(12) United States Patent
Zhang et al.

(10) Patent No.: US 11,447,564 B2
(45) Date of Patent: Sep. 20, 2022

(54) CONSTRUCTS SPECIFICALLY RECOGNIZING GLYPICAN 3 AND USES THEREOF

(71) Applicant: EUREKA THERAPEUTICS, INC., Emeryville, CA (US)

(72) Inventors: Pengbo Zhang, Fremont, CA (US); Yiyang Xu, Pleasanton, CA (US); Javier Morales, San Jose, CA (US); Yoko Nakano, El Cerrito, CA (US); Hong Liu, El Sobrante, CA (US); Jingyi Xiang, Walnut Creek, CA (US); Timothy Acker, San Francisco, CA (US)

(73) Assignee: EUREKA THERAPEUTICS, INC., Emeryville, CA (US)

(*) Notice: Subject to any disclaimer, the term of this patent is extended or adjusted under 35 U.S.C. 154(b) by 107 days.

(21) Appl. No.: 16/608,377

(22) PCT Filed: Apr. 24, 2018

(86) PCT No.: PCT/US2018/029221
§ 371 (c)(1),
(2) Date: Oct. 25, 2019

(87) PCT Pub. No.: WO2018/200586
PCT Pub. Date: Nov. 1, 2018

(65) Prior Publication Data
US 2021/0107992 A1    Apr. 15, 2021

Related U.S. Application Data

(60) Provisional application No. 62/490,586, filed on Apr. 26, 2017.

(51) Int. Cl.
| | | |
|---|---|---|
| C07K 16/30 | (2006.01) |
| A61P 35/00 | (2006.01) |
| C07K 14/725 | (2006.01) |
| C07K 14/705 | (2006.01) |
| C07K 16/28 | (2006.01) |
| G01N 33/574 | (2006.01) |
| A61K 39/00 | (2006.01) |

(52) U.S. Cl.
CPC ............ *C07K 16/303* (2013.01); *A61P 35/00* (2018.01); *C07K 14/7051* (2013.01); *C07K 14/70521* (2013.01); *C07K 16/2809* (2013.01); *G01N 33/57438* (2013.01); *A61K 2039/505* (2013.01); *C07K 2317/21* (2013.01); *C07K 2317/31* (2013.01); *C07K 2317/622* (2013.01); *C07K 2317/73* (2013.01); *C07K 2317/92* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell |
| 4,676,980 A | 6/1987 | Segal |
| 4,816,567 A | 3/1989 | Cabilly |
| 4,975,278 A | 12/1990 | Senter |
| 4,994,560 A | 2/1991 | Kruper, Jr. |
| 5,199,942 A | 4/1993 | Gillis |
| 5,208,020 A | 5/1993 | Chari |
| 5,229,275 A | 7/1993 | Goroff |
| 5,274,119 A | 12/1993 | Frazier |
| 5,342,604 A | 8/1994 | Wilson |
| 5,350,674 A | 9/1994 | Boenisch |
| 5,399,346 A | 3/1995 | Anderson |
| 5,428,139 A | 6/1995 | Kiefer |
| 5,435,990 A | 7/1995 | Cheng |
| 5,489,425 A | 2/1996 | Kruper, Jr. |
| 5,500,362 A | 3/1996 | Robinson |
| 5,505,931 A | 4/1996 | Pribish |
| 5,545,806 A | 8/1996 | Lonberg |
| 5,545,807 A | 8/1996 | Surani |
| 5,567,610 A | 10/1996 | Borrebaeck |
| 5,569,825 A | 10/1996 | Lonberg |
| 5,580,859 A | 12/1996 | Felgner |
| 5,585,362 A | 12/1996 | Wilson |
| 5,589,466 A | 12/1996 | Felgner |
| 5,591,669 A | 1/1997 | Krimpenfort et al. |
| 5,624,821 A | 4/1997 | Winter |
| 5,625,126 A | 4/1997 | Lonberg |
| 5,633,425 A | 5/1997 | Lonberg |
| 5,648,260 A | 7/1997 | Winter |
| 5,652,361 A | 7/1997 | Simon |

(Continued)

FOREIGN PATENT DOCUMENTS

| | | |
|---|---|---|
| EP | 0308936 A2 | 3/1989 |
| EP | 0308936 A3 | 2/1990 |

(Continued)

OTHER PUBLICATIONS

Gura (Science, 1997, 278:1041-1042) (Year: 1997).*
Kaiser (Science, 2006, 313: 1370) (Year: 2006).*
Chames et al (British J. of Pharmacology, 2009, 157, 220-233) (Year: 2009).*
Jena et al. (Blood Aug. 19, 2010 116(7): 1035-1044) (Year: 2010).*
Abhinandan, K.R. et al. (Aug. 2008, e-pub. Jul. 9, 2008). "Analysis and Improvements to Kabat and Structurally Correct Numbering of Antibody Variable Domain," Molecular Immunology 45(14):3832-3839.

(Continued)

*Primary Examiner* — Peter J Reddig
(74) *Attorney, Agent, or Firm* — Morrison & Foerster LLP

(57) ABSTRACT

The present application provides constructs comprising an antibody moiety specifically recognizing Glypican 3 (GPC3), such as a cell surface-bound GPC3. Also provided are methods of making and using these constructs.

25 Claims, 44 Drawing Sheets

Specification includes a Sequence Listing.

(56) References Cited

U.S. PATENT DOCUMENTS

| | | |
|---|---|---|
| 5,661,016 A | 8/1997 | Lonberg |
| 5,696,239 A | 12/1997 | Wilson |
| 5,714,631 A | 2/1998 | Wilson |
| 5,731,168 A | 3/1998 | Carter |
| 5,750,373 A | 5/1998 | Garrard |
| 5,756,065 A | 5/1998 | Wilson |
| 5,808,003 A | 9/1998 | Subramanian |
| 5,821,337 A | 10/1998 | Carter |
| 5,858,358 A | 1/1999 | June et al. |
| 5,883,223 A | 3/1999 | Gray |
| 6,194,551 B1 | 2/2001 | Idusogie |
| 6,326,193 B1 | 12/2001 | Liu |
| 6,352,694 B1 | 3/2002 | June |
| 6,534,055 B1 | 3/2003 | June |
| 6,602,684 B1 | 8/2003 | Umana |
| 6,692,964 B1 | 2/2004 | June |
| 6,737,056 B1 | 5/2004 | Presta |
| 6,797,514 B2 | 9/2004 | Berenson |
| 6,867,041 B2 | 3/2005 | Berenson |
| 6,887,466 B2 | 5/2005 | June |
| 6,905,680 B2 | 6/2005 | June |
| 6,905,874 B2 | 6/2005 | Berenson |
| 7,067,318 B2 | 6/2006 | June |
| 7,144,575 B2 | 12/2006 | June |
| 7,172,869 B2 | 2/2007 | June |
| 7,175,843 B2 | 2/2007 | June |
| 7,232,566 B2 | 6/2007 | June |
| 7,332,581 B2 | 2/2008 | Presta |
| 7,371,826 B2 | 5/2008 | Presta |
| 7,521,541 B2 | 4/2009 | Eigenbrot |
| 7,556,928 B2 | 7/2009 | Jespersen et al. |
| 10,208,285 B2 | 2/2019 | Baeuerle |
| 2002/0164328 A1 | 11/2002 | Shinkawa |
| 2003/0115614 A1 | 6/2003 | Kanda |
| 2003/0157108 A1 | 8/2003 | Presta |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0132140 A1 | 7/2004 | Satoh |
| 2004/0197328 A1* | 10/2004 | Young ............... A61K 51/1096 424/141.1 |
| 2005/0079574 A1 | 4/2005 | Bond |
| 2005/0119455 A1 | 6/2005 | Fuh |
| 2005/0123546 A1 | 6/2005 | Umana |
| 2005/0266000 A1 | 12/2005 | Bond |
| 2006/0121005 A1 | 6/2006 | Berenson |
| 2007/0117126 A1 | 5/2007 | Sidhu |
| 2007/0160598 A1 | 7/2007 | Dennis |
| 2007/0237764 A1 | 10/2007 | Birtalan |
| 2007/0292936 A1 | 12/2007 | Barthelemy |
| 2009/0002360 A1 | 1/2009 | Chen |
| 2014/0170114 A1 | 6/2014 | Kaplan |
| 2014/0322129 A1 | 10/2014 | Leong |
| 2015/0368340 A1* | 12/2015 | Ho ..................... A61P 35/00 424/137.1 |
| 2016/0000842 A1 | 1/2016 | Song et al. |
| 2016/0215261 A1 | 7/2016 | Li et al. |
| 2019/0256571 A1 | 8/2019 | Baeuerle |
| 2019/0276540 A1 | 9/2019 | Baeuerle |
| 2020/0207828 A1 | 7/2020 | Baeuerle |

FOREIGN PATENT DOCUMENTS

| | | |
|---|---|---|
| EP | 0404097 A2 | 12/1990 |
| EP | 1391213 A1 | 2/2004 |
| EP | 1541680 A1 | 6/2005 |
| EP | 3445787 A1 | 2/2019 |
| EP | 3558348 A1 | 10/2019 |
| EP | 3638295 A1 | 4/2020 |
| JP | 2015526387 A | 9/2015 |
| WO | 199100360 A1 | 1/1991 |
| WO | 199220373 A1 | 11/1992 |
| WO | 199308829 A1 | 5/1993 |
| WO | 199311161 A1 | 6/1993 |
| WO | 199321232 A1 | 10/1993 |
| WO | 199411026 A2 | 5/1994 |
| WO | 199411026 A3 | 8/1994 |
| WO | 199429351 A2 | 12/1994 |
| WO | 199429351 A3 | 12/1994 |
| WO | 199429351 A3 | 2/1995 |
| WO | 199704801 A1 | 2/1997 |
| WO | 199717852 A1 | 5/1997 |
| WO | 1997030087 A1 | 8/1997 |
| WO | 199856418 A1 | 12/1998 |
| WO | 1998058964 A1 | 12/1998 |
| WO | 1999022764 A1 | 5/1999 |
| WO | 199951642 A1 | 10/1999 |
| WO | 199954440 A1 | 10/1999 |
| WO | 200042072 A2 | 7/2000 |
| WO | 200061739 A1 | 10/2000 |
| WO | 200042072 A3 | 11/2000 |
| WO | 200129246 A1 | 4/2001 |
| WO | 2001029058 A1 | 4/2001 |
| WO | 0141741 A1 | 6/2001 |
| WO | 200196584 A2 | 12/2001 |
| WO | 200196584 A3 | 1/2003 |
| WO | 2003011878 A2 | 2/2003 |
| WO | 2003084570 A1 | 10/2003 |
| WO | 2003085107 A1 | 10/2003 |
| WO | 2003011878 A3 | 11/2003 |
| WO | 2002031140 A1 | 2/2004 |
| WO | 2004056312 A2 | 7/2004 |
| WO | 2005035586 A1 | 4/2005 |
| WO | 2004056312 A3 | 5/2005 |
| WO | 2003085119 A1 | 8/2005 |
| WO | 2005100402 A1 | 10/2005 |
| WO | 2006006693 A1 | 1/2006 |
| WO | 2006029879 A2 | 3/2006 |
| WO | 2006029879 A3 | 9/2006 |
| WO | 2005035778 A1 | 12/2006 |
| WO | 2005053742 A1 | 6/2007 |
| WO | 2008077546 A1 | 7/2008 |
| WO | 2009012394 A1 | 1/2009 |
| WO | 2009067800 A1 | 6/2009 |
| WO | 2009089004 A1 | 7/2009 |
| WO | 2011056983 A1 | 5/2011 |
| WO | 2011133886 A2 | 10/2011 |
| WO | 2011133886 A3 | 12/2011 |
| WO | 2012145469 A1 | 10/2012 |
| WO | 2013055958 A1 | 4/2013 |
| WO | 2013181543 A1 | 12/2013 |
| WO | 2015142675 A2 | 9/2015 |
| WO | 2015173112 A1 | 11/2015 |
| WO | 2015179658 A2 | 11/2015 |
| WO | 2016049459 A1 | 3/2016 |
| WO | 2017070608 A1 | 4/2017 |
| WO | 2018148454 A1 | 8/2018 |

OTHER PUBLICATIONS

Adolf-Bryfogle, J. et al. (2015, e-pub. Nov. 11, 2014). "PylgClassify: A Database of Antibody CDR Structural Classifications," Nucleic Acids Res. 43:D432-D438.

Al-Lazikani, B. et al. (1997). "Standard Conformations for the Canonical Structures of Immunoglobulins," J. Mol. Biol. 273:927-948.

Allegretta, M. et al. (Jul. 2011). "Therapeutic Potential of Targeting Glypican-3 in Hepatocellular Carcinoma," Anti-Cancer Agents in Medicinal Chemistry (Formerly Current Medicinal Chemistry-Anti-Cancer Agents) 11(6):543-548.

Altman, J. D. et al. (Feb. 2003). "MHC-Peptide Tetramers to Visualize Antigen-Specific T Cells," Current Protocols in Immunology 53(1):17.3.1-17.3.33.

Baldwin, R.W. et al. (Mar. 15, 1986). "Monoclonal Antibodies in Cancer Treatment," Lancet 1(8481)603-605.

Baumhoer, D. et al. (Jun. 1, 2008). "Glypican 3 Expression in Human Nonneoplastic, Preneoplastic, and Neoplastic Tissues: A Tissue Microarray Analysis of 4,387 Tissue Samples," American Journal of Clinical Pathology 129 (6):899-906.

Berg, I.J.M, et al. (Dec. 1998) "Selective Expansion of a Peripheral Blood CD8+ Memory T Cell Subset Expressing Both Granzyme B

(56) References Cited

OTHER PUBLICATIONS and L-Selectin During Primary Viral Infection in Renal Allograft Recipients," Transplant Proc. 30(8):3975-3977.
Boerner, P. et al. (Jul. 1, 1991). "Production of a Antigen-Specific Human Monoclonal Antibodies from in Vitro-Primed Human Splenocytes," J. Immunol. 147(1):86-95.
Brischwein, K. et al. (Mar. 1, 2006, e-pub. Sep. 1, 2005). "MT110: A Novel Bispecific Single-Chain Antibody Construct With High Efficacy in Eradicating Established Tumors," Molecular Immunology 43(8):1129-1143.
Brown, M. et al. (Jun. 5, 1987). "lac Repressor Can Regulate Expression From a Hybrid SV40 Early Promoter Containing a lac Operator in Animal Cells," Cell 49:603-612.
Brüggemann, M. et al. (1993). "Designer Mice: The Production of Human Antibody Repertoires in Transgenic Animals," Year in Immuno. 7:33-40.
Brüggemann, M. et al. (Nov. 1, 1987). "Comparison of the Effector Functions of Human Immunoglobulins Using a Matched Set of Chimeric Antibodies," J. Exp. Med. 166:1351-1361.
Burton, D.R. (1985). "Immunoglobulin G: Functional Sites," Molec. Immunol. 22(3):161-206.
Capel, P.J. et al. (Feb. 1994). "Heterogeneity of Human IgG Fc Receptors," Immunomethods 4(1):25-34.
Capurro, M. et al. (Jul. 1, 2003). "Glypican-3: A Novel Serum and Histochemical Marker For Hepatocellular Carcinoma," Gastroenterology 125(1):89-97.
Chari, R.V.J. et al. (Jan. 1, 1992). "Immunoconjugates Containing Noveal Maytansinoids: Promising Anticancer Drugs," Cancer Res. 52:127-131.
Cheadle, C. et al. (Jan. 1992). "Cloning and Expression of the Variable Regions of Mouse Myeloma Protein Mopc315 in *E. Coli*: Recovery of Active Fv Fragments," Molecular Immunology 29(1):21-30.
Chmielewski, M. (Sep. 2011; e-pub. Jul. 8, 2011). "IL-12 Release by Engineered T Cells Expressing Chimeric Antigen Receptors Can Effectively Muster an Antigen-Independent Macrophage Response on Tumor Cells That Have Shut Down Tumor Antigen Expression," Cancer Research 71(17):5697-5706.
Chothia, C. et al. (Dec. 1989). "Conformations of Immunoglobulin Hypervariable Regions," Nature 342(6252): 877-883.
Chothia, C. et al. (Aug. 20, 1987). "Canonical Structures for the Hypervariable Regions of Immunoglobulins," J. Mol. Biol. 196(4):901-917.
Chothia, C. et al. (Dec. 5, 1985). "Domain Association in Immunoglobulin Molecules. The Packing of Variable Domains," J. Mol. Biol. 186(3):651-663.
Chowdhury, P.S. (2008). "Engineering Hot Spots for Affinity Enhancement of Antibodies," Methods Mol. Biol. 207:179-196.
Clackson, T. et al. (Aug. 15, 1991). "Making Antibody Fragments Using Phage Display Libraries," Nature 352:624-628.
Clipstone, N.A. et al. (Jun. 25, 1992). "Identification of Calcineurin as a Key Signalling Enzyme in T-Lymphocyte Activation," Nature 357(6380):695-697.
Clynes, R. et al. (Jan. 1998). "Fc Receptors are Required in Passive and Active Immunity to Melanoma," Proc. Natl. Acad. Sci. U.S.A. 95:652-656.
Colcher, D. et al. (Jan. 1986). "Use of Monoclonal Antibodies as Radiopharmaceuticals for the Localization of Human Carcinoma Xenografts in Athymic Mice," Methods Enzymol. 121:802-816.
Cole, S.P.C. et al. (1985). "The EBV-Hybridoma Technique and its Applicaton to Human Lung Cancer," in Monoclonal Antibodies and Cancer Therapy, Alan R. Liss, p. 77-96.
Cragg, M.S. et al. (Apr. 1, 2004). "Antibody Specificity Controls in Vivo Effector Mechanisms of Anti-CD20 Reagents," Blood 103(7):2738-2743.
Cragg, M.S. et al. (Feb. 1, 2003). "Complement-Mediated Lysis by Anti-CD20 Mab Correlates With Segregation Into Lipid Rafts," Blood 101(3):1045-1052.
Cunningham, B.C. et al. (Jun. 2, 1989). "High-Resolution Epitope Mapping of hGH-Receptor Interactions by Alanine-Scanning Mutagenesis," Science 244:1081-1085.
Dall'Acqua, W. et al. (1998). "Contribution of Domain Interface Residues to the Stability of Antibody CH3 Domain Homodimers", Biochemistry37:9266-9273.
Datta, R. et al. (Nov. 1992). "Ionizing Radiation Activates Transcription of the EGR1 Gene Via CArG Elements," Proc. Natl. Acad. Sci. USA 89(1):10149-10153.
David, G.S. et al. (1974). "Protein Iodination With Solid State Lactoperoxidase," Biochemistry 13(5):1014-1021.
Daëron, M. (1997). "Fc Receptor Biology," Ann. Rev. Immunol. 15:203-234.
De Haas, M. et al. (Oct. 1995). "Fcγ Receptors of Phagocytes," J. Lab. Clin. Med. 126(4):330-341.
Duncan, A.R. et al. (Apr. 21, 1988). "The Binding Site for C1q on IgG," Nature 322:738-740.
Durand, D. B. et al. (Apr. 1988). "Characterization of Antigen Receptor Response Elements Within The Interleukin-2 Enhancer," Molecular and Cellular Biology 8(4):1715-1724.
Edgar, R.C. (2004, e-pub. Mar. 19, 2004). "MUSCLE: Multiple Sequence Alignment With High Accuracy and High Throughput," Nucleic Acids Research 32(5):1792-1797.
Edgar, R.C. (Aug. 19, 2004). "Muscle: A Multiple Sequence Alignment Method With Reduced Time and Space Complexity," BMC Bioinformatics 5(113):1-19.
Ehrenmann, F. et al. (Jan. 2010, e-pub. Nov. 9, 2009). "IMGT/3Dstructure-DB and IMGT/DomainGapAlign: A Database and a Tool for Immunoglobulins or Antibodies, T Cell Receptors, MHC, IgSF and MhcSF," Nucleic Acids Res. 38:D301-D307.
Fellouse, F.A. et al. (Aug. 24, 2004). "Synthetic Antibodies from a Four-Amino-Acid Code: A Dominant Role for Tyrosine in Antigen Recognition," Proc. Natl. Acad. Sci. USA 101(34):12467-12472.
Feng, M. (e-pub. Mar. 5, 2013). "Therapeutically Targeting Glypican-3 Via a Conformation-Specific Single Domain Antibody in Hepatocellular Carcinoma," PNAS 110(12):E1083-E1091, 9 pages.
Feng, M. et al. (e-pub. Oct. 15, 2013). "Glypican-3 Antibodies: A New Therapeutic Target for Liver Cancer," FEBS Letters 588(2014):377-382.
Ferrara, C. et al. (2006, e-pub. Jan. 24, 2006). "Modulation of Therapeutic Antibody Effector Functions by Glycosylation Engineering: Influence of Golgi Enzyme Localization Domain and Co-Expression of Heterologous β1,4-N-Acetylglucosaminyltransferase III and Golgi α-Mannosidase," Biotechnology and Bioengineering 93(5):851-861.
Fishwild, D.M. et al. (Jul. 1996). "High-Avidity Human IgGK Monoclonal Antibodies from a Novel Strain of Minilocus Transgenic Mice," Nature Biotechnol. 14:845-851.
Fraker, P.J. et al. (Feb. 28, 1978). "Protein and Cell Membrane Iodinations With a Sparingly Soluble Chloroamide, 1,3,4,6-Tetrachloro-3a,6a-Diphenyiglycoluril," Biochem. Biophys. Res. Commun. 80(4):849-857.
Garland, R.J. et al. (Jul. 1999) "The Use of Teflon Cell Culture Bags to Expand Functionally Active CD8+ Cytotoxic T Lymphocytes," J. Immunol Meth. 227(1-2):53-63.
Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.
Ghetie, V. et al. (2000). "Multiple Roles for the Major Histocompatibility Complex Class I-Related Receptor FCRN," Annu. Rev. Immunol. 18:739-766.
Gingrich, J.R. et al. (1998). "Inducible Gene Expression in the Nervous System of Transgenic Mice," Annual Rev. Neurosci. 21:377-405.
Goding, J.W. (1986). "Production of Monoclonal Antibodies." Chapter 3 in Monoclonal Antibodies: Principles and Practice, Academic Press, New York, pp. 59-103.
Gossen, M. et al. (1993). "Anhydrotetracycline, A Novel Effector for Tetracycline Controlled Gene Expression Systems in Eukaryotic Cells," Nucleic Acids Research 21(18):4411-4412.
Griffiths, A.D. et al. (1993). "Human Anti-Self Antibodies with High Specificity from Phage Display Libraries," EMBO J. 12(2):725-734.

(56) References Cited

OTHER PUBLICATIONS

Gu, J. et al. (Jan. 1, 2012). "Generation of Dual-Variable-Domain Immunoglobulin Molecules for Dual-Specific Targeting," Methods in Enzymology 502:25-41.
Guyer, R.L. et al. (Aug. 1976). "Immunoglobulin Binding by Mouse Intestinal Epithelial Cell Receptors," J. Immunol. 117(2):587-593.
Haanen, J.B. et al. (1999), "Selective Expansion of Cross-Reactive CD8+ Memory T Cells by Viral Variants." The Journal of Experimental Medicine 190(9):1319-1328.
Haruyama, Y. et al. (Jan. 7, 2016). "Glypican-3 is a Prognostic Factor and an Immunotherapeutic Target in Hepatocellular Carcinoma," World Journal of Gastroenterology 22(1):275-283.
Hellstrom, I. et al. (Mar. 1985). "Strong Antitumor Activities of IgG3 Antibodies to a Human Melanoma-associated Ganglioside," Proc. Nati. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Hinman, L.M. et al. (Jul. 15, 1993). "Preparation and Characterization of Monoclonal Antibody Conjugates of the Callcheamicins: A Novel and Potent Family of Antitumor Antibiotics," Cancer Research 53:3336-3342.
Hippo, Y. et al. (Apr. 1, 2004)."Identification of Soluble NH2-Terminal Fragment of Glypican-3 as a Serological Marker for Early-Stage Hepatocellular Carcinoma," Cancer Research 64(7):2418-2423.
Ho, M. (Oct. 1, 2011). "Advances in Liver Cancer Antibody Therapies: A Focus on Glypician-3 and Mesothelin," BioDrugs 25(5):275-284.
Hoet, R.M. et al. (2005), "Generation of High-Affinity Human Antibodies by Combining Donor-Derived and Synthetic Complementarity-Determining-Region Divers," Nat Biotechnol, 23(3):344-348.
Holliger, P. et al. (Jul. 1993). "'Diabodies'": Small Bivalent and Bispecific Antibody Fragments, Proceedings of the National Academy of Sciences USA 90:6444-6448.
Honegger, A. et al. (Jun. 8, 2001). "Yet Another Numbering Scheme for Immunoglobulin Variable Domains: An Automatic Modeling and Analysis Tool," J. Mol. Biol. 309:657-670.
Hoogenboom, H.R. et al. (2001). "Overview of Antibody Phage-Display Technology and Its Applications," Chapter 1 in Methods in Molecular Biology, O'Brien et al. ed., Humana Press, Totowa, NJ, 178:1-37.
Hoogenboom, H.R. et al., (Sep. 20, 1992). "By-Passing Immunisation Human Antibodies From Synthetic Repertoires of Germline VH Gene Segments Rearranged In Vitro," J. Mol. Biol. 227(2):381-388.
Hunter, W.M. et al. (May 5, 1962). "Preparation Iodine-131 Labelled Human Growth Hormone of High Specific Activiey," Nature 144:495-496.
Idusogie, E.E. et al. (2000). "Mapping of the C1q Binding Site on Rituxan, a Chimeric Antibody With a Human IgG1 Fc," J. Immunol. 164:4178-4184.
International Preliminary Report on Patentability dated Nov. 7, 2019, for PCT Application No. PCT/US2018/029221 filed on Apr. 24, 2018, 8 pages.
International Search Report and Written Opinion of the International Searching Authority dated Jul. 20, 2018, for PCT Application No. PCT/US2018/029221 filed on Apr. 24, 2018, seventeen pages.
Ishiguro, T. et al. (Dec. 1, 2008). "Anti-Glypican 3 Antibody as a Potential Antitumor Agent for Human Liver Cancer." 68(23):9832-9838.
Jakobovits, A. et al. (Mar. 1993). "Germ-Line Transmission and Expression of a Human-Derived Yeast Artificial Chromosome," Nature 362(6417):255-258.
Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90(6):2551-2555.

Jansen, F.K. et al. (1982). "Immunotoxins: Hybrid Molecules Combining High Specificity and Potent Cytotoxicity," Immunol. Rev. 62:185-216.
Jiang, Y. et al. (e-pub. Jun. 18, 2015). "T-cell Exhaustion in the Tumor Microenvironment," Cell Death & Disease 6(6):e1792-e1792, pages.
Jones, P. et al. (May 29, 1986). "Replacing The Complementarity-Determining Regions in a Human Antibody With Those From A Mouse," Nature 321:522-525.
Kabat, E.A. (1991). Sequences of Proteins of Immunological Interest, 5th ed., Public Health Service, National Institutes of Health, Bethesda, MD, pp. 647-723.
Kabat, E.A. et al. (Oct. 10, 1977). "Unusual Distributions of Amino Acids in Complementarity-Determining (Hypervariable) Segments of Heavy and Light Chains of Immunoglobulins and Their Possible Roles in Specificity of Antibody-Combining Sites," J. Biol. Chem. 252(19):6609-6616.
Kam, N.W.S. et al. (Aug. 16, 2005). "Carbon Nanotubes as Multifunctional Biological Transporters and Near-Infrared Agents for Selective Cancer Cell Destruction," PNAS 102(33):11600-11605, 6 pages.
Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.
Killen, J.A. et al. (Nov. 1, 1984). "Specific Killing of Lymphocytes That Cause Experimental Autoimmune Myasthenia Gravis by Ricin Toxin-Acetylcholine Receptor Conjugates," J. Immunol. 133(5):2549-2553.
Kim, J-K. et al. (1994). "Localization of the Site of the Murine IgGl Molecule That is involved in Binding to the Murine Intestinal Fc Receptor," Eur. J. Immunol. 24:2429-2434.
Kim, J.H. et al. (Apr. 29, 2011). "High Cleavage Efficiency of a 2A Peptide Derived From Porcine Teschovirus-1 in Human Cell Lines, Zebrafish and Mice," PloS one 6(4):e18556, 1-8.
Kohler, G. et al. (Aug. 7, 1975) "Continuous Cultures of Fused Cells Secreting Antibody of Predefined Specificity," Nature 256:495-497.
Kostelny, S.A. et al. (Mar. 1, 1992). "Formation of a Bispecific Antibody by the Use of Leucine Zippers," J. Immunol. 148(5):1547-1553.
Kozbor, D. (Dec. 1984). "A Human Hybrid Myeloma for Production of Human Monoclonal Antibodies," J. Immunol. 133(6):3001-3005.
Labrijn, A.F. et al. (Mar. 26, 2013). "Efficient Generation of stable Bispecific IgG1 by Controlled Fab-arm Exchange," Proc. Natl. Acad. Sci. USA 110(13):5145-5150.
Lee, C.V. et al. (2004). "Bivalent Antibody Phage Display Mimics Natural Immunoglobulin," J. Immunol. Methods 284 (1-2):119-132.
Lee, C.V. et al. (2004). "High-Affinity Human Antibodies From Phage-Displayed Synthetic Fab Libraries With a Single Framework Scaffold," J. Mol. Biol. 340:1073-1093.
Lefranc, M.-P. et al. (2015, e-pub. Nov. 5, 2014). "IMGT®, The International ImMunoGeneTics Information System® 25 Years On," Nucleic Acids Res. 43:D413-0422.
Lefranc, M.P. et al. (Jan. 2003). "IMGT Unique Numbering for Immunoglobulin and T Cell Receptor Variable Domains and Ig Superfamily V-Like Domains," Dev. Comp. Immunol. 27(1):55-77.
Li, W. et al. (2017). "Redirecting T Cells To Glypican-3 With 4-1BB Zeta Chimeric Antigen Receptors Results in Th1 Polarization and Potent Antitumor Activity," Human Gene Therapy 28(5):437-448, 47 pages.
Lindhofer, H. et al. (1995)."Preferential Species-Restricted Heavy/Light Chain Pairing in Rat/Mouse Quadromas. Implications for a Single-Step Purification of Bispecific Antibos," J Immunol 55(1):219-225.
Liu, C. et al. (Aug. 1996). "Eradication of Large Colon Tumor Xenografts by Targeted Delivery of Maytansinoids," Proc. Natl. Acad. Sci. USA 93:8618-8623.
Lode, H.N. et al. (Jul. 15, 1998). "Targeted Therapy with a Novel Enediyene Antibiotic Calicheamicin 011 Effectively Suppresses Growth and Dissemination of Liver Metastases in a Syngeneic Model of Murine Neuroblastoma," Cancer Res. 58:2925-2928.
Lonberg, N. et al. (1995, e-pub. Jul. 10, 2009). "Human Antibodies From Transgenic Mice," Int. Rev. Immunol. 13 (1):65-93.

(56) References Cited

OTHER PUBLICATIONS

Lonberg, N. et al. (Apr. 28, 1994). "Antigen-Specific Human Antibodies From Mice Comprising Four Distinct Genetic Modifications," Nature 368(6474):856-859.
MacCallum, R.M. et al. (Oct. 1996). "Antibody-Antigen Interactions: Contact Analysis and Binding Site Topography," J. Mol. Biol. 262(5):732-745.
Mack, M. et al. (Jul. 1995). "A Small Bispecific Antibody Construct Expressed as a Functional Single-Chain Molecule With High Tumor Cell Cytotoxicity," Proc. Natl. Acad. Sci. USA 92:7021-7025.
Mader, S. et al. (Jun. 1993). "A Steroid-Inducible Promoter for the Controlled Overexpression of Cloned Genes in Eukaryotic Cells." Proc. Natl. Acad. Sci. USA 90:5603-5607.
Mandler, R. et al. (2000). "Synthesis and Evaluation of Antiproliferative Activity of a Geldanamycin-Herceptin TM Immunoconjugate," Bioorganic & Med. Chem. Letters 10:1025-1028.
Mandler, R. et al. (2002, e-pub. Jun. 19, 2002). "Modifications in Synthesis Strategy Improve the Yield and Efficacy of Geldanamycin-Herceptin Immunoconjugates," Bioconjugate Chem. 13:786-791.
Mandler, R. et al. (Oct. 2000). "Immunoconjugates of Geldananlycin and Anti-HER2 Monoclonal Antibodies: Antiproliferative Activity on Human Breast Carcinoma Cell Lines," J. Nat. Cancer Inst. 92(19):1573-1581.
Manome, Y. et al. (Oct. 1993). "Coinduction of c-jun Gene Expression and Internucleosomal DNA Fragmentation by Ionizing Radiation," Biochemistry 32(40):10607-10613.
Marks, J.D. et al. (1991). "By-Passing Immunization Human Antibodies from V-gene Libraries Displayed on Phage," J. Mol. Biol. 222:581-597.
Marks, J.D. et al. (2004) "Selection of Human Antibodies from Phage Display Libraries," Chapter 8 in Methods in Molecular Biology, LO, B.K.C. (ed.), Humana Press Inc., Totowa, NJ, 248:161-176, 29 pages.
Marks, J.D. et al. (Jul. 1992). "By-Passing Immunization: Building High Affinity Human Antibodies by Chain Shuffling," Bio/Technology 10:779-783.
McCafferty, J. et al. (Dec. 6, 1990). "Phage Antibodies: Filamentous Phage Displaying Antibody Variable Domains," Nature 348:552-554.
Milstein, C. et al. (Oct. 6, 1983). "Hybrid Hybridomas and Their Use in Immunohistochemistry," Nature 305:537-539.
Morrison, S.C. et al. (Nov. 1984). "Chimeric Human Antibody Molecules: Mouse Antigen-Binding Domains With Human Constant Region Domains," Proc. Natl. Acad. Sci, USA 81:6851-6855.
Morrison, S.L. (Apr. 28, 1994). "Success in Specification," Nature 368:812-813.
Munson, P.J. et al. (1980). "LIGAND: A Versatile Computerize Approach for Characterization of Ligand-Binding Systems," Anal. Biochem. 107:220-239.
Nakano, K. et al. (2010). "Generation of a Humanized Anti-Glypican 3 Antibody by CDR Grafting and Stability Optimization," Anti-Cancer Drugs 21(10):907-916.
Nakano, K. et al. (e-pub. Nov. 18, 2008). "Anti-Glypican 3 Antibodies Cause ADCC Against Human Hepatocellular Carcinoma Cells," Biochemical and Biophysical Research Communications 378(2009):279-284.
Nakatsura, T. et al. (Jun. 20, 2003). "Glypican-3, Overexpressed Specifically in Human Hepatocellular Carcinoma, is a Novel Tumor Marker," Biochemical and Biophysical Research Communications 306(1):16-25.
Nakatsura, T. et al. (Oct. 1, 2004)."Identification of Glypican-3 as a Novel Tumor Marker for Melanoma," Clinical Cancer Research 10(19):6612-6621.
Neuberger, M. (Jul. 1996). "Generating High-Avidity Human Mabs in Mice," Nature Biotechnology 14:826.
Neuberger, M.S. et al., (Dec. 13, 1984). "Recombinant Antibodies Processing Novel Effector Functions," Nature 312:604-608.
Niculesu-Duvaz, I. et al. (1997). "Antibody-Directed Enzyme Prodrug Therapy (ADEPT): A Review," Adv. Drug Del. Rev. 26:151-172.
Nygren, H. (May 1982). "Conjugation of Horseradish Peroxidase to Fab Fragments With Different Homobifunctional and Heterobifunctional Cross-Linking Reagents. A Comparative Study," J. Histochem. and Cytochem. 30(5):407-412.
Okazaki, A. et al. (Mar. 5, 2004). "Fucose Depletion From Human IgG1 Oligosaccharide Enhances Binding Enthalpy and Association Rate Between IgG1 and FcγRllla," J. Mol. Biol. 336(5):1239-1249.
Pain, D. et al. (1981). "Preparation of Protein A-Peroxidase Monoconjugate Using a Heterobifunctional Reagent, and Its Use in Enzyme Immunoassays," J. Immunol. Methods 40:219-230.
Palucka, K. et al. (Apr. 12, 2012). "Cancer Immunotherapy Via Dendritic Cells," Nature Reviews Cancer 12 (4):265-277.
Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.
Phung, Y. et al. (Sep. 2012). "High Affinity Monoclonal Antibodies to Cell Surface Tumor Antigen Glypican-3 Generated Through a Combination of Peptide Immunization and Flow Cytometry Screening," MABS 4(5):592-599.
Plückthun, A. (1994). "Antibodies from *Escherichia coli*," in Chapter 11 The Pharmacology of Monoclonal Antibodies, vol. 113, Rosenburg and Moore eds., Springer-Verlag, New York, pp. 269-315, 48 pages.
Presta, L.G. (1992). "Antibody Engineering," Current Opinion in Structural Biology 2:593-596.
Pullarkat, V. et al. (Apr. 1, 1999). "A Phase I Study of a HER2/Neu Bispecific Antibody With Granulocyte-Colony-Stimulating Factor in Patients With Metastatic Breast Cancer That Overexpresses HER2/Neu," Cancer Immunology, Immunotherapy 48(1):9-21.
Raag, R. et al. (Jan. 1995). "Single-chain Fvs," The FASEB Journal 9:73-80.
Ramakrishnan, S. et al. (Jan. 1984). "Comparison of the Selective Cytotoxic Effects of Immunotoxins Containing Ricin A Chain or Pokeweed Antiviral Protein and Anti-Thy 1.1 Monoclonal Antibodies," Cancer Res. 44:201-208.
Ravetch, J.V. et al. (1991). "Fc Receptors," Annu. Rev. Immunol. 9:457-492.
Ridgway, J.B.B. et al. (1996). "'Knobs-Into-Holes' Engineering of Antibody CH3 Domains for Heavy Chain Heterodimerization," Protein Engineering 9(7):617-621.
Riechmann, L. et al. (Mar. 24, 1988), "Reshaping Human Antibodies for Therapy," Nature 332:323-329.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Rosenberg, S.A. et al. (Dec. 22, 1988). "Use of Tumor-Infiltrating Lymphocytes and Interleukin-2 in the Immunotherapy of Patients with Metastatic Melanoma—A preliminary Report," The New England Journal of Medicine 319:1676-1680.
Rossi, E.A. et al. (May 2, 2006). "Stably Tethered Multifunctional Structures of Defined Composition Made by the Dock and Lock Method for Use in Cancer Targeting," Proceedings of the National Academy of Sciences 103(18):6841-6846.
Rowland, G.F. et al. (1986). "Drug Localisation and Growth Inhibition Studies of Vindesine-Monoclonal Anti-CEA Conjugates in a Human Tumour Xenograft," Cancer Immunol. Immunother. 21:183-187.
Sanjana, N.E. et al. (Aug. 2014). "Improved Vectors and Genome-Wide Libraries For CRISPR Screening," Nature Methods 11(8):783-784, 5 pages.
Scheraga, H.A. (1992). "Predicting Three-Dimensional Structures of Oligopeptides," Rev. Computational Chem. 3:73-142.
Sergeeva, A. et al. (Apr. 21, 2011, e-pub. Feb. 4, 2011). "An Anti-PR1/HLA-A2 T-Cell Receptor-Like Antibody Mediates Complement-Dependent Cytotoxicity Against Acute Myeloid Leukemia Progenitor Cells," Blood 117 (16):4262-4272.
Shields, R.L. et al. (Mar. 2, 2001). "High Resolution Mapping of the Binding Site on Human IgG1 for FcγRI, FcγRII. FcγRIII, and FcRn and Design of IgG1 Variants With Improved Binding to the FcγR," J. Biol.Chem. 276(9):6591-6604.

(56) References Cited

OTHER PUBLICATIONS

Shirakawa, H. et al. (Aug. 2009). "Glypican-3 Expression is Correlated With Poor Prognosis in Hepatocellular Carcinoma," Cancer Science 100(8):1403-1407.
Shoji-Hosaka, E. et al. (2006). "Enhanced Fc-Dependent Cellular Cytotoxicity of Fc Fusion Proteins Derived from TNF Receptor II and LFA-3 by Fucose Removal from Asn-Linked Oligosaccharides," J. Biochem. 140(6):777-783.
Sidhu, S.S. et al. (2004). "Phage-Displayed Antibody Libraries of Synthetic Heavy Chain Complementarity Determining Regions," J. Mol. Biol. 338(2):299-310.
Spencer, D. M. et al. (Nov. 12, 1993). "Controlling Signal Transduction with Synthetic Ligands," Science 262 (5136):1019-1024.
Suresh, M.R. et al. (1986). "Bispecific Monoclonal Antibodies From Hybrid Hybridomas," Methods in Enzymology 121:210-228, 19 pages.
Syrigos, K. et al. (1999). "Antibody Directed Enzyme Prodrug Therapy (ADEPT): A Review of the Experimental and Clinical Considerations," Anticancer Research 19:605-614.
Thorpe, (1985). "Antibody Carriers of Cytotoxic Agents in Cancer Therapy: A Review," in Monoclonal Antibodies '84: Biological and Clinical Applications, Pincheraet al. (eds.), pp. 475-506.
Tomimatsu, K. et al. (2009, e-pub. Jul. 7, 2009). "Production of Human Monoclonal Antibodies against FcεRIα by a Method Combining In Vitro Immunization with Phage Display," Biosci. Biotechnol. Biochem. 73(7):1465-1469.
Traunecker, A. et al. (1991). "Bispecific Single Chain Molecules (Janusins) Target Cytotoxic Lymphocytes on HIV Infected Cells," EMBO J. 10(12):3655-3659.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.
Ul-Tel, K. et al. (2000). "Sensitive Assay of RNA Interference in Drosophila and Chinese Hamster Cultured Cells Using Firefly Luciferase Gene as Target," FEBS Letters 479:79-82.
Verhoeyen, M. et al. (Oct. 23, 1987) "Reshaping Human Antibodies: Grafting an Antilysozyme Activity," Science 239:1534-1536.
Veri, M.-C. et al. (Jul. 2010). "Therapeutic Control of B Cell Activation via Recruitment of Fcγ Receptor IIb (CD32B) Inhibitory Function With a Novel Bispecific Antibody Scaffold," Arthritis & Rheumatism, 62(7):1933-1943.
Vitetta, E.S. et al. (Nov. 20, 1987). "Redesigning Nature's Poisons to Create Anti-Tumor Reagents," Science 238:1098-1104.
Wang, L. et al. (Aug. 15, 2015). "Glypican-3 is a Biomarker and a Therapeutic Target of Hepatocellular Carcinoma." Hepatobiliary & Pancreatic Diseases International 14(4):361-366.
Wherry, E.J. (Jun. 2011, e-pub. May 18, 2011). "T Cell Exhaustion," Nature immunology 12(6):492-499.
Wright, A. et al. (Jan. 1997). "Effect of Glycosylation on Antibody Function: Implications for Genetics Engineering," Trends Biotechnol. 15:26-32.
Yamane-Ohnuki, N. et al. (Sep. 5, 2004, e-pub Aug. 6, 2004). "Establishment of FUT8 Knockout Chinese Hamster Ovary Cells: An Ideal Host Cell Line For Producing Completely Defucosylated Antibodies With Enhanced Antibody-Dependent Cellular Cytotoxicity," Biotechnology and Bioengineering 87(5):614-622.
Yamauchi, T. et al. (May 2005). "Neuronal Ca2+/Calmodulin-Dependent Protein Kinase Il-Discovery, Progress in a Quarter of a Century, and Perspective: Implication for Learning and Memory," Biological and Pharmaceutical Bulletin 28(8):1342-1354.
Ye, J. et al. (Jul. 2013). "IgBLAST: An Immunoglobulin Variable Domain Sequence Analysis Tool," Nucleic acids research 41(W1):W34-W40.
Yu, X. et al. (Aug. 28, 2015). "Differential Expression of Glypican-3 (GPC3) in Lung Squamous Cell Carcinoma and Lung Adenocarcinoma and its Clinical Significance," Genet Mol Res 14(3):10185-10192.
Zhang, L. et al. (Apr. 2011). "Improving Adoptive T Cell Therapy by Targeting and Controlling IL-12 Expression to the Tumor Environment," Molecular Therapy 19(4):751-759.
Zhang, Y.-F. et al. (Sep. 26, 2016). "Humanization of High-Affinity Antibodies Targeting Glypican-3 in Hepatocellular Carcinoma," Scientific Reports 6(1):1-11.
Zynger, D.L. et al. (2008). "Expression of Glypican 3 in Ovarian and Extragonadal Germ Cell Tumors," American Journal of Clinical Pathology 130(2):224-230.

* cited by examiner

FIG. 1A
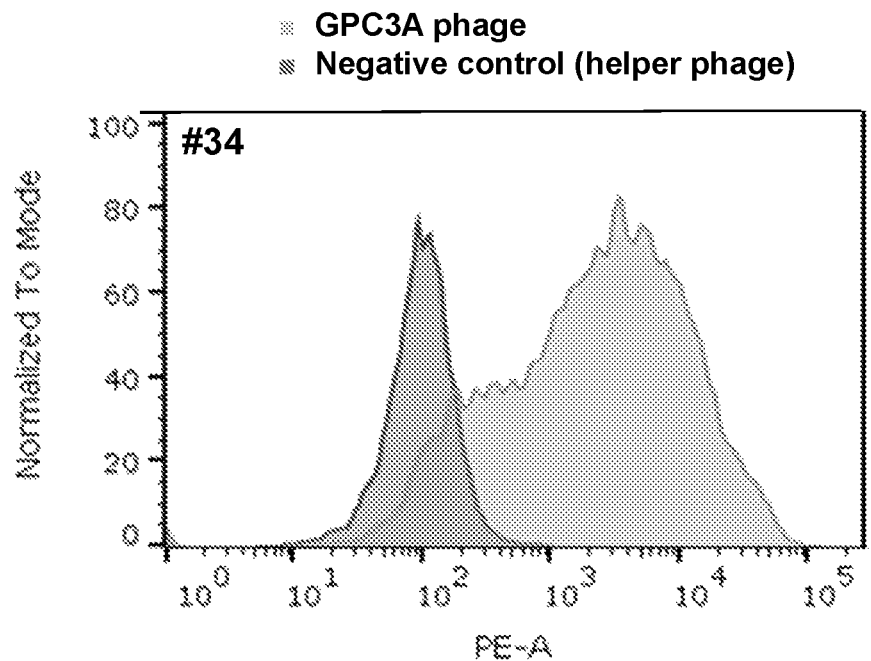
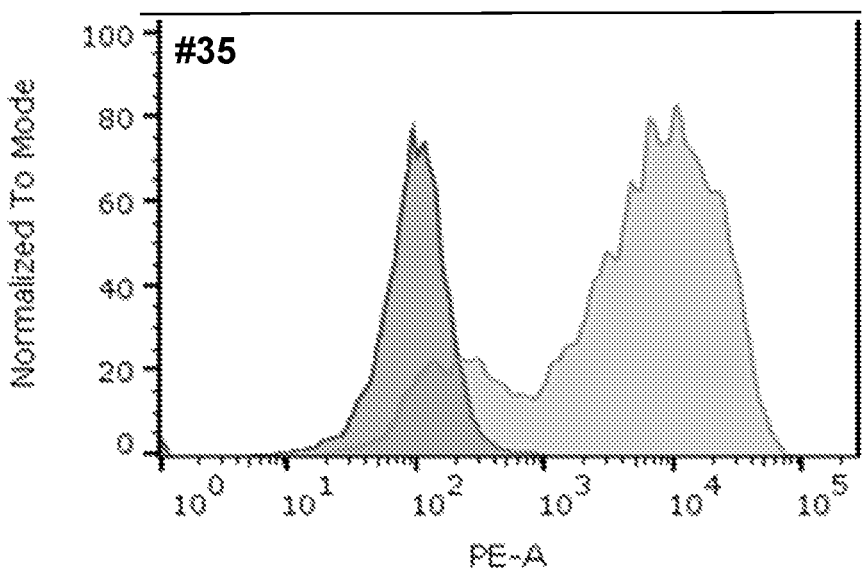

FIG. 1B
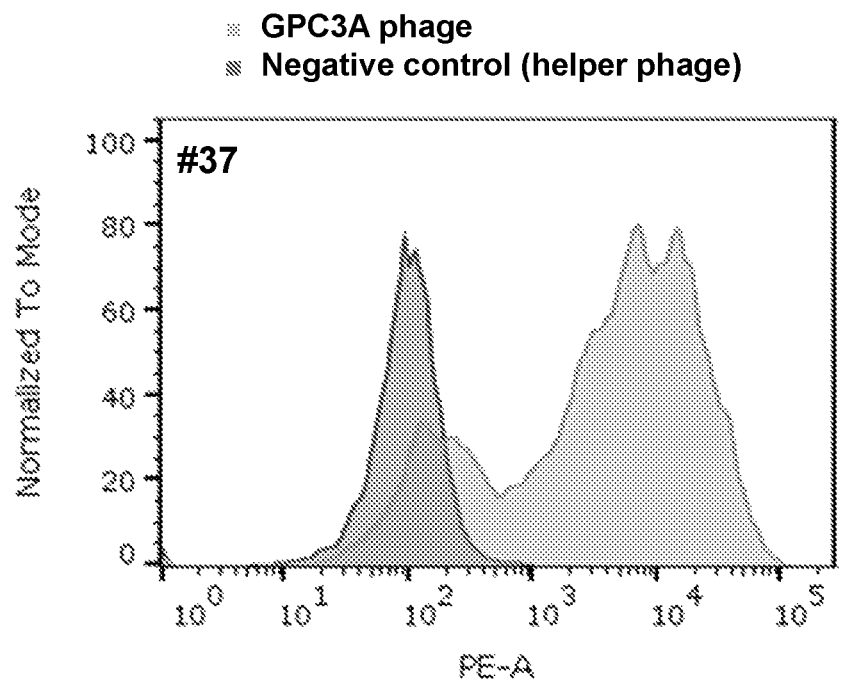
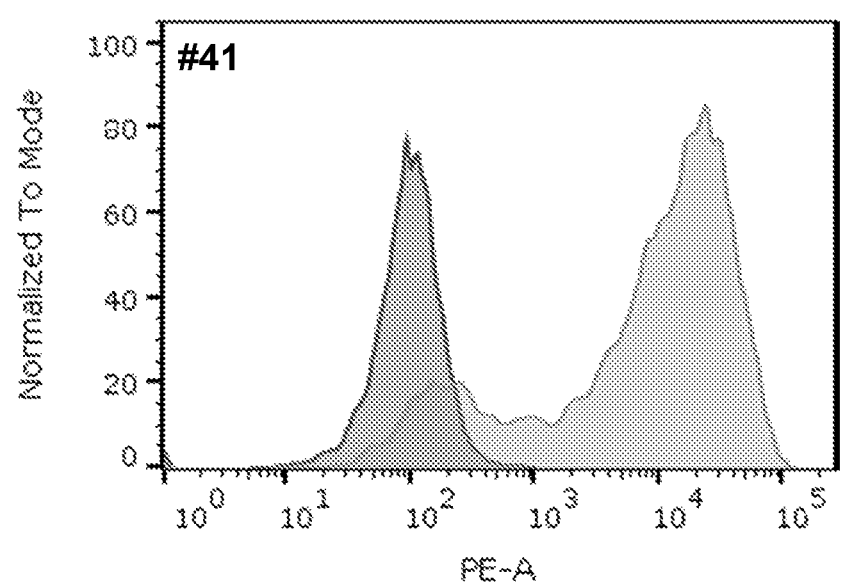

FIG. 1C
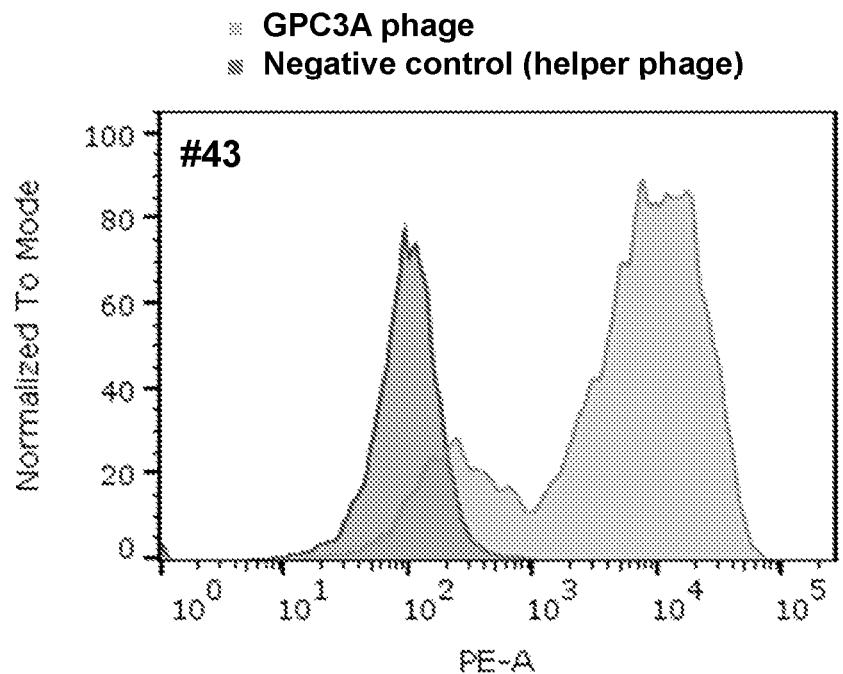
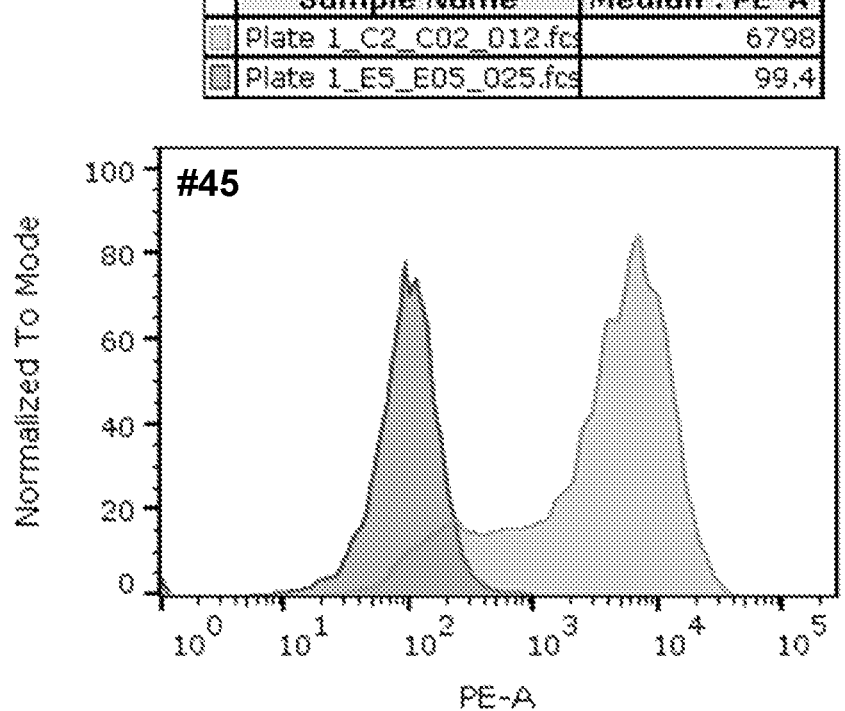

FIG. 1D
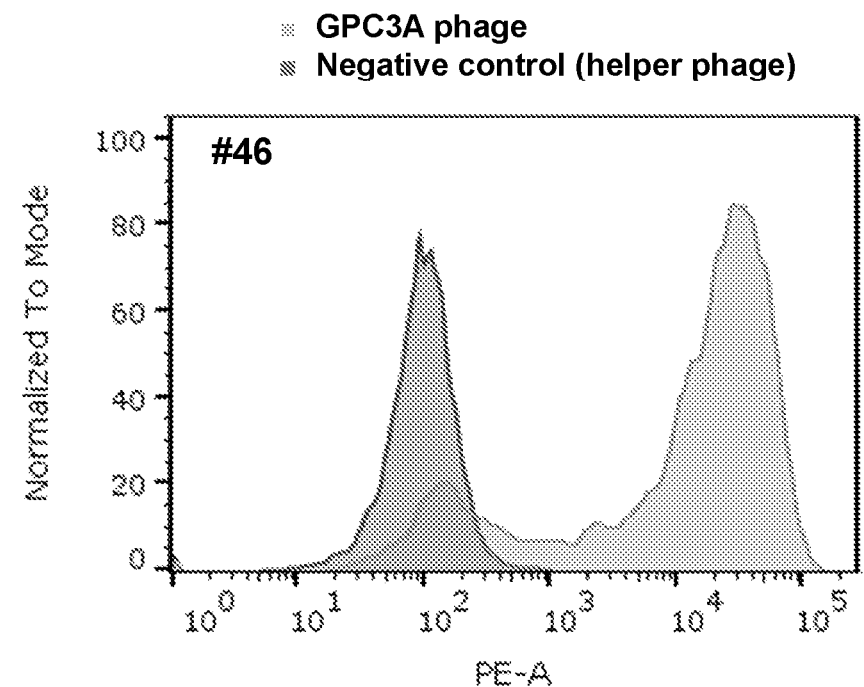
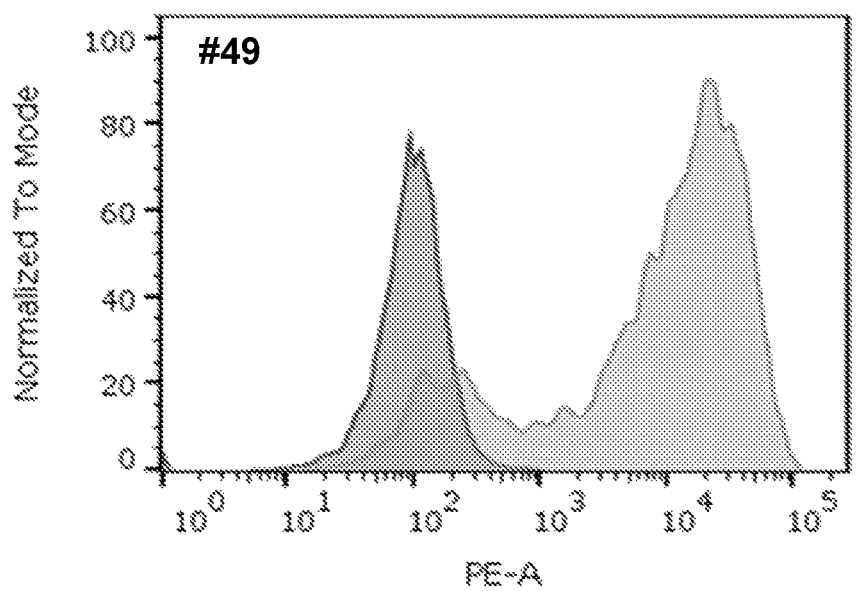

FIG. 1E
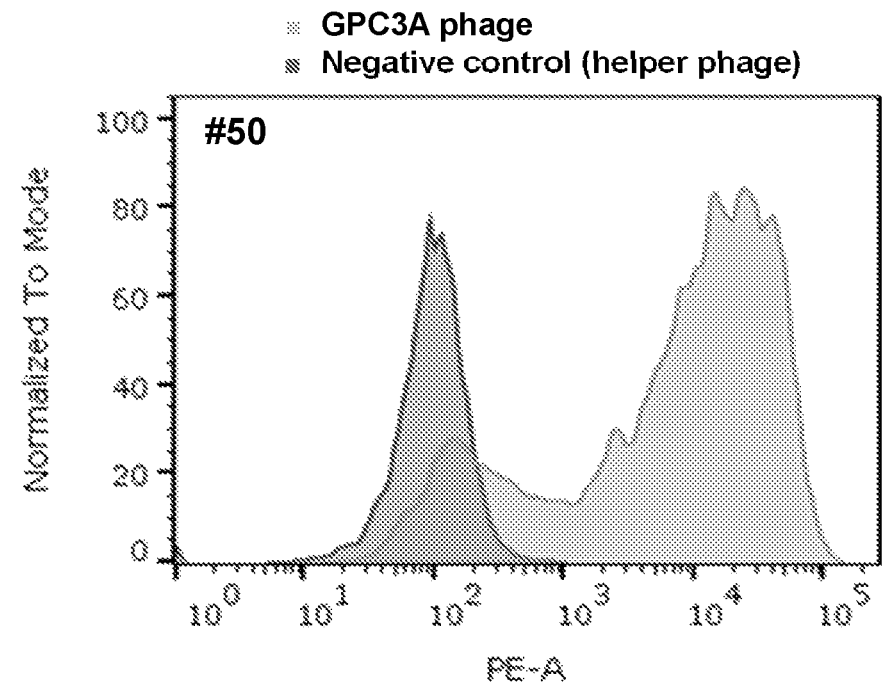
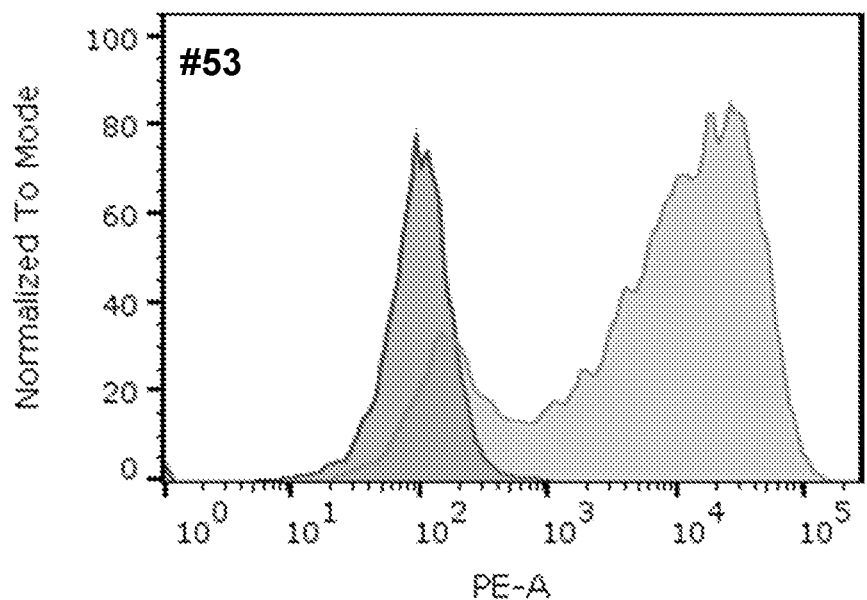

FIG. 1F
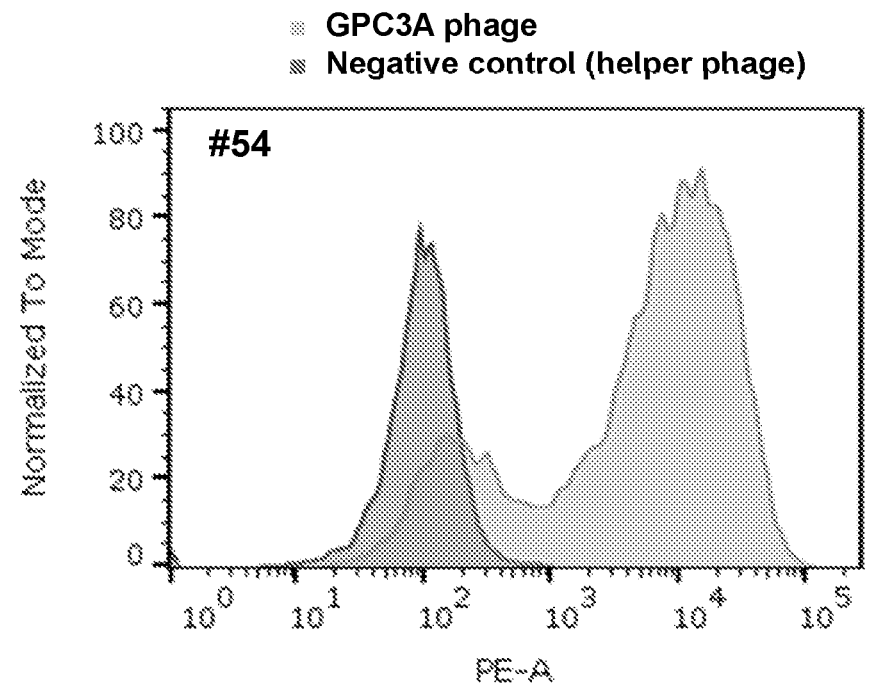
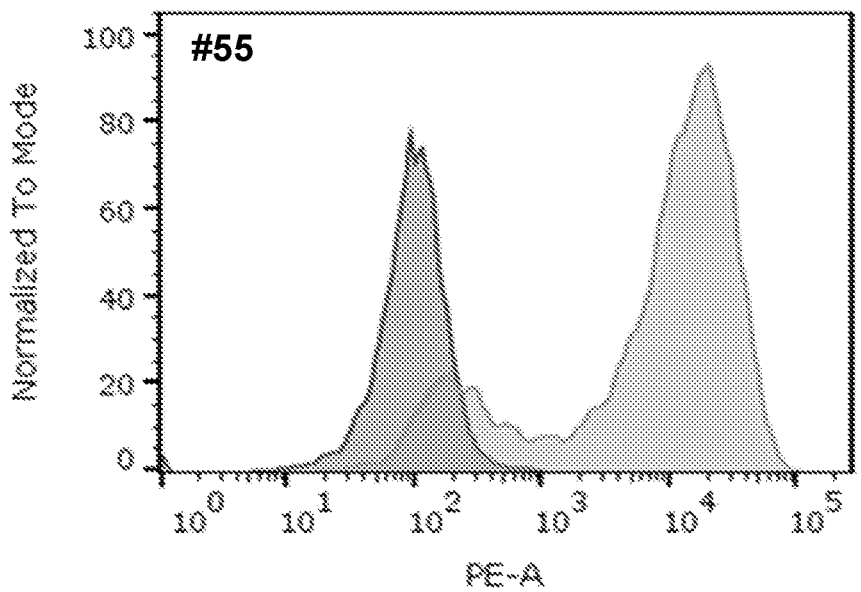

FIG. 1G
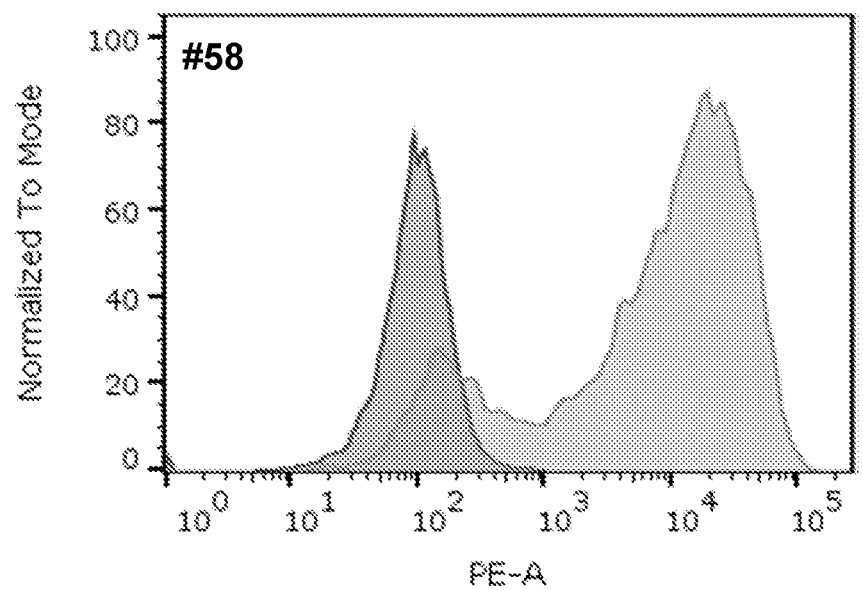
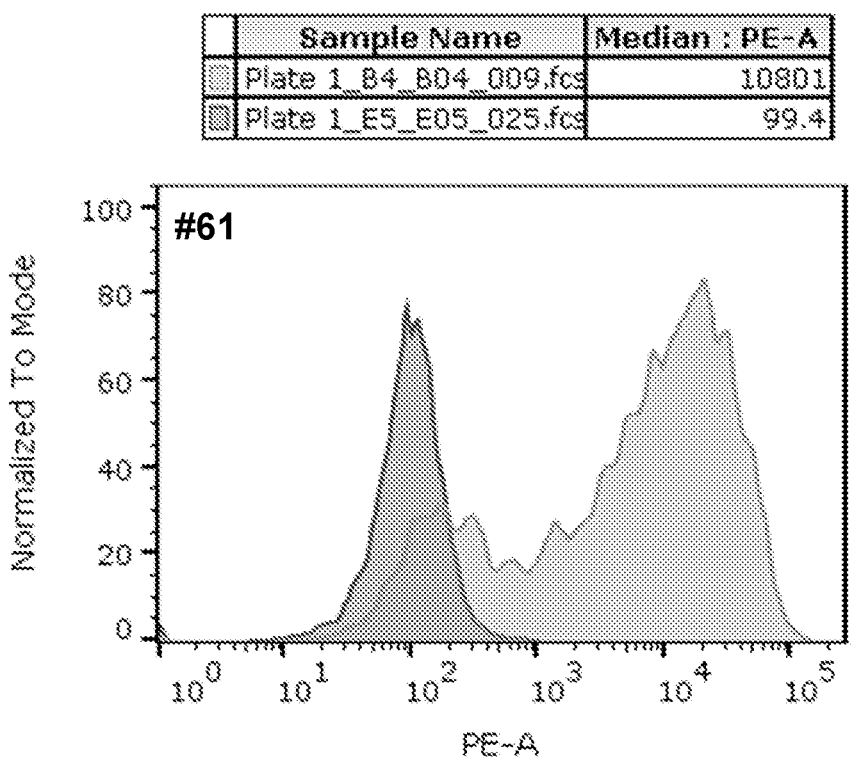

FIG. 3A
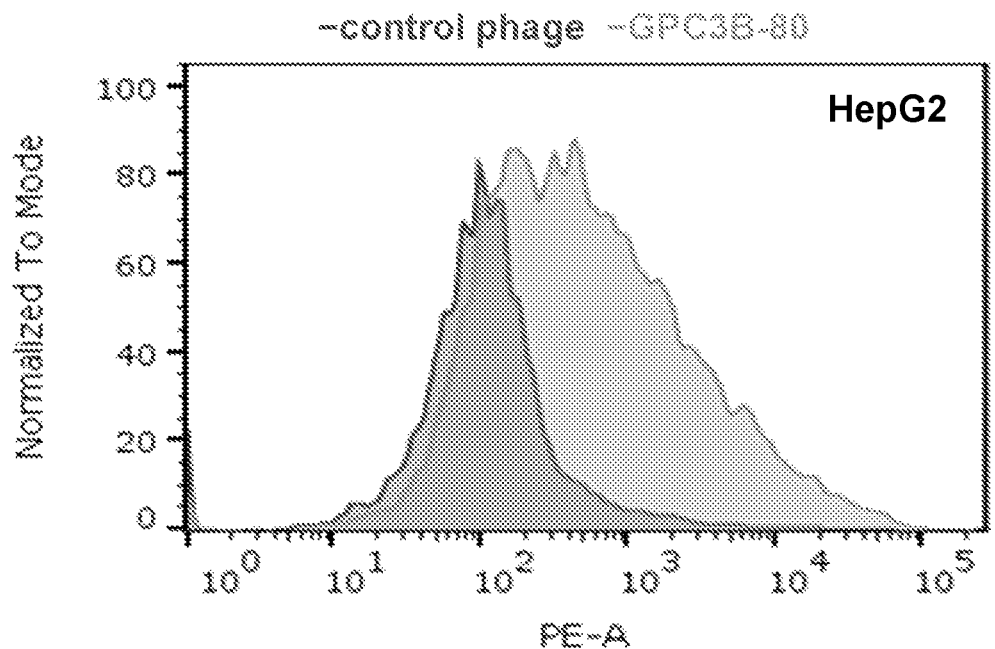
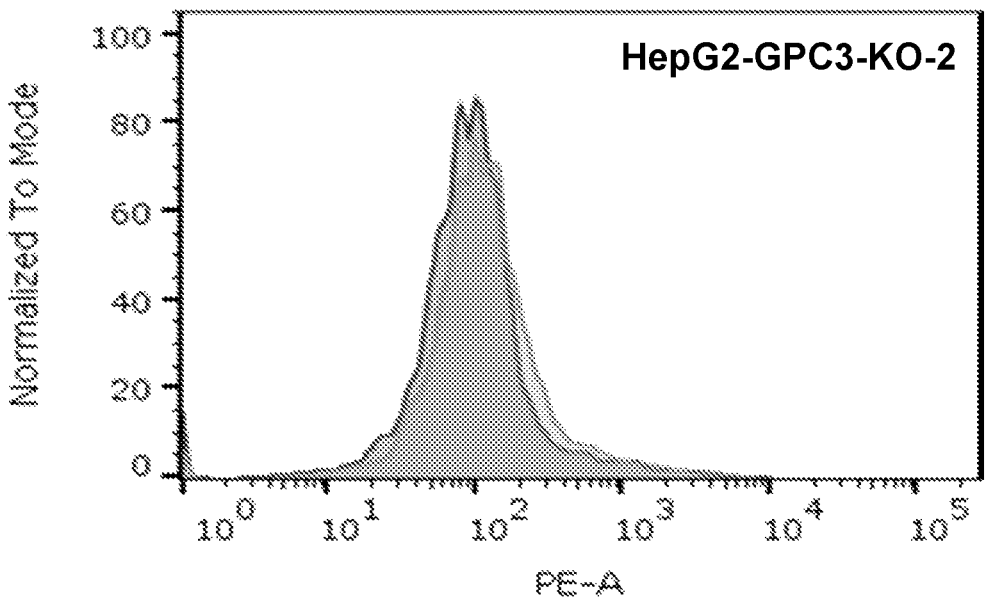

FIG. 3B
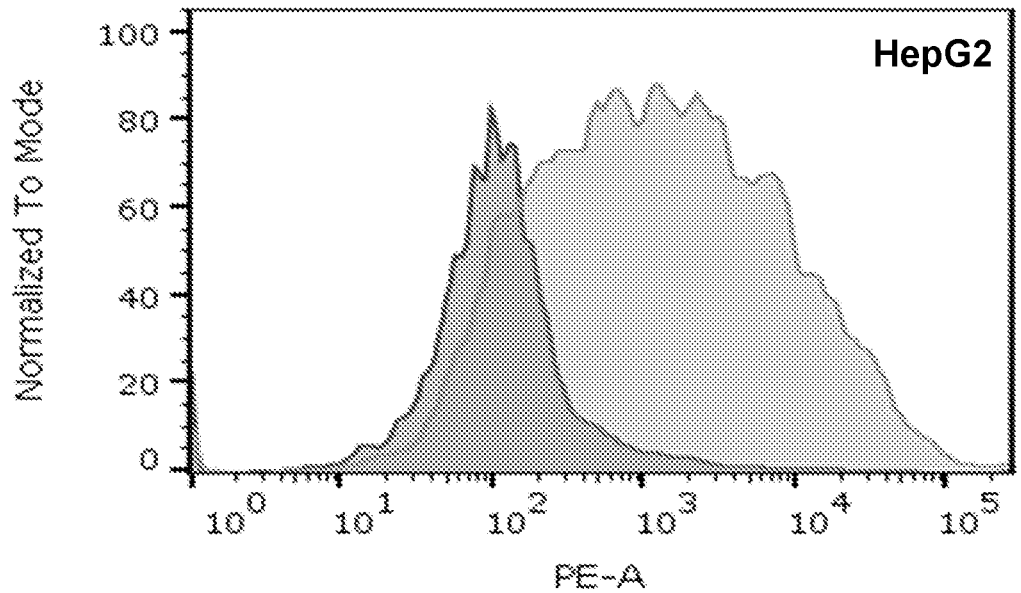
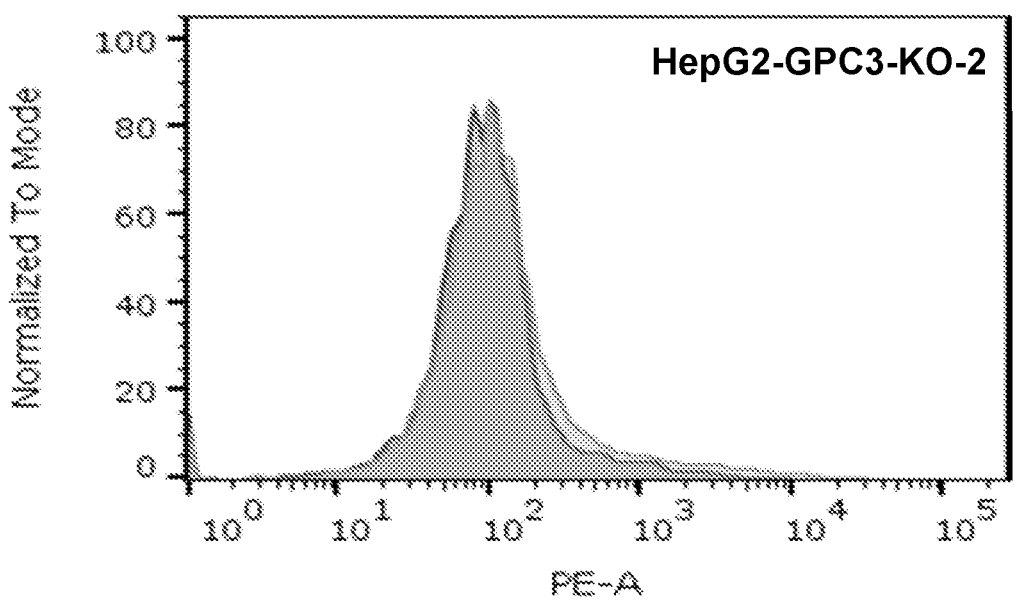

FIG. 3C
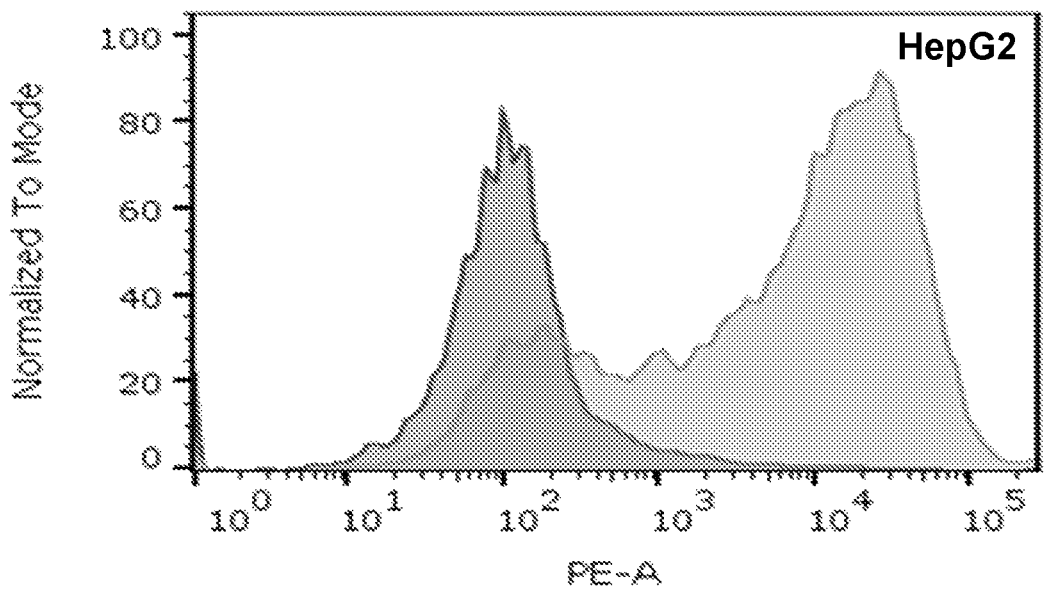
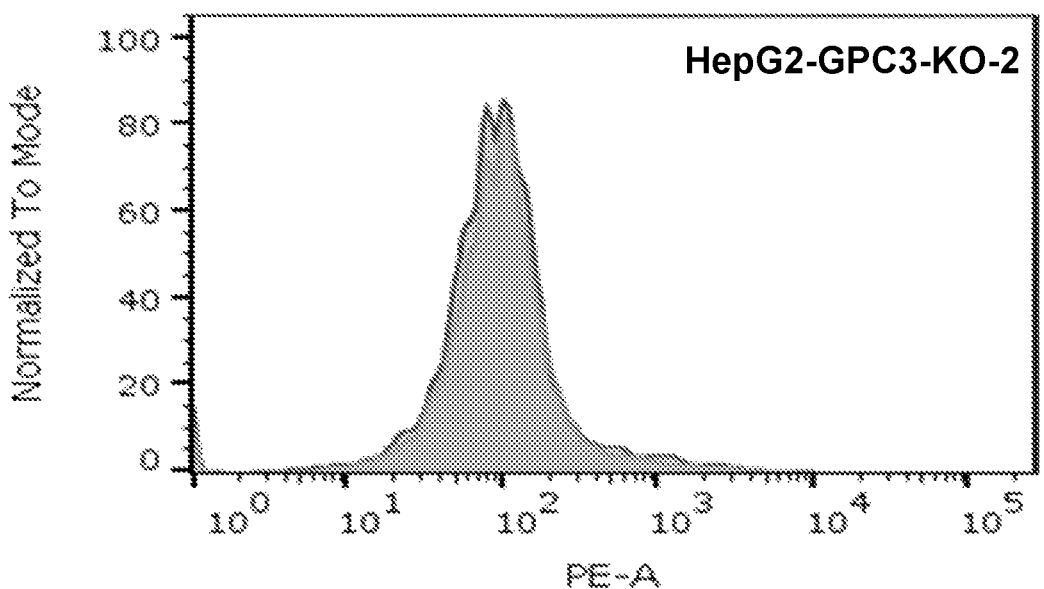

FIG. 3D
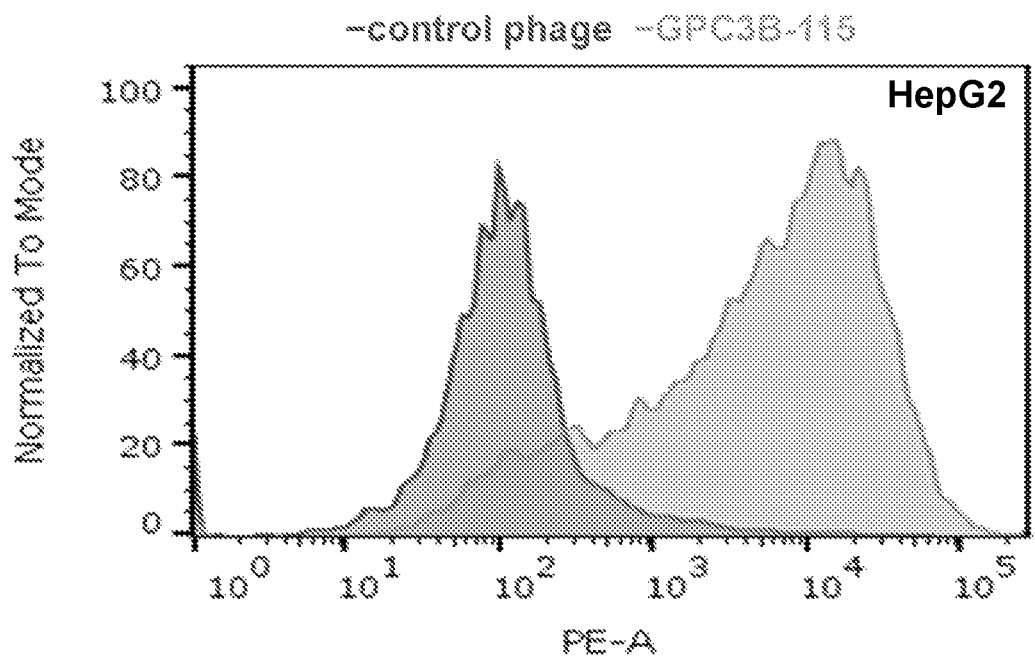
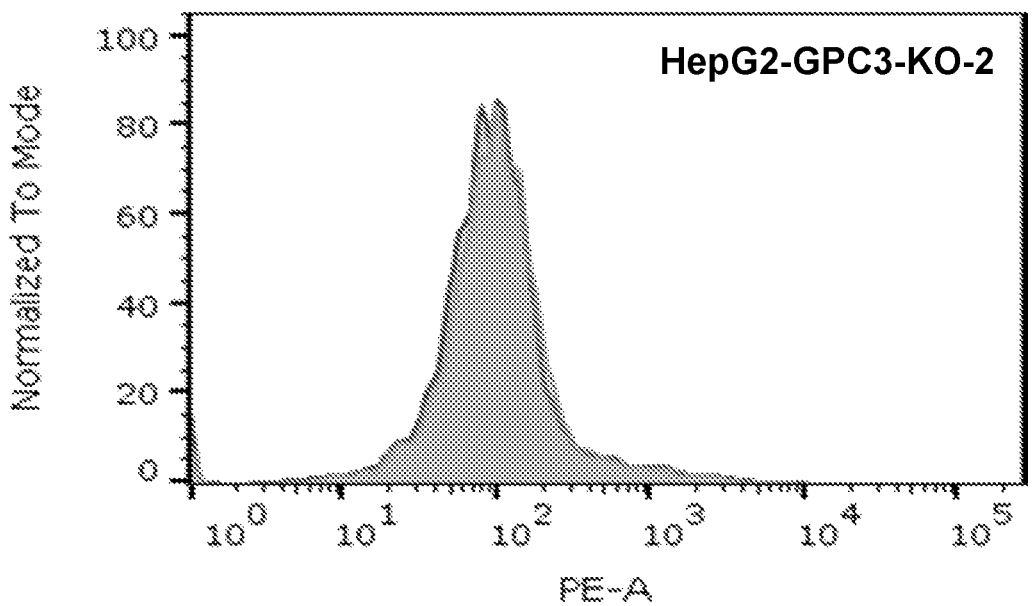

FIG. 4A
-SK-Hep1
-SK-Hep1-GPC3
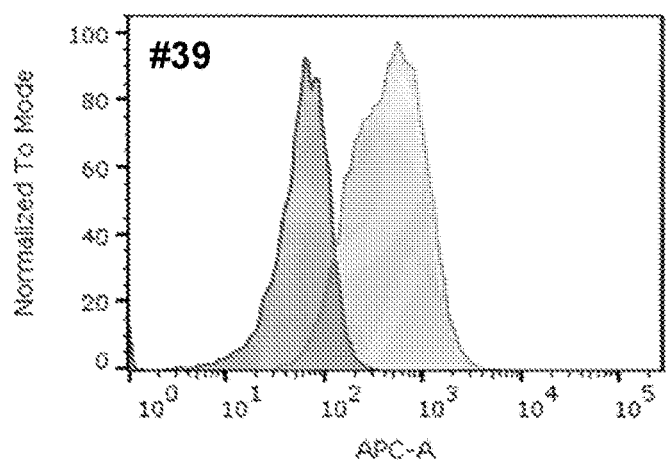
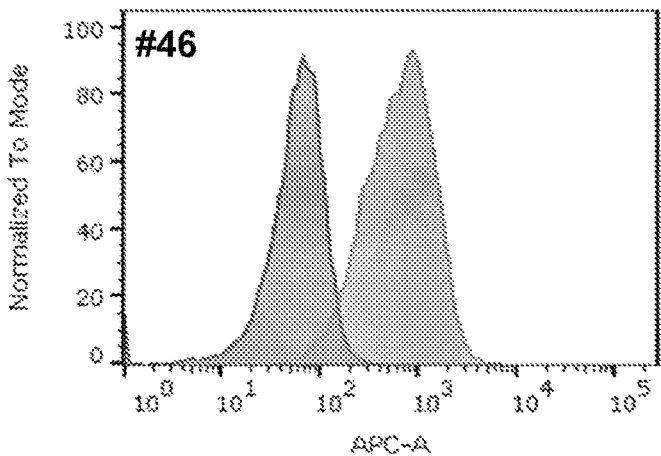
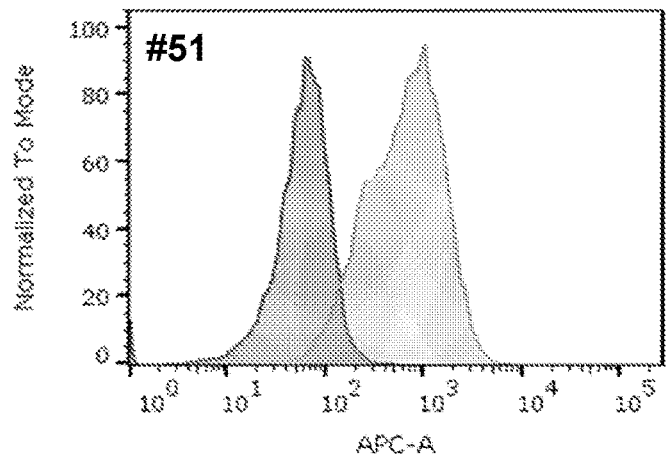

FIG. 4B
-SK-Hep1
-SK-Hep1-GPC3
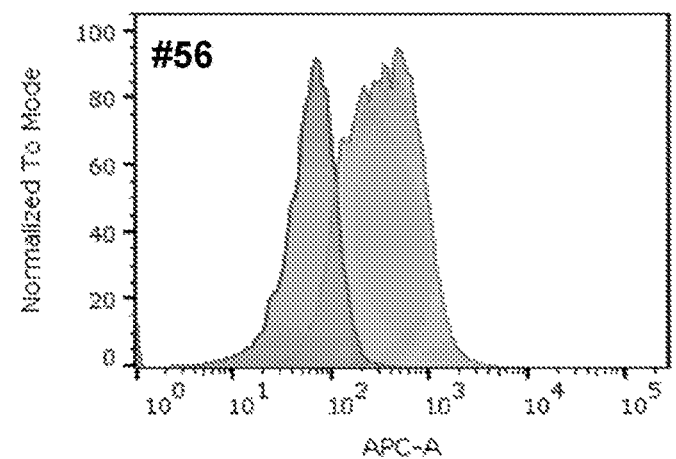
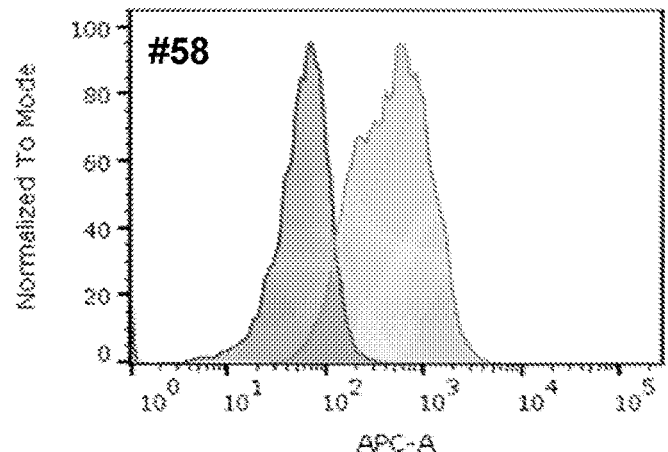
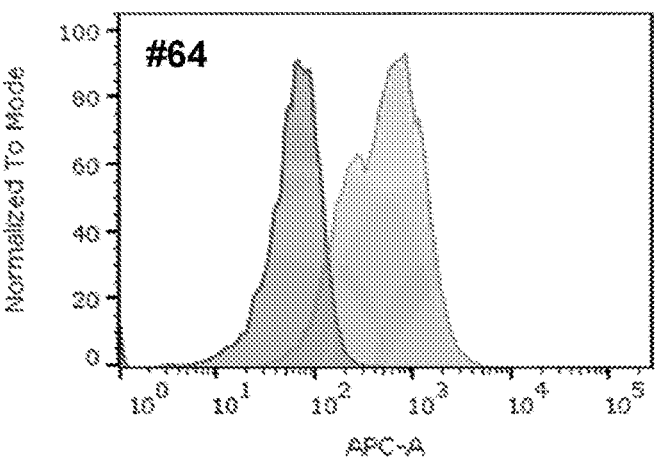

FIG. 5A
—control L2K
—GPC3A L2K
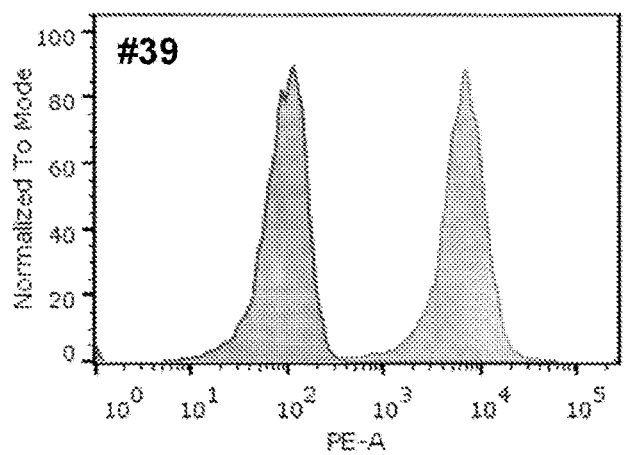
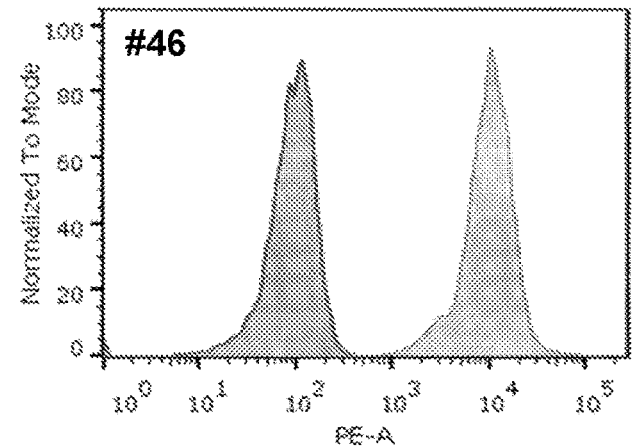
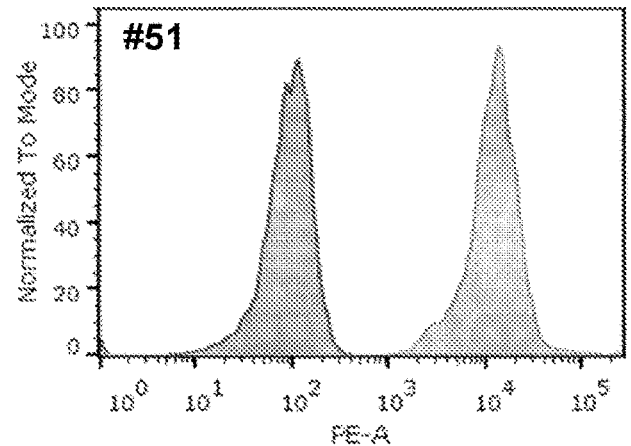

FIG. 5B
—control L2K
—GPC3A L2K
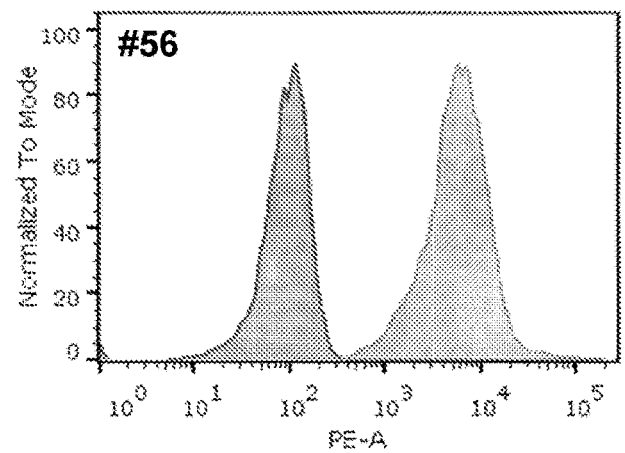
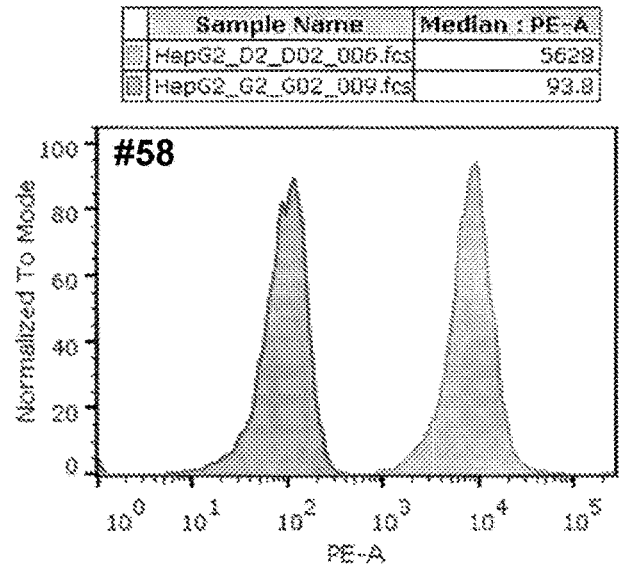
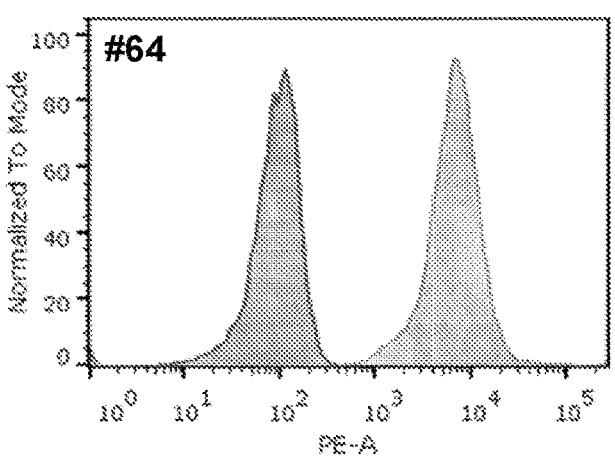

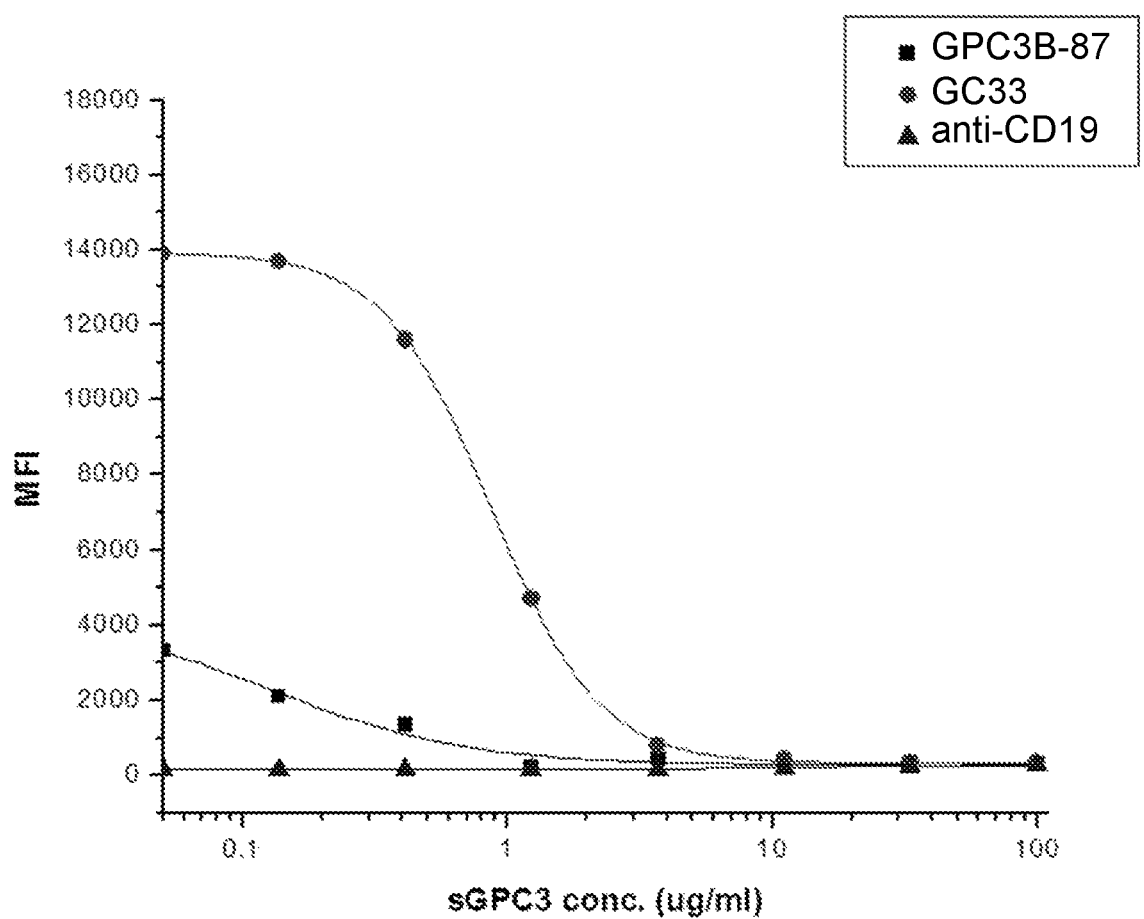
FIG. 10 Competition for L2K binding to HepG2 cells by sGPC3

FIG. 13 Epitope Binning Analysis

FIG. 15A  Binding kinetics between GPC3A L2K clones and GPC3 antigen
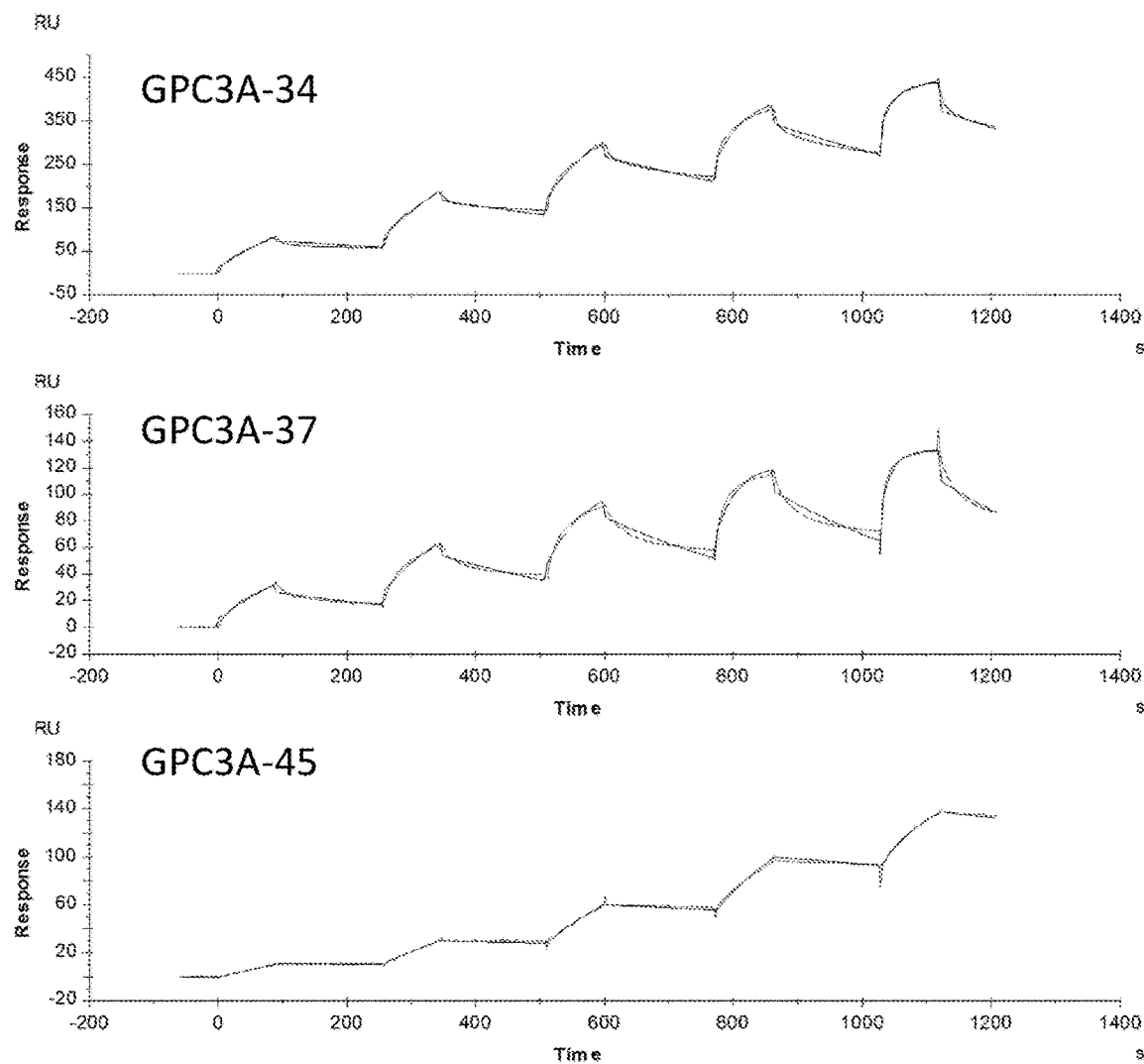

FIG. 15B  Binding kinetics between GPC3A L2K clones and GPC3 antigen
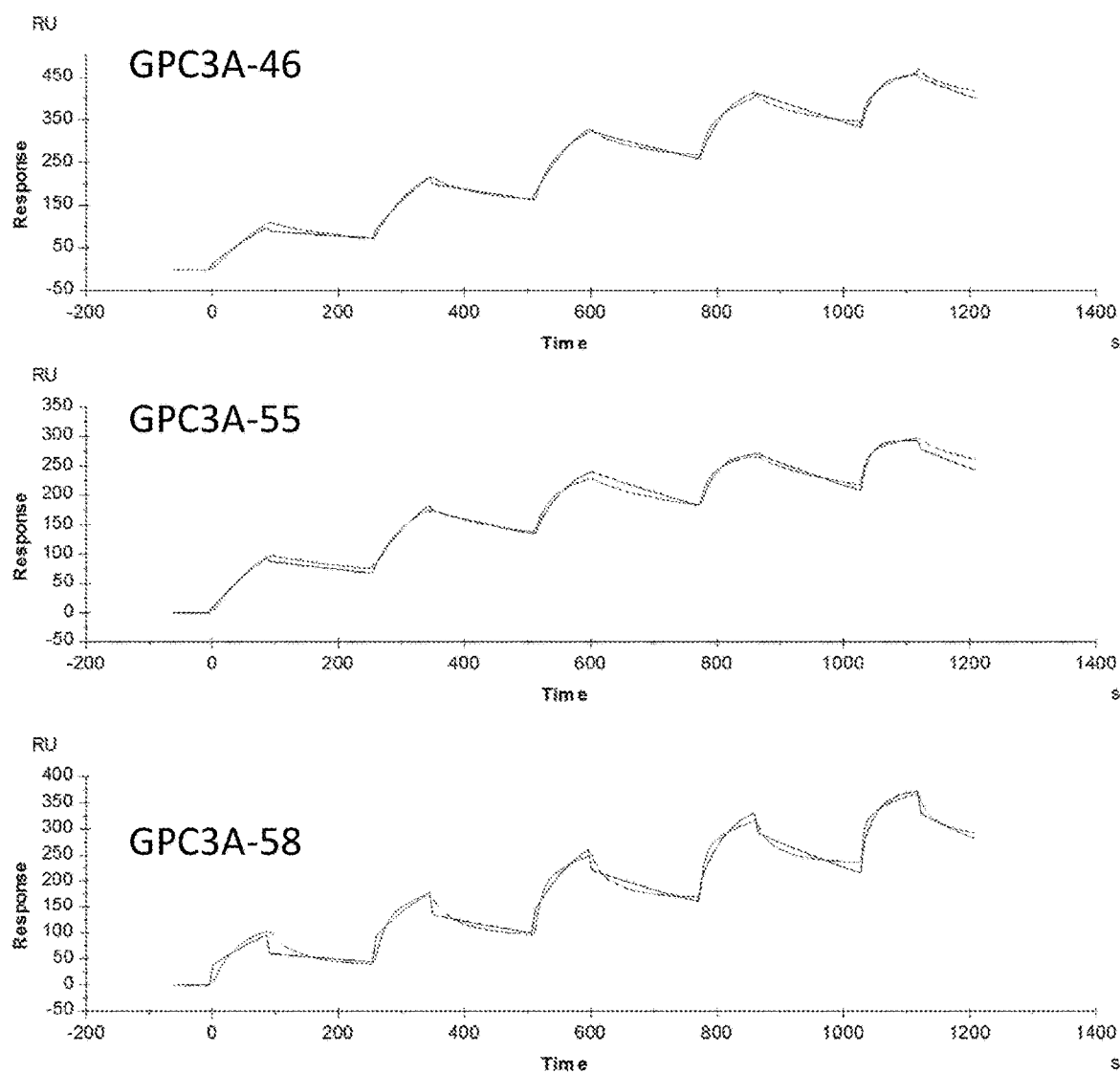

FIG. 22
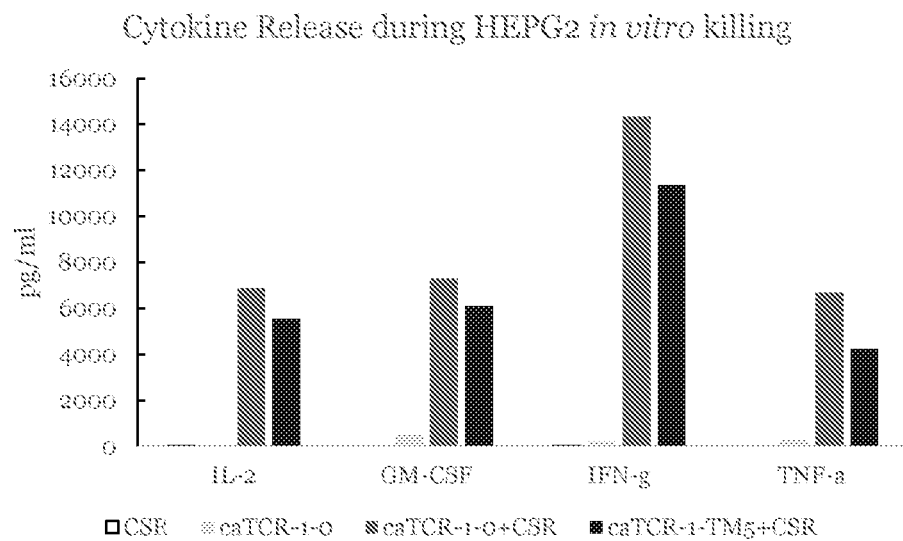
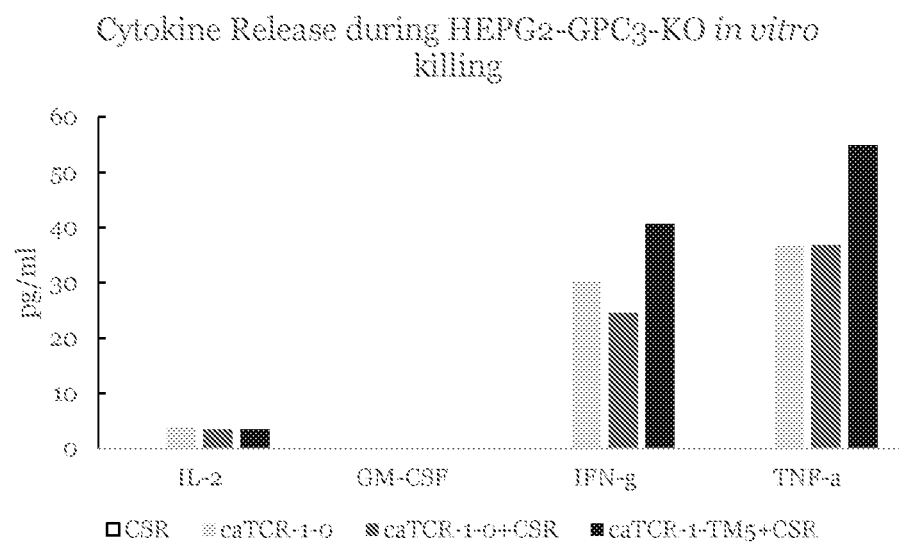

CONSTRUCTS SPECIFICALLY RECOGNIZING GLYPICAN 3 AND USES THEREOF

CROSS-REFERENCE TO RELATED APPLICATION

This application is a U.S. national phase application under 35 U.S.C. § 371 of International Application No. PCT/US2018/029221, filed on Apr. 24, 2018, which claims priority to U.S. Provisional Application No. 62/490,586, filed on Apr. 26, 2017, the contents of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 7500420012000SEQLIST.txt, date recorded: Oct. 14, 2019, size: 394 KB).

FIELD OF THE INVENTION

This invention pertains to antibody constructs that specifically recognize Glypican 3 (GPC3), methods of making, and uses thereof including treating and diagnosing diseases.

BACKGROUND OF THE INVENTION

Glypican 3 (GPC3, also known as SGB, DGSX, MXR7, SDYS, SGBS, OCI-5, SGBS1, GTR2-2) is a cell surface protein that is overexpressed in multiple cancer types, including many solid tumors, such as hepatocellular carcinoma (HCC), melanoma (Nakatsura T et al., *Clin Cancer Res.* 2004), lung squamous cell carcinoma (Yu X et al., *Genet Mol Res.* 2015), ovarian carcinoma (Stadlmann S et al., *Int J Gynecol Pathol.* 2007), yolk sac tumor, choriocarcinoma (Zynger D L et al., *Am J Surg Pathol.* 2006), Wilms' tumor, and liposarcoma (Baumhoer D et al., *Am J Clin Pathol.* 2008). There remains a medical need of developing therapies against various cancers including those overexpressing GPC3.

The GPC3 gene is located on the X chromosome and encodes a 70 kDa precursor protein of 580 amino acids (aa). This precursor protein can be cleaved by Furin between $Arg^{358}$ and $Cys^{359}$ and generate a 40 kDa N-terminal subunit and a 30 kDa C-terminal subunit linked by disulfide bonds. The mature GPC3 is attached to the cell surface by a glycosylphosphatidylinositol (GPI) anchor with two heparin sulfate (HS) chains on the C-terminal region close to the cell membrane. As a member of the heparin sulfate proteoglycan family, GPC3 is an oncofetal protein that is widely expressed in human embryos, and regulates morphogenesis or growth through interaction with signaling factors, such as Wnt, hedgehog signaling, etc. GPC3 is not expressed in normal adult livers; however, during hepatic carcinogenesis, GPC3 has been reported to be reactivated in HCC patients. Yamauchi N et al. examined GPC3 expression in normal, non-neoplastic, and neoplastic liver tissues, and found that GPC3 was present in 84% (47/56) of HCC patients, but absent in normal adult liver, liver cirrhosis or hepatitis (Yamauchi N et al., Modern Pathology 2005). Similar results were reported by other groups (Nakatsura T et al., *Biochem Biophys Res Commun.* 2003; Baumhoer D et al., *Am J Clin Pathol.* 2008; Shirakawa H et al., *Cancer Sci.* 2009; Wang L et al., *Hepatobiliary Pancreat Dis Int* 2015). Studies also showed that GPC3 could be released from cell surface to extracellular environment in different forms in HCC patients, but not in healthy donors. Therefore, GPC3 is currently used as a serum diagnostic marker for HCC (Hippo Y et al., *Cancer Res.* 2004; Capurro M et al., *Gastroenterology* 2003; Haruyama Y and Kataoka H, *World J Gastroenterol.* 2016).

Hepatocellular carcinoma (HCC) is the most common type of liver cancer, accounting for approximately 75% of all liver cancers. Liver cancer is the fifth most common cancer and the second most common cause of death from cancer in the world. Liver cancer incidence has more than tripled since 1980, and liver cancer death rates have increased by almost 3% per year since 2000 (https://www.cancer.org/cancer/liver-cancer/about/what-is-key-statistics.html). Prognosis for liver cancer is very poor with an overall ratio of mortality to incidence of 0.95. Currently liver cancer treatment is mainly limited to chemotherapy or surgery. However, the effect of chemotherapy is often limited because liver cells express ATP binding cassette (ABC) transporters which can export a large range of commonly used chemotherapeutic agents. Another option, surgery, is only available in early staged cancers, in which the 5-year survival rate is 31%. If cancer is diagnosed in the late stages (5-year survival rate: 3-11%), the only approved chemotherapy treatment is the tyrosine kinase inhibitor, sorafenib. This treatment increases the survival rate by only 2-3 months (Fleming B D and Ho M, *Toxins* 2016). Therefore, the development of a novel method to treat liver cancer is desired.

The disclosures of all publications, patents, patent applications and published patent applications referred to herein are hereby incorporated herein by reference in their entirety.

BRIEF SUMMARY OF THE INVENTION

The present application in one aspect provides anti-GPC3 constructs (such as isolated anti-GPC3 constructs) specifically recognizing a cell surface-bound GPC3 (referred to herein as a "native format GPC3," or "native GPC3 (nGPC3)"). In some embodiments, the constructs (referred to herein as "anti-GPC3 constructs") comprise an antibody moiety (referred to herein as an "anti-GPC3 antibody moiety") specifically recognizing native format GPC3.

Thus, in some embodiments, there is provided an anti-GPC3 construct (such as an isolated anti-GPC3 construct) comprising an antibody moiety specifically recognizing a cell surface-bound GPC3. In some embodiments, the antibody moiety specifically recognizes a cell surface-bound GPC3 at a high binding affinity and binds to a soluble GPC3 at a low binding affinity. In some embodiments, the $K_d$ of the anti-GPC3 construct to the cell surface-bound GPC3 is about 0.1 nM to about 2 nM (e.g., about 0.1 nM to about 1 nM, or about 0.1 nM to about 1.5 nM). In some embodiments, the IC50 of a soluble GPC3 to compete binding between the anti-GPC3 construct and the cell surface-bound GPC3 is about 1 µg/ml to about 100 µg/ml (e.g., about 1 µg/ml to about 10 µg/ml, or about 2 µg/ml to about 5 µg/ml). In some embodiments, the cell surface-bound GPC3 comprises the amino acid sequence of SEQ ID NO: 460 or SEQ ID NO: 462. In some embodiments, the cell surface-bound GPC3 is GPC3 expressed on HepG2 cells. In some embodiments, the soluble GPC3 comprises the amino acid sequence of SEQ ID NO: 461 or SEQ ID NO: 463.

In some embodiments according to any of the anti-GPC3 constructs (such as isolated anti-GPC3 constructs) described above, the antibody moiety specifically recognizes an epitope within human GPC3 comprising the amino acid sequence of SEQ ID NO: 460.

In some embodiments according to any of the anti-GPC3 constructs (such as isolated anti-GPC3 constructs) described above, the antibody moiety specifically recognizes an epitope within the amino acid sequence of SEQ ID NO: 461.

In some embodiments according to any of the anti-GPC3 constructs (such as isolated anti-GPC3 constructs) described above, the antibody moiety specifically recognizes an epitope within the amino acid sequence of SEQ ID NO: 462.

In some embodiments according to any of the anti-GPC3 constructs (such as isolated anti-GPC3 constructs) described above, the antibody moiety specifically recognizes an epitope within the amino acid sequence of SEQ ID NO: 463.

In some embodiments according to any of the anti-GPC3 constructs (such as isolated anti-GPC3 constructs) described above, the antibody moiety specifically recognizes an epitope within the N-terminal fragment of GPC3. In some embodiments, the antibody moiety specifically recognizes an epitope within the amino acid sequence of SEQ ID NO: 464.

In some embodiments according to any of the anti-GPC3 constructs (such as isolated anti-GPC3 constructs) described above, the antibody moiety specifically recognizes an epitope within the C-terminal fragment of GPC3. In some embodiments, the antibody moiety specifically recognizes an epitope within the C-terminal fragment of GPC3 lacking heparin sulfate side chain.

In some embodiments according to any of the anti-GPC3 constructs (such as isolated anti-GPC3 constructs) described above, the antibody moiety does not specifically bind to the same or substantially the same GPC3 epitope competitively with GC33. In some embodiments, the antibody moiety does not bind to an epitope within the amino acid sequence of SEQ ID NO: 536. In some embodiments, the antibody moiety does not bind to a fragment comprising the amino acid sequence of SEQ ID NO: 536.

In some embodiments according to any of the anti-GPC3 constructs (such as isolated anti-GPC3 constructs) described above, the GPC3 is expressed on the surface of a cell selected from the group consisting of HepG2, Hep3B, Huh7, JHH-7, and 293.

In some embodiments according to any of the anti-GPC3 constructs (such as isolated anti-GPC3 constructs) described above, GPC3 is expressed on the surface of a cancer cell. In some embodiments, the cancer cell is a liver cancer cell, such as hepatocellular carcinoma (HCC).

The present application in another aspect provides an anti-GPC3 construct (such as an isolated anti-GPC3 construct) comprising an antibody moiety specifically recognizing a cell surface-bound GPC3, wherein the antibody moiety comprises: i) a heavy chain variable domain ($V_H$) comprising a heavy chain complementarity determining region (HC-CDR) 1 comprising the amino acid sequence of any one of SEQ ID NOs: 1-31, or a variant thereof comprising up to about 5 amino acid substitutions, an HC-CDR2 comprising the amino acid sequence of any one of SEQ ID NOs: 52-82, or a variant thereof comprising up to about 5 amino acid substitutions, and an HC-CDR3 comprising the amino acid sequence of any one of SEQ ID NOs: 103-133, or a variant thereof comprising up to about 5 amino acid substitutions; and ii) a light chain variable domain ($V_L$) comprising a light chain complementarity determining region (LC-CDR) 1 comprising the amino acid sequence of any one of SEQ ID NOs: 154-184, or a variant thereof comprising up to about 5 amino acid substitutions, an LC-CDR2 comprising the amino acid sequence of any one of SEQ ID NOs: 205-235, or a variant thereof comprising up to about 3 amino acid substitutions, and an LC-CDR3 comprising the amino acid sequence of any one of SEQ ID NOs: 256-286, or a variant thereof comprising up to about 5 amino acid substitution. In some embodiments, the antibody moiety comprises: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286.

In some embodiments according to any of the anti-GPC3 constructs (such as isolated anti-GPC3 constructs) described above, the antibody moiety comprises: i) a $V_H$ comprising the amino acid sequence of any one of SEQ ID NOs: 307-337, or a variant thereof having at least about 95% sequence identify to any one of SEQ ID NOs: 307-337; and ii) a $V_L$ comprising the amino acid sequence of any one of SEQ ID NOs: 358-388, or a variant thereof having at least about 95% sequence identity to any one of SEQ ID NOs: 358-388. In some embodiments, the antibody moiety comprises: i) a $V_H$ comprising the amino acid sequence of any one of SEQ ID NOs: 307-337; and ii) a $V_L$ comprising the amino acid sequence of any one of SEQ ID NOs: 358-388.

The present application in another aspect provides an anti-GPC3 construct (such as an isolated anti-GPC3 construct) comprising an antibody moiety specifically recognizing a cell surface-bound GPC3, wherein the antibody moiety comprises the HC-CDRs of $V_H$ comprising the amino acid sequence of any one of SEQ ID NOs: 307-337 and LC-CDRs of $V_L$ comprising the amino acid sequence of any one of SEQ ID NOs: 358-388 of an isolated anti-GPC3 construct.

The present application in another aspect provides an isolated anti-GPC3 construct comprising an antibody moiety specifically recognizing GPC3, wherein the antibody moiety comprises: i) a $V_H$ comprising an HC-CDR1 comprising the amino acid sequence of any one of SEQ ID NOs: 32-51, or a variant thereof comprising up to about 5 amino acid substitutions, an HC-CDR2 comprising the amino acid sequence of any one of SEQ ID NOs: 83-102, or a variant thereof comprising up to about 5 amino acid substitutions, and an HC-CDR3 comprising the amino acid sequence of any one of SEQ ID NOs: 134-153, or a variant thereof comprising up to about 5 amino acid substitutions; and ii) a $V_L$ comprising an LC-CDR1 comprising the amino acid sequence of any one of SEQ ID NOs: 185-204, or a variant thereof comprising up to about 5 amino acid substitutions, an LC-CDR2 comprising the amino acid sequence of any one of SEQ ID NOs: 236-255, or a variant thereof comprising up to about 3 amino acid substitutions, and an LC-CDR3 comprising the amino acid sequence of any one of SEQ ID NOs: 287-306, or a variant thereof comprising up to about 5 amino acid substitutions. In some embodiments, the antibody moiety comprises: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306.

In some embodiments according to any of the anti-GPC3 constructs (such as isolated anti-GPC3 constructs) described above, the antibody moiety comprises: i) a $V_H$ comprising the amino acid sequence of any one of SEQ ID NOs: 338-357, or a variant thereof having at least about 95% sequence identify to any one of SEQ ID NOs: 338-357; and ii) a $V_L$ comprising the amino acid sequence of any one of SEQ ID NOs: 389-408, or a variant thereof having at least about 95% sequence identity to any one of SEQ ID NOs: 389-408. In some embodiments, the antibody moiety comprises: i) a $V_H$ comprising the amino acid sequence of any one of SEQ ID NOs: 338-357; and ii) a $V_L$ comprising the amino acid sequence of any one of SEQ ID NOs: 389-408.

The present application in another aspect provides an anti-GPC3 construct (such as an isolated anti-GPC3 construct) comprising an antibody moiety specifically recognizing GPC3, wherein the antibody moiety comprises the HC-CDRs of $V_H$ comprising the amino acid sequence of any one of SEQ ID NOs: 338-357 and LC-CDRs of $V_L$ comprising the amino acid sequence of any one of SEQ ID NOs: 389-408 of an isolated anti-GPC3 construct.

The present application in another aspect provides an anti-GPC3 construct (such as an isolated anti-GPC3 construct) comprising an antibody moiety that specifically binds to GPC3 competitively with the isolated anti-GPC3 construct of any one of the anti-GPC3 constructs described above.

The present application in another aspect provides an anti-GPC3 construct (such as an isolated anti-GPC3 construct) comprising an antibody moiety that specifically binds to the same, or substantially the same, GPC3 epitope competitively with the isolated anti-GPC3 construct of any one of the anti-GPC3 constructs described above.

In some embodiments according to any of the anti-GPC3 constructs (such as isolated anti-GPC3 constructs) described above, the antibody moiety specifically recognizing GPC3 is chimeric, human, partially humanized, fully humanized, or semi-synthetic.

In some embodiments according to any of the anti-GPC3 constructs (such as isolated anti-GPC3 constructs) described above, the antibody moiety specifically recognizing GPC3 is a full-length antibody, a Fab, a Fab', a F(ab')2, an Fv, or a single chain Fv (scFv). In some embodiments, the antibody moiety specifically recognizing GPC3 is an scFv. In some embodiments, the antibody moiety specifically recognizing GPC3 is a Fab or Fab'.

In some embodiments according to any of the anti-GPC3 constructs (such as isolated anti-GPC3 constructs) described above, the antibody moiety specifically recognizing GPC3 is fused to an Fc fragment optionally via a linker. In some embodiments, the Fc fragment is an IgG1 Fc fragment.

In some embodiments according to any of the anti-GPC3 constructs (such as isolated anti-GPC3 constructs) described above, the isolated anti-GPC3 construct is a full-length antibody.

In some embodiments according to any of the anti-GPC3 constructs (such as isolated anti-GPC3 constructs) described above, the isolated anti-GPC3 construct is monospecific.

In some embodiments according to any of the anti-GPC3 constructs (such as isolated anti-GPC3 constructs) described above, the isolated anti-GPC3 construct is multispecific, such as bispecific. In some embodiments, the isolated anti-GPC3 construct is a tandem scFv, a diabody (Db), a single chain diabody (scDb), a dual-affinity retargeting (DART) antibody, a F(ab')2, a dual variable domain (DVD) antibody, a knob-into-hole (KiH) antibody, a dock and lock (DNL) antibody, a chemically cross-linked antibody, a heteromultimeric antibody, or a heteroconjugate antibody. In some embodiments, the isolated anti-GPC3 construct is a tandem scFv comprising two scFvs linked by a peptide linker. In some embodiments, the peptide linker comprises the amino acid sequence of TSGGGGS (SEQ ID NO: 474). In some embodiments, the isolated anti-GPC3 construct further comprises a second antibody moiety specifically recognizing a second antigen. In some embodiments, the second antigen is an antigen on the surface of a T cell, such as cytotoxic T cell, a helper T cell, or a natural killer T cell. In some embodiments, the second antigen is an antigen on the surface of a B cell, a natural killer cell, a dendritic cell, a macrophage, a monocyte, or a neutrophil. In some embodiments, the second antigen is selected from the group consisting of CD3γ, CD3δ, CD3ε, CD3ζ, CD28, OX40, GITR, CD137, CD27, CD40L, and HVEM. In some embodiments, the second antigen is CD3ε. In some embodiments, the isolated anti-GPC3 construct is a tandem scFv comprising an N-terminal scFv specifically recognizing GPC3 and a C-terminal scFv specifically recognizing CD3ε. In some embodiments, the expression of the anti-GPC3 construct is induced by the activation of an engineered T cell. In some embodiments, the engineered T cell is a T cell comprising a chimeric antigen receptor (CAR). In some embodiments, the engineered T cell is a T cell comprising a chimeric antibody-T cell receptor (TCR) construct (caTCR).

In some embodiments according to any of the anti-GPC3 constructs (such as isolated anti-GPC3 constructs) described above, the isolated anti-GPC3 construct is a chimeric antigen receptor (CAR) comprising: (a) an extracellular domain comprising the antibody moiety; (b) a transmembrane domain; and (c) an intracellular signaling domain. In some embodiments, the intracellular signaling domain comprises a CD3ζ intracellular signaling sequence and a CD28 intracellular signaling sequence.

In some embodiments according to any of the anti-GPC3 constructs (such as isolated anti-GPC3 constructs) described above, the isolated anti-GPC3 construct is a chimeric antibody-T cell receptor (TCR) construct (caTCR) comprising: (a) an extracellular domain comprising the antibody moiety; and (b) a T cell receptor module (TCRM) comprising a first TCR domain (TCRD) comprising a first TCR transmembrane domain (TCR-TM) and a second TCRD comprising a second TCR-TM, wherein the TCRM facilitates recruitment of at least one TCR-associated signaling molecule. In some embodiments, the first TCR-TM is derived from one of the transmembrane domains of a first naturally occurring TCR and the second TCR-TM is derived from the other transmembrane domain of the first naturally occurring TCR. In some embodiments, at least one of the TCR-TMs is non-naturally occurring. In some embodiments, the TCRM allows for enhanced recruitment of the at least one TCR-associated signaling molecule as compared to a TCRM comprising the first naturally occurring T cell receptor transmembrane domains. In some embodiments, the first naturally occurring TCR is a γ/δ TCR. In some embodiments, the first naturally occurring TCR is an α/β TCR. In some embodiments, the TCR-associated signaling molecule is selected from the group consisting of CD3δε, CD3γε, and ζζ (also known as CD3ζ or CD3ζζ).

In some embodiments according to any of the anti-GPC3 constructs (such as isolated anti-GPC3 constructs) described above, the isolated anti-GPC3 construct is an immunoconjugate comprising the antibody moiety and an effector molecule. In some embodiments, the effector molecule is a therapeutic agent selected from the group consisting of a drug, a toxin, a radioisotope, a protein, a peptide, and a nucleic acid. In some embodiments, therapeutic agent is a drug or a toxin. In some embodiments, the effector molecule is a label.

The present application in another aspect provides an isolated nucleic acid encoding the polypeptide components of any one of the isolated anti-GPC3 constructs described above.

The present application in another aspect provides a vector comprising an isolated nucleic acid encoding the polypeptide components of any one of the isolated anti-GPC3 constructs described above.

The present application in another aspect provides an isolated host cell comprising any one of the anti-GPC3 constructs described above.

The present application in another aspect provides an isolated host cell comprising an isolated nucleic acid encoding the polypeptide components of any one of the isolated anti-GPC3 constructs described above.

The present application in another aspect provides an isolated host cell comprising a vector comprising an isolated nucleic acid encoding the polypeptide components of any one of the isolated anti-GPC3 constructs described above.

The present application in another aspect provides an effector cell expressing any one of the isolated anti-GPC3 construct described above. In some embodiments, the effector cell is a T cell.

The present application in another aspect provides a pharmaceutical composition comprising any one of the anti-GPC3 construct (such as isolated anti-GPC3 construct) described above, and a pharmaceutically acceptable carrier.

Also provided are kits comprising any one of the isolated anti-GPC3 constructs described above, an isolated nucleic acid encoding the polypeptide components of any one of the isolated anti-GPC3 constructs described above, a vector comprising an nucleic acid encoding the polypeptide components of any one of the isolated anti-GPC3 constructs described above, any one of the isolated cell described above, or any one of the effector cell described above.

The present application in another aspect provides a method of detecting GPC3 in a sample, comprising contacting the sample with any one of the isolated anti-GPC3 immunoconjugate described above comprising an antibody moiety and a label, and detecting the presence of the label. In some embodiments, the sample comprises cells with cell surface-bound GPC3. In some embodiments, the sample comprises soluble GPC3.

The present application in another aspect provides a method of treating an individual having a GPC3-positive disease, comprising administering to the individual: a) an effective amount of any one of the pharmaceutical compositions described above; or b) an effective amount of any one of the effector cells described above. In some embodiments, the administration is via intravenous or intratumoral route. In some embodiments, the administration is to an injection site distal to a first disease site. In some embodiments, the method of treating an individual having a GPC3-positive disease further comprising administering to the individual an additional therapy. In some embodiments, the GPC3-positive disease is cancer, such as HCC, melanoma, lung squamous cell carcinoma, ovarian carcinoma, yolk sac tumor, choriocarcinoma, neuroblastoma, hepatoblastoma, Wilms' tumor, gastric carcinoma, or liposarcoma. In some embodiments the cancer is HCC, such as metastatic HCC.

The present application in another aspect provides a method of diagnosing an individual having a GPC3-positive disease, comprising: a) administering an effective amount of any one of the isolated anti-GPC3 immunoconjugates described above comprising an antibody moiety and a label; and b) determining the level of the label in the individual, wherein a level of the label above a threshold level indicates that the individual has the GPC3-positive disease. In some embodiments, the GPC3-positive disease is cancer, such as HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments the cancer is HCC, such as metastatic HCC.

The present application in another aspect provides a method of diagnosing an individual having an GPC3-positive disease, comprising: a) contacting a sample derived from the individual with any one of the isolated anti-GPC3 immunoconjugates described above comprising an antibody moiety and a label; and b) determining the number of cells bound with the isolated anti-GPC3 construct in the sample, wherein a value for the number of cells bound with the isolated anti-GPC3 construct above a threshold level indicates that the individual has the GPC3-positive disease. In some embodiments, the GPC3-positive disease is cancer, such as HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments the cancer is HCC, such as metastatic HCC.

Also provided are methods of making any of the constructs described herein, articles of manufacture, and kits that are suitable for the methods described herein.

BRIEF DESCRIPTION OF THE DRAWINGS

FIGS. 1A-1G show FACS analysis of the binding of 14 exemplary GPC3A phage clones to GPC3$^+$ HepG2 cells. The binding of helper phages to the GPC3$^+$ HepG2 cells was used as a control.

FIGS. 3A-3D show FACS analysis of the binding of 4 exemplary GPC3B phage clones to GPC3$^+$ HepG2 cell line and HepG2-GPC3-KO-2 cell line. Helper phages were used as a negative control.

FIGS. 4A-4B show FACS analysis of the binding of exemplary GPC3A L2K bispecific antibodies (anti-GPC3× CD3 di-scFvs derived from GPC3A screen) to SK-Hep1-GPC3 cells and GPC3-negative SK-Hep1 cells. The y-axis shows median fluorescence intensity (MFI).

FIGS. 5A-5B show FACS analysis of the binding of exemplary GPC3A L2K bispecific antibodies (anti-GPC3× CD3 di-scFvs derived from GPC3A screen) to GPC3+ HepG2 cells. The binding of a control L2K bispecific antibody to GPC3+ HepG2 cells was used as a negative control.

Figure 7A:
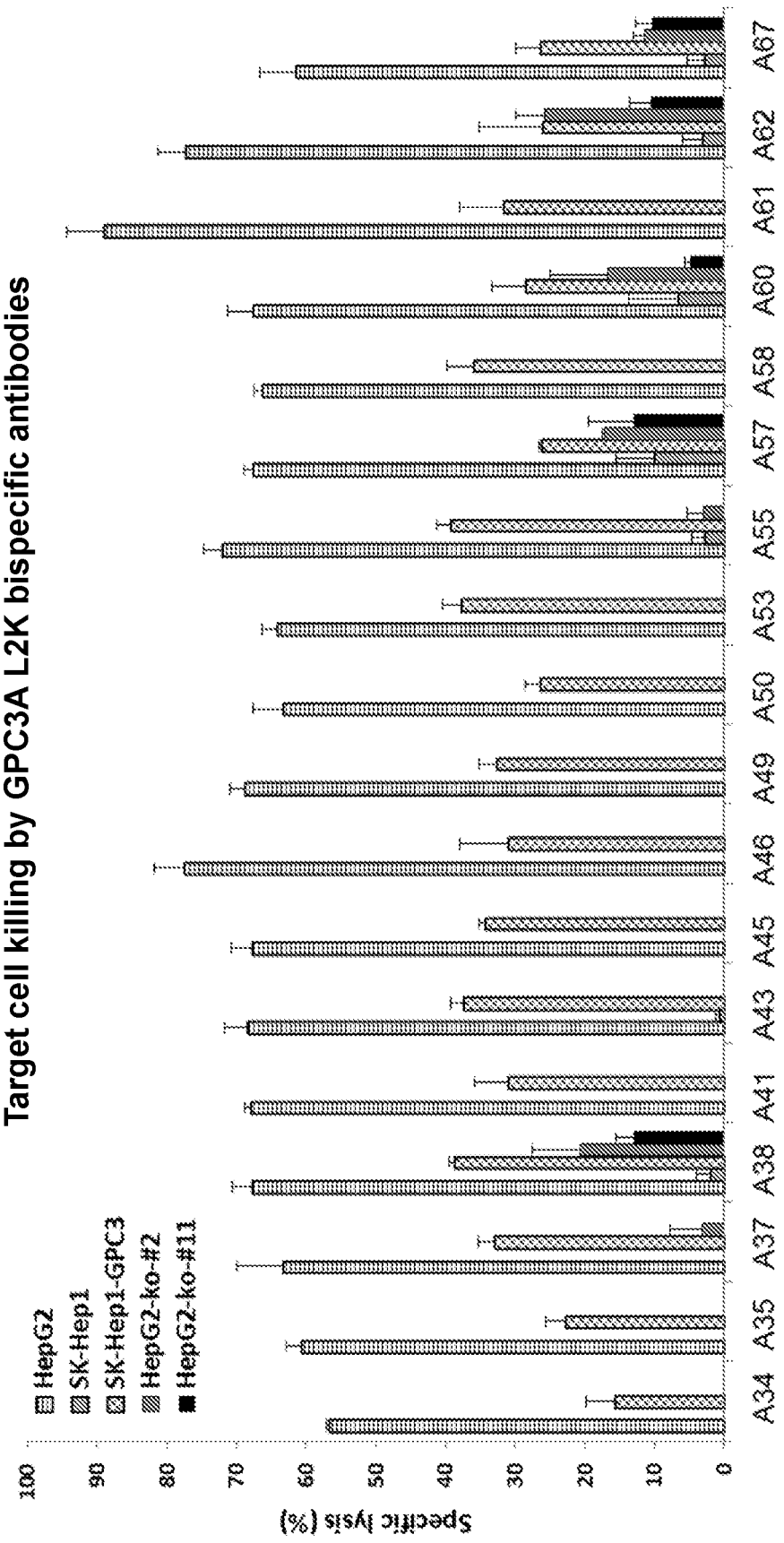
Figure 7B:
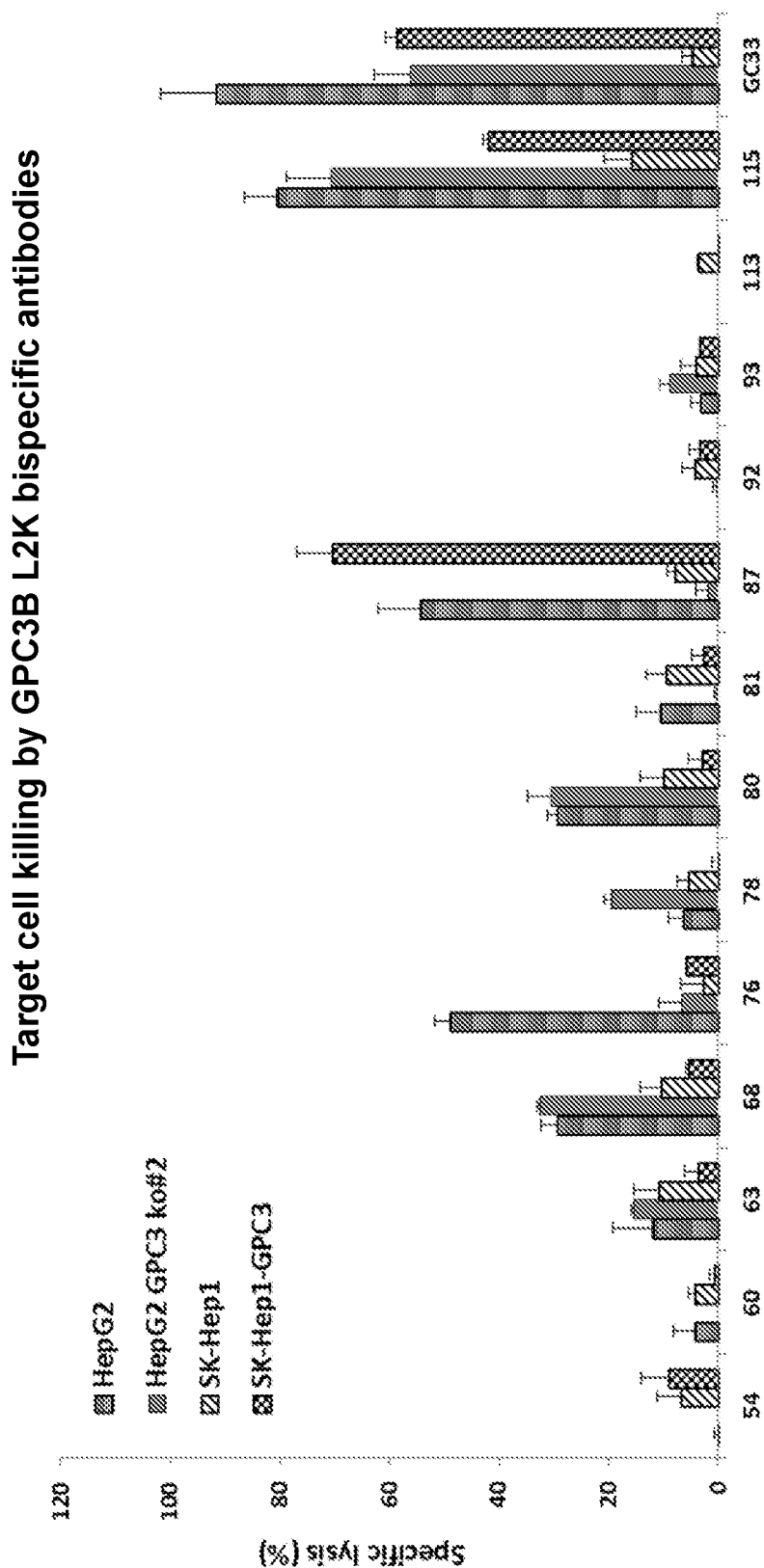

FIG. 7A shows T cell-mediated target cell killing by GPC3A L2K bispecific antibodies, tested on GPC3+ HepG2 cells, GPC3-negative SK-Hep1 cells, SK-Hep1-GPC3 cells, HepG2-GPC3-KO cells (#2 and #11). FIG. 7B shows T cell-mediated target cell killing by GPC3B L2K bispecific antibodies, tested on GPC3+ HepG2 cells, GPC3-negative SK-Hep1 cells, SK-Hep1-GPC3 cells, and HepG2-GPC3-KO-2 cells.

FIG. 8 shows FACS analysis of HepG2 GPC3-knockout cell lines using a commercial mouse anti-human GPC3 antibody (1G12), demonstrating successful generation of HepG2-GPC3-KO cell lines.

Figure 9A:
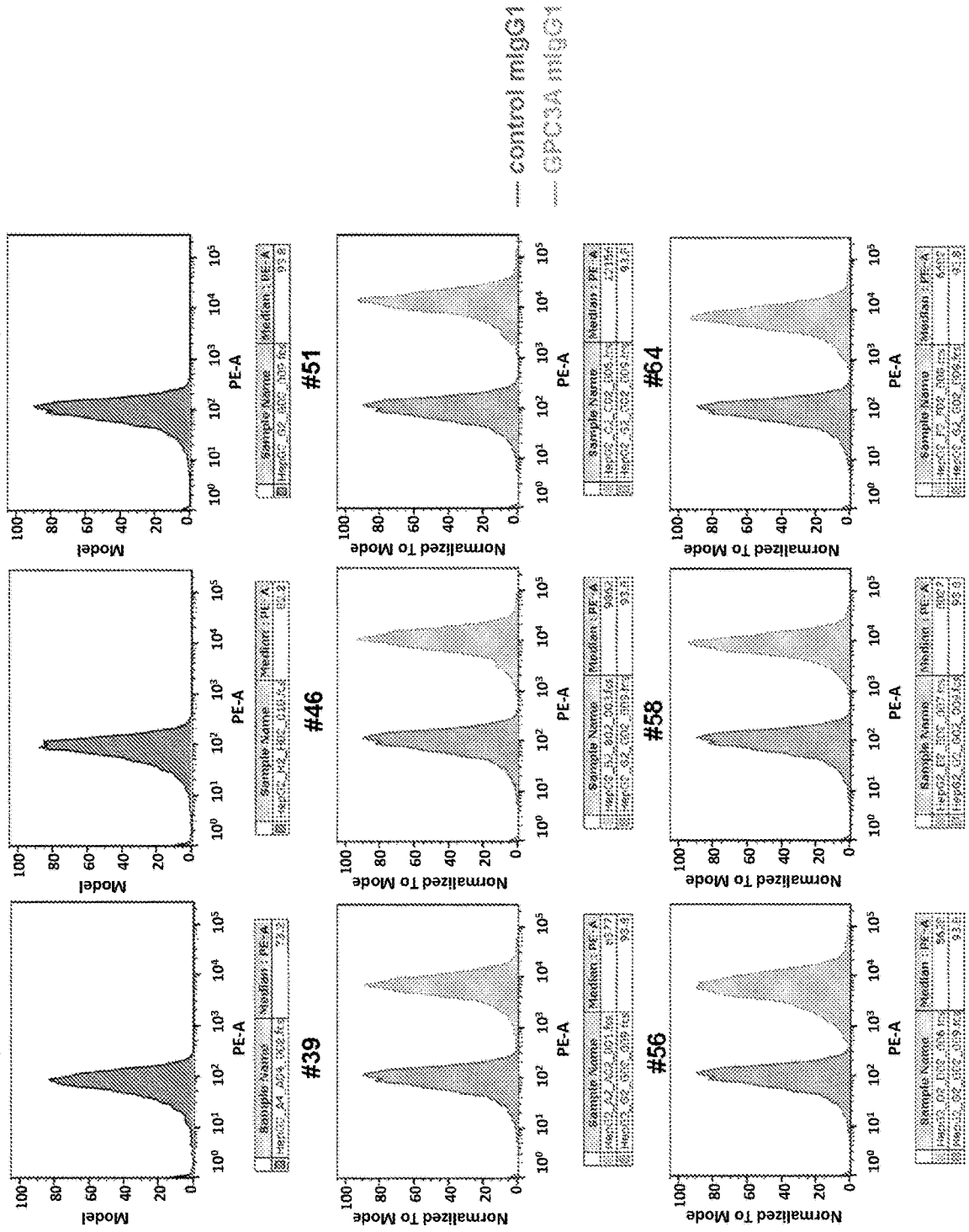
Figure 9B:
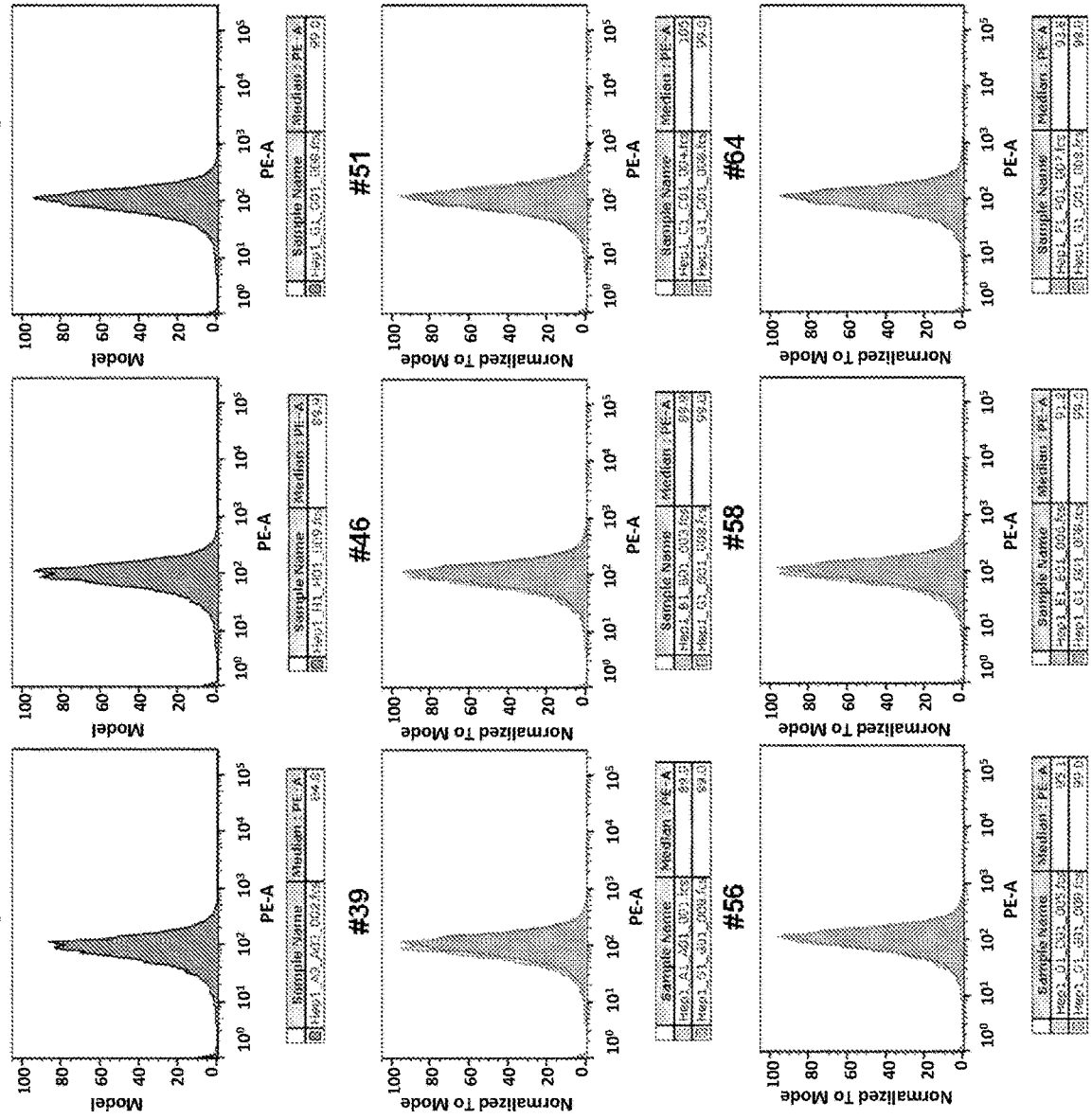

FIG. 9A shows FACS analysis of the binding of anti-human GPC3 (hGPC3) monospecific IgG antibodies with mouse constant domain/Fc region (mIgG1) to GPC3-positive HepG2 cells. FIG. 9B shows FACS analysis of the binding of anti-hGPC3 mIgG1 to GPC3-negative SK-Hep1 cells.

FIG. 10 shows the FACS fluorescence intensity curves indicating competition for HepG2-binding of GPC3 L2K antibodies (GPC3B-87 L2K or GC33 L2K) by soluble GPC3.

Figure 11:
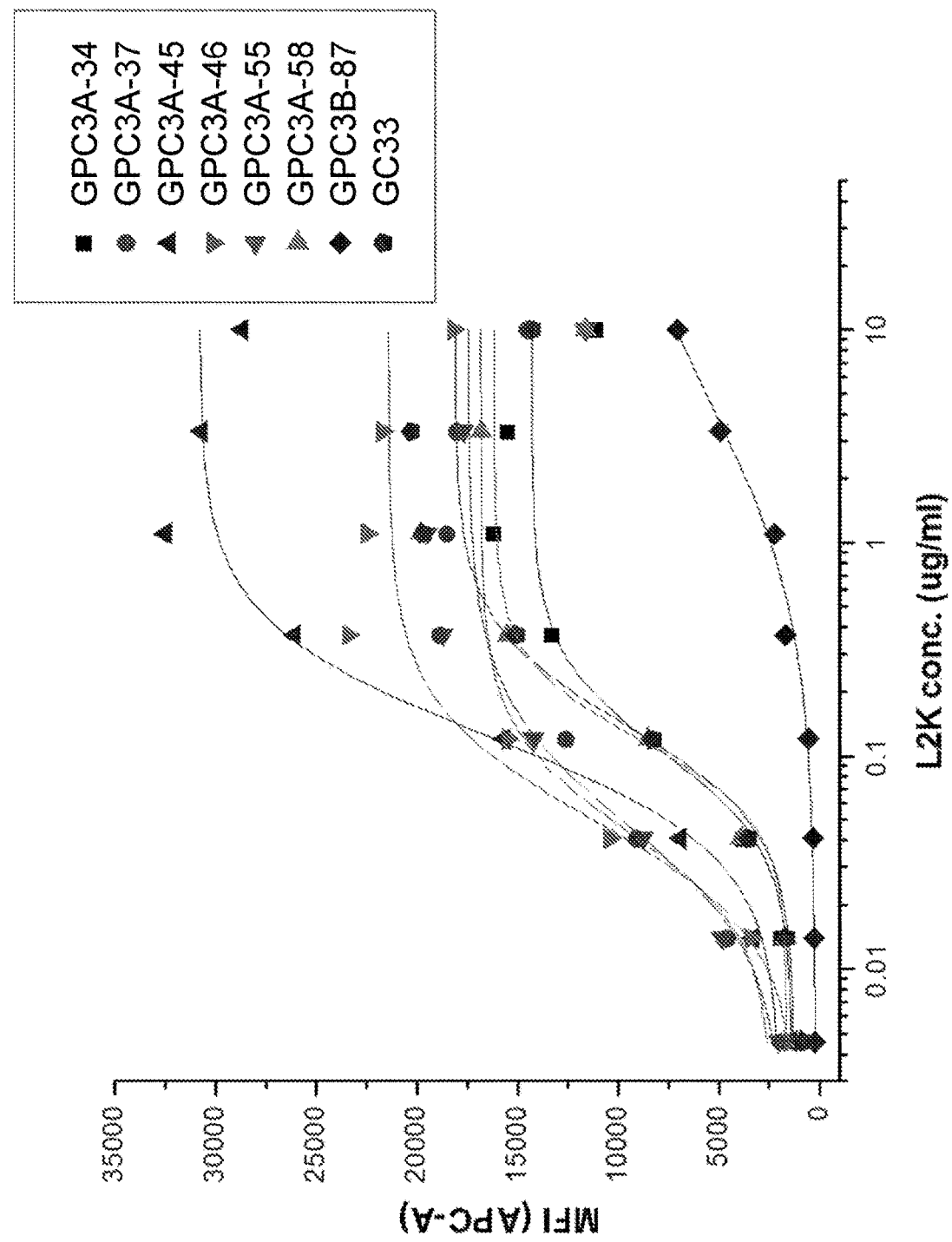

FIG. 11 shows the FACS fluorescence intensity curves indicating the binding affinity of GPC3 LK2 clones towards HepG2 cells.

Figure 12:
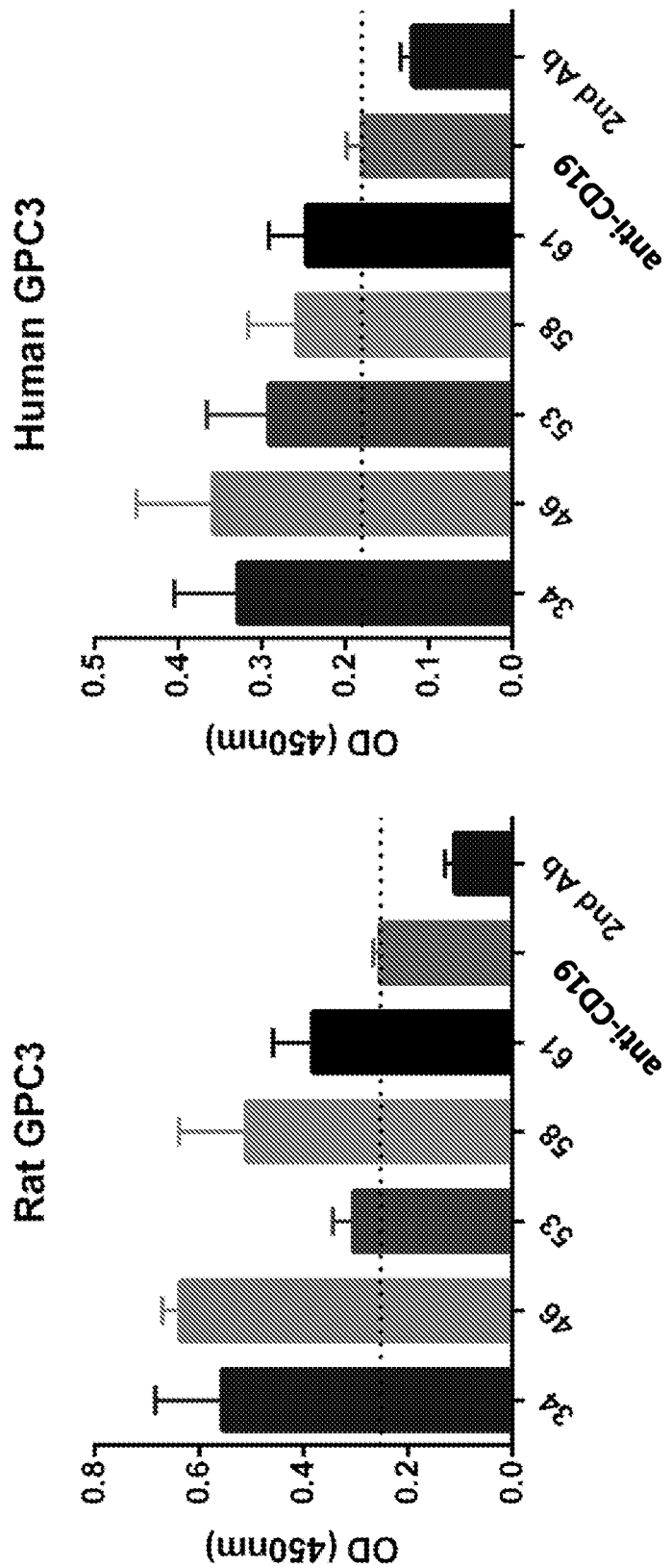

FIG. 12 shows the ELISA analysis of reactivity of GPC3 mIgG1 clones to rat GPC3 and human GPC3 (hGPC3).

Figure 13:
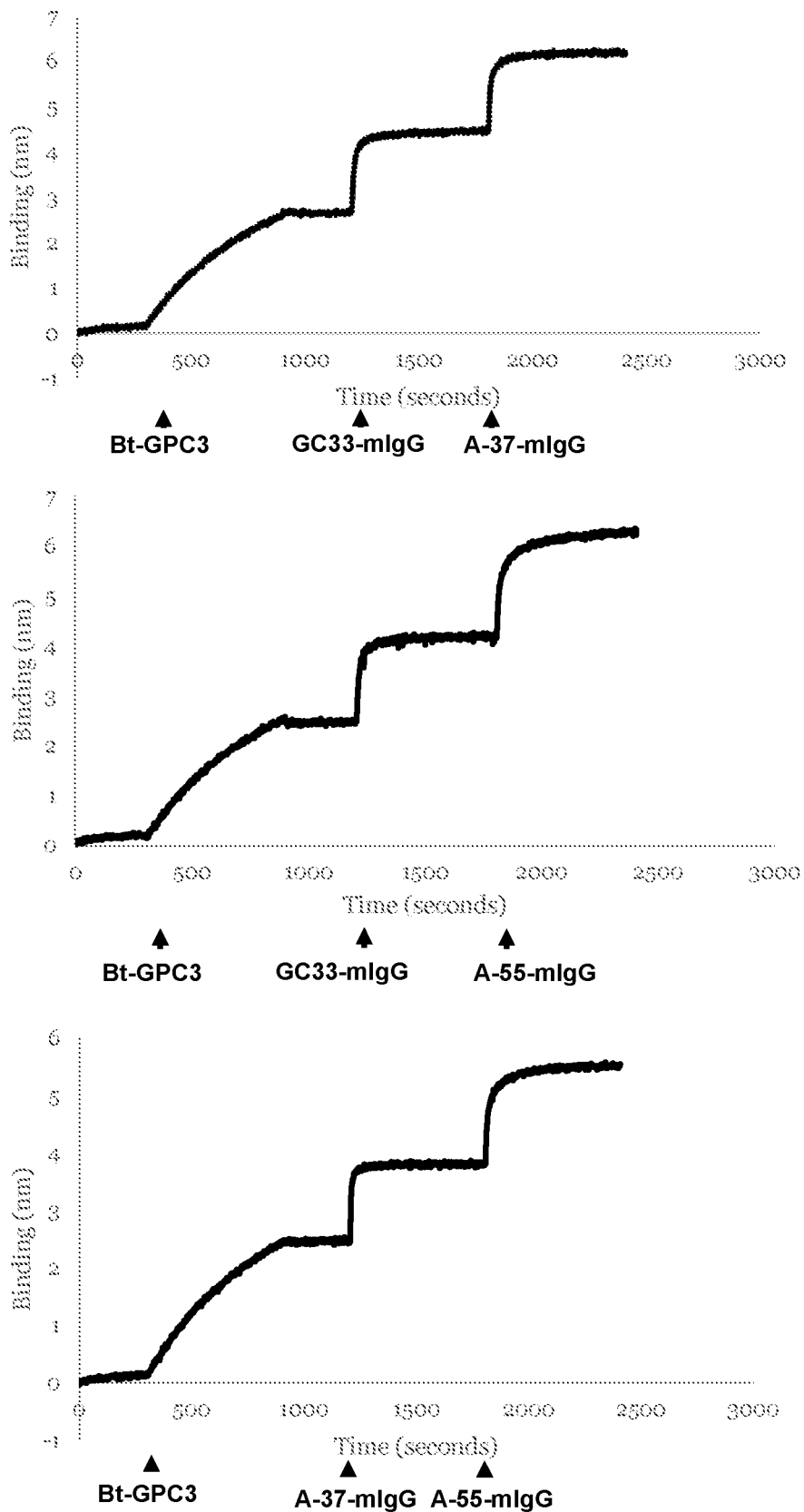
Figure 14:
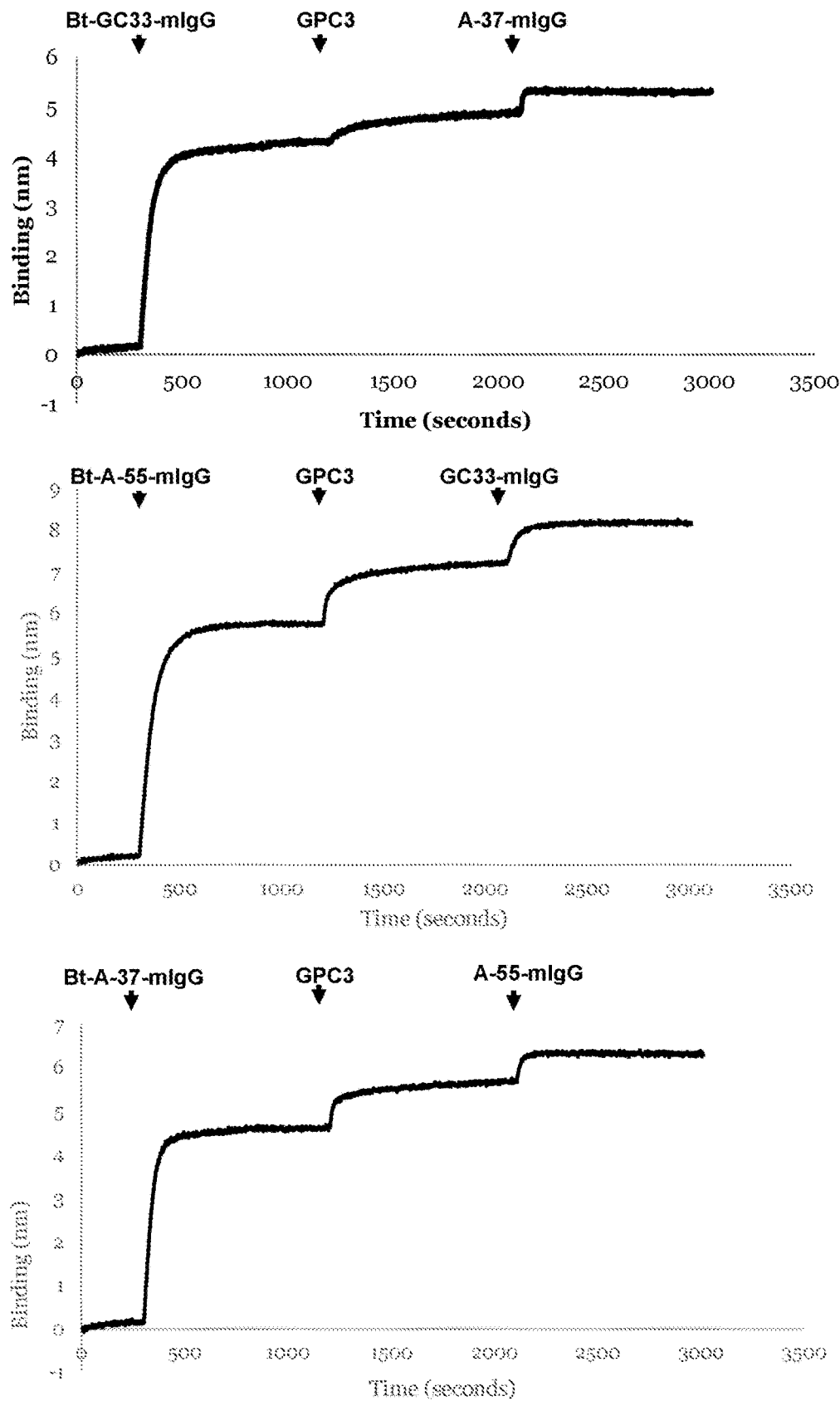

FIG. 13 shows the GPC3 epitope binning analysis of GC33-mIgG, GPC3A-37 mIgG and GPC3A-55 mIgG using a linear format of epitope binning, FIG. 14 shows the GPC3 epitope binning analysis of GC33-mIgG, GPC3A-37 mIgG and GPC3A-55 mIgG using a sandwich format of epitope binning.

FIGS. 15A and 15B show the plotted data from single-cycle kinetics analysis of binding between GPC3A L2K clones and GPC3 antigen.

Figure 16:
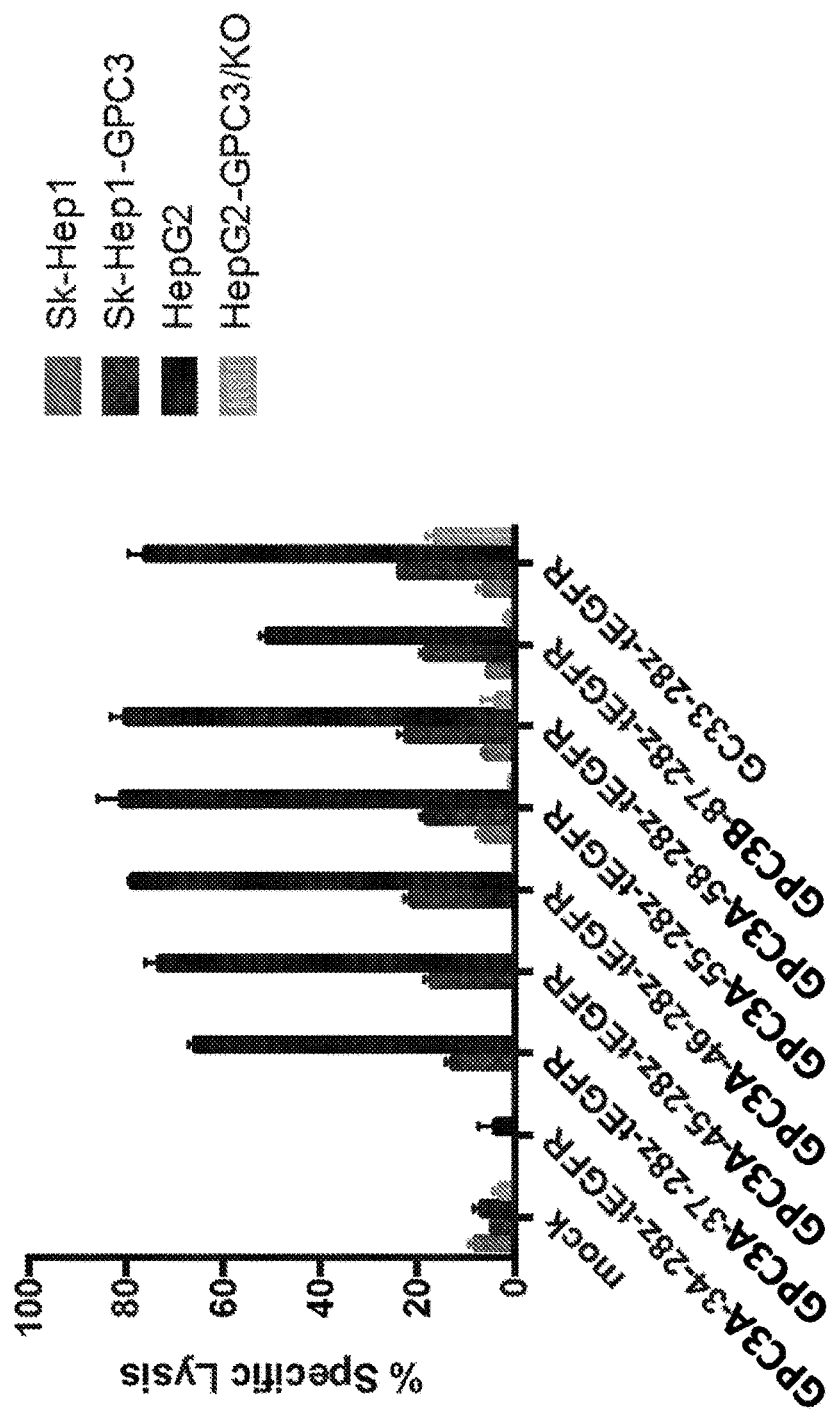
Figure 17A:
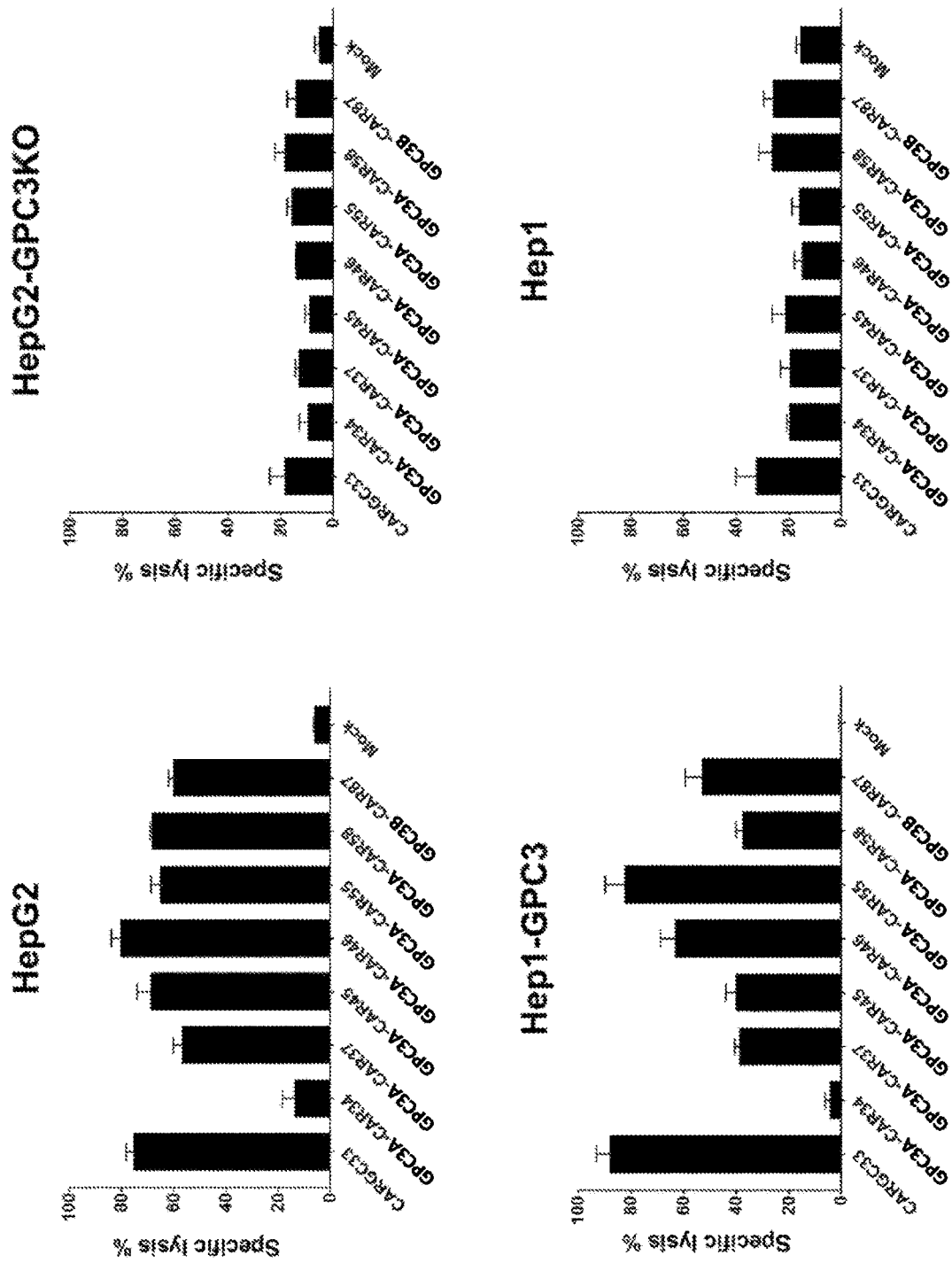
Figure 17B:
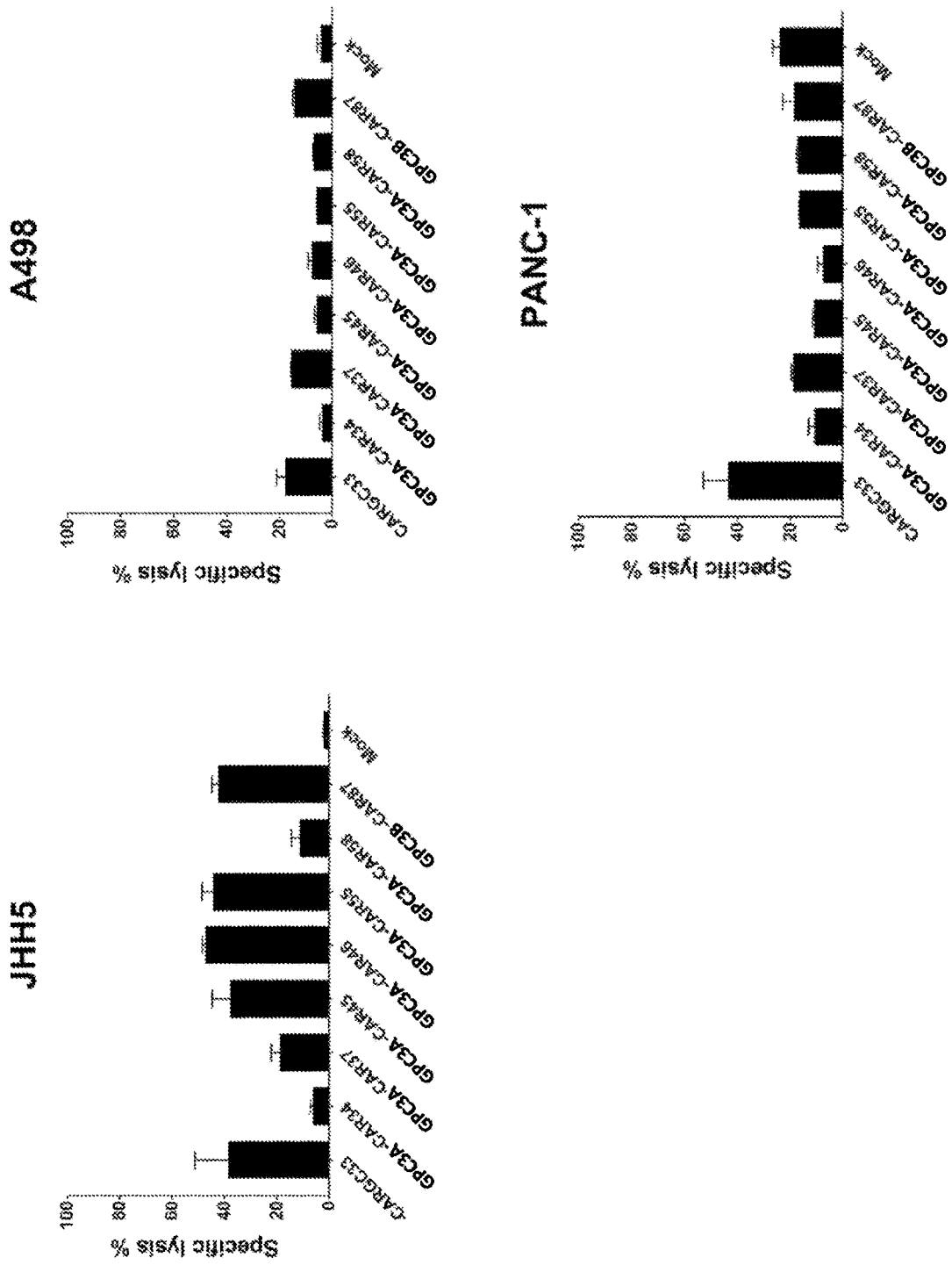

FIG. 16 shows the LDH cytotoxicity analysis in GPC3-positive HepG2 cells, GPC3-negative SK-Hep1 cells, SK-Hep1-GPC3 cells, and HepG2-GPC3-KO cells treated by GPC3A or GPC3B CAR-T cells and GC33 CAR-T cells, FIG. 17A shows the LDH cytotoxicity analysis in GPC3+ HepG2 cells, GPC3-negative SK-Hep1 cells, SK-Hep1-GPC3 cells, and HepG2-GPC3-KO cells treated by GPC3A or GPC3B CAR-T cells and GC33 CAR-T cells. FIG. 17B shows the LDH cytotoxicity analysis in GPC3-positive JHH5 cells, GPC3-negative A-498 cells, and GPC3-negative PANC-1 cells treated by GPC3A or GPC3B CAR-T cells and GC33 CAR-T cells.

Figure 18:
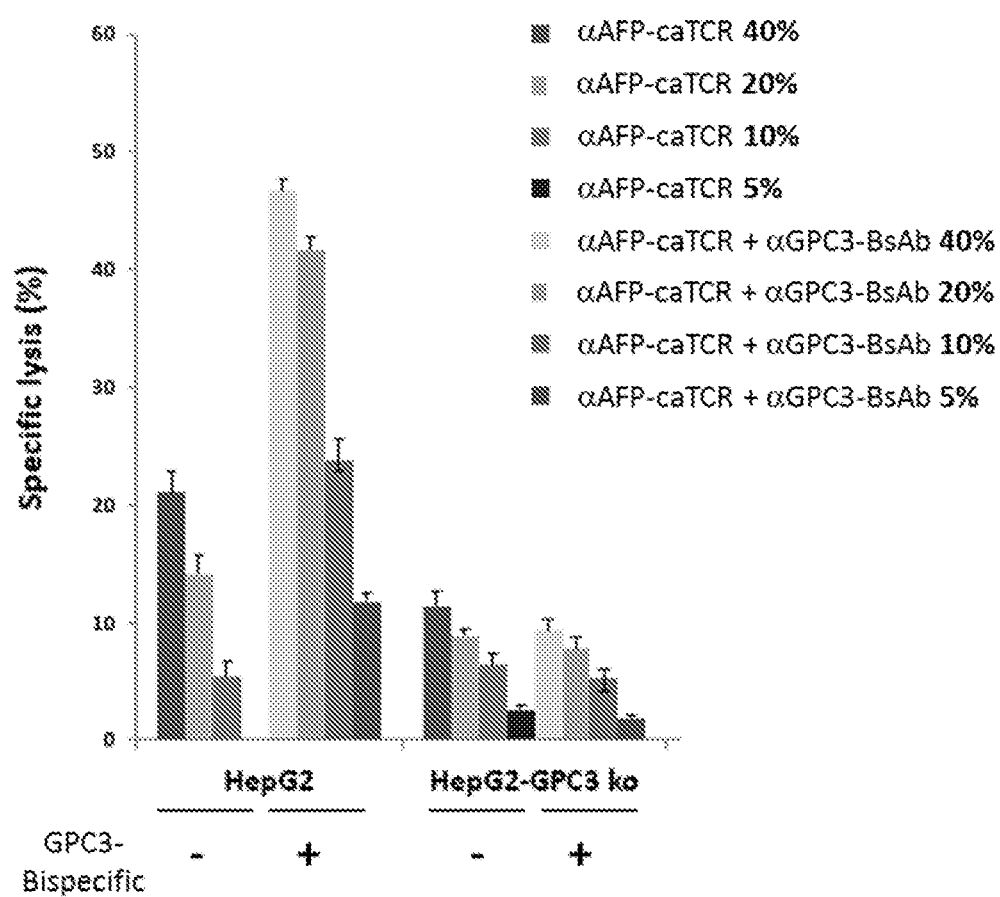

FIG. 18 shows percent specific lysis from the killing of cancer cell lines HepG2 (AFP$^+$/GPC3$^+$) and HepG2-GPC3-KO (AFP$^+$/GPC3$^-$), mediated by T cells transduced with either anti-AFP158/HLA-A*2:01 caTCR alone or anti-AFP158/HLA-A*2:01 caTCR+anti-CD3/anti-GPC3 BsAb at the indicated percent caTCR positivity (5% to 40%).

Figure 19:
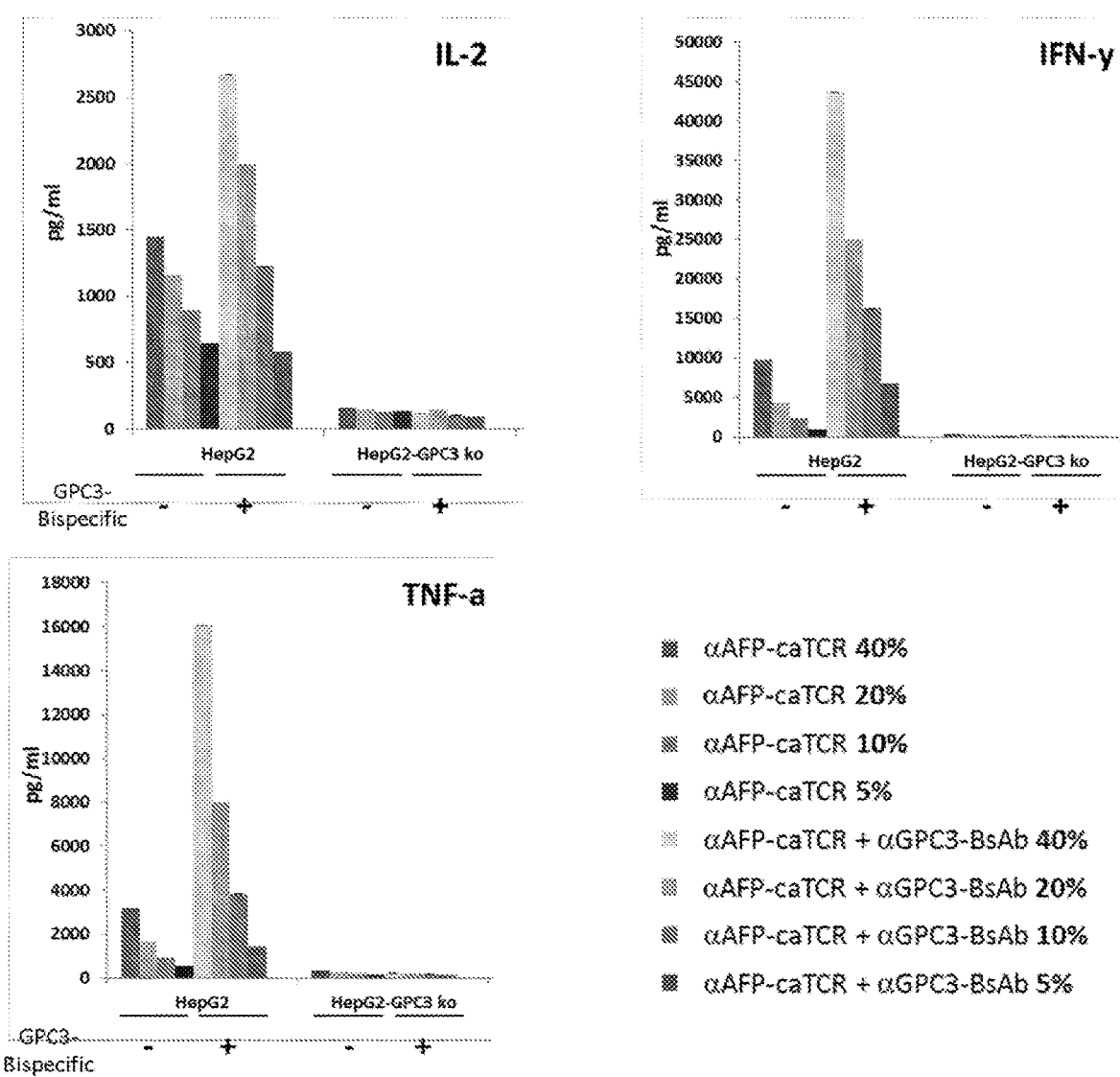

FIG. 19 shows the concentration of cytokines (IL-2, IFN-γ, and TNF-α) found in the supernatant after in vitro killing of cancer cell lines HepG2 and HepG2-GPC3-KO, mediated by T cells transduced with either anti-AFP158/HLA-A*2:01 caTCR alone or anti-AFP158/HLA-A*2:01 caTCR+anti-CD3/anti-GPC3 BsAb at the indicated percent caTCR positivity (5% to 40%).

Figure 20:
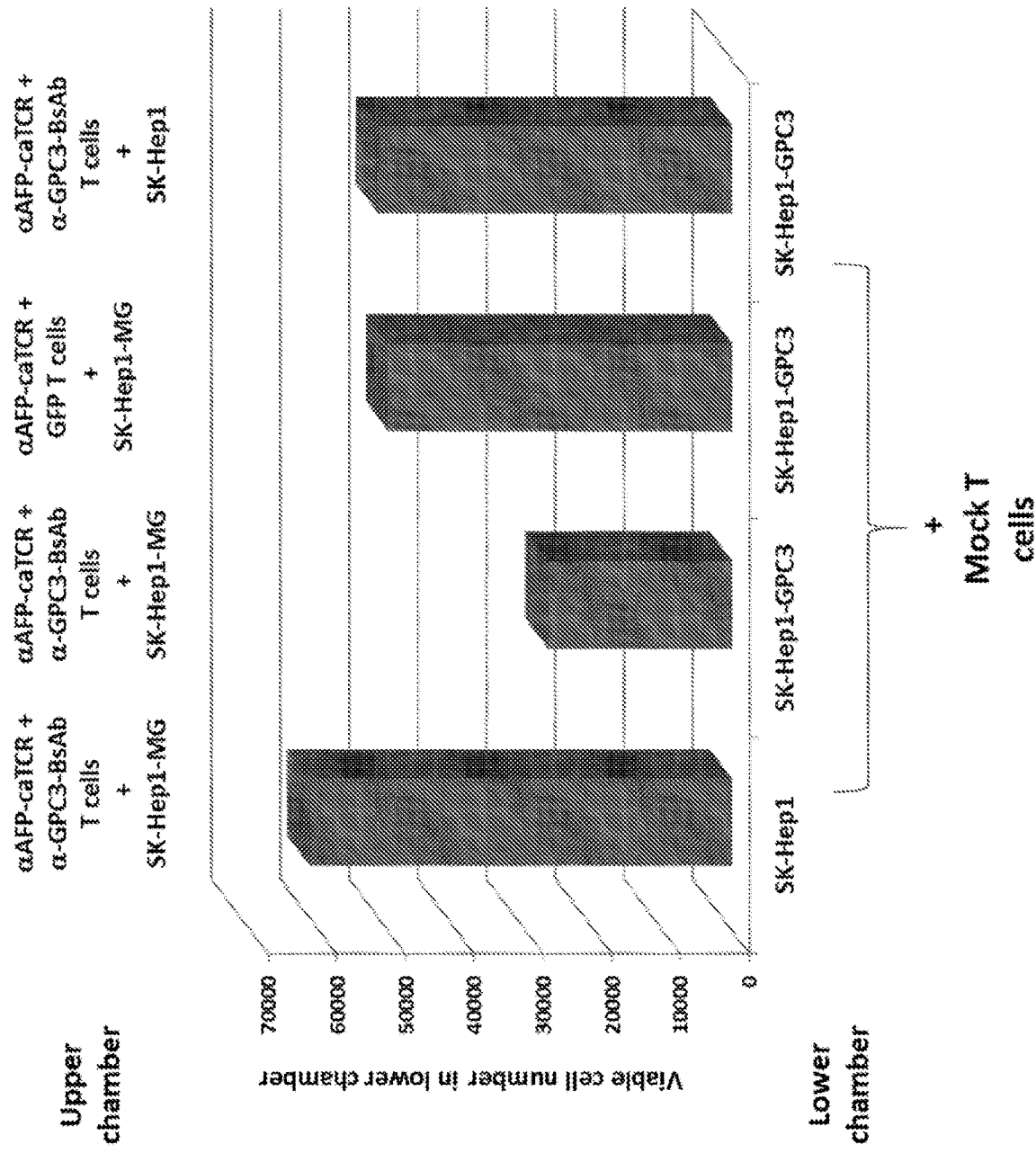

FIG. 20 shows the potentiation of target-specific cancer cell line killing mediated by anti-CD3/anti-GPC3 BsAbs released from activated anti-AFP158/HLA-A*2:01 caTCR+ anti-CD3/anti-GPC3 BsAb T cells. The indicated transduced T cells and target cells were incubated together and separated from the indicated target cells and mock T cells by a membrane permeable to the BsAb, but not the T cells.

Figure 21:
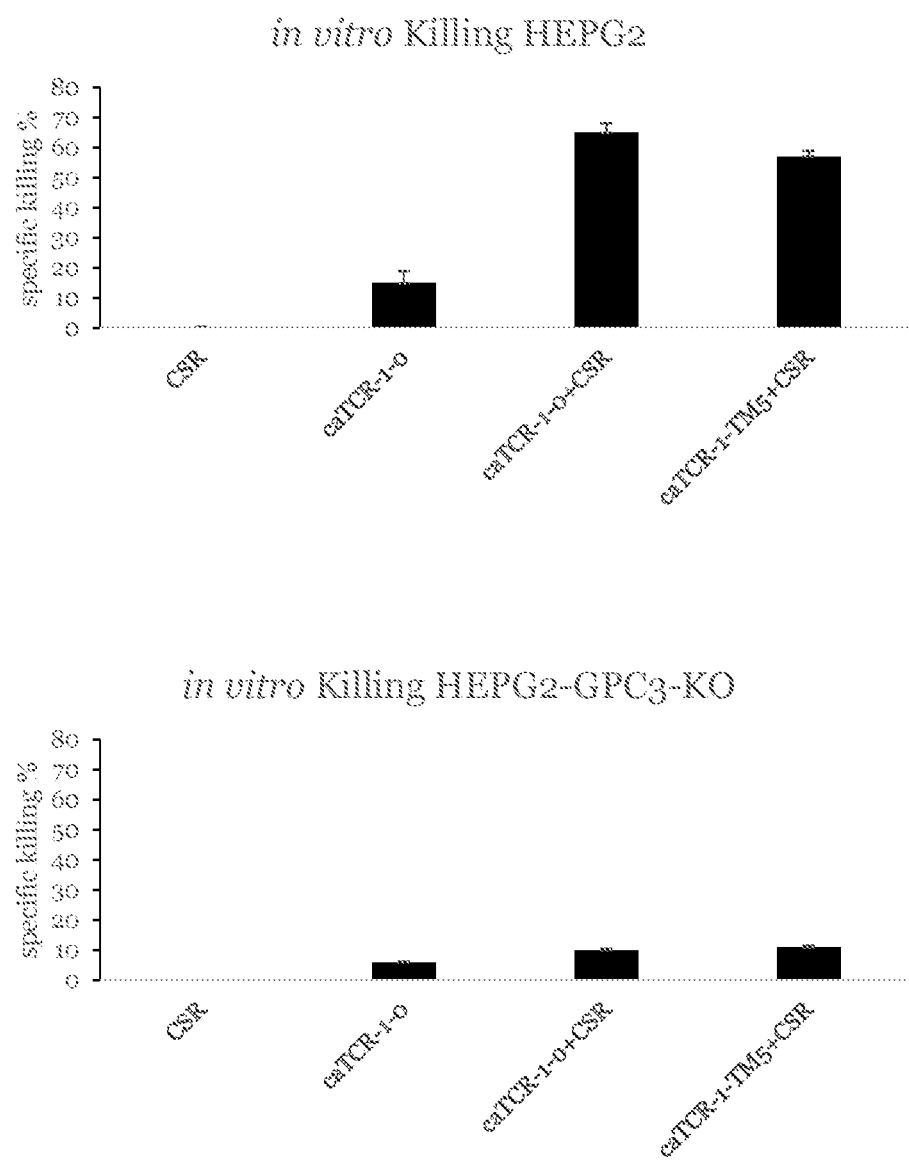

FIG. 21 shows percent specific lysis from the killing of cancer cell lines HepG2 (AFP$^+$/GPC3$^+$) and HepG2-GPC3.ko (AFP$^+$/GPC3$^-$), mediated by T cells transduced with anti-AFP158/HLA-A*2:01 caTCR-1-0 alone, anti-GPC3 CSR alone, or anti-AFP158/HLA-A*2:01 caTCR (1-0 and 1-TM5)+anti-GPC3 CSR.

FIG. 22 shows the concentration of cytokines (IL-2, GM-CSF, IFN-γ, and TNF-α) found in the supernatant after in vitro killing of cancer cell lines HepG2 and HepG2-GPC3-KO, mediated by T cells transduced with anti-AFP158/HLA-A*2:01 caTCR-1-0 alone, anti-GPC3 CSR alone, or anti-AFP158/HLA-A*2:01 caTCR (1-0 and 1-TM5)+anti-GPC3 CSR.

Figure 23:
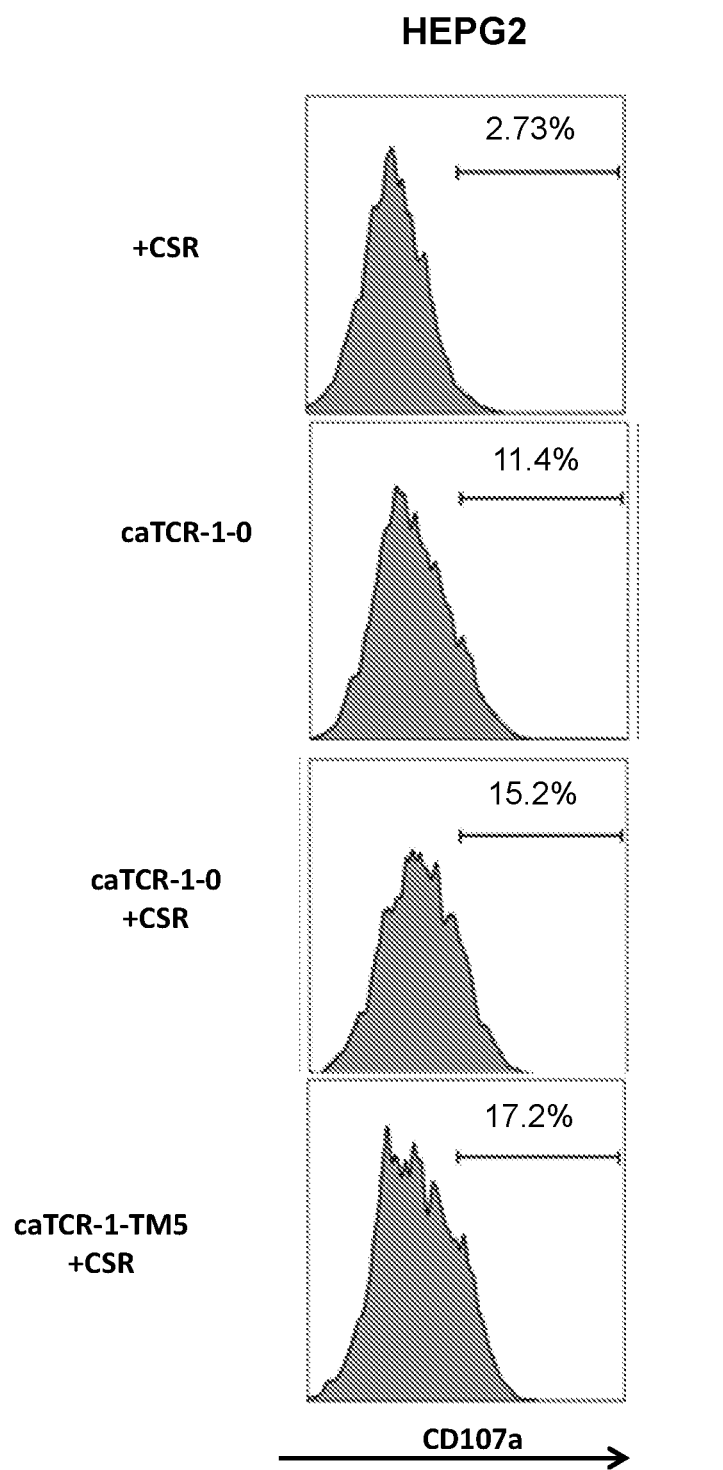

FIG. 23 shows the degranulation activity (as determined by CD107a expression) in T cells transduced with anti-AFP158/HLA-A*2:01 caTCR-1-0 alone, anti-GPC3 CSR alone, or anti-AFP158/HLA-A*2:01 caTCR (1-0 and 1-TM5)+anti-GPC3 CSR following stimulation with cancer cell line HepG2.

Figure 24:
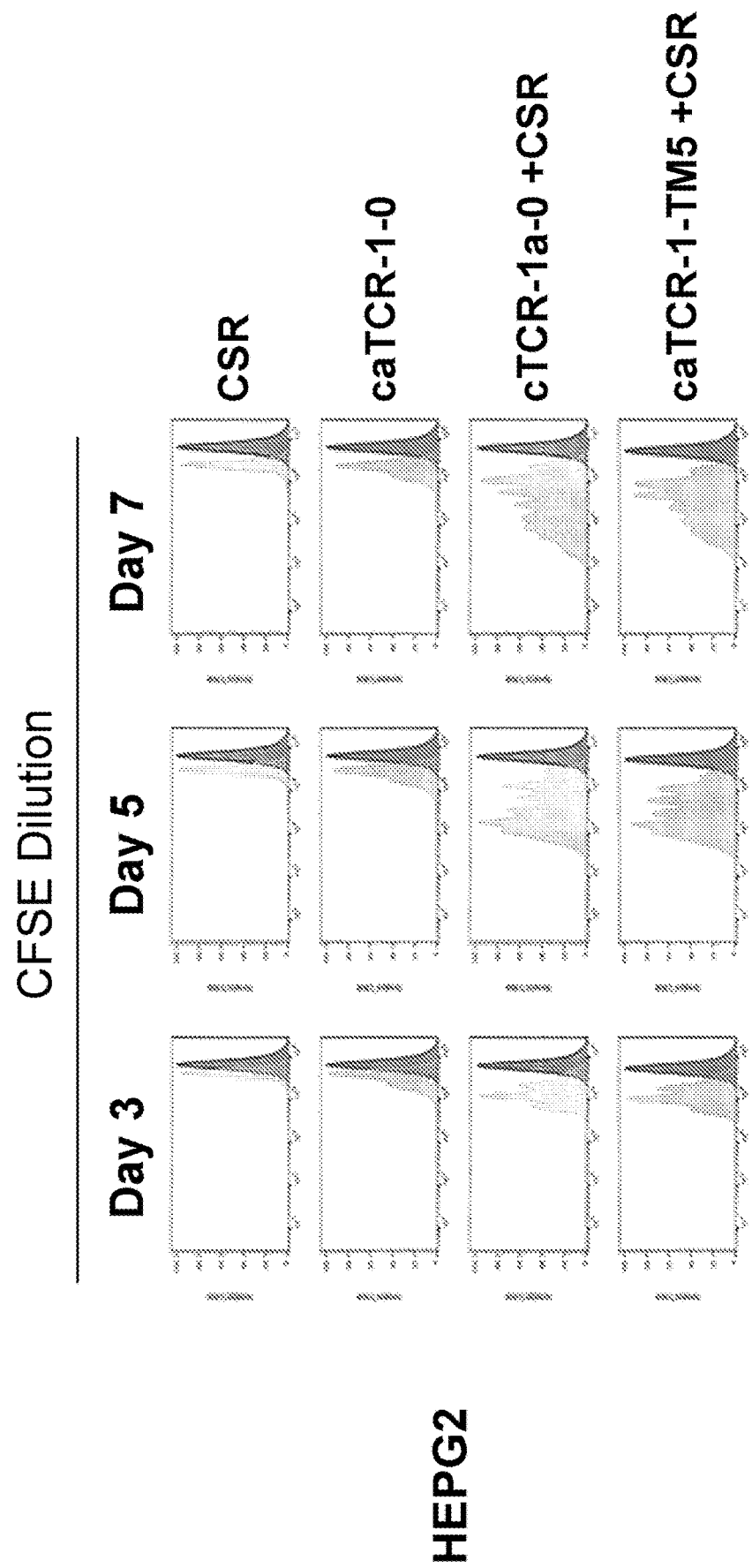

FIG. 24 shows the proliferation (as determined by CFSE dye dilution) of T cells transduced with anti-AFP158/HLA-A*2:01 caTCR-1-0 alone, anti-GPC3 CSR alone, or anti-AFP158/HLA-A*2:01 caTCR (1-0 and 1-TM5)+anti-GPC3 CSR following stimulation with cancer cell line HepG2.

Figure 25:
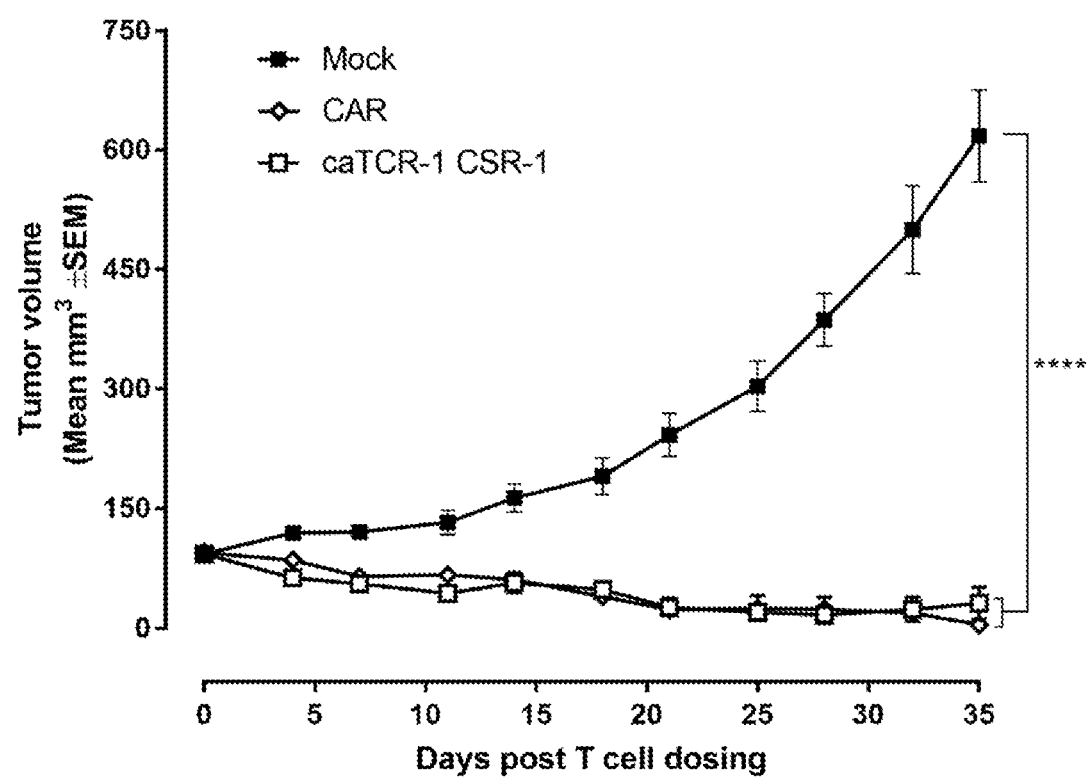

FIG. 25 shows the tumor growth in a subcutaneous mouse model of HepG2 with mock treatment or with a single intratumoral injection of T cells transduced with an anti-AFP CAR, or an anti-AFP CAR in combination with an anti-GPC3 CSR.

DETAILED DESCRIPTION OF THE INVENTION

The present application in one aspect provides constructs (referred to herein as "anti-GPC3 constructs") (such as isolated anti-GPC3 construct) that comprise an antibody moiety (referred to herein as an "anti-GPC3 antibody moiety") specifically recognizing a cell surface-bound GPC3 (referred to herein as a "native format GPC3," or "native GPC3 (nGPC3)"). These anti-GPC3 constructs specifically recognize a cell surface-bound GPC3, as opposed to a non-cell surface bound GPC3 (referred to herein as a "soluble GPC3 (sGPC3)," or "non-native GPC3"), such as circulating GPC3 protein or free GPC3 peptides in the serum.

When armed as anti-CD3 bispecific antibodies or present in a chimeric antigen receptor (CAR) expressed by a T cell, the anti-GPC3 antibody moiety specifically redirected human T cells to kill GPC3-expressing target cells (such as GPC3-expressing cancer cells). This strategy provides a significant technical advantage over using antibodies directed against any format of GPC3 (especially soluble GPC3), because T cell targeting to tumor site can become a lot more efficient and precise, resulting in effective T cell-mediated cancer cell killing without harming normal tissues. Furthermore, when fused to a detectable moiety, the anti-GPC3 antibody moiety allows for diagnosis and prognosis of GPC3-positive diseases or disorders with high sensitivity to changes in the number and distribution of cells expressing GPC3 on the cell surface (such as GPC3-positive tumor cells), a potentially more relevant measure of disease progression than circulating GPC3 levels.

The present application also provides anti-GPC3 constructs (such as isolated anti-GPC3 constructs) comprising an antibody moiety specifically recognizing GPC3 (e.g., nGPC3 and/or sGPC3). These constructs can also be armed as anti-CD3 bispecific antibodies or present in a CAR expressed by a T cell. GPC3 can be expressed on cell surface or released from cell surface to extracellular environment in different forms in cancer patients (such as HCC patients). Thus, these anti-GPC3 constructs can also be fused to a detectable moiety and used for diagnosis and prognosis purposes.

Using phage display technology, we generated multiple monoclonal antibodies that are specific and show high affinity against cell surface-bound human GPC3. Flow cytometry and T-cell mediated cytotoxicity assays demonstrated that these antibodies recognize GPC3-expressing cancer cell lines, in a native format GPC3-restricted manner. When armed as anti-CD3 bispecific antibodies or CAR-T cells, the antibodies re-directed human T cells to kill GPC3-positive target cancer cells. The data presented herein demonstrate that the anti-GPC3 constructs comprising an antibody moiety specifically recognizing cell surface-bound GPC3 described herein can be effective therapeutic agents for cancer indications, such as solid tumor indications (e.g., HCC).

Using phage display technology, we also generated multiple monoclonal antibodies that are specific and high affinity against human GPC3 (e.g., nGPC3 and/or sGPC3). Flow cytometry and T-cell mediated cytotoxicity assays demonstrated that these antibodies specifically recognize GPC3.

The present application thus provides constructs (such as isolated constructs) comprising an antibody moiety specifically recognizing GPC3, such as a cell surface-bound GPC3. The construct can be, for example, anti-GPC3 scFv, anti-GPC3 Fc fusion protein, full-length anti-GPC3 antibodies, multi-specific (such as bispecific) anti-GPC3 molecules (e.g., tandem di-scFv bispecific T cell engager), anti-GPC3 chimeric antigen receptors (CARs), anti-GPC3 chimeric antibody-T cell receptors (caTCRs), and anti-GPC3 immunoconjugates.

In another aspect, there are provided nucleic acids encoding the anti-GPC3 constructs (such as isolated anti-GPC3 constructs) or the anti-GPC3 antibody moiety portion of the constructs (such as those specifically recognizing cell surface-bound GPC3).

In another aspect, there are provided compositions (such as pharmaceutical compositions) comprising an anti-GPC3 construct (such as an isolated anti-GPC3 construct) comprising an antibody moiety specifically recognizing GPC3 (such as a cell surface-bound GPC3). The composition can be a pharmaceutical composition comprising an anti-GPC3 construct (such as a cell surface-bound GPC3) or an effector cell expressing or associated with the anti-GPC3 construct (for example a T cell expressing an anti-GPC3 CAR, a CAR specifically recognizing a cell surface-bound GPC3).

Also provided are methods of making and using the anti-GPC3 constructs (such as isolated anti-GPC3 constructs, or cells expressing or associated with the anti-GPC3 constructs) for treatment or diagnostic purposes, as well as kits and articles of manufacture useful for such methods.

Definitions

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the invention contemplate any one or more of these aspects of treatment.

"Activation" as used herein in relation to T cells, refers to the state of a T cell that has been sufficiently stimulated to induce detectable cellular proliferation. Activation can also be associated with induced cytokine production, and detectable effector functions.

The term "antibody moiety" includes full-length antibodies and antigen-binding fragments thereof. A full-length antibody comprises two heavy chains and two light chains. The variable regions of the light and heavy chains are responsible for antigen binding. The variable regions in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain Fv (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

As used herein, a first antibody moiety "competes" for binding to a target GPC3 (e.g., nGPC3 and/or sGPC3) with a second antibody moiety when the first antibody moiety inhibits target GPC3 binding of the second antibody moiety by at least about 50% (such as at least about any of 55%, 60%, 65%, 70%, 75%, 80%, 85%, 90%, 95%, 98% or 99%) in the presence of an equimolar concentration of the first antibody moiety, or vice versa. A high throughput process for "binning" antibodies based upon their cross-competition is described in PCT Publication No. WO 03/48731.

As use herein, the term "specifically binds," "specifically recognizing," or "is specific for" refers to measurable and reproducible interactions, such as binding between a target and an antibody or antibody moiety, that is determinative of the presence of the target in the presence of a heterogeneous population of molecules, including biological molecules. For example, an antibody or antibody moiety that specifically recognizes a target (which can be an epitope) is an antibody or antibody moiety that binds this target with greater affinity, avidity, more readily, and/or with greater duration than its bindings to other targets. In some embodiments, an antibody or antibody moiety that specifically recognizes an antigen reacts with one or more antigenic determinants of the antigen (such as native format GPC3) with a binding affinity that is at least about 10 times its binding affinity for other targets (such as soluble GPC3).

An "isolated" anti-GPC3 construct as used herein refers to an anti-GPC3 construct that (1) is not associated with proteins found in nature, (2) is free of other proteins from the same source, (3) is expressed by a cell from a different species, or, (4) does not occur in nature.

The term "isolated nucleic acid" as used herein is intended to mean a nucleic acid of genomic, cDNA, or synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); Chothia et al., J. Mol. Biol. 196: 901-917 (1987); Al-Lazikani B. et al., J. Mol. Biol., 273: 927-948 (1997); MacCallum et al., J. Mol. Biol. 262:732-745 (1996); Abhinandan and Martin, Mol. Immunol., 45: 3832-3839 (2008); Lefranc M. P. et al., Dev. Comp. Immunol., 27: 55-77 (2003); and Honegger and Plückthun, J. Mol. Biol., 309:657-670 (2001), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison. CDR prediction algorithms and interfaces are known in the art, including, for example, Abhinandan and Martin, Mol. Immunol., 45: 3832-3839 (2008); Ehrenmann F. et al., Nucleic Acids Res., 38: D301-D307 (2010); and Adolf-Bryfogle J. et al., Nucleic Acids Res., 43: D432-D438 (2015). The contents of the references cited in this paragraph are incorporated herein by reference in their entireties for use in the present invention and for possible inclusion in one or more claims herein.

TABLE 1

CDR DEFINITIONS

| | Kabat[1] | Chothia[2] | MacCallum[3] | IMGT[4] | AHo[5] |
|---|---|---|---|---|---|
| $V_H$ CDR1 | 31-35 | 26-32 | 30-35 | 27-38 | 25-40 |
| $V_H$ CDR2 | 50-65 | 53-55 | 47-58 | 56-65 | 58-77 |
| $V_H$ CDR3 | 95-102 | 96-101 | 93-101 | 105-117 | 109-137 |
| $V_L$ CDR1 | 24-34 | 26-32 | 30-36 | 27-38 | 25-40 |
| $V_L$ CDR2 | 50-56 | 50-52 | 46-55 | 56-65 | 58-77 |
| $V_L$ CDR3 | 89-97 | 91-96 | 89-96 | 105-117 | 109-137 |

[1]Residue numbering follows the nomenclature of Kabat et al., supra
[2]Residue numbering follows the nomenclature of Chothia et al., supra
[3]Residue numbering follows the nomenclature of MacCallum et al., supra
[4]Residue numbering follows the nomenclature of Lefranc et al., supra
[5]Residue numbering follows the nomenclature of Honegger and Plückthun, supra The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., Proc. Natl. Acad. Sci. USA, 81:6851-6855 (1984)).

The term "semi-synthetic" in reference to an antibody or antibody moiety means that the antibody or antibody moiety has one or more naturally occurring sequences and one or more non-naturally occurring (i.e., synthetic) sequences.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32(5):1792-1797, 2004; Edgar, R. C., *BMC Bioinformatics* 5(1):113, 2004).

The terms "Fc receptor" or "FcR" are used to describe a receptor that binds to the Fc region of an antibody. In some embodiments, an FcR of this invention is one that binds an IgG antibody (a γ receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). The term includes allotypes, such as FcγRIIIA allotypes: FcγRIIIA-Phe158, FcγRIIIA-Va1158, FcγRIIA-R131 and/or FcγRIIA-H131. FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "FcRn" refers to the neonatal Fc receptor (FcRn). FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "CH1 domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

A "functional Fc fragment" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art.

An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent $K_d$ or $IC_{50}$ value) than the parent polypeptide or a native sequence IgG Fc. According to some embodiments, the improvement in binding compared to a parent polypeptide is about 3 fold, such as about any of 5, 10, 25, 50, 60, 100, 150, 200, or up to 500 fold, or about 25% to 1000% improvement in binding. The polypeptide variant which "exhibits decreased binding" to an FcR, binds at least one FcR with lower affinity (e.g., higher apparent $K_d$ or higher $IC_{50}$ value) than a parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS (USA)* 95:652-656 (1998).

The polypeptide comprising a variant Fc region which "exhibits increased ADCC" or mediates ADCC in the presence of human effector cells more effectively than a polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g., in an animal model etc. In some embodiments, the variant is from about 5 fold to about 100 fold, e.g. from about 25 to about 50 fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See also, Idusogie et al. *J. Immunol.* 164: 4178-4184 (2000).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

An "effective amount" of an anti-GPC3 construct or composition as disclosed herein, is an amount sufficient to carry out a specifically stated purpose. An "effective amount" can be determined empirically and by known methods relating to the stated purpose.

The term "therapeutically effective amount" refers to an amount of an anti-GPC3 construct or composition as disclosed herein, effective to "treat" a disease or disorder in an individual. In the case of cancer, therapeutically effective amount of the anti-GPC3 construct or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the anti-GPC3 construct or composition as disclosed herein can prevent growth and/or kill existing cancer cells, it can be cytostatic and/or cytotoxic. In some embodiments, therapeutically effective amount is a growth inhibitory amount. In some embodiments, therapeutically effective amount is an amount that extends the survival of a patient. In some embodiments, therapeutically effective amount is an amount that improves progression free survival of a patient.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "label" when used herein refers to a detectable compound or composition which can be conjugated directly or indirectly to the anti-GPC3 antibody moiety. The label may be detectable by itself (e.g., radioisotope labels or fluorescent labels) or, in the case of an enzymatic label, may catalyze chemical alteration of a substrate compound or composition which is detectable.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "or," and "the" include plural referents unless the context clearly dictates otherwise.

Anti-GPC3 Constructs

In one aspect, the present invention provides GPC3-specific constructs (such as isolated anti-GPC3 constructs) that comprise an antibody moiety that specifically binds to GPC3. The specificity of the anti-GPC3 construct derives from an anti-GPC3 antibody moiety, such as a full-length antibody or antigen-binding fragment thereof, which specifically binds to GPC3. In some embodiments, reference to a moiety (such as an antibody moiety) that specifically binds to GPC3 means that the moiety binds to the GPC3 with an affinity that is at least about 10 times (including for example at least about any of 10, $10^2$, $10^3$, $10^4$, $10^5$, $10^6$, or $10^7$ times) its binding affinity for non-target. In some embodiments, the non-target is an antigen that is not GPC3. In some embodiments, for an anti-nGPC3 antibody moiety, the non-target is a soluble GPC3. In some embodiments, for an anti-sGPC3 antibody moiety, the non-target is a cell surface-bound GPC3. Binding affinity can be determined by methods known in the art, such as ELISA, fluorescence activated cell sorting (FACS) analysis, or radioimmunoprecipitation assay (RIA). $K_d$ can be determined by methods known in the art, such as surface plasmon resonance (SPR) assay utilizing, for example, BIACORE™ instruments, or kinetic exclusion assay (KinExA) utilizing, for example, Sapidyne instruments.

Contemplated anti-GPC3 constructs include, for example, anti-GPC3 scFv, anti-GPC3 Fc fusion protein, full-length anti-GPC3 antibodies, multi-specific (such as bispecific) anti-GPC3 molecules (e.g., tandem di-scFv bispecific T cell engager), anti-GPC3 chimeric antigen receptors (CARs), anti-GPC3 chimeric antibody-T cell receptors (caTCRs), and anti-GPC3 immunoconjugates.

The different aspects are discussed in various sections below in further detail.

Although embodiments employing anti-GPC3 constructs comprising an anti-GPC3 antibody moiety that contain human sequences (i.e., human heavy and light chain variable region sequences comprising human CDR sequences) are extensively discussed herein, the present invention also provides non-human anti-GPC3 constructs. In some embodiments, non-human antibody agents comprise human CDR sequences from an antibody agent as described herein and non-human framework sequences. Non-human framework sequences include, in some embodiments, any sequence that can be used for generating synthetic heavy and/or light chain variable regions using one or more human CDR sequences as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. In some embodiments, a provided antibody agent includes an antibody agent generated by grafting one or more human CDR sequences as described herein onto a non-human framework sequence (e.g., a mouse or chicken framework sequence). In many embodiments, provided antibody agents are human antibody agents (e.g., a human monoclonal antibody or fragment thereof, human antigen-binding protein or polypeptide, human multi-specific binding agent [e.g., a human bi-specific antibody], a human polypeptide having one or more structural components of a human immunoglobulin polypeptide).

Anti-GPC3 Antibody Moiety

The anti-GPC3 construct (such as an isolated anti-GPC3 construct) comprises an anti-GPC3 antibody moiety that specifically recognizes GPC3. In some embodiments, the anti-GPC3 antibody moiety specifically recognizes a cell surface-bound GPC3 (referred to herein as "anti-nGPC3 antibody moiety"). In some embodiments, the binding affinity of the anti-nGPC3 antibody moiety to nGPC3 is higher than that to an sGPC3. In some embodiments, the binding affinity of the anti-nGPC3 antibody moiety specifically recognizes a cell surface-bound GPC3 at a high binding affinity and binds to a soluble GPC3 at a low binding affinity. In some embodiments, the cell expressing GPC3 on its surface is HepG2, Hep3B, Huh7, JHH-7, or 293. In some embodiments, the cell presents on its surface abnormally high levels of GPC3. In some embodiments, the cell is a cancer cell. In some embodiments, the cancer cell is in a solid tumor (such as liver cancer, e.g. HCC). In some embodiments, the cancer cell is a metastatic cancer cell (such as metastatic HCC). In some embodiments, the anti-GPC3 antibody moiety specifically recognizes a soluble GPC3 (referred to herein as "anti-sGPC3 antibody moiety"). In some embodiments, the anti-GPC3 antibody moiety specifically recognizes both nGPC3 and sGPC3.

Glypican 3 (GPC3)

Glypican 3 (GPC3) is an oncofetal antigen belonging to the heparin sulfate proteoglycan family existing on the surface of cells, which is involved in cell signaling at the cellular-extracellular matrix interface. GPC3 is expressed in fetal liver and placenta during development and is down-regulated or silenced in normal adult tissues. This developmental stage- and tissue-specific expression manner suggests that GPC3 may be involved in morphogenesis.

The GPC3 gene encodes a 70 kDa precursor protein of 580 amino acids. Upon translocation into the endoplasmic reticulum, the N-terminal signal peptide (SS; residues 1-24) and the C-terminal glycosylphosphatidylinositol (GPI) anchor addition signal (a predicted cleavage site: $S^{560}$) are removed and the latter is replaced with a GPI anchor. The GPC3 precursor protein can be cleaved by Furin between $Arg^{358}$ and $Ser^{359}$ to generate a 40 kDa N-terminal subunit ($Q^{25}$-$R^{358}$) and a 30 kDa C-terminal subunit (starting from $S^{359}$) linked by disulfide bonds. The C-terminus of GPC3 links to the membrane through the GPI anchor and is post-translationally modified with two O-linked heparin sulfate (HS) side chains close to the cell surface. Based on the primary amino acid sequence, the N-terminal subunit, the C-terminal subunit and the two HS glycan chains form the three functional domains of GPC3. The N-terminal and C-terminal subunits form the core protein of GPC3.

The negatively-charged HS chains on GPC3 are functionally important glycosaminoglycans. They can bind positively-charged growth factors, such as HGFs, fibroblast growth factors (FGFs), Wnts, Hedgehog and bone morphogenetic proteins. Thus, the HS chains might serve as "docking sites" for these growth factors, depending on cellular context.

The N-terminal subunit of GPC3 is an N-terminal peptide of GPC3 and of about 40 kDa, which is found in the soluble form of the GPC3 core protein. In some embodiments, the N-terminal subunit is a peptide of an amino acid sequence comprising from Met' to Arg$^{358}$. In some embodiments, the N-terminal subunit is a peptide of an amino acid sequence comprising from Gln$^{25}$ to Arg$^{358}$. In accordance with the invention, fragments of such N-terminal peptide may also be employed, referred to herein as GPC3 N-terminal fragment. In some embodiments, the anti-GPC3 antibody moiety specifically recognizes an epitope existing on the N-terminal subunit of the GPC3 protein. In some embodiments, the antibody moiety specifically recognizing the N-terminal subunit (or fragment thereof) of the GPC3 protein described herein specifically binds to the soluble format of GPC3. In some embodiments, the antibody moiety specifically recognizing the N-terminal subunit (or fragment thereof) of the GPC3 protein specifically binds to the native format of GPC3. In some embodiments, the antibody moiety specifically recognizing the N-terminal subunit (or fragment thereof) of the GPC3 protein can bind to both nGPC3 and sGPC3.

The C-terminal subunit of GPC3 is a C-terminal peptide of GPC3 and of about 30 kDa. Based on the cleavage site mentioned above, in some embodiments, the C-terminal subunit is a peptide of an amino acid sequence comprising from Ser$^{359}$ to His$^{580}$. In some embodiments, the C-terminal subunit is a peptide of an amino acid sequence comprising from Ser$^{359}$ to Ser$^{560}$. In accordance with the invention, fragments of such C-terminal peptide may also be employed, referred to herein as GPC3 C-terminal fragment. In some embodiments, the anti-GPC3 antibody moiety specifically recognizes an epitope existing on the C-terminal subunit of the GPC3 protein. In some embodiments, the antibody moiety specifically recognizing the C-terminal subunit (or fragment thereof) of the GPC3 protein described herein specifically binds to the soluble format of GPC3. In some embodiments, the antibody moiety specifically recognizing the C-terminal subunit (or fragment thereof) of the GPC3 protein specifically binds to the native format of GPC3. In some embodiments, the antibody moiety specifically recognizing the C-terminal subunit (or fragment thereof) of the GPC3 protein can bind to both nGPC3 and sGPC3.

The anti-GPC3 constructs described herein do not bind to the same epitope on GPC3 as known antibodies in the art, such as GC33 (Ishiguro et al., Cancer Res 2008; 68:9832-9838) (e.g., SEQ ID NO: 510). In some embodiments, the anti-GPC3 antibody moiety does not specifically bind to the same or substantially the same GPC3 epitope competitively with GC33. In some embodiments, the anti-GPC3 antibody moiety does not bind to an epitope within the amino acid sequence of SEQ ID NO: 536. In some embodiments, the anti-GPC3 antibody moiety does not bind to a fragment comprising the amino acid sequence of SEQ ID NO: 536.

GPC3 has been reported to be expressed in various cancers and, in particular, HCC, melanoma, lung squamous cell carcinoma, ovarian carcinoma, yolk sac tumor, choriocarcinoma, neuroblastoma, Wilms' tumor, and liposarcoma. Thus, GPC3 may potentially serve as a therapeutic target for both antibody- and cell-based immunotherapy. Particularly, given that GPC3 is highly expressed in HCC, and is expressed in more than 70% of HCC tumors but not normal liver tissue, GPC3 can be a promising candidate for liver cancer therapy. For some patients with GPC3-positive cancers, soluble format of GPC3 can be detected in the blood. Thus, soluble and native formats of GPC3 can both serve as useful biomarkers for cancer diagnosis, such as HCC diagnosis. It was found that GPC3-positive HCC patients have a significantly lower 5-year survival rate than GPC3-negative HCC patients. GPC3 expression is therefore correlated with poor prognosis in HCC.

GPC3 cell surface localization is crucial for cell growth and Wnt activation in HCC. GPC3 binds to Wnt through its core protein. It was hypothesized that GPC3 stimulates Wnt signaling by facilitating and/or stabilizing the interaction of Wnt with Frizzled (Fz), its signaling receptor. Interestingly, it was noted that approximately 50% of HCC patients have secreted GPC3 in the sera. However, it is unclear what form of GPC3 is present in the circulating blood of cancer patients. The extracellular lipase, Notum, may be responsible for cleaving GPC3 from tumor cells into the extracellular environment.

In some embodiments, the anti-GPC3 antibody moiety described herein (against nGPC3 and/or sGPC3) specifically recognizes an epitope within human GPC3. The complete amino acid sequence of an exemplary human GPC3 has UniProt No. P51654 (SEQ ID NO: 460). In some embodiments, the anti-GPC3 antibody moiety specifically recognizes an epitope within human GPC3 comprising the amino acid sequence of SEQ ID NO: 460. In some embodiments, the anti-GPC3 antibody moiety specifically recognizes an epitope within amino acids 1-560 of SEQ ID NO: 460 (SEQ ID NO: 461). In some embodiments, the anti-GPC3 antibody moiety specifically recognizes an epitope within amino acids 25-580 of SEQ ID NO: 460 (SEQ ID NO: 462). In some embodiments, the anti-GPC3 antibody moiety specifically recognizes an epitope within amino acids 25-560 of SEQ ID NO: 460 (SEQ ID NO: 463). In some embodiments, the anti-GPC3 antibody moiety specifically recognizes an epitope within the N-terminal fragment of GPC3. In some embodiments, the anti-GPC3 antibody moiety specifically recognizes an epitope within amino acids 1-358 of SEQ ID NO: 460 (SEQ ID NO: 468). In some embodiments, the anti-GPC3 antibody moiety specifically recognizes an epitope within amino acids 25-358 of SEQ ID NO: 460 (SEQ ID NO: 464). In some embodiments, the anti-GPC3 antibody moiety specifically recognizes an epitope within the C-terminal fragment of GPC3. In some embodiments, the anti-GPC3 antibody moiety specifically recognizes an epitope within amino acids 359-560 of SEQ ID NO: 460 (SEQ ID NO: 465). In some embodiments, the anti-GPC3 antibody moiety specifically recognizes an epitope within amino acids 359-580 of SEQ ID NO: 460 (SEQ ID NO: 466). In some embodiments, the anti-GPC3 antibody moiety specifically recognizes an epitope within GPC3 lacking heparin sulfate side chain. In some embodiments, the anti-GPC3 antibody moiety specifically recognizes an epitope within GPC3 carrying heparin sulfate side chain(s). In some embodiments, the anti-GPC3 antibody moiety specifically recognizes an epitope within the C-terminal fragment of GPC3 lacking heparin sulfate side chain. In some embodiments, the anti-GPC3 antibody moiety specifically recognizes an epitope within amino acids 510-560 of SEQ ID NO: 460 (SEQ ID NO: 467). In some embodiments, the anti- GPC3 antibody moiety specifically recognizes an epitope spanning the Furin cleavage site at amino acids $R^{358}/S^{359}$ of SEQ ID NO: 460. In some embodiments, the anti-GPC3 antibody moiety can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460) In some embodiments, the anti-GPC3 antibody moiety specifically recognizes an epitope within a recombinant human GPC3. In some embodiments, the anti-GPC3 antibody moiety specifically recognizes a cell surface-bound GPC3 at a high binding affinity and binds to a soluble GPC3 at a low binding affinity. In some embodiments, the cell surface-bound GPC3 comprises (and in some embodiments consists of or consists essentially of) the amino acid sequence of SEQ ID NO: 460 or SEQ ID NO: 462. In some embodiments, the soluble GPC3 is circulating GPC3 protein or free GPC3 peptides in the serum. In some embodiments, the soluble GPC3 is a GPC3 protein or peptide present in a solution. In some embodiments, the soluble GPC3 comprises (and in some embodiments consists of or consists essentially of) the amino acid sequence of SEQ ID NO: 461 or SEQ ID NO: 463. In some embodiments, the anti-GPC3 antibody moiety may cross-react with GPC3 from species other than human. In some embodiments, the anti-GPC3 antibody moiety may be completely specific for one or more human GPC3 proteins and may not exhibit species or other types of non-human cross-reactivity.

In some embodiments, the anti-GPC3 antibody moiety cross-reacts with at least one allelic variant of the GPC3 protein (or fragments thereof). In some embodiments, the allelic variant has up to about 30 (such as about any of 1, 2, 3, 4, 5, 6, 7, 8, 9, 10, 15, 20, 25, or 30) amino acid substitutions (such as a conservative substitution) when compared to the naturally occurring GPC3 (or fragments thereof). In some embodiments, the anti-GPC3 antibody moiety does not cross-react with any allelic variant of the GPC3 protein (or fragments thereof).

In some embodiments, the anti-GPC3 antibody moiety cross-reacts with at least one interspecies variant of the GPC3 protein. In some embodiments, for example, the GPC3 protein (or fragments thereof) is human GPC3 and the interspecies variant of the GPC3 protein (or fragments thereof) is a mouse or rat variant thereof. In some embodiments, the anti-GPC3 antibody moiety does not cross-react with any interspecies variant of the GPC3 protein.

In some embodiments, the anti-GPC3 antibody moiety specifically recognizes GPC3 expressed on the cell surface of HepG2, Hep3B, Huh7, JHH-7, or 293 cells. In some embodiments, the anti-GPC3 antibody moiety specifically recognizes GPC3 expressed on the cell surface of a cancer cell (such as solid tumor). In some embodiments, the anti-GPC3 antibody moiety specifically recognizes GPC3 expressed on the cell surface of liver cancer (such as HCC), melanoma, lung squamous cell carcinoma, ovarian carcinoma, yolk sac tumor, choriocarcinoma, neuroblastoma, Wilms' tumor, hepatoblastoma, testicular nonseminomatous germ cell tumor, gastric carcinoma, or liposarcoma.

Binding Affinity

Binding affinity can be indicated by $K_d$, $K_{off}$, $K_{on}$, or $K_a$. The term "$K_{off}$", as used herein, is intended to refer to the off-rate constant for dissociation of an antibody moiety from the antibody moiety/antigen complex, as determined from a kinetic selection set up. The term "$K_{on}$", as used herein, is intended to refer to the on-rate constant for association of an antibody moiety to the antigen to form the antibody moiety/antigen complex. The term equilibrium dissociation constant "$K_d$", as used herein, refers to the dissociation constant of a particular antibody moiety-antigen interaction, and describes the concentration of antigen required to occupy one half of all of the antibody-binding domains present in a solution of antibody molecules at equilibrium, and is equal to $K_{off}/K_{on}$. The measurement of $K_d$ presupposes that all binding agents are in solution. In the case where the antibody moiety is tethered to a cell wall, e.g., in a yeast expression system, the corresponding equilibrium rate constant is expressed as $EC_{50}$, which gives a good approximation of $K_d$. The affinity constant, $K_a$, is the inverse of the dissociation constant, $K_d$.

The dissociation constant ($K_d$) is used as an indicator showing affinity of antibody moieties to antigens. For example, easy analysis is possible by the Scatchard method using antibodies marked with a variety of marker agents, as well as by using BIACORE™ (made by Amersham Biosciences), analysis of biomolecular interactions by surface plasmon resonance, according to the user's manual and attached kit. The $K_d$ value that can be derived using these methods is expressed in units of M (Mols). An antibody moiety that specifically binds to a target may have a $K_d$ of, for example, $\leq 10^{-7}$ M, $\leq 10^{-8}$ M, $\leq 10^{-9}$ M, $\leq 10^{-10}$ M, $\leq 10^{-11}$ M, $\leq 10^{-12}$ M, or $\leq 10^{-13}$ M.

Binding specificity of the antibody moiety can be determined experimentally by methods known in the art. Such methods comprise, but are not limited to, Western blots, ELISA-, RIA-, ECL-, IRMA-, EIA-, BIACORE™-tests and peptide scans. In some embodiments, the binding affinity of the anti-GPC3 antibody moiety is measured by testing the binding affinity of the anti-GPC3 antibody moiety to cells expressing GPC3 on the surface (e.g., HepG2 cells).

In some embodiments, the anti-GPC3 antibody moiety specifically recognizes a cell surface-bound GPC3 (e.g., the binding affinity of the antibody moiety to the cell surface-bound GPC3 is higher than that to a soluble GPC3). In some embodiments, the anti-GPC3 antibody moiety specifically recognizes a cell surface-bound GPC3 at a high binding affinity and binds to a soluble GPC3 at a low binding affinity. In some embodiments, the anti-nGPC3 antibody moiety specifically binds to a cell surface-bound GPC3 in a competitive binding assay with soluble GPC3 antigen, using e.g., flow cytometry. In some embodiments, the anti-nGPC3 antibody moiety specifically binds to a cell surface-bound GPC3 when the anti-nGPC3 antibody moiety has been pre-incubated with soluble GPC3 antigen in a competitive binding assay. For example, in some embodiments, the anti-GPC3 construct comprising an anti-nGPC3 antibody moiety can be pre-incubated with various concentrations of soluble GPC3 antigen (e.g., a recombinant GPC3 fragment), then GPC3+ cells (e.g., HepG2 cells) can be added to the antibody/antigen mixture and incubated, cell surface-bound anti-GPC3 construct can then be detected: the binding of the soluble GPC3 pre-incubated anti-GPC3 construct to GPC3+ cells may not show significant differences when compared to that of anti-GPC3 construct to GPC3+ cells without soluble GPC3 pre-incubation, demonstrating that the anti-GPC3 antibody moiety can specifically recognize a cell surface-bound GPC3, or that the binding affinity of the anti-nGPC3 antibody moiety to the cell surface-bound GPC3 is higher than that to a soluble GPC3, or that the anti-GPC3 antibody moiety specifically recognizes a cell surface-bound GPC3 at a high binding affinity and binds to a soluble GPC3 at a low binding affinity.

In some embodiments, the anti-GPC3 antibody moiety specifically binds to a target GPC3 (e.g., nGPC3 and/or sGPC3) with a $K_d$ of about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). Thus in some embodiments, the $K_d$ of the binding between the anti-nGPC3 antibody moiety and nGPC3, the $K_d$ of the binding between the anti-sGPC3 antibody moiety and sGPC3, or the $K_d$ of the binding between the anti-GPC3 antibody moiety and GPC3 (any format), is about $10^{-7}$ M to about $10^{-13}$ M, about $1\times10^{-7}$ M to about $5\times10^{-13}$ M, about $10^{-7}$ M to about $10^{-12}$ M, about $10^{-7}$ M to about $10^{-11}$ M, about $10^{-7}$ M to about $10^{-10}$ M, about $10^{-7}$ M to about $10^{-9}$ M, about $10^{-8}$ M to about $10^{-13}$ M, about $1\times10^{-8}$ M to about $5\times10^{-13}$ M, about $10^{-8}$ M to about $10^{-12}$ M, about $10^{-8}$ M to about $10^{-11}$ M, about $10^{-8}$ M to about $10^{-10}$ M, about $10^{-8}$ M to about $10^{-9}$ M, about $5\times10^{-9}$ M to about $1\times10^{-13}$ M, about $5\times10^{-9}$ M to about $1\times10^{-12}$ M, about $5\times10^{-9}$ M to about $1\times10^{-11}$ M, about $5\times10^{-9}$ M to about $1\times10^{-10}$ M, about $10^{-9}$ M to about $10^{-13}$ M, about $10^{-9}$ M to about $10^{-12}$ M, about $10^{-9}$ M to about $10^{-11}$ M, about $10^{-9}$ M to about $10^{-10}$ M, about $5\times10^{-10}$ M to about $1\times10^{-13}$ M, about $5\times10^{-10}$ M to about $1\times10^{-12}$ M, about $5\times10^{-10}$ M to about $1\times10^{-11}$ M, about $10^{-10}$ M to about $10^{-13}$ M, about $1\times10^{-10}$ M to about $5\times10^{-13}$ M, about $1\times10^{-10}$ M to about $1\times10^{-12}$ M, about $1\times10^{-10}$ M to about $5\times10^{-12}$ M about $1\times10^{-10}$ M to about $1\times10^{-11}$ M, about $10^{-11}$ M to about $10^{-13}$ M, about $1\times10^{-11}$ M to about $5\times10^{-13}$ M, about $10^{-11}$ M to about $10^{-12}$ M, or about $10^{-12}$ M to about $10^{-13}$ M. In some embodiments, the $K_d$ of the binding between the anti-nGPC3 antibody moiety and nGPC3 is about $10^{-7}$ M to about $10^{-13}$ M.

In some embodiments, the $K_d$ of the binding between the anti-GPC3 antibody moiety and a non-target is more than the $K_d$ of the binding between the anti-GPC3 antibody moiety and the target, and is herein referred to in some embodiments as the binding affinity of the anti-GPC3 antibody moiety to the target (e.g., cell surface-bound GPC3) is higher than that to a non-target (e.g., soluble GPC3). In some embodiments, the non-target is an antigen that is not GPC3. In some embodiments, for an anti-nGPC3 antibody moiety, the non-target is a soluble GPC3. In some embodiments, for an anti-sGPC3 antibody moiety, the non-target is a cell surface-bound GPC3. For example, the $K_d$ of the binding between the anti-nGPC3 antibody moiety and a soluble GPC3 can be at least about 10 times, such as about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between the anti-nGPC3 antibody moiety and a cell surface-bound GPC3. Also for example, the $K_d$ of the binding between the anti-sGPC3 antibody moiety and a cell surface-bound GPC3 can be at least about 10 times, such as about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between the anti-sGPC3 antibody moiety and a soluble GPC3. In some embodiments, the $K_d$ of the binding between the anti-GPC3 antibody moiety (against nGPC3 and/or sGPC3) and a non-GPC3 target can be at least about 10 times, such as about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between the anti-GPC3 antibody moiety and a target GPC3. In some embodiments, the $K_d$ of the binding between the anti-nGPC3 antibody moiety and a soluble GPC3 is at least about 10 times of the $K_d$ of the binding between the anti-nGPC3 antibody moiety and a cell surface-bound GPC3.

In some embodiments, the anti-GPC3 antibody moiety binds to a non-target with a $K_d$ of about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the non-target is an antigen that is not GPC3. In some embodiments, for an anti-nGPC3 antibody moiety, the non-target is a soluble GPC3. In some embodiments, for an anti-sGPC3 antibody moiety, the non-target is a cell surface-bound GPC3. Thus in some embodiments, the $K_d$ of the binding between the anti-GPC3 antibody moiety and a non-GPC3 target, the $K_d$ of the binding between the anti-nGPC3 antibody moiety and a soluble GPC3, or $K_d$ of the binding between the anti-sGPC3 antibody moiety and a cell surface-bound GPC3, is about $10^{-1}$ M to about $10^{-6}$ M, about $1\times10^{-1}$ M to about $5\times10^{-6}$ M, about $10^{-1}$ M to about $10^{-5}$ M, about $1\times10^{-1}$ M to about $5\times10^{-5}$ M, about $10^{-1}$ M to about $10^{-4}$ M, about $1\times10^{-1}$ M to about $5\times10^{-4}$ M, about $10^{-1}$ M to about $10^{-3}$ M, about $1\times10^{-1}$ M to about $5\times10^{-3}$ M, about $10^{-1}$ M to about $10^{-2}$ M, about $10^{-2}$ M to about $10^{-6}$ M, about $1\times10^{-2}$ M to about $5\times10^{-6}$ M, about $10^{-2}$ M to about $10^{-5}$ M, about $1\times10^{-2}$ M to about $5\times10^{-5}$ M, about $10^{-2}$ M to about $10^{-4}$ M, about $1\times10^{-2}$ M to about $5\times10^{-4}$ M, about $10^{-2}$ M to about $10^{-3}$ M, about $10^{-3}$ M to about $10^{-6}$ M, about $1\times10^{-3}$ M to about $5\times10^{-6}$ M, about $10^{-3}$ M to about $10^{-5}$ M, about $1\times10^{-3}$ M to about $5\times10^{-5}$ M, about $10^{-3}$ M to about $10^{-4}$ M, about $10^{-4}$ M to about $10^{-6}$ M, about $1\times10^{-4}$ M to about $5\times10^{-6}$ M, about $10^{-4}$ M to about $10^{-5}$ M, or about $10^{-5}$ M to about $10^{-6}$ M. In some embodiments, the $K_d$ of the binding between the anti-nGPC3 antibody moiety and a soluble GPC3 is about $10^{-1}$ M to about $10^{-6}$ M. In some embodiments, the anti-nGPC3 antibody moiety specifically recognizing a cell surface-bound GPC3 does not bind to a soluble GPC3.

In some embodiments, when referring to that the anti-GPC3 antibody moiety specifically recognizes a target GPC3 (e.g., cell surface-bound GPC3) at a high binding affinity and binds to a non-target (e.g., soluble GPC3) at a low binding affinity, the anti-GPC3 antibody moiety will bind to the target GPC3 (e.g., cell surface-bound GPC3) with a $K_d$ of about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M), and will bind to the non-target (e.g., soluble GPC3) with a $K_d$ of about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M).

In some embodiments, when referring to that the anti-GPC3 antibody moiety specifically recognizes a cell surface-bound GPC3 (e.g., the binding affinity of the antibody moiety to the cell surface-bound GPC3 is higher than that to a soluble GPC3), or when referring to that the anti-GPC3 antibody moiety specifically recognizes a cell surface-bound GPC3 at a high binding affinity while binds to a soluble GPC3 at a low binding affinity, the binding affinity of the anti-GPC3 antibody moiety is compared to a control anti-GPC3 antibody, such as the monoclonal antibody GC33. In some embodiments, the $K_d$ of the binding between GC33 (e.g., SEQ ID NO: 510) and a cell surface-bound GPC3 can be at least about 2 times, such as about 2 times, about 3 times, about 4 times, about 5 times, about 6 times, about 7 times, about 8 times, about 9 times, about 10 times, about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between the anti-nGPC3 antibody moiety described herein and a cell surface-bound GPC3. In some embodiments, the $K_d$ of the anti-GPC3 construct to the cell surface-bound GPC3 is about 0.1 nM to about 2 nM, such as about 0.1 nM to about 0.5 nM, about 0.5 nM to about 1 nM, or about 1.5 to about 2 nM. In some embodiments, the $K_d$ of the binding between the anti-nGPC3 antibody moiety described herein and a soluble GPC3 can be at least about 2 times, such as about 2 times, about 3 times, about 4 times, about 5 times, about 6 times, about 7 times, about 8 times, about 9 times, about 10 times, about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between GC33 (e.g., SEQ ID NO: 510) and a soluble GPC3. In some embodiments, the $K_d$ of the anti-GPC3 construct to the cell surface-bound GPC3 is about 10 nM to about 100 nM, such as about 10 nM to about 20 nM, about 20 nM to about 40 nM, about 40 nM to about 80 nM or about 80 nM to about 100 nM. In some embodiments, the $K_d$ of the binding between a control anti-GPC3 antibody and a cell surface-bound GPC3 can be at least about 2 times, such as about 2 times, about 3 times, about 4 times, about 5 times, about 6 times, about 7 times, about 8 times, about 9 times, about 10 times, about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between the anti-nGPC3 antibody moiety described herein and a cell surface-bound GPC3, wherein the control antibody comprises: i) a $V_H$ comprising the amino acid sequence of SEQ ID NO: 503, or a variant thereof having at least about 95% sequence identify to SEQ ID NO: 503; and ii) a $V_L$ comprising the amino acid sequence of SEQ ID NO: 504, or a variant thereof having at least about 95% sequence identity to SEQ ID NO: 504. In some embodiments, the $K_d$ of the binding between the anti-nGPC3 antibody moiety described herein and a soluble GPC3 can be at least about 2 times, such as about 2 times, about 3 times, about 4 times, about 5 times, about 6 times, about 7 times, about 8 times, about 9 times, about 10 times, about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between a control anti-GPC3 antibody and a soluble GPC3, wherein the control antibody comprises: i) a $V_H$ comprising the amino acid sequence of SEQ ID NO: 503, or a variant thereof having at least about 95% sequence identify to SEQ ID NO: 503; and ii) a $V_L$ comprising the amino acid sequence of SEQ ID NO: 504, or a variant thereof having at least about 95% sequence identity to SEQ ID NO: 504. In some embodiments, the $K_d$ of the binding between a control anti-GPC3 antibody and a cell surface-bound GPC3 can be at least about 2 times, such as about 2 times, about 3 times, about 4 times, about 5 times, about 6 times, about 7 times, about 8 times, about 9 times, about 10 times, about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between the anti-nGPC3 antibody moiety described herein and a cell surface-bound GPC3, wherein the control antibody comprises: i) a $V_H$ comprising an HC-CDR1 comprising the amino acid sequence of SEQ ID NO: 497, an HC-CDR2 comprising the amino acid sequence of SEQ ID NO: 498, and an HC-CDR3 comprising the amino acid sequence of SEQ ID NO: 499; and ii) a $V_L$ comprising an LC-CDR1 comprising the amino acid sequence of SEQ ID NO: 500, an LC-CDR2 comprising the amino acid sequence of SEQ ID NO: 501, and an LC-CDR3 comprising the amino acid sequence of SEQ ID NO: 502. In some embodiments, the $K_d$ of the binding between the anti-nGPC3 antibody moiety described herein and a soluble GPC3 can be at least about 2 times, such as about 2 times, about 3 times, about 4 times, about 5 times, about 6 times, about 7 times, about 8 times, about 9 times, about 10 times, about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between a control anti-GPC3 antibody and a soluble GPC3, wherein the control antibody comprises: i) a $V_H$ comprising an HC-CDR1 comprising the amino acid sequence of SEQ ID NO: 497, an HC-CDR2 comprising the amino acid sequence of SEQ ID NO: 498, and an HC-CDR3 comprising the amino acid sequence of SEQ ID NO: 499; and ii) a $V_L$ comprising an LC-CDR1 comprising the amino acid sequence of SEQ ID NO: 500, an LC-CDR2 comprising the amino acid sequence of SEQ ID NO: 501, and an LC-CDR3 comprising the amino acid sequence of SEQ ID NO: 502.

In some embodiments, the IC50 of a soluble GPC3 to compete binding between the anti-GPC3 construct and a cell surface-bound GPC3 is about 1 μg/ml to about 100 μg/ml, such as about 1 μg/ml to about 5 μg/ml, 1 μg/ml to about 10 μg/ml, about 10 μg/ml to about 20 μg/ml, about 20 μg/ml to about 50 μg/ml, or 50 μg/ml to about 100 μg/ml. In some embodiments, the IC50 of a soluble GPC3 to compete binding between the anti-GPC3 construct and a cell surface-bound GPC3 is at least about any one of 2×, 3×, 4×, 5×, 10×, 20×, 50×, 100×, or more than the IC50 of a soluble GPC3 to compete binding between a control anti-GPC3 antibody (such as GC33) and the cell surface bound GPC3.

Anti-GPC3 Antibody Moiety Format

The anti-GPC3 antibody moiety (against e.g., nGPC3 and/or sGPC3) described herein can be of any antibody or antigen-binding fragment format.

In some embodiments, the anti-GPC3 antibody moiety (against e.g., nGPC3 and/or sGPC3) is a full-length antibody or immunoglobulin derivatives. In some embodiments, the anti-GPC3 antibody moiety is an antigen-binding fragment, for example an antigen-binding fragment selected from the group consisting of a Fab, a Fab', a F(ab')2, an Fv fragment, a disulfide stabilized Fv fragment (dsFv), or a single-chain Fv (scFv). In some embodiments, the anti-GPC3 antibody moiety is an scFv. In some embodiments, the anti-GPC3 antibody moiety is a Fab or Fab'. In some embodiments, the anti-GPC3 antibody moiety is chimeric, human, partially humanized, fully humanized, or semi-synthetic.

In some embodiments, the anti-GPC3 antibody moiety (against nGPC3 and/or sGPC3) is a semi-synthetic antibody moiety comprising fully human sequences and one or more synthetic regions. In some embodiments, the anti-GPC3 antibody moiety is a semi-synthetic antibody moiety comprising a fully human light chain variable domain and a semi-synthetic heavy chain variable domain comprising fully human FR1, HC-CDR1, FR2, HC-CDR2, FR3, and FR4 regions and a synthetic HC-CDR3. In some embodiments, the semi-synthetic heavy chain variable domain comprises a fully synthetic HC-CDR3 having a sequence from about 5 to about 25 (such as about any of 5, 6, 7, 8, 9, 10, 11, 12, 13, 14, 15, 16, 17, 18, 19, 20, 21, 22, 23, 24, or 25) amino acids in length. In some embodiments, the semi-synthetic heavy chain variable domain or the synthetic HC-CDR3 is obtained from a semi-synthetic library (such as a semi-synthetic human library) comprising fully synthetic HC-CDR3s having a sequence from about 5 to about 25 (such as about any of 5, 6, 7, 8, 9, 10, 11, 12, 13, 14, 15, 16, 17, 18, 19, 20, 21, 22, 23, 24, or 25) amino acids in length, wherein each amino acid in the sequence is randomly selected from the standard human amino acids, minus cysteine. In some embodiments, the synthetic HC-CDR3 is from about 5 to about 19 (such as about any of 5, 6, 7, 8, 9, 10, 11, 12, 13, 14, 15, 16, 17, 18 or 19) amino acids in length. In some embodiments, the anti-GPC3 antibody moiety is a semi-synthetic antibody moiety comprising human CDRs and non-human framework sequences. Non-human framework sequences include, in some embodiments, any sequence that can be used for generating synthetic heavy and/or light chain variable regions using one or more human CDR sequences as described herein, including, e.g., mammals, such as mouse, rat, rabbit, pig, bovine (e.g., cow, bull, buffalo), deer, sheep, goat, chicken, cat, dog, ferret, primate (e.g., marmoset, rhesus monkey), etc. In some embodiments, the anti-GPC3 antibody moiety is generated by grafting one or more human CDR sequences as described herein onto a non-human framework sequence (e.g., a mouse or chicken framework sequence).

Anti-GPC3 Antibody Moiety Sequences

The anti-GPC3 antibody moieties in some embodiments comprise specific sequences or certain variants of such sequences. In some embodiments, the amino acid substitutions in the variant sequences do not substantially reduce the ability of the anti-nGPC3 antibody moiety to specifically recognize a cell surface-bound GPC3, the ability of the anti-sGPC3 antibody moiety to specifically recognize soluble GPC3, or the ability of the anti-GPC3 antibody moiety to specifically recognize a target GPC3 (e.g., nGPC3 and/or sGPC3). For example, alterations that do not substantially reduce target GPC3 (e.g., nGPC3 and/or sGPC3) binding affinity may be made. Alterations that substantially improve target GPC3 binding affinity or affect some other property, such as specificity and/or cross-reactivity with related variants of the target GPC3, are also contemplated.

Exemplary antibody sequences are shown in Tables 6-9. The exemplary CDR sequences in Tables 6 and 8 are predicted using the IgBLAST algorithm. See, for example, Ye J. et al. Nucleic Acids Research, 41:W34-W40 (2013), the disclosure of which is incorporated herein by reference in its entirety. Those skilled in the art will recognize that many algorithms are known for prediction of CDR positions in antibody heavy chain and light chain variable regions, and antibody agents comprising CDRs from antibodies described herein, but based on prediction algorithms other than IgBLAST, are within the scope of this invention.

The exemplary antibody heavy chain and light chain variable region sequences in Tables 7 and 9 are delimited according to the INTERNATIONAL IMMUNOGENETICS INFORMATION SYSTEM® (IMGT). See, for example, Lefranc, M.-P. et al., Nucleic Acids Res., 43:D413-422 (2015), the disclosure of which is incorporated herein by reference in its entirety. Those skilled in the art will recognize that antibody agents comprising $V_H$ or $V_L$ sequences from antibodies described herein, but based on algorithms other than IMGT, are within the scope of this invention.

Anti-GPC3 Antibody Moiety Specifically Recognizing a Cell Surface-Bound GPC3

In some embodiments, the anti-GPC3 antibody moiety specifically recognizes a cell surface-bound GPC3 (anti-nGPC3 antibody moiety). In some embodiments, the binding affinity of the anti-nGPC3 antibody moiety to a cell surface-bound GPC3 is higher than that to a soluble GPC3. In some embodiments, the anti-GPC3 antibody moiety specifically recognizes a cell surface-bound GPC3 at a high binding affinity and binds to a soluble GPC3 at a low binding affinity.

In some embodiments, the anti-nGPC3 antibody moiety comprises i) a heavy chain variable domain ($V_H$) comprising an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a light chain variable domain ($V_L$) comprising an LC-CDR3 comprising the amino acid sequence of any one of SEQ ID NOs: 256-286, or a variant thereof comprising up to about 5 (such as about any of 1, 2, 3, 4, or 5) amino acid substitutions.

In some embodiments, the anti-nGPC3 antibody moiety comprises i) a $V_H$ comprising an HC-CDR3 comprising the amino acid sequence of any one of SEQ ID NOs: 103-133; and ii) a $V_L$ comprising an LC-CDR3 comprising the amino acid sequence of any one of SEQ ID NOs: 256-286.

In some embodiments, the anti-nGPC3 antibody moiety comprises i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions.

In some embodiments, the anti-nGPC3 antibody moiety comprises i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286.

In some embodiments, the anti-nGPC3 antibody moiety comprises i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286; or a variant thereof comprising up to about 5 (such as about any of 1, 2, 3, 4, or 5) amino acid substitutions in the LC-CDR sequences.

In some embodiments, the anti-nGPC3 antibody moiety comprises i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; or a variant thereof comprising up to about 5 (such as about any of 1, 2, 3, 4, or 5) amino acid substitutions, wherein the amino acid substitutions are in HC-CDR1 or HC-CDR2; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286; or a variant thereof comprising up to about 5 (such as about any of 1, 2, 3, 4, or 5) amino acid substitutions, wherein the amino acid substitutions are in LC-CDR1 or LC-CDR2.

In some embodiments, the anti-nGPC3 antibody moiety comprises i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286.

In some embodiments, the anti-nGPC3 antibody moiety comprises: a) $V_H$ comprising the amino acid sequence of any one of SEQ ID NOs: 1-31, the amino acid sequence of any one of SEQ ID NOs: 52-82, and the amino acid sequence of any one of SEQ ID NOs: 103-133; and ii) a $V_L$ comprising the amino acid sequence of any one of SEQ ID NOs: 154-184, the amino acid sequence of any one of SEQ ID NOs: 205-235, and the amino acid sequence of any one of SEQ ID NOs: 256-286.

In some embodiments, the anti-nGPC3 antibody moiety comprises: a) a $V_H$ comprising one, two or three CDRs of any one of SEQ ID NOs: 307-337, and b) a $V_L$ comprising one, two or three CDRs of any one of SEQ ID NOs: 358-388. In some embodiments, the anti-nGPC3 antibody moiety comprises: a) a $V_H$ comprising HC-CDR1, HC-CDR2 and HC-CDR3 of the heavy chain variable domain of any one of SEQ ID NOs: 307-337, and b) a VL comprising LC-CDR1, LC-CDR2 and LC-CDR3 of the light chain variable domain of CDRs of any one of SEQ ID NOs: 358-388.

In some embodiments, the anti-nGPC3 antibody moiety comprises: a) a $V_H$ comprising the amino acid sequence of any one of SEQ ID NOs: 307-337, or a variant thereof having at least about 80% (including for example at least about any of 80%, 85%, 90%, 95%, 96%, 97%, 98%, or 99%) sequence identity to any one of SEQ ID NOs: 307-337; and b) a $V_L$ comprising the amino acid sequence of any one of SEQ ID NOs: 358-388, or a variant thereof having at least about 80% (including for example at least about any of 80%, 85%, 90%, 95%, 96%, 97%, 98%, or 99%) sequence identity to any one of SEQ ID NOs: 358-388.

In some embodiments, the anti-nGPC3 antibody moiety comprises: a) a $V_H$ comprising the amino acid sequence of any one of SEQ ID NOs: 307-337; and b) a $V_L$ comprising the amino acid sequence of any one of SEQ ID NOs: 358-388.

In some embodiments, the anti-nGPC3 antibody moiety comprises the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388.

The heavy and light chain variable domains can be combined in various pair-wise combinations to generate a number of anti-nGPC3 antibody moieties. Exemplary anti-nGPC3 antibodies are provided in Tables 6 and 7.

TABLE 6 anti-GPC3 antibody moiety specifically recognizing cell surface-bound GPC3
CDR sequences

| Clone No. | SEQ ID NO: | HCDR1 | SEQ ID NO: | HCDR2 | SEQ ID NO: | HCDR3 | SEQ ID NO: | LCDR1 | SEQ ID NO: | LCDR2 | SEQ ID NO: | LCDR3 |
|---|---|---|---|---|---|---|---|---|---|---|---|---|
| GPC3A-034 | 1 | GGSFSGYY | 52 | INHSGST | 103 | ARGYGGRFDY | 154 | SSNIGSNN | 205 | SNH | 256 | AAWDDSLEGYL |
| GPC3A-035 | 2 | GYTFTGYY | 53 | INPNSGGT | 104 | ARSWTSGFDY | 155 | SSNIGSNY | 206 | KNF | 257 | AAWDDALSGYV |
| GPC3A-037 | 3 | GFTFSSYA | 54 | IYSGGSST | 105 | ARTSYLNHGDY | 156 | RSNIGSDY | 207 | GEN | 258 | GTWDYTLNGVV |
| GPC3A-038 | 4 | GYTFTSYY | 55 | INPSGGST | 106 | ARKVTGYDS | 157 | NIGSKS | 208 | YDS | 259 | QVWDSSSDHVV |
| GPC3A-039 | 5 | GFTFSSYA | 56 | IGTGGGT | 107 | ARYGRKSIDA | 158 | NIGSKS | 209 | YDS | 260 | QVWDSSSDHWV |
| GPC3A-040 | 6 | GYTFTGYY | 57 | INPNSGGT | 108 | ARRGYYGYDS | 159 | SSNIGSNY | 210 | SNN | 261 | AAWDDSLSGYV |
| GPC3A-041 | 7 | GYTFTGYY | 58 | INPNSGGT | 109 | ARSGKYYGDK | 160 | SSNIGSNY | 211 | KNF | 262 | AAWDDALSGYV |
| GPC3A-042 | 8 | GYSFTGYY | 59 | MNPRSGGT | 110 | ARSSYYWADS | 161 | SSDIGSNS | 212 | STQ | 263 | ATWDDSLNGYV |

TABLE 6-continued anti-GPC3 antibody moiety specifically recognizing cell surface-bound GPC3
CDR sequences

| Clone No. | SEQ ID NO: | HCDR1 | SEQ ID NO: | HCDR2 | SEQ ID NO: | HCDR3 | SEQ ID NO: | LCDR1 | SEQ ID NO: | LCDR2 | SEQ ID NO: | LCDR3 |
|---|---|---|---|---|---|---|---|---|---|---|---|---|
| GPC3A-043 | 9 | GYTFTDYY | 60 | VDPEDGET | 111 | ARELRDVAYYPWGVEDF | 162 | SSNIGTNY | 213 | RNN | 264 | AVWDDSLSGVV |
| GPC3A-044 | 10 | GGSFSGYY | 61 | INHSGST | 112 | ARYYVPYLSD | 163 | NIGYKG | 214 | DES | 265 | QVWDSSSDHVV |
| GPC3A-045 | 11 | GFTFSDYY | 62 | ISSSGSTI | 113 | ARASDLYGD | 164 | TSNIGTNT | 215 | SNN | 266 | AAWDDSLNGVV |
| GPC3A-046 | 12 | GYRFSNYG | 63 | ISGSNGNT | 114 | ARGNRRYYSPIIDP | 165 | SSNFGSNT | 216 | SNT | 267 | AAWDDSLTGVV |
| GPC3A-047 | 13 | GYTFTDYY | 64 | INPNSGGT | 115 | ARSDYGSLYBK | 166 | RSNIASND | 217 | KKN | 268 | AAWDENLSGYV |
| GPC3A-048 | 14 | GFTFSSYA | 65 | ISYDGSNK | 116 | ARSSFVATDY | 167 | NIGSKS | 218 | YDS | 269 | QVWDSSSERGV |
| GPC3A-049 | 15 | GYTFTGYY | 66 | INPNSGGT | 117 | ARHGGIGSMRSETQ | 168 | SSNIGSNY | 219 | RNN | 270 | AAWDDSLSG |
| GPC3A-050 | 16 | GYSFTGYY | 67 | MNPRSGGT | 118 | ARSGYRWLDV | 169 | SSNIGSNT | 220 | SNN | 271 | AAWDDSLNGPV |
| GPC3A-051 | 17 | GGAFSSYA | 68 | IIPIFGTA | 119 | ARMLYLSGRYYWDS | 170 | SSNIGAGYD | 221 | GNS | 272 | QSYDSSLSGYV |
| GPC3A-052 | 18 | GYTFTGYY | 69 | INPNSGGT | 120 | ARSHSSGYBK | 171 | SSNIGSNY | 222 | RNN | 273 | AAWDDSLSGYV |
| GPC3A-053 | 19 | GGSISSSSYY | 70 | IYYSGST | 121 | ARWWSGSYDT | 172 | SSNIGSNY | 223 | GNS | 274 | QSYDSSLSGSNV |
| GPC3A-054 | 20 | GYTFTSYG | 71 | ISAYNGNT | 122 | ARIPMYSGSSDY | 173 | SSNIGSNY | 224 | RNN | 275 | AAWDDSLSGYV |
| GPC3A-055 | 21 | GYTFTSYY | 72 | INPSGGST | 123 | ARWHGGPYDY | 174 | NIGSKS | 225 | YDS | 276 | QVWDSSSDHYV |
| GPC3A-056 | 22 | GYSFNDYY | 73 | INPNNGDT | 124 | ARFSTHNWWWPTYDY | 175 | QSISSY | 226 | AAS | 277 | QQSYSTPIT |
| GPC3A-057 | 23 | GFTFSSYA | 74 | ISGSGGST | 125 | ARYNYMSSGFYDR | 176 | NIGSKS | 227 | YDS | 278 | QVWDSSSDHVV |
| GPC3A-058 | 24 | GYTFASHG | 75 | ISPYTGNT | 126 | ARGKRTLASCFDY | 177 | NIGSKS | 228 | DDS | 279 | QVWDSSSDHV |
| GPC3A-059 | 25 | GYTFTRYG | 76 | ISAYSDKT | 127 | ARSRWSYMBV | 178 | NIGSKS | 229 | YDS | 280 | QVWDSSSDHV |
| GPC3A-060 | 26 | GYTFNSYA | 77 | ISAYNGNT | 128 | AREGYGSWAMBQ | 179 | NIGSES | 230 | DDD | 281 | QTWESSTAI |
| GPC3A-061 | 27 | GYTFTSYG | 78 | ISAYNGNT | 129 | ARKGSSQFBQ | 180 | NIGSKS | 231 | YDS | 282 | QVWDSSSDHYV |
| GPC3A-062 | 28 | GGTFSSYA | 79 | IIPKIGTA | 130 | ARMYMDMGWGWGYWDW | 181 | SSNIGAGYD | 232 | GNS | 283 | QSYDSSLSGSYV |
| GPC3A-063 | 29 | GYTFTSYY | 80 | INPSGGSA | 131 | ARDRLASDAFDI | 182 | WSNIGSYT | 233 | GNN | 284 | AAWDENLNGVV |
| GPC3A-064 | 30 | GYTFTIYG | 81 | ISPYNDNT | 132 | ARMGVGWGYAQDS | 183 | NIGSKS | 234 | DDT | 285 | QVWDRSSAHWV |
| GPC3A-067 | 31 | GGTFSSYA | 82 | IIPIFGIT | 133 | ARGAEMSDY | 184 | NIGSKS | 235 | YDS | 286 | QVWDSSSDHVV |

TABLE 7 anti-GPC3 antibody moiety specifically recognizing cell
surface-bound GPC3 $V_H/V_L$ sequences
(CDR sequences are underlined)

| Clone No. | SEQ ID NO: | $V_H$ | SEQ ID NO: | $V_L$ |
|---|---|---|---|---|
| GPC3A-034 | 307 | QVQLQQWGAGLLKPSETLSLTCAVY<u>GGSFSGYYW</u>SWIRQPPGKGLEWIGE<u>INHSGST</u>TNYNPSLKSRVTISVDTSKNQFSLELSSVTAADTAVYYC<u>ARGYGGRFDY</u>WGQGTLVTVSS | 358 | QPVLTQPPSASGTPGQRVTISCSGS<u>SSNIGSNNV</u>IVVYQQLPGAAPKWYS<u>NHRR</u>PSGVPDRFSGSRSGTSASLAISGLQSEDEADYYC<u>AAWDDSLDGYL</u>FGTGTKVTVLG |
| GPC3A-035 | 308 | QVQLVQSGAEVKKPGASVKVSCKASG<u>YTFTGYYMH</u>WVRQAPGQGLEWMGW<u>INPNSGGT</u>NYAQKFQGRVTMTRDTSISTAYMELSRLRSDDTAVYYC<u>ARSWTSGFDY</u>WGQGTLVTVSS | 359 | QAVLTQPPSASQTPGQMVTISCSG<u>TSSNIGSNY</u>VFVVYQQLPGTAPKLLIY<u>KNFQ</u>RPSGVPGRFSGSKSGTAASLAISGLRSEDEADYFC<u>AAWDDALSGYV</u>FGAGTKVTVLG |

TABLE 7-continued anti-GPC3 antibody moiety specifically recognizing cell
surface-bound GPC3 V$_H$/V$_L$ sequences
(CDR sequences are underlined)

| Clone No. | SEQ ID NO: | V$_H$ | SEQ ID NO: | V$_L$ |
|---|---|---|---|---|
| GPC3A-037 | 309 | QVQLVESGGGLVQPGGSLRLSCAASGFTFSSYAMSWVRQAPGKGLEWVSVIYSGGSSTYYADSVKGRFTISRDNSKNTLYLQMNSLRAEDTAVYYCARTSYLNHGDYWGQGTLVTVSS | 360 | QSVLTQPPSVSAAPGQRVTISCSGTRSNIGSDYVSVVYQHLPGTAPKLLVYGDNLRPSGIPDRFSASKSGTSATLGITGLQTGDEADYYCGTWDYTLNGVVFGGGTKLTVLG |
| GPC3A-038 | 310 | QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCARKVTGYDSWGQGTLVTVSS | 361 | QSVLTQPPSVSVAPGKTARITCGGNNIGSKSVHVVYQQKPGQAPVLVIYYDSDRPSGIPERFSGSNSGNTATLTISRVEAGDEADYYCQVWDSSSDHVVFGGGTKLTVLG |
| GPC3A-039 | 311 | QVQLVQSGGGLVHPGGSLRLSCAGSGFTFSSYAMHWVRQAPGKGLEWVSAIGTGGGTYYADSVKGRFTISRDNAKNSLYLQMNSLRAEDTAVYYCARYGRKSIDAWGQGTLVTVSS | 362 | SYVLTQPPSVSVAPGKTARITCGGNNIGSKSVHVVYQQKPGQAPVLVIYYDSDRPSGIPERFSGSNSGNTATLTISRVEAGDEADYYCQVWDSSSDHWVFGGGTKLTVLG |
| GPC3A-040 | 312 | QVQLVQSGAEVKKPGASVTVSCKASGYTFTGYYMHWVRQAPGQGLEWMGWINPNSGGTNYAQKFQGRVTMTRDTSISTAYMELSRLSDDTAVYYCARRGYYGYDSWGQGTLVTVSS | 363 | LPVLTQPPSASGTPGQRVTISCSGSSSNIGSNYVYVVYQQLPGTAPKWYSNNQRPSGVPDRFSGSKSGTSASLAISGLRSEDEADYYCAAWDDSLSGYVFGTGTKVTVLG |
| GPC3A-041 | 313 | EVQLVQSGAEVKKPGASVTVSCKASGYTFTGYYMHWVRQAPGQGLEWMGWINPNSGGTNYAQKFQGRVTMTRDTSISTAYMELSRLSDDTAMYYCARSGKYYGDKWGQGTLVTVSS | 364 | QAVLTQPPSASQTPGQMVTISCSGTSSNIGSNYVFVVYQQLPGTAPKLLIYKNFQRPSGVPGRFSGSKSGTAASLAISGLRSEDEADYFCAAWDDALSGYVFGAGTKVTVLG |
| GPC3A-042 | 314 | QVQLQQSGAEVKKPGASVTVSCKASGYSFTGYYVYWMRQAPGKGLEWMGWMNPRSGGTNYAQKFQGRVTMTRDTSISTAYMELSRLTSDDTAVYYCARSSYYWADSWGQGTLVTVSS | 365 | SYVLTQPPSASGTPGQRVTISCFGSSSDIGSNSVFVVYQQLPGAAPKLLIYSTQYRPSGVPDRFSGSKSGTSASLAISGLQSEDEAEYHCATWDDSLNGYVFGSGTKVTVLG |
| GPC3A-043 | 315 | EVQLVQSGAEVKKPGATVKVSCKVSGYTFTDYYMHWVQQAPGKGLEWMGLVDPEDGETIYAEKFQGRVTITADTSTDTAYMELSSLRSEDTAVYYCARELRDVAYYPWGVEDFWGQGTLVTVSS | 366 | QSVLTQPPSASGTPGQRVTISCSGSSSNIGTNYVYVVYQQLPGTAPKLIIYRNNQRPSGVPDRFSGSESGSASLAISGLRSEDEADYYCAVWDDSLSGVVFGGGTKLTVLG |
| GPC3A-044 | 316 | QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARYYVPYLSDWGQGTLVTVSS | 367 | SYVLTQPPSVSVAPGKTARITCGGDNIGYKGVHVVYQQKPGQAPVLVVYDDSDRPSGIPERFSGSNSGNTATLTISRVEAGDEADYYCQVWDSSSDHVVFGGGTKLTVLG |
| GPC3A-045 | 317 | QMQLVQSGGGLVKPGGSLRLSCAASGFTFSDYYMSWIRQAPGKGLEWVSYISSSGSTIYYADSVKGRFTISRDNAKNSLYLQMNSLRAEDTAVYYCARASDLYGDWGQGTLVTVSS | 368 | QSVLTQPPSVSGTPGQRVIISCPGSTSNIGTNTVWYQQFPGTAPKWYSNNQRPSGVPDRFSGSKSGTSASLAISGLQSEDEADYYCAAWDDSLNGVVFGGGTKLTVLG |
| GPC3A-046 | 318 | QVQLVQSGAEVKKPGASVTVSCKASGYRFSNYGVSWVRQAPGQGLEWMGWISGSNGNTNYAQKFLGRVTMTTDTSTTTAYMELSSLRSDDTAVYYCARGNRRYYSPIIDPWGQGTLVTVSS | 369 | QAVLTQPPSVSGTPGQRVTISCSGSSSNFGSNTVHWYQQVPGTAPKLLIFSNTQRPSEIPDRFSGSKSGTSASLAISGLQSEDEADYYCAAWDDSLTGVVFGGGTKLTVLG |
| GPC3A-047 | 319 | QVQLVQSGAEVKKPGASVKVSCKAPGYTFTGYYMHWVRQAPGQGLEWMGWINPNSGGTNYAQKFQGRVTMTRDTSISTAYMELSRLSDDTAVYYCARSDYGSLYDKWGQGTLVTVSS | 370 | LPVLTQPPSASGTPGQRVTISCSGSRSNIASNDVYWYQQLPGTAPKRLIYKKNQRPSGVPDRFSASKSGTSASLAISGLRSEDEADYYCAAWDDNLSGYVFGTGTKVTVLG |
| GPC3A-048 | 320 | EVQLVESGGGEVQPGRSLRLSCAASGFTFSSYAMHWVRQAPGKGLEWVAVISYDGSNKYYADSVKGRFTISRDNSKNTLYLQMNSLRAEDTAVYYCARSSFVATDYWGQGTLVTVSS | 371 | QPVLTQPPSVSVAPGKTARITCGGNNIGSKSVHVVYQQKPGQAPVLVIYYDSDRPSGIPERFSGSNSGNTATLTISRVEAGDEADYCQVWDSSSDRGVFGGGTKLTVLG |
| GPC3A-049 | 321 | QVQLVQSGAEVKEPGASVKVSCKASGYTFTGYYMHWVRQAPGQGLEWMGWINPNSGGTNYAQKFQGRVTMTRDTSISTAYMELSRLSDDTAVYYCARHGGIGSMRSFDQWGQGTLVTVSS | 372 | QAVLTQPSSASGTPGQRVTISCSGGSSNIGSNYVYVVYQQLPGTAPKLLIYRNNQRPSGVPDRFSGSKSGTSASLAISGLRSEDEADYYCAAWDDSLSGWVFGGRTKLTVLG |
| GPC3A-050 | 322 | QITLKESGAEVKKPGASVKVSCKASGYSFTGYYVYWMRQAPGKGLEWMGWMNPRSGGTNYAQKFQGRVTMTRDTSISTAYMELSRLSDDTATYYCARSGYRWLDVWGQGTLVTVSS | 373 | QAVLTQPSSASGTPGQRVTISCSGSSSNIGSNTVWYQQLPGTAPKLLIYSNNQRPSGVPDRFSGSKSGTSASLAISGLQSEDEADYYCAAWDDSLNGPVFGTGTKVTVLG |

TABLE 7-continued anti-GPC3 antibody moiety specifically recognizing cell
surface-bound GPC3 $V_H/V_L$ sequences
(CDR sequences are underlined)

| Clone No. | SEQ ID NO: | $V_H$ | SEQ ID NO: | $V_L$ |
|---|---|---|---|---|
| GPC3A-051 | 323 | QVQLVQSGAEVKKPGSSVKVSCKAS<u>GGAFSSY AISWVRQAPGQGLEWMGGIIPIFGTANYAQKFQ</u> GRVTITADESTSTAYMELSSLRSEDTAVYYC<u>AR MLYLSGRYYWDS</u>WGQGTLVTVSS | 374 | QAVLTQPSSASGAPGQRVTISCTGG<u>SSNIG AGYDVH</u>WYQQLPGTAPKLLIY<u>GNSNRPSGV</u> PDRFSGSKSGTSASLAITGLQAEDEADYYC <u>QSYDSSLSGYV</u>FGTGTKVTVLG |
| GPC3A-052 | 324 | EVQLVESGAEVKKPGASVKVSCKAS<u>GYTFTGYY MH</u>WVRQAPGQGLEWMG<u>WINPNSGGTNYAQKF</u> QGRVTMTRDTSISTAYMELSRLRSDDTAVYYCA <u>RSHSSGYDK</u>WGQGTLVTVSS | 375 | QAVLTQPSSASGTPGQRVTISCSGS<u>SSNIGS NYV</u>YVVYQQLSGTAPKLLIY<u>RNNQRPSGVPD</u> RFSGSKSGTSASLAISGLRSEDEADYYC<u>AA WDDSLSGYV</u>FGTGTKVTVLG |
| GPC3A-053 | 325 | QLQLQESGPGLVKPSETLSLTCTVS<u>GGSISSSSY YWGWIRQPPGKGLEWIGSIYYSGSTYYNPSLKS</u> RVTISVDTSKNQFSLKLSSVTAADTAVYYC<u>ARW WSGSYDT</u>WGQGTLVTVSS | 376 | QSVLTQPPSASAAPGQRVTISCSGT<u>SSNIGS NYV</u>YVVYQQLPGAAPRLLIY<u>GNSNRPSGV</u> DRFSGSKSGTSASLAITGLQAEDEADYYC<u>Q SYDSSLSGSNV</u>FGTGTKVTVLG |
| GPC3A-054 | 326 | QMQLVQSGAEVKKPGASVKVSCKAS<u>GYTFTSY GIS</u>WVRQAPGQGLEWMG<u>WISAYNGNTNYAQKL</u> QGRVTMTTDTSTSTAYMELRSLRSDDTAVYYC<u>A RIPMYSGSSDY</u>WGQGTLVTVSS | 377 | SYELTQPPSASGTPGQRVTISCSGS<u>SSNIGS NYV</u>YVVYQQLPGTAPKLLIY<u>RNNQRPSGVPD</u> RFSGSKSGTSASLAISGLRSEDEADYYC<u>AA WDDSLSGYV</u>FGTGTKVTVLG |
| GPC3A-055 | 327 | QVQLVQSGAEVKKPGASVKVSCKAS<u>GYTFTSY YMH</u>WVRQAPGQGLEWMG<u>IINPSGGSTSYAQKF</u> QGRVTMTRDTSTSTVYMELSSLRSEDTAVYYC<u>A RWHGGPYDY</u>WGQGTLVTVSS | 378 | QPVLTQPPSVSVAPGKTARITCGGN<u>NIGSKS VHV</u>VYQQKPGQAPVLVIY<u>YDSDRPSGIPERF</u> SGSNSGNTATLTISRVEAGDEADYYC<u>QVWD SSSDHV</u>FGTGTKVTVLG |
| GPC3A-056 | 328 | QVQLQQSGAEVKKPGASVKVSCKAS<u>GYSFNDY YIH</u>WVRQAPGQGLEWMG<u>WINPNNGDTKYEKK WQ</u>GRVTMTRDTSITTAYMELSSLRSDDTAVYYC <u>ARFSTHNWWWPTYDY</u>WGQGTLVTVSS | 379 | DIQLTQSPSSLSASVGDRVTITCRASQ<u>SISSY LN</u>VVYQQKPGKAPKLLIY<u>AASSLQSGVPSRF</u> SGSGSGTDFTLTISSLQPEDFATYYC<u>QQSYS TPIT</u>FGQGTRLEIKR |
| GPC3A-057 | 329 | EVQLVESGGGLIQPGGSLRLSCAAS<u>GFTFSSYA MS</u>WVRQAPGKGLEWVS<u>AISGSGGSTYYADSVK</u> GRFTISRDNSKNTLYLQMNSLRAEDTAVYYC<u>AR YNYMSSGFYDR</u>WGQGTLVTVSS | 380 | EIVLTQSPSVSVAPGKTARITCGGN<u>NIGSKS VHV</u>VYQQKPGQAPVLVIY<u>YDSDRPSGIPERF</u> SGSNSGNTATLTISRVEAGDEADYYC<u>QVWD SSSDHV</u>FGGGTKVEIKR |
| GPC3A-058 | 330 | QVQLVQSGADVRKPGASVKVSCKAS<u>GYTFASH GIS</u>WVRQAPGQGLEWLG<u>WISPYTGNTNYAQKF</u> QGRVTMATDTSTAYMELRSLRSDDTAIYYC<u>A RGKRTLASCFDY</u>WGQGTLVTVSS | 381 | QSVLTQPPSVSVAPGKTARITCGGN<u>NIGSKS VHV</u>VYQQKPGQAPVLVVY<u>DDSDRPSGIPER</u> FSGSNSGNTATLTISRVEAGDEADYYC<u>QVW DSSSDHV</u>FGTGTKVTVLG |
| GPC3A-059 | 331 | QVQLVQSGAEVKKPGASVTVSCKAS<u>GYTFTRY GIT</u>WVRQAPGQGLEWMG<u>WISAYSDKTNYAQKL</u> QGRVTMTTDISTNTAYMELSSLRSEDTAVYYC<u>A RSRWSYMDV</u>WGQGTLVTVSS | 382 | SYVLTQPPSVSVAPGKTARITCGGN<u>NIGSKS VYV</u>VYQQKPGQAPVLVIY<u>YDSDRPSGIPERF</u> SGSNSGNTATLTISRVEAGDEADYYC<u>QVWD SSSDHV</u>FGTGTKVTVLG |
| GPC3A-060 | 332 | QVQLVQSGGEVKKPGASVKVSCKAS<u>GYTFNSY AIS</u>WVRQAPGQGLEWMG<u>WISAYNGNTNYAQKL</u> QGRVTMTTDTSTNTAFMELRSLRSDDTAVYYC<u>A REGYGSWAMDQ</u>WGQGTLVTVSS | 383 | SYVLTQPPSVSVAPGKTARLTCGGN<u>NIGSE SVH</u>VVYQQKPGQAPLLVVY<u>DDDDRPSGIPE</u> RFSGSNSEDTATLTISGTQALDEAEYYC<u>QT WDSSTAI</u>FGTGTKLTVLG |
| GPC3A-061 | 333 | QVQLVQSGAEVKKPGASVKVSCKAS<u>GYTFTSY GIS</u>WVRQTPGQGLEWMG<u>WISAYNGNTNYAQKL</u> QGRVTMTTDTSTAYMELSSLRSEDTAVYYCA <u>RKGSSQFDQ</u>WGQGTLVTVSS | 384 | QPVLTQPPSVSVAPGKTARITCGGN<u>NIGSKS VHV</u>VYQQKPGQAPVLVIY<u>YDSDRPSGIPERF</u> SGSNSGNTATLTISRVEAGDEADYYC<u>QVWD SSSDHY</u>FGTGTKVTVLG |
| GPC3A-062 | 334 | QMQLVQSGSELKKPGASVKVSCKAS<u>GTFSSY AIS</u>WVRQAPGQGLEWMGG<u>IIPKIGTANYAQKFQ</u> GRVTITADESTSTAYMELSSLRSEDTAMYYC<u>AR MYMDMGWGWGYWDW</u>WGQGTLVTVSS | 385 | QSVLTQPPSVSGAPGQRVTISCTGS<u>SSNIGA GYDVH</u>WYQQLPGTAPKLLIY<u>GNSNWPSGV</u> PDRFSGSKSGTSASLAITGLRAEDEADYYC <u>QSYDSSLSGSYV</u>FGTGTKVTVLG |
| GPC3A-063 | 335 | QVQLVQSGAEVKKPGASVKVSCKAS<u>GYTFTSY YMH</u>WVRQAPGQGLEWMG<u>IINPSGGSASYAQKF</u> QGRVTMTRDTSTSTVYMELSSLRSEDTAVYYC<u>A RDRLASDAFDI</u>WGQGTMVTVSS | 386 | QTVVTQPPSASGTPGQRVTISCSGS<u>WSNIG SYT</u>VNWYQHLPGTAPKLLIS<u>GNNQRPSGVP</u> GRFSGSKSGTSASLAISGLQSEDEADYHCA AWDDNLNGVVFGGGTKLTVLG |
| GPC3A-064 | 336 | QMQLVQSGAEVKKPGASVKVSCKAS<u>GYTFTIYG IS</u>WVRQAPGQGLEWMG<u>WISPYNDNTIYAQKVQ</u> GRVTMTTDTSTSTAYMELRSLRSDDTAVYYC<u>AR MGVGWGYAQDS</u>WGQGTLVTVSS | 387 | LPVLTQPPSLSVAPGKTARLTCGGN<u>NIGSKS VHV</u>VYHQKPGQAPVLVVY<u>DDTDRPSGIPERF</u> SGSNSGNTAALTISRVEVGDEADYYC<u>QVWD RSSAHWV</u>FGGGTKLTVLG |

TABLE 7-continued anti-GPC3 antibody moiety specifically recognizing cell
surface-bound GPC3 $V_H/V_L$ sequences
(CDR sequences are underlined)

| Clone No. | SEQ ID NO: | $V_H$ | SEQ ID NO: | $V_L$ |
|---|---|---|---|---|
| GPC3A-067 | 337 | EVQLVQSGAEVKKPGSSVKVSCKASG<u>GTFSSY AI</u>SWVRQAPGQGLEWMGR<u>IIPIFGITNYAQKFQG</u> RVTITADKSTSTAYMELSSLRSEDTAVYYCA<u>RGA EMSDY</u>WGQGTLVTVSS | 388 | QSVLTQPPSVSVAPGKTARITCGG<u>NNIGSKS VH</u>VVYQQKPGQAPVLVIY<u>YDS</u>DRPSGIPERF SGSNSGNTATLTISRVEAGDEADYYC<u>QVWD SSSDHVV</u>FGGGTKLTVLG |

In some embodiments, the anti-nGPC3 antibody moiety comprises: i) a $V_H$ comprising an HC-CDR1 comprising the amino acid sequence of SEQ ID NO: 1, or a variant thereof comprising up to about 5 (such as about any of 1, 2, 3, 4, or 5) amino acid substitutions, an HC-CDR2 comprising the amino acid sequence of SEQ ID NO: 52, or a variant thereof comprising up to about 5 (such as about any of 1, 2, 3, 4, or 5) amino acid substitutions, and an HC-CDR3 comprising the amino acid sequence of SEQ ID NO: 103, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 154, or a variant thereof comprising up to about 5 (such as about any of 1, 2, 3, 4, or 5) amino acid substitutions, an LC-CDR2 comprising the amino acid sequence of SEQ ID NO: 205, or a variant thereof comprising up to about 3 (such as about any of 1, 2, or 3) amino acid substitutions, and an LC-CDR3 comprising the amino acid sequence of SEQ ID NO: 256, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 1, an HC-CDR2 comprising the amino acid sequence of SEQ ID NO: 52, and an HC-CDR3 comprising the amino acid sequence of SEQ ID NO: 103; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 154, an LC-CDR2 comprising the amino acid sequence of SEQ ID NO: 205, and an LC-CDR3 comprising the amino acid sequence of SEQ ID NO: 256; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 1, an HC-CDR2 comprising the amino acid sequence of SEQ ID NO: 52, and an HC-CDR3 comprising the amino acid sequence of SEQ ID NO: 103; and ii) a $V_L$ comprising an LC-CDR1 comprising the amino acid sequence of SEQ ID NO: 154, an LC-CDR2 comprising the amino acid sequence of SEQ ID NO: 205, and an LC-CDR3 comprising the amino acid sequence of SEQ ID NO: 256.

In some embodiments, the anti-nGPC3 antibody moiety comprises: i) a $V_H$ comprising an HC-CDR1 comprising the amino acid sequence of SEQ ID NO: 2, or a variant thereof comprising up to about 5 (such as about any of 1, 2, 3, 4, or 5) amino acid substitutions, an HC-CDR2 comprising the amino acid sequence of SEQ ID NO: 53, or a variant thereof comprising up to about 5 (such as about any of 1, 2, 3, 4, or 5) amino acid substitutions, and an HC-CDR3 comprising the amino acid sequence of SEQ ID NO: 104, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 155, or a variant thereof comprising up to about 5 (such as about any of 1, 2, 3, 4, or 5) amino acid substitutions, an LC-CDR2 comprising the amino acid sequence of SEQ ID NO: 206, or a variant thereof comprising up to about 3 (such as about any of 1, 2, or 3) amino acid substitutions, and an LC-CDR3 comprising the amino acid sequence of SEQ ID NO: 257, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 2, an HC-CDR2 comprising the amino acid sequence of SEQ ID NO: 53, and an HC-CDR3 comprising the amino acid sequence of SEQ ID NO: 104; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 155, an LC-CDR2 comprising the amino acid sequence of SEQ ID NO: 206, and an LC-CDR3 comprising the amino acid sequence of SEQ ID NO: 257; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 2, an HC-CDR2 comprising the amino acid sequence of SEQ ID NO: 53, and an HC-CDR3 comprising the amino acid sequence of SEQ ID NO: 104; and ii) a $V_L$ comprising an LC-CDR1 comprising the amino acid sequence of SEQ ID NO: 155, an LC-CDR2 comprising the amino acid sequence of SEQ ID NO: 206, and an LC-CDR3 comprising the amino acid sequence of SEQ ID NO: 257.

In some embodiments, the anti-nGPC3 antibody moiety comprises: i) a $V_H$ comprising an HC-CDR1 comprising the amino acid sequence of SEQ ID NO: 3, or a variant thereof comprising up to about 5 (such as about any of 1, 2, 3, 4, or 5) amino acid substitutions, an HC-CDR2 comprising the amino acid sequence of SEQ ID NO: 54, or a variant thereof comprising up to about 5 (such as about any of 1, 2, 3, 4, or 5) amino acid substitutions, and an HC-CDR3 comprising the amino acid sequence of SEQ ID NO: 105, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 156, or a variant thereof comprising up to about 5 (such as about any of 1, 2, 3, 4, or 5) amino acid substitutions, an LC-CDR2 comprising the amino acid sequence of SEQ ID NO: 207, or a variant thereof comprising up to about 3 (such as about any of 1, 2, or 3) amino acid substitutions, and an LC-CDR3 comprising the amino acid sequence of SEQ ID NO: 258, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 3, an HC-CDR2 comprising the amino acid sequence of SEQ ID NO: 54, and an HC-CDR3 comprising the amino acid sequence of SEQ ID NO: 105; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 156, an LC-CDR2 comprising the amino acid sequence of SEQ ID NO: 207, and an LC-CDR3 comprising the amino acid sequence of SEQ ID NO: 258; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 3, an HC-CDR2 comprising the amino acid sequence of SEQ ID NO: 54, and an HC-CDR3 comprising the amino acid sequence of SEQ ID NO: 105; and ii) a $V_L$ comprising an LC-CDR1 comprising the amino acid sequence of SEQ ID NO: 156, an LC-CDR2 comprising the amino acid sequence of SEQ ID NO: 207, and an LC-CDR3 comprising the amino acid sequence of SEQ ID NO: 258.

In some embodiments, the anti-nGPC3 antibody moiety comprises: i) a $V_H$ comprising an HC-CDR1 comprising the amino acid sequence of SEQ ID NO: 4, or a variant thereof comprising up to about 5 (such as about any of 1, 2, 3, 4, or 5) amino acid substitutions, an HC-CDR2 comprising the amino acid sequence of SEQ ID NO: 55, or a variant thereof comprising up to about 5 (such as about any of 1, 2, 3, 4, or 5) amino acid substitutions, and an HC-CDR3 comprising the amino acid sequence of SEQ ID NO: 106, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 157, or a variant thereof comprising up to about 5 (such as about any of 1, 2, 3, 4, or 5) amino acid substitutions, an LC-CDR2 comprising the amino acid sequence of SEQ ID NO: 208, or a variant thereof comprising up to about 3 (such as about any of 1, 2, or 3) amino acid substitutions, and an LC-CDR3 comprising the amino acid sequence of SEQ ID NO: 259, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 4, an HC-CDR2 comprising the amino acid sequence of SEQ ID NO: 55, and an HC-CDR3 comprising the amino acid sequence of SEQ ID NO: 106; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 157, an LC-CDR2 comprising the amino acid sequence of SEQ ID NO: 208, and an LC-CDR3 comprising the amino acid sequence of SEQ ID NO: 259; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 4, an HC-CDR2 comprising the amino acid sequence of SEQ ID NO: 55, and an HC-CDR3 comprising the amino acid sequence of SEQ ID NO: 106; and ii) a $V_L$ comprising an LC-CDR1 comprising the amino acid sequence of SEQ ID NO: 157, an LC-CDR2 comprising the amino acid sequence of SEQ ID NO: 208, and an LC-CDR3 comprising the amino acid sequence of SEQ ID NO: 259.

In some embodiments, the anti-nGPC3 antibody moiety comprises: i) a $V_H$ comprising an HC-CDR1 comprising the amino acid sequence of SEQ ID NO: 5, or a variant thereof comprising up to about 5 (such as about any of 1, 2, 3, 4, or 5) amino acid substitutions, an HC-CDR2 comprising the amino acid sequence of SEQ ID NO: 56, or a variant thereof comprising up to about 5 (such as about any of 1, 2, 3, 4, or 5) amino acid substitutions, and an HC-CDR3 comprising the amino acid sequence of SEQ ID NO: 107, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 158, or a variant thereof comprising up to about 5 (such as about any of 1, 2, 3, 4, or 5) amino acid substitutions, an LC-CDR2 comprising the amino acid sequence of SEQ ID NO: 209, or a variant thereof comprising up to about 3 (such as about any of 1, 2, or 3) amino acid substitutions, and an LC-CDR3 comprising the amino acid sequence of SEQ ID NO: 260, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 5, an HC-CDR2 comprising the amino acid sequence of SEQ ID NO: 56, and an HC-CDR3 comprising the amino acid sequence of SEQ ID NO: 107; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 158, an LC-CDR2 comprising the amino acid sequence of SEQ ID NO: 209, and an LC-CDR3 comprising the amino acid sequence of SEQ ID NO: 260; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 5, an HC-CDR2 comprising the amino acid sequence of SEQ ID NO: 56, and an HC-CDR3 comprising the amino acid sequence of SEQ ID NO: 107; and ii) a $V_L$ comprising an LC-CDR1 comprising the amino acid sequence of SEQ ID NO: 158, an LC-CDR2 comprising the amino acid sequence of SEQ ID NO: 209, and an LC-CDR3 comprising the amino acid sequence of SEQ ID NO: 260.

In some embodiments, the anti-nGPC3 antibody moiety comprises: i) a $V_H$ comprising an HC-CDR1 comprising the amino acid sequence of SEQ ID NO: 6, or a variant thereof comprising up to about 5 (such as about any of 1, 2, 3, 4, or 5) amino acid substitutions, an HC-CDR2 comprising the amino acid sequence of SEQ ID NO: 57, or a variant thereof comprising up to about 5 (such as about any of 1, 2, 3, 4, or 5) amino acid substitutions, and an HC-CDR3 comprising the amino acid sequence of SEQ ID NO: 108, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 159, or a variant thereof comprising up to about 5 (such as about any of 1, 2, 3, 4, or 5) amino acid substitutions, an LC-CDR2 comprising the amino acid sequence of SEQ ID NO: 210, or a variant thereof comprising up to about 3 (such as about any of 1, 2, or 3) amino acid substitutions, and an LC-CDR3 comprising the amino acid sequence of SEQ ID NO: 261, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 6, an HC-CDR2 comprising the amino acid sequence of SEQ ID NO: 57, and an HC-CDR3 comprising the amino acid sequence of SEQ ID NO: 108; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 159, an LC-CDR2 comprising the amino acid sequence of SEQ ID NO: 210, and an LC-CDR3 comprising the amino acid sequence of SEQ ID NO: 261; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 6, an HC-CDR2 comprising the amino acid sequence of SEQ ID NO: 57, and an HC-CDR3 comprising the amino acid sequence of SEQ ID NO: 108; and ii) a $V_L$ comprising an LC-CDR1 comprising the amino acid sequence of SEQ ID NO: 159, an LC-CDR2 comprising the amino acid sequence of SEQ ID NO: 210, and an LC-CDR3 comprising the amino acid sequence of SEQ ID NO: 261.

In some embodiments, the anti-nGPC3 antibody moiety comprises: i) a $V_H$ comprising an HC-CDR1 comprising the amino acid sequence of SEQ ID NO: 7, or a variant thereof comprising up to about 5 (such as about any of 1, 2, 3, 4, or 5) amino acid substitutions, an HC-CDR2 comprising the amino acid sequence of SEQ ID NO: 58, or a variant thereof comprising up to about 5 (such as about any of 1, 2, 3, 4, or 5) amino acid substitutions, and an HC-CDR3 comprising the amino acid sequence of SEQ ID NO: 109, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 160, or a variant thereof comprising up to about 5 (such as about any of 1, 2, 3, 4, or 5) amino acid substitutions, an LC-CDR2 comprising the amino acid sequence of SEQ ID NO: 211, or a variant thereof comprising up to about 3 (such as about any of 1, 2, or 3) amino acid substitutions, and an LC-CDR3 comprising the amino acid sequence of SEQ ID NO: 262, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 7, an HC-CDR2 comprising the amino acid sequence of SEQ ID NO: 58, and an HC-CDR3 comprising the amino acid sequence of SEQ ID NO: 109; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 160, an LC-CDR2 comprising the amino acid sequence of SEQ ID NO: 211, and an LC-CDR3 comprising the amino acid sequence of SEQ ID NO: 262; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 7, an HC-CDR2 comprising the amino acid sequence of SEQ ID NO: 58, and an HC-CDR3 comprising the amino acid sequence of SEQ ID NO: 109; and ii) a $V_L$ comprising an LC-CDR1 comprising the amino acid sequence of SEQ ID NO: 160, an LC-CDR2 comprising the amino acid sequence of SEQ ID NO: 211, and an LC-CDR3 comprising the amino acid sequence of SEQ ID NO: 262.

In some embodiments, the anti-nGPC3 antibody moiety comprises: i) a $V_H$ comprising an HC-CDR1 comprising the amino acid sequence of SEQ ID NO: 8, or a variant thereof comprising up to about 5 (such as about any of 1, 2, 3, 4, or 5) amino acid substitutions, an HC-CDR2 comprising the amino acid sequence of SEQ ID NO: 59, or a variant thereof comprising up to about 5 (such as about any of 1, 2, 3, 4, or 5) amino acid substitutions, and an HC-CDR3 comprising the amino acid sequence of SEQ ID NO: 110, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 161, or a variant thereof comprising up to about 5 (such as about any of 1, 2, 3, 4, or 5) amino acid substitutions, an LC-CDR2 comprising the amino acid sequence of SEQ ID NO: 212, or a variant thereof comprising up to about 3 (such as about any of 1, 2, or 3) amino acid substitutions, and an LC-CDR3 comprising the amino acid sequence of SEQ ID NO: 263, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 8, an HC-CDR2 comprising the amino acid sequence of SEQ ID NO: 59, and an HC-CDR3 comprising the amino acid sequence of SEQ ID NO: 110; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 161, an LC-CDR2 comprising the amino acid sequence of SEQ ID NO: 212, and an LC-CDR3 comprising the amino acid sequence of SEQ ID NO: 263; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 8, an HC-CDR2 comprising the amino acid sequence of SEQ ID NO: 59, and an HC-CDR3 comprising the amino acid sequence of SEQ ID NO: 110; and ii) a $V_L$ comprising an LC-CDR1 comprising the amino acid sequence of SEQ ID NO: 161, an LC-CDR2 comprising the amino acid sequence of SEQ ID NO: 212, and an LC-CDR3 comprising the amino acid sequence of SEQ ID NO: 263.

In some embodiments, the anti-nGPC3 antibody moiety comprises: i) a $V_H$ comprising an HC-CDR1 comprising the amino acid sequence of SEQ ID NO: 9, or a variant thereof comprising up to about 5 (such as about any of 1, 2, 3, 4, or 5) amino acid substitutions, an HC-CDR2 comprising the amino acid sequence of SEQ ID NO: 60, or a variant thereof comprising up to about 5 (such as about any of 1, 2, 3, 4, or 5) amino acid substitutions, and an HC-CDR3 comprising the amino acid sequence of SEQ ID NO: 111, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 162, or a variant thereof comprising up to about 5 (such as about any of 1, 2, 3, 4, or 5) amino acid substitutions, an LC-CDR2 comprising the amino acid sequence of SEQ ID NO: 213, or a variant thereof comprising up to about 3 (such as about any of 1, 2, or 3) amino acid substitutions, and an LC-CDR3 comprising the amino acid sequence of SEQ ID NO: 264, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 9, an HC-CDR2 comprising the amino acid sequence of SEQ ID NO: 60, and an HC-CDR3 comprising the amino acid sequence of SEQ ID NO: 111; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 162, an LC-CDR2 comprising the amino acid sequence of SEQ ID NO: 213, and an LC-CDR3 comprising the amino acid sequence of SEQ ID NO: 264; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 9, an HC-CDR2 comprising the amino acid sequence of SEQ ID NO: 60, and an HC-CDR3 comprising the amino acid sequence of SEQ ID NO: 111; and ii) a $V_L$ comprising an LC-CDR1 comprising the amino acid sequence of SEQ ID NO: 162, an LC-CDR2 comprising the amino acid sequence of SEQ ID NO: 213, and an LC-CDR3 comprising the amino acid sequence of SEQ ID NO: 264.

In some embodiments, the anti-nGPC3 antibody moiety comprises: i) a $V_H$ comprising an HC-CDR1 comprising the amino acid sequence of SEQ ID NO: 10, or a variant thereof comprising up to about 5 (such as about any of 1, 2, 3, 4, or 5) amino acid substitutions, an HC-CDR2 comprising the amino acid sequence of SEQ ID NO: 61, or a variant thereof comprising up to about 5 (such as about any of 1, 2, 3, 4, or 5) amino acid substitutions, and an HC-CDR3 comprising the amino acid sequence of SEQ ID NO: 112, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 163, or a variant thereof comprising up to about 5 (such as about any of 1, 2, 3, 4, or 5) amino acid substitutions, an LC-CDR2 comprising the amino acid sequence of SEQ ID NO: 214, or a variant thereof comprising up to about 3 (such as about any of 1, 2, or 3) amino acid substitutions, and an LC-CDR3 comprising the amino acid sequence of SEQ ID NO: 265, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 10, an HC-CDR2 comprising the amino acid sequence of SEQ ID NO: 61, and an HC-CDR3 comprising the amino acid sequence of SEQ ID NO: 112; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 163, an LC-CDR2 comprising the amino acid sequence of SEQ ID NO: 214, and an LC-CDR3 comprising the amino acid sequence of SEQ ID NO: 265; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 10, an HC-CDR2 comprising the amino acid sequence of SEQ ID NO: 61, and an HC-CDR3 comprising the amino acid sequence of SEQ ID NO: 112; and ii) a $V_L$ comprising an LC-CDR1 comprising the amino acid sequence of SEQ ID NO: 163, an LC-CDR2 comprising the amino acid sequence of SEQ ID NO: 214, and an LC-CDR3 comprising the amino acid sequence of SEQ ID NO: 265.

In some embodiments, the anti-nGPC3 antibody moiety comprises: i) a $V_H$ comprising an HC-CDR1 comprising the amino acid sequence of SEQ ID NO: 11, or a variant thereof comprising up to about 5 (such as about any of 1, 2, 3, 4, or 5) amino acid substitutions, an HC-CDR2 comprising the amino acid sequence of SEQ ID NO: 62, or a variant thereof comprising up to about 5 (such as about any of 1, 2, 3, 4, or 5) amino acid substitutions, and an HC-CDR3 comprising the amino acid sequence of SEQ ID NO: 113, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 164, or a variant thereof comprising up to about 5 (such as about any of 1, 2, 3, 4, or 5) amino acid substitutions, an LC-CDR2 comprising the amino acid sequence of SEQ ID NO: 215, or a variant thereof comprising up to about 3 (such as about any of 1, 2, or 3) amino acid substitutions, and an LC-CDR3 comprising the amino acid sequence of SEQ ID NO: 266, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 11, an HC-CDR2 comprising the amino acid sequence of SEQ ID NO: 62, and an HC-CDR3 comprising the amino acid sequence of SEQ ID NO: 113; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 164, an LC-CDR2 comprising the amino acid sequence of SEQ ID NO: 215, and an LC-CDR3 comprising the amino acid sequence of SEQ ID NO: 266; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 11, an HC-CDR2 comprising the amino acid sequence of SEQ ID NO: 62, and an HC-CDR3 comprising the amino acid sequence of SEQ ID NO: 113; and ii) a $V_L$ comprising an LC-CDR1 comprising the amino acid sequence of SEQ ID NO: 164, an LC-CDR2 comprising the amino acid sequence of SEQ ID NO: 215, and an LC-CDR3 comprising the amino acid sequence of SEQ ID NO: 266.

In some embodiments, the anti-nGPC3 antibody moiety comprises: i) a $V_H$ comprising an HC-CDR1 comprising the amino acid sequence of SEQ ID NO: 12, or a variant thereof comprising up to about 5 (such as about any of 1, 2, 3, 4, or 5) amino acid substitutions, an HC-CDR2 comprising the amino acid sequence of SEQ ID NO: 63, or a variant thereof comprising up to about 5 (such as about any of 1, 2, 3, 4, or 5) amino acid substitutions, and an HC-CDR3 comprising the amino acid sequence of SEQ ID NO: 114, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 165, or a variant thereof comprising up to about 5 (such as about any of 1, 2, 3, 4, or 5) amino acid substitutions, an LC-CDR2 comprising the amino acid sequence of SEQ ID NO: 216, or a variant thereof comprising up to about 3 (such as about any of 1, 2, or 3) amino acid substitutions, and an LC-CDR3 comprising the amino acid sequence of SEQ ID NO: 267, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 12, an HC-CDR2 comprising the amino acid sequence of SEQ ID NO: 63, and an HC-CDR3 comprising the amino acid sequence of SEQ ID NO: 114; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 165, an LC-CDR2 comprising the amino acid sequence of SEQ ID NO: 216, and an LC-CDR3 comprising the amino acid sequence of SEQ ID NO: 267; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 12, an HC-CDR2 comprising the amino acid sequence of SEQ ID NO: 63, and an HC-CDR3 comprising the amino acid sequence of SEQ ID NO: 114; and ii) a $V_L$ comprising an LC-CDR1 comprising the amino acid sequence of SEQ ID NO: 165, an LC-CDR2 comprising the amino acid sequence of SEQ ID NO: 216, and an LC-CDR3 comprising the amino acid sequence of SEQ ID NO: 267.

In some embodiments, the anti-nGPC3 antibody moiety comprises: i) a $V_H$ comprising an HC-CDR1 comprising the amino acid sequence of SEQ ID NO: 13, or a variant thereof comprising up to about 5 (such as about any of 1, 2, 3, 4, or 5) amino acid substitutions, an HC-CDR2 comprising the amino acid sequence of SEQ ID NO: 64, or a variant thereof comprising up to about 5 (such as about any of 1, 2, 3, 4, or 5) amino acid substitutions, and an HC-CDR3 comprising the amino acid sequence of SEQ ID NO: 115, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 166, or a variant thereof comprising up to about 5 (such as about any of 1, 2, 3, 4, or 5) amino acid substitutions, an LC-CDR2 comprising the amino acid sequence of SEQ ID NO: 217, or a variant thereof comprising up to about 3 (such as about any of 1, 2, or 3) amino acid substitutions, and an LC-CDR3 comprising the amino acid sequence of SEQ ID NO: 268, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 13, an HC-CDR2 comprising the amino acid sequence of SEQ ID NO: 64, and an HC-CDR3 comprising the amino acid sequence of SEQ ID NO: 115; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 166, an LC-CDR2 comprising the amino acid sequence of SEQ ID NO: 217, and an LC-CDR3 comprising the amino acid sequence of SEQ ID NO: 268; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 13, an HC-CDR2 comprising the amino acid sequence of SEQ ID NO: 64, and an HC-CDR3 comprising the amino acid sequence of SEQ ID NO: 115; and ii) a $V_L$ comprising an LC-CDR1 comprising the amino acid sequence of SEQ ID NO: 166, an LC-CDR2 comprising the amino acid sequence of SEQ ID NO: 217, and an LC-CDR3 comprising the amino acid sequence of SEQ ID NO: 268.

In some embodiments, the anti-nGPC3 antibody moiety comprises: i) a $V_H$ comprising an HC-CDR1 comprising the amino acid sequence of SEQ ID NO: 14, or a variant thereof comprising up to about 5 (such as about any of 1, 2, 3, 4, or 5) amino acid substitutions, an HC-CDR2 comprising the amino acid sequence of SEQ ID NO: 65, or a variant thereof comprising up to about 5 (such as about any of 1, 2, 3, 4, or 5) amino acid substitutions, and an HC-CDR3 comprising the amino acid sequence of SEQ ID NO: 116, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 167, or a variant thereof comprising up to about 5 (such as about any of 1, 2, 3, 4, or 5) amino acid substitutions, an LC-CDR2 comprising the amino acid sequence of SEQ ID NO: 218, or a variant thereof comprising up to about 3 (such as about any of 1, 2, or 3) amino acid substitutions, and an LC-CDR3 comprising the amino acid sequence of SEQ ID NO: 269, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 14, an HC-CDR2 comprising the amino acid sequence of SEQ ID NO: 65, and an HC-CDR3 comprising the amino acid sequence of SEQ ID NO: 116; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 167, an LC-CDR2 comprising the amino acid sequence of SEQ ID NO: 218, and an LC-CDR3 comprising the amino acid sequence of SEQ ID NO: 269; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 14, an HC-CDR2 comprising the amino acid sequence of SEQ ID NO: 65, and an HC-CDR3 comprising the amino acid sequence of SEQ ID NO: 116; and ii) a $V_L$ comprising an LC-CDR1 comprising the amino acid sequence of SEQ ID NO: 167, an LC-CDR2 comprising the amino acid sequence of SEQ ID NO: 218, and an LC-CDR3 comprising the amino acid sequence of SEQ ID NO: 269.

In some embodiments, the anti-nGPC3 antibody moiety comprises: i) a $V_H$ comprising an HC-CDR1 comprising the amino acid sequence of SEQ ID NO: 15, or a variant thereof comprising up to about 5 (such as about any of 1, 2, 3, 4, or 5) amino acid substitutions, an HC-CDR2 comprising the amino acid sequence of SEQ ID NO: 66, or a variant thereof comprising up to about 5 (such as about any of 1, 2, 3, 4, or 5) amino acid substitutions, and an HC-CDR3 comprising the amino acid sequence of SEQ ID NO: 117, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 168, or a variant thereof comprising up to about 5 (such as about any of 1, 2, 3, 4, or 5) amino acid substitutions, an LC-CDR2 comprising the amino acid sequence of SEQ ID NO: 219, or a variant thereof comprising up to about 3 (such as about any of 1, 2, or 3) amino acid substitutions, and an LC-CDR3 comprising the amino acid sequence of SEQ ID NO: 270, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 15, an HC-CDR2 comprising the amino acid sequence of SEQ ID NO: 66, and an HC-CDR3 comprising the amino acid sequence of SEQ ID NO: 117; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 168, an LC-CDR2 comprising the amino acid sequence of SEQ ID NO: 219, and an LC-CDR3 comprising the amino acid sequence of SEQ ID NO: 270; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 15, an HC-CDR2 comprising the amino acid sequence of SEQ ID NO: 66, and an HC-CDR3 comprising the amino acid sequence of SEQ ID NO: 117; and ii) a $V_L$ comprising an LC-CDR1 comprising the amino acid sequence of SEQ ID NO: 168, an LC-CDR2 comprising the amino acid sequence of SEQ ID NO: 219, and an LC-CDR3 comprising the amino acid sequence of SEQ ID NO: 270.

In some embodiments, the anti-nGPC3 antibody moiety comprises: i) a $V_H$ comprising an HC-CDR1 comprising the amino acid sequence of SEQ ID NO: 16, or a variant thereof comprising up to about 5 (such as about any of 1, 2, 3, 4, or 5) amino acid substitutions, an HC-CDR2 comprising the amino acid sequence of SEQ ID NO: 67, or a variant thereof comprising up to about 5 (such as about any of 1, 2, 3, 4, or 5) amino acid substitutions, and an HC-CDR3 comprising the amino acid sequence of SEQ ID NO: 118, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 169, or a variant thereof comprising up to about 5 (such as about any of 1, 2, 3, 4, or 5) amino acid substitutions, an LC-CDR2 comprising the amino acid sequence of SEQ ID NO: 220, or a variant thereof comprising up to about 3 (such as about any of 1, 2, or 3) amino acid substitutions, and an LC-CDR3 comprising the amino acid sequence of SEQ ID NO: 271, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 16, an HC-CDR2 comprising the amino acid sequence of SEQ ID NO: 67, and an HC-CDR3 comprising the amino acid sequence of SEQ ID NO: 118; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 169, an LC-CDR2 comprising the amino acid sequence of SEQ ID NO: 220, and an LC-CDR3 comprising the amino acid sequence of SEQ ID NO: 271; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 16, an HC-CDR2 comprising the amino acid sequence of SEQ ID NO: 67, and an HC-CDR3 comprising the amino acid sequence of SEQ ID NO: 118; and ii) a $V_L$ comprising an LC-CDR1 comprising the amino acid sequence of SEQ ID NO: 169, an LC-CDR2 comprising the amino acid sequence of SEQ ID NO: 220, and an LC-CDR3 comprising the amino acid sequence of SEQ ID NO: 271.

In some embodiments, the anti-nGPC3 antibody moiety comprises: i) a $V_H$ comprising an HC-CDR1 comprising the amino acid sequence of SEQ ID NO: 17, or a variant thereof comprising up to about 5 (such as about any of 1, 2, 3, 4, or 5) amino acid substitutions, an HC-CDR2 comprising the amino acid sequence of SEQ ID NO: 68, or a variant thereof comprising up to about 5 (such as about any of 1, 2, 3, 4, or 5) amino acid substitutions, and an HC-CDR3 comprising the amino acid sequence of SEQ ID NO: 119, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 170, or a variant thereof comprising up to about 5 (such as about any of 1, 2, 3, 4, or 5) amino acid substitutions, an LC-CDR2 comprising the amino acid sequence of SEQ ID NO: 221, or a variant thereof comprising up to about 3 (such as about any of 1, 2, or 3) amino acid substitutions, and an LC-CDR3 comprising the amino acid sequence of SEQ ID NO: 272, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC- CDR1 comprising the amino acid sequence of SEQ ID NO: 17, an HC-CDR2 comprising the amino acid sequence of SEQ ID NO: 68, and an HC-CDR3 comprising the amino acid sequence of SEQ ID NO: 119; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 170, an LC-CDR2 comprising the amino acid sequence of SEQ ID NO: 221, and an LC-CDR3 comprising the amino acid sequence of SEQ ID NO: 272; or a variant thereof comprising up to about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 17, an HC-CDR2 comprising the amino acid sequence of SEQ ID NO: 68, and an HC-CDR3 comprising the amino acid sequence of SEQ ID NO: 119; and ii) a $V_L$ comprising an LC-CDR1 comprising the amino acid sequence of SEQ ID NO: 170, an LC-CDR2 comprising the amino acid sequence of SEQ ID NO: 221, and an LC-CDR3 comprising the amino acid sequence of SEQ ID NO: 272.

In some embodiments, the anti-nGPC3 antibody moiety comprises: i) a $V_H$ comprising an HC-CDR1 comprising the amino acid sequence of SEQ ID NO: 18, or a variant thereof comprising up to about 5 (such as about any of 1, 2, 3, 4, or 5) amino acid substitutions, an HC-CDR2 comprising the amino acid sequence of SEQ ID NO: 69, or a variant thereof comprising up to about 5 (such as about any of 1, 2, 3, 4, or 5) amino acid substitutions, and an HC-CDR3 comprising the amino acid sequence of SEQ ID NO: 120, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 171, or a variant thereof comprising up to about 5 (such as about any of 1, 2, 3, 4, or 5) amino acid substitutions, an LC-CDR2 comprising the amino acid sequence of SEQ ID NO: 222, or a variant thereof comprising up to about 3 (such as about any of 1, 2, or 3) amino acid substitutions, and an LC-CDR3 comprising the amino acid sequence of SEQ ID NO: 273, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 18, an HC-CDR2 comprising the amino acid sequence of SEQ ID NO: 69, and an HC-CDR3 comprising the amino acid sequence of SEQ ID NO: 120; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 171, an LC-CDR2 comprising the amino acid sequence of SEQ ID NO: 222, and an LC-CDR3 comprising the amino acid sequence of SEQ ID NO: 273; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 18, an HC-CDR2 comprising the amino acid sequence of SEQ ID NO: 69, and an HC-CDR3 comprising the amino acid sequence of SEQ ID NO: 120; and ii) a $V_L$ comprising an LC-CDR1 comprising the amino acid sequence of SEQ ID NO: 171, an LC-CDR2 comprising the amino acid sequence of SEQ ID NO: 222, and an LC-CDR3 comprising the amino acid sequence of SEQ ID NO: 273.

In some embodiments, the anti-nGPC3 antibody moiety comprises: i) a $V_H$ comprising an HC-CDR1 comprising the amino acid sequence of SEQ ID NO: 19, or a variant thereof comprising up to about 5 (such as about any of 1, 2, 3, 4, or 5) amino acid substitutions, an HC-CDR2 comprising the amino acid sequence of SEQ ID NO: 70, or a variant thereof comprising up to about 5 (such as about any of 1, 2, 3, 4, or 5) amino acid substitutions, and an HC-CDR3 comprising the amino acid sequence of SEQ ID NO: 121, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 172, or a variant thereof comprising up to about 5 (such as about any of 1, 2, 3, 4, or 5) amino acid substitutions, an LC-CDR2 comprising the amino acid sequence of SEQ ID NO: 223, or a variant thereof comprising up to about 3 (such as about any of 1, 2, or 3) amino acid substitutions, and an LC-CDR3 comprising the amino acid sequence of SEQ ID NO: 274, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 19, an HC-CDR2 comprising the amino acid sequence of SEQ ID NO: 70, and an HC-CDR3 comprising the amino acid sequence of SEQ ID NO: 121; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 172, an LC-CDR2 comprising the amino acid sequence of SEQ ID NO: 223, and an LC-CDR3 comprising the amino acid sequence of SEQ ID NO: 274; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 19, an HC-CDR2 comprising the amino acid sequence of SEQ ID NO: 70, and an HC-CDR3 comprising the amino acid sequence of SEQ ID NO: 121; and ii) a $V_L$ comprising an LC-CDR1 comprising the amino acid sequence of SEQ ID NO: 172, an LC-CDR2 comprising the amino acid sequence of SEQ ID NO: 223, and an LC-CDR3 comprising the amino acid sequence of SEQ ID NO: 274.

In some embodiments, the anti-nGPC3 antibody moiety comprises: i) a $V_H$ comprising an HC-CDR1 comprising the amino acid sequence of SEQ ID NO: 20, or a variant thereof comprising up to about 5 (such as about any of 1, 2, 3, 4, or 5) amino acid substitutions, an HC-CDR2 comprising the amino acid sequence of SEQ ID NO: 71, or a variant thereof comprising up to about 5 (such as about any of 1, 2, 3, 4, or 5) amino acid substitutions, and an HC-CDR3 comprising the amino acid sequence of SEQ ID NO: 122, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 173, or a variant thereof comprising up to about 5 (such as about any of 1, 2, 3, 4, or 5) amino acid substitutions, an LC-CDR2 comprising the amino acid sequence of SEQ ID NO: 224, or a variant thereof comprising up to about 3 (such as about any of 1, 2, or 3) amino acid substitutions, and an LC-CDR3 comprising the amino acid sequence of SEQ ID NO: 275, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 20, an HC-CDR2 comprising the amino acid sequence of SEQ ID NO: 71, and an HC-CDR3 comprising the amino acid sequence of SEQ ID NO: 122; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 173, an LC-CDR2 comprising the amino acid sequence of SEQ ID NO: 224, and an LC-CDR3 comprising the amino acid sequence of SEQ ID NO: 275; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 20, an HC-CDR2 comprising the amino acid sequence of SEQ ID NO: 71, and an HC-CDR3 comprising the amino acid sequence of SEQ ID NO: 122; and ii) a $V_L$ comprising an LC-CDR1 comprising the amino acid sequence of SEQ ID NO: 173, an LC-CDR2 comprising the amino acid sequence of SEQ ID NO: 224, and an LC-CDR3 comprising the amino acid sequence of SEQ ID NO: 275.

In some embodiments, the anti-nGPC3 antibody moiety comprises: i) a $V_H$ comprising an HC-CDR1 comprising the amino acid sequence of SEQ ID NO: 21, or a variant thereof comprising up to about 5 (such as about any of 1, 2, 3, 4, or 5) amino acid substitutions, an HC-CDR2 comprising the amino acid sequence of SEQ ID NO: 72, or a variant thereof comprising up to about 5 (such as about any of 1, 2, 3, 4, or 5) amino acid substitutions, and an HC-CDR3 comprising the amino acid sequence of SEQ ID NO: 123, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 174, or a variant thereof comprising up to about 5 (such as about any of 1, 2, 3, 4, or 5) amino acid substitutions, an LC-CDR2 comprising the amino acid sequence of SEQ ID NO: 225, or a variant thereof comprising up to about 3 (such as about any of 1, 2, or 3) amino acid substitutions, and an LC-CDR3 comprising the amino acid sequence of SEQ ID NO: 276, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 21, an HC-CDR2 comprising the amino acid sequence of SEQ ID NO: 72, and an HC-CDR3 comprising the amino acid sequence of SEQ ID NO: 123; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 174, an LC-CDR2 comprising the amino acid sequence of SEQ ID NO: 225, and an LC-CDR3 comprising the amino acid sequence of SEQ ID NO: 276; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 21, an HC-CDR2 comprising the amino acid sequence of SEQ ID NO: 72, and an HC-CDR3 comprising the amino acid sequence of SEQ ID NO: 123; and ii) a $V_L$ comprising an LC-CDR1 comprising the amino acid sequence of SEQ ID NO: 174, an LC-CDR2 comprising the amino acid sequence of SEQ ID NO: 225, and an LC-CDR3 comprising the amino acid sequence of SEQ ID NO: 276.

In some embodiments, the anti-nGPC3 antibody moiety comprises: i) a $V_H$ comprising an HC-CDR1 comprising the amino acid sequence of SEQ ID NO: 22, or a variant thereof comprising up to about 5 (such as about any of 1, 2, 3, 4, or 5) amino acid substitutions, an HC-CDR2 comprising the amino acid sequence of SEQ ID NO: 73, or a variant thereof comprising up to about 5 (such as about any of 1, 2, 3, 4, or 5) amino acid substitutions, and an HC-CDR3 comprising the amino acid sequence of SEQ ID NO: 124, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 175, or a variant thereof comprising up to about 5 (such as about any of 1, 2, 3, 4, or 5) amino acid substitutions, an LC-CDR2 comprising the amino acid sequence of SEQ ID NO: 226, or a variant thereof comprising up to about 3 (such as about any of 1, 2, or 3) amino acid substitutions, and an LC-CDR3 comprising the amino acid sequence of SEQ ID NO: 277, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 22, an HC-CDR2 comprising the amino acid sequence of SEQ ID NO: 73, and an HC-CDR3 comprising the amino acid sequence of SEQ ID NO: 124; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 175, an LC-CDR2 comprising the amino acid sequence of SEQ ID NO: 226, and an LC-CDR3 comprising the amino acid sequence of SEQ ID NO: 277; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 22, an HC-CDR2 comprising the amino acid sequence of SEQ ID NO: 73, and an HC-CDR3 comprising the amino acid sequence of SEQ ID NO: 124; and ii) a $V_L$ comprising an LC-CDR1 comprising the amino acid sequence of SEQ ID NO: 175, an LC-CDR2 comprising the amino acid sequence of SEQ ID NO: 226, and an LC-CDR3 comprising the amino acid sequence of SEQ ID NO: 277.

In some embodiments, the anti-nGPC3 antibody moiety comprises: i) a $V_H$ comprising an HC-CDR1 comprising the amino acid sequence of SEQ ID NO: 23, or a variant thereof comprising up to about 5 (such as about any of 1, 2, 3, 4, or 5) amino acid substitutions, an HC-CDR2 comprising the amino acid sequence of SEQ ID NO: 74, or a variant thereof comprising up to about 5 (such as about any of 1, 2, 3, 4, or 5) amino acid substitutions, and an HC-CDR3 comprising the amino acid sequence of SEQ ID NO: 125, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 176, or a variant thereof comprising up to about 5 (such as about any of 1, 2, 3, 4, or 5) amino acid substitutions, an LC-CDR2 comprising the amino acid sequence of SEQ ID NO: 227, or a variant thereof comprising up to about 3 (such as about any of 1, 2, or 3) amino acid substitutions, and an LC-CDR3 comprising the amino acid sequence of SEQ ID NO: 278, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 23, an HC-CDR2 comprising the amino acid sequence of SEQ ID NO: 74, and an HC-CDR3 comprising the amino acid sequence of SEQ ID NO: 125; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 176, an LC-CDR2 comprising the amino acid sequence of SEQ ID NO: 227, and an LC-CDR3 comprising the amino acid sequence of SEQ ID NO: 278; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 23, an HC-CDR2 comprising the amino acid sequence of SEQ ID NO: 74, and an HC-CDR3 comprising the amino acid sequence of SEQ ID NO: 125; and ii) a $V_L$ comprising an LC-CDR1 comprising the amino acid sequence of SEQ ID NO: 176, an LC-CDR2 comprising the amino acid sequence of SEQ ID NO: 227, and an LC-CDR3 comprising the amino acid sequence of SEQ ID NO: 278.

In some embodiments, the anti-nGPC3 antibody moiety comprises: i) a $V_H$ comprising an HC-CDR1 comprising the amino acid sequence of SEQ ID NO: 24, or a variant thereof comprising up to about 5 (such as about any of 1, 2, 3, 4, or 5) amino acid substitutions, an HC-CDR2 comprising the amino acid sequence of SEQ ID NO: 75, or a variant thereof comprising up to about 5 (such as about any of 1, 2, 3, 4, or 5) amino acid substitutions, and an HC-CDR3 comprising the amino acid sequence of SEQ ID NO: 126, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 177, or a variant thereof comprising up to about 5 (such as about any of 1, 2, 3, 4, or 5) amino acid substitutions, an LC-CDR2 comprising the amino acid sequence of SEQ ID NO: 228, or a variant thereof comprising up to about 3 (such as about any of 1, 2, or 3) amino acid substitutions, and an LC-CDR3 comprising the amino acid sequence of SEQ ID NO: 279, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 24, an HC-CDR2 comprising the amino acid sequence of SEQ ID NO: 75, and an HC-CDR3 comprising the amino acid sequence of SEQ ID NO: 126; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 177, an LC-CDR2 comprising the amino acid sequence of SEQ ID NO: 228, and an LC-CDR3 comprising the amino acid sequence of SEQ ID NO: 279; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 24, an HC-CDR2 comprising the amino acid sequence of SEQ ID NO: 75, and an HC-CDR3 comprising the amino acid sequence of SEQ ID NO: 126; and ii) a $V_L$ comprising an LC-CDR1 comprising the amino acid sequence of SEQ ID NO: 177, an LC-CDR2 comprising the amino acid sequence of SEQ ID NO: 228, and an LC-CDR3 comprising the amino acid sequence of SEQ ID NO: 279.

In some embodiments, the anti-nGPC3 antibody moiety comprises: i) a $V_H$ comprising an HC-CDR1 comprising the amino acid sequence of SEQ ID NO: 25, or a variant thereof comprising up to about 5 (such as about any of 1, 2, 3, 4, or 5) amino acid substitutions, an HC-CDR2 comprising the amino acid sequence of SEQ ID NO: 76, or a variant thereof comprising up to about 5 (such as about any of 1, 2, 3, 4, or 5) amino acid substitutions, and an HC-CDR3 comprising the amino acid sequence of SEQ ID NO: 127, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 178, or a variant thereof comprising up to about 5 (such as about any of 1, 2, 3, 4, or 5) amino acid substitutions, an LC-CDR2 comprising the amino acid sequence of SEQ ID NO: 229, or a variant thereof comprising up to about 3 (such as about any of 1, 2, or 3) amino acid substitutions, and an LC-CDR3 comprising the amino acid sequence of SEQ ID NO: 280, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 25, an HC-CDR2 comprising the amino acid sequence of SEQ ID NO: 76, and an HC-CDR3 comprising the amino acid sequence of SEQ ID NO: 127; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 178, an LC-CDR2 comprising the amino acid sequence of SEQ ID NO: 229, and an LC-CDR3 comprising the amino acid sequence of SEQ ID NO: 280; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 25, an HC-CDR2 comprising the amino acid sequence of SEQ ID NO: 76, and an HC-CDR3 comprising the amino acid sequence of SEQ ID NO: 127; and ii) a $V_L$ comprising an LC-CDR1 comprising the amino acid sequence of SEQ ID NO: 178, an LC-CDR2 comprising the amino acid sequence of SEQ ID NO: 229, and an LC-CDR3 comprising the amino acid sequence of SEQ ID NO: 280.

In some embodiments, the anti-nGPC3 antibody moiety comprises: i) a $V_H$ comprising an HC-CDR1 comprising the amino acid sequence of SEQ ID NO: 26, or a variant thereof comprising up to about 5 (such as about any of 1, 2, 3, 4, or 5) amino acid substitutions, an HC-CDR2 comprising the amino acid sequence of SEQ ID NO: 77, or a variant thereof comprising up to about 5 (such as about any of 1, 2, 3, 4, or 5) amino acid substitutions, and an HC-CDR3 comprising the amino acid sequence of SEQ ID NO: 128, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 179, or a variant thereof comprising up to about 5 (such as about any of 1, 2, 3, 4, or 5) amino acid substitutions, an LC-CDR2 comprising the amino acid sequence of SEQ ID NO: 230, or a variant thereof comprising up to about 3 (such as about any of 1, 2, or 3) amino acid substitutions, and an LC-CDR3 comprising the amino acid sequence of SEQ ID NO: 281, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 26, an HC-CDR2 comprising the amino acid sequence of SEQ ID NO: 77, and an HC-CDR3 comprising the amino acid sequence of SEQ ID NO: 128; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 179, an LC-CDR2 comprising the amino acid sequence of SEQ ID NO: 230, and an LC-CDR3 comprising the amino acid sequence of SEQ ID NO: 281; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 26, an HC-CDR2 comprising the amino acid sequence of SEQ ID NO: 77, and an HC-CDR3 comprising the amino acid sequence of SEQ ID NO: 128; and ii) a $V_L$ comprising an LC-CDR1 comprising the amino acid sequence of SEQ ID NO: 179, an LC-CDR2 comprising the amino acid sequence of SEQ ID NO: 230, and an LC-CDR3 comprising the amino acid sequence of SEQ ID NO: 281.

In some embodiments, the anti-nGPC3 antibody moiety comprises: i) a $V_H$ comprising an HC-CDR1 comprising the amino acid sequence of SEQ ID NO: 27, or a variant thereof comprising up to about 5 (such as about any of 1, 2, 3, 4, or 5) amino acid substitutions, an HC-CDR2 comprising the amino acid sequence of SEQ ID NO: 78, or a variant thereof comprising up to about 5 (such as about any of 1, 2, 3, 4, or 5) amino acid substitutions, and an HC-CDR3 comprising the amino acid sequence of SEQ ID NO: 129, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 180, or a variant thereof comprising up to about 5 (such as about any of 1, 2, 3, 4, or 5) amino acid substitutions, an LC-CDR2 comprising the amino acid sequence of SEQ ID NO: 231, or a variant thereof comprising up to about 3 (such as about any of 1, 2, or 3) amino acid substitutions, and an LC-CDR3 comprising the amino acid sequence of SEQ ID NO: 282, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 27, an HC-CDR2 comprising the amino acid sequence of SEQ ID NO: 78, and an HC-CDR3 comprising the amino acid sequence of SEQ ID NO: 129; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 180, an LC-CDR2 comprising the amino acid sequence of SEQ ID NO: 231, and an LC-CDR3 comprising the amino acid sequence of SEQ ID NO: 282; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 27, an HC-CDR2 comprising the amino acid sequence of SEQ ID NO: 78, and an HC-CDR3 comprising the amino acid sequence of SEQ ID NO: 129; and ii) a $V_L$ comprising an LC-CDR1 comprising the amino acid sequence of SEQ ID NO: 180, an LC-CDR2 comprising the amino acid sequence of SEQ ID NO: 231, and an LC-CDR3 comprising the amino acid sequence of SEQ ID NO: 282.

In some embodiments, the anti-nGPC3 antibody moiety comprises: i) a $V_H$ comprising an HC-CDR1 comprising the amino acid sequence of SEQ ID NO: 28, or a variant thereof comprising up to about 5 (such as about any of 1, 2, 3, 4, or 5) amino acid substitutions, an HC-CDR2 comprising the amino acid sequence of SEQ ID NO: 79, or a variant thereof comprising up to about 5 (such as about any of 1, 2, 3, 4, or 5) amino acid substitutions, and an HC-CDR3 comprising the amino acid sequence of SEQ ID NO: 130, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 181, or a variant thereof comprising up to about 5 (such as about any of 1, 2, 3, 4, or 5) amino acid substitutions, an LC-CDR2 comprising the amino acid sequence of SEQ ID NO: 232, or a variant thereof comprising up to about 3 (such as about any of 1, 2, or 3) amino acid substitutions, and an LC-CDR3 comprising the amino acid sequence of SEQ ID NO: 283, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 28, an HC-CDR2 comprising the amino acid sequence of SEQ ID NO: 79, and an HC-CDR3 comprising the amino acid sequence of SEQ ID NO: 130; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 181, an LC-CDR2 comprising the amino acid sequence of SEQ ID NO: 232, and an LC-CDR3 comprising the amino acid sequence of SEQ ID NO: 283; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 28, an HC-CDR2 comprising the amino acid sequence of SEQ ID NO: 79, and an HC-CDR3 comprising the amino acid sequence of SEQ ID NO: 130; and ii) a $V_L$ comprising an LC-CDR1 comprising the amino acid sequence of SEQ ID NO: 181, an LC-CDR2 comprising the amino acid sequence of SEQ ID NO: 232, and an LC-CDR3 comprising the amino acid sequence of SEQ ID NO: 283.

In some embodiments, the anti-nGPC3 antibody moiety comprises: i) a $V_H$ comprising an HC-CDR1 comprising the amino acid sequence of SEQ ID NO: 29, or a variant thereof comprising up to about 5 (such as about any of 1, 2, 3, 4, or 5) amino acid substitutions, an HC-CDR2 comprising the amino acid sequence of SEQ ID NO: 80, or a variant thereof comprising up to about 5 (such as about any of 1, 2, 3, 4, or 5) amino acid substitutions, and an HC-CDR3 comprising the amino acid sequence of SEQ ID NO: 131, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 182, or a variant thereof comprising up to about 5 (such as about any of 1, 2, 3, 4, or 5) amino acid substitutions, an LC-CDR2 comprising the amino acid sequence of SEQ ID NO: 233, or a variant thereof comprising up to about 3 (such as about any of 1, 2, or 3) amino acid substitutions, and an LC-CDR3 comprising the amino acid sequence of SEQ ID NO: 284, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 29, an HC-CDR2 comprising the amino acid sequence of SEQ ID NO: 80, and an HC-CDR3 comprising the amino acid sequence of SEQ ID NO: 131; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 182, an LC-CDR2 comprising the amino acid sequence of SEQ ID NO: 233, and an LC-CDR3 comprising the amino acid sequence of SEQ ID NO: 284; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 29, an HC-CDR2 comprising the amino acid sequence of SEQ ID NO: 80, and an HC-CDR3 comprising the amino acid sequence of SEQ ID NO: 131; and ii) a $V_L$ comprising an LC-CDR1 comprising the amino acid sequence of SEQ ID NO: 182, an LC-CDR2 comprising the amino acid sequence of SEQ ID NO: 233, and an LC-CDR3 comprising the amino acid sequence of SEQ ID NO: 284.

In some embodiments, the anti-nGPC3 antibody moiety comprises: i) a $V_H$ comprising an HC-CDR1 comprising the amino acid sequence of SEQ ID NO: 30, or a variant thereof comprising up to about 5 (such as about any of 1, 2, 3, 4, or 5) amino acid substitutions, an HC-CDR2 comprising the amino acid sequence of SEQ ID NO: 81, or a variant thereof comprising up to about 5 (such as about any of 1, 2, 3, 4, or 5) amino acid substitutions, and an HC-CDR3 comprising the amino acid sequence of SEQ ID NO: 132, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 183, or a variant thereof comprising up to about 5 (such as about any of 1, 2, 3, 4, or 5) amino acid substitutions, an LC-CDR2 comprising the amino acid sequence of SEQ ID NO: 234, or a variant thereof comprising up to about 3 (such as about any of 1, 2, or 3) amino acid substitutions, and an LC-CDR3 comprising the amino acid sequence of SEQ ID NO: 285, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 30, an HC-CDR2 comprising the amino acid sequence of SEQ ID NO: 81, and an HC-CDR3 comprising the amino acid sequence of SEQ ID NO: 132; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 183, an LC-CDR2 comprising the amino acid sequence of SEQ ID NO: 234, and an LC-CDR3 comprising the amino acid sequence of SEQ ID NO: 285; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 30, an HC-CDR2 comprising the amino acid sequence of SEQ ID NO: 81, and an HC-CDR3 comprising the amino acid sequence of SEQ ID NO: 132; and ii) a $V_L$ comprising an LC-CDR1 comprising the amino acid sequence of SEQ ID NO: 183, an LC-CDR2 comprising the amino acid sequence of SEQ ID NO: 234, and an LC-CDR3 comprising the amino acid sequence of SEQ ID NO: 285.

In some embodiments, the anti-nGPC3 antibody moiety comprises: i) a $V_H$ comprising an HC-CDR1 comprising the amino acid sequence of SEQ ID NO: 31, or a variant thereof comprising up to about 5 (such as about any of 1, 2, 3, 4, or 5) amino acid substitutions, an HC-CDR2 comprising the amino acid sequence of SEQ ID NO: 82, or a variant thereof comprising up to about 5 (such as about any of 1, 2, 3, 4, or 5) amino acid substitutions, and an HC-CDR3 comprising the amino acid sequence of SEQ ID NO: 133, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 184, or a variant thereof comprising up to about 5 (such as about any of 1, 2, 3, 4, or 5) amino acid substitutions, an LC-CDR2 comprising the amino acid sequence of SEQ ID NO: 235, or a variant thereof comprising up to about 3 (such as about any of 1, 2, or 3) amino acid substitutions, and an LC-CDR3 comprising the amino acid sequence of SEQ ID NO: 286, or a variant thereof comprising up to about 5 (such as about any of 1, 2, 3, 4, or 5) amino acid substitutions. In some embodiments, the anti-nGPC3 antibody moiety comprises: (1) i) a $V_H$ comprising an HC-CDR1 comprising the amino acid sequence of SEQ ID NO: 31, an HC-CDR2 comprising the amino acid sequence of SEQ ID NO: 82, and an HC-CDR3 comprising the amino acid sequence of SEQ ID NO: 133; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 184, an LC-CDR2 comprising the amino acid sequence of SEQ ID NO: 235, and an LC-CDR3 comprising the amino acid sequence of SEQ ID NO: 286; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-nGPC3 antibody moiety comprises i) a $V_H$ comprising an HC-CDR1 comprising the amino acid sequence of SEQ ID NO: 31, an HC-CDR2 comprising the amino acid sequence of SEQ ID NO: 82, and an HC-CDR3 comprising the amino acid sequence of SEQ ID NO: 133; and ii) a $V_L$ comprising an LC-CDR1 comprising the amino acid sequence of SEQ ID NO: 184, an LC-CDR2 comprising the amino acid sequence of SEQ ID NO: 235, and an LC-CDR3 comprising the amino acid sequence of SEQ ID NO: 286.

In some embodiments, the anti-nGPC3 antibody moiety comprises: a) a $V_H$ comprising the amino acid sequence of SEQ ID NO: 307, or a variant thereof having at least about 80% (including for example at least about any of 80%, 85%, 90%, 95%, 96%, 97%, 98%, or 99%) sequence identity to SEQ ID NO: 307; and b) a $V_L$ comprising the amino acid sequence of SEQ ID NO: 358, or a variant thereof having at least about 80% (including for example at least about any of 80%, 85%, 90%, 95%, 96%, 97%, 98%, or 99%) sequence identity to SEQ ID NO: 358. In some embodiments, the anti-nGPC3 antibody moiety comprises: a) a $V_H$ comprising the amino acid sequence of SEQ ID NO: 307; and b) a $V_L$ comprising the amino acid sequence of SEQ ID NO: 358. In some embodiments, the anti-nGPC3 antibody moiety comprises the HC-CDRs of a $V_H$ comprising the amino acid sequence of SEQ ID NO: 307, and the LC-CDRs of a $V_L$ comprising the amino acid sequence of SEQ ID NO: 358.

In some embodiments, the anti-nGPC3 antibody moiety comprises: a) a $V_H$ comprising the amino acid sequence of SEQ ID NO: 308, or a variant thereof having at least about 80% (including for example at least about any of 80%, 85%, 90%, 95%, 96%, 97%, 98%, or 99%) sequence identity to SEQ ID NO: 308; and b) a $V_L$ comprising the amino acid sequence of SEQ ID NO: 359, or a variant thereof having at least about 80% (including for example at least about any of 80%, 85%, 90%, 95%, 96%, 97%, 98%, or 99%) sequence identity to SEQ ID NO: 359. In some embodiments, the anti-nGPC3 antibody moiety comprises: a) a $V_H$ comprising the amino acid sequence of SEQ ID NO: 308; and b) a $V_L$ comprising the amino acid sequence of SEQ ID NO: 359. In some embodiments, the anti-nGPC3 antibody moiety comprises the HC-CDRs of a $V_H$ comprising the amino acid sequence of SEQ ID NO: 308, and the LC-CDRs of a $V_L$ comprising the amino acid sequence of SEQ ID NO: 359.

In some embodiments, the anti-nGPC3 antibody moiety comprises: a) a $V_H$ comprising the amino acid sequence of SEQ ID NO: 309, or a variant thereof having at least about 80% (including for example at least about any of 80%, 85%, 90%, 95%, 96%, 97%, 98%, or 99%) sequence identity to SEQ ID NO: 309; and b) a $V_L$ comprising the amino acid sequence of SEQ ID NO: 360, or a variant thereof having at least about 80% (including for example at least about any of 80%, 85%, 90%, 95%, 96%, 97%, 98%, or 99%) sequence identity to SEQ ID NO: 360. In some embodiments, the anti-nGPC3 antibody moiety comprises: a) a $V_H$ comprising the amino acid sequence of SEQ ID NO: 309; and b) a $V_L$ comprising the amino acid sequence of SEQ ID NO: 360. In some embodiments, the anti-nGPC3 antibody moiety comprises the HC-CDRs of a $V_H$ comprising the amino acid sequence of SEQ ID NO: 309, and the LC-CDRs of a $V_L$ comprising the amino acid sequence of SEQ ID NO: 360.

In some embodiments, the anti-nGPC3 antibody moiety comprises: a) a $V_H$ comprising the amino acid sequence of SEQ ID NO: 310, or a variant thereof having at least about 80% (including for example at least about any of 80%, 85%, 90%, 95%, 96%, 97%, 98%, or 99%) sequence identity to SEQ ID NO: 310; and b) a $V_L$ comprising the amino acid sequence of SEQ ID NO: 361, or a variant thereof having at least about 80% (including for example at least about any of 80%, 85%, 90%, 95%, 96%, 97%, 98%, or 99%) sequence identity to SEQ ID NO: 361. In some embodiments, the anti-nGPC3 antibody moiety comprises: a) a $V_H$ comprising the amino acid sequence of SEQ ID NO: 310; and b) a $V_L$ comprising the amino acid sequence of SEQ ID NO: 361. In some embodiments, the anti-nGPC3 antibody moiety comprises the HC-CDRs of a $V_H$ comprising the amino acid sequence of SEQ ID NO: 310, and the LC-CDRs of a $V_L$ comprising the amino acid sequence of SEQ ID NO: 361.

In some embodiments, the anti-nGPC3 antibody moiety comprises: a) a $V_H$ comprising the amino acid sequence of SEQ ID NO: 311, or a variant thereof having at least about 80% (including for example at least about any of 80%, 85%, 90%, 95%, 96%, 97%, 98%, or 99%) sequence identity to SEQ ID NO: 311; and b) a $V_L$ comprising the amino acid sequence of SEQ ID NO: 362, or a variant thereof having at least about 80% (including for example at least about any of 80%, 85%, 90%, 95%, 96%, 97%, 98%, or 99%) sequence identity to SEQ ID NO: 362. In some embodiments, the anti-nGPC3 antibody moiety comprises: a) a $V_H$ comprising the amino acid sequence of SEQ ID NO: 311; and b) a $V_L$ comprising the amino acid sequence of SEQ ID NO: 362. In some embodiments, the anti-nGPC3 antibody moiety comprises the HC-CDRs of a $V_H$ comprising the amino acid sequence of SEQ ID NO: 311, and the LC-CDRs of a $V_L$ comprising the amino acid sequence of SEQ ID NO: 362.

In some embodiments, the anti-nGPC3 antibody moiety comprises: a) a $V_H$ comprising the amino acid sequence of SEQ ID NO: 312, or a variant thereof having at least about 80% (including for example at least about any of 80%, 85%, 90%, 95%, 96%, 97%, 98%, or 99%) sequence identity to SEQ ID NO: 312; and b) a $V_L$ comprising the amino acid sequence of SEQ ID NO: 363, or a variant thereof having at least about 80% (including for example at least about any of 80%, 85%, 90%, 95%, 96%, 97%, 98%, or 99%) sequence identity to SEQ ID NO: 363. In some embodiments, the anti-nGPC3 antibody moiety comprises: a) a $V_H$ comprising the amino acid sequence of SEQ ID NO: 312; and b) a $V_L$ comprising the amino acid sequence of SEQ ID NO: 363. In some embodiments, the anti-nGPC3 antibody moiety comprises the HC-CDRs of a $V_H$ comprising the amino acid sequence of SEQ ID NO: 312, and the LC-CDRs of a $V_L$ comprising the amino acid sequence of SEQ ID NO: 363.

In some embodiments, the anti-nGPC3 antibody moiety comprises: a) a $V_H$ comprising the amino acid sequence of SEQ ID NO: 313, or a variant thereof having at least about 80% (including for example at least about any of 80%, 85%, 90%, 95%, 96%, 97%, 98%, or 99%) sequence identity to SEQ ID NO: 313; and b) a $V_L$ comprising the amino acid sequence of SEQ ID NO: 364, or a variant thereof having at least about 80% (including for example at least about any of 80%, 85%, 90%, 95%, 96%, 97%, 98%, or 99%) sequence identity to SEQ ID NO: 364. In some embodiments, the anti-nGPC3 antibody moiety comprises: a) a $V_H$ comprising the amino acid sequence of SEQ ID NO: 313; and b) a $V_L$ comprising the amino acid sequence of SEQ ID NO: 364. In some embodiments, the anti-nGPC3 antibody moiety comprises the HC-CDRs of a $V_H$ comprising the amino acid sequence of SEQ ID NO: 313, and the LC-CDRs of a $V_L$ comprising the amino acid sequence of SEQ ID NO: 364.

In some embodiments, the anti-nGPC3 antibody moiety comprises: a) a $V_H$ comprising the amino acid sequence of SEQ ID NO: 314, or a variant thereof having at least about 80% (including for example at least about any of 80%, 85%, 90%, 95%, 96%, 97%, 98%, or 99%) sequence identity to SEQ ID NO: 314; and b) a $V_L$ comprising the amino acid sequence of SEQ ID NO: 365, or a variant thereof having at least about 80% (including for example at least about any of 80%, 85%, 90%, 95%, 96%, 97%, 98%, or 99%) sequence identity to SEQ ID NO: 365. In some embodiments, the anti-nGPC3 antibody moiety comprises: a) a $V_H$ comprising the amino acid sequence of SEQ ID NO: 314; and b) a $V_L$ comprising the amino acid sequence of SEQ ID NO: 365. In some embodiments, the anti-nGPC3 antibody moiety comprises the HC-CDRs of a $V_H$ comprising the amino acid sequence of SEQ ID NO: 314, and the LC-CDRs of a $V_L$ comprising the amino acid sequence of SEQ ID NO: 365.

In some embodiments, the anti-nGPC3 antibody moiety comprises: a) a $V_H$ comprising the amino acid sequence of SEQ ID NO: 315, or a variant thereof having at least about 80% (including for example at least about any of 80%, 85%, 90%, 95%, 96%, 97%, 98%, or 99%) sequence identity to SEQ ID NO: 315; and b) a $V_L$ comprising the amino acid sequence of SEQ ID NO: 366, or a variant thereof having at least about 80% (including for example at least about any of 80%, 85%, 90%, 95%, 96%, 97%, 98%, or 99%) sequence identity to SEQ ID NO: 366. In some embodiments, the anti-nGPC3 antibody moiety comprises: a) a $V_H$ comprising the amino acid sequence of SEQ ID NO: 315; and b) a $V_L$ comprising the amino acid sequence of SEQ ID NO: 366. In some embodiments, the anti-nGPC3 antibody moiety comprises the HC-CDRs of a $V_H$ comprising the amino acid sequence of SEQ ID NO: 315, and the LC-CDRs of a $V_L$ comprising the amino acid sequence of SEQ ID NO: 366.

In some embodiments, the anti-nGPC3 antibody moiety comprises: a) a $V_H$ comprising the amino acid sequence of SEQ ID NO: 316, or a variant thereof having at least about 80% (including for example at least about any of 80%, 85%, 90%, 95%, 96%, 97%, 98%, or 99%) sequence identity to SEQ ID NO: 316; and b) a $V_L$ comprising the amino acid sequence of SEQ ID NO: 367, or a variant thereof having at least about 80% (including for example at least about any of 80%, 85%, 90%, 95%, 96%, 97%, 98%, or 99%) sequence identity to SEQ ID NO: 367. In some embodiments, the anti-nGPC3 antibody moiety comprises: a) a $V_H$ comprising the amino acid sequence of SEQ ID NO: 316; and b) a $V_L$ comprising the amino acid sequence of SEQ ID NO: 367. In some embodiments, the anti-nGPC3 antibody moiety comprises the HC-CDRs of a $V_H$ comprising the amino acid sequence of SEQ ID NO: 316, and the LC-CDRs of a $V_L$ comprising the amino acid sequence of SEQ ID NO: 367.

In some embodiments, the anti-nGPC3 antibody moiety comprises: a) a $V_H$ comprising the amino acid sequence of SEQ ID NO: 317, or a variant thereof having at least about 80% (including for example at least about any of 80%, 85%, 90%, 95%, 96%, 97%, 98%, or 99%) sequence identity to SEQ ID NO: 317; and b) a $V_L$ comprising the amino acid sequence of SEQ ID NO: 368, or a variant thereof having at least about 80% (including for example at least about any of 80%, 85%, 90%, 95%, 96%, 97%, 98%, or 99%) sequence identity to SEQ ID NO: 368. In some embodiments, the anti-nGPC3 antibody moiety comprises: a) a $V_H$ comprising the amino acid sequence of SEQ ID NO: 317; and b) a $V_L$ comprising the amino acid sequence of SEQ ID NO: 368. In some embodiments, the anti-nGPC3 antibody moiety comprises the HC-CDRs of a $V_H$ comprising the amino acid sequence of SEQ ID NO: 317, and the LC-CDRs of a $V_L$ comprising the amino acid sequence of SEQ ID NO: 368.

In some embodiments, the anti-nGPC3 antibody moiety comprises: a) a $V_H$ comprising the amino acid sequence of SEQ ID NO: 318, or a variant thereof having at least about 80% (including for example at least about any of 80%, 85%, 90%, 95%, 96%, 97%, 98%, or 99%) sequence identity to SEQ ID NO: 318; and b) a $V_L$ comprising the amino acid sequence of SEQ ID NO: 369, or a variant thereof having at least about 80% (including for example at least about any of 80%, 85%, 90%, 95%, 96%, 97%, 98%, or 99%) sequence identity to SEQ ID NO: 369. In some embodiments, the anti-nGPC3 antibody moiety comprises: a) a $V_H$ comprising the amino acid sequence of SEQ ID NO: 318; and b) a $V_L$ comprising the amino acid sequence of SEQ ID NO: 369. In some embodiments, the anti-nGPC3 antibody moiety comprises the HC-CDRs of a $V_H$ comprising the amino acid sequence of SEQ ID NO: 318, and the LC-CDRs of a $V_L$ comprising the amino acid sequence of SEQ ID NO: 369.

In some embodiments, the anti-nGPC3 antibody moiety comprises: a) a $V_H$ comprising the amino acid sequence of SEQ ID NO: 319, or a variant thereof having at least about 80% (including for example at least about any of 80%, 85%, 90%, 95%, 96%, 97%, 98%, or 99%) sequence identity to SEQ ID NO: 319; and b) a $V_L$ comprising the amino acid sequence of SEQ ID NO: 370, or a variant thereof having at least about 80% (including for example at least about any of 80%, 85%, 90%, 95%, 96%, 97%, 98%, or 99%) sequence identity to SEQ ID NO: 370. In some embodiments, the anti-nGPC3 antibody moiety comprises: a) a $V_H$ comprising the amino acid sequence of SEQ ID NO: 319; and b) a $V_L$ comprising the amino acid sequence of SEQ ID NO: 370. In some embodiments, the anti-nGPC3 antibody moiety comprises the HC-CDRs of a $V_H$ comprising the amino acid sequence of SEQ ID NO: 319, and the LC-CDRs of a $V_L$ comprising the amino acid sequence of SEQ ID NO: 370.

In some embodiments, the anti-nGPC3 antibody moiety comprises: a) a $V_H$ comprising the amino acid sequence of SEQ ID NO: 320, or a variant thereof having at least about 80% (including for example at least about any of 80%, 85%, 90%, 95%, 96%, 97%, 98%, or 99%) sequence identity to SEQ ID NO: 320; and b) a $V_L$ comprising the amino acid sequence of SEQ ID NO: 371, or a variant thereof having at least about 80% (including for example at least about any of 80%, 85%, 90%, 95%, 96%, 97%, 98%, or 99%) sequence identity to SEQ ID NO: 371. In some embodiments, the anti-nGPC3 antibody moiety comprises: a) a $V_H$ comprising the amino acid sequence of SEQ ID NO: 320; and b) a $V_L$ comprising the amino acid sequence of SEQ ID NO: 371. In some embodiments, the anti-nGPC3 antibody moiety comprises the HC-CDRs of a $V_H$ comprising the amino acid sequence of SEQ ID NO: 320, and the LC-CDRs of a $V_L$ comprising the amino acid sequence of SEQ ID NO: 371.

In some embodiments, the anti-nGPC3 antibody moiety comprises: a) a $V_H$ comprising the amino acid sequence of SEQ ID NO: 321, or a variant thereof having at least about 80% (including for example at least about any of 80%, 85%, 90%, 95%, 96%, 97%, 98%, or 99%) sequence identity to SEQ ID NO: 321; and b) a $V_L$ comprising the amino acid sequence of SEQ ID NO: 372, or a variant thereof having at least about 80% (including for example at least about any of 80%, 85%, 90%, 95%, 96%, 97%, 98%, or 99%) sequence identity to SEQ ID NO: 372. In some embodiments, the anti-nGPC3 antibody moiety comprises: a) a $V_H$ comprising the amino acid sequence of SEQ ID NO: 321; and b) a $V_L$ comprising the amino acid sequence of SEQ ID NO: 372. In some embodiments, the anti-nGPC3 antibody moiety comprises the HC-CDRs of a $V_H$ comprising the amino acid sequence of SEQ ID NO: 321, and the LC-CDRs of a $V_L$ comprising the amino acid sequence of SEQ ID NO: 372.

In some embodiments, the anti-nGPC3 antibody moiety comprises: a) a $V_H$ comprising the amino acid sequence of SEQ ID NO: 322, or a variant thereof having at least about 80% (including for example at least about any of 80%, 85%, 90%, 95%, 96%, 97%, 98%, or 99%) sequence identity to SEQ ID NO: 322; and b) a $V_L$ comprising the amino acid sequence of SEQ ID NO: 373, or a variant thereof having at least about 80% (including for example at least about any of 80%, 85%, 90%, 95%, 96%, 97%, 98%, or 99%) sequence identity to SEQ ID NO: 373. In some embodiments, the anti-nGPC3 antibody moiety comprises: a) a $V_H$ comprising the amino acid sequence of SEQ ID NO: 322; and b) a $V_L$ comprising the amino acid sequence of SEQ ID NO: 373. In some embodiments, the anti-nGPC3 antibody moiety comprises the HC-CDRs of a $V_H$ comprising the amino acid sequence of SEQ ID NO: 322, and the LC-CDRs of a $V_L$ comprising the amino acid sequence of SEQ ID NO: 373.

In some embodiments, the anti-nGPC3 antibody moiety comprises: a) a $V_H$ comprising the amino acid sequence of SEQ ID NO: 323, or a variant thereof having at least about 80% (including for example at least about any of 80%, 85%, 90%, 95%, 96%, 97%, 98%, or 99%) sequence identity to SEQ ID NO: 323; and b) a $V_L$ comprising the amino acid sequence of SEQ ID NO: 374, or a variant thereof having at least about 80% (including for example at least about any of 80%, 85%, 90%, 95%, 96%, 97%, 98%, or 99%) sequence identity to SEQ ID NO: 374. In some embodiments, the anti-nGPC3 antibody moiety comprises: a) a $V_H$ comprising the amino acid sequence of SEQ ID NO: 323; and b) a $V_L$ comprising the amino acid sequence of SEQ ID NO: 374. In some embodiments, the anti-nGPC3 antibody moiety comprises the HC-CDRs of a $V_H$ comprising the amino acid sequence of SEQ ID NO: 323, and the LC-CDRs of a $V_L$ comprising the amino acid sequence of SEQ ID NO: 374.

In some embodiments, the anti-nGPC3 antibody moiety comprises: a) a $V_H$ comprising the amino acid sequence of SEQ ID NO: 324, or a variant thereof having at least about 80% (including for example at least about any of 80%, 85%, 90%, 95%, 96%, 97%, 98%, or 99%) sequence identity to SEQ ID NO: 324; and b) a $V_L$ comprising the amino acid sequence of SEQ ID NO: 375, or a variant thereof having at least about 80% (including for example at least about any of 80%, 85%, 90%, 95%, 96%, 97%, 98%, or 99%) sequence identity to SEQ ID NO: 375. In some embodiments, the anti-nGPC3 antibody moiety comprises: a) a $V_H$ comprising the amino acid sequence of SEQ ID NO: 324; and b) a $V_L$ comprising the amino acid sequence of SEQ ID NO: 375. In some embodiments, the anti-nGPC3 antibody moiety comprises the HC-CDRs of a $V_H$ comprising the amino acid sequence of SEQ ID NO: 324, and the LC-CDRs of a $V_L$ comprising the amino acid sequence of SEQ ID NO: 375.

In some embodiments, the anti-nGPC3 antibody moiety comprises: a) a $V_H$ comprising the amino acid sequence of SEQ ID NO: 325, or a variant thereof having at least about 80% (including for example at least about any of 80%, 85%, 90%, 95%, 96%, 97%, 98%, or 99%) sequence identity to SEQ ID NO: 325; and b) a $V_L$ comprising the amino acid sequence of SEQ ID NO: 376, or a variant thereof having at least about 80% (including for example at least about any of 80%, 85%, 90%, 95%, 96%, 97%, 98%, or 99%) sequence identity to SEQ ID NO: 376. In some embodiments, the anti-nGPC3 antibody moiety comprises: a) a $V_H$ comprising the amino acid sequence of SEQ ID NO: 325; and b) a $V_L$ comprising the amino acid sequence of SEQ ID NO: 376. In some embodiments, the anti-nGPC3 antibody moiety comprises the HC-CDRs of a $V_H$ comprising the amino acid sequence of SEQ ID NO: 325, and the LC-CDRs of a $V_L$ comprising the amino acid sequence of SEQ ID NO: 376.

In some embodiments, the anti-nGPC3 antibody moiety comprises: a) a $V_H$ comprising the amino acid sequence of SEQ ID NO: 326, or a variant thereof having at least about 80% (including for example at least about any of 80%, 85%, 90%, 95%, 96%, 97%, 98%, or 99%) sequence identity to SEQ ID NO: 326; and b) a $V_L$ comprising the amino acid sequence of SEQ ID NO: 377, or a variant thereof having at least about 80% (including for example at least about any of 80%, 85%, 90%, 95%, 96%, 97%, 98%, or 99%) sequence identity to SEQ ID NO: 377. In some embodiments, the anti-nGPC3 antibody moiety comprises: a) a $V_H$ comprising the amino acid sequence of SEQ ID NO: 326; and b) a $V_L$ comprising the amino acid sequence of SEQ ID NO: 377. In some embodiments, the anti-nGPC3 antibody moiety comprises the HC-CDRs of a $V_H$ comprising the amino acid sequence of SEQ ID NO: 326, and the LC-CDRs of a $V_L$ comprising the amino acid sequence of SEQ ID NO: 377.

In some embodiments, the anti-nGPC3 antibody moiety comprises: a) a $V_H$ comprising the amino acid sequence of SEQ ID NO: 327, or a variant thereof having at least about 80% (including for example at least about any of 80%, 85%, 90%, 95%, 96%, 97%, 98%, or 99%) sequence identity to SEQ ID NO: 327; and b) a $V_L$ comprising the amino acid sequence of SEQ ID NO: 378, or a variant thereof having at least about 80% (including for example at least about any of 80%, 85%, 90%, 95%, 96%, 97%, 98%, or 99%) sequence identity to SEQ ID NO: 378. In some embodiments, the anti-nGPC3 antibody moiety comprises: a) a $V_H$ comprising the amino acid sequence of SEQ ID NO: 327; and b) a $V_L$ comprising the amino acid sequence of SEQ ID NO: 378. In some embodiments, the anti-nGPC3 antibody moiety comprises the HC-CDRs of a $V_H$ comprising the amino acid sequence of SEQ ID NO: 327, and the LC-CDRs of a $V_L$ comprising the amino acid sequence of SEQ ID NO: 378.

In some embodiments, the anti-nGPC3 antibody moiety comprises: a) a $V_H$ comprising the amino acid sequence of SEQ ID NO: 328, or a variant thereof having at least about 80% (including for example at least about any of 80%, 85%, 90%, 95%, 96%, 97%, 98%, or 99%) sequence identity to SEQ ID NO: 328; and b) a $V_L$ comprising the amino acid sequence of SEQ ID NO: 379, or a variant thereof having at least about 80% (including for example at least about any of 80%, 85%, 90%, 95%, 96%, 97%, 98%, or 99%) sequence identity to SEQ ID NO: 379. In some embodiments, the anti-nGPC3 antibody moiety comprises: a) a $V_H$ comprising the amino acid sequence of SEQ ID NO: 328; and b) a $V_L$ comprising the amino acid sequence of SEQ ID NO: 379. In some embodiments, the anti-nGPC3 antibody moiety comprises the HC-CDRs of a $V_H$ comprising the amino acid sequence of SEQ ID NO: 328, and the LC-CDRs of a $V_L$ comprising the amino acid sequence of SEQ ID NO: 379.

In some embodiments, the anti-nGPC3 antibody moiety comprises: a) a $V_H$ comprising the amino acid sequence of SEQ ID NO: 329, or a variant thereof having at least about 80% (including for example at least about any of 80%, 85%, 90%, 95%, 96%, 97%, 98%, or 99%) sequence identity to SEQ ID NO: 329; and b) a $V_L$ comprising the amino acid sequence of SEQ ID NO: 380, or a variant thereof having at least about 80% (including for example at least about any of 80%, 85%, 90%, 95%, 96%, 97%, 98%, or 99%) sequence identity to SEQ ID NO: 380. In some embodiments, the anti-nGPC3 antibody moiety comprises: a) a $V_H$ comprising the amino acid sequence of SEQ ID NO: 329; and b) a $V_L$ comprising the amino acid sequence of SEQ ID NO: 380. In some embodiments, the anti-nGPC3 antibody moiety comprises the HC-CDRs of a $V_H$ comprising the amino acid sequence of SEQ ID NO: 329, and the LC-CDRs of a $V_L$ comprising the amino acid sequence of SEQ ID NO: 380.

In some embodiments, the anti-nGPC3 antibody moiety comprises: a) a $V_H$ comprising the amino acid sequence of SEQ ID NO: 330, or a variant thereof having at least about 80% (including for example at least about any of 80%, 85%, 90%, 95%, 96%, 97%, 98%, or 99%) sequence identity to SEQ ID NO: 330; and b) a $V_L$ comprising the amino acid sequence of SEQ ID NO: 381, or a variant thereof having at least about 80% (including for example at least about any of 80%, 85%, 90%, 95%, 96%, 97%, 98%, or 99%) sequence identity to SEQ ID NO: 381. In some embodiments, the anti-nGPC3 antibody moiety comprises: a) a $V_H$ comprising the amino acid sequence of SEQ ID NO: 330; and b) a $V_L$ comprising the amino acid sequence of SEQ ID NO: 381. In some embodiments, the anti-nGPC3 antibody moiety comprises the HC-CDRs of a $V_H$ comprising the amino acid sequence of SEQ ID NO: 330, and the LC-CDRs of a $V_L$ comprising the amino acid sequence of SEQ ID NO: 381.

In some embodiments, the anti-nGPC3 antibody moiety comprises: a) a $V_H$ comprising the amino acid sequence of SEQ ID NO: 331, or a variant thereof having at least about 80% (including for example at least about any of 80%, 85%, 90%, 95%, 96%, 97%, 98%, or 99%) sequence identity to SEQ ID NO: 331; and b) a $V_L$ comprising the amino acid sequence of SEQ ID NO: 382, or a variant thereof having at least about 80% (including for example at least about any of 80%, 85%, 90%, 95%, 96%, 97%, 98%, or 99%) sequence identity to SEQ ID NO: 382. In some embodiments, the anti-nGPC3 antibody moiety comprises: a) a $V_H$ comprising the amino acid sequence of SEQ ID NO: 331; and b) a $V_L$ comprising the amino acid sequence of SEQ ID NO: 382. In some embodiments, the anti-nGPC3 antibody moiety comprises the HC-CDRs of a $V_H$ comprising the amino acid sequence of SEQ ID NO: 331, and the LC-CDRs of a $V_L$ comprising the amino acid sequence of SEQ ID NO: 382.

In some embodiments, the anti-nGPC3 antibody moiety comprises: a) a $V_H$ comprising the amino acid sequence of SEQ ID NO: 332, or a variant thereof having at least about 80% (including for example at least about any of 80%, 85%, 90%, 95%, 96%, 97%, 98%, or 99%) sequence identity to SEQ ID NO: 332; and b) a $V_L$ comprising the amino acid sequence of SEQ ID NO: 383, or a variant thereof having at least about 80% (including for example at least about any of 80%, 85%, 90%, 95%, 96%, 97%, 98%, or 99%) sequence identity to SEQ ID NO: 383. In some embodiments, the anti-nGPC3 antibody moiety comprises: a) a $V_H$ comprising the amino acid sequence of SEQ ID NO: 332; and b) a $V_L$ comprising the amino acid sequence of SEQ ID NO: 383. In some embodiments, the anti-nGPC3 antibody moiety comprises the HC-CDRs of a $V_H$ comprising the amino acid sequence of SEQ ID NO: 332, and the LC-CDRs of a $V_L$ comprising the amino acid sequence of SEQ ID NO: 383.

In some embodiments, the anti-nGPC3 antibody moiety comprises: a) a $V_H$ comprising the amino acid sequence of SEQ ID NO: 333, or a variant thereof having at least about 80% (including for example at least about any of 80%, 85%, 90%, 95%, 96%, 97%, 98%, or 99%) sequence identity to SEQ ID NO: 333; and b) a $V_L$ comprising the amino acid sequence of SEQ ID NO: 384, or a variant thereof having at least about 80% (including for example at least about any of 80%, 85%, 90%, 95%, 96%, 97%, 98%, or 99%) sequence identity to SEQ ID NO: 384. In some embodiments, the anti-nGPC3 antibody moiety comprises: a) a $V_H$ comprising the amino acid sequence of SEQ ID NO: 333; and b) a $V_L$ comprising the amino acid sequence of SEQ ID NO: 384. In some embodiments, the anti-nGPC3 antibody moiety comprises the HC-CDRs of a $V_H$ comprising the amino acid sequence of SEQ ID NO: 333, and the LC-CDRs of a $V_L$ comprising the amino acid sequence of SEQ ID NO: 384.

In some embodiments, the anti-nGPC3 antibody moiety comprises: a) a $V_H$ comprising the amino acid sequence of SEQ ID NO: 334, or a variant thereof having at least about 80% (including for example at least about any of 80%, 85%, 90%, 95%, 96%, 97%, 98%, or 99%) sequence identity to SEQ ID NO: 334; and b) a $V_L$ comprising the amino acid sequence of SEQ ID NO: 385, or a variant thereof having at least about 80% (including for example at least about any of 80%, 85%, 90%, 95%, 96%, 97%, 98%, or 99%) sequence identity to SEQ ID NO: 385. In some embodiments, the anti-nGPC3 antibody moiety comprises: a) a $V_H$ comprising the amino acid sequence of SEQ ID NO: 334; and b) a $V_L$ comprising the amino acid sequence of SEQ ID NO: 385. In some embodiments, the anti-nGPC3 antibody moiety comprises the HC-CDRs of a $V_H$ comprising the amino acid sequence of SEQ ID NO: 334, and the LC-CDRs of a $V_L$ comprising the amino acid sequence of SEQ ID NO: 385.

In some embodiments, the anti-nGPC3 antibody moiety comprises: a) a $V_H$ comprising the amino acid sequence of SEQ ID NO: 335, or a variant thereof having at least about 80% (including for example at least about any of 80%, 85%, 90%, 95%, 96%, 97%, 98%, or 99%) sequence identity to SEQ ID NO: 335; and b) a $V_L$ comprising the amino acid sequence of SEQ ID NO: 386, or a variant thereof having at least about 80% (including for example at least about any of 80%, 85%, 90%, 95%, 96%, 97%, 98%, or 99%) sequence identity to SEQ ID NO: 386. In some embodiments, the anti-nGPC3 antibody moiety comprises: a) a $V_H$ comprising the amino acid sequence of SEQ ID NO: 335; and b) a $V_L$ comprising the amino acid sequence of SEQ ID NO: 386. In some embodiments, the anti-nGPC3 antibody moiety comprises the HC-CDRs of a $V_H$ comprising the amino acid sequence of SEQ ID NO: 335, and the LC-CDRs of a $V_L$ comprising the amino acid sequence of SEQ ID NO: 386.

In some embodiments, the anti-nGPC3 antibody moiety comprises: a) a $V_H$ comprising the amino acid sequence of SEQ ID NO: 336, or a variant thereof having at least about 80% (including for example at least about any of 80%, 85%, 90%, 95%, 96%, 97%, 98%, or 99%) sequence identity to SEQ ID NO: 336; and b) a $V_L$ comprising the amino acid sequence of SEQ ID NO: 387, or a variant thereof having at least about 80% (including for example at least about any of 80%, 85%, 90%, 95%, 96%, 97%, 98%, or 99%) sequence identity to SEQ ID NO: 387. In some embodiments, the anti-nGPC3 antibody moiety comprises: a) a $V_H$ comprising the amino acid sequence of SEQ ID NO: 336; and b) a $V_L$ comprising the amino acid sequence of SEQ ID NO: 387. In some embodiments, the anti-nGPC3 antibody moiety comprises the HC-CDRs of a $V_H$ comprising the amino acid sequence of SEQ ID NO: 336, and the LC-CDRs of a $V_L$ comprising the amino acid sequence of SEQ ID NO: 387.

In some embodiments, the anti-nGPC3 antibody moiety comprises: a) a $V_H$ comprising the amino acid sequence of SEQ ID NO: 337, or a variant thereof having at least about 80% (including for example at least about any of 80%, 85%, 90%, 95%, 96%, 97%, 98%, or 99%) sequence identity to SEQ ID NO: 337; and b) a $V_L$ comprising the amino acid sequence of SEQ ID NO: 388, or a variant thereof having at least about 80% (including for example at least about any of 80%, 85%, 90%, 95%, 96%, 97%, 98%, or 99%) sequence identity to SEQ ID NO: 388. In some embodiments, the anti-nGPC3 antibody moiety comprises: a) a $V_H$ comprising the amino acid sequence of SEQ ID NO: 337; and b) a $V_L$ comprising the amino acid sequence of SEQ ID NO: 388. In some embodiments, the anti-nGPC3 antibody moiety comprises the HC-CDRs of a $V_H$ comprising the amino acid sequence of SEQ ID NO: 337, and the LC-CDRs of a $V_L$ comprising the amino acid sequence of SEQ ID NO: 388.

In some embodiments, the anti-nGPC3 antibody moiety competes for binding to a cell surface-bound GPC3 with a second anti-nGPC3 antibody moiety according to any of the anti-nGPC3 antibody moieties described herein. In some embodiments, the anti-nGPC3 antibody moiety binds to the same, or substantially the same, epitope as the second anti-nGPC3 antibody moiety. In some embodiments, binding of the anti-nGPC3 antibody moiety to a cell surface-bound GPC3 inhibits the binding of a second anti-nGPC3 antibody moiety to the same cell surface-bound GPC3 by at least about 70% (such as by at least about any of 75%, 80%, 85%, 90%, 95%, 98% or 99%), or vice versa. In some embodiments, the anti-nGPC3 antibody moiety and the second anti-nGPC3 antibody moiety cross-compete for binding to the cell surface-bound GPC3, i.e., each of the anti-nGPC3 antibody moieties competes with the other for binding to the cell surface-bound GPC3.

Anti-GPC3 Antibody Moiety Specifically Recognizing GPC3

In some embodiments, the anti-GPC3 antibody moiety specifically recognizes GPC3. In some embodiments, the anti-GPC3 antibody moiety specifically recognizes a cell surface-bound GPC3. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3.

In some embodiments, the anti-GPC3 antibody moiety comprises i) a heavy chain variable domain ($V_H$) comprising an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a light chain variable domain ($V_L$) comprising an LC-CDR3 comprising the amino acid sequence of any one of SEQ ID NOs: 287-306, or a variant thereof comprising up to about 5 (such as about any of 1, 2, 3, 4, or 5) amino acid substitutions.

In some embodiments, the anti-GPC3 antibody moiety comprises i) a $V_H$ comprising an HC-CDR3 comprising the amino acid sequence of any one of SEQ ID NOs: 134-153; and ii) a $V_L$ comprising an LC-CDR3 comprising the amino acid sequence of any one of SEQ ID NOs: 287-306.

In some embodiments, the anti-GPC3 antibody moiety comprises i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions.

In some embodiments, the anti-GPC3 antibody moiety comprises i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306.

In some embodiments, the anti-GPC3 antibody moiety comprises i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306; or a variant thereof comprising up to about 5 (such as about any of 1, 2, 3, 4, or 5) amino acid substitutions in the LC-CDR sequences.

In some embodiments, the anti-GPC3 antibody moiety comprises i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; or a variant thereof comprising up to about 5 (such as about any of 1, 2, 3, 4, or 5) amino acid substitutions, wherein the amino acid substitutions are in HC-CDR1 or HC-CDR2; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306; or a variant thereof comprising up to about 5 (such as about any of 1, 2, 3, 4, or 5) amino acid substitutions, wherein the amino acid substitutions are in LC-CDR1 or LC-CDR2.

In some embodiments, the anti-GPC3 antibody moiety comprises i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306.

In some embodiments, the anti-GPC3 antibody moiety comprises: a) $V_H$ comprising the amino acid sequence of any one of SEQ ID NOs: 32-51, the amino acid sequence of any one of SEQ ID NOs: 83-102, and the amino acid sequence of any one of SEQ ID NOs: 134-153; and ii) a $V_L$ comprising the amino acid sequence of any one of SEQ ID NOs: 185-204, the amino acid sequence of any one of SEQ ID NOs: 236-255, and the amino acid sequence of any one of SEQ ID NOs: 287-306.

In some embodiments, the anti-GPC3 antibody moiety comprises: a) a $V_H$ comprising one, two or three CDRs of any one of SEQ ID NOs: 338-357, and b) a $V_L$ comprising one, two or three CDRs of any one of SEQ ID NOs: 389-408. In some embodiments, the anti-nGPC3 antibody moiety comprises: a) a $V_H$ comprising HC-CDR1, HC-CDR2 and HC-CDR3 of the heavy chain variable domain of any one of SEQ ID NOs: 389-408, and b) a VL comprising LC-CDR1, LC-CDR2 and LC-CDR3 of the light chain variable domain of CDRs of any one of SEQ ID NOs: 358-388.

In some embodiments, the anti-GPC3 antibody moiety comprises: a) a $V_H$ comprising the amino acid sequence of any one of SEQ ID NOs: 338-357, or a variant thereof having at least about 80% (including for example at least about any of 80%, 85%, 90%, 95%, 96%, 97%, 98%, or 99%) sequence identity to any one of SEQ ID NOs: 338-357; and b) a $V_L$ comprising the amino acid sequence of any one of SEQ ID NOs: 389-408, or a variant thereof having at least about 80% (including for example at least about any of 80%, 85%, 90%, 95%, 96%, 97%, 98%, or 99%) sequence identity to any one of SEQ ID NOs: 389-408.

In some embodiments, the anti-GPC3 antibody moiety comprises: a) a $V_H$ comprising the amino acid sequence of any one of SEQ ID NOs: 338-357; and b) a $V_L$ comprising the amino acid sequence of any one of SEQ ID NOs: 389-408.

In some embodiments, the anti-GPC3 antibody moiety comprises the HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408.

The heavy and light chain variable domains can be combined in various pair-wise combinations to generate a number of anti-GPC3 antibody moieties. Exemplary anti-GPC3 antibody moieties are provided in Tables 8 and 9.

TABLE 8 anti-GPC3 antibody moiety CDR sequences

| Clone No. | SEQ ID NO: | HCDR1 | SEQ ID NO: | HCDR2 | SEQ ID NO: | HCDR3 | SEQ ID NO: | LCDR1 | SEQ ID NO: | LCDR2 | SEQ ID NO: | LCDR3 |
|---|---|---|---|---|---|---|---|---|---|---|---|---|
| GPC3B-54 | 32 | GYTFIDYY | 83 | IIPIFGTA | 134 | ARERRYSSSPSDH | 185 | NSNIGSDT | 236 | RCN | 287 | TTWDDSLNGLV |
| GPC3B-60 | 33 | GYTFTSYY | 84 | INPSGGST | 135 | ARSLYSQPYIDG | 186 | NLENKF | 237 | EDN | 288 | QTWDSPTGLFV |
| GPC3B-63 | 34 | GYTFTSYY | 85 | INPSGGST | 136 | ARSLHAMRWSQTMDS | 187 | QSLLHSNGYNY | 238 | LGS | 289 | MQALQTPPT |
| GPC3B-66 | 35 | GYTFIGQY | 86 | INPMTGVT | 137 | ARFSSGYSRDT | 188 | NIGSKS | 239 | YDS | 290 | QVWDSSSDHLYV |
| GPC3B-68 | 36 | GGTFSSYA | 87 | IIPILGIA | 138 | ARYGYEGHDT | 189 | SSNIGNNY | 240 | DNI | 291 | GTWESSLSAGV |
| GPC3B-71 | 37 | GFTFSRYT | 88 | ISSSGSYI | 139 | ARQGHMWYVPVDA | 190 | NIGSKS | 241 | YDS | 292 | QVWDSSSDHYV |
| GPC3B-76 | 38 | GYTFTDYY | 89 | INPNSGGT | 140 | ARNYD | 191 | SSNIGNNY | 242 | CNN | 293 | GTWESSLSAGV |
| GPC3B-78 | 39 | GYTFTSYY | 90 | INPSGGST | 141 | ARGYSSFFDS | 192 | KLGDKY | 243 | QDN | 294 | QTWERSTYV |
| GPC3B-80 | 40 | GGTLSRFA | 91 | IIPIFRTA | 142 | ARMSKYYGSYSSYDE | 193 | SSNIGSNT | 244 | SNN | 295 | AAWDDSLNG |
| GPC3B-81 | 41 | GYTFTGYY | 92 | INPNSGGT | 143 | ARGLWDS | 194 | NIGSKS | 245 | YDS | 296 | QVWDSSSELLYV |
| GPC3B-82 | 42 | GYSFTSYY | 93 | INPSGGST | 144 | ARYPVYMETSDFDS | 195 | SSNIGAGFD | 246 | CNN | 297 | QSFESSLSGWV |
| GPC3B-85 | 43 | GYTFTSYA | 94 | INTNTGNP | 145 | ARSSLYWMGSKWSRQTDM | 196 | SSNIGSNT | 247 | SNN | 298 | AAWDDSLNGYV |
| GPC3B-87 | 44 | GGTFGSYA | 95 | IIPVLGRT | 146 | ARTNDS | 197 | QSLLHSNGYNY | 248 | LGS | 299 | MQALQTPWT |
| GPC3B-92 | 45 | GYTFSNYY | 96 | INPSGGTT | 147 | ARPSMWTSSMGDV | 198 | TLAKRY | 249 | RET | 300 | QSADNSRTFV |
| GPC3B-93 | 46 | GYTFTSYY | 97 | INPSGGST | 148 | ARYTALKPRGIYSVDS | 199 | SGSIASNY | 250 | EDN | 301 | QSYDSSNWV |
| GPC3B-110 | 47 | GGTFTTYS | 98 | IIPTFGTT | 149 | ARYYWRGGSGQGSVTSDY | 200 | SSNIGSNT | 251 | SSN | 302 | AAWDDSLNGPV |
| GPC3B-113 | 48 | GYTLTELS | 99 | FDPEDGET | 150 | ARYSGDY | 201 | SSNIGSNS | 252 | SNN | 303 | AAWDDSLNGVL |

TABLE 8-continued anti-GPC3 antibody moiety CDR sequences

| Clone No. | SEQ ID NO: | HCDR1 | SEQ ID NO: | HCDR2 | SEQ ID NO: | HCDR3 | SEQ ID NO: | LCDR1 | SEQ ID NO: | LCDR2 | SEQ ID NO: | LCDR3 |
|---|---|---|---|---|---|---|---|---|---|---|---|---|
| GPC3B-115 | 49 | GYTFTAYY | 100 | INANTGGT | 151 | ARISGYHSSGWDY | 202 | NIGSKS | 253 | DDS | 304 | QVWDSSSDPLYV |
| GPC3B-119 | 50 | GYTFTSYA | 101 | INTNTGNP | 152 | ARGYYGKYDK | 203 | SSNIGNNY | 254 | CNN | 305 | ATWENSLSALI |
| GPC3B-125 | 51 | GYTFTSYA | 102 | INTNTGNP | 153 | ARQSHDE | 204 | SSDVGGYNY | 255 | EVS | 306 | SSYTSSTTVI |

TABLE 9 anti-GPC3 antibody moiety V$_H$/V$_L$ sequences
(CDR sequences are underlined)

| Clone No. | SEQ ID NO: | V$_H$ | SEQ ID NO: | V$_L$ |
|---|---|---|---|---|
| GPC3B-54 | 338 | EVQLVQSGAEVKKPGASVKLSCKTS<u>GYTFIDYYVY</u>WVRQAPGQGLEWMGG<u>IIPIFGTAN</u>YAQKFQGRVTITADKSTSTAYMELSSLGSEDTAVYYC<u>ARERRYSSSPSDH</u>WGQGTLVTVSS | 389 | QSVLTQPPSASGTPGQRVTISCSGS<u>NSNIGSDT</u>VNVVYQQLPGTAPKLLIY<u>RDN</u>QRPSGVPDRFSGSKSGTSASLAISGLQSEDEADYYC<u>TTWDDSLNGLV</u>FGGGTKVTVLG |
| GPC3B-60 | 339 | EVQLVESGAEVKKPGASVKVSCKAS<u>GYTFTSYYM</u>HWVRQAPGQGLEWMGI<u>INPSGGST</u>SYAQKFQGRVTMTRDTSTSTVYMELSSLRSEDTAVYYC<u>ARSLYSQPYIDGW</u>SQGTLVTVSS | 390 | SYVLTQPPSVSVSPGQTATIACSGD<u>NLENKF</u>VYVVVHQKPGQSPVLVMY<u>EDN</u>KRPSGIPERFSGSNSGNTAALTISGAQPMDEADYYCQ<u>TWDSPTGLF</u>VFGTGTKVTVLG |
| GPC3B-63 | 340 | QVQLVQSGAEVKKPGASVKVSCKAS<u>GYTFTSYYM</u>HWVRQAPGQGLEWMGI<u>INPSGGST</u>SYAQKFQGRVTMTRDTSTSTVYMELSSLRSEDTAVYYC<u>ARSLHAMRWSQTMDSW</u>GQGTLVTVSS | 391 | EIVLTQSPLSLPVTPGEPASISCRSS<u>QSLLHSNGYNYLD</u>WYLQKPGQSPQLLIY<u>LGS</u>NRASGVPDRFSGSGSGTDFTLKISRVEAEDVGVYYC<u>MQALQTPPT</u>FGQGTKVEIKR |
| GPC3B-66 | 341 | QVQLVQSGAEVKRPGASVKVSCKAS<u>GYTFIGQYL</u>HWVRQAPGQGLEWMGR<u>INPMTGVTN</u>YAPKFQGRVTMTRDTSISTGYMEISRLSDDTAVYYC<u>ARFSSGYSRDT</u>WGQGTLVTVSS | 392 | QAVLTQPPSVSVAPGKTASITCGG<u>NNIGSKSV</u>HVVYQQKPGQAPVLVIY<u>YDS</u>RPSGIPERFSGSNSGNTATLTISRVEAGDEADYYC<u>QVWDSSSDHLYV</u>FGTGTKVTVLG |
| GPC3B-68 | 342 | QVQLVQSGAEVKKPGSSVKVSCKAS<u>GGTFSSYAI</u>SWVRQAPGQGLEWMGR<u>IIPILGIAN</u>YAQKFQGRVTITADKSTSTAYMELSSLRSEDTAVYYC<u>ARYGYEGHDT</u>WGQGTLVTVSS | 393 | QSVLTQPPSVSAAPGQKVTISCSGS<u>SSNIGNNY</u>VSVVYQQLPGTAPKLLIY<u>DNI</u>KRPSGIPDRFSGSKSGTSATLGITGLQTGDEADYYC<u>GTWDSSLSAGV</u>FGGGTKLTVLG |
| GPC3B-71 | 343 | EVQLVESGGGLVKPGGSLRLSCAAS<u>GFTFSRYTM</u>NWVRQAPGKGLEWVSS<u>ISSSGSYI</u>YYADSVKGRFTISRDNAKNSLFLQMDSLRAEDTAVYYC<u>ARQGHMWYVPVDAW</u>GQGTLVTVSS | 394 | SYVLTQPPSVSVAPGKTARVTCGG<u>NNIGSKSV</u>HVVYQQKPGQAPVLVMY<u>YDS</u>RPSGIPERFSGSNSGNTATLTISSVEAGDEADYYC<u>QVWDSSSDHYV</u>FGTGTKVTVLG |
| GPC3B-76 | 344 | QMQLVQSGAEVKEPGASVKVSCKAS<u>GYTFTDYYI</u>HWVRQAPGQGLEWMGW<u>INPNSGGT</u>NYAQKFQGRVTMTRDTSISTAYMELSRLSDDTAVYYC<u>ARNYDW</u>GQGTLVTVSS | 395 | QSVVTQPPSVSAAPGQKVTISCSGS<u>SSNIGNNY</u>VSVVYQQLPGTAPKLLIY<u>DNN</u>KRPSGIPDRFSGSKSGTSATLGITGLQTGDEAAYYCG<u>TWDSSLSAGV</u>FGTGTKVTVLG |
| GPC3B-78 | 345 | QMQLVQSGAEVKKPGASVKVSCKAS<u>GYTFTSYY</u>MHWVRQAPGQGLEWMGI<u>INPSGGST</u>SYAQKFQGRVTMTRDTSTSTVYMELSSLRSEDTAVYYC<u>ARGYSSFFDSW</u>GQGTLVTVSS | 396 | LPVLTQPPSVSVSPGQTASITCSGD<u>KLGDKYAY</u>VVVQQKPGQSPVLVIY<u>QDN</u>KRPSGIPERFSGSNSGNTATLTISGTQAMDAADYYC<u>QTWDRSTYV</u>FGTGTKVTVLG |
| GPC3B-80 | 346 | QVQLVQSGAEVKKPGSSVKVSCKAS<u>GGTLSRFAI</u>SWVRQAPGQGLEWMGG<u>IIPIFRTAN</u>YAQKFQGRVTITADESTSTAYMELSSLRSEDTAVYYC<u>ARMSKYYGSYSSYDEW</u>GQGTLVTVSS | 397 | QAVLTQPPSASGTPGQRVTISCSGS<u>SSNIGSNT</u>VNWYQQLPGTAPKLLIY<u>SNN</u>QRPSGVPDRFSGSKSGTSAYLAISGLQSEDEADYYC<u>AAWDDSLNGWGV</u>FGGGTKLTVLG |
| GPC3B-81 | 347 | EVQLVQSGAEVKKPGASVKVSCKAS<u>GYTFTGYYM</u>HWVRQAPGQGLEWMGR<u>INPNSGGT</u>NYAQKFQGRVTMTRDTSISTAYMELSSLRSDDTAVYYC<u>ARGLWDSW</u>GQGTLVTVSS | 398 | SYELTQPPSVSVAPGKTARITCGG<u>NNIGSKSV</u>HVVYQQKPGQAPVLVIY<u>YDS</u>RPSGIPERFSGSNSGNTATLTISRVEAGDEADYYC<u>QVWDSSSDLLYV</u>FGTGTKVTVLG |
| GPC3B-82 | 348 | EVQLVQSGAEVKKPGESLKISCKGS<u>GYSFTSYY</u>MHWVRQAPGQGLEWMGI<u>INPSGGST</u>SYAQKFQGRVTMTRDTSTSTVYMESSLRSEDTAVYYC<u>ARYPVYMETSDFDSW</u>GSRYSGDRLL | 399 | QSVLTQPPSVSGAPGQRVTISCTGS<u>SSNIGAGFD</u>VHVVYQQLPGTAPKLLIY<u>DNN</u>RPSGVPDRFSGSKSDTSASLAITGLQAEDEADYYC<u>QSFDSSLSGWV</u>FGGGTKVTVLG |

TABLE 9-continued anti-GPC3 antibody moiety $V_H/V_L$ sequences
(CDR sequences are underlined)

| Clone No. | SEQ ID NO: $V_H$ | $V_H$ | SEQ ID NO: $V_L$ | $V_L$ |
|---|---|---|---|---|
| GPC3B-85 | 349 | QVQLVQSGSELKKPGASVKVSCKAS<u>GYTFTSYAM</u><br><u>NW</u>VRQAPGQGLEWMG<u>WINTNTGNPTYAQGFTG</u><br>RFVFSLDTSVSTAYLQISSLKAEDTAVYYC<u>ARSSLY</u><br><u>WMGSKWSRQTDMDW</u>GQGTLVTVSS | 400 | QAVLTQPPSASGTPGQRVTISCSGS<u>SSNI</u><br><u>GSNTV</u>NWYQQLPGTAPKLLIY<u>SNNQRPS</u><br>GVPDRFSGSKSGTSASLAISGLQSEDEA<br>DYYC<u>AAWDDSLNGYV</u>FGTGTKVTVLG |
| GPC3B-87 | 350 | EVQLVQSGAEVRKPGSSVKVSCQAS<u>GGTFGSYAI</u><br><u>SW</u>VRQAPGQGLEWMGR<u>IIPVLGRTKYAQKFQGR</u><br>VTVTADTSTSTVYMELTSLTSEDTAVYYC<u>ARTNDS</u><br><u>W</u>GQGTLVTVSS | 401 | DVVMTQSPLSLPVTPGEPASVSCRSS<u>QS</u><br><u>LLHSNGYNYLD</u>VVYLQKPGQSPQLLIY<u>LGS</u><br><u>N</u>RASGVPDRFSGSGSGTDFTLKISRVEA<br>EDVGVYYC<u>MQALQTPWT</u>FGQGTKVEIKR |
| GPC3B-92 | 351 | EVQLVQSGAEVKKPGASVKVSCKAS<u>GYTFSNYYM</u><br><u>H</u>WVRQAPGQGLEWMGI<u>INPSGGTTTYAQKFQGR</u><br>VTMTRDTSTSTVYMELSSLRSEDTAVYYC<u>ARPSM</u><br><u>WTSSMGDV</u>WGQGTLVTVSS | 402 | QSVLTQPPSVSVSPGQTARITCSG<u>ETLAK</u><br><u>RYAH</u>VVYQQKPGQAPVLLIY<u>RDTERPSGI</u><br>PERFSGSSSGTTITLTITGVQAEDEADYY<br>C<u>QSADNSRTFV</u>FGPGTKVTVLG |
| GPC3B-93 | 352 | EVQLVQSGAEVKKPGASVKVSCKAS<u>GYTFTSYYM</u><br><u>H</u>WVRQAPGQGLEWMGI<u>INPSGGSTRYAQKFQGR</u><br>VTMTRDTSTSTVYMELSSLRSEDTAVYYC<u>ARYTAL</u><br><u>KPRGIYSVDSW</u>GQGTLVTVSS | 403 | NFMLTQPHSVSESPGKTVTISCTGS<u>SGSI</u><br><u>ASNYV</u>QVVYQQRPGSAPTTVIY<u>EDNQRPS</u><br>GVPDRFSGSIDSSSNSASLTISGLKTEDE<br>ADYYC<u>QSYDSSNWV</u>FGGGTKLTVLG |
| GPC3B-110 | 353 | EVQLVQSGAEVKKPGSSVKVSCQAS<u>GGTFTTYSI</u><br><u>NW</u>VRQAPGQGLEWMGG<u>IIPTFGTTNYAQNFQDR</u><br>VTISADESTNTAYMELTSLRSEDTAVYYC<u>ARYYWR</u><br><u>GGSGQGSVTSDY</u>WGQGTLVTVSS | 404 | QSVLTQPPSASGTPGQRVTVSCSGS<u>SSN</u><br><u>IGSNTV</u>NWYQQLPGTAPKLLLY<u>SSNQRP</u><br>SGVPDRFSGSRSGTSASLAISGLQSEDE<br>ADYYC<u>AAWDDSLNGPV</u>FGGGTKLTVLG |
| GPC3B-113 | 354 | QVQLVQSGAEVKKPGASVKVSCKVS<u>GYTLTELSM</u><br><u>H</u>WVRQAPGKGLEWMGG<u>FDPEDGETIYAQKFQG</u><br>RVTMTEDTSTDTAYMELSSLRSEDTAVYYC<u>ARYS</u><br><u>GDY</u>WGQGTLVTVSS | 405 | SYELTQPPSASGTPGQRVTISCSGS<u>SSNI</u><br><u>GSNSV</u>SVVYQHLPGVAPKWY<u>SNNQRPS</u><br>GVPDRFSGSKTGTSASLAISGLQSEDEG<br>DYYC<u>AAWDDSLNGVL</u>FGGGTKLTVLG |
| GPC3B-115 | 355 | QVQLVQSGAEVKRPGATIKVSCKTS<u>GYTFTAYYT</u><br><u>H</u>WVRQAPGQGLEWVGR<u>INANTGGTDYAPKFRDR</u><br>VIMTRDTSISTAYMELGRLTSEDTAVYYC<u>ARISGYH</u><br><u>SSGWDY</u>WGQGTLVTVSS | 406 | SYELTQPPSVSVAPGKTARITCGG<u>NNIGS</u><br><u>KSVH</u>VVYQQKPGQAPVLVVY<u>DDSDRPSGI</u><br>PERFSGSNSGNTATLTISRVEAGDEADYY<br>C<u>QVWDSSSDPLYV</u>FGTGTKVTVLG |
| GPC3B-119 | 356 | QVQLVQSGSELKKPGASVKVSCKAS<u>GYTFTSYAM</u><br><u>NW</u>VRQAPGQGLEWMGW<u>INTNTGNPTYAQGFTG</u><br>RFVFSLDTSVSTAYLQISSLKAEDTAVYYC<u>ARGYY</u><br><u>GKYDKW</u>GQGTLVTVSS | 407 | QSVVTQPPSVSAAPGQKVTISCSGS<u>SSNI</u><br><u>GNNYV</u>SVVYQQ1PGTAPKWY<u>DNNKRPS</u><br>GIPDRFSGSRSGTSATLGITGLQTGDEAH<br>YYC<u>ATWDNSLSALI</u>FGGGTKVTVLG |
| GPC3B-125 | 357 | QMQLVQSGSELKKPGASVKVSCKAS<u>GYTFTSYA</u><br><u>MN</u>WVRQAPGQGLEWMGW<u>INTNTGNPTYAQGFT</u><br>GRFVFSLDTSVSTAYLQISSLKAEDTAVYYC<u>ARQS</u><br><u>HDE</u>WGQGTLVTVSS | 408 | QSALTQPASVSGSPGQSITISCTGT<u>SSDV</u><br><u>GGYNYV</u>SWFQQHPGKAPKLIIY<u>EVSNRP</u><br>SGVSDRFSGSKSGSTASLTISGLQAEDEA<br>NYYC<u>SSYTSSTTVI</u>FGGGTKLTVLG |

In some embodiments, the anti-GPC3 antibody moiety comprises: i) a $V_H$ comprising an HC-CDR1 comprising the amino acid sequence of SEQ ID NO: 32, or a variant thereof comprising up to about 5 (such as about any of 1, 2, 3, 4, or 5) amino acid substitutions, an HC-CDR2 comprising the amino acid sequence of SEQ ID NO: 83, or a variant thereof comprising up to about 5 (such as about any of 1, 2, 3, 4, or 5) amino acid substitutions, and an HC-CDR3 comprising the amino acid sequence of SEQ ID NO: 134, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 185, or a variant thereof comprising up to about 5 (such as about any of 1, 2, 3, 4, or 5) amino acid substitutions, an LC-CDR2 comprising the amino acid sequence of SEQ ID NO: 236, or a variant thereof comprising up to about 3 (such as about any of 1, 2, or 3) amino acid substitutions, and an LC-CDR3 comprising the amino acid sequence of SEQ ID NO: 287, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 32, an HC-CDR2 comprising the amino acid sequence of SEQ ID NO: 83, and an HC-CDR3 comprising the amino acid sequence of SEQ ID NO: 134; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 185, an LC-CDR2 comprising the amino acid sequence of SEQ ID NO: 236, and an LC-CDR3 comprising the amino acid sequence of SEQ ID NO: 287; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 32, an HC-CDR2 comprising the amino acid sequence of SEQ ID NO: 83, and an HC-CDR3 comprising the amino acid sequence of SEQ ID NO: 134; and ii) a $V_L$ comprising an LC-CDR1 comprising the amino acid sequence of SEQ ID NO: 185, an LC-CDR2 comprising the amino acid sequence of SEQ ID NO: 236, and an LC-CDR3 comprising the amino acid sequence of SEQ ID NO: 287.

In some embodiments, the anti-GPC3 antibody moiety comprises: i) a $V_H$ comprising an HC-CDR1 comprising the amino acid sequence of SEQ ID NO: 33, or a variant thereof comprising up to about 5 (such as about any of 1, 2, 3, 4, or 5) amino acid substitutions, an HC-CDR2 comprising the amino acid sequence of SEQ ID NO: 84, or a variant thereof comprising up to about 5 (such as about any of 1, 2, 3, 4, or 5) amino acid substitutions, and an HC-CDR3 comprising the amino acid sequence of SEQ ID NO: 135, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 186, or a variant thereof comprising up to about 5 (such as about any of 1, 2, 3, 4, or 5) amino acid substitutions, an LC-CDR2 comprising the amino acid sequence of SEQ ID NO: 237, or a variant thereof comprising up to about 3 (such as about any of 1, 2, or 3) amino acid substitutions, and an LC-CDR3 comprising the amino acid sequence of SEQ ID NO: 288, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 33, an HC-CDR2 comprising the amino acid sequence of SEQ ID NO: 84, and an HC-CDR3 comprising the amino acid sequence of SEQ ID NO: 135; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 186, an LC-CDR2 comprising the amino acid sequence of SEQ ID NO: 237, and an LC-CDR3 comprising the amino acid sequence of SEQ ID NO: 288; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 33, an HC-CDR2 comprising the amino acid sequence of SEQ ID NO: 84, and an HC-CDR3 comprising the amino acid sequence of SEQ ID NO: 135; and ii) a $V_L$ comprising an LC-CDR1 comprising the amino acid sequence of SEQ ID NO: 186, an LC-CDR2 comprising the amino acid sequence of SEQ ID NO: 237, and an LC-CDR3 comprising the amino acid sequence of SEQ ID NO: 288.

In some embodiments, the anti-GPC3 antibody moiety comprises: i) a $V_H$ comprising an HC-CDR1 comprising the amino acid sequence of SEQ ID NO: 34, or a variant thereof comprising up to about 5 (such as about any of 1, 2, 3, 4, or 5) amino acid substitutions, an HC-CDR2 comprising the amino acid sequence of SEQ ID NO: 85, or a variant thereof comprising up to about 5 (such as about any of 1, 2, 3, 4, or 5) amino acid substitutions, and an HC-CDR3 comprising the amino acid sequence of SEQ ID NO: 136, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 187, or a variant thereof comprising up to about 5 (such as about any of 1, 2, 3, 4, or 5) amino acid substitutions, an LC-CDR2 comprising the amino acid sequence of SEQ ID NO: 238, or a variant thereof comprising up to about 3 (such as about any of 1, 2, or 3) amino acid substitutions, and an LC-CDR3 comprising the amino acid sequence of SEQ ID NO: 289, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 34, an HC-CDR2 comprising the amino acid sequence of SEQ ID NO: 85, and an HC-CDR3 comprising the amino acid sequence of SEQ ID NO: 136; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 187, an LC-CDR2 comprising the amino acid sequence of SEQ ID NO: 238, and an LC-CDR3 comprising the amino acid sequence of SEQ ID NO: 289; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 34, an HC-CDR2 comprising the amino acid sequence of SEQ ID NO: 85, and an HC-CDR3 comprising the amino acid sequence of SEQ ID NO: 136; and ii) a $V_L$ comprising an LC-CDR1 comprising the amino acid sequence of SEQ ID NO: 187, an LC-CDR2 comprising the amino acid sequence of SEQ ID NO: 238, and an LC-CDR3 comprising the amino acid sequence of SEQ ID NO: 289.

In some embodiments, the anti-GPC3 antibody moiety comprises: i) a $V_H$ comprising an HC-CDR1 comprising the amino acid sequence of SEQ ID NO: 35, or a variant thereof comprising up to about 5 (such as about any of 1, 2, 3, 4, or 5) amino acid substitutions, an HC-CDR2 comprising the amino acid sequence of SEQ ID NO: 86, or a variant thereof comprising up to about 5 (such as about any of 1, 2, 3, 4, or 5) amino acid substitutions, and an HC-CDR3 comprising the amino acid sequence of SEQ ID NO: 137, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 188, or a variant thereof comprising up to about 5 (such as about any of 1, 2, 3, 4, or 5) amino acid substitutions, an LC-CDR2 comprising the amino acid sequence of SEQ ID NO: 239, or a variant thereof comprising up to about 3 (such as about any of 1, 2, or 3) amino acid substitutions, and an LC-CDR3 comprising the amino acid sequence of SEQ ID NO: 290, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 35, an HC-CDR2 comprising the amino acid sequence of SEQ ID NO: 86, and an HC-CDR3 comprising the amino acid sequence of SEQ ID NO: 137; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 188, an LC-CDR2 comprising the amino acid sequence of SEQ ID NO: 239, and an LC-CDR3 comprising the amino acid sequence of SEQ ID NO: 290; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 35, an HC-CDR2 comprising the amino acid sequence of SEQ ID NO: 86, and an HC-CDR3 comprising the amino acid sequence of SEQ ID NO: 137; and ii) a $V_L$ comprising an LC-CDR1 comprising the amino acid sequence of SEQ ID NO: 188, an LC-CDR2 comprising the amino acid sequence of SEQ ID NO: 239, and an LC-CDR3 comprising the amino acid sequence of SEQ ID NO: 290.

In some embodiments, the anti-GPC3 antibody moiety comprises: i) a $V_H$ comprising an HC-CDR1 comprising the amino acid sequence of SEQ ID NO: 36, or a variant thereof comprising up to about 5 (such as about any of 1, 2, 3, 4, or 5) amino acid substitutions, an HC-CDR2 comprising the amino acid sequence of SEQ ID NO: 87, or a variant thereof comprising up to about 5 (such as about any of 1, 2, 3, 4, or 5) amino acid substitutions, and an HC-CDR3 comprising the amino acid sequence of SEQ ID NO: 138, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 189, or a variant thereof comprising up to about 5 (such as about any of 1, 2, 3, 4, or 5) amino acid substitutions, an LC-CDR2 comprising the amino acid sequence of SEQ ID NO: 240, or a variant thereof comprising up to about 3 (such as about any of 1, 2, or 3) amino acid substitutions, and an LC-CDR3 comprising the amino acid sequence of SEQ ID NO: 291, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 36, an HC-CDR2 comprising the amino acid sequence of SEQ ID NO: 87, and an HC-CDR3 comprising the amino acid sequence of SEQ ID NO: 138; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 189, an LC-CDR2 comprising the amino acid sequence of SEQ ID NO: 240, and an LC-CDR3 comprising the amino acid sequence of SEQ ID NO: 291; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 36, an HC-CDR2 comprising the amino acid sequence of SEQ ID NO: 87, and an HC-CDR3 comprising the amino acid sequence of SEQ ID NO: 138; and ii) a $V_L$ comprising an LC-CDR1 comprising the amino acid sequence of SEQ ID NO: 189, an LC-CDR2 comprising the amino acid sequence of SEQ ID NO: 240, and an LC-CDR3 comprising the amino acid sequence of SEQ ID NO: 291.

In some embodiments, the anti-GPC3 antibody moiety comprises: i) a $V_H$ comprising an HC-CDR1 comprising the amino acid sequence of SEQ ID NO: 37, or a variant thereof comprising up to about 5 (such as about any of 1, 2, 3, 4, or 5) amino acid substitutions, an HC-CDR2 comprising the amino acid sequence of SEQ ID NO: 88, or a variant thereof comprising up to about 5 (such as about any of 1, 2, 3, 4, or 5) amino acid substitutions, and an HC-CDR3 comprising the amino acid sequence of SEQ ID NO: 139, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 190, or a variant thereof comprising up to about 5 (such as about any of 1, 2, 3, 4, or 5) amino acid substitutions, an LC-CDR2 comprising the amino acid sequence of SEQ ID NO: 241, or a variant thereof comprising up to about 3 (such as about any of 1, 2, or 3) amino acid substitutions, and an LC-CDR3 comprising the amino acid sequence of SEQ ID NO: 292, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 37, an HC-CDR2 comprising the amino acid sequence of SEQ ID NO: 88, and an HC-CDR3 comprising the amino acid sequence of SEQ ID NO: 139; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 190, an LC-CDR2 comprising the amino acid sequence of SEQ ID NO: 241, and an LC-CDR3 comprising the amino acid sequence of SEQ ID NO: 292; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 37, an HC-CDR2 comprising the amino acid sequence of SEQ ID NO: 88, and an HC-CDR3 comprising the amino acid sequence of SEQ ID NO: 139; and ii) a $V_L$ comprising an LC-CDR1 comprising the amino acid sequence of SEQ ID NO: 190, an LC-CDR2 comprising the amino acid sequence of SEQ ID NO: 241, and an LC-CDR3 comprising the amino acid sequence of SEQ ID NO: 292.

In some embodiments, the anti-GPC3 antibody moiety comprises: i) a $V_H$ comprising an HC-CDR1 comprising the amino acid sequence of SEQ ID NO: 38, or a variant thereof comprising up to about 5 (such as about any of 1, 2, 3, 4, or 5) amino acid substitutions, an HC-CDR2 comprising the amino acid sequence of SEQ ID NO: 89, or a variant thereof comprising up to about 5 (such as about any of 1, 2, 3, 4, or 5) amino acid substitutions, and an HC-CDR3 comprising the amino acid sequence of SEQ ID NO: 140, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 191, or a variant thereof comprising up to about 5 (such as about any of 1, 2, 3, 4, or 5) amino acid substitutions, an LC-CDR2 comprising the amino acid sequence of SEQ ID NO: 242, or a variant thereof comprising up to about 3 (such as about any of 1, 2, or 3) amino acid substitutions, and an LC-CDR3 comprising the amino acid sequence of SEQ ID NO: 293, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 38, an HC-CDR2 comprising the amino acid sequence of SEQ ID NO: 89, and an HC-CDR3 comprising the amino acid sequence of SEQ ID NO: 140; or a variant thereof comprising up to about 5 (such as about any of 1, 2, 3, 4, or 5) amino acid substitutions in the HC-CDR sequences; and ii) a V$_L$ comprising an LC-CDR1 comprising the amino acid sequence of SEQ ID NO: 191, an LC-CDR2 comprising the amino acid sequence of SEQ ID NO: 242, and an LC-CDR3 comprising the amino acid sequence of SEQ ID NO: 293; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a V$_H$ comprising an HC-CDR1 comprising the amino acid sequence of SEQ ID NO: 38, an HC-CDR2 comprising the amino acid sequence of SEQ ID NO: 89, and an HC-CDR3 comprising the amino acid sequence of SEQ ID NO: 140; and ii) a V$_L$ comprising an LC-CDR1 comprising the amino acid sequence of SEQ ID NO: 191, an LC-CDR2 comprising the amino acid sequence of SEQ ID NO: 242, and an LC-CDR3 comprising the amino acid sequence of SEQ ID NO: 293.

In some embodiments, the anti-GPC3 antibody moiety comprises: i) a V$_H$ comprising an HC-CDR1 comprising the amino acid sequence of SEQ ID NO: 39, or a variant thereof comprising up to about 5 (such as about any of 1, 2, 3, 4, or 5) amino acid substitutions, an HC-CDR2 comprising the amino amino acid sequence of SEQ ID NO: 90, or a variant thereof comprising up to about 5 (such as about any of 1, 2, 3, 4, or 5) amino acid substitutions, and an HC-CDR3 comprising the amino acid sequence of SEQ ID NO: 141, or a variant thereof comprising up to about 5 (such as about any of 1, 2, 3, 4, or 5) amino acid substitutions; and ii) a V$_L$ comprising an LC-CDR1 comprising the amino acid sequence of SEQ ID NO: 192, or a variant thereof comprising up to about 5 (such as about any of 1, 2, 3, 4, or 5) amino acid substitutions, an LC-CDR2 comprising the amino acid sequence of SEQ ID NO: 243, or a variant thereof comprising up to about 3 (such as about any of 1, 2, or 3) amino acid substitutions, and an LC-CDR3 comprising the amino acid sequence of SEQ ID NO: 294, or a variant thereof comprising up to about 5 (such as about any of 1, 2, 3, 4, or 5) amino acid substitutions. In some embodiments, the anti-GPC3 antibody moiety comprises: (1) i) a V$_H$ comprising an HC-CDR1 comprising the amino acid sequence of SEQ ID NO: 39, an HC-CDR2 comprising the amino acid sequence of SEQ ID NO: 90, and an HC-CDR3 comprising the amino acid sequence of SEQ ID NO: 141; or a variant thereof comprising up to about 5 (such as about any of 1, 2, 3, 4, or 5) amino acid substitutions in the HC-CDR sequences; and ii) a V$_L$ comprising an LC-CDR1 comprising the amino acid sequence of SEQ ID NO: 192, an LC-CDR2 comprising the amino acid sequence of SEQ ID NO: 243, and an LC-CDR3 comprising the amino acid sequence of SEQ ID NO: 294; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a V$_H$ comprising an HC-CDR1 comprising the amino acid sequence of SEQ ID NO: 39, an HC-CDR2 comprising the amino acid sequence of SEQ ID NO: 90, and an HC-CDR3 comprising the amino acid sequence of SEQ ID NO: 141; and ii) a V$_L$ comprising an LC-CDR1 comprising the amino acid sequence of SEQ ID NO: 192, an LC-CDR2 comprising the amino acid sequence of SEQ ID NO: 243, and an LC-CDR3 comprising the amino acid sequence of SEQ ID NO: 294.

In some embodiments, the anti-GPC3 antibody moiety comprises: i) a V$_H$ comprising an HC-CDR1 comprising the amino acid sequence of SEQ ID NO: 40, or a variant thereof comprising up to about 5 (such as about any of 1, 2, 3, 4, or 5) amino acid substitutions, an HC-CDR2 comprising the amino acid sequence of SEQ ID NO: 91, or a variant thereof comprising up to about 5 (such as about any of 1, 2, 3, 4, or 5) amino acid substitutions, and an HC-CDR3 comprising the amino acid sequence of SEQ ID NO: 142, or a variant thereof comprising up to about 5 (such as about any of 1, 2, 3, 4, or 5) amino acid substitutions; and ii) a V$_L$ comprising an LC-CDR1 comprising the amino acid sequence of SEQ ID NO: 193, or a variant thereof comprising up to about 5 (such as about any of 1, 2, 3, 4, or 5) amino acid substitutions, an LC-CDR2 comprising the amino acid sequence of SEQ ID NO: 244, or a variant thereof comprising up to about 3 (such as about any of 1, 2, or 3) amino acid substitutions, and an LC-CDR3 comprising the amino acid sequence of SEQ ID NO: 295, or a variant thereof comprising up to about 5 (such as about any of 1, 2, 3, 4, or 5) amino acid substitutions. In some embodiments, the anti-GPC3 antibody moiety comprises: (1) i) a V$_H$ comprising an HC-CDR1 comprising the amino acid sequence of SEQ ID NO: 40, an HC-CDR2 comprising the amino acid sequence of SEQ ID NO: 91, and an HC-CDR3 comprising the amino acid sequence of SEQ ID NO: 142; or a variant thereof comprising up to about 5 (such as about any of 1, 2, 3, 4, or 5) amino acid substitutions in the HC-CDR sequences; and ii) a V$_L$ comprising an LC-CDR1 comprising the amino acid sequence of SEQ ID NO: 193, an LC-CDR2 comprising the amino acid sequence of SEQ ID NO: 244, and an LC-CDR3 comprising the amino acid sequence of SEQ ID NO: 295; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a V$_H$ comprising an HC-CDR1 comprising the amino acid sequence of SEQ ID NO: 40, an HC-CDR2 comprising the amino acid sequence of SEQ ID NO: 91, and an HC-CDR3 comprising the amino acid sequence of SEQ ID NO: 142; and ii) a V$_L$ comprising an LC-CDR1 comprising the amino acid sequence of SEQ ID NO: 193, an LC-CDR2 comprising the amino acid sequence of SEQ ID NO: 244, and an LC-CDR3 comprising the amino acid sequence of SEQ ID NO: 295.

In some embodiments, the anti-GPC3 antibody moiety comprises: i) a V$_H$ comprising an HC-CDR1 comprising the amino acid sequence of SEQ ID NO: 41, or a variant thereof comprising up to about 5 (such as about any of 1, 2, 3, 4, or 5) amino acid substitutions, an HC-CDR2 comprising the amino acid sequence of SEQ ID NO: 92, or a variant thereof comprising up to about 5 (such as about any of 1, 2, 3, 4, or 5) amino acid substitutions, and an HC-CDR3 comprising the amino acid sequence of SEQ ID NO: 143, or a variant thereof comprising up to about 5 (such as about any of 1, 2, 3, 4, or 5) amino acid substitutions; and ii) a V$_L$ comprising an LC-CDR1 comprising the amino acid sequence of SEQ ID NO: 194, or a variant thereof comprising up to about 5 (such as about any of 1, 2, 3, 4, or 5) amino acid substitutions, an LC-CDR2 comprising the amino acid sequence of SEQ ID NO: 245, or a variant thereof comprising up to about 3 (such as about any of 1, 2, or 3) amino acid substitutions, and an LC-CDR3 comprising the amino acid sequence of SEQ ID NO: 296, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 41, an HC-CDR2 comprising the amino acid sequence of SEQ ID NO: 92, and an HC-CDR3 comprising the amino acid sequence of SEQ ID NO: 143; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 194, an LC-CDR2 comprising the amino acid sequence of SEQ ID NO: 245, and an LC-CDR3 comprising the amino acid sequence of SEQ ID NO: 296; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 41, an HC-CDR2 comprising the amino acid sequence of SEQ ID NO: 92, and an HC-CDR3 comprising the amino acid sequence of SEQ ID NO: 143; and ii) a $V_L$ comprising an LC-CDR1 comprising the amino acid sequence of SEQ ID NO: 194, an LC-CDR2 comprising the amino acid sequence of SEQ ID NO: 245, and an LC-CDR3 comprising the amino acid sequence of SEQ ID NO: 296.

In some embodiments, the anti-GPC3 antibody moiety comprises: i) a $V_H$ comprising an HC-CDR1 comprising the amino acid sequence of SEQ ID NO: 42, or a variant thereof comprising up to about 5 (such as about any of 1, 2, 3, 4, or 5) amino acid substitutions, an HC-CDR2 comprising the amino acid sequence of SEQ ID NO: 93, or a variant thereof comprising up to about 5 (such as about any of 1, 2, 3, 4, or 5) amino acid substitutions, and an HC-CDR3 comprising the amino acid sequence of SEQ ID NO: 144, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 195, or a variant thereof comprising up to about 5 (such as about any of 1, 2, 3, 4, or 5) amino acid substitutions, an LC-CDR2 comprising the amino acid sequence of SEQ ID NO: 246, or a variant thereof comprising up to about 3 (such as about any of 1, 2, or 3) amino acid substitutions, and an LC-CDR3 comprising the amino acid sequence of SEQ ID NO: 297, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 42, an HC-CDR2 comprising the amino acid sequence of SEQ ID NO: 93, and an HC-CDR3 comprising the amino acid sequence of SEQ ID NO: 144; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 195, an LC-CDR2 comprising the amino acid sequence of SEQ ID NO: 246, and an LC-CDR3 comprising the amino acid sequence of SEQ ID NO: 297; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 42, an HC-CDR2 comprising the amino acid sequence of SEQ ID NO: 93, and an HC-CDR3 comprising the amino acid sequence of SEQ ID NO: 144; and ii) a $V_L$ comprising an LC-CDR1 comprising the amino acid sequence of SEQ ID NO: 195, LC-CDR2 comprising the amino acid sequence of SEQ ID NO: 246, and an LC-CDR3 comprising the amino acid sequence of SEQ ID NO: 297.

In some embodiments, the anti-GPC3 antibody moiety comprises: i) a $V_H$ comprising an HC-CDR1 comprising the amino acid sequence of SEQ ID NO: 43, or a variant thereof comprising up to about 5 (such as about any of 1, 2, 3, 4, or 5) amino acid substitutions, an HC-CDR2 comprising the amino acid sequence of SEQ ID NO: 94, or a variant thereof comprising up to about 5 (such as about any of 1, 2, 3, 4, or 5) amino acid substitutions, and an HC-CDR3 comprising the amino acid sequence of SEQ ID NO: 145, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 196, or a variant thereof comprising up to about 5 (such as about any of 1, 2, 3, 4, or 5) amino acid substitutions, an LC-CDR2 comprising the amino acid sequence of SEQ ID NO: 247, or a variant thereof comprising up to about 3 (such as about any of 1, 2, or 3) amino acid substitutions, and an LC-CDR3 comprising the amino acid sequence of SEQ ID NO: 298, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 43, an HC-CDR2 comprising the amino acid sequence of SEQ ID NO: 94, and an HC-CDR3 comprising the amino acid sequence of SEQ ID NO: 145; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 196, an LC-CDR2 comprising the amino acid sequence of SEQ ID NO: 247, and an LC-CDR3 comprising the amino acid sequence of SEQ ID NO: 298; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 43, an HC-CDR2 comprising the amino acid sequence of SEQ ID NO: 94, and an HC-CDR3 comprising the amino acid sequence of SEQ ID NO: 145; and ii) a $V_L$ comprising an LC-CDR1 comprising the amino acid sequence of SEQ ID NO: 196, an LC-CDR2 comprising the amino acid sequence of SEQ ID NO: 247, and an LC-CDR3 comprising the amino acid sequence of SEQ ID NO: 298.

In some embodiments, the anti-GPC3 antibody moiety comprises: i) a $V_H$ comprising an HC-CDR1 comprising the amino acid sequence of SEQ ID NO: 44, or a variant thereof comprising up to about 5 (such as about any of 1, 2, 3, 4, or 5) amino acid substitutions, an HC-CDR2 comprising the amino acid sequence of SEQ ID NO: 95, or a variant thereof comprising up to about 5 (such as about any of 1, 2, 3, 4, or 5) amino acid substitutions, and an HC-CDR3 comprising the amino acid sequence of SEQ ID NO: 146, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 197, or a variant thereof comprising up to about 5

(such as about any of 1, 2, 3, 4, or 5) amino acid substitutions, an LC-CDR2 comprising the amino acid sequence of SEQ ID NO: 248, or a variant thereof comprising up to about 3 (such as about any of 1, 2, or 3) amino acid substitutions, and an LC-CDR3 comprising the amino acid sequence of SEQ ID NO: 299, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 44, an HC-CDR2 comprising the amino acid sequence of SEQ ID NO: 95, and an HC-CDR3 comprising the amino acid sequence of SEQ ID NO: 146; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 197, an LC-CDR2 comprising the amino acid sequence of SEQ ID NO: 248, and an LC-CDR3 comprising the amino acid sequence of SEQ ID NO: 299; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 44, an HC-CDR2 comprising the amino acid sequence of SEQ ID NO: 95, and an HC-CDR3 comprising the amino acid sequence of SEQ ID NO: 146; and ii) a $V_L$ comprising an LC-CDR1 comprising the amino acid sequence of SEQ ID NO: 197, an LC-CDR2 comprising the amino acid sequence of SEQ ID NO: 248, and an LC-CDR3 comprising the amino acid sequence of SEQ ID NO: 299.

In some embodiments, the anti-GPC3 antibody moiety comprises: i) a $V_H$ comprising an HC-CDR1 comprising the amino acid sequence of SEQ ID NO: 45, or a variant thereof comprising up to about 5 (such as about any of 1, 2, 3, 4, or 5) amino acid substitutions, an HC-CDR2 comprising the amino acid sequence of SEQ ID NO: 96, or a variant thereof comprising up to about 5 (such as about any of 1, 2, 3, 4, or 5) amino acid substitutions, and an HC-CDR3 comprising the amino acid sequence of SEQ ID NO: 147, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 198, or a variant thereof comprising up to about 5 (such as about any of 1, 2, 3, 4, or 5) amino acid substitutions, an LC-CDR2 comprising the amino acid sequence of SEQ ID NO: 249, or a variant thereof comprising up to about 3 (such as about any of 1, 2, or 3) amino acid substitutions, and an LC-CDR3 comprising the amino acid sequence of SEQ ID NO: 300, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 45, an HC-CDR2 comprising the amino acid sequence of SEQ ID NO: 96, and an HC-CDR3 comprising the amino acid sequence of SEQ ID NO: 147; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 198, an LC-CDR2 comprising the amino acid sequence of SEQ ID NO: 249, and an LC-CDR3 comprising the amino acid sequence of SEQ ID NO: 300; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 45, an HC-CDR2 comprising the amino acid sequence of SEQ ID NO: 96, and an HC-CDR3 comprising the amino acid sequence of SEQ ID NO: 147; and ii) a $V_L$ comprising an LC-CDR1 comprising the amino acid sequence of SEQ ID NO: 198, an LC-CDR2 comprising the amino acid sequence of SEQ ID NO: 249, and an LC-CDR3 comprising the amino acid sequence of SEQ ID NO: 300.

In some embodiments, the anti-GPC3 antibody moiety comprises: i) a $V_H$ comprising an HC-CDR1 comprising the amino acid sequence of SEQ ID NO: 46, or a variant thereof comprising up to about 5 (such as about any of 1, 2, 3, 4, or 5) amino acid substitutions, an HC-CDR2 comprising the amino acid sequence of SEQ ID NO: 97, or a variant thereof comprising up to about 5 (such as about any of 1, 2, 3, 4, or 5) amino acid substitutions, and an HC-CDR3 comprising the amino acid sequence of SEQ ID NO: 148, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 199, or a variant thereof comprising up to about 5 (such as about any of 1, 2, 3, 4, or 5) amino acid substitutions, an LC-CDR2 comprising the amino acid sequence of SEQ ID NO: 250, or a variant thereof comprising up to about 3 (such as about any of 1, 2, or 3) amino acid substitutions, and an LC-CDR3 comprising the amino acid sequence of SEQ ID NO: 301, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 46, an HC-CDR2 comprising the amino acid sequence of SEQ ID NO: 97, and an HC-CDR3 comprising the amino acid sequence of SEQ ID NO: 148; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 199, an LC-CDR2 comprising the amino acid sequence of SEQ ID NO: 250, and an LC-CDR3 comprising the amino acid sequence of SEQ ID NO: 301; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 46, an HC-CDR2 comprising the amino acid sequence of SEQ ID NO: 97, and an HC-CDR3 comprising the amino acid sequence of SEQ ID NO: 148; and ii) a $V_L$ comprising an LC-CDR1 comprising the amino acid sequence of SEQ ID NO: 199, an LC-CDR2 comprising the amino acid sequence of SEQ ID NO: 250, and an LC-CDR3 comprising the amino acid sequence of SEQ ID NO: 301.

In some embodiments, the anti-GPC3 antibody moiety comprises: i) a $V_H$ comprising an HC-CDR1 comprising the amino acid sequence of SEQ ID NO: 47, or a variant thereof comprising up to about 5 (such as about any of 1, 2, 3, 4, or 5) amino acid substitutions, an HC-CDR2 comprising the amino acid sequence of SEQ ID NO: 98, or a variant thereof comprising up to about 5 (such as about any of 1, 2, 3, 4, or 5) amino acid substitutions, and an HC-CDR3 comprising the amino acid sequence of SEQ ID NO: 149, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 200, or a variant thereof comprising up to about 5 (such as about any of 1, 2, 3, 4, or 5) amino acid substitutions, an LC-CDR2 comprising the amino acid sequence of SEQ ID NO: 251, or a variant thereof comprising up to about 3 (such as about any of 1, 2, or 3) amino acid substitutions, and an LC-CDR3 comprising the amino acid sequence of SEQ ID NO: 302, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 47, an HC-CDR2 comprising the amino acid sequence of SEQ ID NO: 98, and an HC-CDR3 comprising the amino acid sequence of SEQ ID NO: 149; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 200, an LC-CDR2 comprising the amino acid sequence of SEQ ID NO: 251, and an LC-CDR3 comprising the amino acid sequence of SEQ ID NO: 302; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 47, an HC-CDR2 comprising the amino acid sequence of SEQ ID NO: 98, and an HC-CDR3 comprising the amino acid sequence of SEQ ID NO: 149; and ii) a $V_L$ comprising an LC-CDR1 comprising the amino acid sequence of SEQ ID NO: 200, an LC-CDR2 comprising the amino acid sequence of SEQ ID NO: 251, and an LC-CDR3 comprising the amino acid sequence of SEQ ID NO: 302.

In some embodiments, the anti-GPC3 antibody moiety comprises: i) a $V_H$ comprising an HC-CDR1 comprising the amino acid sequence of SEQ ID NO: 48, or a variant thereof comprising up to about 5 (such as about any of 1, 2, 3, 4, or 5) amino acid substitutions, an HC-CDR2 comprising the amino acid sequence of SEQ ID NO: 99, or a variant thereof comprising up to about 5 (such as about any of 1, 2, 3, 4, or 5) amino acid substitutions, and an HC-CDR3 comprising the amino acid sequence of SEQ ID NO: 150, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 201, or a variant thereof comprising up to about 5 (such as about any of 1, 2, 3, 4, or 5) amino acid substitutions, an LC-CDR2 comprising the amino acid sequence of SEQ ID NO: 252, or a variant thereof comprising up to about 3 (such as about any of 1, 2, or 3) amino acid substitutions, and an LC-CDR3 comprising the amino acid sequence of SEQ ID NO: 303, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 48, an HC-CDR2 comprising the amino acid sequence of SEQ ID NO: 99, and an HC-CDR3 comprising the amino acid sequence of SEQ ID NO: 150; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 201, an LC-CDR2 comprising the amino acid sequence of SEQ ID NO: 252, and an LC-CDR3 comprising the amino acid sequence of SEQ ID NO: 303; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 48, an HC-CDR2 comprising the amino acid sequence of SEQ ID NO: 99, and an HC-CDR3 comprising the amino acid sequence of SEQ ID NO: 150; and ii) a $V_L$ comprising an LC-CDR1 comprising the amino acid sequence of SEQ ID NO: 201, an LC-CDR2 comprising the amino acid sequence of SEQ ID NO: 252, and an LC-CDR3 comprising the amino acid sequence of SEQ ID NO: 303.

In some embodiments, the anti-GPC3 antibody moiety comprises: i) a $V_H$ comprising an HC-CDR1 comprising the amino acid sequence of SEQ ID NO: 49, or a variant thereof comprising up to about 5 (such as about any of 1, 2, 3, 4, or 5) amino acid substitutions, an HC-CDR2 comprising the amino acid sequence of SEQ ID NO: 100, or a variant thereof comprising up to about 5 (such as about any of 1, 2, 3, 4, or 5) amino acid substitutions, and an HC-CDR3 comprising the amino acid sequence of SEQ ID NO: 151, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 202, or a variant thereof comprising up to about 5 (such as about any of 1, 2, 3, 4, or 5) amino acid substitutions, an LC-CDR2 comprising the amino acid sequence of SEQ ID NO: 253, or a variant thereof comprising up to about 3 (such as about any of 1, 2, or 3) amino acid substitutions, and an LC-CDR3 comprising the amino acid sequence of SEQ ID NO: 304, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 49, an HC-CDR2 comprising the amino acid sequence of SEQ ID NO: 100, and an HC-CDR3 comprising the amino acid sequence of SEQ ID NO: 151; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 202, an LC-CDR2 comprising the amino acid sequence of SEQ ID NO: 253, and an LC-CDR3 comprising the amino acid sequence of SEQ ID NO: 304; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 49, an HC-CDR2 comprising the amino acid sequence of SEQ ID NO: 100, and an HC-CDR3 comprising the amino acid sequence of SEQ ID NO: 151; and ii) a $V_L$ comprising an LC-CDR1 comprising the amino acid sequence of SEQ ID NO: 202, an LC-CDR2 comprising the amino acid sequence of SEQ ID NO: 253, and an LC-CDR3 comprising the amino acid sequence of SEQ ID NO: 304.

In some embodiments, the anti-GPC3 antibody moiety comprises: i) a $V_H$ comprising an HC-CDR1 comprising the amino acid sequence of SEQ ID NO: 50, or a variant thereof comprising up to about 5 (such as about any of 1, 2, 3, 4, or 5) amino acid substitutions, an HC-CDR2 comprising the amino acid sequence of SEQ ID NO: 101, or a variant thereof comprising up to about 5 (such as about any of 1, 2, 3, 4, or 5) amino acid substitutions, and an HC-CDR3 comprising the amino acid sequence of SEQ ID NO: 152, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 203, or a variant thereof comprising up to about 5 (such as about any of 1, 2, 3, 4, or 5) amino acid substitutions, an LC-CDR2 comprising the amino acid sequence of SEQ ID NO: 254, or a variant thereof comprising up to about 3 (such as about any of 1, 2, or 3) amino acid substitutions, and an LC-CDR3 comprising the amino acid sequence of SEQ ID NO: 305, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 50, an HC-CDR2 comprising the amino acid sequence of SEQ ID NO: 101, and an HC-CDR3 comprising the amino acid sequence of SEQ ID NO: 152; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 203, an LC-CDR2 comprising the amino acid sequence of SEQ ID NO: 254, and an LC-CDR3 comprising the amino acid sequence of SEQ ID NO: 305; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 50, an HC-CDR2 comprising the amino acid sequence of SEQ ID NO: 101, and an HC-CDR3 comprising the amino acid sequence of SEQ ID NO: 152; and ii) a $V_L$ comprising an LC-CDR1 comprising the amino acid sequence of SEQ ID NO: 203, an LC-CDR2 comprising the amino acid sequence of SEQ ID NO: 254, and an LC-CDR3 comprising the amino acid sequence of SEQ ID NO: 305.

In some embodiments, the anti-GPC3 antibody moiety comprises: i) a $V_H$ comprising an HC-CDR1 comprising the amino acid sequence of SEQ ID NO: 51, or a variant thereof comprising up to about 5 (such as about any of 1, 2, 3, 4, or 5) amino acid substitutions, an HC-CDR2 comprising the amino acid sequence of SEQ ID NO: 102, or a variant thereof comprising up to about 5 (such as about any of 1, 2, 3, 4, or 5) amino acid substitutions, and an HC-CDR3 comprising the amino acid sequence of SEQ ID NO: 153, or a variant thereof comprising up to about 5 (such as about any of 1, 2, 3, 4, or 5) amino acid substitutions; and ii) a $V_L$ comprising an LC-CDR1 comprising the amino acid sequence of SEQ ID NO: 204, or a variant thereof comprising up to about 5 (such as about any of 1, 2, 3, 4, or 5) amino acid substitutions, an LC-CDR2 comprising the amino acid sequence of SEQ ID NO: 255, or a variant thereof comprising up to about 3 (such as about any of 1, 2, or 3) amino acid substitutions, and an LC-CDR3 comprising the amino acid sequence of SEQ ID NO: 306, or a variant thereof comprising up to about 5 (such as about any of 1, 2, 3, 4, or 5) amino acid substitutions. In some embodiments, the anti-GPC3 antibody moiety comprises: (1) i) a $V_H$ comprising an HC-CDR1 comprising the amino acid sequence of SEQ ID NO: 51, an HC-CDR2 comprising the amino acid sequence of SEQ ID NO: 102, and an HC-CDR3 comprising the amino acid sequence of SEQ ID NO: 153; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of SEQ ID NO: 204, an LC-CDR2 comprising the amino acid sequence of SEQ ID NO: 255, and an LC-CDR3 comprising the amino acid sequence of SEQ ID NO: 306; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, the anti-GPC3 antibody moiety comprises i) a $V_H$ comprising an HC-CDR1 comprising the amino acid sequence of SEQ ID NO: 51, an HC-CDR2 comprising the amino acid sequence of SEQ ID NO: 102, and an HC-CDR3 comprising the amino acid sequence of SEQ ID NO: 153; and ii) a $V_L$ comprising an LC-CDR1 comprising the amino acid sequence of SEQ ID NO: 204, an LC-CDR2 comprising the amino acid sequence of SEQ ID NO: 255, and an LC-CDR3 comprising the amino acid sequence of SEQ ID NO: 306.

In some embodiments, the anti-GPC3 antibody moiety comprises: a) a $V_H$ comprising the amino acid sequence of SEQ ID NO: 338, or a variant thereof having at least about 80% (including for example at least about any of 80%, 85%, 90%, 95%, 96%, 97%, 98%, or 99%) sequence identity to SEQ ID NO: 338; and b) a $V_L$ comprising the amino acid sequence of SEQ ID NO: 389, or a variant thereof having at least about 80% (including for example at least about any of 80%, 85%, 90%, 95%, 96%, 97%, 98%, or 99%) sequence identity to SEQ ID NO: 389. In some embodiments, the anti-GPC3 antibody moiety comprises: a) a $V_H$ comprising the amino acid sequence of SEQ ID NO: 338; and b) a $V_L$ comprising the amino acid sequence of SEQ ID NO: 389. In some embodiments, the anti-GPC3 antibody moiety comprises the HC-CDRs of a $V_H$ comprising the amino acid sequence of SEQ ID NO: 338, and the LC-CDRs of a $V_L$ comprising the amino acid sequence of SEQ ID NO: 389.

In some embodiments, the anti-GPC3 antibody moiety comprises: a) a $V_H$ comprising the amino acid sequence of SEQ ID NO: 339, or a variant thereof having at least about 80% (including for example at least about any of 80%, 85%, 90%, 95%, 96%, 97%, 98%, or 99%) sequence identity to SEQ ID NO: 339; and b) a $V_L$ comprising the amino acid sequence of SEQ ID NO: 390, or a variant thereof having at least about 80% (including for example at least about any of 80%, 85%, 90%, 95%, 96%, 97%, 98%, or 99%) sequence identity to SEQ ID NO: 390. In some embodiments, the anti-GPC3 antibody moiety comprises: a) a $V_H$ comprising the amino acid sequence of SEQ ID NO: 339; and b) a $V_L$ comprising the amino acid sequence of SEQ ID NO: 390. In some embodiments, the anti-GPC3 antibody moiety comprises the HC-CDRs of a $V_H$ comprising the amino acid sequence of SEQ ID NO: 339, and the LC-CDRs of a $V_L$ comprising the amino acid sequence of SEQ ID NO: 390.

In some embodiments, the anti-GPC3 antibody moiety comprises: a) a $V_H$ comprising the amino acid sequence of SEQ ID NO: 340, or a variant thereof having at least about 80% (including for example at least about any of 80%, 85%, 90%, 95%, 96%, 97%, 98%, or 99%) sequence identity to SEQ ID NO: 340; and b) a $V_L$ comprising the amino acid sequence of SEQ ID NO: 391, or a variant thereof having at least about 80% (including for example at least about any of 80%, 85%, 90%, 95%, 96%, 97%, 98%, or 99%) sequence identity to SEQ ID NO: 391. In some embodiments, the anti-GPC3 antibody moiety comprises: a) a $V_H$ comprising the amino acid sequence of SEQ ID NO: 340; and b) a $V_L$ comprising the amino acid sequence of SEQ ID NO: 391. In some embodiments, the anti-GPC3 antibody moiety comprises the HC-CDRs of a $V_H$ comprising the amino acid sequence of SEQ ID NO: 340, and the LC-CDRs of a $V_L$ comprising the amino acid sequence of SEQ ID NO: 391.

In some embodiments, the anti-GPC3 antibody moiety comprises: a) a $V_H$ comprising the amino acid sequence of SEQ ID NO: 341, or a variant thereof having at least about 80% (including for example at least about any of 80%, 85%, 90%, 95%, 96%, 97%, 98%, or 99%) sequence identity to SEQ ID NO: 341; and b) a $V_L$ comprising the amino acid sequence of SEQ ID NO: 392, or a variant thereof having at least about 80% (including for example at least about any of 80%, 85%, 90%, 95%, 96%, 97%, 98%, or 99%) sequence identity to SEQ ID NO: 392. In some embodiments, the anti-GPC3 antibody moiety comprises: a) a $V_H$ comprising the amino acid sequence of SEQ ID NO: 341; and b) a $V_L$ comprising the amino acid sequence of SEQ ID NO: 392. In some embodiments, the anti-GPC3 antibody moiety comprises the HC-CDRs of a $V_H$ comprising the amino acid sequence of SEQ ID NO: 341, and the LC-CDRs of a $V_L$ comprising the amino acid sequence of SEQ ID NO: 392.

In some embodiments, the anti-GPC3 antibody moiety comprises: a) a $V_H$ comprising the amino acid sequence of SEQ ID NO: 342, or a variant thereof having at least about 80% (including for example at least about any of 80%, 85%, 90%, 95%, 96%, 97%, 98%, or 99%) sequence identity to SEQ ID NO: 342; and b) a $V_L$ comprising the amino acid sequence of SEQ ID NO: 393, or a variant thereof having at least about 80% (including for example at least about any of 80%, 85%, 90%, 95%, 96%, 97%, 98%, or 99%) sequence identity to SEQ ID NO: 393. In some embodiments, the anti-GPC3 antibody moiety comprises: a) a $V_H$ comprising the amino acid sequence of SEQ ID NO: 342; and b) a $V_L$ comprising the amino acid sequence of SEQ ID NO: 393. In some embodiments, the anti-GPC3 antibody moiety comprises the HC-CDRs of a $V_H$ comprising the amino acid sequence of SEQ ID NO: 342, and the LC-CDRs of a $V_L$ comprising the amino acid sequence of SEQ ID NO: 393.

In some embodiments, the anti-GPC3 antibody moiety comprises: a) a $V_H$ comprising the amino acid sequence of SEQ ID NO: 343, or a variant thereof having at least about 80% (including for example at least about any of 80%, 85%, 90%, 95%, 96%, 97%, 98%, or 99%) sequence identity to SEQ ID NO: 343; and b) a $V_L$ comprising the amino acid sequence of SEQ ID NO: 394, or a variant thereof having at least about 80% (including for example at least about any of 80%, 85%, 90%, 95%, 96%, 97%, 98%, or 99%) sequence identity to SEQ ID NO: 394. In some embodiments, the anti-GPC3 antibody moiety comprises: a) a $V_H$ comprising the amino acid sequence of SEQ ID NO: 343; and b) a $V_L$ comprising the amino acid sequence of SEQ ID NO: 394. In some embodiments, the anti-GPC3 antibody moiety comprises the HC-CDRs of a $V_H$ comprising the amino acid sequence of SEQ ID NO: 343, and the LC-CDRs of a $V_L$ comprising the amino acid sequence of SEQ ID NO: 394.

In some embodiments, the anti-GPC3 antibody moiety comprises: a) a $V_H$ comprising the amino acid sequence of SEQ ID NO: 344, or a variant thereof having at least about 80% (including for example at least about any of 80%, 85%, 90%, 95%, 96%, 97%, 98%, or 99%) sequence identity to SEQ ID NO: 344; and b) a $V_L$ comprising the amino acid sequence of SEQ ID NO: 395, or a variant thereof having at least about 80% (including for example at least about any of 80%, 85%, 90%, 95%, 96%, 97%, 98%, or 99%) sequence identity to SEQ ID NO: 395. In some embodiments, the anti-GPC3 antibody moiety comprises: a) a $V_H$ comprising the amino acid sequence of SEQ ID NO: 344; and b) a $V_L$ comprising the amino acid sequence of SEQ ID NO: 395. In some embodiments, the anti-GPC3 antibody moiety comprises the HC-CDRs of a $V_H$ comprising the amino acid sequence of SEQ ID NO: 344, and the LC-CDRs of a $V_L$ comprising the amino acid sequence of SEQ ID NO: 395.

In some embodiments, the anti-GPC3 antibody moiety comprises: a) a $V_H$ comprising the amino acid sequence of SEQ ID NO: 345, or a variant thereof having at least about 80% (including for example at least about any of 80%, 85%, 90%, 95%, 96%, 97%, 98%, or 99%) sequence identity to SEQ ID NO: 345; and b) a $V_L$ comprising the amino acid sequence of SEQ ID NO: 396, or a variant thereof having at least about 80% (including for example at least about any of 80%, 85%, 90%, 95%, 96%, 97%, 98%, or 99%) sequence identity to SEQ ID NO: 396. In some embodiments, the anti-GPC3 antibody moiety comprises: a) a $V_H$ comprising the amino acid sequence of SEQ ID NO: 345; and b) a $V_L$ comprising the amino acid sequence of SEQ ID NO: 396. In some embodiments, the anti-GPC3 antibody moiety comprises the HC-CDRs of a $V_H$ comprising the amino acid sequence of SEQ ID NO: 345, and the LC-CDRs of a $V_L$ comprising the amino acid sequence of SEQ ID NO: 396.

In some embodiments, the anti-GPC3 antibody moiety comprises: a) a $V_H$ comprising the amino acid sequence of SEQ ID NO: 346, or a variant thereof having at least about 80% (including for example at least about any of 80%, 85%, 90%, 95%, 96%, 97%, 98%, or 99%) sequence identity to SEQ ID NO: 346; and b) a $V_L$ comprising the amino acid sequence of SEQ ID NO: 397, or a variant thereof having at least about 80% (including for example at least about any of 80%, 85%, 90%, 95%, 96%, 97%, 98%, or 99%) sequence identity to SEQ ID NO: 397. In some embodiments, the anti-GPC3 antibody moiety comprises: a) a $V_H$ comprising the amino acid sequence of SEQ ID NO: 346; and b) a $V_L$ comprising the amino acid sequence of SEQ ID NO: 397. In some embodiments, the anti-GPC3 antibody moiety comprises the HC-CDRs of a $V_H$ comprising the amino acid sequence of SEQ ID NO: 346, and the LC-CDRs of a $V_L$ comprising the amino acid sequence of SEQ ID NO: 397.

In some embodiments, the anti-GPC3 antibody moiety comprises: a) a $V_H$ comprising the amino acid sequence of SEQ ID NO: 347, or a variant thereof having at least about 80% (including for example at least about any of 80%, 85%, 90%, 95%, 96%, 97%, 98%, or 99%) sequence identity to SEQ ID NO: 347; and b) a $V_L$ comprising the amino acid sequence of SEQ ID NO: 398, or a variant thereof having at least about 80% (including for example at least about any of 80%, 85%, 90%, 95%, 96%, 97%, 98%, or 99%) sequence identity to SEQ ID NO: 398. In some embodiments, the anti-GPC3 antibody moiety comprises: a) a $V_H$ comprising the amino acid sequence of SEQ ID NO: 347; and b) a $V_L$ comprising the amino acid sequence of SEQ ID NO: 398. In some embodiments, the anti-GPC3 antibody moiety comprises the HC-CDRs of a $V_H$ comprising the amino acid sequence of SEQ ID NO: 347, and the LC-CDRs of a $V_L$ comprising the amino acid sequence of SEQ ID NO: 398.

In some embodiments, the anti-GPC3 antibody moiety comprises: a) a $V_H$ comprising the amino acid sequence of SEQ ID NO: 348, or a variant thereof having at least about 80% (including for example at least about any of 80%, 85%, 90%, 95%, 96%, 97%, 98%, or 99%) sequence identity to SEQ ID NO: 348; and b) a $V_L$ comprising the amino acid sequence of SEQ ID NO: 399, or a variant thereof having at least about 80% (including for example at least about any of 80%, 85%, 90%, 95%, 96%, 97%, 98%, or 99%) sequence identity to SEQ ID NO: 399. In some embodiments, the anti-GPC3 antibody moiety comprises: a) a $V_H$ comprising the amino acid sequence of SEQ ID NO: 348; and b) a $V_L$ comprising the amino acid sequence of SEQ ID NO: 399. In some embodiments, the anti-GPC3 antibody moiety comprises the HC-CDRs of a $V_H$ comprising the amino acid sequence of SEQ ID NO: 348, and the LC-CDRs of a $V_L$ comprising the amino acid sequence of SEQ ID NO: 399.

In some embodiments, the anti-GPC3 antibody moiety comprises: a) a $V_H$ comprising the amino acid sequence of SEQ ID NO: 349, or a variant thereof having at least about 80% (including for example at least about any of 80%, 85%, 90%, 95%, 96%, 97%, 98%, or 99%) sequence identity to SEQ ID NO: 349; and b) a $V_L$ comprising the amino acid sequence of SEQ ID NO: 400, or a variant thereof having at least about 80% (including for example at least about any of 80%, 85%, 90%, 95%, 96%, 97%, 98%, or 99%) sequence identity to SEQ ID NO: 400. In some embodiments, the anti-GPC3 antibody moiety comprises: a) a $V_H$ comprising the amino acid sequence of SEQ ID NO: 349; and b) a $V_L$ comprising the amino acid sequence of SEQ ID NO: 400. In some embodiments, the anti-GPC3 antibody moiety comprises the HC-CDRs of a $V_H$ comprising the amino acid sequence of SEQ ID NO: 349, and the LC-CDRs of a $V_L$ comprising the amino acid sequence of SEQ ID NO: 400.

In some embodiments, the anti-GPC3 antibody moiety comprises: a) a $V_H$ comprising the amino acid sequence of SEQ ID NO: 350, or a variant thereof having at least about 80% (including for example at least about any of 80%, 85%, 90%, 95%, 96%, 97%, 98%, or 99%) sequence identity to SEQ ID NO: 350; and b) a $V_L$ comprising the amino acid sequence of SEQ ID NO: 401, or a variant thereof having at least about 80% (including for example at least about any of 80%, 85%, 90%, 95%, 96%, 97%, 98%, or 99%) sequence identity to SEQ ID NO: 401. In some embodiments, the anti-GPC3 antibody moiety comprises: a) a $V_H$ comprising the amino acid sequence of SEQ ID NO: 350; and b) a $V_L$ comprising the amino acid sequence of SEQ ID NO: 401. In some embodiments, the anti-GPC3 antibody moiety comprises the HC-CDRs of a $V_H$ comprising the amino acid sequence of SEQ ID NO: 350, and the LC-CDRs of a $V_L$ comprising the amino acid sequence of SEQ ID NO: 401.

In some embodiments, the anti-GPC3 antibody moiety comprises: a) a $V_H$ comprising the amino acid sequence of SEQ ID NO: 351, or a variant thereof having at least about 80% (including for example at least about any of 80%, 85%, 90%, 95%, 96%, 97%, 98%, or 99%) sequence identity to SEQ ID NO: 351; and b) a $V_L$ comprising the amino acid sequence of SEQ ID NO: 402, or a variant thereof having at least about 80% (including for example at least about any of 80%, 85%, 90%, 95%, 96%, 97%, 98%, or 99%) sequence identity to SEQ ID NO: 402. In some embodiments, the anti-GPC3 antibody moiety comprises: a) a $V_H$ comprising the amino acid sequence of SEQ ID NO: 351; and b) a $V_L$ comprising the amino acid sequence of SEQ ID NO: 402. In some embodiments, the anti-GPC3 antibody moiety comprises the HC-CDRs of a $V_H$ comprising the amino acid sequence of SEQ ID NO: 351, and the LC-CDRs of a $V_L$ comprising the amino acid sequence of SEQ ID NO: 402.

In some embodiments, the anti-GPC3 antibody moiety comprises: a) a $V_H$ comprising the amino acid sequence of SEQ ID NO: 352, or a variant thereof having at least about 80% (including for example at least about any of 80%, 85%, 90%, 95%, 96%, 97%, 98%, or 99%) sequence identity to SEQ ID NO: 352; and b) a $V_L$ comprising the amino acid sequence of SEQ ID NO: 403, or a variant thereof having at least about 80% (including for example at least about any of 80%, 85%, 90%, 95%, 96%, 97%, 98%, or 99%) sequence identity to SEQ ID NO: 403. In some embodiments, the anti-GPC3 antibody moiety comprises: a) a $V_H$ comprising the amino acid sequence of SEQ ID NO: 352; and b) a $V_L$ comprising the amino acid sequence of SEQ ID NO: 403. In some embodiments, the anti-GPC3 antibody moiety comprises the HC-CDRs of a $V_H$ comprising the amino acid sequence of SEQ ID NO: 352, and the LC-CDRs of a $V_L$ comprising the amino acid sequence of SEQ ID NO: 403.

In some embodiments, the anti-GPC3 antibody moiety comprises: a) a $V_H$ comprising the amino acid sequence of SEQ ID NO: 353, or a variant thereof having at least about 80% (including for example at least about any of 80%, 85%, 90%, 95%, 96%, 97%, 98%, or 99%) sequence identity to SEQ ID NO: 353; and b) a $V_L$ comprising the amino acid sequence of SEQ ID NO: 404, or a variant thereof having at least about 80% (including for example at least about any of 80%, 85%, 90%, 95%, 96%, 97%, 98%, or 99%) sequence identity to SEQ ID NO: 404. In some embodiments, the anti-GPC3 antibody moiety comprises: a) a $V_H$ comprising the amino acid sequence of SEQ ID NO: 353; and b) a $V_L$ comprising the amino acid sequence of SEQ ID NO: 404. In some embodiments, the anti-GPC3 antibody moiety comprises the HC-CDRs of a $V_H$ comprising the amino acid sequence of SEQ ID NO: 353, and the LC-CDRs of a $V_L$ comprising the amino acid sequence of SEQ ID NO: 404.

In some embodiments, the anti-GPC3 antibody moiety comprises: a) a $V_H$ comprising the amino acid sequence of SEQ ID NO: 354, or a variant thereof having at least about 80% (including for example at least about any of 80%, 85%, 90%, 95%, 96%, 97%, 98%, or 99%) sequence identity to SEQ ID NO: 354; and b) a $V_L$ comprising the amino acid sequence of SEQ ID NO: 405, or a variant thereof having at least about 80% (including for example at least about any of 80%, 85%, 90%, 95%, 96%, 97%, 98%, or 99%) sequence identity to SEQ ID NO: 405. In some embodiments, the anti-GPC3 antibody moiety comprises: a) a $V_H$ comprising the amino acid sequence of SEQ ID NO: 354; and b) a $V_L$ comprising the amino acid sequence of SEQ ID NO: 405. In some embodiments, the anti-GPC3 antibody moiety comprises the HC-CDRs of a $V_H$ comprising the amino acid sequence of SEQ ID NO: 354, and the LC-CDRs of a $V_L$ comprising the amino acid sequence of SEQ ID NO: 405.

In some embodiments, the anti-GPC3 antibody moiety comprises: a) a $V_H$ comprising the amino acid sequence of SEQ ID NO: 355, or a variant thereof having at least about 80% (including for example at least about any of 80%, 85%, 90%, 95%, 96%, 97%, 98%, or 99%) sequence identity to SEQ ID NO: 355; and b) a $V_L$ comprising the amino acid sequence of SEQ ID NO: 406, or a variant thereof having at least about 80% (including for example at least about any of 80%, 85%, 90%, 95%, 96%, 97%, 98%, or 99%) sequence identity to SEQ ID NO: 406. In some embodiments, the anti-GPC3 antibody moiety comprises: a) a $V_H$ comprising the amino acid sequence of SEQ ID NO: 355; and b) a $V_L$ comprising the amino acid sequence of SEQ ID NO: 406. In some embodiments, the anti-GPC3 antibody moiety comprises the HC-CDRs of a $V_H$ comprising the amino acid sequence of SEQ ID NO: 355, and the LC-CDRs of a $V_L$ comprising the amino acid sequence of SEQ ID NO: 406.

In some embodiments, the anti-GPC3 antibody moiety comprises: a) a $V_H$ comprising the amino acid sequence of SEQ ID NO: 356, or a variant thereof having at least about 80% (including for example at least about any of 80%, 85%, 90%, 95%, 96%, 97%, 98%, or 99%) sequence identity to SEQ ID NO: 356; and b) a $V_L$ comprising the amino acid sequence of SEQ ID NO: 407, or a variant thereof having at least about 80% (including for example at least about any of 80%, 85%, 90%, 95%, 96%, 97%, 98%, or 99%) sequence identity to SEQ ID NO: 407. In some embodiments, the anti-GPC3 antibody moiety comprises: a) a $V_H$ comprising the amino acid sequence of SEQ ID NO: 356; and b) a $V_L$ comprising the amino acid sequence of SEQ ID NO: 407. In some embodiments, the anti-GPC3 antibody moiety comprises the HC-CDRs of a $V_H$ comprising the amino acid sequence of SEQ ID NO: 356, and the LC-CDRs of a $V_L$ comprising the amino acid sequence of SEQ ID NO: 407.

In some embodiments, the anti-GPC3 antibody moiety comprises: a) a $V_H$ comprising the amino acid sequence of SEQ ID NO: 357, or a variant thereof having at least about 80% (including for example at least about any of 80%, 85%, 90%, 95%, 96%, 97%, 98%, or 99%) sequence identity to SEQ ID NO: 357; b) a $V_L$ comprising the amino acid sequence of SEQ ID NO: 408, or a variant thereof having at least about 80% (including for example at least about any of 80%, 85%, 90%, 95%, 96%, 97%, 98%, or 99%) sequence identity to SEQ ID NO: 408. In some embodiments, the anti-GPC3 antibody moiety comprises: a) a $V_H$ comprising the amino acid sequence of SEQ ID NO: 357; and b) a $V_L$ comprising the amino acid sequence of SEQ ID NO: 408. In some embodiments, the anti-GPC3 antibody moiety comprises the HC-CDRs of a $V_H$ comprising the amino acid sequence of SEQ ID NO: 357, and the LC-CDRs of a $V_L$ comprising the amino acid sequence of SEQ ID NO: 408.

In some embodiments, the anti-GPC3 antibody moiety competes for binding to a target GPC3 (e.g., nGPC3 and/or sGPC3) with a second anti-GPC3 antibody moiety according to any of the anti-GPC3 antibody moieties described herein. In some embodiments, the anti-GPC3 antibody moiety binds to the same, or substantially the same, epitope as the second anti-GPC3 antibody moiety. In some embodiments, binding of the anti-GPC3 antibody moiety to the target GPC3 inhibits binding of the second anti-GPC3 antibody moiety to the target GPC3 by at least about 70% (such as by at least about any of 75%, 80%, 85%, 90%, 95%, 98% or 99%), or vice versa. In some embodiments, the anti-GPC3 antibody moiety and the second anti-GPC3 antibody moiety cross-compete for binding to the target GPC3, i.e., each of the anti-GPC3 antibody moieties competes with the other for binding to the target GPC3.

In some embodiments, there is provided an anti-GPC3 construct (such as an isolated anti-GPC3 construct) comprising an anti-GPC3 antibody moiety specifically recognizing a cell surface-bound GPC3, wherein the anti-nGPC3 antibody moiety can be any one of the anti-nGPC3 antibody moieties described herein. In some embodiments, there is provided an anti-GPC3 construct (such as an isolated anti-GPC3 construct) comprising an anti-GPC3 antibody moiety specifically recognizing GPC3 (e.g., nGPC3 and/or sGPC3), wherein the anti-GPC3 antibody moiety can be any one of the anti-GPC3 antibody moieties described herein.

For example, in some embodiments, there is provided an anti-GPC3 construct (such as an isolated anti-GPC3 construct) comprising an anti-GPC3 antibody moiety specifically recognizing a cell surface-bound GPC3 (referred to herein as "anti-nGPC3 antibody moiety"; e.g., the binding affinity of the antibody moiety to the cell surface-bound GPC3 is higher than that to a soluble GPC3, or the antibody moiety specifically recognizes a cell surface-bound GPC3 at a high binding affinity and binds to a soluble GPC3 at a low binding affinity). In some embodiments, the anti-nGPC3 antibody moiety specifically recognizes an epitope within human GPC3 comprising the amino acid sequence of SEQ ID NO: 460. In some embodiments, the anti-nGPC3 antibody moiety specifically recognizes an epitope within the amino acid sequence of SEQ ID NO: 461. In some embodiments, the anti-nGPC3 antibody moiety specifically recognizes an epitope within the amino acid sequence of SEQ ID NO: 462. In some embodiments, the anti-nGPC3 antibody moiety specifically recognizes an epitope within the amino acid sequence of SEQ ID NO: 463. In some embodiments, the anti-nGPC3 antibody moiety specifically recognizes an epitope within the N-terminal fragment of GPC3. In some embodiments, the anti-nGPC3 antibody moiety specifically recognizes an epitope within amino acids 1-358 of SEQ ID NO: 460 (SEQ ID NO: 468). In some embodiments, the anti-nGPC3 antibody moiety specifically recognizes an epitope within the amino acid sequence of SEQ ID NO: 464. In some embodiments, the anti-nGPC3 antibody moiety specifically recognizes an epitope within the C-terminal fragment of GPC3. In some embodiments, the anti-nGPC3 antibody moiety specifically recognizes an epitope within amino acids 359-560 of SEQ ID NO: 460 (SEQ ID NO: 465). In some embodiments, the anti-nGPC3 antibody moiety specifically recognizes an epitope within amino acids 359-580 of SEQ ID NO: 460 (SEQ ID NO: 466). In some embodiments, the anti-nGPC3 antibody moiety specifically recognizes an epitope within the C-terminal fragment of GPC3 lacking heparin sulfate side chain. In some embodiments, the anti-nGPC3 antibody moiety specifically recognizes an epitope within amino acids 510-560 of SEQ ID NO: 460 (SEQ ID NO: 467). In some embodiments, the anti-nGPC3 antibody moiety specifically recognizes an epitope spanning the Furin cleavage site at amino acids $R^{358}/S^{359}$ of SEQ ID NO: 460. In some embodiments, the anti-nGPC3 antibody moiety can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460). In some embodiments, the anti-nGPC3 antibody moiety specifically recognizes an epitope within the C-terminal fragment of GPC3 lacking heparin sulfate side chain. In some embodiments, there is provided an anti-GPC3 construct (such as an isolated anti-GPC3 construct) comprising an anti-nGPC3 antibody moiety that competes for binding to nGPC3 with any one of the anti-GPC3 constructs described herein. In some embodiments, there is provided an anti-GPC3 construct (such as an isolated anti-GPC3 construct) comprising an anti-nGPC3 antibody moiety that specifically binds to the same, or substantially the same, nGPC3 epitope competitively with any one of the anti-GPC3 constructs described herein. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the anti-GPC3 construct is non-naturally occurring. In some embodiments, the anti-GPC3 construct is a Fab, a Fab', a F(ab')2, an Fv, or an scFv. In some embodiments, the anti-GPC3 construct is a Fab or a Fab'. In some embodiments, the anti-GPC3 construct is an scFv. In some embodiments, the anti-GPC3 construct comprising an anti-GPC3 antibody moiety fused to an Fc fragment (e.g., IgG1 Fc fragment) optionally via a linker. In some embodiments, the anti-GPC3 construct is a full-length antibody (e.g., monoclonal antibody). In some embodiments, the anti-GPC3 construct is a multi-specific (such as bispecific) molecule, such as tandem di-scFv anti-GPC3 T cell engager (tandem di-scFv anti-GPC3×CD3ε). In some embodiments, the anti-GPC3 construct is a CAR. In some embodiments, the anti-GPC3 construct is a caTCR. In some embodiments, the anti-GPC3 construct is an immunoconjugate. In some embodiments, the anti-GPC3 construct is monospecific. In some embodiments, the anti-GPC3 construct is multispecific (e.g., bispecific). In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-nGPC3 antibody moiety is chimeric, human, partially humanized, fully humanized, or semi-synthetic.

In some embodiments, there is provided an anti-GPC3 construct (such as an isolated anti-GPC3 construct) comprising an anti-GPC3 antibody moiety specifically recognizing a cell surface-bound GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions. In some embodiments, there is provided an anti-GPC3 construct (such as an isolated anti-GPC3 construct) comprising an anti-GPC3 antibody moiety specifically recognizing a cell surface-bound GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, there is provided an anti-GPC3 construct (such as an isolated anti-GPC3 construct) comprising an anti-GPC3 antibody moiety specifically recognizing a cell surface-bound GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286. In some embodiments, there is provided an anti-GPC3 construct (such as an isolated anti-GPC3 construct) comprising an anti-GPC3 antibody moiety specifically recognizing a cell surface-bound GPC3, comprising: i) a $V_H$ comprising the amino acid sequence of any one of SEQ ID NOs: 307-337, or a variant thereof having at least about 80% (including for example at least about any of 80%, 85%, 90%, 95%, 96%, 97%, 98%, or 99%) sequence identity to any one of SEQ ID NOs: 307-337; and ii) a $V_L$ comprising the amino acid sequence of any one of SEQ ID NOs: 358-388, or a variant thereof having at least about 80% (including for example at least about any of 80%, 85%, 90%, 95%, 96%, 97%, 98%, or 99%) sequence identity to any one of SEQ ID NOs: 358-388. In some embodiments, there is provided an anti-GPC3 construct (such as an isolated anti-GPC3 construct) comprising an anti-GPC3 antibody moiety specifically recognizing a cell surface-bound GPC3, comprising: i) a $V_H$ comprising the amino acid sequence of any one of SEQ ID NOs: 307-337; and ii) a $V_L$ comprising the amino acid sequence of any one of SEQ ID NOs: 358-388. In some embodiments, there is provided an anti-GPC3 construct (such as an isolated anti-GPC3 construct) comprising an anti-GPC3 antibody moiety specifically recognizing a cell surface-bound GPC3, comprising the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388. In some embodiments, there is provided an anti-GPC3 construct (such as an isolated anti-GPC3 construct) comprising an anti-nGPC3 antibody moiety that competes for binding to nGPC3 with any one of the anti-GPC3 constructs described herein. In some embodiments, there is provided an anti-GPC3 construct (such as an isolated anti-GPC3 construct) comprising an anti-nGPC3 antibody moiety that specifically binds to the same, or substantially the same, nGPC3 epitope competitively with any one of the anti-GPC3 constructs described herein. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the anti-GPC3 construct is non-naturally occurring. In some embodiments, the anti-GPC3 construct is a Fab, a Fab', a F(ab')2, an Fv, or an scFv. In some embodiments, the anti-GPC3 construct is a Fab or a Fab'. In some embodiments, the anti-GPC3 construct is an scFv. In some embodiments, the anti-GPC3 construct comprising an anti-GPC3 antibody moiety fused to an Fc fragment (e.g., IgG1 Fc fragment) optionally via a linker. In some embodiments, the anti-GPC3 construct is a full-length antibody (e.g., monoclonal antibody). In some embodiments, the anti-GPC3 construct is a multi-specific (such as bispecific) molecule, such as tandem di-scFv anti-GPC3 T cell engager (tandem di-scFv anti-GPC3×CD3ε). In some embodiments, the anti-GPC3 construct is a CAR. In some embodiments, the anti-GPC3 construct is a caTCR. In some embodiments, the anti-GPC3 construct is an immunoconjugate. In some embodiments, the anti-GPC3 construct is monospecific. In some embodiments, the anti-GPC3 construct is multispecific (e.g., bispecific). In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-nGPC3 antibody moiety is chimeric, human, partially humanized, fully humanized, or semi-synthetic.

In some embodiments, there is provided an anti-GPC3 construct (such as an isolated anti-GPC3 construct) comprising an anti-GPC3 antibody moiety specifically recognizing GPC3 (e.g., nGPC3 and/or sGPC3). In some embodiments, there is provided an anti-GPC3 construct (such as an isolated anti-GPC3 construct) comprising an anti-GPC3 antibody moiety specifically recognizing GPC3, comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions. In some embodiments, there is provided an anti-GPC3 construct (such as an isolated anti-GPC3 construct) comprising an anti-GPC3 antibody moiety specifically recognizing GPC3, comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; or a variant thereof comprising up to about 5 (such as about any of 1, 2, 3, 4, or 5) amino acid substitutions in the HC-CDR sequences; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306; or a variant thereof comprising up to about 5 (such as about any of 1, 2, 3, 4, or 5) amino acid substitutions in the LC-CDR sequences. In some embodiments, the amino acid substitutions are in HC-CDR1 or HC-CDR2. In some embodiments, the amino acid substitutions are in LC-CDR1 or LC-CDR2. In some embodiments, there is provided an anti-GPC3 construct (such as an isolated anti-GPC3 construct) comprising an anti-GPC3 antibody moiety specifically recognizing GPC3, comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306. In some embodiments, there is provided an anti-GPC3 construct (such as an isolated anti-GPC3 construct) comprising an anti-GPC3 antibody moiety specifically recognizing GPC3, comprising: i) a $V_H$ comprising the amino acid sequence of any one of SEQ ID NOs: 338-357, or a variant thereof having at least about 80% (including for example at least about any of 80%, 85%, 90%, 95%, 96%, 97%, 98%, or 99%) sequence identity to any one of SEQ ID NOs: 338-357; and ii) a $V_L$ comprising the amino acid sequence of any one of SEQ ID NOs: 389-408, or a variant thereof having at least about 80% (including for example at least about any of 80%, 85%, 90%, 95%, 96%, 97%, 98%, or 99%) sequence identity to any one of SEQ ID NOs: 389-408. In some embodiments, there is provided an anti-GPC3 construct (such as an isolated anti-GPC3 construct) comprising an anti-GPC3 antibody moiety specifically recognizing GPC3, comprising: i) a $V_H$ comprising the amino acid sequence of any one of SEQ ID NOs: 338-357; and ii) a $V_L$ comprising the amino acid sequence of any one of SEQ ID NOs: 389-408. In some embodiments, there is provided an anti-GPC3 construct (such as an isolated anti-GPC3 construct) comprising an anti-GPC3 antibody moiety specifically recognizing GPC3, comprising the HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408. In some embodiments, there is provided an anti-GPC3 construct (such as an isolated anti-GPC3 construct) comprising an anti-GPC3 antibody moiety that competes for binding to GPC3 (e.g., nGPC3 and/or sGPC3) with any one of the anti-GPC3 constructs described herein. In some embodiments, there is provided an anti-GPC3 construct (such as an isolated anti-GPC3 construct) comprising an anti-GPC3 antibody moiety that specifically binds to the same, or substantially the same, GPC3 epitope competitively with any one of the anti-GPC3 constructs described herein. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. n some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the anti-GPC3 construct is non-naturally occurring. In some embodiments, the anti-GPC3 construct is a Fab, a Fab', a F(ab')2, an Fv, or an scFv. In some embodiments, the anti-GPC3 construct is a Fab or a Fab'. In some embodiments, the anti-GPC3 construct is an scFv. In some embodiments, the anti-GPC3 construct comprising an anti-GPC3 antibody moiety fused to an Fc fragment (e.g., IgG1 Fc fragment) optionally via a linker. In some embodiments, the anti-GPC3 construct is a full-length antibody (e.g., monoclonal antibody). In some embodiments, the anti-GPC3 construct is a multi-specific (such as bispecific) molecule, such as tandem di-scFv anti-GPC3 T cell engager (tandem di-scFv anti-GPC3×CD3ε). In some embodiments, the anti-GPC3 construct is a CAR. In some embodiments, the anti-GPC3 construct is a caTCR. In some embodiments, the anti-GPC3 construct is an immunoconjugate. In some embodiments, the anti-GPC3 construct is monospecific. In some embodiments, the anti-GPC3 construct is multispecific (e.g., bispecific). In some embodiments, the $K_d$ of the binding between the anti-GPC3 antibody moiety and a target GPC3 (e.g., nGPC3 and/or sGPC3) is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-GPC3 antibody moiety and a non-target can be at least about 10 times (such as at least about 10, $10^2$, $10^3$, $10^4$, $10^5$, $10^6$, or $10^7$ times) of the $K_d$ of the binding between the anti-GPC3 antibody moiety and the target GPC3. In some embodiments, the $K_d$ of the binding between the anti-GPC3 antibody moiety and a non-target is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-GPC3 antibody moiety is chimeric, human, partially humanized, fully humanized, or semi-synthetic.

Anti-GPC3 scFv

The anti-GPC3 constructs (such as isolated anti-GPC3 constructs) in some embodiments are scFvs (hereinafter referred to as "anti-GPC3 scFv") comprising an anti-GPC3 antibody moiety described herein (targeting e.g., nGPC3 and/or sGPC3). In some embodiments, the anti-GPC3 scFv specifically recognizes a cell surface-bound GPC3. The anti-GPC3-scFv can comprise any one of the anti-GPC3 antibody moieties described herein (see "anti-GPC3 antibody moiety" section). The anti-GPC3 scFv (targeting e.g., nGPC3 and/or sGPC3) can have the configuration of (from N-terminus to C-terminus) $V_L$(GPC3)-L-$V_H$(GPC3), or $V_H$(GPC3)-L-$V_L$(GPC3), wherein L is a linker (such as peptide linker). In some embodiments, the anti-GPC3 scFv is chimeric, human, partially humanized, fully humanized, or semi-synthetic. Exemplary anti-GPC3 scFv sequences are shown in Tables 10-11.

TABLE 10 anti-GPC3 antibody moiety specifically recognizing cell surface-bound GPC3 scFv sequences
(CDR sequences are underlined; linker sequences are bolded)

| Clone No. | SEQ ID NO: | scFv |
|---|---|---|
| GPC3A-034 | 409 | QPVLTQPPSASGTPGQRVTISCSGSSSNIGSNNVIWYQQLPGAAPKWYSNHRRPSGVPDRFSGSRS GTSASLAISGLQSEDEADYYCAAWDDSLDGYLFGTGTKVTVLGSRGGGGSGGGGSGGGGSLEMAQV QLQQWGAGLLKPSETLSLTCAVYGGSFSGYYWSWIRQPPGKGLEWIGEINHSGSTNYNPSLKSRVTIS VDTSKNQFSLELSSVTAADTAVYYCARGYGGRFDYWGQGTLVTVSS |
| GPC3A-035 | 410 | QAVLTQPPSASGTPGQMVTISCSGTSSNIGSNYVFVVYQQLPGTAPKWYKNFQRPSGVPGRFSGSKS GTAASLAISGLRSEDEADYFCAAWDDALSGYVFGAGTKVTVLGSRGGGGSGGGGSGGGGSLEMAQV QLVQSGAEVKKPGASVKVSCKASGYTFTGYYMHWVRQAPGQGLEWMGWINPNSGGTNYAQKFQGR VTMTRDTSISTAYMELSRLRSDDTAVYYCARSWTSGFDYWGQGTLVTVSS |
| GPC3A-037 | 411 | QSVLTQPPSVSAAPGQRVTISCSGTRSNIGSDYVSVVYQHLPGTAPKLLVYGDNLRPSGIPDRFSASKS GTSATLGITGLQTGDEADYYCGTWDYTLNGVVFGGGTKLTVLGSRGGGGSGGGGSGGGGSLEMAQV QLVESGGGLVQPGGSLRLSCAASGFTFSSYAMSWVRQAPGKGLEWVSVIYSGGSSTYYADSVKGRFT ISRDNSKNTLYLQMNSLRAEDTAVYYCARTSYLNHGDYWGQGTLVTVSS |
| GPC3A-038 | 412 | QSVLTQPPSVSVAPGKTARITCGGNNIGSKSVHVVYQQKPGQAPVLVIYYDSDRPSGIPERFSGSNSGN TATLTISRVEAGDEADYYCQVWDSSSDHVVFGGGTKLTVLGSRGGGGSGGGGSGGGGSLEMAQVQL VQSGAEVKKPGASVKVSCKASGYTFTSYYMHWVRQAPGQGLEWMGIINPSGGSTSYAQKFQGRVTM TRDTSTSTVYMELSSLRSEDTAVYYCARKVTGYDSWGQGTLVTVSS |
| GPC3A-039 | 413 | SYVLTQPPSVSVAPGKTARITCGGNNIGSKSVHVVYQQKPGQAPVLVIYYDSDRPSGIPERFSGSNSGN TATLTISRVEAGDEADYYCQVWDSSSDHWVFGGGTKLTVLGSRGGGGSGGGGSGGGGSLEMAQVQ LVQSGGGLVHPGGSLRLSCAGSGFTFSSYAMHWVRQAPGKGLEWVSAIGTGGGTYYADSVKGRFTIS RDNAKNSLYLQMNSLRAEDTAVYYCARYGRKSIDAWGQGTLVTVSS |

TABLE 10-continued anti-GPC3 antibody moiety specifically recognizing cell surface-bound GPC3
scFv sequences
(CDR sequences are underlined; linker sequences are bolded)

| Clone No. | SEQ ID NO: | scFv |
|---|---|---|
| GPC3A-040 | 414 | LPVLTQPPSASGTPGQRVTISCSGS<u>SSNIGSNY</u>VYWYQQLPGTAPKWY<u>SNN</u>QRPSGVPDRFSGSKS GTSASLAISGLRSEDEADYYC<u>AAWDDSLSGYV</u>FGTGTKVTVLGSRGGGGSGGGGSGGGGSLEMAQV QLVQSGAEVKKPGASVTVSCKAS<u>GYTFTGYYMH</u>WVRQAPGQGLEWMGW<u>INPNSGGT</u>NYAQKFQGR VTMTRDTSISTAYMELSRLRSDDTAVYYC<u>ARRGYYGYDS</u>WGQGTLVTVSS |
| GPC3A-041 | 415 | QAVLTQPPSASQTPGQMVTISCSGT<u>SSNIGSNY</u>VFVVYQQLPGTAPKWY<u>KNF</u>QRPSGVPGRFSGSKS GTAASLAISGLRSEDEADYFC<u>AAWDDALSGYV</u>FGAGTKVTVLGSRGGGGSGGGGSGGGGSLEMAEV QLVQSGAEVKKPGASVKVSCKAS<u>GYTFTGYYMH</u>WVRQAPGQGLEWMGW<u>INPNSGGT</u>NYAQKFQGR VTMTRDTSISTAYMELSRLRSDDTAMYYC<u>ARSGKYYGDK</u>WGQGTLVTVSS |
| GPC3A-042 | 416 | SYVLTQPPSASGTPGQRVTISCFGS<u>SSDIGSNS</u>VFWYQQLPGAAPKWY<u>STQ</u>YRPSGVPDRFSGSKS GTSASLAISGLQSEDEAEYHC<u>ATWDDSLNGYV</u>FGSGTKVTVLGSRGGGGSGGGGSGGGGSLEMAQV QLQQSGAEVKKPGASVKVSCKAS<u>GYSFTGYY</u>VYWMRQAPGKGLEWMGW<u>MNPRSGGT</u>NYAQKFQG RVTMTRDTSISTAYMELSRLTSDDTAVYYC<u>ARSSYYWADS</u>WGQGTLVTVSS |
| GPC3A-043 | 417 | QSVLTQPPSASGTPGQRVTISCSGSSSNIGTNYVYWYQQLPGTAPKLIIYRNNQRPSGVPDRFSGSES GTSASLAISGLRSEDEADYYCAVWDDSLSGVVFGGGTKLTVLGSRGGGGSGGGGSGGGGSLEMAEV QLVQSGAEVKKPGATVKVSCKVS<u>GYTFTDYYMH</u>WVQQAPGKGLEWMGL<u>VDPEDGET</u>IYAEKFQGRV TITADTSTDTAYMELSSLRSEDTAVYYC<u>ARELRDVAYYPWGVEDF</u>WGQGTLVTVSS |
| GPC3A-044 | 418 | SYVLTQPPSVSVAPGKTARITCGGD<u>NIGYKG</u>VHWYQQKPGQAPVLVVY<u>DDS</u>DRPSGIPERFSGSNSGN TATLTISRVEAGDEADYYC<u>QVWDSSSDHVV</u>FGGGTKLTVLGSRGGGGSGGGGSGGGGSLEMAQVQL QQWGAGLLKPSETLSLTCAVY<u>GGSFSGYY</u>WSWIRQPPGKGLEWIGE<u>INHSGST</u>NYNPSLKSRVTISVD TSKNQFSLKLSSVTAADTAVYYC<u>ARYYVPYLSD</u>WGQGTLVTVSS |
| GPC3A-045 | 419 | QSVLTQPPSVSGTPGQRVIISCPGT<u>SNIGTNT</u>VNWYQFPGTAPKWY<u>SNN</u>QRPSGVPDRFSGSKSG TSASLAISGLQSEDEADYYC<u>AAWDDSLNGVV</u>FGGGTKLTVLGSRGGGGSGGGGSGGGGSLEMAQM QLVQSGGGLVKPGSLRLSCAAS<u>GFTFSDYYMS</u>WIRQAPGKGLEWVSY<u>ISSSGSTI</u>YYADSVKGRFTIS RDNAKNSLYLQMNSLRAEDTAVYYC<u>ARASDLYGD</u>WGQGTLVTVSS |
| GPC3A-046 | 420 | QAVLTQPPSVSGTPGQRVTISCSGS<u>SSNFGSNT</u>VHVVYQQVPGTAPKLLIF<u>SNT</u>QRPSEIPDRFSGSKS GTSASLAISGLQSEDEADYYC<u>AAWDDSLTGVV</u>FGGGTKLTVLGSRGGGGSGGGGSGGGGSLEMAQV QLVQSGAEVKKPGASVTVSCKAS<u>GYRFSNYG</u>VSWVRQAPGQGLEWMGW<u>ISGSNGNT</u>NYAQKFLGR VTMTDTSTTTAYMELSSLRSDDTAVYYC<u>ARGNRRYYSPIIDP</u>WGQGTLVTVSS |
| GPC3A-047 | 421 | LPVLTTQPPSASGTPGQRVTISCSGS<u>RSNIASND</u>VYWYQQLPGTAPKRLIY<u>KKN</u>QRPSGVPDRFSASKS GTSASLAISGLRSEDEADYYC<u>AAWDDNLSGYV</u>FGTGTKVTVLGSRGGGGSGGGGSGGGGSLEMAQV QLVQSGAEVKKPGASVKVSCKAP<u>GYTFTGYYMH</u>WVRQAPGQGLEWMGW<u>INPNSGGT</u>NYAQKFQGR VTMTRDTSISTAYMELSRLRSDDTAVYYC<u>ARSDYGSLYDK</u>WGQGTLVTVSS |
| GPC3A-048 | 422 | QPVLTQPPSVSVAPGKTARITCGGN<u>NIGSKS</u>VHVVYQQKPGQAPVLVIY<u>YDS</u>DRPSGIPERFSGSNSGN TATLTISRVEAGDEADFYC<u>QVWDSSSDRGV</u>FGGGTKLTVLGSRGGGGSGGGGSGGGGSLEMAEVQL VESGGGEVQPGRSLRLSCAAS<u>GFTFSSYAMH</u>WVRQAPGKGLEWVAV<u>ISYDGSNK</u>YYADSVKGRFTIS RDNSKNTLYLQMNSLRAEDTAVYYC<u>ARSSFVATDY</u>WGQGTLVTVSS |
| GPC3A-049 | 423 | QAVLTQPSSASGTPGQRVTISCSGGS<u>NIGSNY</u>VYWYQQLPGTAPKWY<u>RNN</u>QRPSGVPDRFSGSKS GTSASLAISGLRSEDEADYYC<u>AAWDDSLSGWV</u>FGGRTKLTVLGSRGGGGSGGGGSGGGGSLEMAQV QLVQSGAEVKEPGASVKVSCKAS<u>GYTFTGYYMH</u>WVRQAPGQGLEWMGW<u>INPNSGGT</u>NYAQKFQGR VTMTRDTSISTAYMELSRLRSDDTAVYYC<u>ARHGIGSMRSFDQ</u>WGQGTLVTVSS |
| GPC3A-050 | 424 | QAVLTQPSSASGTPGQRVTISCSGS<u>SSNIGSNT</u>VNVVYQQLPGTAPKWY<u>SNN</u>QRPSGVPDRFSGSKS GTSASLAISGLQSEDEADYYC<u>AAWDDSLNGPV</u>FGTGTKVTVLGSRGGGGSGGGGSGGGGSLEMAQI TLKESGAEVKKPGASVKVSCKAS<u>GYSFTGYY</u>VYWMRQAPGKGLEWMGW<u>MNPRSGGT</u>NYAQKFQGR VTMTRDTSISTAYMELSRLTSDDTATYYC<u>ARSGYRWLDV</u>WGQGTLVTVSS |
| GPC3A-051 | 425 | QAVLTQPSSASGAPGQRVTISCTGGS<u>SNIGAGY</u>DVHWYQQLPGTAPKWY<u>GNS</u>RPSGVPDRFSGSK SGTSASLAITGLQAEDEADYYC<u>QSYDSSLSGYV</u>FGTGTKVTVLGSRGGGGSGGGGSGGGGSLEMAQ VQLVQSGAEVKKPGSSVKVSCKAS<u>GGAFSSYA</u>ISWVRQAPGQGLEWMGG<u>IIPIFGTA</u>NYAQKFQGRVT ITADESTSTAYMELSSLRSEDTAVYYC<u>ARMLYLSGRYYWDS</u>WGQGTLVTVSS |
| GPC3A-052 | 426 | QAVLTQPSSASGTPGQRVTISCSGS<u>SSNIGSNY</u>VYVVYQQLSGTAPKWY<u>RNN</u>QRPSGVPDRFSGSKS GTSASLAISGLRSEDEADYYC<u>AAWDDSLSGYV</u>FGTGTKVTVLGSRGGGGSGGGGSGGGGSLEMAEV QLVESGAEVKKPGASVKVSCKAS<u>GYTFTGYYMH</u>WVRQAPGQGLEWMGW<u>INPNSGGT</u>NYAQKFQGR VTMTRDTSISTAYMELSRLRSDDTAVYYC<u>ARSHSSGYDK</u>WGQGTLVTVSS |
| GPC3A-053 | 427 | QSVLTQPPSASAAPGQRVTISCSGT<u>SSNIGSNY</u>VWWYQQLPGAAPRLLIY<u>GNS</u>NRPSGVPDRFSGSKS GTSASLAITGLQAEDEADYYC<u>QSYDSSLSGSNV</u>FGTGTKVTVLGSRGGGGSGGGGSGGGGSLEMAQ LQLQESGPGLVKPSETLSLTCTVS<u>GGSISSSSYY</u>WGWIRQPPGKGLEWIGS<u>IYYSGST</u>YYNPSLKSRVTI SVDTSKNQFSLKLSSVTAADTAVYYC<u>ARWWSGSYDT</u>WGQGTLVTVSS |

TABLE 10-continued anti-GPC3 antibody moiety specifically recognizing cell surface-bound GPC3 scFv sequences
(CDR sequences are underlined; linker sequences are bolded)

| Clone No. | SEQ ID NO: | scFv |
|---|---|---|
| GPC3A-054 | 428 | SYELTQPPSASGTPGQRVTISCSGS<u>SSNIGSNY</u>VYVVYQQLPGTAPKLLIY<u>RNN</u>QRPSGVPDRFSGSKS GTSASLAISGLRSEDEADYYC<u>AAWDDSLSGYV</u>FGTGTKVTVLGSRGGGGSGGGGSGGGGSLEMAQM QLVQSGAEVKKPGASVKVSCKAS<u>GYTFTSYGI</u>SWVRQAPGQGLEWMGW<u>ISAYNGNT</u>NYAQKLQGRV TMTTDTSTSTAYMELRSLRSDDTAVYYC<u>ARIPMYSGSSDY</u>WGQGTLVTVSS |
| GPC3A-055 | 429 | QPVLTQPPSVSVAPGKTARITCGGN<u>NIGSKS</u>VHVVYQQKPGQAPVLVIY<u>YDS</u>DRPSGIPERFSGSNSGN TATLTISRVEAGDEADYYC<u>QVWDSSSDHYV</u>FGTGTKVTVLGSRGGGGSGGGGSGGGGSLEMAQVQL VQSGAEVKKPGASVKVSCKAS<u>GYTFTSYY</u>MHWVRQAPGQGLEWMGI<u>INPSGGST</u>SYAQKFQGRVTM TRDTSTSTVYMELSSLRSEDTAVYYC<u>ARWHGGPYDY</u>WGQGTLVTVSS |
| GPC3A-056 | 430 | DIQLTQSPSSLSASVGDRVTITCRAS<u>QSISSYL</u>NVVYQQKPGKAPKLLIY<u>AAS</u>SLQSGVPSRFSGSGSGT DFTLTISSLQPEDFATYYC<u>QQSYSTPIT</u>FGQGTRLEIKRSRGGGGSGGGGSGGGGSLEMAQVQLQQS GAEVKKFGASVKVSCKAS<u>GYSFNDYY</u>IHWVRQAPGQGLEWMGW<u>INPNNGDT</u>KYEKKWQGRVTMTR DTSITTAYMELSSLRSDDTAVYYC<u>ARFSTHNWWWPTYDY</u>WGQGTLVTVSS |
| GPC3A-057 | 431 | EIVLTQSPSVSVAPGKTARITCGGN<u>NIGSKS</u>VHWYQQKPGQAPVLVIY<u>YDS</u>DRPSGIPERFSGSNSGNT ATLTISRVEAGDEADYYC<u>QVWDSSSDHVV</u>FGGGTKVEIKRSRGGGGSGGGGSGGGGSLEMAEVQLV ESGGGLIQPGGSLRLSCAAS<u>GFTFSSYA</u>MSWVRQAPGKGLEWVSA<u>ISGSGGST</u>YYADSVKGRFTISRD NSKNTLYLQMNSLRAEDTAVYYC<u>ARYNYMSSGFYDR</u>WGQGTLVTVSS |
| GPC3A-058 | 432 | QSVLTQPPSVSVAPGKTARITCGGN<u>NIGSKS</u>VHVVYQQKPGQAPVLVVY<u>DDS</u>DRPSGIPERFSGSNSGN TATLTISRVEAGDEADYYC<u>QVWDSSSDHVV</u>FGTGTKVTVLGSRGGGGSGGGGSGGGGSLEMAQVQLV QSGADVRKPGASVKVSCKAS<u>GYTFASHG</u>ISWVRQAPGQGLEWLGW<u>ISPYTGNT</u>NYAQKFQGRVTMA TDTSTSTAYMELRSLRSDDTAIYYC<u>ARGKRTLASCFDY</u>WGQGTLVTVSS |
| GPC3A-059 | 433 | SYVLTQPPSVSVAPGKTARITCGGN<u>NIGSKS</u>VYVVYQQKPGQAPVLVIY<u>YDS</u>DRPSGIPERFSGSNSGNT ATLTISRVEAGDEADYYC<u>QVWDSSSDHV</u>FGTGTKVTVLGSRGGGGSGGGGSGGGGSLEMAQVQLVQ SGAEVKKPGASVTVSCKAS<u>GYTFTRYGI</u>TWVRQAPGQGLEWMGW<u>ISAYSDKT</u>NYAQKLQGRVTMTTD ISTNTAYMELSSLRSEDTAVYYC<u>ARSRWSYMDV</u>WGQGTLVTVSS |
| GPC3A-060 | 434 | SYVLTQPPSVSVAPGKTARLTCGGN<u>NIGSES</u>VHVVYQQKPGQAPLLVVY<u>DDD</u>DRPSGIPERFSGSNSE DTATLTISGTQALDEAEYYC<u>QTWDSSTAI</u>FGTGTKLTVLGSRGGGGSGGGGSGGGGSLEMAQVQLVQ SGGEVKKPGASVKVSCKAS<u>GYTFNSYAI</u>SWVRQAPGQGLEWMGW<u>ISAYNGNT</u>NYAQKLQGRVTMTT DTSTNTAFMELRSLRSDDTAVYYC<u>AREGYGSWAMDQ</u>WGQGTLVTVSS |
| GPC3A-061 | 435 | QPVLTQPPSVSVAPGKTARITCGGN<u>NIGSKS</u>VHVVYQQKPGQAPVLVIY<u>YDS</u>DRPSGIPERFSGSNSGN TATLTISRVEAGDEADYYC<u>QVWDSSSDHYV</u>FGTGTKVTVLGSRGGGGSGGGGSGGGGSLEMAQVQL VQSGAEVKKPGASVKVSCKAS<u>GYTFTSYGI</u>SWVRQTPGQGLEWMGW<u>ISAYNGNT</u>NYAQKLQGRVTM TTDTSTSTAYMELSSLRSEDTAVYYC<u>ARKGSSQFDQ</u>WGQGTLVTVSS |
| GPC3A-062 | 436 | QSVLTQPPSVSGAPGQRVTISCTGS<u>SSNIGAGYD</u>VHWYQQLPGTAPKWY<u>GNS</u>NWPSGVPDRFSGSK SGTSASLAITGLRAEDEADYYC<u>QSYDSSLSGSYV</u>FGTGTKVTVLGSRGGGGSGGGGSGGGGSLEMA QMQLVQSGSELKKPGASVKVSCKAS<u>GTFSSYAI</u>SWVRQAPGQGLEWMGG<u>IIPKIGTA</u>NYAQKFQGR VTITADESTSTAYMELSSLRSEDTAMYYC<u>ARMYMDMGWGWGYWDW</u>WGQGTLVTVSS |
| GPC3A-063 | 437 | QTVVTQPPSASGTPGQRVTISCSGS<u>WSNIGSYT</u>VNWYQHLPGTAPKLLIS<u>GNN</u>QRPSGVPGRFSGSKS GTSASLAISGLQSEDEADYHCAAWDDNLNGVVFGGGTKLTVLGSRGGGGSGGGGSGGGGSLEMAQV QLVQSGAEVKKPGASVKVSCKAS<u>GYTFTSYY</u>MHWVRQAPGQGLEWMGI<u>INPSGGSA</u>SYAQKFQGRV TMTRDTSTSTVYMELSSLRSEDTAVYYC<u>ARDRLASDAFD</u>IWGQGTMVTVSS |
| GPC3A-064 | 438 | LPVLTQPPSLSVAPGKTARLTCGGN<u>NIGSKS</u>VHVVYHQKPGQAPVLVVY<u>DDT</u>DRPSGIPERFSGSNSGN TAALTISRVEVGDEADYYC<u>QVWDRSSAHWV</u>FGGGTKLTVLGSRGGGGSGGGGSGGGGSLEMAQMQ LVQSGAEVKKPGASVKVSCKAS<u>GYTFTIYGI</u>SWVRQAPGQGLEWMGW<u>ISPYNDNT</u>IYAQKVQGRVTM TTDTSTSTAYMELRSLRSDDTAVYYC<u>ARMGVGWGYAQDS</u>WGQGTLVTVSS |
| GPC3A-067 | 439 | QSVLTQPPSVSVAPGKTARITCGGN<u>NIGSKS</u>VHVVYQQKPGQAPVLVIY<u>YDS</u>DRPSGIPERFSGSNSGN TATLTISRVEAGDEADYYC<u>QVWDSSSDHVV</u>FGGGTKLTVLGSRGGGGSGGGGSGGGGSLEMAEVQL VQSGAEVKKPGSSVKVSCKAS<u>GGTFSSYAI</u>SWVRQAPGQGLEWMGR<u>IIPIFGIT</u>NYAQKFQGRVTITAD KSTSTAYMELSSLRSEDTAVYYC<u>ARGAEMSDY</u>WGQGTLVTVSS |

TABLE 11 anti-GPC3 antibody moiety scFv sequences
(CDR sequences are underlined; linker sequences are bolded)

| Clone No. | SEQ ID NO: | scFv |
|---|---|---|
| GPC3B-54 | 440 | QSVLTQPPSASGTPGQRVTISCSGS<u>NSNIGSDT</u>VNVVYQQLPGTAPKWY<u>RDN</u>QRPSGVPDRFSGSKSGT SASLAISGLQSEDEADYYC<u>TTWDDSLNGLV</u>FGGGTKVTVLGSRGGGGSGGGGSGGGGS LEMAEVQLVQ SGAEVKKPGASVKLSCKTS<u>GYTFIDYY</u>VYWVRQAPGQGLEWMGG<u>IIPIFGTA</u>NYAQKFQGRVTITADKSTS TAYMELSSLGSEDTAVYYC<u>ARERRYSSSPSDH</u>WGQGTLVTVSS |
| GPC3B-60 | 441 | SYVLTQPPSVSVSPGQTATIACSG<u>DNLENKF</u>VYVVYHQKPGQSPVLVMY<u>EDN</u>KRPSGIPERFSGSNSGNT AALTISGAQPMDEADYYC<u>QTWDSPTGLFV</u>FGTGTKVTVLGSRGGGGSGGGGSGGGGS LEMAEVQLVES GAEVKKPGASVKVSCKAS<u>GYTFTSYY</u>MHWVRQAPGQGLEWMG<u>IINPSGGST</u>SYAQKFQGRVTMTRDTS TSTVYMELSSLRSEDTAVYYC<u>ARSLYSQPYIDG</u>WSQGTLVTVSS |
| GPC3B-63 | 442 | EIVLTQSPLSLPVTPGEPASISCRSS<u>QSLLHSNGYNYLD</u>WYLQKPGQSPQLLIY<u>LGS</u>NRASGVPDRFSGSG SGTDFTLKISRVEAEDVGVYYC<u>MQALQTPPT</u>FGQGTKVEIKRSRGGGGSGGGGSGGGGS LEMAQVQLV QSGAEVKKPGASVKVSCKAS<u>GYTFTSYY</u>MHWVRQAPGQGLEWMG<u>IINPSGGST</u>SYAQKFQGRVTMTRD TSTSTVYMELSSLRSEDTAVYYC<u>ARSLHAMRWSQTMDS</u>WGQGTLVTVSS |
| GPC3B-66 | 443 | QAVLTQPPSVSVAPGKTASITCGG<u>NNIGSKS</u>VHWYQQKPGQAPVLVIY<u>YDS</u>DRPSGIPERFSGSNSGNTA TLTISRVEAG DEADYYC<u>QVWDSSSDHLYV</u>FGTGTKVTVLGSRGGGGSGGGGSGGGGS LEMAQVQLVQS GAEVKRPGASVKVSCKAS<u>GYTFIGQY</u>LHWVRQAPGQGLEWMGR<u>INPMTGVT</u>NYAPKFQGRVTMTRDTSI STGYMEISRLRSDDTAVYYC<u>ARFSSGYSRDT</u>WGQGTLVTVSS |
| GPC3B-68 | 444 | QSVLTQPPSVSAAPGQKVTISCSGS<u>SSNIGNNY</u>VSWYQQLPGTAPKLLIY<u>DNI</u>KRPSGIPDRFSGSKSGTS ATLG ITGLQTGDEADYYC<u>GTWDSSLSAGV</u>FGGGTKLTVLGSRGGGGSGGGGSGGGGS LEMAQVQLVQ SGAEVKKPGSSVKVSCKAS<u>GGTFSSYAI</u>SWVRQAPGQGLEWMGR<u>IIPILGIA</u>NYAQKFQGRVTITADKSTS TAYMELSSLRSEDTAVYYC<u>ARYGYEGHDT</u>WGQGTLVTVSS |
| GPC3B-71 | 445 | SYVLTQPPSVSVAPGKTARVTCGG<u>NNIGSKS</u>VHVVYQQKPGQAPVLVMY<u>YDS</u>DRPSGIPERFSGSNSGNT ATLTISSVEAGDEADYYC<u>QVWDSSSDHYV</u>FGTGTKVTVLGSRGGGGSGGGGSGGGGS LEMAEVQLVES GGGLVKPGGSLRLSCAAS<u>GFTFSRYT</u>MNWVRQAPGKGLEWVS<u>SISSSGSYI</u>YYADSVKGRFTISRDNAKN SLFLQMDSLRAEDTAVYYC<u>ARQGHMWYVPVDA</u>WGQGTLVTVSS |
| GPC3B-76 | 446 | QSVVTQPPSVSAAPGQKVTISCSGS<u>SSNIGNNY</u>VSWYQQLPGTAPKWY<u>DNN</u>KRPSGIPDRFSGSKSGT SATLG ITGLQTGDEAAYYC<u>GTWDSSLSAGV</u>FGTGTKVTVLGSRGGGGSGGGGSGGGGS LEMAQMQLV QSGAEVKEPGASVKVSCKAS<u>GYTFTDYY</u>IHWVRQAPGQGLEWMGW<u>INPNSGGT</u>NYAQKFQGRVTMTR DTSISTAYMELSRLRSDDTAVYYC<u>ARNYD</u>WGQGTLVTVSS |
| GPC3B-78 | 447 | LPVLTQPPSVSVSPGQTASITCSGD<u>KLGDKY</u>AYVVYQQKPGQSPVLVIY<u>QDN</u>KRPSGIPERFSGSNSGNTA TLTISGTQAMDAADYYC<u>QTWDRSTYV</u>FGTGTKVTVLGSRGGGGSGGGGSGGGGS LEMAQMQLVQSGA EVKKPGASVKVSCKAS<u>GYTFTSYY</u>MHWVRQAPGQGLEWMG<u>IINPSGGST</u>SYAQKFQGRVTMTRDTSTS TVYMELSSLRSEDTAVYYC<u>ARGYSSFFDS</u>WGQGTLVTVSS |
| GPC3B-80 | 448 | QAVLTQPPSASGTPGQRVTISCSGS<u>SSNIGSNT</u>VNVVYQQLPGTAPKWY<u>SNN</u>QRPSGVPDRFSGSKSGT SAYLAISGLQSEDEADYYC<u>AAWDDSLNGWGV</u>FGGGTKLTVLGSRGGGGSGGGGSGGGGS LEMAQVQL VQSGAEVKKPGSSVKVSCKAS<u>GGTLSRFAI</u>SWVRQAPGQGLEWMGG<u>IIPIFRTA</u>NYAQKFQGRVTITADE STSTAYMELSSLRSEDTAVYYC<u>ARMSKYYGSYSSYDE</u>WGQGTLVTVSS |
| GPC3B-81 | 449 | SYELTQPPSVSVAPGKTARITCGG<u>NNIGSKS</u>VHWYQQKPGQAPVLVIY<u>YDS</u>DRPSGIPERFSGSNSGNTA TLTISRVEAGDEADYYC<u>QVWDSSSDLLYV</u>FGTGTKVTVLGSRGGGGSGGGGSGGGGS LEMAEVQLVQS GAEVKKPGASVKVSCKAS<u>GYTFTGYY</u>MHWVRQAPGQGLEWMGR<u>INPNSGGT</u>NYAQKFQGRVTMTRDT SISTAYMELSRLRSDDTAVYYC<u>ARGLWDS</u>WGQGTLVTVSS |
| GPC3B-82 | 450 | QSVLTQPPSVSGAPGQRVTISCTGS<u>SSNIGAGFD</u>VHWYQQLPGTAPKWY<u>DNNN</u>RPSGVPDRFSGSKSD TSASLAITGLQAEDEADYYC<u>QSFDSSLSGWV</u>FGGGTKLTVLGSRGGGGSGGGGSGGGGSLEMAEVQLV QSGAEVKKPGESLKISCKGSGYSFTSYYMHWVRQAPGQGLEWMGI<u>INPSGGST</u>SYAQKFQGRVTMTRD TSTSTVYMEMSSLRSEDTAVYYC<u>ARYPVYMETSDFDS</u>WGSRYSGDRLL |
| GPC3B-85 | 451 | QAVLTQPPSASGTPGQRVTISCSGS<u>SSNIGSNT</u>VNVVYQQLPGTAPKWY<u>SNN</u>QRPSGVPDRFSGSKSGT SASLAISGLQSEDEADYYC<u>AAWDDSLNGYV</u>FGTGTKVTVLGSRGGGGSGGGGSGGGGS LEMAQVQLV QSGSELKKPGASVKVSCKAS<u>GYTFTSYAMN</u>WVRQAPGQGLEWMGW<u>INTNTGNPT</u>YAQGFTGRFVFSLD TSVSTAYLQISSLKAEDTAVYYC<u>ARSSLYWMGSKWSRQTDM</u>WGQGTLVTVSS |
| GPC3B-87 | 452 | DVVMTQSPLSLPVTPGEPASVSCRSS<u>QSLLHSNGYNYLD</u>VVYLQKPGQSPQLLIY<u>LGS</u>NRASGVPDRFSG SGSGTDFTLKISRVEAEDVGVYYC<u>MQALQTPWT</u>FGQGTKVEIKRSRGGGGSGGGGSGGGGS LEMAEVQ LVQSGAEVKRPGSSVKVSCQAS<u>GGTFGSYAI</u>SWVRQAPGQGLEWMGR<u>IIPVLGRT</u>KYAQKFQGRVTVTA DTSTSTVYMELTSLTSEDTAVYYC<u>ARTNDS</u>WGQGTLVTVSS |
| GPC3B-92 | 453 | QSVLTQPPSVSVSPGQTARITCSGE<u>TLAKRY</u>AHVVYQQKPGQAPVLLIY<u>RDT</u>ERPSGIPERFSGSSSGTT ITLTITGVQAEDEADYYC<u>QSADNSRTFV</u>FGPGTKVTVLGSRGGGGSGGGGSGGGGS LEMAEVQLVQSGAE VKKPGASVKVSCKAS<u>GYTFSNYY</u>MHWVRQAPGQGLEWMGI<u>INPSGGTT</u>TYAQKFQGRVTMTRDTSTST VYMELSSLRSEDTAVYYC<u>ARPSMVVTSSMGDV</u>WGQGTLVTVSS |

TABLE 11-continued anti-GPC3 antibody moiety scFv sequences
(CDR sequences are underlined; linker sequences are bolded)

| Clone No. | SEQ ID NO: | scFv |
|---|---|---|
| GPC3B-93 | 454 | NFMLTQPHSVSESPGKTVTISCTGS<u>SGSIASNY</u>VQVVYQQRPGSAPTTVIY<u>EDN</u>QRPSGVPDRFSGSIDSS<br>SNSASLTISGLKTEDEADYYC<u>QSYDSSNWV</u>FGGGTKLTVLGSRGGGGSGGGGSGGGGSLEMAEVQLVQ<br>SGAEVKKPGASVKVSCKAS<u>GYTFTSYY</u>MHWVRQAPGQGLEWMG<u>IINPSGGST</u>RYAQKFQGRVTMTRDT<br>STSTVYMELSSLRSEDTAVYYC<u>ARYTALKPRGIYSVDSW</u>GQGTLVTVSS |
| GPC3B-110 | 455 | QSVLTQPPSASGTPGQRVTVSCSGS<u>SSNIGSNT</u>VNWYQQLPGTAPKLLLY<u>SSN</u>QRPSGVPDRFSGSRSG<br>TSASLAISGLQSEDEADYYC<u>AAWDDSLNGPV</u>FGGGTKLTVLGSRGGGGSGGGGSGGGGSLEMAEVQLV<br>QSGAEVKKPGSSVKVSCQAS<u>GGTFTTYS</u>INWVRQAPGQGLEWMGG<u>IIPTFGTT</u>NYAQNFQDRVTISADES<br>TNTAYMELTSLRSEDTAVYYC<u>ARYYWRGGSGQGSVTSDY</u>WGQGTLVTVSS |
| GPC3B-113 | 456 | SYELTQPPSASGTPGQRVTISCSGS<u>SSNIGSNS</u>VSVVYQHLPGVAPKLLIY<u>SNN</u>QRPSGVPDRFSGSKTGT<br>SASLAISGLQSEDEGDYYC<u>AAWDDSLNGVL</u>FGGGTKLTVLGSRGGGGSGGGGSGGGGSLEMAQVQLV<br>QSGAEVKKPGASVKVSCKVS<u>GYTLTELS</u>MHWVRQAPGKGLEWMGG<u>FDPEDGETI</u>YAQKFQGRVTMTED<br>TSTDTAYMELSSLRSEDTAVYYC<u>ARYSGDY</u>WGQGTLVTVSS |
| GPC3B-115 | 457 | SYELTQPPSVSVAPGKTARITCGGN<u>NIGSKS</u>VHWYQQKPGQAPVLVVY<u>DDS</u>DRPSGIPERFSGSNSGNTA<br>TLTISRVEAG DEADYYC<u>QVWDSSSDPLYV</u>FGTGTKVTVLGSRGGGGSGGGGSGGGGSLEMAQVQLVQS<br>GAEVKRPGATIKVSCKTS<u>GYTFTAYY</u>THWVRQAPGQGLEWVGR<u>INANTGGT</u>DYAPKFRDRVIMTRDTSIS<br>TAYMELGRLTSEDTAVYYC<u>ARISGYHSSGWDY</u>WGQGTLVTVSS |
| GPC3B-119 | 458 | QSVVTQPPSVSAAPGQKVTISCSGS<u>SSNIGNNY</u>VSWYQQIPGTAPK<u>WYDNN</u>KRPSGIPDRFSGSRSGTS<br>ATLG ITGLQTGDEAHYYC<u>ATWDNSLSALI</u>FGGGTKVTVLGSRGGGGSGGGGSGGGGSLEMAQVQLVQS<br>GSELKKPGASVKVSCKAS<u>GYTFTSYA</u>MNWVRQAPGQGLEWMGW<u>INTNTGNPT</u>YAQGFTGRFVFSLDTS<br>VSTAYLQISSLKAEDTAVYYC<u>ARGYYGKYDK</u>WGQGTLVTVSS |
| GPC3B-125 | 459 | QSALTQPASVSGSPGQSITISCTGT<u>SSDVGGYNY</u>VSWFQQHPGKAPKLII<u>YEVS</u>NRPSGVSDRFSGSKSG<br>STASLTISGLQAEDEANYYC<u>SSYTSSTTVI</u>FGGGTKLTVLGSRGGGGSGGGGSGGGGSLEMAQMQLVQS<br>GSELKKPGASVKVSCKAS<u>GYTFTSYA</u>MNWVRQAPGQGLEWMGW<u>INTNTGNPT</u>YAQGFTGRFVFSLDTS<br>VSTAYLQISSLKAEDTAVYYC<u>ARQSHDEW</u>GQGTLVTVSS |

Linkers

See "Linkers" subsection under the "Anti-GPC3 Fc fusion protein" section below for all applicable linkers that can be used in the anti-GPC3 scFv described herein. In some embodiments, the linker comprises the amino acid sequence of SRGGGGSGGGGSGGGGSLEMA (SEQ ID NO: 473). In some embodiments, the linker is or comprises a (GGGGS)$_n$ sequence (SEQ ID NO: 471), wherein n is equal to 1, 2, 3, 4, 5, 6, 7, 8, 9, 10 or more. In some embodiments, the linker comprises the amino acid sequence of TSGGGGS (SEQ ID NO: 474). In some embodiments, the linker comprises the amino acid sequence of GEGTSTGSGGSGGSGGAD (SEQ ID NO: 490).

In some embodiments, there is provided an anti-GPC3 construct (e.g., isolated anti-GPC3 construct) comprising an scFv specifically recognizing a cell surface-bound GPC3 (referred to herein as "anti-nGPC3 scFv"; e.g., the binding affinity of the anti-nGPC3 scFv to the cell surface-bound GPC3 is higher than that to a soluble GPC3, or the anti-nGPC3 scFv specifically recognizes a cell surface-bound GPC3 at a high binding affinity and binds to a soluble GPC3 at a low binding affinity). In some embodiments, the anti-nGPC3-scFv specifically recognizes an epitope within human GPC3 comprising the amino acid sequence of SEQ ID NO: 460. In some embodiments, the anti-nGPC3-scFv specifically recognizes an epitope within the amino acid sequence of SEQ ID NO: 461. In some embodiments, the anti-nGPC3-scFv specifically recognizes an epitope within the amino acid sequence of SEQ ID NO: 462. In some embodiments, the anti-nGPC3-scFv specifically recognizes an epitope within the amino acid sequence of SEQ ID NO: 463. In some embodiments, the anti-nGPC3-scFv specifically recognizes an epitope within the N-terminal fragment of GPC3. In some embodiments, the anti-nGPC3-scFv specifically recognizes an epitope within amino acids 1-358 of SEQ ID NO: 460 (SEQ ID NO: 468). In some embodiments, the anti-nGPC3-scFv specifically recognizes an epitope within the amino acid sequence of SEQ ID NO: 464. In some embodiments, the anti-nGPC3-scFv specifically recognizes an epitope within the C-terminal fragment of GPC3. In some embodiments, the anti-nGPC3-scFv specifically recognizes an epitope within amino acids 359-560 of SEQ ID NO: 460 (SEQ ID NO: 465). In some embodiments, the anti-nGPC3-scFv specifically recognizes an epitope within amino acids 359-580 of SEQ ID NO: 460 (SEQ ID NO: 466). In some embodiments, the anti-nGPC3-scFv specifically recognizes an epitope within the C-terminal fragment of GPC3 lacking heparin sulfate side chain. In some embodiments, the anti-nGPC3-scFv specifically recognizes an epitope within amino acids 510-560 of SEQ ID NO: 460 (SEQ ID NO: 467). In some embodiments, the anti-nGPC3-scFv specifically recognizes an epitope spanning the Furin cleavage site at amino acids $R^{358}/S^{359}$ of SEQ ID NO: 460. In some embodiments, the anti-nGPC3-scFv can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460). In some embodiments, the anti-nGPC3-scFv specifically recognizes an epitope within the C-terminal fragment of GPC3 lacking heparin sulfate side chain. In some embodiments, there is provided an anti-GPC3 construct (such as an isolated anti-GPC3 construct) comprising an anti-nGPC3-scFv (e.g., the binding affinity of the anti-nGPC3-scFv to the cell surface-bound GPC3 is higher than that to a soluble GPC3, or the anti-nGPC3-scFv specifically recognizes a cell surface-bound GPC3 at a high binding affinity and binds to a soluble GPC3 at a low binding affinity) that competes for binding to nGPC3 with any one of the anti-GPC3 constructs described herein. In some embodiments, there is provided an anti-GPC3 construct (such as an isolated anti-GPC3 construct) comprising an anti-nGPC3-scFv (e.g., the binding affinity of the anti-nGPC3-scFv to the cell surface-bound GPC3 is higher than that to a soluble GPC3, or the anti-nGPC3-scFv specifically recognizes a cell surface-bound GPC3 at a high binding affinity and binds to a soluble GPC3 at a low binding affinity) that specifically binds to the same, or substantially the same, nGPC3 epitope competitively with any one of the anti-GPC3 constructs described herein. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the anti-GPC3 construct is non-naturally occurring. In some embodiments, the $K_d$ of the binding between the anti-nGPC3-scFv and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3-scFv and an sGPC3 can be at least about 10 times (such as at least about 10, $10^2$, $10^3$, $10^4$, $10^5$, $10^6$, or $10^7$ times) of the $K_d$ of the binding between the anti-nGPC3-scFv and nGPC3. In some embodiments, the $K_d$ of the binding between the anti-nGPC3-scFv and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-nGPC3-scFv is chimeric, human, partially humanized, fully humanized, or semi-synthetic. In some embodiments, the $V_H$ of the anti-nGPC3-scFv is N-terminal to the $V_L$ of the anti-nGPC3-scFv. In some embodiments, the $V_H$ of the anti-nGPC3-scFv is C-terminal to the $V_L$ of the anti-nGPC3-scFv. In some embodiments, the linker between $V_H$ and $V_L$ of the anti-nGPC3-scFv comprises the amino acid sequence of SRGGGGSGGGGSGGGGSLEMA (SEQ ID NO: 473). In some embodiments, the linker between $V_H$ and $V_L$ of the anti-nGPC3-scFv is or comprises a $(GGGGS)_n$ sequence (SEQ ID NO: 471), wherein n is equal to 1, 2, 3, 4, 5, 6, 7, 8, 9, 10 or more. In some embodiments, the linker between $V_H$ and $V_L$ of the anti-nGPC3-scFv comprises the amino acid sequence of GEGTSTGSGGSGGSGGAD (SEQ ID NO: 490). In some embodiments, the anti-nGPC3 scFv further comprises a tag (e.g., a peptide tag for purification purpose). In some embodiments, the tag is N-terminal to the anti-nGPC3 scFv. In some embodiments, the tag is C-terminal to the anti-nGPC3 scFv. In some embodiments, the tag comprises a His-tag and an HA-tag. In some embodiments, the tag comprises the amino acid sequence of TSGQAGQHHHHHHHGAYPYDVPDYAS (SEQ ID NO: 477).

In some embodiments, there is provided an anti-GPC3 construct (such as an isolated anti-GPC3 construct) comprising an anti-GPC3-scFv specifically recognizing a cell surface-bound GPC3. In some embodiments, there is provided an anti-GPC3 construct (such as an isolated anti-GPC3 construct) comprising an anti-GPC3-scFv specifically recognizing a cell surface-bound GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions. In some embodiments, there is provided an anti-GPC3 construct (such as an isolated anti-GPC3 construct) comprising an anti-GPC3-scFv specifically recognizing a cell surface-bound GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286. In some embodiments, there is provided an anti-GPC3 construct (such as an isolated anti-GPC3 construct) comprising an anti-GPC3-scFv specifically recognizing a cell surface-bound GPC3, comprising: i) a $V_H$ comprising the amino acid sequence of any one of SEQ ID NOs: 307-337; and ii) a $V_L$ comprising the amino acid sequence of any one of SEQ ID NOs: 358-388. In some embodiments, there is provided an anti-GPC3 construct (such as an isolated anti-GPC3 construct) comprising an anti-GPC3-scFv specifically recognizing a cell surface-bound GPC3, comprising the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388. In some embodiments, there is provided an anti-GPC3 construct (such as an isolated anti-GPC3 construct) comprising an anti-nGPC3-scFv that competes for binding to nGPC3 with any one of the anti-GPC3 constructs described herein. In some embodiments, there is provided an anti-GPC3 construct (such as an isolated anti-GPC3 construct) comprising an anti-nGPC3-scFv that specifically binds to the same, or substantially the same, nGPC3 epitope competitively with any one of the anti-GPC3 constructs described herein. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the anti-GPC3 construct is non-naturally occurring. In some embodiments, the $K_d$ of the binding between the anti-nGPC3-scFv and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3-scFv and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3-scFv and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-nGPC3-scFv is chimeric, human, partially humanized, fully humanized, or semi-synthetic. In some embodiments, the $V_H$ of the anti-nGPC3-scFv is N-terminal to the $V_L$ of the anti-nGPC3-scFv. In some embodiments, the $V_H$ of the anti-nGPC3-scFv is C-terminal to the $V_L$ of the anti-nGPC3-scFv. In some embodiments, the linker between $V_H$ and $V_L$ of the anti-nGPC3-scFv comprises the amino acid sequence of SRGGGGSGGGGSGGGGSLEMA (SEQ ID NO: 473). In some embodiments, the linker between $V_H$ and $V_L$ of the anti-nGPC3-scFv is or comprises a (GGGGS)$_n$ sequence (SEQ ID NO: 471), wherein n is equal to 1, 2, 3, 4, 5, 6, 7, 8, 9, 10 or more. In some embodiments, the linker between $V_H$ and $V_L$ of the anti-nGPC3-scFv comprises the amino acid sequence of GEGTSTGSGGSGGSGGAD (SEQ ID NO: 490). In some embodiments, there is provided an anti-GPC3 construct (such as an isolated anti-GPC3 construct) comprising an anti-GPC3-scFv specifically recognizing a cell surface-bound GPC3, wherein the anti-nGPC3 scFv comprises the amino acid sequence of any one of SEQ ID NOs: 409-439. In some embodiments, the anti-nGPC3 scFv further comprises a tag (e.g., a peptide tag for purification purpose). In some embodiments, the tag is N-terminal to the anti-nGPC3 scFv. In some embodiments, the tag is C-terminal to the anti-nGPC3 scFv. In some embodiments, the tag comprises a His-tag and an HA-tag. In some embodiments, the tag comprises the amino acid sequence of TSGQAGQHHHHHHHGAYPYDVPDYAS (SEQ ID NO: 477).

In some embodiments, there is provided an anti-GPC3 construct (such as an isolated anti-GPC3 construct) comprising an anti-GPC3-scFv specifically recognizing GPC3 (e.g., nGPC3 and/or sGPC3). In some embodiments, there is provided an anti-GPC3 construct (such as an isolated anti-GPC3 construct) comprising an anti-GPC3-scFv specifically recognizing GPC3 (e.g., nGPC3 and/or sGPC3), comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions. In some embodiments, there is provided an anti-GPC3 construct (such as an isolated anti-GPC3 construct) comprising an anti-GPC3-scFv specifically recognizing GPC3 (e.g., nGPC3 and/or sGPC3), comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306. In some embodiments, there is provided an anti-GPC3 construct (such as an isolated anti-GPC3 construct) comprising an anti-GPC3-scFv specifically recognizing GPC3 (e.g., nGPC3 and/or sGPC3), comprising: i) a $V_H$ comprising the amino acid sequence of any one of SEQ ID NOs: 338-357; and ii) a $V_L$ comprising the amino acid sequence of any one of SEQ ID NOs: 389-408. In some embodiments, there is provided an anti-GPC3 construct (such as an isolated anti-GPC3 construct) comprising an anti-GPC3-scFv specifically recognizing GPC3 (e.g., nGPC3 and/or sGPC3), comprising the HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408. In some embodiments, there is provided an anti-GPC3 construct (such as an isolated anti-GPC3 construct) comprising an anti-GPC3-scFv that competes for binding to GPC3 (e.g., nGPC3 and/or sGPC3) with any one of the anti-GPC3 constructs described herein. In some embodiments, there is provided an anti-GPC3 construct (such as an isolated anti-GPC3 construct) comprising an anti-GPC3-scFv that specifically binds to the same, or substantially the same, GPC3 epitope competitively with any one of the anti-GPC3 constructs described herein. In some embodiments, the anti-GPC3-scFv specifically recognizes a cell surface-bound GPC3. In some embodiments, the binding affinity of the anti-GPC3-scFv to a cell surface-bound GPC3 is higher than that to a soluble GPC3. In some embodiments, the anti-GPC3-scFv specifically recognizes a cell surface-bound GPC3 at a high binding affinity and binds to a soluble GPC3 at a low binding affinity. In some embodiments, the anti-GPC3-scFv specifically recognizes a soluble GPC3. In some embodiments, the binding affinity of the anti-GPC3-scFv to a soluble GPC3 is higher than that to a cell surface-bound GPC3. In some embodiments, the anti-sGPC3-scFv specifically recognizes an epitope within the amino acid sequence of SEQ ID NO: 461. In some embodiments, the anti-sGPC3-scFv specifically recognizes an epitope within amino acids 510-560 of SEQ ID NO: 460 (SEQ ID NO: 467). In some embodiments, the anti-GPC3-scFv specifically recognizes both cell surface-bound GPC3 and soluble GPC3. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the anti-GPC3 construct is non-naturally occurring. In some embodiments, the $K_d$ of the binding between the anti-GPC3-scFv and a target GPC3 (e.g., nGPC3 and/or sGPC3) is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-GPC3-scFv and a non-target can be at least about 10 times (such as at least about 10, $10^2$, $10^3$, $10^4$, $10^5$, $10^6$, or $10^7$ times) of the $K_d$ of the binding between the anti-GPC3-scFv and the target GPC3. In some embodiments, the $K_d$ of the binding between the anti-GPC3-scFv and a non-target is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-GPC3-scFv is chimeric, human, partially humanized, fully humanized, or semi-synthetic. In some embodiments, the $V_H$ of the anti-GPC3-scFv is N-terminal to the $V_L$ of the anti-GPC3-scFv. In some embodiments, the $V_H$ of the anti-GPC3-scFv is C-terminal to the $V_L$ of the anti-GPC3-scFv. In some embodiments, the linker between $V_H$ and $V_L$ of the anti-GPC3-scFv comprises the amino acid sequence of SRGGGGSGGGGSGGGGSLEMA (SEQ ID NO: 473). In some embodiments, the linker between $V_H$ and $V_L$ of the anti-GPC3-scFv is or comprises a $(GGGGS)_n$ sequence (SEQ ID NO: 471), wherein n is equal to 1, 2, 3, 4, 5, 6, 7, 8, 9, 10 or more. In some embodiments, the linker between $V_H$ and $V_L$ of the anti-GPC3-scFv comprises the amino acid sequence of GEGTSTGSGGSGGSGGAD (SEQ ID NO: 490). In some embodiments, there is provided an anti-GPC3 construct (such as an isolated anti-GPC3 construct) comprising an anti-GPC3-scFv specifically recognizing GPC3 (e.g., nGPC3 and/or sGPC3), wherein the anti-GPC3 scFv comprises the amino acid sequence of any one of SEQ ID NOs: 440-459. In some embodiments, the anti-GPC3-scFv further comprises a tag (e.g., a peptide tag for purification purpose). In some embodiments, the tag is N-terminal to the anti-GPC3-scFv. In some embodiments, the tag is C-terminal to the anti-GPC3-scFv. In some embodiments, the tag comprises a His-tag and an HA-tag. In some embodiments, the tag comprises the amino acid sequence of TSGQAGQHHHHHHHGAYPYDVPDYAS (SEQ ID NO: 477).

Anti-GPC3 Fc Fusion Protein

The anti-GPC3 constructs (such as isolated anti-GPC3 constructs) in some embodiments are Fc fusion proteins (hereinafter referred to as "anti-GPC3-Fc fusion protein") comprising an anti-GPC3 antibody moiety described herein fused to an Fc fragment (such as IgG1 Fc fragment). In some embodiments, the anti-GPC3 antibody moiety is fused to an Fc fragment via a linker (such as peptide linker). In some embodiments, the anti-GPC3-Fc fusion protein comprises an antibody comprising an Fc fragment. In some embodiments, the anti-GPC3-Fc fusion protein is a full-length antibody. Any of the anti-GPC3 antibody moieties described in the "anti-GPC3 antibody moiety section" can be employed in the anti-GPC3 Fc fusion protein.

Fc Fragment

The term "Fc region," "Fc domain" or "Fc" refers to a C-terminal non-antigen binding region of an immunoglobulin heavy chain that contains at least a portion of the constant region. The term includes native Fc regions and variant Fc regions. In some embodiments, a human IgG heavy chain Fc region extends from Cys226 to the carboxyl-terminus of the heavy chain. However, the C-terminal lysine (Lys447) of the Fc region may or may not be present, without affecting the structure or stability of the Fc region. Unless otherwise specified herein, numbering of amino acid residues in the IgG or Fc region is according to the EU numbering system for antibodies, also called the EU index, as described in Kabat et al., Sequences of Proteins of Immunological Interest, 5th Ed. Public Health Service, National Institutes of Health, Bethesda, Md., 1991.

In some embodiments, the Fc fragment comprises an immunoglobulin IgG heavy chain constant region comprising a hinge region (starting at Cys226), an IgG CH2 domain and CH3 domain. The term "hinge region" or "hinge sequence" as used herein refers to the amino acid sequence located between the linker and the CH2 domain. In some embodiments, the fusion protein comprises an Fc fragment comprising a hinge region. In some embodiments, the hinge region comprises the amino acid sequence CPPCP (SEQ ID NO: 478), a sequence found in the native IgG1 hinge region, to facilitate dimerization. In some embodiments, the Fc fragment of the fusion protein starts at the hinge region and extends to the C-terminus of the IgG heavy chain. In some embodiments, the fusion protein comprises an Fc fragment that does not comprise the hinge region.

In some embodiments, the fusion protein comprises an Fc fragment selected from the group consisting of Fc fragments from IgG, IgA, IgD, IgE, IgM, and combinations and hybrids thereof. In some embodiments, the Fc fragment is derived from a human IgG. In some embodiments, the Fc fragment comprises the Fc region of human IgG1, IgG2, IgG3, IgG4, or a combination or hybrid IgG. In some embodiments, the Fc fragment is an IgG1 Fc fragment. In some embodiments, the Fc fragment comprises the CH2 and CH3 domains of IgG1. In some embodiments, the Fc fragment is an IgG4 Fc fragment. In some embodiments, the Fc fragment comprises the CH2 and CH3 domains of IgG4. IgG4 Fc is known to exhibit less effector activity than IgG1 Fc, and thus may be desirable for some applications. In some embodiments, the Fc fragment is derived from of a mouse immunoglobulin.

In some embodiments, the IgG CH2 domain starts at Ala231. In some embodiments, the CH3 domain starts at Gly341. It is understood that the C-terminus Lys residue of human IgG can be optionally absent. It is also understood that conservative amino acid substitutions of the Fc region without affecting the desired structure and/or stability of Fc is contemplated within the scope of the invention.

Additionally, anti-GPC3-Fc fusion proteins comprising any of the Fc variants described below, or combinations thereof, are contemplated. In some embodiments, the Fc fragment comprises sequence that has been altered or otherwise changed so that it has enhanced antibody dependent cellular cytotoxicity (ADCC) or complement dependent cytotoxicity (CDC) effector function.

In some embodiments, each chain of the Fc fragment is fused to the same entity. In some embodiments, the anti-GPC3-Fc fusion protein comprises two identical anti-GPC3 antibody moieties described herein (specifically recognizing e.g., nGPC3 and/or sGPC3), each fused with one chain of the Fc fragment. In some embodiments, the two chains of the Fc fragment are identical. In some embodiments, the anti-GPC3-Fc fusion protein (including anti-GPC3-Fc fusion proteins comprising an antibody) comprising the Fc fragment is a homodimer.

In some embodiments, each chain of the Fc fragment is fused to a different entity. In some embodiments, the fusion protein comprises two different anti-GPC3 antibody moieties, each fused to one chain of the Fc fragment. In some embodiments, the two anti-GPC3 antibody moieties are different but both specifically recognize nGPC3. In some embodiments, the two anti-GPC3 antibody moieties are different but both specifically recognize sGPC3. In some embodiments, one anti-GPC3 antibody moiety specifically recognizes nGPC3, and the other anti-GPC3 antibody moiety specifically recognizes sGPC3. In some embodiments, the anti-GPC3-Fc fusion protein is monovalent, i.e., only one anti-GPC3 antibody moiety is fused to one chain of the Fc fragment, and the second chain of the Fc fragment is not fused to an anti-GPC3 antibody moiety. In some embodiments, the anti-GPC3-Fc fusion protein (including anti-GPC3-Fc fusion proteins comprising an antibody) comprising the Fc fragment is a heterodimer.

Heterodimerization of non-identical polypeptides in the anti-GPC3-Fc fusion protein can be facilitated by methods known in the art, including without limitation, heterodimerization by the knob-into-hole technology. The structure and assembly method of the knob-into-hole technology can be found in, e.g., U.S. Pat. Nos. 5,821,333, 7,642,228, US 2011/0287009 and PCT/US2012/059810, hereby incorporated by reference in their entireties. This technology was developed by introducing a "knob" (or a protuberance) by replacing a small amino acid residue with a large one in the CH3 domain of one Fc and introducing a "hole" (or a cavity) in the CH3 domain of the other Fc by replacing one or more large amino acid residues with smaller ones. In some embodiments, one chain of the Fc fragment in the fusion protein comprises a knob, and the second chain of the Fc fragment comprises a hole.

The preferred residues for the formation of a knob are generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the knob has a small side chain volume, such as alanine, asparagine, aspartic acid, glycine, serine, threonine or valine. Exemplary amino acid substitutions in the CH3 domain for forming the knob include without limitation the T366W, T366Y or F405W substitution.

The preferred residues for the formation of a hole are usually naturally occurring amino acid residues and are preferably selected from alanine (A), serine (S), threonine (T) and valine (V). In one embodiment, the original residue for the formation of the hole has a large side chain volume, such as tyrosine, arginine, phenylalanine or tryptophan. Exemplary amino acid substitutions in the CH3 domain for generating the hole include without limitation the T366S, L368A, F405A, Y407A, Y407T and Y407V substitutions. In certain embodiments, the knob comprises T366W substitution, and the hole comprises the T366S/L368A/Y 407V substitutions. It is understood that other modifications to the Fc region known in the art that facilitate heterodimerization are also contemplated and encompassed by the instant application.

Other anti-GPC3 Fc fusion protein variants (such as variants of isolated anti-GPC3-Fc fusion protein, e.g., a full-length anti-GPC3 antibody variant) comprising any of the variants described herein (e.g., Fc variants, effector function variants, glycosylation variants, cysteine engineered variants), or combinations thereof, are contemplated. See "anti-GPC3 variants" section for all applicable variations for the anti-GPC3 Fc fusion protein (e.g., full-length anti-GPC3 antibody).

Linkers

In some embodiments, the anti-GPC3-Fc fusion proteins described herein comprise an anti-GPC3 antibody moiety described herein fused to an Fc fragment via a linker.

The length, the degree of flexibility and/or other properties of the linker used in the anti-GPC3-Fc fusion proteins may have some influence on properties, including but not limited to the affinity, specificity or avidity for the anti-GPC3 antibody moiety, and/or one or more particular antigens or epitopes of the anti-GPC3-Fc fusion protein (such as an antibody comprising an Fc fragment and an anti-GPC3 antibody moiety). For example, longer linkers may be selected to ensure that two adjacent antibody moieties do not sterically interfere with one another. In some embodiments, a linker (such as peptide linker) comprises flexible residues (such as glycine and serine) so that the adjacent antibody moieties are free to move relative to each other. For example, a glycine-serine doublet can be a suitable peptide linker. In some embodiments, the linker is a non-peptide linker. In some embodiments, the linker is a peptide linker. In some embodiments, the linker is a non-cleavable linker. In some embodiments, the linker is a cleavable linker.

Other linker considerations include the effect on physical or pharmacokinetic properties of the resulting anti-GPC3-Fc fusion protein, such as solubility, lipophilicity, hydrophilicity, hydrophobicity, stability (more or less stable as well as planned degradation), rigidity, flexibility, immunogenicity, modulation of antibody moiety binding, the ability to be incorporated into a micelle or liposome, and the like.

Non-Peptide Linkers

Any one or all of the linkers described herein can be accomplished by any chemical reaction that will bind the two molecules so long as the components or fragments retain their respective activities, i.e. binding to target GPC3 (e.g., nGPC3 and/or sGPC3), binding to FcR, or ADCC/CDC. This linkage can include many chemical mechanisms, for instance covalent binding, affinity binding, intercalation, coordinate binding and complexation. In some embodiments, the binding is covalent binding. Covalent binding can be achieved either by direct condensation of existing side chains or by the incorporation of external bridging molecules. Many bivalent or polyvalent linking agents are useful in coupling protein molecules, such as an Fc fragment to the anti-GPC3 antibody moiety of the present invention. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents (see Killen and Lindstrom, Jour. Immun. 133:1335-2549 (1984); Jansen et al., Immunological Reviews 62:185-216 (1982); and Vitetta et al., Science 238:1098 (1987)).

Linkers that can be applied in the present application are described in the literature (see, for example, Ramakrishnan, S. et al., Cancer Res. 44:201-208 (1984) describing use of MBS (M-maleimidobenzoyl-N-hydroxysuccinimide ester)). In some embodiments, non-peptide linkers used herein include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to anti-GPC3-Fc fusion proteins with differing physio-chemical properties. For example, sulfo-NHS esters of alkyl carboxylates are more stable than sulfo-NHS esters of aromatic carboxylates. NETS-ester containing linkers are less soluble than sulfo-NHS esters. Further, the linker SMPT contains a sterically hindered disulfide bond, and can form fusion protein with increased stability. Disulfide linkages, are in general, less stable than other linkages because the disulfide linkage is cleaved in vitro, resulting in less fusion protein available. Sulfo-NHS, in particular, can enhance the stability of carbodimide couplings. Carbodimide couplings (such as EDC)

when used in conjunction with sulfo-NHS, forms esters that are more resistant to hydrolysis than the carbodimide coupling reaction alone.

Peptide Linkers

Any one or all of the linkers described herein can be peptide linkers. The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker comprises the amino acid sequence of CPPCP (SEQ ID NO: 478), a sequence found in the native IgG1 hinge region.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids (aa) long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 aa to about 10 aa, about 1 aa to about 20 aa, about 1 aa to about 30 aa, about 5 aa to about 15 aa, about 10 aa to about 25 aa, about 5 aa to about 30 aa, about 10 aa to about 30 aa, about 30 aa to about 50 aa, about 50 aa to about 100 aa, or about 1 aa to about 100 aa.

An essential technical feature of such peptide linker is that said peptide linker does not comprise any polymerization activity. The characteristics of a peptide linker, which comprise the absence of the promotion of secondary structures, are known in the art and described, e.g., in Dall'Acqua et al. (Biochem. (1998) 37, 9266-9273), Cheadle et al. (Mol Immunol (1992) 29, 21-30) and Raag and Whitlow (FASEB (1995) 9(1), 73-80). A particularly preferred amino acid in context of the "peptide linker" is Gly. Furthermore, peptide linkers that also do not promote any secondary structures are preferred. The linkage of the molecules to each other can be provided by, e.g., genetic engineering. Methods for preparing fused and operatively linked antibody constructs and expressing them in mammalian cells or bacteria are well-known in the art (e.g. WO 99/54440, Ausubel, Current Protocols in Molecular Biology, Green Publishing Associates and Wiley Interscience, N. Y. 1989 and 1994 or Sambrook et al., Molecular Cloning: A Laboratory Manual, Cold Spring Harbor Laboratory Press, Cold Spring Harbor, N. Y., 2001).

In some embodiments, the peptide linker is a stable linker, which is not cleavable by protease, such as by Matrix metalloproteinases (MMPs).

In some embodiments, the peptide linker tends not to adopt a rigid three-dimensional structure, but rather provide flexibility to a polypeptide (e.g., first and/or second components), such as providing flexibility between the anti-GPC3 antibody moiety and the Fc fragment. In some embodiments, the peptide linker is a flexible linker. Exemplary flexible linkers include glycine polymers $(G)_n$, glycine-serine polymers (including, for example, $(GS)_n$ (SEQ ID NO: 469), $(GSGGS)_n$ (SEQ ID NO: 470), $(GGGGS)_n$ (SEQ ID NO: 471), and $(GGGS)_n$ (SEQ ID NO: 472), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11 173-142 (1992)). The ordinarily skilled artisan will recognize that design of an anti-GPC3-Fc fusion protein can include linkers that are all or partially flexible, such that the linker can include a flexible linker portion as well as one or more portions that confer less flexible structure to provide a desired fusion protein structure.

In some embodiments, the anti-GPC3 antibody moiety and the Fc fragment are linked together by a linker of sufficient length to enable the anti-GPC3-Fc fusion protein to fold in such a way as to permit binding to target GPC3 (e.g., nGPC3 and/or sGPC3), as well as to FcR. In some embodiments, the linker comprises the amino acid sequence of SRGGGGSGGGGSGGGGSLEMA (SEQ ID NO: 473). In some embodiments, the linker is or comprises a $(GGGGS)_n$ sequence (SEQ ID NO: 471), wherein n is equal to 1, 2, 3, 4, 5, 6, 7, 8, 9, 10 or more. In some embodiments, the linker comprises the amino acid sequence of TSGGGGS (SEQ ID NO: 474). In some embodiments, the linker comprises the amino acid sequence of GEGTSTGSGGSGGSGGAD (SEQ ID NO: 490).

Natural linkers adopt various conformations in secondary structure, such as helical, β-strand, coil/bend and turns, to exert their functions. Linkers in an α-helix structure might serve as rigid spacers to effectively separate protein domains, thus reducing their unfavorable interactions. Non-helical linkers with Pro-rich sequence could increase the linker rigidity and function in reducing inter-domain interference. In some embodiments, the anti-GPC3 antibody moiety (specifically recognizing e.g., nGPC3 and/or sGPC3) and the Fc fragment (or an antibody comprising an Fc fragment) is linked together by an α-helical linker with an amino acid sequence of $A(EAAAK)_4A$ (SEQ ID NO: 475).

Anti-GPC3-Fc Fusion Protein Sequences

In some embodiments, the anti-GPC3 construct (such as an isolated anti-GPC3 construct) is an anti-GPC3-Fc fusion protein comprising an anti-GPC3 antibody moiety fused to an Fc fragment (such as IgG1 Fc fragment) optionally via a linker (such as peptide linker). In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-GPC3 antibody moiety specifically recognizes both cell surface-bound GPC3 and soluble GPC3. In some embodiments, the anti-GPC3 antibody moiety (targeting e.g., nGPC3 and/or sGPC3) is a Fab, a Fab', an Fc, or an scFv. In some embodiments, the anti-GPC3 antibody moiety is chimeric, human, partially humanized, fully humanized, or semi-synthetic. In some embodiments, the anti-GPC3-Fc fusion protein is a full-length antibody. In some embodiments, the full-length anti-GPC3 antibody is a monoclonal antibody. In some embodiments, the anti-GPC3-Fc fusion protein (such as a full-length anti-GPC3 antibody) is monospecific. In some embodiments, the anti-GPC3-Fc fusion protein is monovalent. In some embodiments, the anti-GPC3-Fc fusion protein (such as a full-length anti-GPC3 antibody) is multivalent. In some embodiments, the anti-GPC3-Fc fusion protein (such as a full-length anti-GPC3 antibody) is multispecific. In some embodiments, the linker comprises the amino acid sequence of (GGGGS)$_n$ (SEQ ID NO: 471), wherein n is equal to 1, 2, 3, 4, 5, 6, 7, 8, 9, 10 or more. In some embodiments, the linker comprises the amino acid sequence of CPPCP (SEQ ID NO: 478).

Thus, for example, in some embodiments, there is provided an anti-GPC3-Fc fusion protein comprising: a) an anti-GPC3 antibody moiety specifically recognizing a cell surface-bound GPC3 (e.g., the binding affinity of the anti-GPC3 antibody moiety to a cell surface-bound GPC3 is higher than that to a soluble GPC3, or the anti-GPC3 antibody moiety specifically recognizes a cell surface-bound GPC3 at a high binding affinity and binds to a soluble GPC3 at a low binding affinity); and b) an Fc fragment. In some embodiments, the anti-nGPC3 antibody moiety specifically recognizes an epitope within human GPC3 comprising the amino acid sequence of SEQ ID NO: 460. In some embodiments, the anti-nGPC3 antibody moiety specifically recognizes an epitope within the amino acid sequence of SEQ ID NO: 461. In some embodiments, the anti-nGPC3 antibody moiety specifically recognizes an epitope within the amino acid sequence of SEQ ID NO: 462. In some embodiments, the anti-nGPC3 antibody moiety specifically recognizes an epitope within the amino acid sequence of SEQ ID NO: 463. In some embodiments, the anti-nGPC3 antibody moiety specifically recognizes an epitope within the N-terminal fragment of GPC3. In some embodiments, the anti-nGPC3 antibody moiety specifically recognizes an epitope within amino acids 1-358 of SEQ ID NO: 460 (SEQ ID NO: 468). In some embodiments, the anti-nGPC3 antibody moiety specifically recognizes an epitope within the amino acid sequence of SEQ ID NO: 464. In some embodiments, the anti-nGPC3 antibody moiety specifically recognizes an epitope within the C-terminal fragment of GPC3. In some embodiments, the anti-nGPC3 antibody moiety specifically recognizes an epitope within amino acids 359-560 of SEQ ID NO: 460 (SEQ ID NO: 465). In some embodiments, the anti-nGPC3 antibody moiety specifically recognizes an epitope within amino acids 359-580 of SEQ ID NO 460 (SEQ ID NO: 466). In some embodiments, the anti-nGPC3 antibody moiety specifically recognizes an epitope within the C-terminal fragment of GPC3 lacking heparin sulfate side chain. In some embodiments, the anti-nGPC3 antibody moiety specifically recognizes an epitope within amino acids 510-560 of SEQ ID NO: 460 (SEQ ID NO: 467). In some embodiments, the anti-nGPC3 antibody moiety specifically recognizes an epitope spanning the Furin cleavage site at amino acids R$^{358}$/S$^{359}$ of SEQ ID NO: 460. In some embodiments, the anti-nGPC3 antibody moiety can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460). In some embodiments, the anti-nGPC3 antibody moiety specifically recognizes an epitope within the C-terminal fragment of GPC3 lacking heparin sulfate side chain. In some embodiments, there is provided an anti-GPC3-Fc fusion protein comprising: a) an anti-nGPC3 antibody moiety that competes for binding to nGPC3 with any one of the anti-GPC3 constructs described herein (e.g., the binding affinity of the anti-GPC3 antibody moiety to a cell surface-bound GPC3 is higher than that to a soluble GPC3, or the anti-GPC3 antibody moiety specifically recognizes a cell surface-bound GPC3 at a high binding affinity and binds to a soluble GPC3 at a low binding affinity); and b) an Fc fragment. In some embodiments, there is provided an anti-GPC3-Fc fusion protein comprising an anti-nGPC3 antibody moiety that specifically binds to the same, or substantially the same, nGPC3 epitope competitively with any one of the anti-GPC3 constructs described herein (e.g., the binding affinity of the anti-GPC3 antibody moiety to a cell surface-bound GPC3 is higher than that to a soluble GPC3, or the anti-GPC3 antibody moiety specifically recognizes a cell surface-bound GPC3 at a high binding affinity and binds to a soluble GPC3 at a low binding affinity); and b) an Fc fragment. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the anti-nGPC3 antibody moiety and the Fc fragment are connected via a linker (such as peptide linker). In some embodiments, the linker comprises the amino acid sequence of (GGGGS)$_n$ (SEQ ID NO: 471), wherein n is equal to 1, 2, 3, 4, 5, 6, 7, 8, 9, 10 or more. In some embodiments, the linker comprises the amino acid sequence of CPPCP (SEQ ID NO: 478). In some embodiments, the Fc fragment comprises an IgG1 Fc sequence. In some embodiments, the Fc fragment comprises a human IgG1 Fc sequence. In some embodiments, the Fc fragment comprises a mouse IgG1 Fc sequence. In some embodiments, the anti-GPC3-Fc fusion protein is a full-length antibody. In some embodiments, the full-length anti-GPC3 antibody is a monoclonal antibody. In some embodiments, the anti-GPC3-Fc fusion protein (such as a full-length anti-GPC3 antibody) is monospecific. In some embodiments, the anti-GPC3-Fc fusion protein is monovalent. In some embodiments, the anti-GPC3-Fc fusion protein (such as a full-length anti-GPC3 antibody) is multivalent. In some embodiments, the anti-GPC3-Fc fusion protein (such as a full-length anti-GPC3 antibody) is multispecific. In some embodiments, the anti-nGPC3 antibody moiety is a Fab or a Fab'. In some embodiments, the anti-nGPC3 antibody moiety is an scFv. In some embodiments, the anti-GPC3 antibody moiety is chimeric, human, partially humanized, fully humanized, or semi-synthetic. In some embodiments, the K$_d$ of the binding between the anti-nGPC3 antibody moiety and nGPC3 is about 10$^{-7}$ M to about 10$^{-13}$ M (such as about 10$^{-7}$ M to about 10$^{-13}$ M, about 10$^{-9}$ M to about 10$^{-13}$ M, or about 10$^{-10}$ M to about 10$^{-12}$ M). In some embodiments, the K$_d$ of the binding between the anti-nGPC3 antibody moiety and an sGPC3 can be at least about 10 times (such as at least about 10, 10$^2$, 10$^3$, 10$^4$, 10$^5$, 10$^6$, or 10$^7$ times) of the K$_d$ of the binding between the anti-nGPC3 antibody moiety and nGPC3. In some embodiments, the K$_d$ of the binding between the anti-nGPC3 antibody moiety and an sGPC3 is about 10$^{-1}$ M to about 10$^{-6}$ M (such as about 10$^{-1}$ M to about 10$^{-6}$ M, about 10$^{-1}$ M to about 10$^{-5}$ M, or about 10$^{-2}$ M to about 10$^{-4}$ M).

In some embodiments, there is provided an anti-GPC3-Fc fusion protein comprising: a) an anti-nGPC3 antibody moiety comprising: i) a V$_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a V$_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions; and b) an Fc fragment. In some embodiments, there is provided an anti-GPC3-Fc fusion protein comprising: a) an anti-nGPC3 antibody moiety comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286; and b) an Fc fragment. In some embodiments, there is provided an anti-GPC3-Fc fusion protein comprising: a) an anti-nGPC3 antibody moiety comprising: i) a $V_H$ comprising the amino acid sequence of any one of SEQ ID NOs: 307-337; and ii) a $V_L$ comprising the amino acid sequence of any one of SEQ ID NOs: 358-388; and b) an Fc fragment. In some embodiments, there is provided an anti-GPC3-Fc fusion protein comprising: a) an anti-nGPC3 antibody moiety comprising: i) the HC-CDRs of a $V_H$ comprising the amino acid sequence of any one of SEQ ID NOs: 307-337; and ii) the LC-CDRs of a $V_L$ comprising the amino acid sequence of any one of SEQ ID NOs: 358-388; and b) an Fc fragment. In some embodiments, there is provided an anti-GPC3-Fc fusion protein comprising a) an anti-nGPC3 antibody moiety that competes for binding to nGPC3 with any one of the anti-GPC3 constructs described herein; and b) an Fc fragment. In some embodiments, there is provided an anti-GPC3-Fc fusion protein comprising a) an anti-nGPC3 antibody moiety that specifically binds to the same, or substantially the same, nGPC3 epitope competitively with any one of the anti-GPC3 constructs described herein; and b) an Fc fragment. In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-nGPC3 antibody moiety and the Fc fragment are connected via a linker (such as peptide linker). In some embodiments, the linker comprises the amino acid sequence of $(GGGGS)_n$ (SEQ ID NO: 471), wherein n is equal to 1, 2, 3, 4, 5, 6, 7, 8, 9, 10 or more. In some embodiments, the linker comprises the amino acid sequence of CPPCP (SEQ ID NO: 478). In some embodiments, the Fc fragment comprises an IgG1 Fc sequence. In some embodiments, the Fc fragment comprises a human IgG1 Fc sequence. In some embodiments, the Fc fragment comprises a mouse IgG1 Fc sequence. In some embodiments, the anti-GPC3-Fc fusion protein is a full-length antibody. In some embodiments, the full-length anti-GPC3 antibody is a monoclonal antibody. In some embodiments, the anti-GPC3-Fc fusion protein (such as a full-length anti-GPC3 antibody) is monospecific. In some embodiments, the anti-GPC3-Fc fusion protein is monovalent. In some embodiments, the anti-GPC3-Fc fusion protein (such as a full-length anti-GPC3 antibody) is multivalent. In some embodiments, the anti-GPC3-Fc fusion protein (such as a full-length anti-GPC3 antibody) is multispecific. In some embodiments, the anti-nGPC3 antibody moiety is a Fab or a Fab'. In some embodiments, the anti-nGPC3 antibody moiety is an scFv. In some embodiments, the anti-nGPC3 antibody moiety is chimeric, human, partially humanized, fully humanized, or semi-synthetic.

In some embodiments, the anti-GPC3-Fc fusion protein (such as a full-length anti-GPC3 antibody) comprising an anti-nGPC3 antibody moiety competes for binding to a cell surface-bound GPC3 with a second anti-GPC3-Fc fusion protein (such as a second full-length anti-GPC3 antibody) comprising an anti-nGPC3 antibody moiety according to any of the anti-GPC3-Fc fusion proteins (such as a full-length anti-GPC3 antibody) described herein. In some embodiments, the anti-GPC3-Fc fusion protein (such as a full-length anti-GPC3 antibody) comprising an anti-nGPC3 antibody moiety binds to the same, or substantially the same, epitope as the second anti-GPC3-Fc fusion protein (such as a second full-length anti-GPC3 antibody) comprising an anti-nGPC3 antibody moiety. In some embodiments, binding of the anti-GPC3-Fc fusion protein (such as a full-length anti-GPC3 antibody) comprising an anti-nGPC3 antibody moiety to the cell surface-bound GPC3 inhibits binding of the second anti-GPC3-Fc fusion protein (such as a full-length anti-GPC3 antibody) comprising an anti-nGPC3 antibody moiety to the same cell surface-bound GPC3 by at least about 70% (such as by at least about any of 75%, 80%, 85%, 90%, 95%, 98% or 99%), or vice versa. In some embodiments, the anti-GPC3-Fc fusion protein (such as a full-length anti-GPC3 antibody) comprising an anti-nGPC3 antibody moiety and the second anti-GPC3-Fc fusion protein (such as a second full-length anti-GPC3 antibody) comprising an anti-nGPC3 antibody moiety cross-compete for binding to the cell surface-bound GPC3, i.e., each of the anti-GPC3-Fc fusion proteins (such as full-length anti-GPC3 antibodies) competes with the other for binding to the cell surface-bound GPC3.

In some embodiments, there is provided an anti-GPC3-Fc fusion protein (such as a full-length anti-GPC3 antibody) comprising: a) an anti-GPC3 antibody moiety specifically recognizing GPC3 (e.g., nGPC3 and/or sGPC3), comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs:

287-306, or a variant thereof comprising up to about 5 (such as about any of 1, 2, 3, 4, or 5) amino acid substitutions; and b) an Fc fragment. In some embodiments, there is provided an anti-GPC3-Fc fusion protein comprising: a) an anti-GPC3 antibody moiety specifically recognizing GPC3 (e.g., nGPC3 and/or sGPC3), comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306; and b) an Fc fragment. In some embodiments, there is provided an anti-GPC3-Fc fusion protein comprising: a) an anti-GPC3 antibody moiety specifically recognizing GPC3 (e.g., nGPC3 and/or sGPC3), comprising: i) a $V_H$ comprising the amino acid sequence of any one of SEQ ID NOs: 338-357; and ii) a $V_L$ comprising the amino acid sequence of any one of SEQ ID NOs: 389-408; and b) an Fc fragment. In some embodiments, there is provided an anti-GPC3-Fc fusion protein comprising: a) an anti-GPC3 antibody moiety specifically recognizing GPC3 (e.g., nGPC3 and/or sGPC3), comprising: i) the HC-CDRs of a $V_H$ comprising the amino acid sequence of any one of SEQ ID NOs: 338-357; and ii) the LC-CDRs of a $V_L$ comprising the amino acid sequence of any one of SEQ ID NOs: 389-408; and b) an Fc fragment. In some embodiments, there is provided an anti-GPC3-Fc fusion protein comprising a) an anti-GPC3 antibody moiety that competes for binding to GPC3 (e.g., nGPC3 and/or sGPC3) with any one of the anti-GPC3 constructs described herein; and b) an Fc fragment. In some embodiments, there is provided an anti-GPC3-Fc fusion protein comprising a) an anti-GPC3 antibody moiety that specifically binds to the same, or substantially the same, GPC3 epitope competitively with any one of the anti-GPC3 constructs described herein; and b) an Fc fragment. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the $K_d$ of the binding between the anti-GPC3 antibody moiety and target GPC3 (e.g., nGPC3 and/or sGPC3) is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-GPC3 antibody moiety and non-target can be at least about 10 times (such as at least about 10, $10^2$, $10^3$, $10^4$, $10^5$, $10^6$, or $10^7$ times) of the $K_d$ of the binding between the anti-GPC3 antibody moiety and target GPC3. In some embodiments, the $K_d$ of the binding between the anti-GPC3 antibody moiety and non-target is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-GPC3 antibody moiety and the Fc fragment are connected via a linker (such as peptide linker). In some embodiments, the linker comprises the amino acid sequence of $(GGGGS)_n$ (SEQ ID NO: 471), wherein n is equal to 1, 2, 3, 4, 5, 6, 7, 8, 9, 10 or more. In some embodiments, the linker comprises the amino acid sequence of CPPCP (SEQ ID NO: 478). In some embodiments, the Fc fragment comprises an IgG1 Fc sequence. In some embodiments, the Fc fragment comprises a human IgG1 Fc sequence. In some embodiments, the Fc fragment comprises a mouse IgG1 Fc sequence. In some embodiments, the anti-GPC3-Fc fusion protein is a full-length antibody. In some embodiments, the full-length anti-GPC3 antibody is a monoclonal antibody. In some embodiments, the anti-GPC3-Fc fusion protein (such as a full-length anti-GPC3 antibody) is monospecific. In some embodiments, the anti-GPC3-Fc fusion protein is monovalent. In some embodiments, the anti-GPC3-Fc fusion protein (such as a full-length anti-GPC3 antibody) is multivalent. In some embodiments, the anti-GPC3-Fc fusion protein (such as a full-length anti-GPC3 antibody) is multispecific. In some embodiments, the anti-GPC3 antibody moiety is a Fab or a Fab'. In some embodiments, the anti-GPC3 antibody moiety is an scFv. In some embodiments, the anti-GPC3 antibody moiety is chimeric, human, partially humanized, fully humanized, or semi-synthetic.

In some embodiments, the anti-GPC3-Fc fusion protein (such as a full-length anti-GPC3 antibody) comprising an anti-GPC3 antibody moiety competes for binding to a target GPC3 (e.g., nGPC3 and/or sGPC3) with a second anti-GPC3-Fc fusion protein (such as a second full-length anti-GPC3 antibody) comprising an anti-GPC3 antibody moiety according to any of the anti-GPC3-Fc fusion proteins (such as a full-length anti-GPC3 antibody) described herein. In some embodiments, the anti-GPC3-Fc fusion protein (such as a full-length anti-GPC3 antibody) comprising an anti-GPC3 antibody moiety binds to the same, or substantially the same, epitope as the second anti-GPC3-Fc fusion protein (such as a second full-length anti-GPC3 antibody) comprising an anti-GPC3 antibody moiety. In some embodiments, binding of the anti-GPC3-Fc fusion protein (such as a full-length anti-GPC3 antibody) comprising an anti-GPC3 antibody moiety to the target GPC3 (e.g., nGPC3 and/or sGPC3) inhibits binding of the second anti-GPC3-Fc fusion protein (such as a full-length anti-GPC3 antibody) comprising an anti-GPC3 antibody moiety to the target GPC3 by at least about 70% (such as by at least about any of 75%, 80%, 85%, 90%, 95%, 98% or 99%), or vice versa. In some embodiments, the anti-GPC3-Fc fusion protein (such as a full-length anti-GPC3 antibody) comprising an anti-GPC3 antibody moiety and the second anti-GPC3-Fc fusion protein (such as a second full-length anti-GPC3 antibody) comprising an anti-GPC3 antibody moiety cross-compete for binding to the target GPC3 (e.g., nGPC3 and/or sGPC3), i.e., each of the anti-GPC3-Fc fusion proteins (such as full-length anti-GPC3 antibodies) competes with the other for binding to the target GPC3.

In some embodiments, there is provided a full-length anti-GPC3 antibody (such as an isolated full-length anti-GPC3 antibody) comprising: a) an anti-GPC3 antibody moiety specifically recognizing a cell surface-bound GPC3 (e.g., the binding affinity of the anti-GPC3 antibody moiety to a cell surface-bound GPC3 is higher than that to a soluble GPC3, or the anti-GPC3 antibody moiety specifically recognizes a cell surface-bound GPC3 at a high binding affinity and binds to a soluble GPC3 at a low binding affinity); and b) an Fc fragment. In some embodiments, the Fc fragment comprises an IgG1 Fc sequence (e.g., human or mouse IgG1 Fc sequence). In some embodiments, the anti-nGPC3 antibody moiety specifically recognizes an epitope within human GPC3 comprising the amino acid sequence of SEQ ID NO: 460. In some embodiments, the anti-nGPC3 antibody moiety specifically recognizes an epitope within the amino acid sequence of SEQ ID NO: 461. In some embodiments, the anti-nGPC3 antibody moiety specifically recognizes an epitope within the amino acid sequence of SEQ ID NO: 462. In some embodiments, the anti-nGPC3 antibody moiety specifically recognizes an epitope within the amino acid sequence of SEQ ID NO: 463. In some embodiments, the anti-nGPC3 antibody moiety specifically recognizes an epitope within the N-terminal fragment of GPC3. In some embodiments, the anti-nGPC3 antibody moiety specifically recognizes an epitope within amino acids 1-358 of SEQ ID NO: 460 (SEQ ID NO: 468). In some embodiments, the anti-nGPC3 antibody moiety specifically recognizes an epitope within the amino acid sequence of SEQ ID NO: 464. In some embodiments, the anti-nGPC3 antibody moiety specifically recognizes an epitope within the C-terminal fragment of GPC3. In some embodiments, the anti-nGPC3 antibody moiety specifically recognizes an epitope within amino acids 359-560 of SEQ ID NO: 460 (SEQ ID NO: 465). In some embodiments, the anti-nGPC3 antibody moiety specifically recognizes an epitope within amino acids 359-580 of SEQ ID NO: 460 (SEQ ID NO: 466). In some embodiments, the anti-nGPC3 antibody moiety specifically recognizes an epitope within the C-terminal fragment of GPC3 lacking heparin sulfate side chain. In some embodiments, the anti-nGPC3 antibody moiety specifically recognizes an epitope within amino acids 510-560 of SEQ ID NO: 460 (SEQ ID NO: 467). In some embodiments, the anti-nGPC3 antibody moiety specifically recognizes an epitope spanning the Furin cleavage site at amino acids $R^{358}/S^{359}$ of SEQ ID NO: 460. In some embodiments, the anti-nGPC3 antibody moiety can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460. In some embodiments, the anti-nGPC3 antibody moiety specifically recognizes an epitope within the C-terminal fragment of GPC3 lacking heparin sulfate side chain. In some embodiments, there is provided a full-length anti-GPC3-Fc fusion protein comprising: a) an anti-nGPC3 antibody moiety that competes for binding to nGPC3 with any one of the anti-GPC3 constructs described herein (e.g., the binding affinity of the anti-GPC3 antibody moiety to a cell surface-bound GPC3 is higher than that to a soluble GPC3, or the anti-GPC3 antibody moiety specifically recognizes a cell surface-bound GPC3 at a high binding affinity and binds to a soluble GPC3 at a low binding affinity); and b) an Fc fragment. In some embodiments, there is provided a full-length anti-GPC3-Fc fusion protein comprising a) an anti-nGPC3 antibody moiety (e.g., the binding affinity of the anti-GPC3 antibody moiety to a cell surface-bound GPC3 is higher than that to a soluble GPC3, or the anti-GPC3 antibody moiety specifically recognizes a cell surface-bound GPC3 at a high binding affinity and binds to a soluble GPC3 at a low binding affinity) that specifically binds to the same, or substantially the same, nGPC3 epitope competitively with any one of the anti-GPC3 constructs described herein; and b) an Fc fragment. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the full-length anti-GPC3 antibody is non-naturally occurring. In some embodiments, the full-length anti-GPC3 antibody is monoclonal. In some embodiments, the full-length anti-GPC3 antibody is monospecific. In some embodiments, the full-length anti-GPC3 antibody is multi-specific (e.g., bispecific). In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-nGPC3 antibody moiety is chimeric, human, partially humanized, fully humanized, or semi-synthetic. In some embodiments, the full-length anti-GPC3 antibody comprises a mouse IgG1 heavy chain constant domain ($C_H$) comprising the amino acid sequence of SEQ ID NO: 507. In some embodiments, the full-length anti-GPC3 antibody comprises a mouse λ light chain constant domain ($C_L$) comprising the amino acid sequence of SEQ ID NO: 508. For example, in some embodiments, the full-length anti-GPC3 antibody comprises a heavy chain comprising the amino acid sequence of SEQ ID NO: 505, and a light chain comprising the amino acid sequence of SEQ ID NO: 506. In some embodiments, the heavy and/or light chain of the full-length anti-GPC3 antibody optionally comprises an N-terminal signal peptide. In some embodiments, the signal peptide comprises the amino acid sequence of SEQ ID NO: 509.

In some embodiments, there is provided a full-length anti-GPC3 antibody (such as an isolated full-length anti-GPC3 antibody) comprising: a) an anti-GPC3 antibody moiety specifically recognizing a cell surface-bound GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions; and b) an Fc fragment. In some embodiments, there is provided a full-length anti-GPC3 antibody (such as an isolated full-length anti-GPC3 antibody) comprising: a) an anti-GPC3 antibody moiety specifically recognizing a cell surface-bound GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286; and b) an Fc fragment. In some embodiments, there is provided a full-length anti-GPC3 antibody (such as an isolated full-length anti-GPC3 antibody) comprising: a) an anti-GPC3 antibody moiety specifically recognizing a cell surface-bound GPC3, comprising: i) a $V_H$ comprising the amino acid sequence of any one of SEQ ID NOs: 307-337; and ii) a $V_L$ comprising the amino acid sequence of any one of SEQ ID NOs: 358-388. In some embodiments, there is provided a full-length anti-GPC3 antibody (such as an isolated full-length anti-GPC3 antibody) comprising: a) an anti-GPC3 antibody moiety specifically recognizing a cell surface-bound GPC3, comprising the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388. In some embodiments, there is provided a full-length anti-GPC3 antibody (such as an isolated full-length anti-GPC3 antibody) comprising: a) an anti-GPC3 antibody moiety that specifically binds to a cell surface-bound GPC3 competitively with any of the anti-GPC3 constructs described herein; and an Fc fragment. In some embodiments, there is provided a full-length anti-GPC3 antibody (such as an isolated full-length anti-GPC3 antibody) comprising an anti-nGPC3 antibody moiety that specifically binds to the same, or substantially the same, nGPC3 epitope competitively with any one of the anti-GPC3 constructs described herein; and an Fc fragment. In some embodiments, the Fc fragment comprises an IgG1 Fc sequence (e.g., human or mouse IgG1 Fc sequence). In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the full-length anti-GPC3 antibody is non-naturally occurring. In some embodiments, the full-length anti-GPC3 antibody is monoclonal. In some embodiments, the full-length anti-GPC3 antibody is monospecific. In some embodiments, the full-length anti-GPC3 antibody is multispecific (e.g., bispecific). In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-nGPC3 antibody moiety is chimeric, human, partially humanized, fully humanized, or semi-synthetic. In some embodiments, the full-length anti-GPC3 antibody comprises a mouse IgG1 heavy chain constant domain ($C_H$) comprising the amino acid sequence of SEQ ID NO: 507. In some embodiments, the full-length anti-GPC3 antibody comprises a mouse λ, light chain constant domain ($C_L$) comprising the amino acid sequence of SEQ ID NO: 508. For example, in some embodiments, the full-length anti-GPC3 antibody comprises a heavy chain comprising the amino acid sequence of SEQ ID NO: 505, and a light chain comprising the amino acid sequence of SEQ ID NO: 506. In some embodiments, the heavy and/or light chain of the full-length anti-GPC3 antibody optionally comprises an N-terminal signal peptide. In some embodiments, the signal peptide comprises the amino acid sequence of SEQ ID NO: 509.

In some embodiments, there is provided a full-length anti-GPC3 antibody (such as an isolated full-length anti-GPC3 antibody) comprising: a) an anti-GPC3 antibody moiety specifically recognizing GPC3 (e.g., nGPC3 and/or sGPC3), comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions; and b) an Fc fragment. In some embodiments, there is provided a full-length anti-GPC3 antibody (such as an isolated full-length anti-GPC3 antibody) comprising: a) an anti-GPC3 antibody moiety specifically recognizing GPC3 (e.g., nGPC3 and/or sGPC3), comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306; and b) an Fc fragment. In some embodiments, there is provided a full-length anti-GPC3 antibody (such as an isolated full-length anti-GPC3 antibody) comprising: a) an anti-GPC3 antibody moiety specifically recognizing GPC3 (e.g., nGPC3 and/or sGPC3), comprising: i) a $V_H$ comprising the amino acid sequence of any one of SEQ ID NOs: 338-357; and ii) a $V_L$ comprising the amino acid sequence of any one of SEQ ID NOs: 389-408. In some embodiments, there is provided a full-length anti-GPC3 antibody (such as an isolated full-length anti-GPC3 antibody) comprising: a) an anti-GPC3 antibody moiety specifically recognizing GPC3 (e.g., nGPC3 and/or sGPC3), comprising the HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408. In some embodiments, there is provided a full-length anti-GPC3 antibody (such as an isolated full-length anti-GPC3 antibody) comprising: a) an anti-GPC3 antibody moiety that specifically binds to a target GPC3 (e.g., nGPC3 and/or sGPC3) competitively with any of the anti-GPC3 constructs described herein; and an Fc fragment. In some embodiments, there is provided a full-length anti-GPC3 antibody (such as an isolated full-length anti-GPC3 antibody) comprising an anti-GPC3 antibody moiety that specifically binds to the same, or substantially the same, GPC3 epitope competitively with any one of the anti-GPC3 constructs described herein; and an Fc fragment. In some embodiments, the Fc fragment comprises an IgG1 Fc sequence (e.g., human or mouse IgG1 Fc sequence). In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the anti-GPC3 construct is non-naturally occurring. In some embodiments, the full-length anti-GPC3 antibody is monoclonal. In some embodiments, the full-length anti-GPC3 antibody is monospecific. In some embodiments, the full-length anti-GPC3 antibody is multispecific (e.g., bispecific). In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the $K_d$ of the binding between the anti-GPC3 antibody moiety and a target GPC3 (e.g., nGPC3 and/or sGPC3) is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-GPC3 antibody moiety and a non-target can be at least about 10 times (such as at least about 10, $10^2$, $10^3$, $10^4$, $10^5$, $10^6$, or $10^7$ times) of the $K_d$ of the binding between the anti-GPC3 antibody moiety and the target GPC3. In some embodiments, the $K_d$ of the binding between the anti-GPC3 antibody moiety and a non-target is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-GPC3 antibody moiety is chimeric, human, partially humanized, fully humanized, or semi-synthetic. In some embodiments, the full-length anti-GPC3 antibody comprises a mouse IgG1 heavy chain constant domain ($C_H$) comprising the amino acid sequence of SEQ ID NO: 507. In some embodiments, the full-length anti-GPC3 antibody comprises a mouse λ, light chain constant domain ($C_L$) comprising the amino acid sequence of SEQ ID NO: 508. In some embodiments, the heavy and/or light chain of the full-length anti-GPC3 antibody optionally comprises an N-terminal signal peptide. In some embodiments, the signal peptide comprises the amino acid sequence of SEQ ID NO: 509.

Multi-Specific Anti-GPC3 Molecules

The anti-GPC3 constructs (such as isolated anti-GPC3 constructs) in some embodiments comprise a multi-specific (e.g., bispecific) anti-GPC3 molecule comprising an anti-GPC3 antibody moiety according to any one of the anti-GPC3 antibody moieties described herein, and a second binding moiety (such as a second antibody moiety) specifically recognizing a second antigen. In some embodiments, the multi-specific anti-GPC3 molecule comprises an anti-GPC3 antibody moiety and a second antibody moiety specifically recognizing a second antigen. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-GPC3 antibody moiety specifically recognizes both cell surface-bound GPC3 and soluble GPC3.

Multi-specific molecules are molecules that have binding specificities for at least two different antigens or epitopes (e.g., bispecific antibodies have binding specificities for two antigens or epitopes). Multi-specific molecules with more than two valencies and/or specificities are also contemplated. For example, trispecific antibodies can be prepared (Tutt et al. *J. Immunol.* 147: 60 (1991)). It is to be appreciated that one of skill in the art could select appropriate features of individual multi-specific molecules described herein to combine with one another to form a multi-specific anti-GPC3 molecule of the invention.

Thus, for example, in some embodiments, there is provided a multi-specific (e.g., bispecific) anti-GPC3 molecule comprising a) an anti-GPC3 antibody moiety (e.g., scFv) specifically recognizing a target GPC3 (e.g., nGPC3 and/or sGPC3), and b) a second binding moiety (such as a second antibody moiety, e.g., scFv) specifically recognizing a second antigen. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-GPC3 antibody moiety specifically recognizes both cell surface-bound GPC3 and soluble GPC3. In some embodiments, the second binding moiety specifically recognizes the same format of GPC3 (e.g., nGPC3 and/or sGPC3) as the anti-GPC3 antibody moiety. In some embodiments, the second binding moiety specifically recognizes a different GPC3 epitope compared to the anti-GPC3 antibody moiety. In some embodiments, the second binding moiety specifically recognizes a different format of GPC3 compared to the anti-GPC3 antibody moiety. For example, in some embodiments, the second binding moiety specifically recognizes an sGPC3 (or both sGPC3 and nGPC3), while the anti-GPC3 antibody moiety specifically recognizes nGPC3 (with no or little binding to sGPC3). In some embodiments, the second binding moiety specifically recognizes a second antigen that is not GPC3. In some embodiments, the second binding moiety specifically recognizes a second antigen on the surface of a cell, such as a cytotoxic cell. In some embodiments, the second binding moiety specifically binds to an antigen on the surface of a lymphocyte, such as a T cell, a B cell, a natural killer (NK) cell, a neutrophil, a monocyte, a macrophage, or a dendritic cell. In some embodiments, the second binding moiety specifically binds to an effector T cell, such as a cytotoxic T cell (also known as cytotoxic T lymphocyte (CTL) or T killer cell) or natural killer T (NKT) cell. In some embodiments, the second binding moiety specifically binds to a second antigen on the surface of an effector cell, including for example CD3γ, CD3δ, CD3ε, CD3ζ, CD27, CD28, CD16a, CD40L, CD56, CD68, CD137, OX40, GITR, HVEM and GDS2D. In some embodiments, the anti-GPC3 antibody moiety is chimeric, human, partially humanized, fully humanized, or semi-synthetic. In some embodiments, the anti-GPC3 antibody moiety is a full-length antibody, a Fab, a Fab', a F(ab')2, an Fv, or an scFv. In some embodiments, the second binding moiety is chimeric, human, partially humanized, fully humanized, or semi-synthetic. In some embodiments, the multi-specific anti-GPC3 molecule further comprises at least one (such as at least about any of 2, 3, 4, 5, or more) additional antibody moieties.

In some embodiments, there is provided a multi-specific (e.g., bispecific) anti-GPC3 molecule comprising a) an anti-GPC3 antibody moiety (e.g., scFv) specifically recognizing a cell surface-bound GPC3 (e.g., the binding affinity of the anti-nGPC3 antibody moiety to the cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity), and b) a second binding moiety (such as a second antibody moiety, e.g., scFv) specifically recognizing a second antigen (e.g., CD3 on T cell). In some embodiments, the anti-nGPC3 antibody moiety specifically recognizes an epitope within human GPC3 comprising the amino acid sequence of SEQ ID NO: 460. In some embodiments, the anti-nGPC3 antibody moiety specifically recognizes an epitope within the amino acid sequence of SEQ ID NO: 461. In some embodiments, the anti-nGPC3 antibody moiety specifically recognizes an epitope within the amino acid sequence of SEQ ID NO: 462. In some embodiments, the anti-nGPC3 antibody moiety specifically recognizes an epitope within the amino acid sequence of SEQ ID NO: 463. In some embodiments, the anti-nGPC3 antibody moiety specifically recognizes an epitope within the N-terminal fragment of GPC3. In some embodiments, the anti-nGPC3 antibody moiety specifically recognizes an epitope within amino acids 1-358 of SEQ ID NO: 460 (SEQ ID NO: 468). In some embodiments, the anti-nGPC3 antibody moiety specifically recognizes an epitope within the amino acid sequence of SEQ ID NO: 464. In some embodiments, the anti-nGPC3 antibody moiety specifically recognizes an epitope within the C-terminal fragment of GPC3. In some embodiments, the anti-nGPC3 antibody moiety specifically recognizes an epitope within amino acids 359-560 of SEQ ID NO: 460 (SEQ ID NO: 465). In some embodiments, the anti-nGPC3 antibody moiety specifically recognizes an epitope within amino acids 359-580 of SEQ ID NO: 460 (SEQ ID NO: 466). In some embodiments, the anti-nGPC3 antibody moiety specifically recognizes an epitope within the C-terminal fragment of GPC3 lacking heparin sulfate side chain. In some embodiments, the anti-nGPC3 antibody moiety specifically recognizes an epitope within amino acids 510-560 of SEQ ID NO: 460 (SEQ ID NO: 467). In some embodiments, the anti-nGPC3 antibody moiety specifically recognizes an epitope spanning the Furin cleavage site at amino acids $R^{358}/S^{359}$ of SEQ ID NO: 460. In some embodiments, the anti-nGPC3 antibody moiety can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460. In some embodiments, the anti-nGPC3 antibody moiety specifically recognizes an epitope within the C-terminal fragment of GPC3 lacking heparin sulfate side chain. In some embodiments, there is provided a multi-specific (e.g., bispecific) anti-GPC3 molecule comprising: a) an anti-nGPC3 antibody moiety (e.g., scFv; e.g., the binding affinity of the anti-nGPC3 antibody moiety to the cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that competes for binding to nGPC3 with any one of the anti-GPC3 constructs described herein; and b) a second binding moiety (such as a second antibody moiety, e.g., scFv) specifically recognizing a second antigen (e.g., CD3 on T cell). In some embodiments, there is provided a multi-specific (e.g., bispecific) anti-GPC3 molecule comprising: a) an anti-nGPC3 antibody moiety (e.g., scFv; e.g., the binding affinity of the anti-nGPC3 antibody moiety to the cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that specifically binds to the same, or substantially the same, nGPC3 epitope competitively with any one of the anti-GPC3 constructs described herein; and b) a second binding moiety (such as a second antibody moiety, e.g., scFv) specifically recognizing a second antigen (e.g., CD3 on T cell). In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the first and/or the second antibody moieties are chimeric, human, partially humanized, fully humanized, or semi-synthetic. In some embodiments, the first and/or the second antibody moieties are full-length antibody, a Fab, a Fab', a F(ab')2, an Fv, or an scFv. In some embodiments, the first and/or the second antibody moiety is scFv. In some embodiments, the first and the second antibody moieties are connected by a linker (e.g., SEQ ID NO: 474). In some embodiments, the first anti-GPC3 antibody moiety is N-terminal to the second antibody moiety. In some embodiments, the effector cell is T cell (e.g., cytotoxic T cell, helper T cell, or natural killer T cell), B cell, NK cell, dendritic cell, macrophage, monocyte, or a neutrophil. In some embodiments, the second antigen is CD3γ, CD3δ, CD3ε, CD3ζ, CD28, OX40, GITR, CD137, CD27, CD40L, or HVEM.

In some embodiments, there is provided a multi-specific (e.g., bispecific) anti-GPC3 molecule comprising a) an anti-GPC3 antibody moiety (e.g., scFv) specifically recognizing a cell surface-bound GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions; and b) a second binding moiety (such as a second antibody moiety, e.g., scFv) specifically recognizing a second antigen (e.g., CD3 on T cell). In some embodiments, there is provided a multi-specific (e.g., bispecific) anti-GPC3 molecule comprising a) an anti-GPC3 antibody moiety (e.g., scFv) specifically recognizing a cell surface-bound GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286; and b) a second binding moiety (such as a second antibody moiety, e.g., scFv) specifically recognizing a second antigen (e.g., CD3 on T cell). In some embodiments, there is provided a multi-specific (e.g., bispecific) anti-GPC3 molecule comprising a) an anti-GPC3 antibody moiety (e.g., scFv) specifically recognizing a cell surface-bound GPC3, comprising: i) a $V_H$ comprising the amino acid sequence of any one of SEQ ID NOs: 307-337; and ii) a $V_L$ comprising the amino acid sequence of any one of SEQ ID NOs: 358-388; and b) a second binding moiety (such as a second antibody moiety, e.g., scFv) specifically recognizing a second antigen (e.g., CD3 on T cell). In some embodiments, there is provided a multi-specific (e.g., bispecific) anti-GPC3 molecule comprising a) an anti-GPC3 antibody moiety (e.g., scFv) specifically recognizing a cell surface-bound GPC3, comprising the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388; and b) a second binding moiety (such as a second antibody moiety, e.g., scFv) specifically recognizing a second antigen (e.g., CD3 on T cell). In some embodiments, there is provided a multi-specific (e.g., bispecific) anti-GPC3 molecule comprising a) an anti-GPC3 antibody moiety (e.g., scFv) specifically recognizing a cell surface-bound GPC3, wherein the anti-nGPC3 antibody moiety competes for binding to the cell surface-bound GPC3 with a second anti-nGPC3 antibody moiety according to any of the anti-nGPC3 antibody moieties described herein; and b) a second binding moiety (such as a second antibody moiety, e.g., scFv) specifically recognizing a second antigen (e.g., CD3 on T cell). In some embodiments, there is provided a multi-specific (e.g., bispecific) anti-GPC3 molecule comprising: a) an anti-nGPC3 antibody moiety (e.g., scFv) that specifically binds to the same, or substantially the same, nGPC3 epitope competitively with any one of the anti-GPC3 constructs described herein; and b) a second binding moiety (such as a second antibody moiety, e.g., scFv) specifically recognizing a second antigen (e.g., CD3 on T cell). In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the first and/or the second antibody moieties are chimeric, human, partially humanized, fully humanized, or semi-synthetic. In some embodiments, the first and/or the second antibody moieties are full-length antibody, a Fab, a Fab', a F(ab')2, an Fv, or an scFv. In some embodiments, the first and/or the second antibody moiety is scFv. In some embodiments, the first and the second antibody moieties are connected by a linker (e.g., SEQ ID NO: 474). In some embodiments, the first anti-GPC3 antibody moiety is N-terminal to the second antibody moiety. In some embodiments, the effector cell is T cell (e.g., cytotoxic T cell, helper T cell, or natural killer T cell), B cell, NK cell, dendritic cell, macrophage, monocyte, or a neutrophil. In some embodiments, the second antigen is CD3γ, CD3δ, CD3ε, CD3ζ, CD28, OX40, GITR, CD137, CD27, CD40L, or HVEM.

In some embodiments, there is provided a multi-specific (e.g., bispecific) anti-GPC3 molecule comprising a) an anti-GPC3 antibody moiety (e.g., scFv) specifically recognizing GPC3 (e.g., nGPC3 and/or sGPC3), comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions; and b) a second binding moiety (such as a second antibody moiety, e.g., scFv) specifically recognizing a second antigen (e.g., CD3 on T cell). In some embodiments, there is provided a multi-specific (e.g., bispecific) anti-GPC3 molecule comprising a) an anti-GPC3 antibody moiety (e.g., scFv) specifically recognizing GPC3, comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306; and b) a second binding moiety (such as a second antibody moiety, e.g., scFv) specifically recognizing a second antigen (e.g., CD3 on T cell). In some embodiments, there is provided a multi-specific (e.g., bispecific) anti-GPC3 molecule comprising a) an anti-GPC3 antibody moiety (e.g., scFv) specifically recognizing GPC3, comprising: i) a $V_H$ comprising the amino acid sequence of any one of SEQ ID NOs: 338-357; and ii) a $V_L$ comprising the amino acid sequence of any one of SEQ ID NOs: 389-408; and b) a second binding moiety (such as a second antibody moiety, e.g., scFv) specifically recognizing a second antigen (e.g., CD3 on T cell). In some embodiments, there is provided a multi-specific (e.g., bispecific) anti-GPC3 molecule comprising a) an anti-GPC3 antibody moiety (e.g., scFv) specifically recognizing GPC3, comprising the HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408; and b) a second binding moiety (such as a second antibody moiety, e.g., scFv) specifically recognizing a second antigen (e.g., CD3 on T cell). In some embodiments, there is provided a multi-specific (e.g., bispecific) anti-GPC3 molecule comprising a) an anti-GPC3 antibody moiety (e.g., scFv) specifically recognizing GPC3, wherein the anti-GPC3 antibody moiety competes for binding to the target GPC3 (e.g., nGPC3 and/or sGPC3) with a second anti-GPC3 antibody moiety according to any of the anti-GPC3 antibody moieties described herein; and b) a second binding moiety (such as a second antibody moiety, e.g., scFv) specifically recognizing a second antigen (e.g., CD3 on T cell). In some embodiments, there is provided a multi-specific (e.g., bispecific) anti-GPC3 molecule comprising: a) an anti-GPC3 antibody moiety (e.g., scFv) that specifically binds to the same, or substantially the same, GPC3 epitope competitively with any one of the anti-GPC3 constructs described herein; and b) a second binding moiety (such as a second antibody moiety, e.g., scFv) specifically recognizing a second antigen (e.g., CD3 on T cell). In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the $K_d$ of the binding between the anti-GPC3 antibody moiety and target GPC3 (e.g., gGPC3 and/or sGPC3) is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-GPC3 antibody moiety and a non-target can be at least about 10 times (such as at least about 10, $10^2$, $10^3$, $10^4$, $10^5$, $10^6$, or $10^7$ times) of the $K_d$ of the binding between the anti-GPC3 antibody moiety and the target GPC3. In some embodiments, the $K_d$ of the binding between the anti-GPC3 antibody moiety and a non-target is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the first and/or the second antibody moieties are chimeric, human, partially humanized, fully humanized, or semi-synthetic. In some embodiments, the first and/or the second antibody moieties are full-length antibody, a Fab, a Fab', a F(ab')2, an Fv, or an scFv. In some embodiments, the first and/or the second antibody moiety is scFv. In some embodiments, the first and the second antibody moieties are connected by a linker (e.g., SEQ ID NO: 474). In some embodiments, the first anti-GPC3 antibody moiety is N-terminal to the second antibody moiety. In some embodiments, the effector cell is T cell (e.g., cytotoxic T cell, helper T cell, or natural killer T cell), B cell, NK cell, dendritic cell, macrophage, monocyte, or a neutrophil. In some embodiments, the second antigen is CD3γ, CD3δ, CD3ε, CD3ζ, CD28, OX40, GITR, CD137, CD27, CD40L, or HVEM.

In some embodiments, the multi-specific anti-GPC3 molecule is, for example, a diabody (Db), a single-chain diabody (scDb), a tandem scDb (Tandab), a linear dimeric scDb (LD-scDb), a circular dimeric scDb (CD-scDb), a di-diabody, a tandem scFv, a tandem di-scFv (e.g., a bispecific T cell engager), a tandem tri-scFv, a tri(a) body, a bispecific Fab2, a di-miniantibody, a tetrabody, an scFv-Fc-scFv fusion, a dual-affinity retargeting (DART) antibody, a dual variable domain (DVD) antibody, an IgG-scFab, an scFab-ds-scFv, an Fv2-Fc, an IgG-scFv fusion, a dock and lock (DNL) antibody, a knob-into-hole (KiH) antibody (bispecific IgG prepared by the KiH technology), a DuoBody (bispecific IgG prepared by the Duobody technology), a heteromultimeric antibody, or a heteroconjugate antibody. In some embodiments, the multi-specific anti-GPC3 molecule is a tandem scFv (e.g., a tandem di-scFv, such as a bispecific T cell engager).

Second Antigen

In some embodiments, the anti-GPC3 construct (such as an isolated anti-GPC3 construct) comprises a multi-specific (e.g., bispecific) anti-GPC3 molecule comprising an anti-GPC3 antibody moiety (such as an anti-nGPC3 antibody moiety) and a second antibody moiety (e.g. scFv) specifically recognizing a second antigen. In some embodiments, the second antigen is also GPC3 but comprises a different epitope compared to that recognized by the anti-GPC3 antibody moiety. In some embodiments, the second antigen is not GPC3. In some embodiments, the second antigen is a tumor antigen. In some embodiments, the second antigen is a cell surface molecule. In some embodiments, the second antigen is a cell surface molecule on an effector cell.

Exemplary tumor antigens that can be recognized by the second antibody moiety described herein include, but are not limited to, alpha fetoprotein (AFP), CA15-3, CA27-29, CA19-9, CA-125, calretinin, carcinoembryonic antigen, CD34, CD99, CD117, chromogranin, cytokeratin, desmin, epithelial membrane protein (EMA), Factor VIII, CD31 FL1, glial fibrillary acidic protein (GFAP), gross cystic disease fluid protein (GCDFP-15), HMB-45, human chorionic gonadotropin (hCG), inhibin, keratin, CD45, a lymphocyte marker, MART-1 (Melan-A), Myo Dl, muscle-specific actin (MSA), neurofilament, neuron-specific enolase (NSE), placental alkaline phosphatase (PLAP), prostate-specific antigen, S100 protein, smooth muscle actin (SMA), synaptophysin, thyroglobulin, thyroid transcription factor-1, tumor M2-PK, and vimentin.

In some embodiments, the multi-specific (e.g., bispecific) anti-GPC3 molecules described herein can be engineered to facilitate killing (e.g., cytotoxic lysis or phagocytosis) of tumor cells by directing (or recruiting) an effector cell (such as a cytotoxic T cell) to a tumor site. In some embodiments, tumor cytotoxicitiy can be tested using an LDH Cytotoxicity Assay. In some embodiments, the multi-specific (e.g., bispecific) anti-GPC3 molecule can effectively direct an effector cell (e.g., T cell, NK cell, CAR-T cell, caTCR-T cell) to a target cell in an immunosuppressive environment, such as an immunosuppressive tumor environment.

Exemplary effector cells include without limitation a T cell, a B cell, a natural killer (NK) cell, a dendritic cell (DC), a macrophage, a monocyte, a neutrophil, a natural killer T (NKT) cell, an antibody-dependent cytotoxic cell, a chimeric antigen receptor (CAR) effector cell (e.g., CAR-T), a chimeric antibody-T cell receptor (TCR) construct (caTCR) effector cell (see caTCR section below), or the like. In some embodiments, the effector cell is a T cell (e.g., a cytotoxic T cell, a helper T cell, or an NKT cell). In some embodiments, the effector cell is a cytotoxic T cell. In some embodiments, the effector cell is allogenic. In some embodiments, the effector cell is autologous.

A cell surface molecule of the present invention is a molecule found on the external cell wall or plasma membrane of a specific cell type or a limited number of cell types. Examples of cell surface molecules include, but are not limited to, membrane proteins such as receptors, transporters, ion channels, proton pumps, and G protein-coupled receptors; extracellular matrix molecules such as adhesion molecules (e.g., integrins, cadherins, selectins, or NCAMS); see, e.g., U.S. Pat. No. 7,556,928, which is incorporated herein by reference in its entirety. Cell surface molecules on an effector cell include but not limited to CD3 (e.g., CD3γ, CD3δ, CD3ε, or CD3ζ), CD4, CD5, CD7, CD8, CD13, CD14, CD16, CD27 (TNFRSF7), CD28, CD31, CD38, CD40L (TNFSF5 or CD154), CD56, CD64, CD68, CD89, CD94, CD137 (TNFRSF9 or 4-1BB), CD278, NKp46, NKp30, NKG2D, MAC-1/MAC-3, IL-2Ra, OX40 (TNFRSF4 or CD134), GITR, HVEM (TNFRSF14 or CD270), Ly49, or an invariant TCR.

The skilled artisan will recognize that immune cells have different cell surface molecules. For example, CD3 is a cell surface molecule on T cells, whereas CD16, NKG2D, or NKp30 are cell surface molecules on NK cells, and CD3 or an invariant TCR are the cell surface molecules on NKT-cells. In some embodiments, e.g., wherein the effector cell is a T cell, the activation molecule is one or more of CD3 (e.g., CD3γ, CD3δ or CD3ε), CD27, CD28, CD40, CD134, CD137, and CD278. In some embodiments, e.g., wherein the effector cell is a NK cell, the cell surface molecule is CD16, NKG2D, or NKp30; or wherein the effector cell is a NKT-cell, the cell surface molecule is CD3 or an invariant TCR.

In some embodiments, the second antibody moiety binds specifically to CD3. CD3 is an antigen expressed by T cells and comprises three different polypeptide chains (ε, δ and γ chains). The three CD3 polypeptide chains associate with the T cell receptor (TCR) and the ζ-chain to form the TCR complex, which has the function of activating signaling cascades in T cells. Currently, many therapeutic strategies target the TCR signal transduction to treat diseases using anti-human CD3 monoclonal antibodies. The skilled artisan will recognize that the TCR complex is an octomeric complex of variable TCR α and β chains with three dimeric signaling modules CD3δ/ε, CD3γ/ε and CD3ζ/ζ or ζ/η. Although in some embodiments the second antibody moiety (such as an scFv) described herein binds to CD3ε, targeting other CD3 molecules, especially CD3ζ, or the TCR α and β chains, is also encompassed in the disclosure.

In some embodiments, there is provided a multi-specific (e.g., bispecific) anti-GPC3 molecule comprising a) an anti-GPC3 antibody moiety (e.g. scFv) specifically recognizing a target GPC3 (e.g., nGPC3 and/or sGPC3), and b) a second antibody moiety (e.g. scFv) that binds specifically to CD3. In some embodiments, the second antibody moiety specifically binds to CD3ε. In some embodiments, the second antibody moiety specifically binds to an agonistic epitope of CD3ε. The term "agonistic epitope," as used herein, means (a) an epitope that, upon binding of the multi-specific molecule, optionally upon binding of several multi-specific molecules on the same cell, allows said multi-specific molecules to activate TCR signaling and induce T cell activation, and/or (b) an epitope that is solely composed of amino acid residues of the epsilon chain of CD3 and is accessible for binding by the multi-specific molecule, when presented in its natural context on T cells (i.e. surrounded by the TCR, the CD3γ chain, etc.), and/or (c) an epitope that, upon binding of the multi-specific molecule, does not lead to stabilization of the spatial position of CD3ε relative to CD3γ.

In some embodiments, there is provided a multi-specific (e.g., bispecific) anti-GPC3 molecule comprising a) an anti-GPC3 antibody moiety (e.g. scFv) specifically recognizing a target GPC3 (e.g., nGPC3 and/or sGPC3), and b) a second antibody moiety (e.g. scFv) that binds specifically to an antigen on the surface of an effector cell, including for example CD3γ, CD3δ, CD3ε, CD3ζ, CD28, CD16a, CD56, CD68, and GDS2D.

In some embodiments, there is provided a multi-specific (e.g., bispecific) anti-GPC3 molecule comprising a) an anti-GPC3 antibody moiety (e.g. scFv) specifically recognizing a target GPC3 (e.g., nGPC3 and/or sGPC3), and b) a second antibody moiety (e.g. scFv) that binds specifically to a component of the complement system, such as C1q. C1q is a subunit of the C1 enzyme complex that activates the serum complement system.

In some embodiments, the second antibody moiety specifically binds to an Fc receptor. In some embodiments, the second antibody moiety specifically binds to an Fcγ receptor (FcγR). The FcγR may be an FcγRIII present on the surface of NK cells or one of FcγRI, FcγRIIA, FcγRIIBI, FcγRIIB2, and FcγRIIIB present on the surface of macrophages, monocytes, neutrophils and/or dendritic cells. In some embodiments, the second antibody moiety is an Fc region or functional fragment thereof. A "functional fragment" as used in this context refers to a fragment of an antibody Fc region that is still capable of binding to an FcR, in particular to an FcγR, with sufficient specificity and affinity to allow an FcγR bearing effector cell, in particular a macrophage, a monocyte, a neutrophil and/or a dendritic cell, to kill the target cell by cytotoxic lysis or phagocytosis. A functional Fc fragment is capable of competitively inhibiting the binding of the original, full-length Fc portion to an FcR such as the activating FcγRI. In some embodiments, a functional Fc fragment retains at least 30%, 40%, 50%, 60%, 70%, 80%, 90% or 95% of its affinity to an activating FcγR. In some embodiments, the Fc region or functional fragment thereof is an enhanced Fc region or functional fragment thereof. The term "enhanced Fc region", as used herein, refers to an Fc region that is modified to enhance Fc receptor-mediated effector-functions, in particular antibody-dependent cell-mediated cytotoxicity (ADCC), complement-dependent cytotoxicity (CDC), and antibody-mediated phagocytosis. This can be achieved as known in the art, for example by altering the Fc region in a way that leads to an increased affinity for an activating receptor (e.g. FcγRIIIA (CD16A) expressed on NK cells) and/or a decreased binding to an inhibitory receptor (e.g. FcγRIIB1/B2 (CD32B)). In yet other embodiments, the second antibody moiety is an antibody or antigen-binding fragment thereof that specifically binds to an FcR, in particular to an FcγR, with sufficient specificity and affinity to allow an FcγR bearing effector cell, in particular a macrophage, a monocyte, a neutrophil and/or a dendritic cell, to kill the target cell by cytotoxic lysis or phagocytosis.

In some embodiments, the multi-specific (e.g., bispecific) anti-GPC3 molecule allows killing of GPC3+ cells (such as HCC cells) and/or can effectively redirect CTLs to lyse cells expressing GPC3 on the target cell surface. In some embodiments, the multi-specific anti-GPC3 molecule of the present invention shows an in vitro $EC_{50}$ ranging from 10 to 500 ng/ml, and is able to induce redirected lysis of about 50% of the target cells through CTLs at a ratio of CTLs to target cells of from about 1:1 to about 50:1 (such as from about 1:1 to about 15:1, or from about 2:1 to about 10:1).

In some embodiments, the multi-specific (e.g., bispecific) anti-GPC3 molecule is capable of cross-linking a stimulated or unstimulated CTL and the target cell (such as GPC3+ cells, e.g. HCC cell) in such a way that the target cell is lysed. This offers the advantage that no generation of target-specific T cell clones or common antigen presentation by dendritic cells is required for the multi-specific anti-GPC3 molecule to exert its desired activity. In some embodiments, the multi-specific (e.g., bispecific) anti-GPC3 molecule of the present invention is capable of redirecting CTLs to lyse the target cells (such as GPC3+ cells, e.g. HCC cell) in the absence of other activating signals. In some embodiments, the second antibody moiety of the multi-specific anti-GPC3 molecule specifically binds to CD3 (e.g., specifically binds to CDR), and signaling through CD28 and/or IL-2 is not required for redirecting CTLs to lyse the target cells.

Methods for measuring the preference of the multi-specific (e.g., bispecific) anti-GPC3 molecule to simultaneously bind to two antigens (e.g., antigens on two different cells) are within the normal capabilities of a person skilled in the art. For example, when the second binding moiety (e.g., second antibody moiety) specifically binds to CD3, the multi-specific anti-GPC3 molecule may be contacted with a mixture of CD3+/GPC3− cells and CD3−/GPC3+ cells. The number of multi-specific anti-GPC3 molecule-positive single cells and the number of cells cross-linked by multi-specific anti-GPC3 molecules may then be assessed by microscopy or fluorescence-activated cell sorting (FACS) as known in the art.

In some embodiments, the multi-specific (e.g., bispecific) anti-GPC3 molecule comprises a) an anti-GPC3 antibody moiety (e.g., scFv) specifically recognizing a target GPC3 (e.g., nGPC3 and/or sGPC3), and b) a second antibody moiety (e.g., scFv) that binds specifically to CD3ε on a T cell (herein after referred to as "anti-CD3 antibody moiety"). In some embodiments, anti-CD3 antibody moiety (e.g., scFv) comprises: i) a $V_H$ comprising an HC-CDR1 comprising the amino acid sequence of SEQ ID NO: 479, an HC-CDR2 comprising the amino acid sequence of SEQ ID NO: 480, and an HC-CDR3 comprising the amino acid sequence of SEQ ID NO: 481; and ii) a $V_L$ comprising an LC-CDR1 comprising the amino acid sequence of SEQ ID NO: 482, an LC-CDR2 comprising the amino acid sequence of SEQ ID NO: 483, and an LC-CDR3 comprising the amino acid sequence of SEQ ID NO: 484. In some embodiments, anti-CD3 antibody moiety (e.g., scFv) comprises: i) a $V_H$ comprising the amino acid sequence of SEQ ID NO: 485; and ii) a $V_L$ comprising the amino acid sequence of SEQ ID NO: 486. In some embodiments, anti-CD3 antibody moiety (e.g., scFv) comprises: i) a $V_H$ comprising the amino acid sequence of SEQ ID NO: 485; and ii) a $V_L$ comprising the amino acid sequence of SEQ ID NO: 486. In some embodiments, the anti-CD3 antibody moiety is an scFv. In some embodiments, the anti-CD3-scFv comprises the amino acid sequence of SEQ ID NO: 487.

Linkers

In some embodiments, the anti-GPC3 antibody moiety (e.g., scFv) specifically recognizing a target GPC3 (e.g., nGPC3 and/or sGPC3) and the second antibody moiety (e.g., scFv) specifically recognizing a second antigen (e.g., CD3 on T cells) are connected by a linker (such as a peptide linker). See "Linkers" subsection under the "Anti-GPC3 Fc fusion protein" section for all applicable linkers that can be used in the multi-specific anti-GPC3 molecules described herein. In some embodiments, the linker comprises the amino acid sequence of SRGGGGSGGGGSGGGGSLEMA (SEQ ID NO: 473). In some embodiments, the linker is or comprises a $(GGGGS)_n$ sequence (SEQ ID NO: 471), wherein n is equal to 1, 2, 3, 4, 5, 6, 7, 8, 9, 10 or more. In some embodiments, the linker comprises the amino acid sequence of TSGGGGS (SEQ ID NO: 474). In some embodiments, the linker comprises the amino acid sequence of GEGTSTGSGGSGGSGGAD (SEQ ID NO: 490).

Tandem scFv

The multi-specific anti-GPC3 molecule in some embodiments is a tandem scFv comprising a first scFv comprising an anti-GPC3 antibody moiety specifically recognizing GPC3 (referred to herein as "anti-GPC3 scFv"; recognizing nGPC3 and/or sGPC3) and a second scFv specifically recognizing a second antigen (also referred to herein as a "tandem scFv multi-specific anti-GPC3 antibody"). In some embodiments, the tandem scFv multi-specific anti-GPC3 antibody further comprises at least one (such as at least about any of 2, 3, 4, 5, or more) additional scFv.

In some embodiments, there is provided a tandem scFv multi-specific (e.g., bispecific) anti-GPC3 antibody comprising a) a first scFv specifically recognizing GPC3, and b)

a second scFv specifically recognizing a second antigen (e.g., CD3 on T cell), wherein the tandem scFv multi-specific anti-GPC3 antibody is a tandem di-scFv or a tandem tri-scFv. In some embodiments, the tandem scFv multi-specific anti-GPC3 antibody is a tandem di-scFv. In some embodiments, the tandem scFv multi-specific anti-GPC3 antibody is a bispecific T-cell engager. In some embodiments, the first anti-GPC3 scFv specifically recognizes a cell surface-bound GPC3. In some embodiments, the binding affinity of the first anti-nGPC3 scFv to a cell surface-bound GPC3 is higher than that to a soluble GPC3. In some embodiments, the first anti-nGPC3 scFv specifically recognizes a cell surface-bound GPC3 at a high binding affinity and binds to a soluble GPC3 at a low binding affinity. In some embodiments, the first anti-GPC3 scFv specifically recognizes a soluble GPC3. In some embodiments, the binding affinity of the first anti-sGPC3 scFv to a soluble GPC3 is higher than that to a cell surface-bound GPC3. In some embodiments, the first anti-GPC3 scFv specifically recognizes both cell surface-bound GPC3 and soluble GPC3. In some embodiments, the second scFv specifically binds to a different GPC3 epitope. In some embodiments, the second scFv specifically recognizes a second antigen that is not GPC3. In some embodiments, the second scFv specifically recognizes a second antigen on the surface of a cell, such as a cytotoxic cell. In some embodiments, the second scFv specifically binds to an antigen on the surface of a lymphocyte, such as a T cell (e.g., CTL, helper T cell, or NKT), a B cell, a natural killer (NK) cell, a neutrophil, a monocyte, a macrophage, or a dendritic cell. In some embodiments, the second scFv specifically binds to an effector T cell, such as a CTL or NKT cell. In some embodiments, the second scFv specifically binds to a second antigen on the surface of an effector cell, including for example CD3γ, CD3δ, CD3ε, CD3ζ, CD27, CD28, CD16a, CD40L, CD56, CD68, CD137, OX40, GITR, HVEM and GDS2D. In some embodiments, the first anti-GPC3 scFv is chimeric, human, partially humanized, fully humanized, or semi-synthetic. In some embodiments, the second scFv is chimeric, human, partially humanized, fully humanized, or semi-synthetic. In some embodiments, both the first and second scFvs are chimeric, human, partially humanized, fully humanized, or semi-synthetic. In some embodiments, the tandem scFv multi-specific anti-GPC3 antibody further comprises at least one (such as at least about any of 2, 3, 4, 5, or more) additional scFv. In some embodiments, the first anti-GPC3 scFv and the second scFv are connected by a linker (e.g., peptide linker). In some embodiments, the linker comprises the amino acid sequence of (GGGGS)$_n$ (SEQ ID NO: 471), wherein n is equal to 1, 2, 3, 4, 5, 6, 7, 8, 9, 10 or more. In some embodiments, the linker comprises the amino acid sequence of TSGGGGS (SEQ ID NO: 474). In some embodiments, the first anti-GPC3 scFv is N-terminal to the second scFv. In some embodiments, the first anti-GPC3 scFv is C-terminal to the second scFv. In some embodiments, the tandem scFv multi-specific (e.g., bispecific) anti-GPC3 antibody further comprises a tag (e.g., a peptide tag for purification purpose). In some embodiments, the tag is N-terminal to the tandem scFv multi-specific (e.g., bispecific) anti-GPC3 antibody. In some embodiments, the tag is C-terminal to the tandem scFv multi-specific (e.g., bispecific) anti-GPC3 antibody. In some embodiments, the tag comprises the amino acid sequence of HHHHHH (SEQ ID NO: 476).

In some embodiments, the tandem scFv multi-specific anti-GPC3 antibody is a tandem di-scFv comprising two scFvs (referred to herein as "tandem di-scFv bispecific anti-GPC3 antibody"). The tandem di-scFv bispecific anti-GPC3 antibody can have $V_H$ and $V_L$ assembled in any configurations, such as the configurations listed below (from N-terminus to C-terminus), wherein X is the second antigen specifically bound by the second scFv, L1, L2, and L3 are optional linkers (such as peptide linkers). See "Linkers" subsection under the "Anti-GPC3 Fc fusion protein" section for all applicable linkers. In some embodiments, the linker (L1, L2, or L3) comprises the amino acid sequence of SRGGGGSGGGGSGGGGSLEMA (SEQ ID NO: 473). In some embodiments, the linker (L1, L2, or L3) is or comprises a (GGGGS)$_n$ sequence (SEQ ID NO: 471), wherein n is equal to 1, 2, 3, 4, 5, 6, 7, 8, 9, 10 or more. In some embodiments, the linker (L1, L2, or L3) comprises the amino acid sequence of TSGGGGS (SEQ ID NO: 474). In some embodiments, the linker (L1, L2, or L3) comprises the amino acid sequence of GEGTSTGSGGSGGSGGAD (SEQ ID NO: 490).

In some embodiments, the multi-specific anti-GPC3 antibody is a tandem di-scFv having one of the following structures:

$V_L$(GPC3)-L1-$V_H$(GPC3)-L2-$V_L$(X)-L3-$V_H$(X);
$V_L$(GPC3)-L1-$V_H$(GPC3)-L2-$V_H$(X)-L3-$V_L$(X);
$V_H$(GPC3)-L1-$V_L$(GPC3)-L2-$V_L$(X)-L3-$V_H$(X);
$V_H$(GPC3)-L1-$V_L$(GPC3)-L2-$V_H$(X)-L3-$V_L$(X);
$V_L$(X)-L1-$V_H$(X)-L2-$V_L$(GPC3)-L3-$V_H$(GPC3);
$V_L$(X)-L1-$V_H$(X)-L2-$V_H$(GPC3)-L3-$V_L$(GPC3);
$V_H$(X)-L1-$V_L$(X)-L2-$V_L$(GPC3)-L3-$V_H$(GPC3);
$V_H$(X)-L1-$V_L$(X)-L2-$V_H$(GPC3)-L3-$V_L$(GPC3);
$V_L$(GPC3)-L1-$V_H$(X)-L2-$V_L$(X)-L3-$V_H$(GPC3);
$V_L$(GPC3)-L1-$V_L$(X)-L2-$V_H$(X)-L3-$V_H$(GPC3);
$V_H$(GPC3)-L1-$V_H$(X)-L2-$V_L$(X)-L3-$V_L$(GPC3);
$V_H$(GPC3)-L1-$V_L$(X)-L2-$V_H$(X)-L3-$V_L$(GPC3);
$V_L$(X)-L1-$V_H$(GPC3)-L2-$V_L$(GPC3)-L3-$V_H$(X);
$V_L$(X)-L1-$V_L$(GPC3)-L2-$V_H$(GPC3)-L3-$V_H$(X);
$V_H$(X)-L1-$V_H$(GPC3)-L2-$V_L$(GPC3)-L3-$V_L$(X); or
$V_H$(X)-L1-$V_L$(GPC3)-L2-$V_H$(GPC3)-L3-$V_L$(X).

In some embodiments, there is provided a tandem scFv multi-specific (e.g., bispecific) anti-GPC3 antibody comprising a) a first scFv specifically recognizing a cell surface-bound GPC3 (e.g., the binding affinity of the first anti-nGPC3 scFv to a cell surface-bound GPC3 is higher than that to a soluble GPC3, or the first anti-nGPC3 scFv specifically recognizes a cell surface-bound GPC3 at a high binding affinity and binds to a soluble GPC3 at a low binding affinity), and b) a second scFv specifically recognizing a second antigen (such as a second antigen on an effector cell, e.g., CD3 on T cell). In some embodiments, the first anti-nGPC3 scFv specifically recognizes an epitope within human GPC3 comprising the amino acid sequence of SEQ ID NO: 460. In some embodiments, the first anti-nGPC3 scFv specifically recognizes an epitope within the amino acid sequence of SEQ ID NO: 461. In some embodiments, the first anti-nGPC3 scFv specifically recognizes an epitope within the amino acid sequence of SEQ ID NO: 462. In some embodiments, the first anti-nGPC3 scFv specifically recognizes an epitope within the amino acid sequence of SEQ ID NO: 463. In some embodiments, the first anti-nGPC3 scFv specifically recognizes an epitope within the N-terminal fragment of GPC3. In some embodiments, the first anti-nGPC3 scFv specifically recognizes an epitope within amino acids 1-358 of SEQ ID NO: 460 (SEQ ID NO: 468). In some embodiments, the first anti-nGPC3 scFv specifically recognizes an epitope within the amino acid sequence of SEQ ID NO: 464. In some embodiments, the first anti-nGPC3 scFv specifically recognizes an epitope within the C-terminal fragment of GPC3. In some embodiments, the first antinGPC3 scFv specifically recognizes an epitope within amino acids 359-560 of SEQ ID NO: 460 (SEQ ID NO: 465). In some embodiments, the first anti-nGPC3 scFv specifically recognizes an epitope within amino acids 359-580 of SEQ ID NO: 460 (SEQ ID NO: 466). In some embodiments, the first anti-nGPC3 scFv specifically recognizes an epitope within the C-terminal fragment of GPC3 lacking heparin sulfate side chain. In some embodiments, the first anti-nGPC3 scFv specifically recognizes an epitope within amino acids 510-560 of SEQ ID NO: 460 (SEQ ID NO: 467). In some embodiments, the first anti-nGPC3 scFv specifically recognizes an epitope spanning the Furin cleavage site at amino acids $R^{358}/S^{359}$ of SEQ ID NO: 460. In some embodiments, the first anti-nGPC3 scFv can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460. In some embodiments, the first anti-nGPC3 scFv specifically recognizes an epitope within the C-terminal fragment of GPC3 lacking heparin sulfate side chain. In some embodiments, there is provided a tandem scFv multi-specific (e.g., bispecific) anti-GPC3 antibody comprising a) a first anti-nGPC3 scFv (e.g., the binding affinity of the first anti-nGPC3 scFv to a cell surface-bound GPC3 is higher than that to a soluble GPC3, or the first anti-nGPC3 scFv specifically recognizes a cell surface-bound GPC3 at a high binding affinity and binds to a soluble GPC3 at a low binding affinity) that competes for binding to nGPC3 with any one of the anti-GPC3 constructs described herein; and b) a second scFv specifically recognizing a second antigen (such as a second antigen on an effector cell, e.g., CD3 on T cell). In some embodiments, there is provided a tandem scFv multi-specific (e.g., bispecific) anti-GPC3 antibody comprising a) a first anti-nGPC3 scFv (e.g., the binding affinity of the first anti-nGPC3 scFv to a cell surface-bound GPC3 is higher than that to a soluble GPC3, or the first anti-nGPC3 scFv specifically recognizes a cell surface-bound GPC3 at a high binding affinity and binds to a soluble GPC3 at a low binding affinity) that specifically binds to the same, or substantially the same, nGPC3 epitope competitively with any one of the anti-GPC3 constructs described herein; and b) a second scFv specifically recognizing a second antigen (such as a second antigen on an effector cell, e.g., CD3 on T cell). In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the first anti-nGPC3 scFv and the second scFv are connected by a linker (e.g., peptide linker). In some embodiments, the linker comprises the amino acid sequence of $(GGGGS)_n$ (SEQ ID NO: 471), wherein n is equal to 1, 2, 3, 4, 5, 6, 7, 8, 9, 10 or more. In some embodiments, the linker comprises the amino acid sequence of TSGGGGS (SEQ ID NO: 474). In some embodiments, the first anti-nGPC3 scFv is N-terminal to the second scFv. In some embodiments, the first anti-nGPC3 scFv is chimeric, human, partially humanized, fully humanized, or semi-synthetic. In some embodiments, the second scFv is chimeric, human, partially humanized, fully humanized, or semi-synthetic. In some embodiments, both the first and second scFvs are chimeric, human, partially humanized, fully humanized, or semi-synthetic. In some embodiments, the $K_d$ of the binding between the anti-nGPC3-scFv and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3-scFv and an sGPC3 can be at least about 10 times (such as at least about 10, $10^2$, $10^3$, $10^4$, $10^5$, $10^6$, or $10^7$ times) of the $K_d$ of the binding between the anti-nGPC3-scFv and nGPC3. In some embodiments, the $K_d$ of the binding between the anti-nGPC3-scFv and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the second scFv specifically binds to an antigen on the surface of a lymphocyte, such as a T cell (e.g., CTL, helper T cell, or NKT), a B cell, a natural killer (NK) cell, a neutrophil, a monocyte, a macrophage, or a dendritic cell. In some embodiments, the second scFv specifically binds to an effector T cell, such as a CTL or NKT cell. In some embodiments, the second scFv specifically binds to a second antigen on the surface of an effector cell, including for example CD3γ, CD3δ, CD3ε, CD3ζ, CD27, CD28, CD16a, CD40L, CD56, CD68, CD137, OX40, GITR, HVEM and GDS2D.

In some embodiments, there is provided a tandem scFv multi-specific (e.g., bispecific) anti-GPC3 antibody comprising a) a first scFv specifically recognizing a cell surface-bound GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions, and b) a second scFv specifically recognizing a second antigen (such as a second antigen on an effector cell, e.g., CD3 on T cell). In some embodiments, there is provided a tandem scFv multi-specific (e.g., bispecific) anti-GPC3 antibody comprising a) a first scFv specifically recognizing a cell surface-bound GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286, and b) a second scFv specifically recognizing a second antigen (such as a second antigen on an effector cell, e.g., CD3 on T cell). In some embodiments, there is provided a tandem scFv multi-specific (e.g., bispecific) anti-GPC3 antibody comprising a) a first scFv specifically recognizing a cell surface-bound GPC3, comprising: a $V_H$ comprising the amino acid sequence of any one of SEQ ID NOs: 307-337; and ii) a $V_L$ comprising the amino acid sequence of any one of SEQ ID NOs: 358-388, and b) a second scFv specifically recognizing a second antigen (such as a second antigen on an effector cell, e.g., CD3 on T cell). In some embodiments, there is provided a tandem scFv multi-specific (e.g., bispecific) anti-GPC3 antibody comprising a) a first scFv specifically recognizing a cell surface-bound GPC3, comprising the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388; and b) a second scFv specifically recognizing a second antigen (such as a second antigen on an effector cell, e.g., CD3 on T cell). In some embodiments, there is provided a tandem scFv multi-specific (e.g., bispecific) anti-GPC3 antibody comprising a) a first anti-nGPC3 scFv that competes for binding to nGPC3 with any one of the anti-GPC3 constructs described herein; and b) a second scFv specifically recognizing a second antigen (such as a second antigen on an effector cell, e.g., CD3 on T cell). In some embodiments, there is provided a tandem scFv multi-specific (e.g., bispecific) anti-GPC3 antibody comprising a) a first anti-nGPC3 scFv that specifically binds to the same, or substantially the same, nGPC3 epitope competitively with any one of the anti-GPC3 constructs described herein; and b) a second scFv specifically recognizing a second antigen (such as a second antigen on an effector cell, e.g., CD3 on T cell). In some embodiments, the $K_d$ of the binding between the anti-nGPC3-scFv and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3-scFv and an sGPC3 can be at least about 10 times (such as at least about 10, $10^2$, $10^3$, $10^4$, $10^5$, $10^6$, or $10^7$ times) of the $K_d$ of the binding between the anti-nGPC3-scFv and nGPC3. In some embodiments, the $K_d$ of the binding between the anti-nGPC3-scFv and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the first anti-nGPC3 scFv and the second scFv are connected by a linker (e.g., peptide linker). In some embodiments, the linker comprises the amino acid sequence of (GGGGS)$_n$ (SEQ ID NO: 471), wherein n is equal to 1, 2, 3, 4, 5, 6, 7, 8, 9, 10 or more. In some embodiments, the linker comprises the amino acid sequence of TSGGGGS (SEQ ID NO: 474). In some embodiments, the first anti-nGPC3 scFv is N-terminal to the second scFv. In some embodiments, the first anti-nGPC3 scFv is chimeric, human, partially humanized, fully humanized, or semi-synthetic. In some embodiments, the second scFv is chimeric, human, partially humanized, fully humanized, or semi-synthetic. In some embodiments, both the first and second scFvs are chimeric, human, partially humanized, fully humanized, or semi-synthetic. In some embodiments, the second scFv specifically binds to an antigen on the surface of a lymphocyte, such as a T cell (e.g., CTL, helper T cell, or NKT), a B cell, a natural killer (NK) cell, a neutrophil, a monocyte, a macrophage, or a dendritic cell. In some embodiments, the second scFv specifically binds to an effector T cell, such as a CTL or NKT cell. In some embodiments, the second scFv specifically binds to a second antigen on the surface of an effector cell, including for example CD3γ, CD3δ, CD3ε, CD3ζ, CD27, CD28, CD16a, CD40L, CD56, CD68, CD137, OX40, GITR, HVEM and GDS2D.

In some embodiments, there is provided a tandem scFv multi-specific (e.g., bispecific) anti-GPC3 antibody comprising a) a first scFv specifically recognizing GPC3 (e.g., nGPC3 and/or sGPC3), comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions, and b) a second scFv specifically recognizing a second antigen (such as a second antigen on an effector cell, e.g., CD3 on T cell). In some embodiments, there is provided a tandem scFv multi-specific (e.g., bispecific) anti-GPC3 antibody comprising a) a first scFv specifically recognizing GPC3, comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306, and b) a second scFv specifically recognizing a second antigen (such as a second antigen on an effector cell, e.g., CD3 on T cell). In some embodiments, there is provided a tandem scFv multi-specific (e.g., bispecific) anti-GPC3 antibody comprising a) a first scFv specifically recognizing GPC3, comprising: a $V_H$ comprising the amino acid sequence of any one of SEQ ID NOs: 338-357; and ii) a $V_L$ comprising the amino acid sequence of any one of SEQ ID NOs: 389-408, and b) a second scFv specifically recognizing a second antigen (such as a second antigen on an effector cell, e.g., CD3 on T cell). In some embodiments, there is provided a tandem scFv multi-specific (e.g., bispecific) anti-GPC3 antibody comprising a) a first scFv specifically recognizing GPC3, comprising the HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408; and b) a second scFv specifically recognizing a second antigen (such as a second antigen on an effector cell, e.g., CD3 on T cell). In some embodiments, there is provided a tandem scFv multi-specific (e.g., bispecific) anti-GPC3 antibody comprising a) a first anti-GPC3 scFv that competes for binding to GPC3 with any one of the anti-GPC3 constructs described herein; and b) a second scFv specifically recognizing a second antigen (such as a second antigen on an effector cell, e.g., CD3 on T cell). In some embodiments, there is provided a tandem scFv multi-specific (e.g., bispecific) anti-GPC3 antibody comprising a) a first anti-GPC3 scFv that specifically binds to the same, or substantially the same, GPC3 epitope competitively with any one of the anti-GPC3 constructs described herein; and b) a second scFv specifically recognizing a second antigen (such as a second antigen on an effector cell, e.g., CD3 on T cell). In some embodiments, the first anti-GPC3 antibody moiety specifically recognizes a cell surface-bound GPC3. In some embodiments, the binding affinity of the first anti-nGPC3 antibody moiety to a cell surface-bound GPC3 is higher than that to a soluble GPC3. In some embodiments, the first anti-GPC3 antibody moiety specifically recognizes a cell surface-bound GPC3 at a high binding affinity and binds to a soluble GPC3 at a low binding affinity. In some embodiments, the first anti-GPC3 antibody moiety specifically recognizes a soluble GPC3. In some embodiments, the binding affinity of the first anti-sGPC3 antibody moiety to a soluble GPC3 is higher than that to a cell surface-bound GPC3. In some embodiments, the first anti-sGPC3 antibody moiety specifically recognizes an epitope within the amino acid sequence of SEQ ID NO: 461. In some embodiments, the first anti-sGPC3 antibody moiety specifically recognizes an epitope within amino acids 510-560 of SEQ ID NO: 460 (SEQ ID NO: 467). In some embodiments, the first anti-GPC3 antibody moiety specifically recognizes both cell surface-bound GPC3 and soluble GPC3. In some embodiments, the $K_d$ of the binding between the first anti-GPC3-scFv and a target GPC3 (e.g., nGPC3 and/or sGPC3) is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the first anti-GPC3-scFv and a non-target can be at least about 10 times (such as at least about 10, $10^2$, $10^3$, $10^4$, $10^5$, $10^6$, or $10^7$ times) of the $K_d$ of the binding between the anti-GPC3-scFv and the target GPC3. In some embodiments, the $K_d$ of the binding between the anti-GPC3-scFv and a non-target is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the first anti-GPC3 scFv and the second scFv are connected by a linker (e.g., peptide linker). In some embodiments, the linker comprises the amino acid sequence of (GGGGS)$_n$ (SEQ ID NO: 471), wherein n is equal to 1, 2, 3, 4, 5, 6, 7, 8, 9, 10 or more. In some embodiments, the linker comprises the amino acid sequence of TSGGGGS (SEQ ID NO: 474). In some embodiments, the first anti-GPC3 scFv is N-terminal to the second scFv. In some embodiments, the first anti-GPC3 scFv is chimeric, human, partially humanized, fully humanized, or semi-synthetic. In some embodiments, the second scFv is chimeric, human, partially humanized, fully humanized, or semi-synthetic. In some embodiments, both the first and second scFvs are chimeric, human, partially humanized, fully humanized, or semi-synthetic. In some embodiments, the second scFv specifically binds to an antigen on the surface of a lymphocyte, such as a T cell (e.g., CTL, helper T cell, or NKT), a B cell, a natural killer (NK) cell, a neutrophil, a monocyte, a macrophage, or a dendritic cell. In some embodiments, the second scFv specifically binds to an effector T cell, such as a CTL or NKT cell. In some embodiments, the second scFv specifically binds to a second antigen on the surface of an effector cell, including for example CD3γ, CD3δ, CD3ε, CD3ζ, CD27, CD28, CD16a, CD40L, CD56, CD68, CD137, OX40, GITR, HVEM and GDS2D.

In some embodiments, there is provided a tandem di-scFv bispecific anti-GPC3 antibody comprising a) a first scFv specifically recognizing GPC3, and b) a second scFv specifically recognizing CD3ε on the cell surface of a T cell. In some embodiments, the tandem di-scFv bispecific anti-GPC3 antibody is a bispecific T-cell engager. In some embodiments, the first anti-GPC3 scFv specifically recognizes a cell surface-bound GPC3. In some embodiments, the binding affinity of the first anti-nGPC3 scFv to a cell surface-bound GPC3 is higher than that to a soluble GPC3. In some embodiments, the first anti-nGPC3 scFv specifically recognizes a cell surface-bound GPC3 at a high binding affinity and binds to a soluble GPC3 at a low binding affinity. In some embodiments, the first anti-GPC3 scFv specifically recognizes a soluble GPC3. In some embodiments, the binding affinity of the first anti-sGPC3 scFv to a soluble GPC3 is higher than that to a cell surface-bound GPC3. In some embodiments, the first anti-GPC3 scFv specifically recognizes both cell surface-bound GPC3 and soluble GPC3. In some embodiments, the first anti-GPC3 scFv is chimeric, human, partially humanized, fully humanized, or semi-synthetic. In some embodiments, the second scFv is chimeric, human, partially humanized, fully humanized, or semi-synthetic. In some embodiments, both the first and second scFvs are chimeric, human, partially humanized, fully humanized, or semi-synthetic. In some embodiments, the first anti-GPC3 scFv and the second scFv are connected by a linker (e.g., peptide linker). In some embodiments, the linker comprises the amino acid sequence of (GGGGS)$_n$ (SEQ ID NO: 471), wherein n is equal to 1, 2, 3, 4, 5, 6, 7, 8, 9, 10 or more. In some embodiments, the linker comprises the amino acid sequence of TSGGGGS (SEQ ID NO: 474). In some embodiments, the first anti-GPC3 scFv is N-terminal to the second anti-CD3-scFv. In some embodiments, anti-CD3-scFv comprises: i) a $V_H$ comprising an HC-CDR1 comprising the amino acid sequence of SEQ ID NO: 479, an HC-CDR2 comprising the amino acid sequence of SEQ ID NO: 480, and an HC-CDR3 comprising the amino acid sequence of SEQ ID NO: 481; and ii) a $V_L$ comprising an LC-CDR1 comprising the amino acid sequence of SEQ ID NO: 482, an LC-CDR2 comprising the amino acid sequence of SEQ ID NO: 483, and an LC-CDR3 comprising the amino acid sequence of SEQ ID NO: 484. In some embodiments, anti-CD3-scFv comprises: i) a $V_H$ comprising the amino acid sequence of SEQ ID NO: 485; and ii) a $V_L$ comprising the amino acid sequence of SEQ ID NO: 486. In some embodiments, anti-CD3-scFv comprises: i) a $V_H$ comprising the amino acid sequence of SEQ ID NO: 485; and ii) a $V_L$ comprising the amino acid sequence of SEQ ID NO: 486. In some embodiments, the anti-CD3-scFv comprises the amino acid sequence of SEQ ID NO: 487.

In some embodiments, there is provided a tandem di-scFv bispecific anti-GPC3 antibody comprising a) a first scFv specifically recognizing a cell surface-bound GPC3 (e.g., the binding affinity of the first anti-nGPC3 scFv to a cell surface-bound GPC3 is higher than that to a soluble GPC3, or the first anti-nGPC3 scFv specifically recognizes a cell surface-bound GPC3 at a high binding affinity and binds to a soluble GPC3 at a low binding affinity), and b) a second scFv specifically recognizing CD3ε on the cell surface of a T cell. In some embodiments, the first anti-nGPC3 scFv specifically recognizes an epitope within human GPC3 comprising the amino acid sequence of SEQ ID NO: 460. In some embodiments, the first anti-nGPC3 scFv specifically recognizes an epitope within the amino acid sequence of SEQ ID NO: 461. In some embodiments, the first anti-nGPC3 scFv specifically recognizes an epitope within the amino acid sequence of SEQ ID NO: 462. In some embodiments, the first anti-nGPC3 scFv specifically recognizes an epitope within the amino acid sequence of SEQ ID NO: 463. In some embodiments, the first anti-nGPC3 scFv specifically recognizes an epitope within the N-terminal fragment of GPC3. In some embodiments, the first anti-nGPC3 scFv specifically recognizes an epitope within amino acids 1-358 of SEQ ID NO: 460 (SEQ ID NO: 468). In some embodiments, the first anti-nGPC3 scFv specifically recognizes an epitope within the amino acid sequence of SEQ ID NO: 464. In some embodiments, the first anti-nGPC3 scFv specifically recognizes an epitope within the C-terminal fragment of GPC3. In some embodiments, the first anti-nGPC3 scFv specifically recognizes an epitope within amino acids 359-560 of SEQ ID NO: 460 (SEQ ID NO: 465). In some embodiments, the first anti-nGPC3 scFv specifically recognizes an epitope within amino acids 359-580 of SEQ ID NO: 460 (SEQ ID NO: 466). In some embodiments, the first anti-nGPC3 scFv specifically recognizes an epitope within the C-terminal fragment of GPC3 lacking heparin sulfate side chain. In some embodiments, the first anti-nGPC3 scFv specifically recognizes an epitope within amino acids 510-560 of SEQ ID NO: 460 (SEQ ID NO: 467). In some embodiments, the first anti-nGPC3 scFv specifically recognizes an epitope spanning the Furin cleavage site at amino acids $R^{358}/S^{359}$ of SEQ ID NO: 460. In some embodiments, the first anti-nGPC3 scFv can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460). In some embodiments, the first anti-nGPC3 scFv specifically recognizes an epitope within the C-terminal fragment of GPC3 lacking heparin sulfate side chain. In some embodiments, there is provided a tandem di-scFv bispecific anti-GPC3 antibody comprising: a) a first anti-nGPC3-scFv (e.g., the binding affinity of the first anti-nGPC3 scFv to a cell surface-bound GPC3 is higher than that to a soluble GPC3, or the first anti-nGPC3 scFv specifically recognizes a cell surface-bound GPC3 at a high binding affinity and binds to a soluble GPC3 at a low binding affinity) that competes for binding to nGPC3 with any one of the anti-GPC3 constructs described herein; and b) a second scFv specifically recognizing CD3ε on the cell surface of a T cell. In some embodiments, there is provided a tandem di-scFv bispecific anti-GPC3 antibody comprising: a) a first anti-nGPC3-scFv (e.g., the binding affinity of the first anti-nGPC3 scFv to a cell surface-bound GPC3 is higher than that to a soluble GPC3, or the first anti-nGPC3 scFv specifically recognizes a cell surface-bound GPC3 at a high binding affinity and binds to a soluble GPC3 at a low binding affinity) that specifically binds to the same, or substantially the same, nGPC3 epitope competitively with any one of the anti-GPC3 constructs described herein; and b) a second scFv specifically recognizing CD3ε on the cell surface of a T cell. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the first anti-nGPC3 scFv and the second scFv are connected by a linker (e.g., peptide linker). In some embodiments, the linker comprises the amino acid sequence of $(GGGGS)_n$ (SEQ ID NO: 471), wherein n is equal to 1, 2, 3, 4, 5, 6, 7, 8, 9, 10 or more. In some embodiments, the linker comprises the amino acid sequence of TSGGGGS (SEQ ID NO: 474). In some embodiments, the first anti-nGPC3 scFv is N-terminal to the second scFv. In some embodiments, the first anti-nGPC3 scFv is chimeric, human, partially humanized, fully humanized, or semi-synthetic. In some embodiments, the second scFv is chimeric, human, partially humanized, fully humanized, or semi-synthetic. In some embodiments, both the first and second scFvs are chimeric, human, partially humanized, fully humanized, or semi-synthetic. In some embodiments, the $K_d$ of the binding between the anti-nGPC3-scFv and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3-scFv and an sGPC3 can be at least about 10 times (such as at least about 10, $10^2$, $10^3$, $10^4$, $10^5$, $10^6$, or $10^7$ times) of the $K_d$ of the binding between the anti-nGPC3-scFv and nGPC3. In some embodiments, the $K_d$ of the binding between the anti-nGPC3-scFv and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, anti-CD3-scFv comprises: i) a $V_H$ comprising an HC-CDR1 comprising the amino acid sequence of SEQ ID NO: 479, an HC-CDR2 comprising the amino acid sequence of SEQ ID NO: 480, and an HC-CDR3 comprising the amino acid sequence of SEQ ID NO: 481; and ii) a $V_L$ comprising an LC-CDR1 comprising the amino acid sequence of SEQ ID NO: 482, an LC-CDR2 comprising the amino acid sequence of SEQ ID NO: 483, and an LC-CDR3 comprising the amino acid sequence of SEQ ID NO: 484. In some embodiments, anti-CD3-scFv comprises: i) a $V_H$ comprising the amino acid sequence of SEQ ID NO: 485; and ii) a $V_L$ comprising the amino acid sequence of SEQ ID NO: 486. In some embodiments, anti-CD3-scFv comprises: i) a $V_H$ comprising the amino acid sequence of SEQ ID NO: 485; and ii) a $V_L$ comprising the amino acid sequence of SEQ ID NO: 486. In some embodiments, the anti-CD3-scFv comprises the amino acid sequence of SEQ ID NO: 487. In some embodiments, the tandem di-scFv bispecific anti-GPC3 antibody further comprises a tag (e.g., a peptide tag for purification purpose). In some embodiments, the tag is N-terminal to the tandem di-scFv bispecific anti-GPC3 antibody. In some embodiments, the tag is C-terminal to the tandem di-scFv bispecific anti-GPC3 antibody. In some embodiments, the tag comprises the amino acid sequence of HHHHHH (SEQ ID NO: 476).

In some embodiments, there is provided a tandem di-scFv bispecific anti-GPC3 antibody comprising a) a first scFv specifically recognizing a cell surface-bound GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions, and b) a second scFv specifically recognizing CD3ε on the cell surface of a T cell. In some embodiments, there is provided a tandem di-scFv bispecific anti-GPC3 antibody comprising a) a first scFv specifically recognizing a cell surface-bound GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286, and b) a second scFv specifically recognizing CD3ε on the cell surface of a T cell. In some embodiments, there is provided a tandem di-scFv bispecific anti-GPC3 antibody comprising a) a first scFv specifically recognizing a cell surface-bound GPC3, comprising: a $V_H$ comprising the amino acid sequence of any one of SEQ ID NOs: 307-337; and ii) a $V_L$ comprising the amino acid sequence of any one of SEQ ID NOs: 358-388, and b) a second scFv specifically recognizing CD3ε on the cell surface of a T cell. In some embodiments, there is provided a tandem di-scFv bispecific anti-GPC3 antibody comprising a) a first scFv specifically recognizing a cell surface-bound GPC3, comprising the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388; and b) a second scFv specifically recognizing CD3ε on the cell surface of a T cell. In some embodiments, there is provided a tandem di-scFv bispecific anti-GPC3 antibody comprising: a) a first anti-nGPC3-scFv that competes for binding to nGPC3 with any one of the anti-GPC3 constructs described herein; and b) a second scFv specifically recognizing CD3ε on the cell surface of a T cell. In some embodiments, there is provided a tandem di-scFv bispecific anti-GPC3 antibody comprising: a) a first anti-nGPC3-scFv that specifically binds to the same, or substantially the same, nGPC3 epitope competitively with any one of the anti-GPC3 constructs described herein; and b) a second scFv specifically recognizing CD3ε on the cell surface of a T cell. In some embodiments, the $K_d$ of the binding between the anti-nGPC3-scFv and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3-scFv and an sGPC3 can be at least about 10 times (such as at least about 10, $10^2$, $10^3$, $10^4$, $10^5$, $10^6$, or $10^7$ times) of the $K_d$ of the binding between the anti-nGPC3-scFv and nGPC3. In some embodiments, the $K_d$ of the binding between the anti-nGPC3-scFv and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the first anti-nGPC3 scFv and the second scFv are connected by a linker (e.g., peptide linker). In some embodiments, the linker comprises the amino acid sequence of (GGGGS)$_n$ (SEQ ID NO: 471), wherein n is equal to 1, 2, 3, 4, 5, 6, 7, 8, 9, 10 or more. In some embodiments, the linker comprises the amino acid sequence of TSGGGGS (SEQ ID NO: 474). In some embodiments, the first anti-nGPC3 scFv is N-terminal to the second scFv. In some embodiments, the first anti-nGPC3 scFv is chimeric, human, partially humanized, fully humanized, or semi-synthetic. In some embodiments, the second scFv is chimeric, human, partially humanized, fully humanized, or semi-synthetic. In some embodiments, both the first and second scFvs are chimeric, human, partially humanized, fully humanized, or semi-synthetic. In some embodiments, the anti-nGPC3 scFv comprises the amino acid sequence of any one of SEQ ID NOs: 409-439. In some embodiments, anti-CD3-scFv comprises: i) a $V_H$ comprising an HC-CDR1 comprising the amino acid sequence of SEQ ID NO: 479, an HC-CDR2 comprising the amino acid sequence of SEQ ID NO: 480, and an HC-CDR3 comprising the amino acid sequence of SEQ ID NO: 481; and ii) a $V_L$ comprising an LC-CDR1 comprising the amino acid sequence of SEQ ID NO: 482, an LC-CDR2 comprising the amino acid sequence of SEQ ID NO: 483, and an LC-CDR3 comprising the amino acid sequence of SEQ ID NO: 484. In some embodiments, anti-CD3-scFv comprises: i) a $V_H$ comprising the amino acid sequence of SEQ ID NO: 485; and ii) a $V_L$ comprising the amino acid sequence of SEQ ID NO: 486. In some embodiments, anti-CD3-scFv comprises: i) a $V_H$ comprising the amino acid sequence of SEQ ID NO: 485; and ii) a $V_L$ comprising the amino acid sequence of SEQ ID NO: 486. In some embodiments, the anti-CD3-scFv comprises the amino acid sequence of SEQ ID NO: 487. In some embodiments, there is provided a tandem di-scFv bispecific anti-GPC3 antibody comprising a) a first scFv specifically recognizing a cell surface-bound GPC3; and b) a second scFv specifically recognizing CD3ε on the cell surface of a T cell, wherein the tandem di-scFv bispecific anti-GPC3 antibody comprises the amino acid sequence of any one of SEQ ID NOs: 488 and 511-515. In some embodiments, the tandem di-scFv bispecific anti-GPC3 antibody further comprises a tag (e.g., a peptide tag for purification purpose). In some embodiments, the tag is N-terminal to the tandem di-scFv bispecific anti-GPC3 antibody. In some embodiments, the tag is C-terminal to the tandem di-scFv bispecific anti-GPC3 antibody. In some embodiments, the tag comprises the amino acid sequence of HHHHHH (SEQ ID NO: 476).

In some embodiments, there is provided a tandem di-scFv bispecific anti-GPC3 antibody comprising a) a first scFv specifically recognizing GPC3 (e.g., nGPC3 and/or sGPC3), comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions, and b) a second scFv specifically recognizing CD3ε on the cell surface of a T cell. In some embodiments, there is provided a tandem di-scFv bispecific anti-GPC3 antibody comprising a) a first scFv specifically recognizing GPC3 (e.g., nGPC3 and/or sGPC3), comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153, wherein the amino acid substitutions are in HC-CDR1 or HC-CDR2; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306, and b) a second scFv specifically recognizing CD3ε on the cell surface of a T cell. In some embodiments, there is provided a tandem di-scFv bispecific anti-GPC3 antibody comprising a) a first scFv specifically recognizing GPC3 (e.g., nGPC3 and/or sGPC3), comprising: a $V_H$ comprising the amino acid sequence of any one of SEQ ID NOs: 338-357; and ii) a $V_L$ comprising the amino acid sequence of any one of SEQ ID NOs: 389-408, and b) a second scFv specifically recognizing CD3ε on the cell surface of a T cell. In some embodiments, there is provided a tandem di-scFv bispecific anti-GPC3 antibody comprising a) a first scFv specifically recognizing GPC3 (e.g., nGPC3 and/or sGPC3), comprising the HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408; and b) a second scFv specifically recognizing CD3ε on the cell surface of a T cell. In some embodiments, there is provided a tandem di-scFv bispecific anti-GPC3 antibody comprising: a) a first anti-GPC3-scFv that competes for binding to target GPC3 (e.g., nGPC3 and/or sGPC3) with any one of the anti-GPC3 constructs described herein; and b) a second scFv specifically recognizing CD3ε on the cell surface of a T cell. In some embodiments, there is provided a tandem di-scFv bispecific anti-GPC3 antibody comprising: a) a first anti-GPC3-scFv that specifically binds to the same, or substantially the same, GPC3 epitope competitively with any one of the anti-GPC3 constructs described herein; and b) a second scFv specifically recognizing CD3ε on the cell surface of a T cell. In some embodiments, the first anti-GPC3 antibody moiety specifically recognizes a cell surface-bound GPC3. In some embodiments, the binding affinity of the first anti-nGPC3 antibody moiety to a cell surface-bound GPC3 is higher than that to a soluble GPC3. In some embodiments, the first anti-nGPC3 antibody moiety specifically recognizes a cell surface-bound GPC3 at a high binding affinity and binds to a soluble GPC3 at a low binding affinity. In some embodiments, the first anti-GPC3 antibody moiety specifically recognizes a soluble GPC3. In some embodiments, the binding affinity of the first anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the first anti-GPC3 antibody moiety specifically recognizes both cell surface-bound GPC3 and soluble GPC3. In some embodiments, the $K_d$ of the binding between the anti-GPC3-scFv and target GPC3 (e.g., nGPC3 and/or sGPC3) is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-GPC3-scFv and an non-target can be at least about 10 times (such as at least about 10, $10^2$, $10^3$, $10^4$, $10^5$, $10^6$, or $10^7$ times) of the $K_d$ of the binding between the anti-GPC3-scFv and target GPC3. In some embodiments, the $K_d$ of the binding between the anti-GPC3 antibody moiety and a non-target is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the first anti-GPC3 scFv and the second anti-CD3-scFv are connected by a linker (e.g., peptide linker). In some embodiments, the linker comprises the amino acid sequence of (GGGGS)$_n$ (SEQ ID NO: 471), wherein n is equal to 1, 2, 3, 4, 5, 6, 7, 8, 9, 10 or more. In some embodiments, the linker comprises the amino acid sequence of TSGGGGS (SEQ ID NO: 474). In some embodiments, the first anti-GPC3 scFv is N-terminal to the second scFv. In some embodiments, the first anti-GPC3 scFv is chimeric, human, partially humanized, fully humanized, or semi-synthetic. In some embodiments, the second scFv is chimeric, human, partially humanized, fully humanized, or semi-synthetic. In some embodiments, both the first and second scFvs are chimeric, human, partially humanized, fully humanized, or semi-synthetic. In some embodiments, the anti-GPC3 scFv comprises the amino acid sequence of any one of SEQ ID NOs: 440-459. In some embodiments, anti-CD3-scFv comprises: i) a $V_H$ comprising an HC-CDR1 comprising the amino acid sequence of SEQ ID NO: 479, an HC-CDR2 comprising the amino acid sequence of SEQ ID NO: 480, and an HC-CDR3 comprising the amino acid sequence of SEQ ID NO: 481; and ii) a $V_L$ comprising an LC-CDR1 comprising the amino acid sequence of SEQ ID NO: 482, an LC-CDR2 comprising the amino acid sequence of SEQ ID NO: 483, and an LC-CDR3 comprising the amino acid sequence of SEQ ID NO: 484. In some embodiments, anti-CD3-scFv comprises: i) a $V_H$ comprising the amino acid sequence of SEQ ID NO: 485; and ii) a $V_L$ comprising the amino acid sequence of SEQ ID NO: 486. In some embodiments, anti-CD3-scFv comprises: i) a $V_H$ comprising the amino acid sequence of SEQ ID NO: 485; and ii) a $V_L$ comprising the amino acid sequence of SEQ ID NO: 486. In some embodiments, the anti-CD3-scFv comprises the amino acid sequence of SEQ ID NO: 487. In some embodiments, there is provided a tandem di-scFv bispecific anti-GPC3 antibody comprising a) a first scFv specifically recognizing GPC3 (e.g., nGPC3 and/or sGPC3); and b) a second scFv specifically recognizing CD3ε on the cell surface of a T cell, wherein the tandem di-scFv bispecific anti-GPC3 antibody comprises the amino acid sequence exemplified by SEQ ID NO: 489. In some embodiments, the tandem di-scFv bispecific anti-GPC3 antibody further comprises a tag (e.g., a peptide tag for purification purpose). In some embodiments, the tag is N-terminal to the tandem di-scFv bispecific anti-GPC3 antibody. In some embodiments, the tag is C-terminal to the tandem di-scFv bispecific anti-GPC3 antibody. In some embodiments, the tag comprises the amino acid sequence of HHHHHH (SEQ ID NO: 476).

Inducible Expression

In some embodiments, the expression of the multi-specific (e.g., bispecific) anti-GPC3 molecule (e.g., anti-GPC3×CD3 tandem di-scFv T cell engager) is inducible. In some embodiments, an effector cell (e.g., T cell, CAR-T cell, caTCR T cell) comprises a nucleic acid sequence encoding the multi-specific (e.g., bispecific) anti-GPC3 molecule (e.g., anti-GPC3×CD3 bispecific T cell engager) operably linked to an inducible promoter, including any inducible promoter described herein (e.g., see "Nucleic Acids" section). In some embodiments, the expression of the multi-specific (e.g., bispecific) anti-GPC3 molecule (e.g., anti-GPC3×CD3 tandem di-scFv T cell engager) in the effector cell (e.g., T cell, CAR-T cell, caTCR T cell) is inducible upon signaling through a signaling receptor on the effector cell (e.g., TCR, CAR, caTCR). In some such embodiments, a CAR-T cell comprises a nucleic acid sequence encoding the multi-specific (e.g., bispecific) anti-GPC3 molecule (e.g., anti-GPC3×CD3 tandem di-scFv T cell engager) operably linked to a promoter or regulatory element responsive to signaling through the CAR. In some such embodiments, a caTCR-T cell comprises a nucleic acid sequence encoding the multi-specific (e.g., bispecific) anti-GPC3 molecule (e.g., anti-GPC3×CD3 tandem di-scFv T cell engager) operably linked to a promoter or regulatory element responsive to signaling through the caTCR. In some embodiments, the nucleic acid sequence encoding the multi-specific (e.g., bispecific) anti-GPC3 molecule (e.g., anti-GPC3×CD3 tandem di-scFv T cell engager) is operably linked to a nuclear-factor of the activated T-cell (NFAT)-derived promoter. In some embodiments, the NFAT-derived promoter is an NFAT-derived minimal promoter (see for example Durand, D. et. al., *Molec. Cell. Biol.* 8, 1715-1724 (1988); Clipstone, N A, Crabtree, G R. *Nature.* 1992 357(6380): 695-7; Chmielewski, M., et al. *Cancer research* 71.17 (2011): 5697-5706; and Zhang, L., et al. *Molecular therapy* 19.4 (2011): 751-759). The NFAT family of transcription factors are important regulators of T cell activation. In some embodiments, the nucleic acid sequence encoding the multi-specific (e.g., bispecific) anti-GPC3 molecule (e.g., anti-GPC3×CD3 tandem di-scFv T cell engager) is operably linked to an IL-2 promoter.

In some embodiments, there is provided an engineered immune cell (such as a T cell) expressing on its surface a dimeric caTCR and expressing or capable of expressing a multi-specific (e.g., bispecific) anti-GPC3 molecule (e.g., anti-GPC3×CD3 bispecific antibody) according to any one of the multispecific anti-GPC3 molecule described herein, wherein the engineered immune cell comprises: a) a first caTCR nucleic acid sequence encoding a first caTCR polypeptide chain of the caTCR; b) a second caTCR nucleic acid sequence encoding a second caTCR polypeptide chain of the caTCR; and c) a nucleic acid sequence encoding the multispecific anti-GPC3 molecule, wherein the caTCR localizes to the surface of the immune cell and the multispecific anti-GPC3 molecule is capable of being secreted from the immune cell. In some embodiments, the first caTCR nucleic acid sequence is contained in a first vector (such as a viral vector, e.g., a lentiviral vector), the second caTCR nucleic acid sequence is contained in a second vector (such as a viral vector, e.g., a lentiviral vector), and the nucleic acid sequence encoding the multispecific anti-GPC3 molecule is contained in a third vector (such as a viral vector, e.g., a lentiviral vector). In some embodiments, some or all of the first and second caTCR nucleic acid sequences and the nucleic acid sequence encoding the multispecific anti-GPC3 molecule are contained in the same vector (such as a viral vector, e.g., a lentiviral vector). In some embodiments, each of the first and second caTCR nucleic acid sequences and the nucleic acid sequence encoding the multispecific anti-GPC3 molecule are, individually, operably linked to a promoter. In some embodiments, some or all of the nucleic acid sequences are under the control of a single promoter. In some embodiments, some or all of the promoters have the same sequence. In some embodiments, some or all of the promoters have different sequences. In some embodiments, some or all of the promoters are inducible. In some embodiments, the nucleic acid sequences encoding the caTCR are under the control of one or more constitutive promoters, such as a EF1-alpha promoter (e.g., a EF1-alpha promoter comprising the nucleic acid sequence of SEQ ID NO: 527). In some embodiments, the nucleic acid sequence encoding the multispecific anti-GPC3 molecule is under the control of an inducible promoter. In some embodiments, the inducible promoter is inducible upon activation of the immune cell. In some embodiments, the inducible promoter is an NFAT-derived promoter, e.g., an NFAT-derived promoter comprising the nucleic acid sequence of SEQ ID NO: 524 or 526. In some embodiments, some or all of the vectors are viral vectors (such as lentiviral vectors). In some embodiments, the immune cell does not express the TCR subunits from which the TCR-TMs of the caTCR are derived. For example, in some embodiments, the immune cell is an αβ T cell and the TCR-TMs of the introduced caTCR comprise sequences derived from TCR δ and γ chains, or the immune cell is a γδ T cell and the TCR-TMs of the introduced caTCR comprise sequences derived from TCR α and β chains. In some embodiments, the immune cell is modified to block or decrease the expression of one or both of its endogenous TCR subunits. For example, in some embodiments, the immune cell is an αβ T cell modified to block or decrease the expression of the TCR α and/or β chains, or the immune cell is a γδ T cell modified to block or decrease the expression of the TCR γ and/or δ chains. In some embodiments, the immune cell is selected from the group consisting of a cytotoxic T cell, a helper T cell, a natural killer T cell, and a suppressor T cell. In some embodiments, some or all of the vectors are viral vectors (such as lentiviral vectors) integrated into the host genome of the immune cell. In some embodiments, the caTCR specifically recognizes an AFP/MHC class I complex (e.g., AFP158/HLA-A*02:01). In some embodiments, the caTCR comprises a first polypeptide comprising the amino acid sequence of SEQ ID NO: 522 and a second polypeptide comprising the amino acid sequence of SEQ ID NO: 523. In some embodiments, the multispecific anti-GPC3 molecule comprises the amino acid sequence of SEQ ID NO: 511.

Chimeric Antigen Receptor (CAR) and CAR Effector Cells

The anti-GPC3 construct in some embodiments is a CAR comprising an anti-GPC3 antibody moiety (also referred to herein as an "anti-GPC3 CAR"). Any one of the anti-GPC3 antibody moieties described herein can be employed in the anti-GPC3 CAR. Also provided is a CAR effector cell (e.g., T cell) comprising a CAR comprising an anti-GPC3 antibody moiety (also referred to herein as an "anti-GPC3 CAR effector cell", e.g., "anti-GPC3 CAR T cell"). In some embodiments, the anti-GPC3 CAR comprises an anti-GPC3 antibody moiety specifically recognizing a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 CAR comprises an anti-GPC3 antibody moiety specifically recognizing a soluble GPC3.

The anti-GPC3 CAR comprises a) an extracellular domain comprising an anti-GPC3 antibody moiety that specifically binds to GPC3 (e.g., nGPC3 and/or sGPC3), and b) an intracellular signaling domain. A transmembrane domain may be present between the extracellular domain and the intracellular domain.

Between the extracellular domain and the transmembrane domain of the anti-GPC3 CAR, or between the intracellular domain and the transmembrane domain of the anti-GPC3 CAR, there may be a spacer domain. The spacer domain can be any oligo- or polypeptide that functions to link the transmembrane domain to the extracellular domain or the intracellular domain in the polypeptide chain. A spacer domain may comprise up to about 300 amino acids, including for example about 10 to about 100, or about 25 to about 50 amino acids.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the α, β, δ, or γ chain of the T-cell receptor, CD28, CD3ε, CD3ζ, CD45, CD4, CD5, CD8, CD9, CD16, CD22, CD33, CD37, CD64, CD80, CD86, CD134, CD137, or CD154. In some embodiments, the transmembrane domain may be synthetic, in which case it may comprise predominantly hydrophobic residues such as leucine and valine. In some embodiments, a triplet of phenylalanine, tryptophan and valine may be found at each end of a synthetic transmembrane domain. In some embodiments, a short oligo- or polypeptide linker, having a length of, for example, between about 2 and about 10 (such as about any of 2, 3, 4, 5, 6, 7, 8, 9, or 10) amino acids in length may form the linkage between the transmembrane domain and the intracellular signaling domain of the anti-GPC3 CAR. In some embodiments, the linker is a glycine-serine doublet.

In some embodiments, the transmembrane domain that is naturally associated with one of the sequences in the intracellular domain of the anti-GPC3 CAR is used (e.g., if an anti-GPC3 CAR intracellular domain comprises a CD28 co-stimulatory sequence, the transmembrane domain of the anti-GPC3 CAR is derived from the CD28 transmembrane domain). In some embodiments, the transmembrane domain can be selected or modified by amino acid substitution to avoid binding of such domains to the transmembrane domains of the same or different surface membrane proteins to minimize interactions with other members of the receptor complex.

The intracellular signaling domain of the anti-GPC3 CAR is responsible for activation of at least one of the normal effector functions of the immune cell in which the anti-GPC3 CAR has been placed in. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term "intracellular signaling sequence" is thus meant to include any truncated portion of the intracellular signaling domain sufficient to transduce the effector function signal.

Examples of intracellular signaling domains for use in the anti-GPC3 CAR of the invention include the cytoplasmic sequences of the TCR and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of intracellular signaling sequence: those that initiate antigen-dependent primary activation through the TCR (primary signaling sequences) and those that act in an antigen-independent manner to provide a secondary or co-stimulatory signal (co-stimulatory signaling sequences).

Primary signaling sequences regulate primary activation of the TCR complex either in a stimulatory way, or in an inhibitory way. Primary signaling sequences that act in a stimulatory manner may contain signaling motifs which are known as immunoreceptor tyrosine-based activation motifs or ITAMs. The anti-GPC3 CAR constructs in some embodiments comprise one or more ITAMs.

Examples of ITAM containing primary signaling sequences that are of particular use in the invention include those derived from TCRζ, FcRγ, FcRβ, CD3γ, CD3δ, CD3ε, CD5, CD22, CD79a, CD79b, and CD66d.

In some embodiments, the anti-GPC3 CAR comprises a primary signaling sequence derived from CD3ζ. For example, the intracellular signaling domain of the CAR can comprise the CD3ζ intracellular signaling sequence by itself or combined with any other desired intracellular signaling sequence(s) useful in the context of the anti-GPC3 CAR of the invention. For example, the intracellular domain of the anti-GPC3 CAR can comprise a CD3ζ intracellular signaling sequence and a costimulatory signaling sequence. The costimulatory signaling sequence can be a portion of the intracellular domain of a costimulatory molecule including, for example, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like.

In some embodiments, the intracellular signaling domain of the anti-GPC3 CAR comprises the intracellular signaling sequence of CD3ζ and the intracellular signaling sequence of CD28. In some embodiments, the intracellular signaling domain of the anti-GPC3 CAR comprises the intracellular signaling sequence of CD3ζ and the intracellular signaling sequence of 4-1BB. In some embodiments, the intracellular signaling domain of the anti-GPC3 CAR comprises the intracellular signaling sequence of CD3ζ and the intracellular signaling sequences of CD28 and 4-1BB.

Thus, for example, in some embodiments, there is provided an anti-GPC3 CAR comprising a) an extracellular domain comprising an anti-GPC3 antibody moiety that specifically binds to a cell surface bound-GPC3 (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity), b) a transmembrane domain, and c) an intracellular signaling domain. In some embodiments, the anti-nGPC3 antibody moiety specifically recognizes an epitope within human GPC3 comprising the amino acid sequence of SEQ ID NO: 460. In some embodiments, the anti-nGPC3 antibody moiety specifically recognizes an epitope within the amino acid sequence of SEQ ID NO: 461. In some embodiments, the anti-nGPC3 antibody moiety specifically recognizes an epitope within the amino acid sequence of SEQ ID NO: 462. In some embodiments, the anti-nGPC3 antibody moiety specifically recognizes an epitope within the amino acid sequence of SEQ ID NO: 463. In some embodiments, the anti-nGPC3 antibody moiety specifically recognizes an epitope within the N-terminal fragment of GPC3. In some embodiments, the anti-nGPC3 antibody moiety specifically recognizes an epitope within amino acids 1-358 of SEQ ID NO: 460 (SEQ ID NO: 468). In some embodiments, the anti-nGPC3 antibody moiety specifically recognizes an epitope within the amino acid sequence of SEQ ID NO: 464.

In some embodiments, the anti-nGPC3 antibody moiety specifically recognizes an epitope within the C-terminal fragment of GPC3. In some embodiments, the anti-nGPC3 antibody moiety specifically recognizes an epitope within amino acids 359-560 of SEQ ID NO: 460 (SEQ ID NO: 465). In some embodiments, the anti-nGPC3 antibody moiety specifically recognizes an epitope within amino acids 359-580 of SEQ ID NO: 460 (SEQ ID NO: 466). In some embodiments, the anti-nGPC3 antibody moiety specifically recognizes an epitope within the C-terminal fragment of GPC3 lacking heparin sulfate side chain. In some embodiments, the anti-nGPC3 antibody moiety specifically recognizes an epitope within amino acids 510-560 of SEQ ID NO: 460 (SEQ ID NO: 467). In some embodiments, the anti-nGPC3 antibody moiety specifically recognizes an epitope spanning the Furin cleavage site at amino acids $R^{358}/S^{359}$ of SEQ ID NO: 460. In some embodiments, the anti-nGPC3 antibody moiety can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460). In some embodiments, the anti-nGPC3 antibody moiety specifically recognizes an epitope within the C-terminal fragment of GPC3 lacking heparin sulfate side chain. In some embodiments, there is provided an anti-GPC3 CAR comprising a) an extracellular domain comprising an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that competes for binding to nGPC3 with any one of the anti-GPC3 constructs described herein, b) a transmembrane domain, and c) an intracellular signaling domain. In some embodiments, there is provided an anti-GPC3 CAR comprising a) an extracellular domain comprising an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that specifically binds to the same, or substantially the same, nGPC3 epitope competitively with any one of the anti-GPC3 constructs described herein, b) a transmembrane domain, and c) an intracellular signaling domain. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence. In some embodiments, the anti-GPC3 CAR comprises an extracellular domain comprising an anti-GPC3 antibody moiety that specifically binds to a cell surface bound-GPC3 (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) described herein fused to the N-terminus of SEQ ID NO: 494. In some embodiments, the anti-nGPC3 antibody moiety is a Fab or a Fab'. In some embodiments, the anti-nGPC3 antibody moiety is an scFv. In some embodiments, the anti-nGPC3 antibody moiety is chimeric, human, humanized, or semi-synthetic. In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M).

In some embodiments, there is provided an anti-GPC3 CAR comprising a) an extracellular domain comprising an anti-GPC3 antibody moiety that specifically binds to a cell surface bound-GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions, b) a transmembrane domain, and c) an intracellular signaling domain. In some embodiments, there is provided an anti-GPC3 CAR comprising a) an extracellular domain comprising an anti-GPC3 antibody moiety that specifically binds to a cell surface bound-GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286, b) a transmembrane domain, and c) an intracellular signaling domain. In some embodiments, there is provided an anti-GPC3 CAR comprising a) an extracellular domain comprising an anti-GPC3 antibody moiety that specifically binds to a cell surface bound-GPC3, comprising: i) a $V_H$ comprising the amino acid sequence of any one of SEQ ID NOs: 307-337; and ii) a $V_L$ comprising the amino acid sequence of any one of SEQ ID NOs: 358-388, b) a transmembrane domain, and c) an intracellular signaling domain. In some embodiments, there is provided an anti-GPC3 CAR comprising a) an extracellular domain comprising an anti-GPC3 antibody moiety that specifically binds to a cell surface bound-GPC3, comprising: the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388, b) a transmembrane domain, and c) an intracellular signaling domain. In some embodiments, there is provided an anti-GPC3 CAR comprising a) an extracellular domain comprising an anti-nGPC3 antibody moiety that competes for binding to nGPC3 with any one of the anti-GPC3 constructs described herein, b) a transmembrane domain, and c) an intracellular signaling domain. In some embodiments, there is provided an anti-GPC3 CAR comprising a) an extracellular domain comprising an anti-nGPC3 antibody moiety that specifically binds to the same, or substantially the same, nGPC3 epitope competitively with any one of the anti-GPC3 constructs described herein, b) a transmembrane domain, and c) an intracellular signaling domain. In some embodiments, the anti-GPC3 CAR comprises an extracellular domain comprising an anti-GPC3 antibody moiety that specifically binds to a cell surface bound-GPC3 described herein fused to the N-terminus of SEQ ID NO: 494. For example, in some embodiments, the anti-GPC3 CAR comprises the amino acid sequence of SEQ ID NO: 491. In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence. In some embodiments, the anti-nGPC3 antibody moiety is a Fab or a Fab'. In some embodiments, the anti-nGPC3 antibody moiety is an scFv. In some embodiments, the anti-nGPC3 antibody moiety is chimeric, human, humanized, or semi-synthetic.

In some embodiments, there is provided an anti-GPC3 CAR comprising a) an extracellular domain comprising an anti-GPC3 antibody moiety that specifically binds GPC3 (e.g., nGPC3 and/or sGPC3), b) a transmembrane domain, and c) an intracellular signaling domain. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-GPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence. In some embodiments, the anti-GPC3 antibody moiety is a Fab or a Fab'. In some embodiments, the anti-GPC3 antibody moiety is an scFv. In some embodiments, the anti-GPC3 antibody moiety is chimeric, human, humanized, or semi-synthetic.

In some embodiments, there is provided an anti-GPC3 CAR comprising a) an extracellular domain comprising an anti-GPC3 antibody moiety that specifically binds to GPC3 (e.g., nGPC3 and/or sGPC3), comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions, b) a transmembrane domain, and c) an intracellular signaling domain. In some embodiments, there is provided an anti-GPC3 CAR comprising a) an extracellular domain comprising an anti-GPC3 antibody moiety that specifically binds to a cell surface bound-GPC3 (e.g., nGPC3 and/or sGPC3), comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306, b) a transmembrane domain, and c) an intracellular signaling domain. In some embodiments, there is provided an anti-GPC3 CAR comprising a) an extracellular domain comprising an anti-GPC3 antibody moiety that specifically binds to a cell surface bound-GPC3 (e.g., nGPC3 and/or sGPC3), comprising: i) a $V_H$ comprising the amino acid sequence of any one of SEQ ID NOs: 338-357; and ii) a $V_L$ comprising the amino acid sequence of any one of SEQ ID NOs: 389-408, b) a transmembrane domain, and c) an intracellular signaling domain. In some embodiments, there is provided an anti-GPC3 CAR comprising a) an extracellular domain comprising an anti-GPC3 antibody moiety that specifically binds to a cell surface bound-GPC3 (e.g., nGPC3 and/or sGPC3), comprising: the HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408, b) a transmembrane domain, and c) an intracellular signaling domain. In some embodiments, there is provided an anti-GPC3 CAR comprising a) an extracellular domain comprising an anti-GPC3 antibody moiety that competes for binding to a target GPC3 (e.g., nGPC3 and/or sGPC3) with any one of the anti-GPC3 constructs described herein, b) a transmembrane domain, and c) an intracellular signaling domain. In some embodiments, there is provided an anti-GPC3 CAR comprising a) an extracellular domain comprising an anti-GPC3 antibody moiety that specifically binds to the same, or substantially the same, GPC3 epitope competitively with any one of the anti-GPC3 constructs described herein, b) a transmembrane domain, and c) an intracellular signaling domain. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 intracellular signaling sequence. In some embodiments, the intracellular domain comprises a CD3ζ intracellular signaling sequence and a CD28 intracellular signaling sequence.

In some embodiments, the anti-GPC3 antibody moiety is a Fab or a Fab'. In some embodiments, the anti-GPC3 antibody moiety is an scFv. In some embodiments, the anti-GPC3 antibody moiety is chimeric, human, humanized, or semi-synthetic. In some embodiments, the anti-GPC3 CAR comprises an extracellular domain comprising an anti-GPC3 antibody moiety that specifically binds to GPC3 (e.g., nGPC3 and/or sGPC3) described herein fused to the N-terminus of SEQ ID NO: 494. In some embodiments, the $K_d$ of the binding between the anti-GPC3 antibody moiety and a target GPC3 (e.g., nGPC3 and/or sGPC3) is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-GPC3 antibody moiety and a non-target can be at least about 10 times (such as at least about 10, $10^2$, $10^3$, $10^4$, $10^5$, $10^6$, or $10^7$ times) of the $K_d$ of the binding between the anti-GPC3 antibody moiety and the target GPC3. In some embodiments, the $K_d$ of the binding between the anti-GPC3 antibody moiety and a non-target is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M).

In some embodiments, there is provided an anti-GPC3 CAR comprising a) an extracellular domain comprising an anti-GPC3 antibody moiety that specifically binds to a cell surface bound-GPC3 (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity), b) a transmembrane domain, and c) an intracellular signaling domain comprising a CD3ζ intracellular signaling sequence and a CD28 intracellular signaling sequence. In some embodiments, the anti-nGPC3 antibody moiety specifically recognizes an epitope within human GPC3 comprising the amino acid sequence of SEQ ID NO: 460. In some embodiments, the anti-nGPC3 antibody moiety specifically recognizes an epitope within the amino acid sequence of SEQ ID NO: 461. In some embodiments, the anti-nGPC3 antibody moiety specifically recognizes an epitope within the amino acid sequence of SEQ ID NO: 462. In some embodiments, the anti-nGPC3 antibody moiety specifically recognizes an epitope within the amino acid sequence of SEQ ID NO: 463. In some embodiments, the anti-nGPC3 antibody moiety specifically recognizes an epitope within the N-terminal fragment of GPC3. In some embodiments, the anti-GPC3 antibody moiety specifically recognizes an epitope within amino acids 1-358 of SEQ ID NO: 460 (SEQ ID NO: 468). In some embodiments, the anti-nGPC3 antibody moiety specifically recognizes an epitope within the amino acid sequence of SEQ ID NO: 464. In some embodiments, the anti-nGPC3 antibody moiety specifically recognizes an epitope within the C-terminal fragment of GPC3. In some embodiments, the anti-nGPC3 antibody moiety specifically recognizes an epitope within amino acids 359-560 of SEQ ID NO: 460 (SEQ ID NO: 465). In some embodiments, the anti-nGPC3 antibody moiety specifically recognizes an epitope within amino acids 359-580 of SEQ ID NO: 460 (SEQ ID NO: 466). In some embodiments, the anti-nGPC3 antibody moiety specifically recognizes an epitope within the C-terminal fragment of GPC3 lacking heparin sulfate side chain. In some embodiments, the anti-nGPC3 antibody moiety specifically recognizes an epitope within amino acids 510-560 of SEQ ID NO: 460 (SEQ ID NO: 467). In some embodiments, the anti-nGPC3 antibody moiety specifically recognizes an epitope spanning the Furin cleavage site at amino acids $R^{358}/S^{359}$ of SEQ ID NO: 460. In some embodiments, the anti-nGPC3 antibody moiety can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460. In some embodiments, the anti-nGPC3 antibody moiety specifically recognizes an epitope within the C-terminal fragment of GPC3 lacking heparin sulfate side chain. In some embodiments, there is provided an anti-GPC3 CAR comprising a) an extracellular domain comprising an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that competes for binding to nGPC3 with any one of the anti-GPC3 constructs described herein, b) a transmembrane domain, and c) an intracellular signaling domain comprising a CD3ζ intracellular signaling sequence and a CD28 intracellular signaling sequence. In some embodiments, there is provided an anti-GPC3 CAR comprising a) an extracellular domain comprising an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that specifically binds to the same, or substantially the same, nGPC3 epitope competitively with any one of the anti-GPC3 constructs described herein, b) a transmembrane domain, and c) an intracellular signaling domain comprising a CD3ζ intracellular signaling sequence and a CD28 intracellular signaling sequence. In some embodiments, the anti-GPC3 CAR comprises an extracellular domain comprising an anti-GPC3 antibody moiety that specifically binds to a cell surface bound-GPC3 described herein fused to the N-terminus of SEQ ID NO: 494. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-nGPC3 antibody moiety is chimeric, human, partially humanized, fully humanized, or semi-synthetic. In some embodiments, the anti-nGPC3 antibody moiety is a Fab or a Fab'. In some embodiments, the anti-nGPC3 antibody moiety is an scFv.

In some embodiments, there is provided an anti-GPC3 CAR comprising a) an extracellular domain comprising an anti-GPC3 antibody moiety that specifically binds to a cell surface bound-GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions, b) a transmembrane domain, and c) an intracellular signaling domain comprising a CD3ζ intracellular signaling sequence and a CD28 intracellular signaling sequence. In some embodiments, there is provided an anti-GPC3 CAR comprising a) an extracellular domain comprising an anti-GPC3 antibody moiety that specifically binds to a cell surface bound-GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286, b) a transmembrane domain, and c) an intracellular signaling domain comprising a CD3ζ intracellular signaling sequence and a CD28 intracellular signaling sequence. In some embodiments, there is provided an anti-GPC3 CAR comprising a) an extracellular domain comprising an anti-GPC3 antibody moiety that specifically binds to a cell surface bound-GPC3, comprising: i) a $V_H$ comprising the amino acid sequence of any one of SEQ ID NOs: 307-337; and ii) a $V_L$ comprising the amino acid sequence of any one of SEQ ID NOs: 358-388, b) a transmembrane domain, and c) an intracellular signaling domain comprising a CD3ζ intracellular signaling sequence and a CD28 intracellular signaling sequence. In some embodiments, there is provided an anti-GPC3 CAR comprising a) an extracellular domain comprising an anti-GPC3 antibody moiety that specifically binds to a cell surface bound-GPC3, comprising: the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388, b) a transmembrane domain, and c) an intracellular signaling domain comprising a CD3ζ intracellular signaling sequence and a CD28 intracellular signaling sequence. In some embodiments, there is provided an anti-GPC3 CAR comprising a) an extracellular domain comprising an anti-nGPC3 antibody moiety that competes for binding to nGPC3 with any one of the anti-GPC3 constructs described herein, b) a transmembrane domain, and c) an intracellular signaling domain comprising a CD3ζ intracellular signaling sequence and a CD28 intracellular signaling sequence. In some embodiments, there is provided an anti-GPC3 CAR comprising a) an extracellular domain comprising an antinGPC3 antibody moiety that specifically binds to the same, or substantially the same, nGPC3 epitope competitively with any one of the anti-GPC3 constructs described herein, b) a transmembrane domain, and c) an intracellular signaling domain comprising a CD3ζ intracellular signaling sequence and a CD28 intracellular signaling sequence. In some embodiments, the anti-GPC3 CAR comprises an extracellular domain comprising an anti-GPC3 antibody moiety that specifically binds to a cell surface bound-GPC3 described herein fused to the N-terminus of SEQ ID NO: 494. For example, in some embodiments, the anti-GPC3 CAR comprises the amino acid sequence of SEQ ID NO: 491. In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-nGPC3 antibody moiety is a Fab or a Fab'. In some embodiments, the anti-nGPC3 antibody moiety is an scFv. In some embodiments, the anti-nGPC3 antibody moiety is chimeric, human, humanized, or semi-synthetic.

In some embodiments, there is provided an anti-GPC3 CAR comprising a) an extracellular domain comprising an anti-GPC3 antibody moiety that specifically binds to GPC3 (e.g., nGPC3 and/or sGPC3), comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions, b) a transmembrane domain, and c) an intracellular signaling domain comprising a CD3ζ intracellular signaling sequence and a CD28 intracellular signaling sequence. In some embodiments, there is provided an anti-GPC3 CAR comprising a) an extracellular domain comprising an anti-GPC3 antibody moiety that specifically binds to GPC3 (e.g., nGPC3 and/or sGPC3), comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306, b) a transmembrane domain, and c) an intracellular signaling domain comprising a CD3ζ intracellular signaling sequence and a CD28 intracellular signaling sequence. In some embodiments, there is provided an anti-GPC3 CAR comprising a) an extracellular domain comprising an anti-GPC3 antibody moiety that specifically binds to GPC3 (e.g., nGPC3 and/or sGPC3), comprising: i) a $V_H$ comprising the amino acid sequence of any one of SEQ ID NOs: 338-357; and ii) a $V_L$ comprising the amino acid sequence of any one of SEQ ID NOs: 389-408, b) a transmembrane domain, and c) an intracellular signaling domain. In some embodiments, there is provided an anti-GPC3 CAR comprising a) an extracellular domain comprising an anti-GPC3 antibody moiety that specifically binds to GPC3 (e.g., nGPC3 and/or sGPC3), comprising: the HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408, b) a transmembrane domain, and c) an intracellular signaling domain comprising a CD3ζ intracellular signaling sequence and a CD28 intracellular signaling sequence. In some embodiments, there is provided an anti-GPC3 CAR comprising a) an extracellular domain comprising an anti-GPC3 antibody moiety that competes for binding to a target GPC3 (e.g., nGPC3 and/or sGPC3) with any one of the anti-GPC3 constructs described herein, b) a transmembrane domain, and c) an intracellular signaling domain comprising a CD3ζ intracellular signaling sequence and a CD28 intracellular signaling sequence. In some embodiments, there is provided an anti-GPC3 CAR comprising a) an extracellular domain comprising an anti-GPC3 antibody moiety that specifically binds to the same, or substantially the same, GPC3 epitope competitively with any one of the anti-GPC3 constructs described herein, b) a transmembrane domain, and c) an intracellular signaling domain comprising a CD3ζ intracellular signaling sequence and a CD28 intracellular signaling sequence. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the anti-GPC3 antibody moiety is a Fab or a Fab'. In some embodiments, the anti-GPC3 antibody moiety is an scFv. In some embodiments, the anti-GPC3 antibody moiety is chimeric, human, humanized, or semi-synthetic. In some embodiments, the anti-GPC3 CAR comprises an extracellular domain comprising an anti-GPC3 antibody moiety that specifically binds to GPC3 (e.g., nGPC3 and/or sGPC3) described herein fused to the N-terminus of SEQ ID NO:

494. In some embodiments, the $K_d$ of the binding between the anti-GPC3 antibody moiety and a target GPC3 (e.g., nGPC3 and/or sGPC3) is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-GPC3 antibody moiety and a non-target can be at least about 10 times (such as at least about 10, $10^2$, $10^3$, $10^4$, $10^5$, $10^6$, or $10^7$ times) of the $K_d$ of the binding between the anti-GPC3 antibody moiety and the target GPC3. In some embodiments, the $K_d$ of the binding between the anti-GPC3 antibody moiety and a non-target is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M).

Also provided herein are effector cells (such as lymphocytes, e.g., T cells) expressing an anti-GPC3 CAR.

Also provided is a method of producing an effector cell expressing an anti-GPC3 CAR, the method comprising introducing a vector comprising a nucleic acid encoding the anti-GPC3 CAR into the effector cell. In some embodiments, introducing the vector into the effector cell comprises transducing the effector cell with the vector. In some embodiments, introducing the vector into the effector cell comprises transfecting the effector cell with the vector. Transduction or transfection of the vector into the effector cell can be carried about using any method known in the art.

In some embodiments, there is provided an anti-GPC3 CAR effector cell (such as lymphocytes, e.g., T cells) comprising a nucleic acid sequence encoding a multi-specific (e.g., bispecific) anti-GPC3 molecule (e.g., anti-GPC3×CD3 bispecific T cell engager) described herein operably linked to an inducible promoter. In some embodiments, the expression of the multi-specific (e.g., bispecific) anti-GPC3 molecule (e.g., anti-GPC3×CD3 tandem di-scFv T cell engager) in the anti-GPC3 CAR effector cell is inducible upon signaling through the anti-GPC3 CAR. In some embodiments, the nucleic acid sequence encoding the multi-specific (e.g., bispecific) anti-GPC3 molecule (e.g., anti-GPC3×CD3 tandem di-scFv T cell engager) is operably linked to an NFAT-derived promoter. In some embodiments, the NFAT-derived promoter is an NFAT-derived minimal promoter. In some embodiments, the nucleic acid sequence encoding the multi-specific (e.g., bispecific) anti-GPC3 molecule (e.g., anti-GPC3×CD3 tandem di-scFv T cell engager) is operably linked to an IL-2 promoter.

Chimeric Antibody-T Cell Receptor (TCR) Construct (caTCR) and caTCR Effector Cells The anti-GPC3 construct in some embodiments is a chimeric antibody-T cell receptor construct (caTCR) comprising an anti-GPC3 antibody moiety (also referred to herein as an "anti-GPC3 caTCR"). Exemplary caTCRs are provided in PCT/US2016/058305, incorporated herein by reference. Any of the anti-GPC3 antibody moieties (targeting e.g., nGPC3 and/or sGPC3) described herein can be employed in the anti-GPC3 caTCR. The anti-GPC3 caTCR can specifically bind to GPC3 and is capable of recruiting at least one TCR-associated signaling molecule (such as CD3δε, CD3γε, and/or ζζ). Also provided is a caTCR effector cell (e.g., T cell) comprising a caTCR comprising an anti-GPC3 antibody moiety (also referred to herein as an "anti-GPC3 caTCR effector cell", e.g., "anti-GPC3 caTCR T cell"). In some embodiments, the anti-GPC3 caTCR comprises an anti-GPC3 antibody moiety specifically recognizing a cell surface-bound GPC3. In some embodiments, the binding affinity of the anti-nGPC3 antibody moiety to a cell surface-bound GPC3 is higher than that to a soluble GPC3. In some embodiments, the anti-GPC3 caTCR comprises an anti-GPC3 antibody moiety specifically recognizing a soluble GPC3.

In some embodiments, there is provided an anti-GPC3 caTCR comprising a) an antigen-binding module comprising an antibody moiety specifically recognizing GPC3 (e.g., nGPC3 and/or sGPC3) described herein, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, the anti-GPC3 caTCR comprises naturally occurring TCR domains. In some embodiments, the anti-GPC3 caTCR comprises at least one non-naturally occurring TCR domain. The anti-GPC3 caTCR comprises an antigen-binding module comprising an anti-GPC3 antibody moiety that provides the antigen specificity and a TCRM that allows for CD3 recruitment and signaling. The antigen-binding module is not a naturally occurring T cell receptor antigen-binding moiety. In some embodiments, the antigen-binding module is linked to the N-terminus of a polypeptide chain in the TCRM. In some embodiments, the antigen-binding module is an antibody moiety. In some embodiments, the anti-GPC3 antibody moiety is a Fab, a Fab', a F(ab')2, an Fv, or an scFv. In some embodiments, the anti-GPC3 antibody moiety is a Fab or a Fab'. In some embodiments, the anti-GPC3 antibody moiety is an scFv. The TCRM comprises a transmembrane module derived from the transmembrane domains of one or more TCRs (TCR-TMs), such as an αβ and/or γδ TCR, and optionally further comprises one or both of the connecting peptides or fragments thereof of a TCR and/or one or more TCR intracellular domains or fragments thereof. In some embodiments, the TCRM comprises two polypeptide chains, each polypeptide chain comprising, from N-terminus to C-terminus, a connecting peptide, a transmembrane domain, and optionally a TCR intracellular domain. In some embodiments, the TCRM comprises one or more non-naturally occurring TCR domains. For example, in some embodiments, the TCRM comprises one or two non-naturally occurring TCR transmembrane domains. A non-naturally occurring TCR domain may be a corresponding domain of a naturally occurring TCR modified by substitution of one or more amino acids, and/or by replacement of a portion of the corresponding domain with a portion of an analogous domain from another TCR. The anti-GPC3 caTCR may comprise a first polypeptide chain and a second polypeptide chain, wherein the first and second polypeptide chains together form the antigen-binding module and the TCRM. In some embodiments, the first and second polypeptide chains are separate polypeptide chains, and the caTCR is a multimer, such as a dimer. In some embodiments, the first and second polypeptide chains are covalently linked, such as by a peptide linkage, or by another chemical linkage, such as a disulfide linkage. In some embodiments, the first polypeptide chain and the second polypeptide chain are linked by at least one disulfide bond. In some embodiments, the anti-GPC3 caTCR further comprises one or more T cell co-stimulatory signaling sequences. The one or more co-stimulatory signaling sequences can be, individually, all or a portion of the intracellular domain of a co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the one or more co-stimulatory signaling sequences are between the first TCR-TM and the first TCR intracellular domain and/or between the second TCR-TM and the second TCR intracellular domain. In some embodiments, the one or more co-stimulatory signaling sequences are C-terminal to the first TCRD and/or the second TCRD. In some embodiments, the anti-GPC3 caTCR lacks a T cell co-stimulatory signaling sequence. In some embodiments, the anti-GPC3 caTCR further comprises a stabilization module comprising a first stabilization domain and a second stabilization domain, wherein the first and second stabilization domains have a binding affinity for each other that stabilizes the anti-GPC3 caTCR. In some embodiments, the stabilization module is located between the antigen-binding module and the TCRM. In some embodiments, the anti-GPC3 caTCR further comprises a spacer module between any two caTCR modules or domains. In some embodiments, the spacer module comprises one or more peptide linkers connecting two caTCR modules or domains. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the anti-GPC3 antibody moiety is chimeric, human, partially humanized, fully humanized, or semi-synthetic. In some embodiments, there is provided an anti-GPC3 caTCR comprising: a) a first polypeptide chain comprising a first antigen-binding domain comprising $V_H$ and $C_H1$ antibody domains and a first T cell receptor domain (TCRD) comprising a first transmembrane domain of a first TCR subunit; and b) a second polypeptide chain comprising a second antigen-binding domain comprising $V_L$ and $C_L$ antibody domains and a second TCRD comprising a second transmembrane domain of a second TCR subunit, wherein the $V_H$ and $C_H1$ domains of the first antigen-binding domain and the $V_L$ and $C_L$ domains of the second antigen-binding domain form an antigen-binding module that specifically binds to GPC3, and wherein the first TCRD and the second TCRD form a T cell receptor module (TCRM) that is capable of recruiting at least one TCR-associated signaling module. In some embodiments, the antigen-binding module comprises a disulfide bond between a residue in the $C_H1$ domain and a residue in the $C_L$ domain. In some embodiments, there is provided an anti-GPC3 caTCR comprising: a) a first polypeptide chain comprising a first antigen-binding domain comprising a $V_H$ antibody domain and a first TCRD comprising a first transmembrane domain of a first TCR subunit; and b) a second polypeptide chain comprising a second antigen-binding domain comprising a $V_L$ antibody domains and a second TCRD comprising a second transmembrane domain of a second TCR subunit, wherein the $V_H$ domain of the first antigen-binding domain and the $V_L$ domain of the second antigen-binding domain form an antigen-binding module that specifically binds to GPC3, wherein the first TCRD and the second TCRD form a T cell receptor module (TCRM) that is capable of recruiting at least one TCR-associated signaling module. In some embodiments, the TCR-TM comprises the amino acid sequence of SEQ ID NO: 495. In some embodiments, the TCR-TM comprises the amino acid sequence of SEQ ID NO: 496.

In some embodiments, the TCRM described herein comprises a) a first T cell receptor domain (TCRD) comprising a first TCR transmembrane domain (TCR-TM) and b) a second TCRD comprising a second TCR-TM, wherein the TCRM facilitates recruitment of at least one TCR-associated signaling molecule. In some embodiments, both of the TCR-TMs are naturally occurring. In some embodiments, at least one of the TCR-TMs is non-naturally occurring. In some embodiments, both of the TCR-TMs are non-naturally occurring. In some embodiments, the first TCR-TM is derived from one of the transmembrane domains of a T cell receptor (such as an αβ TCR or a γδ TCR) and the second TCR-TM is derived from the other transmembrane domain of the T cell receptor. In some embodiments, the TCRM allows for enhanced recruitment of the at least one TCR-associated signaling molecule as compared to a TCRM comprising the transmembrane domains of the T cell receptor. Recruitment of TCR-associated signaling molecules can be determined by methods known in the art, such as FACS analysis for TCR-CD3 complex surface expression or co-immunoprecipitation of CD3 subunits with the caTCR.

In some embodiments, the antigen-binding module comprises a first antigen-binding domain comprising a $V_H$ antibody domain (such as any of the $V_H$ antibody domain described herein for anti-GPC3 antibody moieties) and a second antigen-binding domain comprising a $V_L$ antibody domain (such as any of the $V_L$ antibody domain described herein for anti-GPC3 antibody moieties). In some embodiments, the $V_H$ antibody domain and $V_L$ antibody domain CDRs are derived from the same antibody moiety. In some embodiments, some of the $V_H$ antibody domain and $V_L$ antibody domain CDRs are derived from different antibody moieties. In some embodiments, the $V_H$ antibody domain and/or $V_L$ antibody domain are human, humanized, chimeric, semi-synthetic, or fully synthetic.

In some embodiments, the caTCR comprises an antigen-binding module described herein linked to a TCRM described herein, optionally including a stabilization module. For example, in some embodiments, the caTCR comprises the antigen-binding module linked to the N-terminus of one or both of the TCRDs. In some embodiments, the caTCR comprises a stabilization module between a TCRM and an antigen-binding module. In some embodiments, the caTCR further comprises a spacer module between any two caTCR modules or domains. In some embodiments, the spacer module comprises one or more peptide linkers between about 5 to about 70 (such as about any of 5, 10, 15, 20, 25, 30, 35, 40, 45, 50, 55, 60, 65, or 70, including any ranges between these values) amino acids in length. In some embodiments, the caTCR further comprises one or more accessory intracellular domains. In some embodiments, the one or more accessory intracellular domains are carboxy-terminal to the first and/or second TCRD. In some embodiments, the one or more accessory intracellular domains are between the first TCR-TM and the first TCR intracellular domain and/or between the second TCR-TM and the second TCR intracellular domain. In some embodiments, the one or more accessory intracellular domains comprise, individually, a TCR co-stimulatory domain. In some embodiments, the TCR co-stimulatory domain comprises all or a portion of the intracellular domain of an immune co-stimulatory molecule (such as CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like). In some embodiments, the TCR co-stimulatory domain comprises all or a portion of the amino acid sequence of any one of SEQ ID NOs: 51-56, or a variant thereof.

In some embodiments, there is provided an anti-GPC3 caTCR comprising a) an antigen-binding module comprising an antibody moiety specifically recognizing a cell surface-bound GPC3 (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity), and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising: a) a first polypeptide chain comprising a first antigen-binding domain comprising $V_H$ and $C_H1$ antibody domains and a first T cell receptor domain (TCRD) comprising a first transmembrane domain of a first TCR subunit; and b) a second polypeptide chain comprising a second antigen-binding domain comprising $V_L$ and $C_L$ antibody domains and a second TCRD comprising a second transmembrane domain of a second TCR subunit, wherein the $V_H$ and $C_H1$ domains of the first antigen-binding domain and the $V_L$ and $C_L$ domains of the second antigen-binding domain form an antigen-binding module that specifically binds to cell surface bound-GPC3 (e.g., the binding affinity of the $V_H$ and $V_L$ to a cell surface-bound GPC3 is higher than that to a soluble GPC3, or the $V_H$ and $V_L$ specifically recognizes a cell surface-bound GPC3 at a high binding affinity and binds to a soluble GPC3 at a low binding affinity), and wherein the first TCRD and the second TCRD form a T cell receptor module (TCRM) that is capable of recruiting at least one TCR-associated signaling module. In some embodiments, the antigen-binding module comprises a disulfide bond between a residue in the $C_H1$ domain and a residue in the $C_L$ domain. In some embodiments, there is provided an anti-GPC3 caTCR comprising: a) a first polypeptide chain comprising a first antigen-binding domain comprising a $V_H$ antibody domain and a first TCRD comprising a first transmembrane domain of a first TCR subunit; and b) a second polypeptide chain comprising a second antigen-binding domain comprising a $V_L$ antibody domains and a second TCRD comprising a second transmembrane domain of a second TCR subunit, wherein the $V_H$ domain of the first antigen-binding domain and the $V_L$ domain of the second antigen-binding domain form an antigen-binding module that specifically binds to cell surface bound-GPC3 (e.g., the binding affinity of the $V_H$ and $V_L$ to a cell surface-bound GPC3 is higher than that to a soluble GPC3, or the $V_H$ and $V_L$ specifically recognizes a cell surface-bound GPC3 at a high binding affinity and binds to a soluble GPC3 at a low binding affinity), wherein the first TCRD and the second TCRD form a T cell receptor module (TCRM) that is capable of recruiting at least one TCR-associated signaling module. In some embodiments, the anti-nGPC3 antibody moiety specifically recognizes an epitope within human GPC3 comprising the amino acid sequence of SEQ ID NO: 460. In some embodiments, the anti-nGPC3 antibody moiety specifically recognizes an epitope within the amino acid sequence of SEQ ID NO: 461. In some embodiments, the anti-nGPC3 antibody moiety specifically recognizes an epitope within the amino acid sequence of SEQ ID NO: 462. In some embodiments, the anti-nGPC3 antibody moiety specifically recognizes an epitope within the amino acid sequence of SEQ ID NO: 463. In some embodiments, the anti-nGPC3 antibody moiety specifically recognizes an epitope within the N-terminal fragment of GPC3. In some embodiments, the anti-GPC3 antibody moiety specifically recognizes an epitope within amino acids 1-358 of SEQ ID NO: 460 (SEQ ID NO: 468). In some embodiments, the anti-nGPC3 antibody moiety specifically recognizes an epitope within the amino acid sequence of SEQ ID NO: 464. In some embodiments, the anti-nGPC3 antibody moiety specifically recognizes an epitope within the C-terminal fragment of GPC3. In some embodiments, the anti-nGPC3 antibody moiety specifically recognizes an epitope within amino acids 359-560 of SEQ ID NO: 460 (SEQ ID NO: 465). In some embodiments, the anti-nGPC3 antibody moiety specifically recognizes an epitope within amino acids 359-580 of SEQ ID NO: 460 (SEQ ID NO: 466). In some embodiments, the anti-nGPC3 antibody moiety specifically recognizes an epitope within the C-terminal fragment of GPC3 lacking heparin sulfate side chain. In some embodiments, the anti-nGPC3 antibody moiety specifically recognizes an epitope within amino acids 510-560 of SEQ ID NO: 460 (SEQ ID NO: 467). In some embodiments, the anti-nGPC3 antibody moiety specifically recognizes an epitope spanning the Furin cleavage site at amino acids $R^{358}/S^{359}$ of SEQ ID NO: 460. In some embodiments, the anti-nGPC3 antibody moiety can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460. In some embodiments, the anti-nGPC3 antibody moiety specifically recognizes an epitope within the C-terminal fragment of GPC3 lacking heparin sulfate side chain. In some embodiments, there is provided an anti-GPC3 caTCR comprising a) an antigen-binding module comprising an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that competes for binding to nGPC3 with any one of the anti-GPC3 constructs described herein, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising a) an antigen-binding module comprising an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that specifically binds to the same, or substantially the same, nGPC3 epitope competitively with any one of the anti-GPC3 constructs described herein, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-nGPC3 antibody moiety is chimeric, human, partially humanized, fully humanized, or semi-synthetic. In some embodiments, the anti-nGPC3 antibody moiety is a Fab or a Fab'. In some embodiments, the anti-nGPC3 antibody moiety is an scFv. In some embodiments, the anti-nGPC3 antibody moiety is human, humanized, chimeric, or synthetic. In some embodiments, the anti-nGPC3 antibody moiety is linked to the N-terminus of the first and/or second TCRDs. In some embodiments, the first naturally occurring TCR is a γ/δ TCR. In some embodiments, the first naturally occurring TCR is an α/β TCR. In some embodiments, at least one of the TCR-TMs is non-naturally occurring. In some embodiments, the first and second TCR-TMs are non-naturally occurring. In some embodiments, the first TCR-TM comprises up to 5 (such as any of 1, 2, 3, 4, or 5) amino acid substitutions compared to the transmembrane domain from which it is derived and/or the second TCR-TM comprises up to 5 (such as any of 1, 2, 3, 4, or 5) amino acid substitutions compared to the transmembrane domain from which it is derived. In some embodiments, the TCRM comprises a transmembrane module derived from the transmembrane domains of one or more TCRs (TCR-TMs), such as an αβ and/or γδ TCR, and optionally further comprises one or both of the connecting peptides or fragments thereof of a TCR and/or one or more TCR intracellular domains or fragments thereof. In some embodiments, the TCRM comprises two polypeptide chains, each polypeptide chain comprising, from amino terminus to carboxy terminus, a connecting peptide, a transmembrane domain, and optionally a TCR intracellular domain. In some embodiments, anti-GPC3 caTCR may comprise a first polypeptide chain and a second polypeptide chain, wherein the first and second polypeptide chains together form the antigen-binding module and the TCRM. In some embodiments, the first and second polypeptide chains are separate polypeptide chains, and the caTCR is a multimer, such as a dimer. In some embodiments, the first and second polypeptide chains are covalently linked, such as by a peptide linkage, or by another chemical linkage, such as a disulfide linkage. In some embodiments, the first polypeptide chain and the second polypeptide chain are linked by at least one disulfide bond. In some embodiments, the caTCR further comprises one or more T cell co-stimulatory signaling sequences. The one or more co-stimulatory signaling sequences can be, individually, all or a portion of the intracellular domain of a co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the one or more co-stimulatory signaling sequences are between the first TCR-TM and the first TCR intracellular domain and/or between the second TCR-TM and the second TCR intracellular domain. In some embodiments, the one or more co-stimulatory signaling sequences are carboxy-terminal to the first TCRD and/or the second TCRD. In some embodiments, the caTCR lacks a T cell co-stimulatory signaling sequence. In some embodiments, the caTCR further comprises a stabilization module comprising a first stabilization domain and a second stabilization domain, wherein the first and second stabilization domains have a binding affinity for each other that stabilizes the caTCR. In some embodiments, the stabilization module is located between the antigen-binding module and the TCRM. In some embodiments, the stabilization module comprises a first stabilization domain comprising a $C_H1$ antibody domain or variant thereof and a second stabilization domain comprising a $C_L$ antibody domain or variant thereof. In some embodiments, the caTCR further comprises a spacer module between any two caTCR modules or domains. In some embodiments, the TCRM is capable of recruiting at least one TCR-associated signaling molecule selected from the group consisting of CD3δε, CD3γε, and ζζ). In some embodiments, the TCRM allows for enhanced recruitment of the at least one TCR-associated signaling molecule as compared to a TCRM comprising the naturally occurring T cell receptor transmembrane domains. In some embodiments, the TCRM promotes caTCR-CD3 complex formation. In some embodiments, there is a spacer module between any two caTCR modules or domains. In some embodiments, the anti-GPC3 caTCR is a heteromultimer, such as a heterodimer. For example, in some embodiments, the anti-GPC3 caTCR is a heterodimer comprising a first polypeptide chain comprising the first TCRD and a second polypeptide chain comprising the second TCRD, wherein the antibody moiety is linked to the first and/or second polypeptide chains. In some embodiments, the TCRM comprises one or more non-naturally occurring TCR domains. In some embodiments, the TCR-TM comprises the amino acid sequence of SEQ ID NO: 495. In some embodiments, the TCR-TM comprises the amino acid sequence of SEQ ID NO: 496.

In some embodiments, there is provided an anti-GPC3 caTCR comprising a) a an antigen-binding module comprising an antibody moiety specifically recognizing a cell surface-bound GPC3, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising a) an antigen-binding module comprising an antibody moiety specifically recognizing a cell surface-bound GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising a) an antigen-binding module comprising an antibody moiety specifically recognizing a cell surface-bound GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising a) an antigen-binding module comprising an antibody moiety specifically recognizing a cell surface-bound GPC3, comprising: i) a $V_H$ comprising the amino acid sequence of any one of SEQ ID NOs: 307-337; and ii) a $V_L$ comprising the amino acid sequence of any one of SEQ ID NOs: 358-388, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising a) an antigen-binding module comprising an antibody moiety specifically recognizing a cell surface-bound GPC3, comprising the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising a) an antigen-binding module comprising an anti-nGPC3 antibody moiety that competes for binding to nGPC3 with any one of the anti-GPC3 constructs described herein, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising a) an antigen-binding module comprising an anti-nGPC3 antibody moiety that specifically binds to the same, or substantially the same, nGPC3 epitope competitively with any one of the anti-GPC3 constructs described herein, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising: a) a first polypeptide chain comprising a first antigen-binding domain comprising $V_H$ comprising the amino acid sequence of any one of SEQ ID NOs: 307-337 and $C_H1$ antibody domains and a first T cell receptor domain (TCRD) comprising a first transmembrane domain of a first TCR subunit; and b) a second polypeptide chain comprising a second antigen-binding domain comprising $V_L$ comprising the amino acid sequence of any one of SEQ ID NOs: 358-388 and $C_L$ antibody domains and a second TCRD comprising a second transmembrane domain of a second TCR subunit, wherein the $V_H$ and $C_H1$ domains of the first antigen-binding domain and the $V_L$ and $C_L$ domains of the second antigen-binding domain form an antigen-binding module that specifically binds to cell surface bound-GPC3, and wherein the first TCRD and the second TCRD form a T cell receptor module (TCRM) that is capable of recruiting at least one TCR-associated signaling module. In some embodiments, the antigen-binding module comprises a disulfide bond between a residue in the $C_H1$ domain and a residue in the $C_L$ domain. In some embodiments, there is provided an anti-GPC3 caTCR comprising: a) a first polypeptide chain comprising a first antigen-binding domain comprising a $V_H$ antibody domain comprising the amino acid sequence of any one of SEQ ID NOs: 307-337 and a first TCRD comprising a first transmembrane domain of a first TCR subunit; and b) a second polypeptide chain comprising a second antigen-binding domain comprising a $V_L$ antibody domains comprising the amino acid sequence of any one of SEQ ID NOs: 358-388 and a second TCRD comprising a second transmembrane domain of a second TCR subunit, wherein the $V_H$ domain of the first antigen-binding domain and the $V_L$ domain of the second antigen-binding domain form an antigen-binding module that specifically binds to cell surface bound-GPC3, wherein the first TCRD and the second TCRD form a T cell receptor module (TCRM) that is capable of recruiting at least one TCR-associated signaling module. In some embodiments, the anti-GPC3 caTCR comprises two polypeptide chains, comprising amino acid sequence of SEQ ID NO: 492 and SEQ ID NO: 493. In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the anti-nGPC3 antibody moiety is a Fab or a Fab'. In some embodiments, the anti-nGPC3 antibody moiety is an scFv. In some embodiments, the anti-nGPC3 antibody moiety is human, humanized, chimeric, or synthetic. In some embodiments, the anti-nGPC3 antibody moiety is linked to the N-terminus of the first and/or second TCRDs. In some embodiments, the first naturally occurring TCR is a γ/δ TCR. In some embodiments, the first naturally occurring TCR is an α/β TCR. In some embodiments, at least one of the TCR-TMs is non-naturally occurring. In some embodiments, the first and second TCR-TMs are non-naturally occurring. In some embodiments, the first TCR-TM comprises up to 5 (such as any of 1, 2, 3, 4, or 5) amino acid substitutions compared to the transmembrane domain from which it is derived and/or the second TCR-TM comprises up to 5 (such as any of 1, 2, 3, 4, or 5) amino acid substitutions compared to the transmembrane domain from which it is derived. In some embodiments, the TCRM comprises a transmembrane module derived from the transmembrane domains of one or more TCRs (TCR-TMs), such as an αβ and/or γδ TCR, and optionally further comprises one or both of the connecting peptides or fragments thereof of a TCR and/or one or more TCR intracellular domains or fragments thereof. In some embodiments, the TCRM comprises two polypeptide chains, each polypeptide chain comprising, from amino terminus to carboxy terminus, a connecting peptide, a transmembrane domain, and optionally a TCR intracellular domain. In some embodiments, anti-GPC3 caTCR may comprise a first polypeptide chain and a second polypeptide chain, wherein the first and second polypeptide chains together form the antigen-binding module and the TCRM. In some embodiments, the first and second polypeptide chains are separate polypeptide chains, and the caTCR is a multimer, such as a dimer. In some embodiments, the first and second polypeptide chains are covalently linked, such as by a peptide linkage, or by another chemical linkage, such as a disulfide linkage. In some embodiments, the first polypeptide chain and the second polypeptide chain are linked by at least one disulfide bond. In some embodiments, the caTCR further comprises one or more T cell co-stimulatory signaling sequences. The one or more co-stimulatory signaling sequences can be, individually, all or a portion of the intracellular domain of a co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the one or more co-stimulatory signaling sequences are between the first TCR-TM and the first TCR intracellular domain and/or between the second TCR-TM and the second TCR intracellular domain. In some embodiments, the one or more co-stimulatory signaling sequences are carboxy-terminal to the first TCRD and/or the second TCRD. In some embodiments, the caTCR lacks a T cell co-stimulatory signaling sequence. In some embodiments, the caTCR further comprises a stabilization module comprising a first stabilization domain and a second stabilization domain, wherein the first and second stabilization domains have a binding affinity for each other that stabilizes the caTCR. In some embodiments, the stabilization module is located between the antigen-binding module and the TCRM. In some embodiments, the stabilization module comprises a first stabilization domain comprising a $C_H1$ antibody domain or variant thereof and a second stabilization domain comprising a $C_L$ antibody domain or variant thereof. In some embodiments, the caTCR further comprises a spacer module between any two caTCR modules or domains. In some embodiments, the TCRM is capable of recruiting at least one TCR-associated signaling molecule selected from the group consisting of CD3δε, CD3γε, and ζζ). In some embodiments, the TCRM allows for enhanced recruitment of the at least one TCR-associated signaling molecule as compared to a TCRM comprising the naturally occurring T cell receptor transmembrane domains. In some embodiments, the TCRM promotes caTCR-CD3 complex formation. In some embodiments, there is a spacer module between any two caTCR modules or domains. In some embodiments, the anti-GPC3 caTCR is a heteromultimer, such as a heterodimer. For example, in some embodiments, the anti-GPC3 caTCR is a heterodimer comprising a first polypeptide chain comprising the first TCRD and a second polypeptide chain comprising the second TCRD, wherein the antibody moiety is linked to the first and/or second polypeptide chains. In some embodiments, the TCRM comprises one or more non-naturally occurring TCR domains. In some embodiments, the TCR-TM comprises the amino acid sequence of SEQ ID NO: 495. In some embodiments, the TCR-TM comprises the amino acid sequence of SEQ ID NO: 496.

In some embodiments, there is provided an anti-GPC3 caTCR comprising a) an antigen-binding module comprising an antibody moiety specifically recognizing GPC3 (e.g., nGPC3 and/or sGPC3), and b) a TCRM comprising first and second TCR-TMs derived from the transmembrane domains of a naturally occurring TCR (such as an αβTCR or a γδTCR), wherein the TCRM is capable of recruiting at least one TCR-associated signaling molecule. In some embodiments, there is provided an anti-GPC3 caTCR comprising a) an antigen-binding module comprising an antibody moiety specifically recognizing GPC3, comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising a) an antigen-binding module comprising an antibody moiety specifically recognizing GPC3 (e.g., nGPC3 and/or sGPC3), comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306, and b) a TCRM comprising first and second TCR-TMs derived from the transmembrane domains of a naturally occurring TCR (such as an αβTCR or a γδTCR), wherein the TCRM is capable of recruiting at least one TCR-associated signaling molecule. In some embodiments, there is provided an anti-GPC3 caTCR comprising a) an antigen-binding module comprising an antibody moiety specifically recognizing GPC3 (e.g., nGPC3 and/or sGPC3), comprising: i) a $V_H$ comprising the amino acid sequence of any one of SEQ ID NOs: 338-357; and ii) a $V_L$ comprising the amino acid sequence of any one of SEQ ID NOs: 389-408, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising a) an antigen-binding module comprising an antibody moiety specifically recognizing (e.g., nGPC3 and/or sGPC3), comprising HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising a) an antigen-binding module comprising an anti-GPC3 antibody moiety that competes for binding to GPC3 (e.g., nGPC3 and/or sGPC3) with any one of the anti-GPC3 constructs described herein, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising a) an antigen-binding module comprising an anti-GPC3 antibody moiety that specifically binds to the same, or substantially the same, GPC3 epitope competitively with any one of the anti-GPC3 constructs described herein, and b) aa T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided an anti-GPC3 caTCR comprising: a) a first polypeptide chain comprising a first antigen-binding domain comprising $V_H$ comprising the amino acid sequence of any one of SEQ ID NOs: 338-357 and $C_H1$ antibody domains and a first T cell receptor domain (TCRD) comprising a first transmembrane domain of a first TCR subunit; and b) a second polypeptide chain comprising a second antigen-binding domain comprising $V_L$ comprising the amino acid sequence of any one of SEQ ID NOs: 389-408 and $C_L$ antibody domains and a second TCRD comprising a second transmembrane domain of a second TCR subunit, wherein the $V_H$ and $C_H1$ domains of the first antigen-binding domain and the $V_L$ and $C_L$ domains of the second antigen-binding domain form an antigen-binding module that specifically binds to GPC3 (e.g., nGPC3 and/or sGPC3), and wherein the first TCRD and the second TCRD form a T cell receptor module (TCRM) that is capable of recruiting at least one TCR-associated signaling module. In some embodiments, the antigen-binding module comprises a disulfide bond between a residue in the $C_H1$ domain and a residue in the $C_L$ domain. In some embodiments, there is provided an anti-GPC3 caTCR comprising: a) a first polypeptide chain comprising a first antigen-binding domain comprising a $V_H$ antibody domain comprising the amino acid sequence of any one of SEQ ID NOs: 338-357 and a first TCRD comprising a first transmembrane domain of a first TCR subunit; and b) a second polypeptide chain comprising a second antigen-binding domain comprising a $V_L$ antibody domains comprising the amino acid sequence of any one of SEQ ID NOs: 389-408 and a second TCRD comprising a second transmembrane domain of a second TCR subunit, wherein the $V_H$ domain of the first antigen-binding domain and the $V_L$ domain of the second antigen-binding domain form an antigen-binding module that specifically binds to GPC3 (e.g., nGPC3 and/or sGPC3), wherein the first TCRD and the second TCRD form a T cell receptor module (TCRM) that is capable of recruiting at least one TCR-associated signaling module. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the anti-GPC3 antibody moiety is a Fab or a Fab'. In some embodiments, the anti-GPC3 antibody moiety is an scFv. In some embodiments, the $K_d$ of the binding between the anti-GPC3 antibody moiety and a target GPC3 (e.g., nGPC3 and/or sGPC3) is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-GPC3 antibody moiety and a non-target can be at least about 10 times (such as at least about 10, $10^2$, $10^3$, $10^4$, $10^5$, $10^6$, or $10^7$ times) of the $K_d$ of the binding between the anti-GPC3 antibody moiety and the target GPC3. In some embodiments, the $K_d$ of the binding between the anti-GPC3 antibody moiety and a non-target is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the anti-nGPC3 antibody moiety is human, humanized, chimeric, or synthetic. In some embodiments, the anti-nGPC3 antibody moiety is linked to the N-terminus of the first and/or second TCRDs. In some embodiments, the first naturally occurring TCR is a γ/δ TCR. In some embodiments, the first naturally occurring TCR is an α/β TCR. In some embodiments, at least one of the TCR-TMs is non-naturally occurring. In some embodiments, the first and second TCR-TMs are non-naturally occurring. In some embodiments, the first TCR-TM comprises up to 5 (such as any of 1, 2, 3, 4, or 5) amino acid substitutions compared to the transmembrane domain from which it is derived and/or the second TCR-TM comprises up to 5 (such as any of 1, 2, 3, 4, or 5) amino acid substitutions compared to the transmembrane domain from which it is derived. In some embodiments, the TCRM comprises a transmembrane module derived from the transmembrane domains of one or more TCRs (TCR-TMs), such as an αβ and/or γδ TCR, and optionally further comprises one or both of the connecting peptides or fragments thereof of a TCR and/or one or more TCR intracellular domains or fragments thereof. In some embodiments, the TCRM comprises two polypeptide chains, each polypeptide chain comprising, from amino terminus to carboxy terminus, a connecting peptide, a transmembrane domain, and optionally a TCR intracellular domain. In some embodiments, anti-GPC3 caTCR may comprise a first polypeptide chain and a second polypeptide chain, wherein the first and second polypeptide chains together form the antigen-binding module and the TCRM. In some embodiments, the first and second polypeptide chains are separate polypeptide chains, and the caTCR is a multimer, such as a dimer. In some embodiments, the first and second polypeptide chains are covalently linked, such as by a peptide linkage, or by another chemical linkage, such as a disulfide linkage. In some embodiments, the first polypeptide chain and the second polypeptide chain are linked by at least one disulfide bond. In some embodiments, the caTCR further comprises one or more T cell co-stimulatory signaling sequences. The one or more co-stimulatory signaling sequences can be, individually, all or a portion of the intracellular domain of a co-stimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the one or more co-stimulatory signaling sequences are between the first TCR-TM and the first TCR intracellular domain and/or between the second TCR-TM and the second TCR intracellular domain. In some embodiments, the one or more co-stimulatory signaling sequences are carboxy-terminal to the first TCRD and/or the second TCRD. In some embodiments, the caTCR lacks a T cell co-stimulatory signaling sequence. In some embodiments, the caTCR further comprises a stabilization module comprising a first stabilization domain and a second stabilization domain, wherein the first and second stabilization domains have a binding affinity for each other that stabilizes the caTCR. In some embodiments, the stabilization module is located between the antigen-binding module and the TCRM. In some embodiments, the stabilization module comprises a first stabilization domain comprising a $C_H1$ antibody domain or variant thereof and a second stabilization domain comprising a $C_L$ antibody domain or variant thereof. In some embodiments, the caTCR further comprises a spacer module between any two caTCR modules or domains. In some embodiments, the TCRM is capable of recruiting at least one TCR-associated signaling molecule selected from the group consisting of CD3δε, CD3γε, and ζζ. In some embodiments, the TCRM allows for enhanced recruitment of the at least one TCR-associated signaling molecule as compared to a TCRM comprising the naturally occurring T cell receptor transmembrane domains. In some embodiments, the TCRM promotes caTCR-CD3 complex formation. In some embodiments, there is a spacer module between any two caTCR modules or domains. In some embodiments, the anti-GPC3 caTCR is a heteromultimer, such as a heterodimer. For example, in some embodiments, the anti-GPC3 caTCR is a heterodimer comprising a first polypeptide chain comprising the first TCRD and a second polypeptide chain comprising the second TCRD, wherein the antibody moiety is linked to the first and/or second polypeptide chains. In some embodiments, the TCRM comprises one or more non-naturally occurring TCR domains. In some embodiments, the TCR-TM comprises the amino acid sequence of SEQ ID NO: 495. In some embodiments, the TCR-TM comprises the amino acid sequence of SEQ ID NO: 496.

Also provided herein are effector cells (such as lymphocytes, e.g., T cells) expressing an anti-GPC3 caTCR.

Also provided is a method of producing an effector cell expressing an anti-GPC3 caTCR, the method comprising introducing a vector comprising a nucleic acid encoding the anti-GPC3 caTCR into the effector cell. In some embodiments, introducing the vector into the effector cell comprises transducing the effector cell with the vector. In some embodiments, introducing the vector into the effector cell comprises transfecting the effector cell with the vector. Transduction or transfection of the vector into the effector cell can be carried about using any method known in the art.

In some embodiments, there is provided an anti-GPC3 caTCR effector cell (such as lymphocytes, e.g., T cells) comprising a nucleic acid sequence encoding a multi-specific (e.g., bispecific) anti-GPC3 molecule (e.g., anti-GPC3× CD3 bispecific T cell engager) described herein operably linked to an inducible promoter. In some embodiments, the expression of the multi-specific (e.g., bispecific) anti-GPC3 molecule (e.g., anti-GPC3×CD3 tandem di-scFv T cell engager) in the anti-GPC3 caTCR effector cell is inducible upon signaling through the anti-GPC3 caTCR. In some embodiments, the nucleic acid sequence encoding the multi-specific (e.g., bispecific) anti-GPC3 molecule (e.g., anti-GPC3×CD3 tandem di-scFv T cell engager) is operably linked to an NFAT-derived promoter. In some embodiments, the NFAT-derived promoter is an NFAT-derived minimal promoter. In some embodiments, the nucleic acid sequence encoding the multi-specific (e.g., bispecific) anti-GPC3 molecule (e.g., anti-GPC3×CD3 tandem di-scFv T cell engager) is operably linked to an IL-2 promoter.

Chimeric Co-Stimulatory Receptor (CSR) Constructs

The anti-GPC3 construct in some embodiments is a chimeric co-stimulatory receptor (CSR) that specifically binds to GPC3 and is capable of stimulating an immune cell on the surface of which it is functionally expressed upon target ligand binding. The CSR comprises a ligand-binding module that provides the ligand-binding specificity, a transmembrane module, and a co-stimulatory immune cell signaling module that allows for stimulating the immune cell. The CSR lacks a functional primary immune cell signaling sequence. In some embodiments, the CSR lacks any primary immune cell signaling sequence. In some embodiments, the CSR comprises a single polypeptide chain comprising the ligand-binding module, transmembrane module, and co-stimulatory signaling module. In some embodiments, the CSR comprises a first polypeptide chain and a second polypeptide chain, wherein the first and second polypeptide chains together form the ligand-binding module, transmembrane module, and co-stimulatory signaling module. In some embodiments, the first and second polypeptide chains are separate polypeptide chains, and the CSR is a multimer, such as a dimer. In some embodiments, the first and second polypeptide chains are covalently linked, such as by a peptide linkage, or by another chemical linkage, such as a disulfide linkage. In some embodiments, the first polypeptide chain and the second polypeptide chain are linked by at least one disulfide bond. In some embodiments, the expression of the CSR in the caTCR plus CSR immune cell is inducible. In some embodiments, the expression of the CSR in the caTCR plus CSR immune cell is inducible upon signaling through the caTCR.

In some embodiments, there is provided a CSR that specifically binds to GPC3, comprising a) an scFv comprising a VH domain having the amino acid sequence of SEQ ID NO: 309 and a VL domain having the amino acid sequence of SEQ ID NO: 360; and b) a fragment of CD28 comprising, consisting essentially of, or consisting of the amino acid sequence of SEQ ID NO: 530. In some embodiments, the scFv comprises, consists essentially of, or consists of the amino acid sequence of SEQ ID NO: 441. In some embodiments, the CSR comprises, from amino terminus to carboxy terminus, the scFv, a peptide linker having the amino acid sequence AAA, and the fragment of CD28. In some embodiments, the CSR comprises, consists essentially of, or consists of the amino acid sequence of SEQ ID NO: 530.

In some embodiments, there is provided an immune cell (such as a T cell) comprising nucleic acid encoding a caTCR (such as a caTCR that specifically binds to an AFP/MHC class I molecule, e.g., AFP158/HLA-A02) and an anti-GPC3 CSR according to any of the CSRs described herein, wherein the caTCR and CSR are expressed from the nucleic acid and localized to the immune cell surface. In some embodiments, the nucleic acid comprises a first caTCR nucleic acid sequence encoding a first caTCR polypeptide chain of the caTCR, a second caTCR nucleic acid sequence encoding a second caTCR polypeptide chain of the caTCR, and a CSR nucleic acid sequence encoding a CSR polypeptide chain of the CSR. In some embodiments, the first and second caTCR nucleic acid sequences and CSR nucleic acid sequence are each contained in different vectors. In some embodiments, some or all of the nucleic acid sequences are contained in the same vector. Vectors may be selected, for example, from the group consisting of mammalian expression vectors and viral vectors (such as those derived from retroviruses, adenoviruses, adeno-associated viruses, herpes viruses, and lentiviruses). In some embodiments, one or more of the vectors is integrated into the host genome of the immune cell. In some embodiments, the first and second caTCR nucleic acid sequences and CSR nucleic acid sequence are each under the control of different promoters. In some embodiments, some or all of the promoters have the same sequence. In some embodiments, some or all of the promoters have different sequences. In some embodiments, some or all of the nucleic acid sequences are under the control of a single promoter. In some embodiments, some or all of the promoters are inducible. In some embodiments, the immune cell is selected from the group consisting of a cytotoxic T cell, a helper T cell, a natural killer T cell, and a suppressor T cell.

Immunoconjugates

The anti-GPC3 constructs (such as isolated anti-GPC3 constructs) in some embodiments comprise an immunoconjugate comprising an anti-GPC3 antibody moiety according to any of the anti-GPC3 antibody moieties described herein attached to an effector molecule (also referred to herein as an "anti-GPC3 immunoconjugate"). In some embodiments the effector molecule is a therapeutic agent, such as drug, a toxin, a radioisotope, a protein, a peptide, a carbohydrate, a lipid, or a nucleic acid. In some embodiments the effector molecule is a cancer therapeutic agent, which is either cytotoxic, cytostatic or otherwise provides some therapeutic benefit. In some embodiments, therapeutic agents for use in accordance with the present invention may have a biological activity relevant to modulation of the immune system and/or enhancement of T-cell mediated cytotoxicity. In some embodiments, the effector molecule is a label, which can generate a detectable signal, either directly or indirectly. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-GPC3 antibody moiety specifically recognizes both cell surface-bound GPC3 and soluble GPC3. In some embodiments, the anti-GPC3 antibody moiety is a full-length antibody, a Fab, a Fab', a F(ab')2, an Fv, or an scFv. In some embodiments, the anti-GPC3 antibody moiety is chimeric, human, partially humanized, fully humanized, or semi-synthetic.

In some embodiments, there is provided an anti-GPC3 immunoconjugate comprising an anti-GPC3 antibody moiety and a therapeutic agent (also referred to herein as an "antibody-drug conjugate", or "ADC"). In some embodiments, therapeutic agent is a toxin that is either cytotoxic, cytostatic or otherwise prevents or reduces the ability of the target cells to divide. The use of ADCs for the local delivery of cytotoxic or cytostatic agents, i.e., drugs to kill or inhibit tumor cells in the treatment of cancer (Syrigos and Epenetos, *Anticancer Research* 19:605-614 (1999); Niculescu-Duvaz and Springer, *Adv. Drg. Del. Rev.* 26:151-172 (1997); U.S. Pat. No. 4,975,278) allows targeted delivery of the drug moiety to target cells, and intracellular accumulation therein, where systemic administration of these unconjugated therapeutic agents may result in unacceptable levels of toxicity to normal cells as well as the target cells sought to be eliminated (Baldwin et al., *Lancet* (Mar. 15, 1986):603-605 (1986); Thorpe, (1985) "Antibody Carriers Of Cytotoxic Agents In Cancer Therapy: A Review," in Monoclonal Antibodies '84: Biological And Clinical Applications, A. Pinchera et al. (eds.), pp. 475-506). Maximal efficacy with minimal toxicity is sought thereby.

Therapeutic agents used in anti-GPC3 immunoconjugates include, for example, daunomycin, doxorubicin, methotrexate, and vindesine (Rowland et al., *Cancer Immunol. Immunother.* 21:183-187 (1986)). Toxins used in anti-GPC3 immunoconjugates include bacterial toxins such as diphtheria toxin, plant toxins such as ricin, small molecule toxins such as geldanamycin (Mandler et al., *J. Nat. Cancer Inst.* 92(19):1573-1581 (2000); Mandler et al., *Bioorganic & Med. Chem. Letters* 10:1025-1028 (2000); Mandler et al., *Bioconjugate Chem.* 13:786-791 (2002)), maytansinoids (EP 1391213; Liu et al., *Proc. Natl. Acad. Sci. USA* 93:8618-8623 (1996)), and calicheamicin (Lode et al., *Cancer Res.* 58:2928 (1998); Hinman et al., *Cancer Res.* 53:3336-3342 (1993)). The toxins may exert their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Enzymatically active toxins and fragments thereof that can be used include, for example, diphtheria A chain, nonbinding active fragments of diphtheria toxin, exotoxin A chain (from *Pseudomonas aeruginosa*), ricin A chain, abrin A chain, modeccin A chain,α-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993.

In some embodiments, the anti-GPC3 immunoconjugate comprises an anti-GPC3 antibody moiety and one or more small molecule toxins, such as a calicheamicin, maytansinoids, dolastatins, aurostatins, a trichothecene, and CC1065, and the derivatives of these toxins that have toxin activity, are also contemplated herein.

In some embodiments, there is provided an anti-GPC3 immunoconjugate comprising a therapeutic agent that has an intracellular activity. In some embodiments, the anti-GPC3 immunoconjugate is internalized and therapeutic agent is a cytotoxin that blocks the protein synthesis of the cell, therein leading to cell death. In some embodiments, therapeutic agent is a cytotoxin comprising a polypeptide having ribosome-inactivating activity including, for example, gelonin, bouganin, saporin, ricin, ricin A chain, bryodin, diphtheria toxin, restrictocin, *Pseudomonas* exotoxin A and variants thereof. In some embodiments, where therapeutic agent is a cytotoxin comprising a polypeptide having a ribosome-inactivating activity, the anti-GPC3 immunoconjugate must be internalized upon binding to the target cell in order for the protein to be cytotoxic to the cells.

In some embodiments, there is provided an anti-GPC3 immunoconjugate comprising a therapeutic agent that acts to disrupt DNA. In some embodiments, therapeutic agent that acts to disrupt DNA is, for example, selected from the group consisting of enediyne (e.g., calicheamicin and esperamicin) and non-enediyne small molecule agents (e.g., bleomycin, methidiumpropyl-EDTA-Fe(II)). Other cancer therapeutic agents useful in accordance with the present application include, without limitation, daunorubicin, doxorubicin, distamycin A, cisplatin, mitomycin C, ecteinascidins, duocarmycin/CC-1065, and bleomycin/pepleomycin.

The present invention further contemplates an anti-GPC3 immunoconjugate formed between the anti-GPC3 antibody moiety and a compound with nucleolytic activity (e.g., a ribonuclease or a DNA endonuclease such as a deoxyribonuclease; DNase).

In some embodiments, the anti-GPC3 immunoconjugate comprises an agent that acts to disrupt tubulin. Such agents may include, for example, rhizoxin/maytansine, paclitaxel, vincristine and vinblastine, colchicine, auristatin dolastatin 10 MMAE, and peloruside A.

In some embodiments, the anti-GPC3 immunoconjugate comprises an alkylating agent including, for example, Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholinodoxorubicin NSC 357704, cyclodisone NSC 348948, dianhydrogalactitol NSC 132313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobroman NSC 25154, porfiromycin NSC 56410, spirohydantoin mustard NSC 172112, teroxirone NSC 296934, tetraplatin NSC 363812, thio-tepa NSC 6396, triethylenemelamine NSC 9706, uracil nitrogen mustard NSC 34462, and Yoshi-864 NSC 102627.

In some embodiments, the cancer therapeutic agent portion of the anti-GPC3 immunoconjugate of the present application may comprise an antimitotic agent including, without limitation, allocolchicine NSC 406042, Halichondrin B NSC 609395, colchicine NSC 757, colchicine derivative NSC 33410, dolastatin 10 NSC 376128 (NG—auristatin derived), maytansine NSC 153858, rhizoxin NSC 332598, taxol NSC 125973, taxol derivative NSC 608832, thiocolchicine NSC 361792, trityl cysteine NSC 83265, vinblastine sulfate NSC 49842, and vincristine sulfate NSC 67574.

In some embodiments, the anti-GPC3 immunoconjugate comprises a topoisomerase I inhibitor including, without limitation, camptothecin NSC 94600, camptothecin, Na salt NSC 100880, aminocamptothecin NSC 603071, camptothecin derivative NSC 95382, camptothecin derivative NSC 107124, camptothecin derivative NSC 643833, camptothecin derivative NSC 629971, camptothecin derivative NSC 295500, camptothecin derivative NSC 249910, camptothecin derivative NSC 606985, camptothecin derivative NSC 374028, camptothecin derivative NSC 176323, camptothecin derivative NSC 295501, camptothecin derivative NSC 606172, camptothecin derivative NSC 606173, camptothecin derivative NSC 610458, camptothecin derivative NSC 618939, camptothecin derivative NSC 610457, camptothecin derivative NSC 610459, camptothecin derivative NSC 606499, camptothecin derivative NSC 610456, camptothecin derivative NSC 364830, camptothecin derivative NSC 606497, and morpholinodoxorubicin NSC 354646.

In some embodiments, the anti-GPC3 immunoconjugate comprises a topoisomerase II inhibitor including, without limitation, doxorubicin NSC 123127, amonafide NSC 308847, m-AMSA NSC 249992, anthrapyrazole derivative NSC 355644, pyrazoloacridine NSC 366140, bisantrene HCL NSC 337766, daunorubicin NSC 82151, deoxydoxorubicin NSC 267469, mitoxantrone NSC 301739, menogaril NSC 269148, N,N-dibenzyl daunomycin NSC 268242, oxanthrazole NSC 349174, rubidazone NSC 164011, VM-26 NSC 122819, and VP-16 NSC 141540.

In some embodiments, the anti-GPC3 immunoconjugate comprises an RNA or DNA antimetabolite including, without limitation, L-alanosine NSC 153353, 5-azacytidine NSC 102816, 5-fluorouracil NSC 19893, acivicin NSC 163501, aminopterin derivative NSC 132483, aminopterin derivative NSC 184692, aminopterin derivative NSC 134033, an antifol NSC 633713, an antifol NSC 623017, Baker's soluble antifol NSC 139105, dichlorallyl lawsone NSC 126771, brequinar NSC 368390, ftorafur (pro-drug) NSC 148958, 5,6-dihydro-5-azacytidine NSC 264880, methotrexate NSC 740, methotrexate derivative NSC 174121, N-(phosphonoacetyl)-L-aspartate (PALA) NSC 224131, pyrazofurin NSC 143095, trimetrexate NSC 352122, 3-HP NSC 95678, 2'-deoxy-5-fluorouridine NSC 27640, 5-HP NSC 107392,α-TGDR NSC 71851, aphidicolin glycinate NSC 303812, ara-C NSC 63878, 5-aza-2'-deoxycytidine NSC 127716,β-TGDR NSC 71261, cyclocytidine NSC 145668, guanazole NSC 1895, hydroxyurea NSC 32065, inosine glycodialdehyde NSC 118994, macbecin Il NSC 330500, pyrazoloimidazole NSC 51143, thioguanine NSC 752, and thiopurine NSC 755.

In some embodiments, the anti-GPC3 immunoconjugate comprises a highly radioactive atom. A variety of radioactive isotopes are available for the production of radioconjugated antibodies. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu.

In some embodiments, the anti-GPC3 antibody moiety can be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

In some embodiments, an anti-GPC3 immunoconjugate may comprise an anti-GPC3 antibody moiety conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such anti-GPC3 immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibody moieties by recombinant DNA techniques well known in the art. See, e.g., Neuberger et al., *Nature* 312:604-608 (1984).

In some embodiments, therapeutic portion of the anti-GPC3 immunoconjugates may be a nucleic acid. Nucleic acids that may be used include, but are not limited to, anti-sense RNA, genes or other polynucleotides, including nucleic acid analogs such as thioguanine and thiopurine.

The present application further provides anti-GPC3 immunoconjugates comprising an anti-GPC3 antibody moiety attached to an effector molecule, wherein the effector molecule is a label, which can generate a detectable signal, indirectly or directly. These anti-GPC3 immunoconjugates can be used for research or diagnostic applications, such as for the in vivo detection of cancer. The label is preferably capable of producing, either directly or indirectly, a detectable signal. For example, the label may be radio-opaque or a radioisotope, such as $^3$H, actinium-225, astatine-211, bismuth-212, carbon-14, chromium-51, chlorine-36, cobalt-57, cobalt-58, copper-67, Europium-152, gallium-67, hydrogen-3, iodine-123, iodine-124, iodine-125, iodine-131, indium-111, iron-59, lead-212, lutetium-177, phosphorus-32, radium-223, radium-224, rhenium-186, rhenium-188, selenium-75, sulphur-35, technicium-99m, thorium-227, yttrium-90, or zirconium-89; a fluorescent (fluorophore) or chemiluminescent (chromophore) compound, such as fluorescein isothiocyanate, rhodamine, luciferin, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, HEX, 6-JOE, Oregon Green 488, Oregon Green 500, Oregon Green 514, Pacific Blue, REG, Renographin, ROX, TAMRA, TET, Tetramethylrhodamine, and/or Texas Red; an enzyme, such as alkaline phosphatase, β-galactosidase or horseradish peroxidase; an imaging agent; or a metal ion, e.g., chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II), and/or bismuth (III). In some embodiments, the label is a radioactive atom for scintigraphic studies, for example $^{99}$Tc or $^{123}$I, or a spin label for nuclear magnetic resonance (NMR) imaging (also known as magnetic resonance imaging, MM), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

In some embodiments, the anti-GPC3 immunoconjugate is detectable indirectly. For example, a secondary antibody that is specific for the anti-GPC3 immunoconjugate and contains a detectable label can be used to detect the anti-GPC3 immunoconjugate.

In some embodiments, there is provided an anti-GPC3 immunoconjugate comprising a) an anti-GPC3 antibody moiety that specifically binds to a cell surface-bound GPC3 (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity), and b) an effector molecule. In some embodiments, the anti-nGPC3 antibody moiety specifically recognizes an epitope within human GPC3 comprising the amino acid sequence of SEQ ID NO: 460. In some embodiments, the anti-nGPC3 antibody moiety specifically recognizes an epitope within the amino acid sequence of SEQ ID NO: 461. In some embodiments, the anti-nGPC3 antibody moiety specifically recognizes an epitope within amino acids 25-580 of SEQ ID NO: 460 (SEQ ID NO: 463). In some embodiments, the anti-nGPC3 antibody moiety specifically recognizes an epitope within the amino acid sequence of SEQ ID NO: 463. In some embodiments, the anti-nGPC3 antibody moiety specifically recognizes an epitope within the N-terminal fragment of GPC3. In some embodiments, the anti-nGPC3 antibody moiety specifically recognizes an epitope within amino acids 1-358 of SEQ ID NO: 460 (SEQ ID NO: 468). In some embodiments, the anti-nGPC3 antibody moiety specifically recognizes an epitope within the amino acid sequence of SEQ ID NO: 464. In some embodiments, the anti-nGPC3 antibody moiety specifically recognizes an epitope within the C-terminal fragment of GPC3. In some embodiments, the anti-nGPC3 antibody moiety specifically recognizes an epitope within amino acids 359-560 of SEQ ID NO: 460 (SEQ ID NO: 465). In some embodiments, the anti-nGPC3 antibody moiety specifically recognizes an epitope within amino acids 359-580 of SEQ ID NO: 460 (SEQ ID NO: 466). In some embodiments, the anti-nGPC3 antibody moiety specifically recognizes an epitope within the C-terminal fragment of GPC3 lacking heparin sulfate side chain. In some embodiments, the anti-nGPC3 antibody moiety specifically recognizes an epitope within amino acids 510-560 of SEQ ID NO: 460 (SEQ ID NO: 467). In some embodiments, the anti-nGPC3 antibody moiety specifically recognizes an epitope spanning the Furin cleavage site at amino acids $R^{358}/S^{359}$ of SEQ ID NO: 460. In some embodiments, the anti-nGPC3 antibody moiety can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460). In some embodiments, the anti-nGPC3 antibody moiety specifically recognizes an epitope within the C-terminal fragment of GPC3 lacking heparin sulfate side chain. In some embodiments, there is provided an anti-GPC3 immunoconjugate comprising a) an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that competes for binding to nGPC3 with any one of the anti-GPC3 constructs described herein, and b) an effector molecule. In some embodiments, there is provided an anti-GPC3 immunoconjugate comprising a) an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that specifically binds to the same, or substantially the same, nGPC3 epitope competitively with any one of the anti-GPC3 constructs described herein, and b) an effector molecule. In some embodiments, the GPC3 is expressed on the surface of a cell selected from the group consisting of HepG2, Hep3B, Huh7, JHH-7, and 293. In some embodiments, the GPC3 is expressed on the surface of a cancer cell (such as liver cancer cell, e.g., HCC). In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the effector molecule is covalently attached to the anti-GPC3 antibody moiety. In some embodiments, the effector molecule is a therapeutic agent selected, for example, from the group consisting of a drug, a toxin, a radioisotope, a protein, a peptide, and a nucleic acid. In some embodiments, the effector molecular is a cancer therapeutic agent. In some embodiments, the cancer therapeutic agent is a chemotherapeutic. In some embodiments, the cancer therapeutic agent is a highly radioactive atom selected, for example, from the group consisting of $^{211}$At, $^{131}$I, $^{125}$I $^{90}$Y, $^{186}$Re, $^{188}$Re, $^{153}$Sm, $^{212}$Bi, $^{32}$P, and $^{212}$Pb. In some embodiments, the effector molecule is a label that can generate a detectable signal, either directly or indirectly. In some embodiments, the label is a radioisotope selected, for example, from the group consisting of $^{3}$H, $^{14}$C, $^{32}$P, $^{35}$S, $^{123}$I, $^{125}$I, and $^{131}$I. In some embodiments, the anti-nGPC3 antibody moiety is a full-length antibody, a Fab, a Fab', a F(ab')2, an Fv, or an scFv. In some embodiments, the anti-nGPC3 antibody moiety is a Fab or a Fab'. In some embodiments, the anti-nGPC3 antibody moiety is an scFv. In some embodiments, the anti-GPC3 antibody moiety is chimeric, human, humanized, or semi-synthetic.

In some embodiments, there is provided an anti-GPC3 immunoconjugate comprising a) an anti-GPC3 antibody moiety that specifically binds to a cell surface-bound GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions, and b) an effector molecule. In some embodiments, there is provided an anti-GPC3 immunoconjugate comprising a) an anti-GPC3 antibody moiety that specifically binds to a cell surface-bound GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286, and b) an effector molecule. In some embodiments, there is provided an anti-GPC3 immunoconjugate comprising a) an anti-GPC3 antibody moiety that specifically binds to a cell surface-bound GPC3, comprising: i) a $V_H$ comprising the amino acid sequence of any one of SEQ ID NOs: 307-337; and ii) a $V_L$ comprising the amino acid sequence of any one of SEQ ID NOs: 358-388, and b) an effector molecule. In some embodiments, there is provided an anti-GPC3 immunoconjugate comprising a) an anti-GPC3 antibody moiety that specifically binds to a cell surface-bound GPC3, comprising the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388, and b) an effector molecule. In some embodiments, there is provided an anti-GPC3 immunoconjugate comprising a) an anti-nGPC3 antibody moiety that competes for binding to nGPC3 with any one of the anti-GPC3 constructs described herein, and b) an effector molecule. In some embodiments, there is provided an anti-GPC3 immunoconjugate comprising a) an anti-nGPC3 antibody moiety that specifically binds to the same, or substantially the same, nGPC3 epitope competitively with any one of the anti-GPC3 constructs described herein, and b) an effector molecule. In some embodiments, the $K_d$ of the binding between the anti-nGPC3 antibody moiety and nGPC3 is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-nGPC3 antibody moiety and an sGPC3 can be at least about 10 times (such as at least about 10, $10^2$, $10^3$, $10^4$, $10^5$, $10^6$, or $10^7$ times) of the $K_d$ of the binding between the anti-nGPC3 antibody moiety and nGPC3. In some embodiments, the $K_d$ of the binding between the anti-nGPC3 antibody moiety and an sGPC3 is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the effector molecule is covalently attached to the anti-GPC3 antibody moiety. In some embodiments, the effector molecule is a therapeutic agent selected, for example, from the group consisting of a drug, a toxin, a radioisotope, a protein, a peptide, and a nucleic acid. In some embodiments, the effector molecular is a cancer therapeutic agent. In some embodiments, the cancer therapeutic agent is a chemotherapeutic. In some embodiments, the cancer therapeutic agent is a highly radioactive atom selected, for example, from the group consisting of $^{211}$At, $^{131}$I, $^{125}$I, $^{90}$Y, $^{186}$Re $^{188}$Re $^{153}$Sm, $^{212}$Bi, $^{32}$P, and $^{212}$Pb. In some embodiments, the effector molecule is a label that can generate a detectable signal, either directly or indirectly. In some embodiments, the label is a radioisotope selected, for example, from the group consisting of $^{3}$H, $^{14}$C, $^{32}$P, $^{35}$S, $^{123}$I, $^{125}$I, and $^{131}$I. In some embodiments, the anti-nGPC3 antibody moiety is a full-length antibody, a Fab, a Fab', a F(ab')2, an Fv, or an scFv. In some embodiments, the anti-nGPC3 antibody moiety is a Fab or a Fab'. In some embodiments, the anti-nGPC3 antibody moiety is an scFv. In some embodiments, the anti-nGPC3 antibody moiety is chimeric, human, humanized, or semi-synthetic.

In some embodiments, there is provided an anti-GPC3 immunoconjugate comprising a) an anti-GPC3 antibody moiety that specifically binds to GPC3 (e.g., nGPC3 and/or sGPC3), comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions, and b) an effector molecule. In some embodiments, there is provided an anti-GPC3 immunoconjugate comprising a) an anti-GPC3 antibody moiety that specifically binds to GPC3 (e.g., nGPC3 and/or sGPC3), comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306, and b) an effector molecule. In some embodiments, there is provided an anti-GPC3 immunoconjugate comprising a) an anti-GPC3 antibody moiety that specifically binds to GPC3 (e.g., nGPC3 and/or sGPC3), comprising: i) a $V_H$ comprising the amino acid sequence of any one of SEQ ID NOs: 338-357; and ii) a $V_L$ comprising the amino acid sequence of any one of SEQ ID NOs: 389-408, and b) an effector molecule. In some embodiments, there is provided an anti-GPC3 immunoconjugate comprising a) an anti-GPC3 antibody moiety that specifically binds to GPC3 (e.g., nGPC3 and/or sGPC3), comprising the HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408, and b) an effector molecule. In some embodiments, there is provided an anti-GPC3 immunoconjugate comprising a) an anti-GPC3 antibody moiety that competes for binding to GPC3 (e.g., nGPC3 and/or sGPC3) with any one of the anti-GPC3 constructs described herein, and b) an effector molecule. In some embodiments, there is provided an anti-GPC3 immunoconjugate comprising a) an anti-GPC3 antibody moiety that specifically binds to the same, or substantially the same, GPC3 epitope competitively with any one of the anti-GPC3 constructs described herein, and b) an effector molecule. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the $K_d$ of the binding between the anti-GPC3 antibody moiety and a target GPC3 (e.g., nGPC3 and/or sGPC3) is about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M). In some embodiments, the $K_d$ of the binding between the anti-GPC3 antibody moiety and a non-target can be at least about 10 times (such as at least about 10, $10^2$, $10^3$, $10^4$, $10^5$, $10^6$, or $10^7$ times) of the $K_d$ of the binding between the anti-GPC3 antibody moiety and the target GPC3. In some embodiments, the $K_d$ of the binding between the anti-GPC3 antibody moiety and a non-target is about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the effector molecule is covalently attached to the anti-GPC3 antibody moiety. In some embodiments, the effector molecule is a therapeutic agent selected, for example, from the group consisting of a drug, a toxin, a radioisotope, a protein, a peptide, and a nucleic acid. In some embodiments, the effector molecular is a cancer therapeutic agent. In some embodiments, the cancer therapeutic agent is a chemotherapeutic. In some embodiments, the cancer therapeutic agent is a highly radioactive atom selected, for example, from the group consisting of $^{211}At$, $^{131}I$, $^{125}I$, $^{90}Y$, $^{186}Re$, $^{188}Re$, $^{153}Sm$, $^{212}Bi$, and $^{212}Pb$. In some embodiments, the effector molecule is a label that can generate a detectable signal, either directly or indirectly. In some embodiments, the label is a radioisotope selected, for example, from the group consisting of $^3H$, $^{14}C$, $^{32}P$, $^{35}S$, $^{123}I$, $^{125}I$, and $^{131}I$ In some embodiments, the anti-GPC3 antibody moiety is a full-length antibody, a Fab, a Fab', a F(ab')2, an Fv, or an scFv. In some embodiments, the anti-GPC3 antibody moiety is a Fab or a Fab'. In some embodiments, the anti-GPC3 antibody moiety is an scFv. In some embodiments, the anti-GPC3 antibody moiety is chimeric, human, humanized, or semi-synthetic.

Nucleic Acids

Nucleic acid molecules encoding the anti-GPC3 constructs (such as isolated anti-GPC3 constructs) or anti-GPC3 antibody moieties are also contemplated. In some embodiments, there is provided a nucleic acid (or a set of nucleic acids) encoding a full-length anti-GPC3 antibody. In some embodiments, there is provided a nucleic acid (or a set of nucleic acids) encoding an anti-GPC3 scFv. In some embodiments, there is provided a nucleic acid (or a set of nucleic acids) encoding an anti-GPC3 Fc fusion protein. In some embodiments, there is provided a nucleic acid (or a set of nucleic acids) encoding a multi-specific anti-GPC3 molecule (e.g., a multi-specific anti-GPC3 antibody, a bispecific anti-GPC3 antibody, or a bispecific T-cell engager anti-GPC3 antibody), or polypeptide portion thereof. In some embodiments, there is provided a nucleic acid (or a set of nucleic acids) encoding an anti-GPC3 CAR. In some embodiments, there is provided a nucleic acid (or a set of nucleic acids) encoding an anti-GPC3 caTCR. In some embodiments, there is provided a nucleic acid (or a set of nucleic acids) encoding an anti-GPC3 immunoconjugate, or polypeptide portion thereof. In some embodiments, the nucleic acid (or a set of nucleic acids) encoding the anti-GPC3 construct described herein may further comprises a nucleic acid sequence encoding a peptide tag (such as protein purification tag, e.g., His-tag, HA tag).

Also contemplated here are isolated host cell comprising an anti-GPC3 construct, an isolated nucleic acid encoding the polypeptide components of the anti-GPC3 construct, or a vector comprising a nucleic acid encoding the polypeptide components of the anti-GPC3 construct described herein.

The present application also includes variants to these nucleic acid sequences. For example, the variants include nucleotide sequences that hybridize to the nucleic acid sequences encoding the anti-GPC3 constructs (such as isolated anti-GPC3 constructs) or anti-GPC3 antibody moieties of the present application under at least moderately stringent hybridization conditions.

The present invention also provides vectors in which a nucleic acid of the present invention is inserted.

In brief summary, the expression of an anti-GPC3 construct (e.g., anti-GPC3 CAR, anti-GPC3 caTCR) or polypeptide portion thereof by a natural or synthetic nucleic acid encoding the anti-GPC3 construct or polypeptide portion thereof can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Factor-1a (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence to which it is operatively linked when such expression is desired, or turning off the expression when expression is not desired. Examples of inducible promoters include, but are not limited to, a metallothionine promoter, a glucocorticoid promoter, a progesterone promoter, and a tetracycline promoter.

As mentioned above, in some embodiments, the expression of the multi-specific (e.g., bispecific) anti-GPC3 molecule (e.g., anti-GPC3×CD3 tandem di-scFv T cell engager) is inducible. In some embodiments, an effector cell (e.g., T cell, CAR-T cell, caTCR T cell) comprises a nucleic acid sequence encoding the multi-specific (e.g., bispecific) anti-GPC3 molecule (e.g., anti-GPC3×CD3 bispecific T cell engager) operably linked to an inducible promoter, including any inducible promoter described herein. In some embodiments, the expression of the multi-specific (e.g., bispecific) anti-GPC3 molecule (e.g., anti-GPC3×CD3 tandem di-scFv T cell engager) in the effector cell (e.g., T cell, CAR-T cell, caTCR T cell) is inducible upon signaling through a signaling receptor on the effector cell (e.g., TCR, CAR, caTCR). In some embodiments, the nucleic acid sequence encoding the multi-specific (e.g., bispecific) anti-GPC3 molecule (e.g., anti-GPC3×CD3 tandem di-scFv T cell engager) is operably linked to an NFAT-derived promoter. In some embodiments, the NFAT-derived promoter is an NFAT-derived minimal promoter. In some embodiments, the nucleic acid sequence encoding the multi-specific (e.g., bispecific) anti-GPC3 molecule (e.g., anti-GPC3×CD3 tandem di-scFv T cell engager) is operably linked to an IL-2 promoter.

Inducible Promoters

The use of an inducible promoter provides a molecular switch capable of turning on expression of the polynucleotide sequence which it is operatively linked when such expression is desired, or turning off the expression when expression is not desired. Exemplary inducible promoter systems for use in eukaryotic cells include, but are not limited to, hormone-regulated elements (e.g., see Mader, S. and White, J. H. (1993) Proc. Natl. Acad. Sci. USA 90:5603-5607), synthetic ligand-regulated elements (see, e.g., Spencer, D. M. et al 1993) Science 262: 1019-1024) and ionizing radiation-regulated elements (e.g., see Manome, Y. et al. (1993) Biochemistry 32: 10607-10613; Datta, R. et al. (1992) Proc. Natl. Acad. Sci. USA 89: 1014-10153). Further exemplary inducible promoter systems for use in in vitro or in vivo mammalian systems are reviewed in Gingrich et al. (1998) Annual Rev. Neurosci 21:377-405. In some embodiments, the inducible promoter system for use to express the multi-specific (e.g., bispecific) anti-GPC3 molecule is the Tet system. In some embodiments, the inducible promoter system for use to express the multi-specific (e.g., bispecific) anti-GPC3 molecule is the lac repressor system from E. coli. In some embodiments, the inducible promoter system for use to express the multi-specific (e.g., bispecific) anti-GPC3 molecule is NFAT-derived promoter.

An exemplary inducible promoter system for use in the present invention is the Tet system. Such systems are based on the Tet system described by Gossen et al. (1993). In an exemplary embodiment, a polynucleotide of interest is under the control of a promoter that comprises one or more Tet operator (TetO) sites. In the inactive state, Tet repressor (TetR) will bind to the TetO sites and repress transcription from the promoter. In the active state, e.g., in the presence of an inducing agent such as tetracycline (Tc), anhydrotetracycline, doxycycline (Dox), or an active analog thereof, the inducing agent causes release of TetR from TetO, thereby allowing transcription to take place. Doxycycline is a member of the tetracycline family of antibiotics having the chemical name of 1-dimethylamino-2,4a,5,7,12-pentahydroxy-11-methyl-4,6-dioxo-1,4a,11,11a,12,12α-hexahydrotetracene-3-carboxamide.

In one embodiment, a TetR is codon-optimized for expression in mammalian cells, e.g., murine or human cells. Most amino acids are encoded by more than one codon due to the degeneracy of the genetic code, allowing for substantial variations in the nucleotide sequence of a given nucleic acid without any alteration in the amino acid sequence encoded by the nucleic acid. However, many organisms display differences in codon usage, also known as "codon bias" (i.e., bias for use of a particular codon(s) for a given amino acid). Codon bias often correlates with the presence of a predominant species of tRNA for a particular codon, which in turn increases efficiency of mRNA translation. Accordingly, a coding sequence derived from a particular organism (e.g., a prokaryote) may be tailored for improved expression in a different organism (e.g., a eukaryote) through codon optimization.

Other specific variations of the Tet system include the following "Tet-Off" and "Tet-On" systems. In the Tet-Off system, transcription is inactive in the presence of Tc or Dox. In that system, a tetracycline-controlled transactivator protein (tTA), which is composed of TetR fused to the strong transactivating domain of VP16 from Herpes simplex virus, regulates expression of a target nucleic acid that is under transcriptional control of a tetracycline-responsive promoter element (TRE). The TRE is made up of TetO sequence concatamers fused to a promoter (commonly the minimal promoter sequence derived from the human cytomegalovirus (hCMV) immediate-early promoter). In the absence of Tc or Dox, tTA binds to the TRE and activates transcription of the target gene. In the presence of Tc or Dox, tTA cannot bind to the TRE, and expression from the target gene remains inactive.

Conversely, in the Tet-On system, transcription is active in the presence of Tc or Dox. The Tet-On system is based on a reverse tetracycline-controlled transactivator, rtTA. Like tTA, rtTA is a fusion protein comprised of the TetR repressor and the VP16 transactivation domain. However, a four amino acid change in the TetR DNA binding moiety alters rtTA's binding characteristics such that it can only recognize the tetO sequences in the TRE of the target transgene in the presence of Dox. Thus, in the Tet-On system, transcription of the TRE-regulated target gene is stimulated by rtTA only in the presence of Dox.

Another inducible promoter system is the lac repressor system from E. coli (See Brown et al., Cell 49:603-612 (1987)). The lac repressor system functions by regulating transcription of a polynucleotide of interest operably linked to a promoter comprising the lac operator (lacO). The lac repressor (lacR) binds to LacO, thus preventing transcription of the polynucleotide of interest. Expression of the polynucleotide of interest is induced by a suitable inducing agent, e.g., isopropyl-β-D-thiogalactopyranoside (IPTG).

Another exemplary inducible promoter system for use in the present invention is the NFAT system. The NFAT family of transcription factors are important regulators of T cell activation. NFAT response elements are found, for example, in the IL-2 promoter (see for example Durand, D. et. al., *Molec. Cell. Biol.* 8, 1715-1724 (1988); Clipstone, N A, Crabtree, G R. *Nature.* 1992 357(6380): 695-7; Chmielewski, M., et al. *Cancer research* 71.17 (2011): 5697-5706; and Zhang, L., et al. *Molecular therapy* 19.4 (2011): 751-759).

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter.

Such promoter regions may be linked to a reporter gene and used to evaluate agents for the ability to modulate promoter-driven transcription.

In some embodiments, there is provided nucleic acid encoding an anti-GPC3 CAR and/or a multi-specific (e.g., bispecific) anti-GPC3 molecule (e.g., anti-GPC3×CD3 tandem di-scFv T cell engager) according to any of the anti-GPC3 CARs and multi-specific (e.g., bispecific) anti-GPC3 molecules described herein. In some embodiments, the nucleic acid comprises one or more nucleic acid sequences encoding all of the polypeptide chains of the anti-GPC3 CAR. In some embodiments, the nucleic acid comprises one or more nucleic acid sequences encoding all of the polypeptide chains of the multi-specific (e.g., bispecific) anti-GPC3 molecule. In some embodiments, the nucleic acid comprises one or more nucleic acid sequences encoding all of the polypeptide chains of the anti-GPC3 CAR and the multi-specific (e.g., bispecific) anti-GPC3 molecule. In some embodiments, each of the one or more nucleic acid sequences are contained in separate vectors. In some embodiments, at least some of the nucleic acid sequences are contained in the same vector. In some embodiments, all of the nucleic acid sequences are contained in the same vector. Vectors may be selected, for example, from the group consisting of mammalian expression vectors and viral vectors (such as those derived from retroviruses, adenoviruses, adeno-associated viruses, herpes viruses, and lentiviruses).

In some embodiments, the anti-GPC3 CAR is a monomer comprising a single polypeptide chain (e.g., anti-GPC3 scFv-CAR) and the multi-specific (e.g., bispecific) anti-GPC3 molecule is a monomer comprising a single multi-specific (e.g., bispecific) anti-GPC3 polypeptide chain (e.g., anti-GPC3×CD3 tandem di-scFv T cell engager), and the nucleic acid comprises a first nucleic acid sequence encoding the anti-GPC3 CAR polypeptide chain, and a second nucleic acid sequence encoding the multi-specific (e.g., bispecific) anti-GPC3 polypeptide chain. In some embodiments, the first nucleic acid sequence is contained in a first vector, and the second nucleic acid sequence is contained in a second vector. In some embodiments, the first and second nucleic acid sequences are contained in the same vector. In some embodiments, the first nucleic acid sequence is under the control of a first promoter, and the second nucleic acid sequence is under the control of a second promoter. In some embodiments, one or both of the first and second promoters have the same sequence. In some embodiments, one or both of the first and second promoters have different sequences. In some embodiments, one or both of the first and second nucleic acid sequences are expressed as a single transcript under the control of a single promoter in a multicistronic vector. See for example Kim, J H, et al., PLoS One 6(4): e18556, 2011. In some embodiments, one or both of the promoters are inducible. In some embodiments, the promoter controlling the nucleic acid sequence encoding the multi-specific (e.g., bispecific) anti-GPC3 polypeptide chain is inducible (such as inducible through the activation of the anti-GPC3 CAR). In some embodiments, the inducible promoter is an NFAT-derived promoter.

In some embodiments, there is provided nucleic acid encoding an anti-GPC3 caTCR and/or a multi-specific (e.g., bispecific) anti-GPC3 molecule (e.g., anti-GPC3×CD3 tandem di-scFv T cell engager) according to any of the anti-GPC3 caTCRs and multi-specific (e.g., bispecific) anti-GPC3 molecules described herein. In some embodiments, the nucleic acid comprises one or more nucleic acid sequences encoding all of the polypeptide chains of the anti-GPC3 caTCR. In some embodiments, the nucleic acid comprises one or more nucleic acid sequences encoding all of the polypeptide chains of the multi-specific (e.g., bispecific) anti-GPC3 molecule. In some embodiments, the nucleic acid comprises one or more nucleic acid sequences encoding all of the polypeptide chains of the anti-GPC3 caTCR and the multi-specific (e.g., bispecific) anti-GPC3 molecule. In some embodiments, each of the one or more nucleic acid sequences are contained in separate vectors. In some embodiments, at least some of the nucleic acid sequences are contained in the same vector. In some embodiments, all of the nucleic acid sequences are contained in the same vector. Vectors may be selected, for example, from the group consisting of mammalian expression vectors and viral vectors (such as those derived from retroviruses, adenoviruses, adeno-associated viruses, herpes viruses, and lentiviruses).

In some embodiments, the anti-GPC3 caTCR is a dimer comprising a first caTCR polypeptide chain and a second caTCR polypeptide chain and the multi-specific (e.g., bispecific) anti-GPC3 molecule is a monomer comprising a single multi-specific (e.g., bispecific) anti-GPC3 polypeptide chain (e.g., anti-GPC3×CD3 tandem di-scFv T cell engager), and the nucleic acid comprises a first nucleic acid sequence encoding the first caTCR polypeptide chain, a second nucleic acid encoding the second caTCR chain, and a third nucleic acid sequence encoding the multi-specific (e.g., bispecific) anti-GPC3 polypeptide chain. In some embodiments, the first nucleic acid sequence is contained in a first vector, the second nucleic acid sequence is contained in a second vector, and the third nucleic acid sequence is contained in a third vector. In some embodiments, the first and second nucleic acid sequences are contained in a first vector, and the third nucleic acid sequence is contained in a second vector. In some embodiments, the first and third nucleic acid sequences are contained in a first vector, and the second nucleic acid sequence is contained in a second vector. In some embodiments, the second and third nucleic acid sequences are contained in a first vector, and the first nucleic acid sequence is contained in a second vector. In some embodiments, the first, the second, and the third nucleic acid sequences are contained in the same vector. In some embodiments, the first nucleic acid sequence is under the control of a first promoter, the second nucleic acid sequence is under the control of a second promoter, and the third nucleic acid sequence is under the control of a third promoter. In some embodiments, some (such as all) of the first, second, and third promoters have the same sequence. In some embodiments, some (such as all) of the first, second, and third promoters have different sequences. In some embodiments, some (such as all) of the first, second, and third nucleic acid sequences are expressed as a single transcript under the control of a single promoter in a multicistronic vector. See for example Kim, J H, et al., PLoS One 6(4):e18556, 2011. In some embodiments, one or more of the promoters are inducible. In some embodiments, the promoter controlling the nucleic acid sequence encoding the multi-specific (e.g., bispecific) anti-GPC3 polypeptide chain is inducible (such as inducible through the activation of the anti-GPC3 caTCR). In some embodiments, the inducible promoter is an NFAT-derived promoter.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method of inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Preparation of Anti-GPC3 Constructs and Anti-GPC3 Antibody Moieties

In some embodiments, the anti-GPC3 construct or anti-GPC3 antibody moiety is a monoclonal antibody. In some embodiments, the anti-GPC3 construct is an anti-GPC3 CAR or anti-GPC3 caTCR which comprises an anti-GPC3 antibody moiety, the anti-GPC3 antibody moiety (e.g., Fab, Fab', F(ab')2, Fv, or scFv) comprises sequences derived from a monoclonal antibody. In some embodiments, the anti-GPC3 antibody moiety comprises $V_H$ and $V_L$ domains, or variants thereof, from the monoclonal antibody. In some embodiments, the anti-GPC3 antibody moiety further comprises $C_H1$ and $C_L$ domains, or variants thereof, from the monoclonal antibody. Monoclonal antibodies can be prepared, e.g., using hybridoma methods, such as those described by Kohler and Milstein, Nature, 256:495 (1975) and Sergeeva et al., Blood, 117(16):4262-4272, using the phage display methods described herein and in the Examples below, or using recombinant DNA methods (see, e.g., U.S. Pat. No. 4,816,567).

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest, or a complex comprising at least two molecules, such as a complex comprising a peptide and an MHC protein. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. See, e.g., Goding, Monoclonal Antibodies: Principles and Practice (New York: Academic Press, 1986), pp. 59-103. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, J. Immunol., 133:3001 (1984); Brodeur et al. Monoclonal Antibody Production Techniques and Applications (Marcel Dekker, Inc.: New York, 1987) pp. 51-63.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones can be sub cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In some embodiments, according to any of the anti-GPC3 constructs described herein comprising an anti-GPC3 antibody moiety, the anti-GPC3 antibody moiety comprises sequences from a clone selected from an antibody moiety library (such as a phage library presenting scFv or Fab fragments). The clone may be identified by screening combinatorial libraries for antibody fragments with the desired activity or activities. For example, a variety of methods are known in the art for generating phage display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N.J., 2001) and further described, e.g., in McCafferty et al., *Nature* 348:552-554; Clackson et al., *Nature* 352: 624-628 (1991); Marks et al., *J. Mol. Biol.* 222: 581-597 (1992); Marks and Bradbury, *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as scFv fragments or as Fab fragments. Libraries from immunized sources provide high-affinity antibodies to the immunogen without the requirement of constructing hybridomas. Alternatively, the naïve repertoire can be cloned (e.g., from human) to provide a single source of antibodies to a wide range of non-self and also self-antigens without any immunization as described by Griffiths et al., *EMBO J*, 12: 725-734 (1993). Finally, naïve libraries can also be made synthetically by cloning unrearranged V-gene segments from stem cells and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

The anti-GPC3 constructs can be prepared using phage display to screen libraries for anti-GPC3 antibody moieties specific to the target GPC3 (e.g., nGPC3 and/or sGPC3). The library can be a human scFv phage display library having a diversity of at least one×$10^9$ (such as at least about any of $1\times10^9$, $2.5\times10^9$, $5\times10^9$, $7.5\times10^9$, $1\times10^{10}$, $2.5\times10^{10}$, $5\times10^{10}$, $7.5\times10^{10}$, or $1\times10^{11}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al., *Nat. Biotechnol.* 23(3):344-348, 2005). In some embodiments, the heavy chain CDR3 of the semi-synthetic human library has a length from about 5 to about 24 (such as about any of 5, 6, 7, 8, 9, 10, 11, 12, 13, 14, 15, 16, 17, 18, 19, 20, 21, 22, 23, or 24) amino acids. In some embodiments, the library is a fully-synthetic phage display library. In some embodiments, the library is a non-human phage display library.

Phage clones that bind to the target GPC3 (e.g., nGPC3 and/or sGPC3) with high affinity can be selected by iterative binding of phage to the target GPC3, which is bound to a solid support (such as, for example, beads for solution panning or mammalian cells for cell panning), followed by removal of non-bound phage and by elution of specifically bound phage. In an example of solution panning, GPC3 polypeptide can be biotinylated for immobilization to a solid support. The biotinylated GPC3 is mixed with the phage library and a solid support, such as streptavidin-conjugated DYNABEADS® M-280, and then GPC3-phage-bead complexes are isolated. The bound phage clones are then eluted and used to infect an appropriate host cell, such as *E. coli* XL1-Blue, for expression and purification. In an example of cell panning, SK-Hep1 cells over-expressing GPC3 on cell surface are mixed with the phage library, after which the cells are collected and the bound clones are eluted and used to infect an appropriate host cell for expression and purification (all see Examples). The panning can be performed for multiple (such as about any of 2, 3, 4, 5, 6 or more) rounds with solution panning, cell panning, or a combination of both, to enrich for phage clones binding specifically to the target GPC3. Enriched phage clones can be tested for specific binding to the target GPC3 by any methods known in the art, including for example ELISA and FACS.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). Hybridoma cells as described above or GPC3-specific phage clones of the invention can serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains and/or framework regions in place of the homologous non-human sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention or can be substituted for the variable domains of one antigen-combining site of an antibody of the invention to create a chimeric bivalent antibody.

The antibodies can be monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using any method known in the art.

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. In some embodiments, the first heavy-chain constant region (CH1) containing the site necessary for light-chain binding is present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., *Methods in Enzymology,* 121: 210 (1986).

Human and Humanized Antibodies

The anti-GPC3 constructs (e.g., anti-GPC3 CAR or caTCR) or anti-GPC3 antibody moieties can be humanized antibodies or human antibodies. Humanized forms of non-human (e.g., murine) antibody moieties are chimeric immunoglobulins, immunoglobulin chains, or fragments thereof (such as Fv, Fab, Fab', F(ab')$_2$, scFv, or other antigen-binding subsequences of antibodies) that typically contain minimal sequence derived from non-human immunoglobulin. Humanized antibody moieties include human immunoglobulins, immunoglobulin chains, or fragments thereof (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibody moieties can also comprise residues that are found neither in the recipient antibody moiety nor in the imported CDR or framework sequences. In general, the humanized antibody moiety can comprise substantially all of at least one, and typically two, variable domains, in which all or substantially all of the CDR regions correspond to those of a non-human immunoglobulin, and all or substantially all of the FR regions are those of a human immunoglobulin consensus sequence. See, e.g., Jones et al., *Nature,* 321: 522-525 (1986); Riechmann et al., *Nature,* 332: 323-329 (1988); Presta, *Curr. Op. Struct. Biol.,* 2:593-596 (1992).

Generally, a humanized antibody moiety has one or more amino acid residues introduced into it from a source that is non-human. These non-human amino acid residues are often referred to as "import" residues, which are typically taken from an "import" variable domain. According to some embodiments, humanization can be essentially performed following the method of Winter and co-workers (Jones et al., *Nature,* 321: 522-525 (1986); Riechmann et al., *Nature,* 332: 323-327 (1988); Verhoeyen et al., *Science,* 239: 1534-1536 (1988)), by substituting rodent CDRs or CDR sequences for the corresponding sequences of a human antibody moiety. Accordingly, such "humanized" antibody moieties are antibody moieties (U.S. Pat. No. 4,816,567), wherein substantially less than an intact human variable domain has been substituted by the corresponding sequence from a non-human species. In practice, humanized antibody moieties are typically human antibody moieties in which some CDR residues and possibly some FR residues are substituted by residues from analogous sites in rodent antibodies.

As an alternative to humanization, human antibody moieties can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *PNAS USA,* 90:2551 (1993); Jakobovits et al., *Nature,* 362:255-258 (1993); Bruggemann et al., *Year in Immunol.,* 7:33 (1993); U.S. Pat. Nos. 5,545,806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; and 5,661,016, and Marks et al., *Bio/Technology,* 10: 779-783 (1992); Lonberg et al., *Nature,* 368: 856-859 (1994); Morrison, *Nature,* 368: 812-813 (1994); Fishwild et al., *Nature Biotechnology,* 14: 845-851 (1996); Neuberger, *Nature Biotechnology,* 14: 826 (1996); Lonberg and Huszar, *Intern. Rev. Immunol.,* 13: 65-93 (1995).

Human antibodies may also be generated by in vitro activated B cells (see U.S. Pat. Nos. 5,567,610 and 5,229,275) or by using various techniques known in the art, including phage display libraries. Hoogenboom and Winter, *J. Mol. Biol.,* 227:381 (1991); Marks et al., *J. Mol. Biol.,* 222:581 (1991). The techniques of Cole et al. and Boerner et al. are also available for the preparation of human monoclonal antibodies. Cole et al., *Monoclonal Antibodies and Cancer Therapy,* Alan R. Liss, p. 77 (1985) and Boerner et al., *J. Immunol.,* 147(1): 86-95 (1991).

Multi-Specific Antibodies

In some embodiments, the anti-GPC3 construct (such as an isolated anti-GPC3 construct) is a multi-specific antibody (e.g., tandem di-scFv bispecific anti-GPC3 antibody). Suitable methods for making multi-specific (e.g., bispecific) antibodies are well known in the art. For example, the production of bispecific antibodies based on the co-expression of two immunoglobulin heavy-chain/light-chain pairs, where the two pairs each have different specificities, and upon association result in a heterodimeric antibody (see, e.g., Milstein and Cuello, *Nature,* 305: 537-539 (1983); WO 93/08829, and Traunecker et al., *EMBO J.* 10: 3655 (1991)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker et al., *EMBO*, 10: 3655-3659 (1991). Alternatively, the combining of heavy and light chains can be directed by taking advantage of species-restricted pairing (see, e.g., Lindhofer et al., *J. Immunol.*, 155:219-225 (1995)) and the pairing of heavy chains can be directed by use of "knob-into hole" engineering of CH3 domains (see, e.g., U.S. Pat. No. 5,731,168; Ridgway et al., *Protein Eng.*, 9(7):617-621 (1996)). Multispecific antibodies may also be made by engineering electrostatic steering effects for making antibody Fc-heterodimeric molecules (see, e.g., WO 2009/089004A1). In yet another method, stable bispecific antibodies can be generated by controlled Fab-arm exchange, where two parental antibodies having distinct antigen specificity and matched point mutations in the CH3 domains are mixed in reducing condition to allow for separation, reassembly, and reoxidation to form highly pure bispecific antibodies. Labrigin et al., *Proc. Natl. Acad. Sci.*, 110(13):5145-5150 (2013). Such antibodies, comprising a mixture of heavy-chain/light-chain pairs, are also referred to herein as "heteromultimeric antibodies".

Antibodies or antigen-binding fragments thereof having different specificities can also be chemically cross-linked to generate multi-specific heteroconjugate antibodies. For example, two F(ab')2 molecules, each having specificity for a different antigen, can be chemically linked. Pullarkat et al., *Trends Biotechnol.*, 48:9-21 (1999). Such antibodies have, for example, been proposed to target immune-system cells to unwanted cells (U.S. Pat. No. 4,676,980), and for treatment of HIV infection. WO 91/00360; WO 92/200373; EP 03089. It is contemplated that the antibodies can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

In some embodiments, multi-specific antibodies can be prepared using recombinant DNA techniques. For example, a bispecific antibody can be engineered by fusing two scFvs, such as by fusing them through a peptide linker, resulting in a tandem scFv. One example of a tandem scFv is a bispecific T cell engager. Bispecific T cell engagers are made by linking an anti-CD3 scFv to an scFv specific for a surface antigen of a target cell, such as GPC3, resulting in the redirection of T cells to the target cells (e.g., HCC cells). Mack et al., *Proc. Natl. Acad. Sci.*, 92:7021-7025 (1995); Brischwein et al., *Mol. Immunol.*, 43(8):1129-1143 (2006). By shortening the length of a peptide linker between two variable domains, they can be prevented from self-assembling and forced to pair with domains on a second polypeptide, resulting in a compact bispecific antibody called a diabody (Db). Holliger et al., *Proc. Natl. Acad. Sci.*, 90:6444-6448 (1993). The two polypeptides of a Db each comprise a $V_H$ connected to a $V_L$ by a linker which is too short to allow pairing between the two domains on the same chain. Accordingly, the $V_H$ and VL domains of one polypeptide are forced to pair with the complementary $V_L$ and $V_H$ domains of another polypeptide, thereby forming two antigen-binding sites. In a modification of this format, the two polypeptides are linked by another peptide linker, resulting in a single chain diabody (scDb). In yet another modification of the Db format, dual-affinity retargeting (DART) bispecific antibodies can be generated by introducing a disulfide linkage between cysteine residues at the C-terminus of each polypeptide, optionally including domains prior to the C-terminal cysteine residues that drive assembly of the desired heterodimeric structure. Veri et al., *Arthritis Rheum.*, 62(7):1933-1943 (2010). Dual-variable-domain immunoglobulins (DVD-Ig™), in which the target-binding variable domains of two monoclonal antibodies are combined via naturally occurring linkers to yield a tetravalent, bispecific antibody, are also known in the art. Gu and Ghayur, *Methods Enzymol.*, 502:25-41 (2012). In yet another format, Dock and Lock (DNL), bispecific antibodies are prepared by taking advantage of the dimerization of a peptide (DDD2) derived from the regulatory subunit of human cAMP-dependent protein kinase (PKA) with a peptide (AD2) derived from the anchoring domains of human A kinase anchor proteins (AKAPs). Rossi et al., *Proc. Natl. Acad. Sci.*, 103:6841-6846 (2006).

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). This method can also be utilized for the production of antibody homodimers.

Anti-GPC3 Variants

In some embodiments, amino acid sequence variants of the anti-GPC3 constructs (e.g., anti-GPC3 full-length antibody) provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, anti-GPC3 antibody variants having one or more amino acid substitutions are provided. Sites of interest for substitutional mutagenesis include the HVRs and FRs. Amino acid substitutions may be introduced into an antibody of interest and the products screened for a desired activity, e.g., retained/improved antigen binding, decreased immunogenicity, or improved ADCC or CDC.

Conservative substitutions are shown in Table 2 below.

TABLE 2

CONSERVATIVE SUBSTITITIONS

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |

TABLE 2-continued

CONSERVATIVE SUBSTITITIONS

| Original Residue | Exemplary Substitutions | Preferred Substitutions |
|---|---|---|
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:
 a. hydrophobic: Norleucine, Met, Ala, Val, Leu, Ile;
 b. neutral hydrophilic: Cys, Ser, Thr, Asn, Gln;
 c. acidic: Asp, Glu;
 d. basic: His, Lys, Arg;
 e. residues that influence chain orientation: Gly, Pro;
 f. aromatic: Trp, Tyr, Phe.

Non-conservative substitutions will entail exchanging a member of one of these classes for another class.

An exemplary substitutional variant is an affinity matured antibody moiety, which may be conveniently generated, e.g., using phage display-based affinity maturation techniques. Briefly, one or more CDR residues are mutated and the variant antibody moieties displayed on phage and screened for a particular biological activity (e.g., binding affinity). Alterations (e.g., substitutions) may be made in HVRs, e.g., to improve antibody moiety affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody moiety variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex can be determined to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Fc Region Variants

In some embodiments, one or more amino acid modifications may be introduced into the Fc region of a full-length anti-GPC3 antibody or anti-GPC3 Fc fusion protein provided herein, thereby generating an Fc region variant. In some embodiments, the Fc region variant has enhanced ADCC effector function, often related to binding to Fc receptors (FcRs). In some embodiments, the Fc region variant has decreased ADCC effector function. There are many examples of changes or mutations to Fc sequences that can alter effector function. For example, WO 00/42072 and Shields et al. *J. Biol. Chem.* 9(2): 6591-6604 (2001) describe antibody variants with improved or diminished binding to FcRs. The contents of those publications are specifically incorporated herein by reference.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., an anti-GPC3 antibody). The typical ADCC involves activation of NK cells by antibodies. An NK cell expresses CD16 which is an Fc receptor. This receptor recognizes, and binds to, the Fc portion of an antibody bound to the surface of a target cell. The most common Fc receptor on the surface of an NK cell is called CD16 or FcγRIII Binding of the Fc receptor to the Fc region of an antibody results in NK cell activation, release of cytolytic granules and consequent target cell apoptosis. The contribution of ADCC to tumor cell killing can be measured with a specific test that uses NK-92 cells that have been transfected with a high-affinity FcR. Results are compared to wild-type NK-92 cells that do not express the FcR.

In some embodiments, the invention contemplates an anti-GPC3 construct variant (such as an isolated anti-GPC3 construct variant) comprising an Fc region that possesses some but not all effector functions, which makes it a desirable candidate for applications in which the half-life of the anti-GPC3 construct in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, there is provided an anti-GPC3 construct (such as an isolated anti-GPC3 construct, e.g., anti-GPC3-Fc fusion protein, a full-length anti-GPC3 antibody) variant comprising a variant Fc region comprising one or more amino acid substitutions which improve ADCC. In some embodiments, the variant Fc region comprises one or more amino acid substitutions which improve ADCC, wherein the substitutions are at positions 298, 333, and/or 334 of the variant Fc region (EU numbering of residues). In some embodiments, the anti-GPC3 construct (e.g., full-length anti-GPC3 antibody) variant comprises the following amino acid substitution in its variant Fc region: S298A, E333A, and K334A.

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

In some embodiments, there is provided an anti-GPC3 construct (such as an isolated anti-GPC3 construct, e.g., anti-GPC3-Fc fusion protein, a full-length anti-GPC3 antibody) variant comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-GPC3 constructs (such as isolated anti-GPC3 constructs, e.g., anti-GPC3-Fc fusion protein, full-length anti-GPC3 antibodies) comprising any of the Fc variants described herein, or combinations thereof, are contemplated.

Glycosylation Variants

In some embodiments, an anti-GPC3 construct (such as an isolated anti-GPC3 construct, e.g., anti-GPC3-Fc fusion protein, a full-length anti-GPC3 antibody) provided herein is altered to increase or decrease the extent to which the anti-GPC3 construct is glycosylated. Addition or deletion of glycosylation sites to an anti-GPC3 construct may be conveniently accomplished by altering the amino acid sequence of the anti-GPC3 construct or polypeptide portion thereof such that one or more glycosylation sites is created or removed.

Where the anti-GPC3 construct comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-GPC3 construct of the invention may be made in order to create anti-GPC3 construct variants with certain improved properties.

The N-glycans attached to the CH2 domain of Fc is heterogeneous. Antibodies or Fc fusion proteins generated in CHO cells are fucosylated by fucosyltransferase activity. See Shoji-Hosaka et al., *J. Biochem.* 2006, 140:777-83. Normally, a small percentage of naturally occurring afucosylated IgGs may be detected in human serum. N-glycosylation of the Fc is important for binding to FcγR; and afucosylation of the N-glycan increases Fc's binding capacity to FcγRIIIa. Increased FcγRIIIa binding can enhance ADCC, which can be advantageous in certain antibody therapeutic applications in which cytotoxicity is desirable.

In some embodiments, an enhanced effector function can be detrimental when Fc-mediated cytotoxicity is undesirable. In some embodiments, the Fc fragment or CH2 domain is not glycosylated. In some embodiments, the N-glycosylation site in the CH2 domain is mutated to prevent from glycosylation.

In some embodiments, anti-GPC3 construct (such as an isolated anti-GPC3 construct, e.g., an anti-GPC3-Fc fusion protein, a full-length anti-GPC3 antibody) variants are provided comprising an Fc region wherein a carbohydrate structure attached to the Fc region has reduced fucose or lacks fucose, which may improve ADCC function. Specifically, anti-GPC3 constructs are contemplated herein that have reduced fusose relative to the amount of fucose on the same anti-GPC3 construct produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In some embodiments, the anti-GPC3 construct is one wherein less than about 50%, 40%, 30%, 20%, 10%, or 5% of the N-linked glycans thereon comprise fucose. For example, the amount of fucose in such an anti-GPC3 construct may be from 1% to 80%, from 1% to 65%, from 5% to 65% or from 20% to 40%. In some embodiments, the anti-GPC3 construct is one wherein none of the N-linked glycans thereon comprise fucose, i.e., wherein the anti-GPC3 construct is completely without fucose, or has no fucose or is afucosylated. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as α-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-GPC3 construct (such as an isolated anti-GPC3 construct, e.g., an anti-GPC3-Fc fusion protein, a full-length anti-GPC3 antibody) variants are further provided with bisected oligosaccharides, e.g., in which a biantennary oligosaccharide attached to the Fc region of the anti-GPC3 construct is bisected by GlcNAc. Such anti-GPC3 construct (such as an isolated anti-GPC3 construct, e.g., an anti-GPC3-Fc fusion protein, a full-length anti-GPC3 antibody) variants may have reduced fucosylation and/or improved ADCC function. Examples of such antibody variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering*, 93(5): 851-861 (2006). Anti-GPC3 construct (such as full-length anti-GPC3 antibody) variants with at least one galactose residue in the oligosaccharide attached to the Fc region are also provided. Such anti-GPC3 construct variants may have improved CDC function. Such antibody variants are described, e.g., in WO 1997/30087 (Patel et al.); WO 1998/58964 (Raju, S.); and WO 1999/22764 (Raju, S.).

In some embodiments, the anti-GPC3 construct (such as an isolated anti-GPC3 construct, e.g., an anti-GPC3-Fc fusion protein, a full-length anti-GPC3 antibody) variants comprising an Fc region are capable of binding to an FcγRIII. In some embodiments, the anti-GPC3 construct (such as an isolated anti-GPC3 construct, e.g., an anti-GPC3-Fc fusion protein, a full-length anti-GPC3 antibody) variants comprising an Fc region have ADCC activity in the presence of human effector cells (e.g., T cell) or have increased ADCC activity in the presence of human effector cells compared to the otherwise same anti-GPC3 construct (such as an isolated anti-GPC3 construct, e.g., an anti-GPC3-Fc fusion protein, a full-length anti-GPC3 antibody) comprising a human wild-type IgG1Fc region.

Cysteine Engineered Variants

In some embodiments, it may be desirable to create cysteine engineered anti-GPC3 constructs (such as an isolated anti-GPC3 construct, e.g., an anti-GPC3-Fc fusion protein, a full-length anti-GPC3 antibody) in which one or more amino acid residues are substituted with cysteine residues. In some embodiments, the substituted residues occur at accessible sites of the anti-GPC3 construct. By substituting those residues with cysteine, reactive thiol groups are thereby positioned at accessible sites of the anti-GPC3 construct and may be used to conjugate the anti-GPC3 construct to other moieties, such as drug moieties or linker-drug moieties, to create an anti-GPC3 immunoconjugate, as described further herein. Cysteine engineered anti-GPC3 constructs (such as full-length anti-GPC3 antibodies) may be generated as described, e.g., in U.S. Pat. No. 7,521,541.

Derivatives

In some embodiments, an anti-GPC3 construct (such as an isolated anti-GPC3 construct, e.g., an anti-GPC3-Fc fusion protein, a full-length anti-GPC3 antibody) provided herein may be further modified to contain additional non-proteinaceous moieties that are known in the art and readily available. The moieties suitable for derivatization of the anti-GPC3 construct include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the anti-GPC3 construct may vary, and if more than one polymer are attached, they can be the same or different molecules. In general, the number and/or type of polymers used for derivatization can be determined based on considerations including, but not limited to, the particular properties or functions of the anti-GPC3 construct to be improved, whether the anti-GPC3 construct derivative will be used in a therapy under defined conditions, etc.

In some embodiments, conjugates of an anti-GPC3 construct (such as an isolated anti-GPC3 construct, e.g., a full-length anti-GPC3 antibody) and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the anti-GPC3 construct-nonproteinaceous moiety are killed.

CAR Effector Cell and caTCR Effector Cell Preparation

The present invention in one aspect provides effector cells (such as lymphocytes, for example T cells) expressing an anti-GPC3 CAR. Exemplary methods of preparing effector cells (such as T cells) expressing the anti-GPC3 CARs (anti-GPC3 CAR effector cells, such as anti-GPC3 CAR T cells) are provided herein.

In some embodiments, an anti-GPC3 CAR effector cell (such as T cell) can be generated by introducing a vector (including for example a lentiviral vector) comprising an anti-GPC3 CAR (for example a CAR comprising an anti-GPC3 antibody moiety and CD28 and CD3 intracellular signaling sequences) into the effector cell (such as T cell). In some embodiments, the anti-GPC3 CAR effector cells (such as T cells) of the invention are able to replicate in vivo, resulting in long-term persistence that can lead to sustained control of a GPC3-positive disease (such as cancer, e.g., HCC). In some embodiments, the anti-GPC3 CAR effector cell (such as T cell) further expresses a multi-specific (e.g., bispecific) anti-GPC3 molecule described herein, by introducing a vector (including for example a lentiviral vector) comprising a multi-specific (e.g., bispecific) anti-GPC3 molecule (e.g., anti-GPC3×CD3 tandem di-scFv T cell engager) into the effector cell (such as T cell). In some embodiments, the nucleic acids encoding the anti-GPC3 CAR and the multi-specific (e.g., bispecific) anti-GPC3 molecules are contained in the same vector. In some embodiments, the nucleic acid encoding the multi-specific (e.g., bispecific) anti-GPC3 molecule is under control of an inducible promoter. In some embodiments, the expression of the multi-specific (e.g., bispecific) anti-GPC3 molecule is inducible through the activation of the anti-GPC3 CAR. In some embodiments, the inducible promoter is an NFAT-derived promoter.

In some embodiments, the anti-GPC3 CAR T cell expresses an anti-GPC3 CAR comprising an anti-GPC3 antibody moiety (also referred to herein as an "anti-GPC3 CAR T cell"). In some embodiments, the anti-GPC3 CAR T cell expresses an anti-GPC3 CAR comprising an extracellular domain comprising an anti-GPC3 antibody moiety and an intracellular domain comprising intracellular signaling sequences of CD3 and CD28. In some embodiments, the anti-GPC3 CAR T cell expresses an anti-GPC3 CAR comprising an anti-GPC3 antibody moiety, and a multi-specific (e.g., bispecific) anti-GPC3 molecule (e.g., anti-GPC3×CD3 tandem di-scFv T cell engager) described herein. The anti-GPC3 CART cells of the invention can undergo robust in vivo T cell expansion and can establish GPC3-specific memory cells that persist at high levels for an extended amount of time in blood and bone marrow. In some embodiments, the anti-GPC3 CAR T cells of the invention infused into a patient can eliminate GPC3$^+$ cells, such as GPC3$^+$ cancer cells (e.g., HCC cells), in vivo in patients having an GPC3-positive disease.

The present invention in another aspect provides effector cells (such as lymphocytes, for example T cells) expressing an anti-GPC3 caTCR. Exemplary methods of preparing effector cells (such as T cells) expressing the anti-GPC3 caTCRs (anti-GPC3 caTCR effector cells, such as anti-GPC3 caTCR T cells) are provided herein.

In some embodiments, an anti-GPC3 caTCR effector cell (such as T cell) can be generated by introducing a vector (including for example a lentiviral vector) comprising an anti-GPC3 caTCR into the effector cell (such as T cell). In some embodiments, the anti-GPC3 caTCR effector cells (such as T cells) of the invention are able to replicate in vivo, resulting in long-term persistence that can lead to sustained control of an GPC3-positive disease (such as cancer, e.g., HCC). In some embodiments, the anti-GPC3 caTCR effector cell (such as T cell) further expresses a multi-specific (e.g., bispecific) anti-GPC3 molecule described herein, by introducing a vector (including for example a lentiviral vector) comprising a multi-specific (e.g., bispecific) anti-GPC3 molecule (e.g., anti-GPC3×CD3 tandem di-scFv T cell engager) into the effector cell (such as T cell). In some embodiments, the nucleic acids encoding the anti-GPC3 caTCR and the multi-specific (e.g., bispecific) anti-GPC3 molecules are contained in the same vector. In some embodiments, the nucleic acid encoding the multi-specific (e.g., bispecific) anti-GPC3 molecule is under control of an inducible promoter. In some embodiments, the expression of the multi-specific (e.g., bispecific) anti-GPC3 molecule is inducible through the activation of the anti-GPC3 caTCR. In some embodiments, the inducible promoter is an NFAT-derived promoter.

In some embodiments, the anti-GPC3 caTCR T cell expresses an anti-GPC3 caTCR comprising an anti-GPC3 antibody moiety (also referred to herein as an "anti-GPC3 caTCR T cell"). In some embodiments, the anti-GPC3 caTCR T cell expresses an anti-GPC3 caTCR comprising an extracellular domain comprising an anti-GPC3 antibody moiety and a T cell receptor module (TCRM) comprising a first TCR domain (TCRD) comprising a first TCR transmembrane domain (TCR-TM) and a second TCRD comprising a second TCR-TM, wherein the TCRM facilitates recruitment of at least one TCR-associated signaling molecule. In some embodiments, the TCR-TM is derived from an αβTCR or a γδTCR. In some embodiments, the anti-GPC3 caTCR T cell expresses an anti-GPC3 caTCR comprising an anti-GPC3 antibody moiety, and a multi-specific (e.g., bispecific) anti-GPC3 molecule (e.g., anti-GPC3×CD3 tandem di-scFv T cell engager) described herein. The anti-GPC3 caTCR T cells of the invention can undergo robust in vivo T cell expansion and can establish GPC3-specific memory cells that persist at high levels for an extended amount of time in blood and bone marrow. In some embodiments, the anti-GPC3 caTCR T cells of the invention infused into a patient can eliminate GPC3$^+$ cells, such as GPC3$^+$ cancer cells (e.g., HCC cells), in vivo in patients having an GPC3-positive disease.

In some embodiments, the invention relates to administering a genetically modified T cell expressing an anti-GPC3 CAR or a genetically modified T cell expressing an anti-GPC3 caTCR for the treatment of a patient having an GPC3-positive disease or at risk of having an GPC3-positive disease using lymphocyte infusion. In some embodiments, autologous lymphocyte infusion is used in the treatment. Autologous PBMCs are collected from a patient in need of treatment and T cells are activated and expanded using the methods described herein and known in the art and then infused back into the patient.

In some embodiments, the anti-GPC3 CAR T cell expresses the anti-GPC3 CAR with even cell surface distribution. In some embodiments, the anti-GPC3 caTCR T cell expresses the anti-GPC3 caTCR with even cell surface distribution. Even cell surface distribution can be characterized, for example, by staining patterns with continuous appearance and even thickness or signal intensity. For example, in some embodiments, a composition, such as a pharmaceutical composition, comprising anti-GPC3 CAR T cells (or anti-GPC3 caTCR T cells) comprises fewer than about 10% (such as fewer than about 10, 9, 8, 7, 6, 5, 4, 3, 2, or 1%) cells with aggregation of the anti-GPC3 CAR (or anti-GPC3 caTCR) on the cell surface. Aggregation can be characterized, for example, by staining patterns with uneven thickness or signal intensity, or discontinuous, lumpy, punctate, and/or uneven distribution patterns. In some embodiments, the anti-GPC3 CAR T cell expresses the anti-GPC3 CAR with less than about 10% (such as less than about 10, 9, 8, 7, 6, 5, 4, 3, 2, or 1%) aggregation of the anti-GPC3 CAR on the cell surface. In some embodiments, the anti-GPC3 caTCR T cell expresses the anti-GPC3 caTCR with less than about 10% (such as less than about 10, 9, 8, 7, 6, 5, 4, 3, 2, or 1%) aggregation of the anti-GPC3 caTCR on the cell surface. In some embodiments, the anti-GPC3 CAR T cell has a low level of antigen-independent anti-GPC3 CAR activation. In some embodiments, the anti-GPC3 caTCR T cell has a low level of antigen-independent anti-GPC3 caTCR activation. In some embodiments, the anti-GPC3 CAR T cell or anti-GPC3 caTCR T cell has a low level of T cell exhaustion. T cell exhaustion naturally occurs during conditions of extended immune activation, such as with cancer or chronic infection, where T cells become dysfunctional. T cell exhaustion may be characterized by impaired effector function, prolonged expression of inhibitory receptors, and/or an altered transcriptional state compared to functional effector or memory T cells. Optimal clearance of tumor cells and infections is prevented by T cell exhaustion. T cell exhaustion of the anti-GPC3 CAR T cell or anti-GPC3 caTCR T cell can be characterized by any means known in the art, for example, by determining its functional and/or phenotypic profile (Wherry, E. J., Nature immunology 12(6): 492-499, 2011; Jiang, Y., et al., Cell death & disease 6(6): e1792, 2015). For example, in some embodiments, the anti-GPC3 CAR T cell or anti-GPC3 caTCR T cell expresses low levels of one or more markers of T cell exhaustion, including, for example, PD-1, LAG-3, TIM-3, CTLA-4, BTLA, and TIGIT. In some embodiments, the anti-GPC3 CAR T cell or anti-GPC3 caTCR T cell maintains levels characteristic of non-exhausted T cells for IL-2 production, TNF-α production, IFN-γ production, and granzyme B production, and/or maintains ex vivo killing capacity in the presence of target cells, suggesting that the anti-GPC3 CAR T cell or the anti-GPC3 caTCR T cell is not undergoing self-activation and premature exhaustion.

Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments of the present invention, any number of T cell lines available in the art may be used. In some embodiments of the present invention, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as $Ca^{2+}$-free, $Mg^{2+}$-free PBS, PlasmaLyte A, or other saline solutions with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45R^+$ T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In some embodiments, the time period ranges from 30 minutes to 36 hours or longer and all integer values there between. In some embodiments, the time period is at least one, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such as in isolating tumor infiltrating lymphocytes (TIL) from tumor tissue or from immune-compromised individuals. Further, use of longer incubation times can increase the efficiency of capture of $CD8^+$ T cells. Thus, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD-14, CD20, CD11b, CD-16, HLA-DR, and CD8. In some embodiments, it may be desirable to enrich for or positively select for regulatory T cells which typically express $CD4^+$, $CD25^+$, CD62Lhi, $GITR^+$, and $FoxP3^+$. Alternatively, in some embodiments, T regulatory cells are depleted by anti-CD25 conjugated beads or other similar methods of selection.

For isolation of a desired population of cells by positive or negative selection, the concentration of cells and surface (e.g., particles such as beads) can be varied. In some embodiments, it may be desirable to significantly decrease the volume in which beads and cells are mixed together (i.e., increase the concentration of cells), to ensure maximum contact of cells and beads. For example, in some embodiments, a concentration of about 2 billion cells/ml is used. In some embodiments, a concentration of about 1 billion cells/ml is used. In some embodiments, greater than about 100 million cells/ml is used. In some embodiments, a concentration of cells of about any of 10, 15, 20, 25, 30, 35, 40, 45, or 50 million cells/ml is used. In some embodiments, a concentration of cells of about any of 75, 80, 85, 90, 95, or 100 million cells/ml is used. In some embodiments, a concentration of about 125 or about 150 million cells/ml is used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In some embodiments of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in some embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Whether prior to or after genetic modification of the T cells to express a desirable anti-GPC3 CAR or anti-GPC3 caTCR (and in some embodiments further co-expressing a multi-specific (e.g., bispecific) anti-GPC3 molecule), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated, such as by contact with an anti-CD3 antibody, or antigen-binding fragment thereof, or an anti-CD3 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol. Meth.* 227(1-2):53-63, 1999).

Immunoconjugate Preparation

The anti-GPC3 immunoconjugates may be prepared using any methods known in the art. See, e.g., WO 2009/067800, WO 2011/133886, and U.S. Patent Application Publication No. 2014322129, incorporated by reference herein in their entirety.

The anti-GPC3 antibody moiety of an anti-GPC3 immunoconjugate may be "attached to" the effector molecule by any means by which the anti-GPC3 antibody moiety can be associated with, or linked to, the effector molecule. For example, the anti-GPC3 antibody moiety of an anti-GPC3 immunoconjugate may be attached to the effector molecule by chemical or recombinant means. Chemical means for preparing fusions or conjugates are known in the art and can be used to prepare the anti-GPC3 immunoconjugate. The method used to conjugate the anti-GPC3 antibody moiety and effector molecule must be capable of joining the binding protein with the effector molecule without interfering with the ability of the binding protein to bind to the antigen on the target cell.

The anti-GPC3 antibody moiety of an anti-GPC3 immunoconjugate may be linked indirectly to the effector molecule. For example, the anti-GPC3 antibody moiety of an anti-GPC3 immunoconjugate may be directly linked to a liposome containing the effector molecule of one of several types. The effector molecule(s) and/or the anti-GPC3 antibody moiety may also be bound to a solid surface.

In some embodiments, the anti-GPC3 antibody moiety of an anti-GPC3 immunoconjugate and the effector molecule are both proteins and can be conjugated using techniques well known in the art. There are several hundred crosslinkers available that can conjugate two proteins. (See for example "Chemistry of Protein Conjugation and Crosslinking". 1991, Shans Wong, CRC Press, Ann Arbor). The crosslinker is generally chosen based on the reactive functional groups available or inserted on the anti-GPC3 antibody moiety and/or effector molecule. In addition, if there are no reactive groups, a photoactivatible crosslinker can be used. In certain instances, it may be desirable to include a spacer between the anti-GPC3 antibody moiety and the effector molecule.

Crosslinking agents known to the art include the homobifunctional agents: glutaraldehyde, dimethyladipimidate and Bis(diazobenzidine) and the heterobifunctional agents: m Maleimidobenzoyl-N-Hydroxysuccinimide and Sulfo-m Maleimidobenzoyl-N-Hydroxysuccinimide.

In some embodiments, the anti-GPC3 antibody moiety of an anti-GPC3 immunoconjugate may be engineered with specific residues for chemical attachment of the effector molecule. Specific residues used for chemical attachment of molecule known to the art include lysine and cysteine. The crosslinker is chosen based on the reactive functional groups inserted on the anti-GPC3 antibody moiety, and available on the effector molecule.

An anti-GPC3 immunoconjugate may also be prepared using recombinant DNA techniques. In such a case a DNA sequence encoding the anti-GPC3 antibody moiety is fused to a DNA sequence encoding the effector molecule, resulting in a chimeric DNA molecule. The chimeric DNA sequence is transfected into a host cell that expresses the fusion protein. The fusion protein can be recovered from the cell culture and purified using techniques known in the art.

Examples of attaching an effector molecule, which is a label, to the binding protein include the methods described in Hunter, et al., *Nature* 144:945 (1962); David, et al., *Biochemistry* 13:1014 (1974); Pain, et al., *J. Immunol. Meth.* 40:219 (1981); Nygren, *J. Histochem. and Cytochem.* 30:407 (1982); Wensel and Meares, *Radioimmunoimaging And Radioimmunotherapy*, Elsevier, N.Y. (1983); and Colcher et al., "Use of Monoclonal Antibodies as Radiopharmaceuticals for the Localization of Human Carcinoma Xenografts in Athymic Mice", *Meth. Enzymol.*, 121:802-16 (1986).

The radio- or other labels may be incorporated in the immunoconjugate in known ways. For example, the peptide may be biosynthesized or may be synthesized by chemical amino acid synthesis using suitable amino acid precursors involving, for example, fluorine-19 in place of hydrogen. Labels such as $^{99}$Tc or $^{123}$I $^{186}$Re, $^{188}$Re and $^{111}$In can be attached via a cysteine residue in the peptide. Yttrium-90 can be attached via a lysine residue. The IODOGEN method (Fraker et al., *Biochem. Biophys. Res. Commun.* 80:49-57 (1978)) can be used to incorporate iodine-123. "Monoclonal Antibodies in Immunoscintigraphy" (Chatal, CRC Press 1989) describes other methods in detail.

Immunoconjugates of the anti-GPC3 antibody moiety and a cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCI), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene tnaminepentaacetic acid (MX-DTPA) is an exemplary chelating agent for conjugation of radionucleotide to the antibody. See, e.g., WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

The anti-GPC3 immunoconjugates of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Pharmaceutical Compositions

Also provided herein are compositions (such as pharmaceutical compositions, also referred to herein as formulations) comprising an anti-GPC3 construct (such as an isolated anti-GPC3 construct), nucleic acid encoding the construct, vector comprising the nucleic acid encoding the construct, host cell comprising the nucleic acid or vector, or effector cell comprising the nucleic acid or vector. In some embodiments, the composition further comprises a cell (such as an effector cell, e.g., a T cell) associated with the anti-GPC3 construct. In some embodiments, there is provided a pharmaceutical composition comprising an anti-GPC3 construct and optionally a pharmaceutically acceptable carrier. In some embodiments, the pharmaceutical composition further comprises a cell (such as an effector cell, e.g., a T cell, CAR-T cell, caTCR-T cell) associated with the anti-GPC3 construct.

Suitable formulations of the anti-GPC3 constructs (such as isolated anti-GPC3 constructs) are obtained by mixing an anti-GPC3 construct having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be treated herein. Lipofectins or liposomes can be used to deliver the anti-GPC3 constructs of this invention into cells.

The formulation herein may also contain one or more active compounds in addition to the anti-GPC3 construct (such as an isolated anti-GPC3 construct) as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent in addition to the anti-GPC3 construct. Such molecules are suitably present in combination in amounts that are effective for the purpose intended. The effective amount of such other agents depends on the amount of anti-GPC3 construct present in the formulation, the type of disease or disorder or treatment, and other factors discussed above. These are generally used in the same dosages and with administration routes as described herein or about from 1 to 99% of the heretofore employed dosages.

The anti-GPC3 constructs (such as isolated anti-GPC3 constructs) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980). Sustained-release preparations may be prepared.

Sustained-release preparations of the anti-GPC3 constructs (such as isolated anti-GPC3 constructs) can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D (−)-3-hydroxybutyric acid. While polymers such as ethylene-vinyl acetate and lactic acid-glycolic acid enable release of molecules for over 100 days, certain hydro gels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization of anti-GPC3 constructs depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In some embodiments, the anti-GPC3 construct (such as an isolated anti-GPC3 construct) is formulated in a buffer comprising a citrate, NaCl, acetate, succinate, glycine, polysorbate 80 (Tween 80), or any combination of the foregoing. In some embodiments, the anti-GPC3 construct is formulated in a buffer comprising about 100 mM to about 150 mM glycine. In some embodiments, the anti-GPC3 construct is formulated in a buffer comprising about 50 mM to about 100 mM NaCl. In some embodiments, the anti-GPC3 construct is formulated in a buffer comprising about 10 mM to about 50 mM acetate. In some embodiments, the anti-GPC3 construct is formulated in a buffer comprising about 10 mM to about 50 mM succinate. In some embodiments, the anti-GPC3 construct is formulated in a buffer comprising about 0.005% to about 0.02% polysorbate 80. In some embodiments, the anti-GPC3 construct is formulated in a buffer having a pH between about 5.1 and 5.6. In some embodiments, the anti-GPC3 construct is formulated in a buffer comprising 10 mM citrate, 100 mM NaCl, 100 mM glycine, and 0.01% polysorbate 80, wherein the formulation is at pH 5.5.

The formulations to be used for in vivo administration must be sterile. This is readily accomplished by, e.g., filtration through sterile filtration membranes.

Methods for Treatment Using Anti-GPC3 Constructs

The anti-GPC3 constructs (such as isolated anti-GPC3 constructs) and/or compositions of the invention can be administered to individuals (e.g., mammals such as humans) to treat a disease and/or disorder involving abnormally high GPC3 expression (also referred to herein as an "GPC3-positive" disease or disorder), including, for example, cancer (such as hepatocellular carcinoma (HCC)). The present application thus in some embodiments provides a method of treating an GPC3-positive disease (such as cancer) in an individual comprising administering to the individual an effective amount of a composition (such as a pharmaceutical composition) comprising an anti-GPC3 construct comprising an anti-GPC3 antibody moiety, such as any one of the anti-GPC3 constructs described herein. In some embodiments, the composition further comprises a cell (such as an effector cell, e.g., T cell) associated with the anti-GPC3 construct (e.g., anti-GPC3 CAR or anti-GPC3 caTCR). In some embodiments, there is provided a method of treating an GPC3-positive disease (such as cancer) in an individual comprising administering to the individual an effective amount of a composition (such as a pharmaceutical composition) comprising an anti-GPC3 construct (e.g., anti-GPC3×CD3 tandem di-scFv T cell engager), wherein the expression of the anti-GPC3 construct is inducible upon signaling through a signaling receptor (e.g., TCR, CAR, caTCR) on an effector cell (e.g., T cell). In some embodiments, there is provided a method of treating an GPC3-positive disease (such as cancer) in an individual comprising administering to the individual an effective amount of a composition (such as a pharmaceutical composition) comprising an effector cell (e.g., T cell, CAR-T cell, caTCR-T cell), wherein the effector cell induces expression of an anti-GPC3 construct (e.g., anti-GPC3×CD3 tandem di-scFv T cell engager) through the activation of the effector cell signaling receptor (e.g., TCR, CAR, caTCR). In some embodiments, the nucleic acid encoding the anti-GPC3 construct (e.g., anti-GPC3×CD3 tandem di-scFv T cell engager) is operably linked to an inducible promoter, such as a signaling receptor (e.g., TCR, CAR, caTCR)-activation dependent promoter. In some embodiments, the inducible promoter is an NFAT-derived promoter, such as an NFAT-derived minimal promoter. In some embodiments, the inducible promoter is an IL-2 promoter. In some embodiments, the effector cell is an anti-GPC3 CAR-T cell. In some embodiments, the effector cell is an anti-GPC3 caTCR-T cell.

In some embodiments, the cancer is selected, for example, from the group consisting of HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, and liposarcoma. In some embodiments, the cancer is HCC. In some embodiments, the cancer is hepatocellular carcinoma and the treating comprises preventing the spread of the cancer, e.g., inhibiting (such as preventing) metastasis of the cancer. In some embodiments, the cancer is metastatic HCC. In some embodiments, the individual is human.

For example, in some embodiments, there is provided a method of treating an individual having a GPC3-positive disease comprising administering to the individual an effective amount of a composition comprising an anti-GPC3 construct (such as an isolated anti-GPC3 construct) comprising an anti-GPC3 antibody moiety that specifically binds to GPC3 (e.g., nGPC3 and/or sGPC3). In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-GPC3 antibody moiety specifically recognizes both cell surface-bound GPC3 and soluble GPC3. In some embodiments, the anti-GPC3 construct is non-naturally occurring. In some embodiments, the anti-GPC3 construct is an scFv. In some embodiments, the anti-GPC3 construct is a full-length antibody. In some embodiments, the anti-GPC3 construct is a multi-specific molecule (e.g., a bispecific T cell engager). In some embodiments, the anti-GPC3 construct is a CAR or caTCR. In some embodiments, the anti-GPC3 construct is an immunoconjugate. In some embodiments, the composition further comprises a cell (such as an effector cell, e.g., T cell) associated with the anti-GPC3 construct. In some embodiments, the composition comprises an effector cell (e.g., T cell, CAR-T cell, caTCR-T cell), wherein the effector cell induces expression of an anti-GPC3 construct (e.g., anti-GPC3×CD3 tandem di-scFv T cell engager) through the activation of the effector cell signaling receptor (e.g., TCR, CAR, caTCR). In some embodiments, the nucleic acid encoding the anti-GPC3 construct (e.g., anti-GPC3×CD3 tandem di-scFv T cell engager) is operably linked to an inducible promoter, such as a signaling receptor (e.g., TCR, CAR, caTCR)-activation dependent promoter. In some embodiments, the inducible promoter is an NFAT-derived promoter, such as an NFAT-derived minimal promoter. In some embodiments, the inducible promoter is an IL-2 promoter. In some embodiments, the effector cell is an anti-GPC3 CAR-T cell. In some embodiments, the effector cell is an anti-GPC3 caTCR-T cell. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the cancer is HCC and the treating comprises preventing the spread of the cancer, e.g., inhibiting (such as preventing) metastasis of the cancer. In some embodiments, the cancer is metastatic HCC. In some embodiments, the individual is human.

In some embodiments, there is provided a method of treating an individual having a GPC3-positive disease (e.g., cancer) comprising administering to the individual an effective amount of a composition comprising an anti-GPC3 construct (such as an isolated anti-GPC3 construct) comprising an anti-GPC3 antibody moiety that specifically binds to a cell surface-bound GPC3 (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity). In some embodiments, the anti-nGPC3 antibody moiety specifically recognizes an epitope within human GPC3 comprising the amino acid sequence of SEQ ID NO: 460. In some embodiments, the anti-nGPC3 antibody moiety specifically recognizes an epitope within the amino acid sequence of SEQ ID NO: 461. In some embodiments, the anti-nGPC3 antibody moiety specifically recognizes an epitope within the amino acid sequence of SEQ ID NO: 462. In some embodiments, the anti-nGPC3 antibody moiety specifically recognizes an epitope within the amino acid sequence of SEQ ID NO: 463. In some embodiments, the anti-nGPC3 antibody moiety specifically recognizes an epitope within the N-terminal fragment of GPC3. In some embodiments, the anti-nGPC3 antibody moiety specifically recognizes an epitope within amino acids 1-358 of SEQ ID NO: 460 (SEQ ID NO: 468). In some embodiments, the anti-nGPC3 antibody moiety specifically recognizes an epitope within the amino acid sequence of SEQ ID NO: 464. In some embodiments, the anti-nGPC3 antibody moiety specifically recognizes an epitope within the C-terminal fragment of GPC3. In some embodiments, the anti-nGPC3 antibody moiety specifically recognizes an epitope within amino acids 359-560 of SEQ ID NO: 460 (SEQ ID NO: 465). In some embodiments, the anti-nGPC3 antibody moiety specifically recognizes an epitope within amino acids 359-580 of SEQ ID NO: 460 (SEQ ID NO: 466). In some embodiments, the anti-nGPC3 antibody moiety specifically recognizes an epitope within the C-terminal fragment of GPC3 lacking heparin sulfate side chain. In some embodiments, the anti-nGPC3 antibody moiety specifically recognizes an epitope within amino acids 510-560 of SEQ ID NO: 460 (SEQ ID NO: 467). In some embodiments, the anti-nGPC3 antibody moiety specifically recognizes an epitope spanning the Furin cleavage site at amino acids $R^{358}/S^{359}$ of SEQ ID NO: 460. In some embodiments, the anti-nGPC3 antibody moiety can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460). In some embodiments, the anti-nGPC3 antibody moiety specifically recognizes an epitope within the C-terminal fragment of GPC3 lacking heparin sulfate side chain. In some embodiments, there is provided a method of treating an individual having a GPC3-positive disease (e.g., cancer) comprising administering to the individual an effective amount of a composition comprising an anti-GPC3 construct (such as an isolated anti-GPC3 construct) comprising an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that competes for binding to nGPC3 with any one of the anti-GPC3 constructs described herein. In some embodiments, there is provided a method of treating an individual having a GPC3-positive disease (e.g., cancer) comprising administering to the individual an effective amount of a composition comprising an anti-GPC3 construct (such as an isolated anti-GPC3 construct) comprising an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that specifically binds to the same, or substantially the same, nGPC3 epitope competitively with any one of the anti-GPC3 constructs described herein. In some embodiments, the anti-GPC3 construct is non-naturally occurring. In some embodiments, the anti-GPC3 construct is an scFv. In some embodiments, the anti-GPC3 construct is a full-length antibody. In some embodiments, the anti-GPC3 construct is a multi-specific molecule (e.g., a bispecific T cell engager). In some embodiments, the anti-GPC3 construct is a CAR or caTCR. In some embodiments, the anti-GPC3 construct is an immunoconjugate. In some embodiments, the composition further comprises a cell (such as an effector cell, e.g., T cell, CAR-T cell, caTCR-T cell) associated with the anti-GPC3 construct. In some embodiments, the effector cell (e.g., T cell, CAR-T cell, caTCR-T cell) induces the expression of the anti-GPC3 construct (e.g., anti-GPC3×CD3 tandem di-scFv T cell engager) through the activation of the effector cell signaling receptor (e.g., TCR, CAR, caTCR). In some embodiments, the expression of the anti-GPC3 construct (e.g., anti-GPC3×CD3 tandem di-scFv T cell engager) is under control of an inducible promoter, such as a signaling receptor (e.g., TCR, CAR, caTCR)-activation dependent promoter. In some embodiments, the inducible promoter is an NFAT-derived promoter, such as an NFAT-derived minimal promoter. In some embodiments, the inducible promoter is an IL-2 promoter. In some embodiments, the effector cell is an anti-GPC3 CAR-T cell. In some embodiments, the effector cell is an anti-GPC3 caTCR-T cell. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the cancer is HCC and the treating comprises preventing the spread of the cancer, e.g., inhibiting (such as preventing) metastasis of the cancer. In some embodiments, the cancer is metastatic HCC. In some embodiments, the individual is human.

In some embodiments, there is provided a method of treating an individual having a GPC3-positive disease (e.g., cancer) comprising administering to the individual an effective amount of a composition comprising an anti-GPC3 construct (such as an isolated anti-GPC3 construct) comprising an anti-GPC3 antibody moiety that specifically binds to a cell surface-bound GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions. In some embodiments, there is provided a method of treating an individual having a GPC3-positive disease comprising administering to the individual an effective amount of a composition comprising an anti-GPC3 construct (such as an isolated anti-GPC3 construct) comprising an anti-GPC3 antibody moiety that specifically binds to a cell surface-bound GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286. In some embodiments, there is provided a method of treating an individual having a GPC3-positive disease comprising administering to the individual an effective amount of a composition comprising an anti-GPC3 construct (such as an isolated anti-GPC3 construct) comprising an anti-GPC3 antibody moiety that specifically binds to a cell surface-bound GPC3, comprising: i) a $V_H$ comprising the amino acid sequence of any one of SEQ ID NOs: 307-337; and ii) a $V_L$ comprising the amino acid sequence of any one of SEQ ID NOs: 358-388. In some embodiments, there is provided a method of treating an individual having a GPC3-positive disease comprising administering to the individual an effective amount of a composition comprising an anti-GPC3 construct (such as an isolated anti-GPC3 construct) comprising an anti-GPC3 antibody moiety that specifically binds to a cell surface-bound GPC3, comprising the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388. In some embodiments, there is provided a method of treating an individual having a GPC3-positive disease (e.g., cancer) comprising administering to the individual an effective amount of a composition comprising an anti-GPC3 construct (such as an isolated anti-GPC3 construct) comprising an anti-nGPC3 antibody moiety that competes for binding to nGPC3 with any one of the anti-GPC3 constructs described herein. In some embodiments, there is provided a method of treating an individual having a GPC3-positive disease (e.g., cancer) comprising administering to the individual an effective amount of a composition comprising an anti-GPC3 construct (such as an isolated anti-GPC3 construct) comprising an anti-nGPC3 antibody moiety that specifically binds to the same, or substantially the same, nGPC3 epitope competitively with any one of the anti-GPC3 constructs described herein. In some embodiments, the anti-GPC3 construct is non-naturally occurring. In some embodiments, the anti-GPC3 construct is an scFv. In some embodiments, the anti-GPC3 construct is a full-length antibody. In some embodiments, the anti-GPC3 construct is a multi-specific molecule (e.g., a bispecific T cell engager). In some embodiments, the anti-GPC3 construct is a CAR or caTCR. In some embodiments, the anti-GPC3 construct is an immunoconjugate. In some embodiments, the composition further comprises a cell (such as an effector cell, e.g., T cell, CAR-T cell, caTCR-T cell) associated with the anti-GPC3 construct. In some embodiments, the effector cell (e.g., T cell, CAR-T cell, caTCR-T cell) induces the expression of the anti-GPC3 construct (e.g., anti-GPC3×CD3 tandem di-scFv T cell engager) through the activation of the effector cell signaling receptor (e.g., TCR, CAR, caTCR). In some embodiments, the expression of the anti-GPC3 construct (e.g., anti-GPC3× CD3 tandem di-scFv T cell engager) is under control of an inducible promoter, such as a signaling receptor (e.g., TCR, CAR, caTCR)-activation dependent promoter. In some embodiments, the inducible promoter is an NFAT-derived promoter, such as an NFAT-derived minimal promoter. In some embodiments, the inducible promoter is an IL-2 promoter. In some embodiments, the effector cell is an anti-GPC3 CAR-T cell. In some embodiments, the effector cell is an anti-GPC3 caTCR-T cell. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the cancer is HCC and the treating comprises preventing the spread of the cancer, e.g., inhibiting (such as preventing) metastasis of the cancer. In some embodiments, the cancer is metastatic HCC. In some embodiments, the individual is human.

In some embodiments, there is provided a method of treating an individual having a GPC3-positive disease comprising administering to the individual an effective amount of a composition comprising an anti-GPC3 construct (such as an isolated anti-GPC3 construct) comprising an anti-GPC3 antibody moiety that specifically binds to GPC3 (e.g., nGPC3 and/or sGPC3), comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions. In some embodiments, there is provided a method of treating an individual having a GPC3-positive disease comprising administering to the individual an effective amount of a composition comprising an anti-GPC3 construct (such as an isolated anti-GPC3 construct) comprising an anti-GPC3 antibody moiety that specifically binds to GPC3 (e.g., nGPC3 and/or sGPC3), comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306. In some embodiments, there is provided a method of treating an individual having a GPC3-positive disease comprising administering to the individual an effective amount of a composition comprising an anti-GPC3 construct (such as an isolated anti-GPC3 construct) comprising an anti-GPC3 antibody moiety that specifically binds to GPC3 (e.g., nGPC3 and/or sGPC3), comprising: i) a $V_H$ comprising the amino acid sequence of any one of SEQ ID NOs: 338-357; and ii) a $V_L$ comprising the amino acid sequence of any one of SEQ ID NOs: 389-408. In some embodiments, there is provided a method of treating an individual having a GPC3-positive disease comprising administering to the individual an effective amount of a composition comprising an anti-GPC3 construct (such as an isolated anti-GPC3 construct) comprising an anti-GPC3 antibody moiety that specifically binds to GPC3 (e.g., nGPC3 and/or sGPC3), comprising the HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408. In some embodiments, there is provided a method of treating an individual having a GPC3-positive disease (e.g., cancer) comprising administering to the individual an effective amount of a composition comprising an anti-GPC3 construct (such as an isolated anti-GPC3 construct) comprising an anti-GPC3 antibody moiety that competes for binding to GPC3 (e.g., nGPC3 and/or sGPC3) with any one of the anti-GPC3 constructs described herein. In some embodiments, there is provided a method of treating an individual having a GPC3-positive disease (e.g., cancer) comprising administering to the individual an effective amount of a composition comprising an anti-GPC3 construct (such as an isolated anti-GPC3 construct) comprising an anti-nGPC3 antibody moiety that specifically binds to the same, or substantially the same, GPC3 epitope competitively with any one of the anti-GPC3 constructs described herein. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the anti-GPC3 construct is non-naturally occurring. In some embodiments, the anti-GPC3 construct is an scFv. In some embodiments, the anti-GPC3 construct is a full-length antibody. In some embodiments, the anti-GPC3 construct is a multi-specific molecule (e.g., a bispecific T cell engager). In some embodiments, the anti-GPC3 construct is a CAR or caTCR. In some embodiments, the anti-GPC3 construct is an immunoconjugate. In some embodiments, the composition further comprises a cell (such as an effector cell, e.g., T cell, CAR-T cell, caTCR-T cell) associated with the anti-GPC3 construct. In some embodiments, the effector cell (e.g., T cell, CAR-T cell, caTCR-T cell) induces the expression of the anti-GPC3 construct (e.g., anti-GPC3×CD3 tandem di-scFv T cell engager) through the activation of the effector cell signaling receptor (e.g., TCR, CAR, caTCR). In some embodiments, the expression of the anti-GPC3 construct (e.g., anti-GPC3×CD3 tandem di-scFv T cell engager) is under control of an inducible promoter, such as a signaling receptor (e.g., TCR, CAR, caTCR)-activation dependent promoter. In some embodiments, the inducible promoter is an NFAT-derived promoter, such as an NFAT-derived minimal promoter. In some embodiments, the inducible promoter is an IL-2 promoter. In some embodiments, the effector cell is an anti-GPC3 CAR-T cell. In some embodiments, the effector cell is an anti-GPC3 caTCR-T cell. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the cancer is HCC and the treating comprises preventing the spread of the cancer, e.g., inhibiting (such as preventing) metastasis of the cancer. In some embodiments, the cancer is metastatic HCC. In some embodiments, the individual is human.

In some embodiments, there is provided a method of treating metastatic HCC in an individual comprising administering to the individual an effective amount of a composition comprising an anti-GPC3 construct (such as an isolated anti-GPC3 construct) according to any of the embodiments described above. In some embodiments, the composition further comprises a cell (such as an effector cell, e.g., T cell, CAR-T cell, caTCR-T cell) associated with the anti-GPC3 construct. In some embodiments, the individual is human.

In some embodiments, there is provided a method of inhibiting (such as preventing) metastasis of hepatocellular carcinoma in an individual comprising administering to the individual an effective amount of a composition comprising an anti-GPC3 construct (such as an isolated anti-GPC3 construct) according to any of the embodiments described above. In some embodiments, the individual is human.

In some embodiments of any of the methods for treating a GPC3-positive disease described above, the anti-GPC3 construct (such as an isolated anti-GPC3 construct) is conjugated to a cell (such as an immune cell, e.g., a T cell) prior to being administered to the individual. Thus, for example, there is provided a method of treating an GPC3-positive disease in an individual comprising a) conjugating any one of the anti-GPC3 constructs described herein to a cell (such as an immune cell, e.g., a T cell) to form an anti-GPC3 construct/cell conjugate, and b) administering to the individual an effective amount of a composition comprising the anti-GPC3 construct/cell conjugate. In some embodiments, the cell is derived from the individual. In some embodiments, the cell is not derived from the individual. In some embodiments, the anti-GPC3 construct is conjugated to the cell by covalent linkage to a molecule on the surface of the cell. In some embodiments, the anti-GPC3 construct is conjugated to the cell by non-covalent linkage to a molecule on the surface of the cell. In some embodiments, the anti-GPC3 construct is conjugated to the cell by insertion of a portion of the anti-GPC3 construct into the outer membrane of the cell. In some embodiments, the anti-GPC3 construct is non-naturally occurring. In some embodiments, the anti-GPC3 construct is a full-length antibody. In some embodiments, the anti-GPC3 construct is a multi-specific (such as bispecific) molecule. In some embodiments, the anti-GPC3 construct is a chimeric antigen receptor. In some embodiments, the anti-GPC3 construct is a caTCR. In some embodiments, the method of treating an individual having a GPC3-positive disease comprises administering to the individual an effective amount of anti-GPC3 CAR T cell. In some embodiments, the method of treating an individual having a GPC3-positive disease comprises administering to the individual an effective amount of anti-GPC3 caTCR T cell. In some embodiments, the anti-GPC3 construct is an immunoconjugate. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the cancer is HCC and the treating comprises preventing the spread of the cancer, e.g., inhibiting (such as preventing) metastasis of the cancer. In some embodiments, the cancer is metastatic HCC. In some embodiments, the individual is human.

In some embodiments of any of the methods for treating a GPC3-positive disease described above, the anti-GPC3 construct (such as an isolated anti-GPC3 construct, e.g., anti-GPC3×CD3 bispecific T cell engager) is expressed upon activation of an effector cell (e.g., a T cell, CAR-T cell, caTCR-T cell) through its signaling receptor (e.g., TCR, CAR, caTCR). In some embodiments, the effector cell comprises a nucleic acid sequence encoding the anti-GPC3 construct (such as an isolated anti-GPC3 construct, e.g., anti-GPC3×CD3 bispecific T cell engager) operably linked to an inducible promoter, such as a signaling receptor (e.g., TCR, CAR, caTCR)-activation dependent promoter. In some embodiments, the inducible promoter is an NFAT-derived promoter, such as an NFAT-derived minimal promoter. In some embodiments, the inducible promoter is an IL-2 promoter. In some embodiments, the effector cell is an anti-GPC3 CAR-T cell. In some embodiments, the effector cell is an anti-GPC3 caTCR-T cell. Thus, for example, there is provided a method of treating an GPC3-positive disease in an individual comprising a) introducing a nucleic acid encoding any one of the anti-GPC3 constructs described herein to an effector cell (e.g., T cell, CAR-T cell, caTCR-T cell), wherein the nucleic acid is operably linked to an inducible promoter (such as a signaling receptor (e.g., TCR, CAR, caTCR)-activation dependent promoter), and b) administering to the individual an effective amount of a composition comprising the effector cell. In some embodiments, the cell is derived from the individual. In some embodiments, the cell is not derived from the individual. In some embodiments, the anti-GPC3 construct is non-naturally occurring. In some embodiments, the anti-GPC3 construct is an scFv. In some embodiments, the anti-GPC3 construct is a full-length antibody. In some embodiments, the anti-GPC3 construct is a multi-specific (such as bispecific) molecule. In some embodiments, the anti-GPC3 construct is a chimeric antigen receptor. In some embodiments, the anti-GPC3 construct is a caTCR. In some embodiments, the method of treating an individual having a GPC3-positive disease comprises administering to the individual an effective amount of anti-GPC3 CAR T cell. In some embodiments, the method of treating an individual having a GPC3-positive disease comprises administering to the individual an effective amount of anti-GPC3 caTCR T cell. In some embodiments, the anti-GPC3 construct is an immunoconjugate. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the cancer is HCC and the treating comprises preventing the spread of the cancer, e.g., inhibiting (such as preventing) metastasis of the cancer. In some embodiments, the cancer is metastatic HCC. In some embodiments, the individual is human.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old). In some embodiments, the individual is diagnosed with or genetically prone to one or more of the diseases or disorders described herein (such as HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma). In some embodiments, the individual has one or more risk factors associated with one or more diseases or disorders described herein.

The present application in some embodiments provides a method of delivering an anti-GPC3 construct (such as any one of the anti-GPC3 constructs described herein, e.g., an isolated anti-GPC3 construct) to a cell expressing GPC3 on its surface in an individual, or an individual having soluble GPC3 (e.g., having circulating GPC3 protein or free GPC3 peptides in the serum), the method comprising administering to the individual a composition comprising the anti-GPC3 construct. In some embodiments, the anti-GPC3 construct to be delivered is associated with a cell (such as an effector cell, e.g., a T cell). In some embodiments, the method comprises administering to the individual an anti-GPC3 CAR T cell. In some embodiments, the method comprises administering to the individual an anti-GPC3 caTCR T cell.

Many diagnostic methods for cancer (such as HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma) or any other disease exhibiting abnormal GPC3 expression and the clinical delineation of those diseases are known in the art. Such methods include, but are not limited to, e.g., immunohistochemistry, PCR, and fluorescent in situ hybridization (FISH).

In some embodiments, the anti-GPC3 constructs (such as isolated anti-GPC3 constructs) and/or compositions of the invention are administered in combination with a second, third, or fourth agent (including, e.g., an antineoplastic agent, a growth inhibitory agent, a cytotoxic agent, or a chemotherapeutic agent) to treat diseases or disorders involving abnormal GPC3 expression. In some embodiments, the agent includes, for example, IFN receptor agonists, Hsp90 inhibitors, enhancers of p53 expression, and chemotherapeutic agents. In some embodiments, the agent is an IFN receptor agonist including, for example, IFNγ, IFNβ, and IFNα. In some embodiments, the agent is an Hsp90 inhibitor including, for example, tanespimycin (17-AAG), alvespimycin (17-DMAG), retaspimycin (IPI-504), IPI-493, CNF2024/BIIB021, MPC-3100, Debio 0932 (CUDC-305), PU-H71, Ganetespib (STA-9090), NVP-AUY922 (VER-52269), HSP990, KW-2478, AT13387, SNX-5422, DS-2248, and XL888. In some embodiments, the agent is an enhancer of p53 expression including, for example, 5-fluorouracil and nutlin-3. In some embodiments, the agent is a chemotherapeutic agent including, for example, topotecan, etoposide, cisplatin, paclitaxel, and vinblastine.

Cancer treatments can be evaluated by, e.g., tumor regression, tumor weight or size shrinkage, time to progression, duration of survival, progression free survival, overall response rate, duration of response, quality of life, protein expression and/or activity. Approaches to determining efficacy of therapy can be employed, including for example, measurement of response through radiological imaging.

In some embodiments, the efficacy of treatment is measured as the percentage tumor growth inhibition (% TGI), calculated using the equation $100-(T/C \times 100)$, where T is the mean relative tumor volume of the treated tumor, and C is the mean relative tumor volume of a non-treated tumor. In some embodiments, the % TGI is about 10%, about 20%, about 30%, about 40%, about 50%, about 60%, about 70%, about 80%, about 90%, about 91%, about 92%, about 93%, about 94%, about 95%, or more than 95%.

Dosing and Method of Administering the Anti-GPC3 Construct Compositions

The dose of the anti-GPC3 construct (such as isolated anti-GPC3 construct or administered in the format of anti-GPC3 CAR T cell or anti-GPC3 caTCR T cell) compositions administered to an individual (such as a human) may vary with the particular composition, the mode of administration, and the type of disease being treated. In some embodiments, the amount of the composition (such as composition comprising isolated anti-GPC3 construct, anti-GPC3 CAR T cell, or anti-GPC3 caTCR T cell) is effective to result in an objective response (such as a partial response or a complete response). In some embodiments, the amount of the anti-GPC3 construct composition is sufficient to result in a complete response in the individual. In some embodiments, the amount of the anti-GPC3 construct composition is sufficient to result in a partial response in the individual. In some embodiments, the amount of the anti-GPC3 construct composition administered (for example when administered alone) is sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the anti-GPC3 construct composition. Responses of an individual to the treatment of the methods described herein can be determined, for example, based on RECIST levels.

In some embodiments, the amount of the composition (such as composition comprising isolated anti-GPC3 construct, anti-GPC3 CAR T cell, or anti-GPC3 caTCR T cell) is sufficient to prolong progress-free survival of the individual. In some embodiments, the amount of the composition is sufficient to prolong overall survival of the individual. In some embodiments, the amount of the composition (for example when administered along) is sufficient to produce clinical benefit of more than about any of 50%, 60%, 70%, or 77% among a population of individuals treated with the anti-GPC3 construct composition.

In some embodiments, the amount of the composition (such as composition comprising isolated anti-GPC3 construct, anti-GPC3 CAR T cell, or anti-GPC3 caTCR T cell), alone or in combination with a second, third, and/or fourth agent, is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of the anti-GPC3 construct (such as an isolated anti-GPC3 construct, e.g., an anti-GPC3 scFv, full-length anti-GPC3 antibody, multi-specific anti-GPC3 molecule, anti-GPC3 CAR, anti-GPC3 caTCR, or anti-GPC3 immunoconjugate) in the composition is below the level that induces a toxicological effect (i.e., an effect above a clinically acceptable level of toxicity) or is at a level where a potential side effect can be controlled or tolerated when the composition is administered to the individual.

In some embodiments, the amount of the composition is close to a maximum tolerated dose (MTD) of the composition following the same dosing regimen. In some embodiments, the amount of the composition is more than about any of 80%, 90%, 95%, or 98% of the MTD.

In some embodiments, the amount of an anti-GPC3 construct (such as an isolated anti-GPC3 construct, e.g., full-length anti-GPC3 antibody, multi-specific anti-GPC3 molecule, or anti-GPC3 immunoconjugate) in the composition is included in a range of about 0.001 µg to about 1000 µg.

In some embodiments of any of the above aspects, the effective amount of an anti-GPC3 construct (such as an isolated anti-GPC3 construct, e.g., full-length anti-GPC3 antibody, multi-specific anti-GPC3 molecule, or anti-GPC3 immunoconjugate) in the composition is in the range of about 0.1 µg/kg to about 100 mg/kg of total body weight.

The anti-GPC3 construct compositions can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used. In some embodiments, the composition is administered intravenously. In some embodiments, the composition is administered intraportally. In some embodiments, the composition is administered intraarterially. In some embodiments, the composition is administered intraperitoneally. In some embodiments, the composition is administered intrahepatically. In some embodiments, the composition is administered by hepatic arterial infusion. In some embodiments, the administration is to an injection site distal to a first disease site.

Anti-GPC3 CAR Effector Cell Therapy and Anti-GPC3 caTCR Effector Cell Therapy

The present application also provides methods of using an anti-GPC3 CAR or anti-GPC3 caTCR to redirect the specificity of an effector cell (such as a primary T cell) to GPC3 (such as cell surface-bound GPC3 or soluble GPC3). Thus, the present invention also provides a method of stimulating an effector cell-mediated response (such as a T cell-mediated immune response) to a target cell population or tissue comprising GPC-expressing cells in a mammal, comprising the step of administering to the mammal an effector cell (such as a T cell) that expresses an anti-GPC3 CAR or anti-GPC3 caTCR. In some embodiments, the anti-GPC3 CAR effector cell or the anti-GPC3 caTCR effector cell further comprises a nucleic acid encoding a multi-specific (e.g., bispecific) anti-GPC3 molecule (e.g., anti-GPC3×CD3 bispecific T cell engager) operably linked to an inducible promoter. In some embodiments, the expression of the multi-specific (e.g., bispecific) anti-GPC3 molecule (e.g., anti-GPC3×CD3 tandem di-scFv T cell engager) in the anti-GPC3 CAR effector cell or the anti-GPC3 caTCR effector cell is inducible upon signaling through the anti-GPC3 CAR or anti-GPC3 caTCR (respectively). In some embodiments, the inducible promoter is an NFAT-derived promoter, such as an NFAT-derived minimal promoter. In some embodiments, the inducible promoter is an IL-2 promoter.

Anti-GPC3 CAR effector cells (such as T cells) expressing the anti-GPC3 CAR (optionally further expressing an anti-GPC3 bispecific T cell engager) can be infused to a recipient in need thereof. Anti-GPC3 caTCR effector cells (such as T cells) expressing the anti-GPC3 caTCR (optionally further expressing an anti-GPC3 bispecific T cell engager) can be infused to a recipient in need thereof. The infused cell is able to kill cells expressing GPC3 on its cell surface in the recipient. In some embodiments, unlike antibody therapies, anti-GPC3 CAR effector cells (such as T cells) or anti-GPC3 caTCR effector cells (such as T cells) are able to replicate in vivo resulting in long-term persistence that can lead to sustained tumor control.

In some embodiments, the anti-GPC3 CAR effector cells are anti-GPC3 CAR T cells that can undergo robust in vivo T cell expansion and can persist for an extended amount of time. In some embodiments, the anti-GPC3 CAR T cells of the invention develop into specific memory T cells that can be reactivated to inhibit any additional tumor formation or growth.

In some embodiments, the anti-GPC3 caTCR effector cells are anti-GPC3 caTCR T cells that can undergo robust in vivo T cell expansion and can persist for an extended amount of time. In some embodiments, the anti-GPC3 caTCR T cells of the invention develop into specific memory T cells that can be reactivated to inhibit any additional tumor formation or growth.

The anti-GPC3 CAR T cells or anti-GPC3 caTCR T cells of the invention may also serve as a type of vaccine for ex vivo immunization and/or in vivo therapy in a mammal. In some embodiments, the mammal is a human. In some embodiments, the anti-GPC3 CAR T cell or the anti-GPC3 caTCR T cell further comprises a nucleic acid encoding a multi-specific (e.g., bispecific) anti-GPC3 molecule (e.g., anti-GPC3×CD3 bispecific T cell engager) operably linked to an inducible promoter. In some embodiments, the expression of the multi-specific (e.g., bispecific) anti-GPC3 molecule (e.g., anti-GPC3×CD3 tandem di-scFv T cell engager) is inducible upon signaling through the anti-GPC3 CAR or anti-GPC3 caTCR. In some embodiments, the inducible promoter is an NFAT-derived promoter, such as an NFAT-derived minimal promoter. In some embodiments, the inducible promoter is an IL-2 promoter.

With respect to ex vivo immunization, at least one of the following occurs in vitro prior to administering the cell into a mammal: i) expansion of the cells, ii) introducing a nucleic acid encoding an anti-GPC3 CAR or anti-GPC3 caTCR to the cells, and/or iii) cryopreservation of the cells. In some embodiments, the cells are further in vitro manipulated by introducing a nucleic acid encoding a multi-specific (e.g., bispecific) anti-GPC3 molecule (e.g., anti-GPC3×CD3 bispecific T cell engager) operably linked to an inducible promoter. In some embodiments, the inducible promoter is an NFAT-derived promoter, such as an NFAT-derived minimal promoter. In some embodiments, the inducible promoter is an IL-2 promoter.

Ex vivo procedures are well known in the art and are discussed more fully below. Briefly, cells are isolated from a mammal (preferably a human) and genetically modified (i.e., transduced or transfected in vitro) with a vector expressing an anti-GPC3 CAR or an anti-GPC3 caTCR disclosed herein. The anti-GPC3 CAR effector cell or anti-GPC3 caTCR effector cell can be administered to a mammalian recipient to provide a therapeutic benefit. The mammalian recipient may be a human and the anti-GPC3 CAR cell (or anti-GPC3 caTCR cell) can be autologous with respect to the recipient. Alternatively, the cells can be allogeneic, syngeneic or xenogeneic with respect to the recipient. In some embodiments, the anti-GPC3 CAR effector cell or the anti-GPC3 caTCR effector cell further comprises a nucleic acid encoding a multi-specific (e.g., bispecific) anti-GPC3 molecule (e.g., anti-GPC3×CD3 bispecific T cell engager) operably linked to an inducible promoter, wherein the inducible promoter is responsive to signaling through the anti-GPC3 CAR or anti-GPC3 caTCR.

The procedure for ex vivo expansion of hematopoietic stem and progenitor cells is described in U.S. Pat. No. 5,199,942, incorporated herein by reference, can be applied to the cells of the present invention. Other suitable methods are known in the art; therefore the present invention is not limited to any particular method of ex vivo expansion of the cells. Briefly, ex vivo culture and expansion of T cells comprises: (1) collecting CD34$^+$ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

The anti-GPC3 CAR effector cells (such as T cells) or anti-GPC3 caTCR effector cells (such as T cells) of the present invention may be administered either alone, or as a pharmaceutical composition in combination with diluents and/or with other components such as IL-2 or other cytokines or cell populations. Briefly, pharmaceutical compositions of the present invention may comprise anti-GPC3 CAR effector cells (such as T cells) or anti-GPC3 caTCR effector cells (such as T cells), in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In some embodiments, anti-GPC3 CAR effector cell (such as T cell) compositions or anti-GPC3 caTCR effector cell (such as T cell) compositions are formulated for intravenous administration.

The precise amount of the anti-GPC3 CAR effector cell (such as T cell) compositions or the anti-GPC3 caTCR effector cell (such as T cell) compositions of the present invention to be administered can be determined by a physician with consideration of individual differences in age, weight, tumor size, extent of infection or metastasis, and condition of the patient (subject). In some embodiments, a pharmaceutical composition comprising the anti-GPC3 CAR effector cells (such as T cells) or the anti-GPC3 caTCR effector cells (such as T cells) is administered at a dosage of about $10^4$ to about $10^9$ cells/kg body weight, such any of about $10^4$ to about $10^5$, about $10^5$ to about $10^6$, about $10^6$ to about $10^7$, about $10^7$ to about $10^8$, or about $10^8$ to about $10^9$ cells/kg body weight, including all integer values within those ranges. Anti-GPC3 CAR effector cell (such as T cell) compositions or anti-GPC3 caTCR effector cell (such as T cell) compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regimen for a particular patient can readily be determined by one skilled in the art of medicine by monitoring the patient for signs of disease and adjusting the treatment accordingly.

In some embodiments, it may be desired to administer activated anti-GPC3 CAR T cells or activated anti-GPC3 caTCR T cells to a subject and then subsequently redraw blood (or have an apheresis performed), activate T cells therefrom according to the present invention, and reinfuse the patient with these activated and expanded T cells. This process can be carried out multiple times every few weeks. In some embodiments, T cells can be activated from blood draws of from 10 cc to 400 cc. In some embodiments, T cells are activated from blood draws of 20 cc, 30 cc, 40 cc, 50 cc, 60 cc, 70 cc, 80 cc, 90 cc, or 100 cc.

The administration of the anti-GPC3 CAR effector cells (such as T cells) or anti-GPC3 caTCR effector cells (such as T cells) may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In some embodiments, the anti-GPC3 CAR effector cell (such as T cell) compositions or the anti-GPC3 caTCR effector cell (such as T cell) compositions of the present invention are administered to a patient by intradermal or subcutaneous injection. In some embodiments, the anti-GPC3 CAR effector cell (such as T cell) compositions or the anti-GPC3 caTCR effector cell (such as T cell) compositions of the present invention are administered by i.v. injection. The compositions of anti-GPC3 CAR effector cells (such as T cells) or anti-GPC3 caTCR effector cells (such as T cells) may be injected directly into a tumor, lymph node, or site of infection.

Thus, for example, in some embodiments, there is provided a method of treating an GPC3-positive disease (e.g., HCC) in an individual comprising administering to the individual an effective amount of a composition comprising an effector cell (such as a T cell) expressing an anti-GPC3 CAR comprising a) an extracellular domain comprising an anti-GPC3 antibody moiety that specifically binds to a cell surface bound-GPC3 (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity), b) a transmembrane domain, and c) an intracellular signaling domain comprising a CD3ζ intracellular signaling sequence and a CD28 intracellular signaling sequence. In some embodiments, the anti-nGPC3 antibody moiety specifically recognizes an epitope within human GPC3 comprising the amino acid sequence of SEQ ID NO: 460. In some embodiments, the anti-nGPC3 antibody moiety specifically recognizes an epitope within the amino acid sequence of SEQ ID NO: 461. In some embodiments, the anti-nGPC3 antibody moiety specifically recognizes an epitope within the amino acid sequence of SEQ ID NO: 462. In some embodiments, the anti-nGPC3 antibody moiety specifically recognizes an epitope within the amino acid sequence of SEQ ID NO: 463. In some embodiments, the anti-nGPC3 antibody moiety specifically recognizes an epitope within the N-terminal fragment of GPC3. In some embodiments, the anti-nGPC3 antibody moiety specifically recognizes an epitope within amino acids 1-358 of SEQ ID NO: 460 (SEQ ID NO: 468). In some embodiments, the anti-nGPC3 antibody moiety specifically recognizes an epitope within the amino acid sequence of SEQ ID NO: 464. In some embodiments, the anti-nGPC3 antibody moiety specifically recognizes an epitope within the C-terminal fragment of GPC3. In some embodiments, the anti-nGPC3 antibody moiety specifically recognizes an epitope within amino acids 359-560 of SEQ ID NO: 460 (SEQ ID NO: 465). In some embodiments, the anti-nGPC3 antibody moiety specifically recognizes an epitope within amino acids 359-580 of SEQ ID NO: 460 (SEQ ID NO: 466). In some embodiments, the anti-nGPC3 antibody moiety specifically recognizes an epitope within the C-terminal fragment of GPC3 lacking heparin sulfate side chain. In some embodiments, the anti-nGPC3 antibody moiety specifically recognizes an epitope within amino acids 510-560 of SEQ ID NO: 460 (SEQ ID NO: 467). In some embodiments, the anti-nGPC3 antibody moiety specifically recognizes an epitope spanning the Furin cleavage site at amino acids $R^{358}/S^{359}$ of SEQ ID NO: 460. In some embodiments, the anti-nGPC3 antibody moiety can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460). In some embodiments, the anti-nGPC3 antibody moiety specifically recognizes an epitope within the C-terminal fragment of GPC3 lacking heparin sulfate side chain. In some embodiments, there is provided a method of treating an GPC3-positive disease in an individual comprising administering to the individual an effective amount of a composition comprising an effector cell (such as a T cell) expressing an anti-GPC3 CAR comprising a) an extracellular domain comprising an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that competes for binding to nGPC3 with any one of the anti-GPC3 constructs described herein, b) a transmembrane domain, and c) an intracellular signaling domain comprising a CD3ζ intracellular signaling sequence and a CD28 intracellular signaling sequence. In some embodiments, there is provided a method of treating an GPC3-positive disease in an individual comprising administering to the individual an effective amount of a composition comprising an effector cell (such as a T cell) expressing an anti-GPC3 CAR comprising a) an extracellular domain comprising an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that specifically binds to the same, or substantially the same, nGPC3 epitope competitively with any one of the anti-GPC3 constructs described herein, b) a transmembrane domain, and c) an intracellular signaling domain comprising a CD3ζ intracellular signaling sequence and a CD28 intracellular signaling sequence. In some embodiments, the anti-GPC3 CAR comprises an extracellular domain comprising an anti-GPC3 antibody moiety that specifically binds to a cell surface bound-GPC3 described herein fused to the N-terminus of SEQ ID NO: 494. In some embodiments, the effector cell (such as a T cell) expressing the anti-GPC3 CAR further comprises a nucleic acid encoding a multi-specific (e.g., bispecific) anti-GPC3 molecule (e.g., anti-GPC3×CD3 bispecific T cell engager) operably linked to an inducible promoter. In some embodiments, the expression of the multi-specific (e.g., bispecific) anti-GPC3 molecule (e.g., anti-GPC3×CD3 tandem di-scFv T cell engager) is inducible upon signaling through the anti-GPC3 CAR. In some embodiments, the inducible promoter is an NFAT-derived promoter, such as an NFAT-derived minimal promoter. In some embodiments, the inducible promoter is an IL-2 promoter. In some embodiments, the anti-nGPC3 antibody moiety is chimeric, human, partially humanized, fully humanized, or semi-synthetic. In some embodiments, the anti-nGPC3 antibody moiety is a Fab, a Fab', a F(ab')2, an Fv, or an scFv. In some embodiments, the anti-nGPC3 antibody moiety is a Fab or a Fab'. In some embodiments, the anti-nGPC3 antibody moiety is an scFv. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the cancer is metastatic HCC. In some embodiments, the cancer is HCC and the treating comprises preventing the spread of the cancer, e.g., inhibiting (such as preventing) metastasis of the cancer. In some embodiments, the cancer is metastatic HCC. In some embodiments, the administration is via intravenous, intraperitoneal, or intratumoral route. In some embodiments, the administration is via intravenous route. In some embodiments, the administration is via intratumoral route. In some embodiments, the administration comprises local injection an injection site distal to a site of the GPC3-positive disease (such as an GPC3-positive tumor). In some embodiments, the injection site is a first GPC3-positive tumor (i.e., the administration is via intratumoral route). In some embodiments, the site of the GPC3-positive disease is a second GPC3-positive tumor. In some embodiments, the injection site is a first GPC3-positive tumor and the site of the GPC3-positive disease is a second GPC3-positive tumor. In some embodiments, the individual is human.

In some embodiments, there is provided a method of treating an GPC3-positive disease (e.g., HCC) in an individual comprising administering to the individual an effective amount of a composition comprising an effector cell (such as a T cell) expressing an anti-GPC3 CAR comprising a) an extracellular domain comprising an anti-GPC3 antibody moiety that specifically binds to a cell surface bound-GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions, b) a transmembrane domain, and c) an intracellular signaling domain comprising a CD3ζ intracellular signaling sequence and a CD28 intracellular signaling sequence. In some embodiments, there is provided a method of treating an GPC3-positive disease (e.g., HCC) in an individual comprising administering to the individual an effective amount of a composition comprising an effector cell (such as a T cell) expressing an anti-GPC3 CAR comprising a) an extracellular domain comprising an anti-GPC3 antibody moiety that specifically binds to a cell surface bound-GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286, b) a transmembrane domain, and c) an intracellular signaling domain comprising a CD3ζ intracellular signaling sequence and a CD28 intracellular signaling sequence. In some embodiments, there is provided a method of treating an GPC3-positive disease (e.g., HCC) in an individual comprising administering to the individual an effective amount of a composition comprising an effector cell (such as a T cell) expressing an anti-GPC3 CAR comprising a) an extracellular domain comprising an anti-GPC3 antibody moiety that specifically binds to a cell surface bound-GPC3, comprising: i) a $V_H$ comprising the amino acid sequence of any one of SEQ ID NOs: 307-337; and ii) a $V_L$ comprising the amino acid sequence of any one of SEQ ID NOs: 358-388, b) a transmembrane domain, and c) an intracellular signaling domain comprising a CD3ζ intracellular signaling sequence and a CD28 intracellular signaling sequence. In some embodiments, there is provided a method of treating an GPC3-positive disease (e.g., HCC) in an individual comprising administering to the individual an effective amount of a composition comprising an effector cell (such as a T cell) expressing an anti-GPC3 CAR comprising a) an extracellular domain comprising an anti-GPC3 antibody moiety that specifically binds to a cell surface bound-GPC3, comprising the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388, b) a transmembrane domain, and c) an intracellular signaling domain comprising a CD3ζ intracellular signaling sequence and a CD28 intracellular signaling sequence. In some embodiments, there is provided a method of treating an GPC3-positive disease in an individual comprising administering to the individual an effective amount of a composition comprising an effector cell (such as a T cell) expressing an anti-GPC3 CAR comprising a) an extracellular domain comprising an anti-nGPC3 antibody moiety that competes for binding to nGPC3 with any one of the anti-GPC3 constructs described herein, b) a transmembrane domain, and c) an intracellular signaling domain comprising a CD3ζ intracellular signaling sequence and a CD28 intracellular signaling sequence. In some embodiments, there is provided a method of treating an GPC3-positive disease in an individual comprising administering to the individual an effective amount of a composition comprising an effector cell (such as a T cell) expressing an anti-GPC3 CAR comprising a) an extracellular domain comprising an anti-nGPC3 antibody moiety that specifically binds to the same, or substantially the same, nGPC3 epitope competitively with any one of the anti-GPC3 constructs described herein, b) a transmembrane domain, and c) an intracellular signaling domain comprising a CD3ζ intracellular signaling sequence and a CD28 intracellular signaling sequence. In some embodiments, the anti-GPC3 CAR comprises an extracellular domain comprising an anti-GPC3 antibody moiety that specifically binds to a cell surface bound-GPC3 described herein fused to the N-terminus of SEQ ID NO: 494. For example, in some embodiments, the anti-GPC3 CAR comprises the amino acid sequence of any one of SEQ ID NOs: 491 and 516-521. In some embodiments, the effector cell (such as a T cell) expressing the anti-GPC3 CAR further comprises a nucleic acid encoding a multi-specific (e.g., bispecific) anti-GPC3 molecule (e.g., anti-GPC3×CD3 bispecific T cell engager) operably linked to an inducible promoter. In some embodiments, the expression of the multi-specific (e.g., bispecific) anti-GPC3 molecule (e.g., anti-GPC3×CD3 tandem di-scFv T cell engager) is inducible upon signaling through the anti-GPC3 CAR. In some embodiments, the inducible promoter is an NFAT-derived promoter, such as an NFAT-derived minimal promoter. In some embodiments, the inducible promoter is an IL-2 promoter. In some embodiments, the anti-nGPC3 antibody moiety is chimeric, human, partially humanized, fully humanized, or semi-synthetic. In some embodiments, the anti-nGPC3 antibody moiety is a Fab, a Fab', a F(ab')2, an Fv, or an scFv. In some embodiments, the anti-nGPC3 antibody moiety is a Fab or a Fab'. In some embodiments, the anti-nGPC3 antibody moiety is an scFv. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the cancer is HCC and the treating comprises preventing the spread of the cancer, e.g., inhibiting (such as preventing) metastasis of the cancer. In some embodiments, the cancer is metastatic HCC. In some embodiments, the administration is via intravenous, intraperitoneal, or intratumoral route. In some embodiments, the administration is via intravenous route. In some embodiments, the administration is via intratumoral route. In some embodiments, the administration comprises local injection an injection site distal to a site of the GPC3-positive disease (such as an GPC3-positive tumor). In some embodiments, the injection site is a first GPC3-positive tumor (i.e., the administration is via intratumoral route). In some embodiments, the site of the GPC3-positive disease is a second GPC3-positive tumor. In some embodiments, the injection site is a first GPC3-positive tumor and the site of the GPC3-positive disease is a second GPC3-positive tumor. In some embodiments, the individual is human.

In some embodiments, there is provided a method of treating an GPC3-positive disease (e.g., HCC) in an individual comprising administering to the individual an effective amount of a composition comprising an effector cell (such as a T cell) expressing an anti-GPC3 CAR comprising a) an extracellular domain comprising an anti-GPC3 antibody moiety that specifically binds to GPC3 (e.g., nGPC3 and/or sGPC3), comprising: i) a $V_H$ comprising an HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions, b) a transmembrane domain, and c) an intracellular signaling domain comprising a CD3ζ intracellular signaling sequence and a CD28 intracellular signaling sequence. In some embodiments, there is provided a method of treating an GPC3-positive disease (e.g., HCC) in an individual comprising administering to the individual an effective amount of a composition comprising an effector cell (such as a T cell) expressing an anti-GPC3 CAR comprising a) an extracellular domain comprising an anti-GPC3 antibody moiety that specifically binds to GPC3 (e.g., nGPC3 and/or sGPC3), comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306, b) a transmembrane domain, and c) an intracellular signaling domain comprising a CD3ζ intracellular signaling sequence and a CD28 intracellular signaling sequence. In some embodiments, there is provided a method of treating an GPC3-positive disease (e.g., HCC) in an individual comprising administering to the individual an effective amount of a composition comprising an effector cell (such as a T cell) expressing an anti-GPC3 CAR comprising a) an extracellular domain comprising an anti-GPC3 antibody moiety that specifically binds to GPC3 (e.g., nGPC3 and/or sGPC3), comprising: i) a $V_H$ comprising the amino acid sequence of any one of SEQ ID NOs: 338-357; and ii) a $V_L$ comprising the amino acid sequence of any one of SEQ ID NOs: 389-408, b) a transmembrane domain, and c) an intracellular signaling domain comprising a CD3ζ intracellular signaling sequence and a CD28 intracellular signaling sequence. In some embodiments, there is provided a method of treating an GPC3-positive disease (e.g., HCC) in an individual comprising administering to the individual an effective amount of a composition comprising an effector cell (such as a T cell) expressing an anti-GPC3 CAR comprising a) an extracellular domain comprising an anti-GPC3 antibody moiety that specifically binds to GPC3 (e.g., nGPC3 and/or sGPC3), comprising the HC-CDRs of a $V_H$ comprising the amino acid sequence of any one of SEQ ID NOs: 338-357, and the LC-CDRs of a $V_L$ comprising the amino acid sequence of any one of SEQ ID NOs: 389-408, b) a transmembrane domain, and c) an intracellular signaling domain comprising a CD3ζ intracellular signaling sequence and a CD28 intracellular signaling sequence. In some embodiments, there is provided a method of treating an GPC3-positive disease in an individual comprising administering to the individual an effective amount of a composition comprising an effector cell (such as a T cell) expressing an anti-GPC3 CAR comprising a) an extracellular domain comprising an anti-GPC3 antibody moiety that competes for binding to GPC3 (e.g., nGPC3 and/or sGPC3) with any one of the anti-GPC3 constructs described herein, b) a transmembrane domain, and c) an intracellular signaling domain comprising a CD3ζ intracellular signaling sequence and a CD28 intracellular signaling sequence. In some embodiments, there is provided a method of treating an GPC3-positive disease in an individual comprising administering to the individual an effective amount of a composition comprising an effector cell (such as a T cell) expressing an anti-GPC3 CAR comprising a) an extracellular domain comprising an anti-GPC3 antibody moiety that specifically binds to the same, or substantially the same, GPC3 epitope competitively with any one of the anti-GPC3 constructs described herein, b) a transmembrane domain, and c) an intracellular signaling domain comprising a CD3ζ intracellular signaling sequence and a CD28 intracellular signaling sequence. In some embodiments, the anti-GPC3 CAR comprises an extracellular domain comprising an anti-GPC3 antibody moiety that specifically binds to GPC3 (e.g., nGPC3 and/or sGPC3) described herein fused to the N-terminus of SEQ ID NO: 494. In some embodiments, the effector cell (such as a T cell) expressing the anti-GPC3 CAR further comprises a nucleic acid encoding a multi-specific (e.g., bispecific) anti-GPC3 molecule (e.g., anti-GPC3×CD3 bispecific T cell engager) operably linked to an inducible promoter. In some embodiments, the expression of the multi-specific (e.g., bispecific) anti-GPC3 molecule (e.g., anti-GPC3×CD3 tandem di-scFv T cell engager) is inducible upon signaling through the anti-GPC3 CAR. In some embodiments, the inducible promoter is an NFAT-derived promoter, such as an NFAT-derived minimal promoter. In some embodiments, the inducible promoter is an IL-2 promoter. In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the anti-GPC3 antibody moiety is chimeric, human, partially humanized, fully humanized, or semi-synthetic. In some embodiments, the anti-GPC3 antibody moiety is a Fab, a Fab', a F(ab')2, an Fv, or an scFv. In some embodiments, the anti-GPC3 antibody moiety is a Fab or a Fab'. In some embodiments, the anti-GPC3 antibody moiety is an scFv. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the cancer is HCC and the treating comprises preventing the spread of the cancer, e.g., inhibiting (such as preventing) metastasis of the cancer. In some embodiments, the cancer is metastatic HCC. In some embodiments, the administration is via intravenous, intraperitoneal, or intratumoral route. In some embodiments, the administration is via intravenous route. In some embodiments, the administration is via intratumoral route. In some embodiments, the administration comprises local injection an injection site distal to a site of the GPC3-positive disease (such as an GPC3-positive tumor). In some embodiments, the injection site is a first GPC3-positive tumor (i.e., the administration is via intratumoral route). In some embodiments, the site of the GPC3-positive disease is a second GPC3-positive tumor. In some embodiments, the injection site is a first GPC3-positive tumor and the site of the GPC3-positive disease is a second GPC3-positive tumor. In some embodiments, the individual is human.

In some embodiments, there is provided a method of treating an GPC3-positive disease (e.g., HCC) in an individual comprising administering to the individual an effective amount of a composition comprising an effector cell (such as a T cell) expressing an anti-GPC3 caTCR comprising a) an antigen-binding module comprising an anti-GPC3 antibody moiety that specifically binds to a cell surface bound-GPC3 (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity), and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, the anti-nGPC3 antibody moiety specifically recognizes an epitope within human GPC3 comprising the amino acid sequence of SEQ ID NO: 460. In some embodiments, the anti-nGPC3 antibody moiety specifically recognizes an epitope within the amino acid sequence of SEQ ID NO: 461. In some embodiments, the anti-nGPC3 antibody moiety specifically recognizes an epitope within the amino acid sequence of SEQ ID NO: 462. In some embodiments, the anti-nGPC3 antibody moiety specifically recognizes an epitope within the amino acid sequence of SEQ ID NO: 463. In some embodiments, the anti-nGPC3 antibody moiety specifically recognizes an epitope within the N-terminal fragment of GPC3. In some embodiments, the anti-nGPC3 antibody moiety specifically recognizes an epitope within amino acids 1-358 of SEQ ID NO: 460 (SEQ ID NO: 468). In some embodiments, the anti-nGPC3 antibody moiety specifically recognizes an epitope within the amino acid sequence of SEQ ID NO: 464. In some embodiments, the anti-nGPC3 antibody moiety specifically recognizes an epitope within the C-terminal fragment of GPC3. In some embodiments, the anti-nGPC3 antibody moiety specifically recognizes an epitope within amino acids 359-560 of SEQ ID NO: 460 (SEQ ID NO: 465). In some embodiments, the anti-nGPC3 antibody moiety specifically recognizes an epitope within amino acids 359-580 of SEQ ID NO: 460 (SEQ ID NO: 466). In some embodiments, the anti-nGPC3 antibody moiety specifically recognizes an epitope within the C-terminal fragment of GPC3 lacking heparin sulfate side chain. In some embodiments, the anti-nGPC3 antibody moiety specifically recognizes an epitope within amino acids 510-560 of SEQ ID NO: 460 (SEQ ID NO: 467). In some embodiments, the anti-nGPC3 antibody moiety specifically recognizes an epitope spanning the Furin cleavage site at amino acids $R^{358}/S^{359}$ of SEQ ID NO: 460. In some embodiments, the anti-nGPC3 antibody moiety can specifically bind to a full-length mature human GPC3 (e.g., amino acids 25-560 or 25-580 of SEQ ID NO: 460) but does not bind to an N-terminal fragment of human GPC3 (e.g., amino acids 25-358 of SEQ ID NO: 460) or to a C-terminal fragment of human GPC3 (e.g., amino acids 359-560 or 359-580 of SEQ ID NO: 460). In some embodiments, the anti-nGPC3 antibody moiety specifically recognizes an epitope within the C-terminal fragment of GPC3 lacking heparin sulfate side chain. In some embodiments, there is provided a method of treating an GPC3-positive disease in an individual comprising administering to the individual an effective amount of a composition comprising an effector cell (such as a T cell) expressing an anti-GPC3 caTCR comprising a) an antigen-binding module comprising an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that competes for binding to nGPC3 with any one of the anti-GPC3 constructs described herein, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease in an individual comprising administering to the individual an effective amount of a composition comprising an effector cell (such as a T cell) expressing an anti-GPC3 caTCR comprising a) an antigen-binding module comprising an anti-nGPC3 antibody moiety (e.g., the binding affinity of the anti-nGPC3 antibody moiety to a cell surface-bound GPC3 is higher than that to a soluble GPC3, or the anti-nGPC3 antibody moiety specifically recognizes a cell surface-bound GPC3 at a high binding affinity and binds to a soluble GPC3 at a low binding affinity) that specifically binds to the same, or substantially the same, nGPC3 epitope competitively with any one of the anti-GPC3 constructs described herein, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease in an individual comprising administering to the individual an effective amount of a composition comprising an effector cell (such as a T cell) expressing an anti-GPC3 caTCR comprising: a) a first polypeptide chain comprising a first antigen-binding domain comprising $V_H$ and $C_H1$ antibody domains and a first T cell receptor domain (TCRD) comprising a first transmembrane domain of a first TCR subunit; and b) a second polypeptide chain comprising a second antigen-binding domain comprising $V_L$ and $C_L$ antibody domains and a second TCRD comprising a second transmembrane domain of a second TCR subunit, wherein the $V_H$ and $C_H1$ domains of the first antigen-binding domain and the $V_L$ and $C_L$ domains of the second antigen-binding domain form an antigen-binding module that specifically binds to cell surface bound-GPC3 (e.g., the binding affinity of the $V_H$ and $V_L$ to a cell surface-bound GPC3 is higher than that to a soluble GPC3, or the $V_H$ and $V_L$ specifically recognizes a cell surface-bound GPC3 at a high binding affinity and binds to a soluble GPC3 at a low binding affinity), and wherein the first TCRD and the second TCRD form a T cell receptor module (TCRM) that is capable of recruiting at least one TCR-associated signaling module. In some embodiments, the antigen-binding module comprises a disulfide bond between a residue in the $C_H1$ domain and a residue in the $C_L$ domain. In some embodiments, there is provided a method of treating an GPC3-positive disease in an individual comprising administering to the individual an effective amount of a composition comprising an effector cell (such as a T cell) expressing an anti-GPC3 caTCR comprising: a) a first polypeptide chain comprising a first antigen-binding domain comprising a $V_H$ antibody domain and a first TCRD comprising a first transmembrane domain of a first TCR subunit; and b) a second polypeptide chain comprising a second antigen-binding domain comprising a $V_L$ antibody domains and a second TCRD comprising a second transmembrane domain of a second TCR subunit, wherein the $V_H$ domain of the first antigen-binding domain and the $V_L$ domain of the second antigen-binding domain form an antigen-binding module that specifically binds to cell surface bound-GPC3 (e.g., the binding affinity of the $V_H$ and $V_L$ to a cell surface-bound GPC3 is higher than that to a soluble GPC3, or the $V_H$ and $V_L$ specifically recognizes a cell surface-bound GPC3 at a high binding affinity and binds to a soluble GPC3 at a low binding affinity), wherein the first TCRD and the second TCRD form a T cell receptor module (TCRM) that is capable of recruiting at least one TCR-associated signaling module. In some embodiments, the effector cell (such as a T cell) expressing the anti-GPC3 caTCR further comprises a nucleic acid encoding a multi-specific (e.g., bispecific) anti-GPC3 molecule (e.g., anti-GPC3×CD3 bispecific T cell engager) operably linked to an inducible promoter. In some embodiments, the expression of the multi-specific (e.g., bispecific) anti-GPC3 molecule (e.g., anti-GPC3×CD3 tandem di-scFv T cell engager) is inducible upon signaling through the anti-GPC3 caTCR. In some embodiments, the inducible promoter is an NFAT-derived promoter, such as an NFAT-derived minimal promoter. In some embodiments, the inducible promoter is an IL-2 promoter. In some embodiments, the first TCR-TM is derived from one of the transmembrane domains of a naturally occurring T cell receptor (such as an αβ TCR or a γδ TCR). In some embodiments, the anti-nGPC3 antibody moiety is chimeric, human, partially humanized, fully humanized, or semi-synthetic. In some embodiments, the anti-nGPC3 antibody moiety is a Fab, a Fab', a F(ab')2, an Fv, or an scFv. In some embodiments, the anti-nGPC3 antibody moiety is a Fab or a Fab'. In some embodiments, the anti-nGPC3 antibody moiety is an scFv. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the cancer is HCC and the treating comprises preventing the spread of the cancer, e.g., inhibiting (such as preventing) metastasis of the cancer. In some embodiments, the cancer is metastatic HCC. In some embodiments, the administration is via intravenous, intraperitoneal, or intratumoral route. In some embodiments, the administration is via intravenous route. In some embodiments, the administration is via intratumoral route. In some embodiments, the administration comprises local injection an injection site distal to a site of the GPC3-positive disease (such as an GPC3-positive tumor). In some embodiments, the injection site is a first GPC3-positive tumor (i.e., the administration is via intratumoral route). In some embodiments, the site of the GPC3-positive disease is a second GPC3-positive tumor. In some embodiments, the injection site is a first GPC3-positive tumor and the site of the GPC3-positive disease is a second GPC3-positive tumor. In some embodiments, the individual is human.

In some embodiments, there is provided a method of treating an GPC3-positive disease (e.g., HCC) in an individual comprising administering to the individual an effective amount of a composition comprising an effector cell (such as a T cell) expressing an anti-GPC3 caTCR comprising a) an antigen-binding module comprising an anti-GPC3 antibody moiety that specifically binds to a cell surface bound-GPC3, comprising: i) a $V_H$ comprising an HC-CDR1 comprising the amino acid sequence of any one of SEQ ID NOs: 1-31, or a variant thereof comprising up to about 5 (such as about any of 1, 2, 3, 4, or 5) amino acid substitutions, an HC-CDR2 comprising the amino acid sequence of any one of SEQ ID NOs: 52-82, or a variant thereof comprising up to about 5 (such as about any of 1, 2, 3, 4, or 5) amino acid substitutions, and an HC-CDR3 comprising the amino acid sequence of any one of SEQ ID NOs: 103-133, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 154-184, or a variant thereof comprising up to about 5 (such as about any of 1, 2, 3, 4, or 5) amino acid substitutions, an LC-CDR2 comprising the amino acid sequence of any one of SEQ ID NOs: 205-235, or a variant thereof comprising up to about 3 (such as about any of 1, 2, or 3) amino acid substitutions, and an LC-CDR3 comprising the amino acid sequence of any one of SEQ ID NOs: 256-286, or a variant thereof comprising up to about 5 (such as about any of 1, 2, 3, 4, or 5) amino acid substitutions, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease (e.g., HCC) in an individual comprising administering to the individual an effective amount of a composition comprising an effector cell (such as a T cell) expressing an anti-GPC3 caTCR comprising a) an antigen-binding module comprising an anti-GPC3 antibody moiety that specifically binds to a cell surface bound-GPC3, comprising: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease (e.g., HCC) in an individual comprising administering to the individual an effective amount of a composition comprising an effector cell (such as a T cell) expressing an anti-GPC3 caTCR comprising a) an antigen-binding module comprising an anti-GPC3 antibody moiety that specifically binds to a cell surface bound-GPC3, comprising: i) a $V_H$ comprising the amino acid sequence of any one of SEQ ID NOs: 307-337; and ii) a $V_L$ comprising the amino acid sequence of any one of SEQ ID NOs: 358-388, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease (e.g., HCC) in an individual comprising administering to the individual an effective amount of a composition comprising an effector cell (such as a T cell) expressing an anti-GPC3 caTCR comprising a) an antigen-binding module comprising an anti-GPC3 antibody moiety that specifically binds to a cell surface bound-GPC3, comprising the HC-CDRs of a $V_H$ comprising the amino acid sequence of any one of SEQ ID NOs: 307-337, and the LC-CDRs of a $V_L$ comprising the amino acid sequence of any one of SEQ ID NOs: 358-388, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease in an individual comprising administering to the individual an effective amount of a composition comprising an effector cell (such as a T cell) expressing an anti-GPC3 caTCR comprising a) an antigen-binding module comprising an anti-nGPC3 antibody moiety that competes for binding to nGPC3 with any one of the anti-GPC3 constructs described herein, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease in an individual comprising administering to the individual an effective amount of a composition comprising an effector cell (such as a T cell) expressing an anti-GPC3 caTCR comprising a) an antigen-binding module comprising an anti-nGPC3 antibody moiety that specifically binds to the same, or substantially the same, nGPC3 epitope competitively with any one of the anti-GPC3 constructs described herein, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease in an individual comprising administering to the individual an effective amount of a composition comprising an effector cell (such as a T cell) expressing an anti-GPC3 caTCR comprising: a) a first polypeptide chain comprising a first antigen-binding domain comprising $V_H$ comprising the amino acid sequence of any one of SEQ ID NOs: 307-337 and $C_H1$ antibody domains and a first T cell receptor domain (TCRD) comprising a first transmembrane domain of a first TCR subunit; and b) a second polypeptide chain comprising a second antigen-binding domain comprising $V_L$ comprising the amino acid sequence of any one of SEQ ID NOs: 358-388 and $C_L$ antibody domains and a second TCRD comprising a second transmembrane domain of a second TCR subunit, wherein the $V_H$ and $C_H1$ domains of the first antigen-binding domain and the $V_L$ and $C_L$ domains of the second antigen-binding domain form an antigen-binding module that specifically binds to cell surface bound-GPC3, and wherein the first TCRD and the second TCRD form a T cell receptor module (TCRM) that is capable of recruiting at least one TCR-associated signaling module. In some embodiments, the antigen-binding module comprises a disulfide bond between a residue in the $C_H1$ domain and a residue in the $C_L$ domain. In some embodiments, there is provided a method of treating an GPC3-positive disease in an individual comprising administering to the individual an effective amount of a composition comprising an effector cell (such as a T cell) expressing an anti-GPC3 caTCR comprising: a) a first polypeptide chain comprising a first antigen-binding domain comprising a $V_H$ antibody domain comprising the amino acid sequence of any one of SEQ ID NOs: 307-337 and a first TCRD comprising a first transmembrane domain of a first TCR subunit; and b) a second polypeptide chain comprising a second antigen-binding domain comprising a $V_L$ antibody domains comprising the amino acid sequence of any one of SEQ ID NOs: 358-388 and a second TCRD comprising a second transmembrane domain of a second TCR subunit, wherein the $V_H$ domain of the first antigen-binding domain and the $V_L$ domain of the second antigen-binding domain form an antigen-binding module that specifically binds to cell surface bound-GPC3, wherein the first TCRD and the second TCRD form a T cell receptor module (TCRM) that is capable of recruiting at least one TCR-associated signaling module. In some embodiments, the anti-GPC3 caTCR comprises two polypeptide chains, comprising amino acid sequences of SEQ ID NO: 492 and SEQ ID NO: 493. In some embodiments, the effector cell (such as a T cell) expressing the anti-GPC3 caTCR further comprises a nucleic acid encoding a multi-specific (e.g., bispecific) anti-GPC3 molecule (e.g., anti-GPC3×CD3 bispecific T cell engager) operably linked to an inducible promoter. In some embodiments, the expression of the multi-specific (e.g., bispecific) anti-GPC3 molecule (e.g., anti-GPC3×CD3 tandem di-scFv T cell engager) is inducible upon signaling through the anti-GPC3 caTCR. In some embodiments, the inducible promoter is an NFAT-derived promoter, such as an NFAT-derived minimal promoter. In some embodiments, the inducible promoter is an IL-2 promoter. In some embodiments, the first TCR-TM is derived from one of the transmembrane domains of a naturally occurring T cell receptor (such as an αβ TCR or a γδ TCR). In some embodiments, the anti-nGPC3 antibody moiety is chimeric, human, partially humanized, fully humanized, or semi-synthetic. In some embodiments, the anti-nGPC3 antibody moiety is a Fab, a Fab', a F(ab')2, an Fv, or an scFv. In some embodiments, the anti-nGPC3 antibody moiety is a Fab or a Fab'. In some embodiments, the anti-nGPC3 antibody moiety is an scFv. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the cancer is HCC and the treating comprises preventing the spread of the cancer, e.g., inhibiting (such as preventing) metastasis of the cancer. In some embodiments, the cancer is metastatic HCC. In some embodiments, the administration is via intravenous, intraperitoneal, or intratumoral route. In some embodiments, the administration is via intravenous route. In some embodiments, the administration is via intratumoral route. In some embodiments, the administration comprises local injection an injection site distal to a site of the GPC3-positive disease (such as an GPC3-positive tumor). In some embodiments, the injection site is a first GPC3-positive tumor (i.e., the administration is via intratumoral route). In some embodiments, the site of the GPC3-positive disease is a second GPC3-positive tumor. In some embodiments, the injection site is a first GPC3-positive tumor and the site of the GPC3-positive disease is a second GPC3-positive tumor. In some embodiments, the individual is human.

In some embodiments, there is provided a method of treating an GPC3-positive disease (e.g., HCC) in an individual comprising administering to the individual an effective amount of a composition comprising an effector cell (such as a T cell) expressing an anti-GPC3 caTCR comprising a) an antigen-binding module comprising an anti-GPC3 antibody moiety that specifically binds to GPC3 (e.g., nGPC3 and/or sGPC3), comprising: i) a $V_H$ comprising a HC-CDR1 comprising the amino acid sequence of any one of SEQ ID NOs: 32-51, or a variant thereof comprising up to about 5 (such as about any of 1, 2, 3, 4, or 5) amino acid substitutions, an HC-CDR2 comprising the amino acid sequence of any one of SEQ ID NOs: 83-102, or a variant thereof comprising up to about 5 (such as about any of 1, 2, 3, 4, or 5) amino acid substitutions, and an HC-CDR3 comprising the amino acid sequence of any one of SEQ ID NOs: 134-153, or a variant thereof comprising up to about 5 (such as about any of 1, 2, 3, 4, or 5) amino acid substitutions; and ii) a $V_L$ comprising an LC-CDR1 comprising the amino acid sequence of any one of SEQ ID NOs: 185-204, or a variant thereof comprising up to about 5 (such as about any of 1, 2, 3, 4, or 5) amino acid substitutions, an LC-CDR2 comprising the amino acid sequence of any one of SEQ ID NOs: 236-255, or a variant thereof comprising up to about 3 (such as about any of 1, 2, or 3) amino acid substitutions, and an LC-CDR3 comprising the amino acid sequence of any one of SEQ ID NOs: 287-306, or a variant thereof comprising up to about 5 (such as about any of 1, 2, 3, 4, or 5) amino acid substitutions, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease (e.g., HCC) in an individual comprising administering to the individual an effective amount of a composition comprising an effector cell (such as a T cell) expressing an anti-GPC3 caTCR comprising a) an antigen-binding module comprising an anti-GPC3 antibody moiety that specifically binds to GPC3 (e.g., nGPC3 and/or sGPC3), comprising: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a V$_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease (e.g., HCC) in an individual comprising administering to the individual an effective amount of a composition comprising an effector cell (such as a T cell) expressing an anti-GPC3 caTCR comprising a) an antigen-binding module comprising an anti-GPC3 antibody moiety that specifically binds to GPC3 (e.g., nGPC3 and/or sGPC3), comprising: i) a V$_H$ comprising the amino acid sequence of any one of SEQ ID NOs: 338-357; and ii) a V$_L$ comprising the amino acid sequence of any one of SEQ ID NOs: 389-408, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease (e.g., HCC) in an individual comprising administering to the individual an effective amount of a composition comprising an effector cell (such as a T cell) expressing an anti-GPC3 caTCR comprising a) an antigen-binding module comprising an anti-GPC3 antibody moiety that specifically binds to GPC3 (e.g., nGPC3 and/or sGPC3), comprising the HC-CDRs of a V$_H$ comprising the amino acid sequence of any one of SEQ ID NOs: 338-357, and the LC-CDRs of a V$_L$ comprising the amino acid sequence of any one of SEQ ID NOs: 389-408, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease in an individual comprising administering to the individual an effective amount of a composition comprising an effector cell (such as a T cell) expressing an anti-GPC3 caTCR comprising a) an antigen-binding module comprising an anti-GPC3 antibody moiety that competes for binding to GPC3 (e.g., nGPC3 and/or sGPC3) with any one of the anti-GPC3 constructs described herein, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease in an individual comprising administering to the individual an effective amount of a composition comprising an effector cell (such as a T cell) expressing an anti-GPC3 caTCR comprising a) an antigen-binding module comprising an anti-GPC3 antibody moiety that specifically binds to the same, or substantially the same, GPC3 epitope competitively with any one of the anti-GPC3 constructs described herein, and b) a T cell receptor module (TCRM) comprising a first TCR domain (TCRD) comprising a first TCR transmembrane domain (TCR-TM) derived from one of the transmembrane domains of a naturally occurring TCR (such as an αβTCR or a γδTCR) and a second TCRD comprising a second TCR-TM derived from the other transmembrane domain of the naturally occurring TCR (such as an αβTCR or a γδTCR), wherein the TCRM facilitates recruitment of at least one TCR-associated signaling molecule (such as CD3δε, CD3γε, and/or ζζ), and wherein the antibody moiety is linked to the first and/or second TCRDs. In some embodiments, there is provided a method of treating an GPC3-positive disease in an individual comprising administering to the individual an effective amount of a composition comprising an effector cell (such as a T cell) expressing an anti-GPC3 caTCR comprising: a) a first polypeptide chain comprising a first antigen-binding domain comprising V$_H$ comprising the amino acid sequence of any one of SEQ ID NOs: 338-357 and C$_H$1 antibody domains and a first T cell receptor domain (TCRD) comprising a first transmembrane domain of a first TCR subunit; and b) a second polypeptide chain comprising a second antigen-binding domain comprising V$_L$ comprising the amino acid sequence of any one of SEQ ID NOs: 389-408 and C$_L$ antibody domains and a second TCRD comprising a second transmembrane domain of a second TCR subunit, wherein the V$_H$ and C$_H$1 domains of the first antigen-binding domain and the V$_L$ and C$_L$ domains of the second antigen-binding domain form an antigen-binding module that specifically binds to GPC3 (e.g., nGPC3 and/or sGPC3), and wherein the first TCRD and the second TCRD form a T cell receptor module (TCRM) that is capable of recruiting at least one TCR-associated signaling module. In some embodiments, the antigen-binding module comprises a disulfide bond between a residue in the C$_H$1 domain and a residue in the C$_L$ domain. In some embodiments, there is provided a method of treating an GPC3-positive disease in an individual comprising administering to the individual an effective amount of a composition comprising an effector cell (such as a T cell) expressing an anti-GPC3 caTCR comprising: a) a first polypeptide chain comprising a first antigen-binding domain comprising a V$_H$ antibody domain comprising the amino acid sequence of any one of SEQ ID NOs: 338-357 and a first TCRD comprising a first transmembrane domain of a first TCR subunit; and b) a second polypeptide chain comprising a second antigen-binding domain comprising a V$_L$ antibody domains comprising the amino acid sequence of any one of SEQ ID NOs: 389-408 and a second TCRD comprising a second transmembrane domain of a second TCR subunit, wherein the $V_H$ domain of the first antigen-binding domain and the $V_L$ domain of the second antigen-binding domain form an antigen-binding module that specifically binds to GPC3 (e.g., nGPC3 and/or sGPC3), wherein the first TCRD and the second TCRD form a T cell receptor module (TCRM) that is capable of recruiting at least one TCR-associated signaling module. In some embodiments, the effector cell (such as a T cell) expressing the anti-GPC3 caTCR further comprises a nucleic acid encoding a multi-specific (e.g., bispecific) anti-GPC3 molecule (e.g., anti-GPC3×CD3 bispecific T cell engager) operably linked to an inducible promoter. In some embodiments, the expression of the multi-specific (e.g., bispecific) anti-GPC3 molecule (e.g., anti-GPC3×CD3 tandem di-scFv T cell engager) is inducible upon signaling through the anti-GPC3 caTCR. In some embodiments, the inducible promoter is an NFAT-derived promoter, such as an NFAT-derived minimal promoter. In some embodiments, the inducible promoter is an IL-2 promoter. In some embodiments, the first TCR-TM is derived from one of the transmembrane domains of a naturally occurring T cell receptor (such as an αβ TCR or a γδ TCR). In some embodiments, the anti-GPC3 antibody moiety specifically recognizes a cell surface-bound GPC3. In some embodiments, the binding affinity of the anti-nGPC3 antibody moiety to a cell surface-bound GPC3 is higher than that to a soluble GPC3. In some embodiments, the anti-nGPC3 antibody moiety specifically recognizes a cell surface-bound GPC3 at a high binding affinity and binds to a soluble GPC3 at a low binding affinity. In some embodiments, the anti-GPC3 antibody moiety specifically recognizes a soluble GPC3. In some embodiments, the binding affinity of the anti-sGPC3 antibody moiety to a soluble GPC3 is higher than that to a cell surface-bound GPC3. In some embodiments, the anti-sGPC3 antibody moiety specifically recognizes an epitope within the amino acid sequence of SEQ ID NO: 461. In some embodiments, the anti-sGPC3 antibody moiety specifically recognizes an epitope within amino acids 510-560 of SEQ ID NO: 460 (SEQ ID NO: 467). In some embodiments, the anti-GPC3 antibody moiety specifically recognizes both cell surface-bound GPC3 and soluble GPC3. In some embodiments, the anti-GPC3 antibody moiety is chimeric, human, partially humanized, fully humanized, or semi-synthetic. In some embodiments, the anti-GPC3 antibody moiety is a Fab, a Fab', a F(ab')2, an Fv, or an scFv. In some embodiments, the anti-GPC3 antibody moiety is a Fab or a Fab'. In some embodiments, the anti-GPC3 antibody moiety is an scFv. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the cancer is HCC and the treating comprises preventing the spread of the cancer, e.g., inhibiting (such as preventing) metastasis of the cancer. In some embodiments, the cancer is metastatic HCC. In some embodiments, the administration is via intravenous, intraperitoneal, or intratumoral route. In some embodiments, the administration is via intravenous route. In some embodiments, the administration is via intratumoral route. In some embodiments, the administration comprises local injection an injection site distal to a site of the GPC3-positive disease (such as an GPC3-positive tumor). In some embodiments, the injection site is a first GPC3-positive tumor (i.e., the administration is via intratumoral route). In some embodiments, the site of the GPC3-positive disease is a second GPC3-positive tumor. In some embodiments, the injection site is a first GPC3-positive tumor and the site of the GPC3-positive disease is a second GPC3-positive tumor. In some embodiments, the individual is human.

In some embodiments, there is provided a method of treating metastatic HCC in an individual comprising administering to the individual an effective amount of a composition comprising an effector cell (such as a T cell) expressing an anti-GPC3 CAR or anti-GPC3 caTCR according to any of the embodiments described above. In some embodiments, the individual is human. In some embodiments, the effector cell (such as a T cell) expressing the anti-GPC3 CAR or anti-GPC3 caTCR further comprises a nucleic acid encoding the multi-specific (e.g., bispecific) anti-GPC3 molecule (e.g., anti-GPC3×CD3 bispecific T cell engager) operably linked to an inducible promoter. In some embodiments, the expression of the multi-specific (e.g., bispecific) anti-GPC3 molecule (e.g., anti-GPC3×CD3 bispecific T cell engager) is inducible upon signaling through the anti-GPC3 CAR or anti-GPC3 caTCR. In some embodiments, the inducible promoter is an NFAT-derived promoter, such as an NFAT-derived minimal promoter. In some embodiments, the inducible promoter is an IL-2 promoter.

In some embodiments, there is provided a method of inhibiting (such as preventing) metastasis of HCC in an individual comprising administering to the individual an effective amount of a composition comprising an effector cell (such as a T cell) expressing an anti-GPC3 CAR or anti-GPC3 caTCR according to any of the embodiments described above. In some embodiments, the individual is human. In some embodiments, the effector cell (such as a T cell) expressing the anti-GPC3 CAR or anti-GPC3 caTCR further comprises a nucleic acid encoding the multi-specific (e.g., bispecific) anti-GPC3 molecule (e.g., anti-GPC3×CD3 bispecific T cell engager) operably linked to an inducible promoter. In some embodiments, the expression of the multi-specific (e.g., bispecific) anti-GPC3 molecule (e.g., anti-GPC3×CD3 bispecific T cell engager) is inducible upon signaling through the anti-GPC3 CAR or anti-GPC3 caTCR. In some embodiments, the inducible promoter is an NFAT-derived promoter, such as an NFAT-derived minimal promoter. In some embodiments, the inducible promoter is an IL-2 promoter.

In some embodiments, there is provided a method of priming T cells in an individual comprising administering to the individual an effective amount of a composition comprising an effector cell (such as a T cell) expressing an anti-GPC3 CAR according to any of the anti-GPC3 CARs described above. In some embodiments, there is provided a method of priming T cells in an individual comprising administering to the individual an effective amount of a composition comprising an effector cell (such as a T cell) expressing an anti-GPC3 caTCR according to any of the anti-GPC3 caTCRs described above. In some embodiments, the individual has an GPC3-positive disease. In some embodiments, the GPC3-positive disease is cancer. In some embodiments, the cancer is, for example, HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma. In some embodiments, the cancer is HCC. In some embodiments, the administration is via intravenous, intraperitoneal, or intratumoral route. In some embodiments, the administration is via intravenous route. In some embodiments, the administration is via intratumoral route. In some embodiments, the administration is to an injection site distal to a first disease site. In some embodiments, the individual is human.

In some embodiments, according to any of the methods described above, the method further comprising administering antigen presenting cells, or APCs, (such as monocytes or monocyte-differentiated dendritic cells) to the individual. Dendritic cells can be generated ex vivo via culturing monocytes with specific cytokines (Palucka and Banchereau, Nature Reviews Cancer 12:265-277, 2012). In some embodiments, the APCs are administered simultaneously with the effector cell composition. In some embodiments, the APCs are administered concurrently with the effector cell composition. In some embodiments, the APCs are administered sequentially with the effector cell composition. In some embodiments, the APCs are administered via the same route as the effector cell composition. In some embodiments, the APCs are administered to the same site as the effector cell composition. In some embodiments, the effector cell composition comprises the APCs.

Cancers

The anti-GPC3 constructs (such as isolated anti-GPC3 constructs), anti-GPC3 CAR cells, and anti-GPC3 caTCR cells in some embodiments can be useful for treating cancer. Cancers that may be treated using any of the methods described herein include tumors that are not vascularized, or not yet substantially vascularized, as well as vascularized tumors. The cancers may comprise solid tumors. Types of cancers to be treated with the anti-GPC3 constructs, anti-GPC3 CAR cells, and anti-GPC3 caTCR cells of the invention include, but are not limited to, carcinoma, blastoma, sarcoma, benign and malignant tumors, and malignancies e.g., sarcomas, carcinomas, and melanomas. Adult tumors/cancers and pediatric tumors/cancers are also included.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers (e.g., lung squamous cell carcinoma), ovarian cancer, yolk sac tumor (endodermal sinus tumor), prostate cancer, hepatocellular carcinoma (HCC), squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In some embodiments, the cancer that can be treated by the present invention is HCC. GPC3 is highly expressed in HCC and HCC cell lines, e.g., HepG2, Hep3B, HT17, HuH6, HuH7 and PLC/PRF/5. GPC3 expression is correlated with poor prognosis in HCC. In some embodiments, the HCC is early stage HCC, non-metastatic HCC, primary HCC, advanced HCC, locally advanced HCC, metastatic HCC, HCC in remission, or recurrent HCC. In some embodiments, the HCC is localized resectable (i.e., tumors that are confined to a portion of the liver that allows for complete surgical removal), localized unresectable (i.e., the localized tumors may be unresectable because crucial blood vessel structures are involved or because the liver is impaired), or unresectable (i.e., the tumors involve all lobes of the liver and/or has spread to involve other organs (e.g., lung, lymph nodes, bone). In some embodiments, the HCC is, according to TNM classifications, a stage I tumor (single tumor without vascular invasion), a stage II tumor (single tumor with vascular invasion, or multiple tumors, none greater than 5 cm), a stage III tumor (multiple tumors, any greater than 5 cm, or tumors involving major branch of portal or hepatic veins), a stage IV tumor (tumors with direct invasion of adjacent organs other than the gallbladder, or perforation of visceral peritoneum), N1 tumor (regional lymph node metastasis), or M1 tumor (distant metastasis). In some embodiments, the HCC is, according to AJCC (American Joint Commission on Cancer) staging criteria, stage T1, T2, T3, or T4 HCC. In some embodiments, the HCC is any one of liver cell carcinomas, fibrolamellar variants of HCC, and mixed hepatocellular cholangiocarcinomas.

In some embodiments, the GPC3-positive cancer is yolk sac tumor (YST, endodermal sinus tumor). In some embodiments, the GPC3-positive cancer is ovarian carcinoma. In some embodiments, the GPC3-positive cancer is choriocarcinoma. In some embodiments, the GPC3-positive cancer is testicular nonseminomatous germ cell tumor.

YST is the most common testicular tumor in children under 3 and is also known as infantile embryonal carcinoma. Unlike the pure form typical of infants, adult YSTs are often found in combination with other kinds of germ cell tumor, particularly teratoma and embryonal carcinoma. Although pure teratoma is usually benign, YST is malignant.

GPC3 is expressed in a less than 20% of ovarian carcinomas, but in more than 60% of ovarian clear-cell carcinomas, suggesting that GPC3 may represent a potential biomarker for ovarian clear-cell carcinomas. GPC3 immunostaining may be beneficial in the diagnosis of YST and choriocarcinoma.

Choriocarcinoma is a malignant, trophoblastic cancer usually at placenta. Choriocarcinoma occurs rarely in primary locations other than the placenta; very rarely, it occurs in testicles. Pure choriocarcinoma of the adult testis is rare, but represents the most aggressive pathologic variant of germ cell tumors (GCTs) in adults. It is characterized with early hematogenous and lymphatic metastatic spread. Patients have very poor prognosis due to the early spread and inherent resistance to anticancer drugs.

GPC3 might be used as a tumor marker for the diagnosis of melanoma, especially in the early stages of the disease, since GPC3 mRNA and protein have been found in >80% of melanomas and melanocytic nevus.

Expression of GPC3 is also found in neuroblastoma, hepatoblastoma, Wilms' tumor cells, testicular nonseminomatous germ cell tumors, and a distinct group of gastric carcinomas called GPC3-GC. Thus, in some embodiments, the present invention can be used for treating or diagnosing these GPC3-positive diseases.

Cancer treatments can be evaluated by, e.g., tumor regression, tumor weight or size shrinkage, time to progression, duration of survival, progression free survival, overall response rate, duration of response, quality of life, protein expression and/or activity. Approaches to determining efficacy of therapy can be employed, including for example, measurement of response through radiological imaging.

Methods for Diagnosis, Detection and Imaging Using Anti-GPC3 Constructs

Labeled anti-GPC3 antibody moieties and derivatives and analogs thereof (e.g., anti-GPC3 immunoconjugates comprising a label), which specifically bind to an GPC3 (either cell surface-bound or soluble), can be used for diagnostic purposes to detect, diagnose, or monitor diseases and/or disorders associated with the expression, aberrant expression and/or activity of GPC3, including any of the diseases and disorders described above, such as cancer (e.g., HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma). For example, the anti-GPC3 antibody moieties of the invention can be used in in situ, in vivo, ex vivo, and in vitro diagnostic assays or imaging assays.

Additional embodiments of the invention include methods of detecting GPC3 in a sample, comprising contacting the sample with an anti-GPC3 construct (such as an isolated anti-GPC3 construct, e.g., anti-GPC3 immunoconjugate comprising a label) described herein, and detecting the presence of the label. In some embodiments, the sample comprises cells with cell surface-bound GPC3. In some embodiments, the sample comprises soluble GPC3.

Additional embodiments of the invention include methods of diagnosing a disease or disorder associated with expression or aberrant expression of GPC3 in an individual (e.g., a mammal, such as a human). The methods comprise detecting cell surface-bound GPC3 or soluble GPC3 in the individual. In some embodiments, there is provided a method of diagnosing a disease or disorder associated with expression or aberrant expression of GPC3 in an individual (e.g., a mammal, such as a human) comprising (a) administering an effective amount of a labeled anti-GPC3 antibody moiety (e.g., anti-GPC3 immunoconjugate comprising a label) according to any of the embodiments described above to the individual; and (b) determining the level of the label in the individual, such that a level of the label above a threshold level indicates that the individual has the GPC3-positive disease or disorder. In some embodiments, the GPC3-positive disease or disorder is cancer. In some embodiments, the cancer is selected, for example, from the group consisting of HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, and liposarcoma. In some embodiments, the cancer is HCC. In some embodiments, the cancer is metastatic HCC. In some embodiments, the cancer is metastatic HCC, and the method further comprises determining the level of the label in the individual's blood. In some embodiments, there is provided a method of diagnosing HCC (e.g., metastatic HCC) in an individual (e.g., a mammal, such as a human) comprising (a) administering an effective amount of a labeled anti-GPC3 antibody moiety (e.g., anti-GPC3 immunoconjugate comprising a label) according to any of the embodiments described above to the individual; and (b) determining the level of the label in the individual, such that a level of the label above a threshold level indicates that the individual has HCC (e.g., metastatic HCC). The threshold level can be determined by various methods, including, for example, by detecting the label according to the method of diagnosing described above in a first set of individuals that have the disease or disorder and a second set of individuals that do not have the disease or disorder, and setting the threshold to a level that allows for discrimination between the first and second sets. In some embodiments, the threshold level is zero, and the method comprises determining the presence or absence of the label in the individual. In some embodiments, the method further comprises waiting for a time interval following the administering of step (a) to permit the labeled anti-GPC3 antibody moiety (e.g., anti-GPC3 immunoconjugate comprising a label) to preferentially concentrate at sites in the individual where GPC3 is expressed (e.g., GPC3-positive tumor site, and for unbound labeled anti-GPC3 antibody moiety to be cleared). In some embodiments, the method further comprises subtracting a background level of the label. Background level can be determined by various methods, including, for example, by detecting the label in the individual prior to administration of the labeled anti-GPC3 antibody moiety (e.g., anti-GPC3 immunoconjugate comprising a label), or by detecting the label according to the method of diagnosing described above in an individual that does not have the disease or disorder. In some embodiments, the individual is human.

In some embodiments, there is provided a method of diagnosing a disease or disorder associated with expression or aberrant expression of GPC3 in an individual (e.g., a mammal, such as a human), comprising (a) contacting a labeled anti-GPC3 antibody moiety (e.g., anti-GPC3 immunoconjugate comprising a label) according to any of the embodiments described above with a sample (such as whole blood or homogenized tissue) derived from the individual; and (b) determining the number of cells bound with the labeled anti-GPC3 antibody moiety in the sample, such that a value for the number of cells bound with the labeled anti-GPC3 antibody moiety above a threshold level indicates that the individual has the disease or disorder. In some embodiments, the disease or disorder is cancer. In some embodiments, the cancer is selected, for example, from the group consisting of HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, and liposarcoma. In some embodiments, the cancer is HCC. In some embodiments, the cancer is metastatic HCC, and the sample is a blood sample (such as whole blood). In some embodiments, the cancer is metastatic HCC. In some embodiments, there is provided a method of diagnosing HCC (e.g., metastatic HCC) in an individual (e.g., a mammal, such as a human), comprising (a) contacting a labeled anti-GPC3 antibody moiety according to any of the embodiments described above with a sample (such as whole blood) derived from the individual; and (b) determining the number of cells bound with the labeled anti-GPC3 antibody moiety in the sample, such that a value for the number of cells bound with the labeled anti-GPC3 antibody moiety above a threshold level indicates that the individual has HCC (e.g., metastatic HCC). The threshold level can be determined by various methods, including, for example, by determining the number of cells bound with the labeled anti-GPC3 antibody moiety according to the method of diagnosing described above in a first set of individuals that have the disease or disorder and a second set of individuals that do not have the disease or disorder, and setting the threshold to a level that allows for discrimination between the first and second sets. In some embodiments, the threshold level is zero, and the method comprises determining the presence or absence of cells bound with the labeled anti-GPC3 antibody moiety in the sample. In some embodiments, the method further comprises subtracting a background level of the number of cells bound with the labeled anti-GPC3 antibody moiety. Background level can be determined by various methods, including, for example, by determining the number of cells bound with the labeled anti-GPC3 antibody moiety in the individual prior to administration of the labeled anti-GPC3 antibody moiety, or by determining the number of cells bound with the labeled anti-GPC3 antibody moiety according to the method of diagnosing described above in an individual that does not have the disease or disorder. In some embodiments, the individual is human.

Anti-GPC3 antibody moieties of the invention can be used to assay levels of GPC3 in a biological sample using methods known to those of skill in the art. Suitable antibody labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), samarium ($^{153}$Sm), lutetium ($^{177}$Lu), gadolinium ($^{159}$Gd), promethium ($^{149}$Pm), lanthanum ($^{140}$La), ytterbium ($^{175}$Yb), holmium ($^{166}$Ho), yttrium ($^{90}$Y), scandium ($^{47}$Sc), rhenium ($^{186}$Re, $^{188}$Re), praseodymium ($^{142}$Pr), rhodium ($^{105}$Rh), and ruthenium ($^{97}$Ru); luminol; fluorescent labels, such as fluorescein and rhodamine; and biotin.

Techniques known in the art may be applied to labeled anti-GPC3 antibody moieties (e.g., anti-GPC3 immunoconjugate comprising a label) of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003). Aside from the above assays, various in vivo and ex vivo assays are available to the skilled practitioner. For example, one can expose cells within the body of the subject to an anti-GPC3 antibody moiety which is optionally labeled with a detectable label, e.g., a radioactive isotope, and binding of the anti-GPC3 antibody moiety to the cells can be evaluated, e.g., by external scanning for radioactivity or by analyzing a sample (e.g., a biopsy or other biological sample) derived from a subject previously exposed to the anti-GPC3 antibody moiety.

Articles of Manufacture and Kits

In some embodiments of the invention, there is provided an article of manufacture containing materials useful for the treatment of an GPC3-positive disease such as cancer (for example HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma), for delivering an anti-GPC3 construct (such as an isolated anti-GPC3 construct) to a cell expressing GPC3 on its surface, or for isolation or detection of cells expressing GPC3 on cell surface, or for isolation or detection of soluble GPC3 in an individual. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein and may have a sterile access port (for example the container may be an intravenous solution bag or a vial having a stopper pierceable by a hypodermic injection needle). At least one active agent in the composition is an anti-GPC3 construct of the invention. The label or package insert indicates that the composition is used for treating the particular condition. The label or package insert will further comprise instructions for administering the anti-GPC3 construct composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating cancer (such as HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma).

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of an GPC3-positive disease or disorder described herein, for delivering an anti-GPC3 construct (such as an isolated anti-GPC3 construct) to a cell expressing GPC3 on its surface, or for isolation or detection of cells expressing GPC3 on cell surface, or for isolation or detection of soluble GPC3 in an individual, optionally in combination with the articles of manufacture. Kits of the invention include one or more containers comprising an anti-GPC3 construct composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an anti-GPC3 construct (such as an isolated anti-GPC3 construct, e.g., an anti-GPC3 scFv, a full-length anti-GPC3 antibody, a multi-specific anti-GPC3 molecule (such as a bispecific anti-GPC3 antibody), or an anti-GPC3 immunoconjugate). In some embodiments, the kit comprises a) a composition comprising an anti-GPC3 construct, and b) an effective amount of at least one other agent, wherein the other agent enhances the effect (e.g., treatment effect, detecting effect) of the anti-GPC3 construct. In some embodiments, the kit comprises a) a composition comprising an anti-GPC3 construct, and b) instructions for administering the anti-GPC3 construct composition to an individual for treatment of an GPC3-positive disease, such as HCC. In some embodiments, the kit comprises a) a composition comprising an anti-GPC3 construct, b) an effective amount of at least one other agent, wherein the other agent enhances the effect (e.g., treatment effect, detecting effect) of the anti-GPC3 construct, and c) instructions for administering the anti-GPC3 construct composition and the other agent(s) to an individual for treatment of an GPC3-positive disease, such as HCC. The anti-GPC3 construct and the other agent(s) can be present in separate containers or in a single container. For example, the kit may comprise one distinct composition or two or more compositions wherein one composition comprises an anti-GPC3 construct and another composition comprises another agent.

In some embodiments, the kit comprises a) a composition comprising an anti-GPC3 construct (such as an isolated anti-GPC3 construct, e.g., an anti-GPC3 scFv, a full-length anti-GPC3 antibody, a multi-specific anti-GPC3 molecule (such as a bispecific anti-GPC3 antibody), or an anti-GPC3 immunoconjugate), and b) instructions for combining the anti-GPC3 construct with cells (such as effector cells, e.g., immune cells, derived from an individual, CAR-T cell, or caTCR-T cell) to form a composition comprising anti-GPC3 construct/cell conjugates and administering the anti-GPC3 construct/cell conjugate composition to the individual for treatment of an GPC3-positive disease (such as HCC). In some embodiments, the kit comprises a) a composition comprising an anti-GPC3 construct, and b) a cell (such as a cytotoxic cell, e.g., cytotoxic T cell, CAR-T cell, or caTCR-T cell). In some embodiments, the kit comprises a) a composition comprising an anti-GPC3 construct, b) a cell (such as a cytotoxic cell, e.g., cytotoxic T cell, CAR-T cell, or caTCR-T cell), and c) instructions for combining the anti-GPC3 construct with the cell to form a composition comprising anti-GPC3 construct/cell conjugates and administering the anti-GPC3 construct/cell conjugate composition to an individual for the treatment of an GPC3-positive disease, such as HCC. In some embodiments, the kit comprises a composition comprising an anti-GPC3 construct in association with a cell (such as a cytotoxic cell, e.g., cytotoxic T cell, CAR-T cell, or caTCR-T cell). In some embodiments, the kit comprises a) a composition comprising an anti-GPC3 construct in association with a cell (such as a cytotoxic cell, e.g., cytotoxic T cell, CAR-T cell, or caTCR-T cell), and b) instructions for administering the composition to an individual for the treatment of an GPC3-positive disease, such as HCC. In some embodiments, the association is by conjugation of the anti-GPC3 construct to a molecule on the surface of the cell. In some embodiments, the association is by insertion of a portion of the anti-GPC3 construct (e.g., anti-GPC3 CAR, anti-GPC3 caTCR) into the outer membrane of the cell.

In some embodiments, the kit comprises a nucleic acid (or set of nucleic acids) encoding an anti-GPC3 construct (such as an isolated anti-GPC3 construct, e.g., an anti-GPC3 scFv, a full-length anti-GPC3 antibody, a multi-specific anti-GPC3 molecule (such as a bispecific anti-GPC3 antibody), an anti-GPC3 CAR, an anti-GPC3caTCR, or an anti-GPC3 immunoconjugate) or polypeptide portions thereof. In some embodiments, the kit comprises a) a nucleic acid (or set of nucleic acids) encoding an anti-GPC3 construct (e.g., anti-GPC3×CD3 tandem di-scFv T cell engager) or polypeptide portions thereof, and b) a host cell (such as an effector cell, e.g., T cell, CAR-T cell, or caTCR-T cell) for expressing the nucleic acid (or set of nucleic acids). In some embodiments, the kit comprises a) a nucleic acid (or set of nucleic acids) encoding an anti-GPC3 construct (e.g., anti-GPC3×CD3 tandem di-scFv T cell engager) or polypeptide portions thereof, and b) instructions for i) expressing the anti-GPC3 construct in a host cell (such as an effector cell, e.g., a T cell, CAR-T cell, or caTCR-T cell), ii) preparing a composition comprising the anti-GPC3 construct or the host cell expressing the anti-GPC3 construct, and iii) administering the composition comprising the anti-GPC3 construct or the host cell expressing the anti-GPC3 construct to an individual for the treatment of an GPC3-positive disease, such as HCC. In some embodiments, the host cell is derived from the individual. In some embodiments, the kit comprises a) a nucleic acid (or set of nucleic acids) encoding an anti-GPC3 construct (e.g., anti-GPC3×CD3 tandem di-scFv T cell engager) or polypeptide portions thereof, b) a host cell (such as an effector cell, e.g., T cell, CAR-T cell, or caTCR-T cell) for expressing the nucleic acid (or set of nucleic acids), and c) instructions for i) expressing the anti-GPC3 construct in the host cell, ii) preparing a composition comprising the anti-GPC3 construct or the host cell expressing the anti-GPC3 construct, and iii) administering the composition comprising the anti-GPC3 construct or the host cell expressing the anti-GPC3 construct to an individual for the treatment of an GPC3-positive disease, such as HCC. In some embodiments, the expression of the anti-GPC3 construct (e.g., anti-GPC3×CD3 tandem di-scFv T cell engager) or polypeptide portions thereof is inducible. In some embodiments, the nucleic acid (or set of nucleic acids) encoding an anti-GPC3 construct (e.g., anti-GPC3×CD3 tandem di-scFv T cell engager) or polypeptide portions thereof are under control of inducible promoter(s). In some embodiments, the expression of the anti-GPC3 construct (e.g., anti-GPC3× CD3 tandem di-scFv T cell engager) or polypeptide portions thereof in the effector cell (e.g., T cell, CAR-T cell, caTCR T cell) is inducible upon signaling through a signaling receptor on the effector cell (e.g., TCR, CAR, caTCR). For example, in some embodiments, the nucleic acid (or set of nucleic acids) encoding the anti-GPC3 construct (e.g., anti-GPC3×CD3 tandem di-scFv T cell engager) or polypeptide portions thereof are under control of inducible promoter(s) responsive to signaling through CAR on the CAR-T cell, upon introducing the nucleic acid (or set of nucleic acids) encoding the anti-GPC3 construct (e.g., anti-GPC3×CD3 tandem di-scFv T cell engager) or polypeptide portions thereof into the CAR-T cell, and introducing the composition comprising the anti-GPC3 construct or the host cell expressing the anti-GPC3 construct to an individual carrying GPC3-positive disease according to the kit instructions. In some embodiments, the nucleic acid (or set of nucleic acids) encoding the anti-GPC3 construct (e.g., anti-GPC3×CD3 tandem di-scFv T cell engager) or polypeptide portions thereof are under control of inducible promoter(s) responsive to signaling through caTCR on an caTCR-T cell, upon introducing the nucleic acid (or set of nucleic acids) encoding the anti-GPC3 construct (e.g., anti-GPC3×CD3 tandem di-scFv T cell engager) or polypeptide portions thereof into the caTCR-T cell, and introducing the composition comprising the anti-GPC3 construct or the host cell expressing the anti-GPC3 construct to an individual carrying GPC3-positive disease according to the kit instructions. In some embodiments, the nucleic acid (or set of nucleic acids) encoding the anti-GPC3 construct (e.g., anti-GPC3×CD3 tandem di-scFv T cell engager) or polypeptide portions thereof is operably linked to an NFAT-derived promoter. In some embodiments, the NFAT-derived promoter is an NFAT-derived minimal promoter. In some embodiments, the nucleic acid (or set of nucleic acids) encoding the anti-GPC3 construct (e.g., anti-GPC3×CD3 tandem di-scFv T cell engager) or polypeptide portions thereof is operably linked to an IL-2 promoter.

In some embodiments, the kit comprises a nucleic acid encoding an anti-GPC3 CAR. In some embodiments, the kit comprises a vector comprising a nucleic acid encoding an anti-GPC3 CAR. In some embodiments, the kit comprises a) a vector comprising a nucleic acid encoding an anti-GPC3 CAR, and b) instructions for i) introducing the vector into effector cells, such as T cells derived from an individual, ii)

preparing a composition comprising the anti-GPC3 CAR effector cells, and iii) administering the anti-GPC3 CAR effector cell composition to the individual for treatment of an GPC3-positive disease, such as HCC.

In some embodiments, the kit comprises a first nucleic acid encoding an anti-GPC3 CAR, and a second nucleic acid encoding a multi-specific (e.g., bispecific) anti-GPC3 molecule (e.g., anti-GPC3×CD3 tandem di-scFv T cell engager). In some embodiments, the kit comprises a first vector comprising a nucleic acid encoding an anti-GPC3 CAR, and a second vector comprising a nucleic acid encoding a multi-specific (e.g., bispecific) anti-GPC3 molecule (e.g., anti-GPC3×CD3 tandem di-scFv T cell engager). In some embodiments, the kit comprises a vector comprising a first nucleic acid encoding an anti-GPC3 CAR, and a second nucleic acid encoding a multi-specific (e.g., bispecific) anti-GPC3 molecule (e.g., anti-GPC3×CD3 tandem di-scFv T cell engager). In some embodiments, the kit comprises a) a first vector comprising a nucleic acid encoding an anti-GPC3 CAR, and a second vector comprising a nucleic acid encoding a multi-specific (e.g., bispecific) anti-GPC3 molecule (e.g., anti-GPC3×CD3 tandem di-scFv T cell engager), and b) instructions for i) introducing the vectors into effector cells, such as T cells derived from an individual, ii) preparing a composition comprising the anti-GPC3 CAR effector cells and the multi-specific (e.g., bispecific) anti-GPC3 molecule, and iii) administering the anti-GPC3 CAR effector cell and the multi-specific (e.g., bispecific) anti-GPC3 molecule composition to the individual for treatment of an GPC3-positive disease, such as HCC. In some embodiments, the kit comprises a) a vector comprising a first nucleic acid encoding an anti-GPC3 CAR, and a second nucleic acid encoding a multi-specific (e.g., bispecific) anti-GPC3 molecule (e.g., anti-GPC3×CD3 tandem di-scFv T cell engager), and b) instructions for i) introducing the vector into effector cells, such as T cells derived from an individual, ii) preparing a composition comprising the anti-GPC3 CAR effector cells and the multi-specific (e.g., bispecific) anti-GPC3 molecule, and iii) administering the anti-GPC3 CAR effector cell and the multi-specific (e.g., bispecific) anti-GPC3 molecule composition to the individual for treatment of an GPC3-positive disease, such as HCC. In some embodiments, the nucleic acid encoding the multi-specific (e.g., bispecific) anti-GPC3 molecule (e.g., anti-GPC3×CD3 tandem di-scFv T cell engager) is under control of an inducible promoter. In some embodiments, the expression of the multi-specific (e.g., bispecific) anti-GPC3 molecule (e.g., anti-GPC3×CD3 tandem di-scFv T cell engager) is inducible through the signaling of the anti-GPC3-CAR (e.g., in a GPC3-positive disease environment). In some embodiments, the nucleic acid encoding the multi-specific (e.g., bispecific) anti-GPC3 molecule (e.g., anti-GPC3×CD3 tandem di-scFv T cell engager) is under control of an NFAT-derived promoter. In some embodiments, the NFAT-derived promoter is an NFAT-derived minimal promoter. In some embodiments, the nucleic acid encoding the multi-specific (e.g., bispecific) anti-GPC3 molecule (e.g., anti-GPC3×CD3 tandem di-scFv T cell engager) is under control of an IL-2 promoter.

In some embodiments, the kit comprises a nucleic acid encoding an anti-GPC3 caTCR. In some embodiments, the kit comprises a vector comprising a nucleic acid encoding an anti-GPC3 caTCR. In some embodiments, the kit comprises a) a vector comprising a nucleic acid encoding an anti-GPC3 caTCR, and b) instructions for i) introducing the vector into effector cells, such as T cells derived from an individual, ii) preparing a composition comprising the anti-GPC3 caTCR effector cells, and iii) administering the anti-GPC3 caTCR effector cell composition to the individual for treatment of an GPC3-positive disease, such as HCC.

In some embodiments, the kit comprises a first nucleic acid encoding an anti-GPC3 caTCR, and a second nucleic acid encoding a multi-specific (e.g., bispecific) anti-GPC3 molecule (e.g., anti-GPC3×CD3 tandem di-scFv T cell engager). In some embodiments, the kit comprises a first vector comprising a nucleic acid encoding an anti-GPC3 caTCR, and a second vector comprising a nucleic acid encoding a multi-specific (e.g., bispecific) anti-GPC3 molecule (e.g., anti-GPC3×CD3 tandem di-scFv T cell engager). In some embodiments, the kit comprises a vector comprising a first nucleic acid encoding an anti-GPC3 caTCR, and a second nucleic acid encoding a multi-specific (e.g., bispecific) anti-GPC3 molecule (e.g., anti-GPC3×CD3 tandem di-scFv T cell engager). In some embodiments, the kit comprises a) a first vector comprising a nucleic acid encoding an anti-GPC3 caTCR, and a second vector comprising a nucleic acid encoding a multi-specific (e.g., bispecific) anti-GPC3 molecule (e.g., anti-GPC3×CD3 tandem di-scFv T cell engager), and b) instructions for i) introducing the vectors into effector cells, such as T cells derived from an individual, ii) preparing a composition comprising the anti-GPC3 caTCR effector cells and the multi-specific (e.g., bispecific) anti-GPC3 molecule, and iii) administering the anti-GPC3 caTCR effector cell and the multi-specific (e.g., bispecific) anti-GPC3 molecule composition to the individual for treatment of an GPC3-positive disease, such as HCC. In some embodiments, the kit comprises a) a vector comprising a first nucleic acid encoding an anti-GPC3 caTCR, and a second nucleic acid encoding a multi-specific (e.g., bispecific) anti-GPC3 molecule (e.g., anti-GPC3×CD3 tandem di-scFv T cell engager), and b) instructions for i) introducing the vector into effector cells, such as T cells derived from an individual, ii) preparing a composition comprising the anti-GPC3 caTCR effector cells and the multi-specific (e.g., bispecific) anti-GPC3 molecule, and iii) administering the anti-GPC3 caTCR effector cell and the multi-specific (e.g., bispecific) anti-GPC3 molecule composition to the individual for treatment of an GPC3-positive disease, such as HCC. In some embodiments, the nucleic acid encoding the multi-specific (e.g., bispecific) anti-GPC3 molecule (e.g., anti-GPC3×CD3 tandem di-scFv T cell engager) is under control of an inducible promoter. In some embodiments, the expression of the multi-specific (e.g., bispecific) anti-GPC3 molecule (e.g., anti-GPC3×CD3 tandem di-scFv T cell engager) is inducible through the signaling of the anti-GPC3 caTCR (e.g., in a GPC3-positive disease environment). In some embodiments, the nucleic acid encoding the multi-specific (e.g., bispecific) anti-GPC3 molecule (e.g., anti-GPC3×CD3 tandem di-scFv T cell engager) is under control of an NFAT-derived promoter. In some embodiments, the NFAT-derived promoter is an NFAT-derived minimal promoter. In some embodiments, the nucleic acid encoding the multi-specific (e.g., bispecific) anti-GPC3 molecule (e.g., anti-GPC3×CD3 tandem di-scFv T cell engager) is under control of an IL-2 promoter.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the anti-GPC3 construct compositions generally include information as to dosage, dosing schedule, and route of administration for the intended treatment. The containers may be unit doses, bulk packages (e.g., multi-dose packages) or subunit doses. For example, kits may be provided that contain sufficient dosages of an anti-GPC3 construct (such as an isolated anti-GPC3 construct, e.g., an anti-GPC3 scFv, a full-length anti-GPC3 antibody, a multi-specific anti-GPC3 molecule (such as a bispecific anti-GPC3 antibody), an anti-GPC3 CAR, an anti-GPC3 caTCR, or an anti-GPC3 immunoconjugate) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the anti-GPC3 construct and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXEMPLARY EMBODIMENTS

Embodiment 1. An isolated anti-Glypican 3 (GPC3) construct comprising an antibody moiety specifically recognizing a cell surface-bound GPC3.

Embodiment 2. The isolated anti-GPC3 construct of embodiment 1, wherein the antibody moiety specifically recognizes a cell surface-bound GPC3 at a high binding affinity and binds to a soluble GPC3 at a low binding affinity.

Embodiment 3. The isolated anti-GPC3 construct of embodiment 2, wherein the $K_d$ of the anti-GPC3 construct to the cell surface-bound GPC3 is about 0.1 nM to about 2 nM.

Embodiment 4. The isolated anti-GPC3 construct of embodiment 2 or 3, wherein the IC50 of a soluble GPC3 to compete binding between the anti-GPC3 construct and the cell surface-bound GPC3 is about 1 µg/ml to about 100 µg/ml.

Embodiment 5. The isolated anti-GPC3 construct of embodiment 1, wherein the antibody moiety specifically recognizes a cell surface-bound GPC3 at a low binding affinity, and binds to a soluble GPC3 at a high binding affinity.

Embodiment 6. The isolated anti-GPC3 construct of embodiment 5, wherein the $K_d$ of the anti-GPC3 construct to the cell surface-bound GPC3 is about 10 nM to about 100 nM.

Embodiment 7. The isolated anti-GPC3 construct of embodiment 5 or 6, wherein the IC50 of a soluble GPC3 to compete binding between the anti-GPC3 construct and the cell surface-bound GPC3 is about 0.01 µg/ml to about 1 µg/ml.

Embodiment 8. The isolated anti-GPC3 construct of any one of embodiments 3-7, wherein the cell surface-bound GPC3 is GPC3 expressed on HepG2 cells.

Embodiment 9. The isolated anti-GPC3 construct of any one of embodiments 1-8, wherein the cell surface-bound GPC3 comprises the amino acid sequence of SEQ ID NO: 460 or SEQ ID NO: 462.

Embodiment 10. The isolated anti-GPC3 construct of any one of embodiments 1-9, wherein the soluble GPC3 comprises the amino acid sequence of SEQ ID NO: 461 or SEQ ID NO: 463.

Embodiment 11. The isolated anti-GPC3 construct of any one of embodiments 1-10, wherein the antibody moiety specifically recognizes an epitope within human GPC3 comprising the amino acid sequence of SEQ ID NO: 460.

Embodiment 12. The isolated anti-GPC3 construct of embodiment 11, wherein the antibody moiety specifically recognizes an epitope within amino acids 1-560 of SEQ ID NO: 460 (SEQ ID NO: 461).

Embodiment 13. The isolated anti-GPC3 construct of embodiment 11, wherein the antibody moiety specifically recognizes an epitope within amino acids 25-580 of SEQ ID NO: 460 (SEQ ID NO: 462).

Embodiment 14. The isolated anti-GPC3 construct of embodiment 11 or 12, wherein the antibody moiety specifically recognizes an epitope within amino acids 25-560 of SEQ ID NO: 460 (SEQ ID NO: 463).

Embodiment 15. The isolated anti-GPC3 construct of any one of embodiments 1-15, wherein the antibody moiety specifically recognizes an epitope within the N-terminal fragment of GPC3.

Embodiment 16. The isolated anti-GPC3 construct of embodiment 15, wherein the antibody moiety specifically recognizes an epitope within amino acids 25-358 of SEQ ID NO: 460 (SEQ ID NO: 464).

Embodiment 17. The isolated anti-GPC3 construct of any one of embodiments 1-15, wherein the antibody moiety specifically recognizes an epitope within the C-terminal fragment of GPC3.

Embodiment 18. The isolated anti-GPC3 construct of embodiment 17, wherein the antibody moiety specifically recognizes an epitope within the C-terminal fragment of GPC3 lacking heparin sulfate side chain.

Embodiment 19. The isolated anti-GPC3 construct of any one of embodiments 1-18, wherein the antibody moiety does not specifically bind to the same or substantially the same GPC3 epitope competitively with GC33.

Embodiment 20. The isolated anti-GPC3 construct of embodiment 19, wherein the antibody moiety does not bind to an epitope within amino acids 524-565 of SEQ ID NO: 460 (SEQ ID NO: 536).

Embodiment 21. The isolated anti-GPC3 construct of embodiment 19 or 20, wherein the antibody moiety does not bind to a fragment comprising amino acids 524-565 of SEQ ID NO: 460 (SEQ ID NO: 536).

Embodiment 22. The isolated anti-GPC3 construct of any one of embodiments 1-21, wherein the GPC3 is expressed on the surface of a cell selected from the group consisting of HepG2, Hep3B, Huh7, JHH-7, and 293.

Embodiment 23. The isolated anti-GPC3 construct of any one of embodiments 1-22, wherein the GPC3 is expressed on the surface of a cancer cell.

Embodiment 24. The isolated anti-GPC3 construct of embodiment 23, wherein the cancer cell is a liver cancer cell.

Embodiment 25. The isolated anti-GPC3 construct of embodiment 24, wherein the cancer cell is hepatocellular carcinoma (HCC).

Embodiment 26. An isolated anti-GPC3 construct comprising an antibody moiety specifically recognizing a cell surface-bound GPC3, wherein the antibody moiety comprises: i) a heavy chain variable domain ($V_H$) comprising a heavy chain complementarity determining region (HC-CDR) 1 comprising the amino acid sequence of any one of SEQ ID NOs: 1-31, or a variant thereof comprising up to about 5 amino acid substitutions, an HC-CDR2 comprising the amino acid sequence of any one of SEQ ID NOs: 52-82, or a variant thereof comprising up to about 5 amino acid substitutions, and an HC-CDR3 comprising the amino acid sequence of any one of SEQ ID NOs: 103-133, or a variant thereof comprising up to about 5 amino acid substitutions; and ii) a light chain variable domain ($V_L$) comprising a light chain complementarity determining region (LC-CDR) 1 comprising the amino acid sequence of any one of SEQ ID NOs: 154-184, or a variant thereof comprising up to about 5 amino acid substitutions, an LC-CDR2 comprising the amino acid sequence of any one of SEQ ID NOs: 205-235, or a variant thereof comprising up to about 3 amino acid substitutions, and an LC-CDR3 comprising the amino acid sequence of any one of SEQ ID NOs: 256-286, or a variant thereof comprising up to about 5 amino acid substitution.

Embodiment 27. The isolated anti-GPC3 construct of embodiment 26, wherein the antibody moiety comprises: i) a $V_H$ comprising an HC-CDR1 comprising the amino acid sequence of any one of SEQ ID NOs: 1-31, an HC-CDR2 comprising the amino acid sequence of any one of SEQ ID NOs: 52-82, and an HC-CDR3 comprising the amino acid sequence of any one of SEQ ID NOs: 103-133; and ii) a $V_L$ comprising an LC-CDR1 comprising the amino acid sequence of any one of SEQ ID NOs: 154-184, an LC-CDR2 comprising the amino acid sequence of any one of SEQ ID NOs: 205-235, and an LC-CDR3 comprising the amino acid sequence of any one of SEQ ID NOs: 256-286.

Embodiment 28. The isolated anti-GPC3 construct of embodiment 26 or 27, wherein the antibody moiety comprises: i) a $V_H$ comprising the amino acid sequence of any one of SEQ ID NOs: 307-337, or a variant thereof having at least about 95% sequence identify to any one of SEQ ID NOs: 307-337; and ii) a $V_L$ comprising the amino acid sequence of any one of SEQ ID NOs: 358-388, or a variant thereof having at least about 95% sequence identity to any one of SEQ ID NOs: 358-388.

Embodiment 29. The isolated anti-GPC3 construct of embodiment 28, wherein the antibody moiety comprises: i) a $V_H$ comprising the amino acid sequence of any one of SEQ ID NOs: 307-337; and ii) a $V_L$ comprising the amino acid sequence of any one of SEQ ID NOs: 358-388.

Embodiment 30. An isolated anti-GPC3 construct comprising an antibody moiety specifically recognizing a cell surface-bound GPC3, wherein the antibody moiety comprises the HC-CDRs of $V_H$ comprising the amino acid sequence of any one of SEQ ID NOs: 307-337; and LC-CDRs of $V_L$ comprising the amino acid sequence of any one of SEQ ID Nos: 358-388.

Embodiment 31. An isolated anti-GPC3 construct comprising an antibody moiety specifically recognizing a cell surface-bound GPC3, wherein the antibody moiety comprises: i) a VH comprising the amino acid sequence of any one of SEQ ID NOs: 1-31, the amino acid sequence of any one of SEQ ID NOs: 52-82, and the amino acid sequence of any one of SEQ ID NOs: 103-133; and ii) a $V_L$ comprising the amino acid sequence of any one of SEQ ID NOs: 154-184, the amino acid sequence of any one of SEQ ID NOs: 205-235, and the amino acid sequence of any one of SEQ ID NOs: 256-286.

Embodiment 32. An isolated anti-GPC3 construct comprising an antibody moiety specifically recognizing GPC3, wherein the antibody moiety comprises: i) a $V_H$ comprising an HC-CDR1 comprising the amino acid sequence of any one of SEQ ID NOs: 32-51, or a variant thereof comprising up to about 5 amino acid substitutions, an HC-CDR2 comprising the amino acid sequence of any one of SEQ ID NOs: 83-102, or a variant thereof comprising up to about 5 amino acid substitutions, and an HC-CDR3 comprising the amino acid sequence of any one of SEQ ID NOs: 134-153, or a variant thereof comprising up to about 5 amino acid substitutions; and ii) a $V_L$ comprising an LC-CDR1 comprising the amino acid sequence of any one of SEQ ID NOs: 185-204, or a variant thereof comprising up to about 5 amino acid substitutions, an LC-CDR2 comprising the amino acid sequence of any one of SEQ ID NOs: 236-255, or a variant thereof comprising up to about 3 amino acid substitutions, and an LC-CDR3 comprising the amino acid sequence of any one of SEQ ID NOs: 287-306, or a variant thereof comprising up to about 5 amino acid substitutions.

Embodiment 33. The isolated anti-GPC3 construct of embodiment 32, wherein the antibody moiety comprises: i) a $V_H$ comprising an HC-CDR1 comprising the amino acid sequence of any one of SEQ ID NOs: 32-51, an HC-CDR2 comprising the amino acid sequence of any one of SEQ ID NOs: 83-102, and an HC-CDR3 comprising the amino acid sequence of any one of SEQ ID NOs: 134-153; and ii) a $V_L$ comprising an LC-CDR1 comprising the amino acid sequence of any one of SEQ ID NOs: 185-204, an LC-CDR2 comprising the amino acid sequence of any one of SEQ ID NOs: 236-255, and an LC-CDR3 comprising the amino acid sequence of any one of SEQ ID NOs: 287-306.

Embodiment 34. The isolated anti-GPC3 construct of embodiment 32 or 33, wherein the antibody moiety comprises: i) a $V_H$ comprising the amino acid sequence of any one of SEQ ID NOs: 338-357, or a variant thereof having at least about 95% sequence identify to any one of SEQ ID NOs: 338-357; and ii) a $V_L$ comprising the amino acid sequence of any one of SEQ ID NOs: 389-408, or a variant thereof having at least about 95% sequence identity to any one of SEQ ID NOs: 389-408.

Embodiment 35. The isolated anti-GPC3 construct of embodiment 34, wherein the antibody moiety comprises: i) a $V_H$ comprising the amino acid sequence of any one of SEQ ID NOs: 338-357; and ii) a $V_L$ comprising the amino acid sequence of any one of SEQ ID NOs: 389-408.

Embodiment 36. An isolated anti-GPC3 construct comprising an antibody moiety specifically recognizing GPC3, wherein the antibody moiety comprises the HC-CDRs of $V_H$ comprising the amino acid sequence of any one of SEQ ID NOs: 338-357; and LC-CDRs of $V_L$ comprising the amino acid sequence of any one of SEQ ID NOs: 389-408.

Embodiment 37. An isolated anti-GPC3 construct comprising an antibody moiety specifically recognizing a cell surface-bound GPC3, wherein the antibody moiety comprises: i) a VH comprising the amino acid sequence of any one of SEQ ID NOs: 32-51, the amino acid sequence of any one of SEQ ID NOs: 83-102, and the amino acid sequence of any one of SEQ ID NOs: 134-153; and ii) a $V_L$ comprising the amino acid sequence of any one of SEQ ID NOs: 185-204, the amino acid sequence of any one of SEQ ID NOs: 236-255, and the amino acid sequence of any one of SEQ ID NOs: 287-306.

Embodiment 38. An isolated anti-GPC3 construct comprising an antibody moiety that specifically binds to GPC3 competitively with the isolated anti-GPC3 construct of any one of embodiments 1-37.

Embodiment 39. An isolated anti-GPC3 construct comprising an antibody moiety that specifically binds to the same, or substantially the same, GPC3 epitope competitively with the isolated anti-GPC3 construct of any one of embodiments 1-37.

Embodiment 40. The isolated anti-GPC3 construct of any one of embodiments 1-39, wherein the antibody moiety specifically recognizing GPC3 is chimeric, human, partially humanized, fully humanized, or semi-synthetic.

Embodiment 41. The isolated anti-GPC3 construct of any one of embodiments 1-40, wherein the antibody moiety specifically recognizing GPC3 is a full-length antibody, a Fab, a Fab', a F(ab')2, an Fv, or a single chain Fv (scFv).

Embodiment 42. The isolated anti-GPC3 construct of embodiment 41, wherein the antibody moiety specifically recognizing GPC3 is an scFv.

Embodiment 43. The isolated anti-GPC3 construct of embodiment 41, wherein the antibody moiety specifically recognizing GPC3 is a Fab or Fab'.

Embodiment 44. The isolated anti-GPC3 construct of any one of embodiments 1-43, wherein the antibody moiety specifically recognizing GPC3 is fused to an Fc fragment optionally via a linker.

Embodiment 45. The isolated anti-GPC3 construct of embodiment 44, wherein the Fc fragment is an IgG1 Fc fragment.

Embodiment 46. The isolated anti-GPC3 construct of any one of embodiments 1-40 and 44-45, wherein the isolated anti-GPC3 construct is a full-length antibody.

Embodiment 47. The isolated anti-GPC3 construct of any one of embodiments 1-46, wherein the isolated anti-GPC3 construct is monospecific.

Embodiment 48. The isolated anti-GPC3 construct of any one of embodiments 1-46, wherein the isolated anti-GPC3 construct is multispecific.

Embodiment 49. The isolated anti-GPC3 construct of embodiment 48, wherein the isolated anti-GPC3 construct is bispecific.

Embodiment 50. The isolated anti-GPC3 construct of embodiment 48 or 49, wherein the isolated anti-GPC3 construct is a tandem scFv, a diabody (Db), a single chain diabody (scDb), a dual-affinity retargeting (DART) antibody, a F(ab')2, a dual variable domain (DVD) antibody, a knob-into-hole (KiH) antibody, a dock and lock (DNL) antibody, a chemically cross-linked antibody, a heteromultimeric antibody, or a heteroconjugate antibody.

Embodiment 51. The isolated anti-GPC3 construct of embodiment 50, wherein the isolated anti-GPC3 construct is a tandem scFv comprising two scFvs linked by a peptide linker.

Embodiment 52. The isolated anti-GPC3 construct of embodiment 51, wherein the peptide linker comprises the amino acid sequence of TSGGGS (SEQ ID NO: 474).

Embodiment 53. The isolated anti-GPC3 construct of any one of embodiments 48-52, wherein the isolated anti-GPC3 construct further comprises a second antibody moiety specifically recognizing a second antigen.

Embodiment 54. The isolated anti-GPC3 construct of embodiment 53, wherein the second antigen is an antigen on the surface of a T cell.

Embodiment 55. The isolated anti-GPC3 construct of embodiment 54, wherein the second antigen is selected from the group consisting of CD3γ, CD3δ, CD3ε, CD3ζ, CD28, OX40, GITR, CD137, CD27, CD40L, and HVEM.

Embodiment 56. The isolated anti-GPC3 construct of embodiment 55, wherein the second antigen is CD3ε.

Embodiment 57. The isolated anti-GPC3 construct of embodiment 56, wherein the isolated anti-GPC3 construct is a tandem scFv comprising an N-terminal scFv specifically recognizing GPC3 and a C-terminal scFv specifically recognizing CD3ε.

Embodiment 58. The isolated anti-GPC3 construct of embodiment 53, wherein the second antigen is an antigen on the surface of a B cell, a natural killer cell, a dendritic cell, a macrophage, a monocyte, or a neutrophil.

Embodiment 59. The isolated anti-GPC3 construct of any one of embodiments 1-43, wherein the isolated anti-GPC3 construct is a chimeric antigen receptor (CAR) comprising: (a) an extracellular domain comprising the antibody moiety; (b) a transmembrane domain; and (c) an intracellular signaling domain.

Embodiment 60. The isolated anti-GPC3 construct of embodiment 59, wherein the intracellular signaling domain comprises a CD3ζ intracellular signaling sequence and a CD28 intracellular signaling sequence.

Embodiment 61. The isolated anti-GPC3 construct of any one of embodiments 1-43, wherein the isolated anti-GPC3 construct is a chimeric antibody-T cell receptor (TCR) construct (caTCR) comprising: (a) an extracellular domain comprising the antibody moiety; and (b) a T cell receptor module (TCRM) comprising a first TCR domain (TCRD) comprising a first TCR transmembrane domain (TCR-TM) and a second TCRD comprising a second TCR-TM, wherein the TCRM facilitates recruitment of at least one TCR-associated signaling molecule.

Embodiment 62. The isolated anti-GPC3 construct of embodiment 61, wherein the first TCR-TM is derived from one of the transmembrane domains of a first naturally occurring TCR and the second TCR-TM is derived from the other transmembrane domain of the first naturally occurring TCR.

Embodiment 63. The isolated anti-GPC3 construct of embodiment 61, wherein the at least one of the TCR-TMs is non-naturally occurring.

Embodiment 64. The isolated anti-GPC3 construct of embodiment 63, wherein the TCRM allows for enhanced recruitment of the at least one TCR-associated signaling molecule as compared to a TCRM comprising the first naturally occurring T cell receptor transmembrane domains.

Embodiment 65. The isolated anti-GPC3 construct of embodiment 62, wherein the first naturally occurring TCR is a γ/δ TCR.

Embodiment 66. The isolated anti-GPC3 construct of embodiment 62, wherein the first naturally occurring TCR is an α/β TCR.

Embodiment 67. The isolated anti-GPC3 construct of any one of embodiments 61-66, wherein the TCR-associated signaling molecule is selected from the group consisting of CD3δε, CD3γε, and ζζ.

Embodiment 68. The isolated anti-GPC3 construct of any one of embodiments 1-58, wherein the isolated anti-GPC3 construct is an immunoconjugate comprising the antibody moiety and an effector molecule.

Embodiment 69. The isolated anti-GPC3 construct of embodiment 68, wherein the effector molecule is a therapeutic agent selected from the group consisting of a drug, a toxin, a radioisotope, a protein, a peptide, and a nucleic acid.

Embodiment 70. The isolated anti-GPC3 construct of embodiment 69, wherein therapeutic agent is a drug or a toxin.

Embodiment 71. The isolated anti-GPC3 construct of embodiment 68, wherein the effector molecule is a label.

Embodiment 72. An isolated nucleic acid encoding the polypeptide components of the isolated anti-GPC3 construct of any one of embodiments 1-71.

Embodiment 73. A vector comprising the isolated nucleic acid of embodiment 72.

Embodiment 74. An isolated host cell comprising the anti-GPC3 construct of any one of embodiments 1-71, isolated nucleic acid of embodiment 72, or the vector of 73.

Embodiment 75. An effector cell expressing the isolated anti-GPC3 construct of any one of embodiments 53-67.

Embodiment 76. The effector cell of embodiment 75, wherein the effector cell is a T cell.

Embodiment 77. The effector cell of embodiment 76, wherein the T cell is selected from the group consisting of a cytotoxic T cell, a helper T cell, and a natural killer T cell.

Embodiment 78. The effector cell of any one of embodiments 75-77, wherein the expression of the anti-GPC3 construct is induced by activation of the effector cell.

Embodiment 79. The effector cell of any one of embodiments 75-78, wherein the effector cell further comprises a chimeric antibody-T cell receptor (TCR) construct (caTCR).

Embodiment 80. A pharmaceutical composition comprising the isolated anti-GPC3 construct of any one of embodiments 1-71 or the effector cell of any one of embodiments 75-79, and a pharmaceutically acceptable carrier.

Embodiment 81. A kit comprising the isolated anti-GPC3 construct of any one of embodiments 1-71, the isolated nucleic acid of embodiment 72, the vector of embodiment 73, the isolated host cell of embodiment 74, the effector cell of any one of embodiments 75-79, or the pharmaceutical composition of embodiment 80.

Embodiment 82. A method of detecting GPC3 in a sample, comprising contacting the sample with the isolated anti-GPC3 construct of embodiment 71 and detecting the presence of the label.

Embodiment 83. The method of embodiment 82, wherein the sample comprises cells with cell surface-bound GPC3.

Embodiment 84. The method of embodiment 83, wherein the sample comprises soluble GPC3.

Embodiment 85. A method of treating an individual having a GPC3-positive disease, comprising administering to the individual an effective amount of the pharmaceutical composition of embodiment 80.

Embodiment 86. The method of embodiment 85, wherein the administration is via intravenous or intratumoral route.

Embodiment 87. The method of embodiment 85, wherein the administration is to an injection site distal to a first disease site.

Embodiment 88. The method of any one of embodiments 85-87, further comprising administering to the individual an additional therapy.

Embodiment 89. A method of diagnosing an individual having a GPC3-positive disease, comprising: a) administering an effective amount of the isolated anti-GPC3 construct of embodiment 71 to the individual; and b) determining the level of the label in the individual, wherein a level of the label above a threshold level indicates that the individual has the GPC3-positive disease.

Embodiment 90. A method of diagnosing an individual having an GPC3-positive disease, comprising: a) contacting a sample derived from the individual with the isolated anti-GPC3 construct of embodiment 71; and b) determining the number of cells bound with the isolated anti-GPC3 construct in the sample, wherein a value for the number of cells bound with the isolated anti-GPC3 construct above a threshold level indicates that the individual has the GPC3-positive disease.

Embodiment 91. The method of any one of embodiments 85-90, wherein the GPC3-positive disease is cancer.

Embodiment 92. The method of embodiment 91, wherein the cancer is selected from the group consisting of HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, and liposarcoma.

Embodiment 93. The method of embodiment 92, wherein the cancer is HCC.

Embodiment 94. The method of embodiment 93, wherein the cancer is metastatic HCC.

Embodiment 95. A method of producing an isolated anti-GPC3 construct, comprising: (a) culturing a host cell comprising the isolated nucleic acid of embodiment 72 or the vector of embodiment 73, or the isolated host cell of embodiment 74 under conditions effective to express the anti-GPC3 construct; and (b) obtaining the expressed anti-GPC3 construct from said host cell.

Embodiment 96. The method of embodiment 95, wherein step (a) further comprises producing a host cell comprising the isolated nucleic acid or the vector.

EXAMPLES

Materials and Methods

Cell lines HepG2 and SK-Hep1 were obtained from the American Type Culture Collection. HepG2 is human hepatocellular carcinoma cell line (ATCC HB-8065). SK-Hep1 is a liver endothelial adenocarcinoma cell line (ATCC HTB-52). Cell lines were cultured in RPMI 1640 or DMEM supplemented with 10% FBS at 37° C./5% $CO_2$.

FITC-labeled anti-His antibody was purchased from Thermo Fisher Scientific (Cat MA1-81891) for detection of bispecific anti-GPC3 T cell engager antibody described herein, which bears a 6xHis tag at the C-terminus.

GC33 is a monoclonal antibody derived from mice immunized with a human C-terminal GPC3 fragment consisting of amino acids 524-565 (Ishiguro et al., Cancer Res 2008; 68:9832-9838). The GC33 antibody used in FIG. 7B was purchased from Roche Diagnostics (Cat. 790-4564).

Generation of Recombinant Human GPC3 Fragments

The recombinant human $GPC3_{(560)}$ protein comprises amino acids 1-560 of the full-length human GPC3 precursor protein (SEQ ID NO: 461), which comprises the extracellular domain of human GPC3 lacking the GPI anchor site, and further fused at its C-terminus a 6xHis tag. The recombinant human $GPC3_{(560)}$ protein was expressed from the lentiviral vector pCDH EF1-MCS (System Biosciences).

Biotinylated $GPC3_{(560)}$ (bt-$GPC3_{(560)}$) was prepared according to standard protocols (Altman, J. D. & Davis, M. M., Current Protocols in Immunology 17.3.1-17.3.33, 2003). Briefly, DNA encoding the BirA substrate peptide (BSP) was ligated to the C-terminus of the recombinant human $GPC3_{(560)}$ protein (SEQ ID NO: 461) and cloned into vector pET-27b, transformed into E. coli BL21 cells, then isolated as inclusion bodies from bacterial culture. $GPC3_{(560)}$-BSP protein was concentrated by ultrafiltration and further purified through size-exclusion chromatography. $GPC3_{(560)}$-BSP peptide was then biotinylated via BirA-mediated enzymatic reaction and subsequently purified by high-resolution anion-exchange chromatography.

The GPC3-51mer fragment represents amino acids 510-560 of the full-length human GPC3 precursor protein (SEQ ID NO: 467), this peptide and the biotinylated form of the peptide was synthesized by Elim Biopharmaceuticals.

Generation of SK-Hep1-GPC3 Cells

SK-Hep1 cells over-expressing GPC3 protein were made by Eureka Therapeutics using full-length human GPC3 (SEQ ID NO: 460) carried on a lentivirus vector (pCDH EF1-MCS, System Biosciences), referred to herein as "SK-Hep1-GPC3".

Generation of HepG2 GPC3 Knockout (HepG2-GPC3-KO) Cells

HepG2 GPC3 knock out cell lines HepG2-GPC3-KO-2, KO-3, and KO-11 were generated using a commercial CRISPR-Cas9 vector as described (lentiCRISPR-V2, Ori-Gene; Sanjana et al., Nat Methods. 2014; 11:783-784). GPC3-specific guide RNA (gRNA) sequences were cloned into the lentiCRISPR-V2 backbone and the vector was used to transform Stbl3 bacteria. Positive clones were sequenced and transfected into HEK 293FT cells to create GPC3-CRISPR lentivirus. HepG2 cells were infected and cultured under selection for 2 weeks and measured for GPC3 expression by FACS analysis.

FACS Analysis

FACS was performed using a commercial mouse anti-human GPC3 antibody (1G12, Santa Cruz Biotech sc-65443), which binds to the C-terminal portion of GPC3. 50 µl of IG12 antibody was diluted 50, 100 and 200 times in PBS plus 5% FBS and incubated for one hour at 4° C. with GPC3+ HepG2 cells. The cells were washed in PBS and a PE-conjugated mouse anti-IgG secondary antibody (Vector Labs #EI-2007) was added at a 1:200 dilution in PBS with 5% FBS and incubated for another 30 minutes at 4° C. in the dark. The cells were washed twice with PBS and fixed.

FACS analysis results are summarized in FIG. 8. All 13 HepG2-GPC3-KO cell lines generated were negative for anti-hGPC3 antibody (1G12) binding, demonstrating successful knockout of GPC3 expression in HepG2 cells. Sequencing analysis further confirmed that HepG2-GPC3-KO cell lines KO #2, KO #3, and KO #11 were GPC3 negative. Of the 13 HepG2-GPC3-KO cell lines, HepG2-GPC3-KO-2, HepG2-GPC3-KO-3, and HepG2-GPC3-KO-11 cell lines were used for further study.

Panning of Phage Display Libraries

Eureka Therapeutics E-ALPHA™ phage library (human scFv phage library) was screened by panning for GPC3 reactive phage clones. Isolation and FACS analysis of phage clones were performed with the following reagents: mouse anti-M13 mAb (Thermo Fisher Scientific (#MA1-12900), PE-anti-mouse IgG (Vector Labs (#EI-2007) and fixation buffer (Biolegend #420801). Control mouse anti-GPC3 antibody (Clone 1G12) was purchased from Santa Cruz Biotech (#SC-65443).

ELISA Panning

ELISA panning was performed in 96-well plates coated with streptavidin, blocked and coated with biotinylated GPC3 peptide target (bt-GPC3$_{(560)}$ or bt-GPC3-51mer), then incubated with the phage library (with human scFv expressed on the phage capsid). After washing away unbound phages, the bound phages were eluted, amplified and re-panned over the course of several rounds of selection. ELISA-panned clones were then screened for binding to GPC3-expressing HepG2 cells.

Bead Panning

Bead panning was performed on DYNABEADS® coated with streptavidin and bt-GPC3-51mer peptide. The phage library was added for incubation. After washing away unbound phages, the bead-bound phages were eluted with trypsin and put through several rounds of bead-GPC3-51mer incubation, washing and elution. Positive phage clones were further tested for binding to GPC3+ HepG2 cells and GPC3− HepG2-GPC3-KO cells.

Cell Panning

Cell panning was performed by incubating phage clones with GPC3 expressing SK-Hep1-GPC3 cells in suspension. Unbound phages were removed by washing. Cells with bound phages were incubated with mouse anti-M13 antibody followed by PE-conjugated anti-mouse secondary antibody, then confirmed by flow cytometry. The phage clones selected against SK-Hep1-GPC3 cells were further screened against GPC3+ HepG2 cells and GPC3− HepG2-GPC3-KO cells.

Example 1. Generation and Selection of Human Antibody Constructs Specific for Human GPC3

This example demonstrates the production of human antibody constructs specific for human GPC3 (hGPC3). In particular, this example demonstrates the production of human scFvs that specifically bind to human GPC3 in native format (cell surface-bound GPC3). Human antibody constructs described herein were developed using naïve or semi-synthetic human antibody libraries generated from normal donors and/or autoimmune disease donors and were selected based on high specificity for human GPC3 via panning against cell surface-bound human GPC3 in its native conformation. Thus, these human anti-GPC3 antibody constructs (e.g., anti-GPC3 scFv) provide a valuable source of antibody components for the construction of, e.g., full-length IgG, multi-specific anti-GPC3 antibody molecules, anti-GPC3 CARs, or anti-GPC3 caTCRs.

An exemplary outline for the development of anti-human GPC3 constructs is set forth in Table 3. The process started with identification of human GPC3-specific and biologically active antibody constructs from Eureka Therapeutics E-ALPHA™ phage library.

TABLE 3

| Stage | Methodology |
| --- | --- |
| Primary panning with E-ALPHA ™ phage library | Cell Panning, ELISA Panning |
| | FACS screening of phage clones |
| Clone Characterization | Binding to HepG2 cells |
| | Target cancer cell killing |
| | Human liver cancer cell binding |
| | Screen against GPC3 knockout cell line |
| Creation of bispecific antibodies | Cloning of hGPC3-specific phage clones and anti-CDε scFvs into an expression vector |

A collection of human scFv antibody phage display libraries (diversity=10×10$^{10}$) constructed at Eureka Therapeutics (trademarked as E-ALPHA™ phage libraries) was used for the selection of human antibody constructs (e.g., scFv) specific for human GPC3. E-ALPHA™ phage libraries included naïve libraries comprising fully naïve human heavy and light chain repertoires, and semi-synthetic libraries containing fully naïve human light chain repertoires and semi-synthetic heavy chain with completely randomized heavy chain CDR3 regions. The naïve antibody repertoires were cloned from PBMCs and spleens of healthy donors or from PBMCs of autoimmune disease (such as systemic lupus erythematosus and rheumatoid arthritis) donors.

Panning Strategies and Phage Library Screening Against Cell Surface-Bound GPC3 (GPC3A)

Panning Against GPC3+ Cells

The E-APLPHA™ scFv phage libraries were screened (panned) against human GPC3 by co-incubation with recombinant GPC3-expressing SK-Hep1 cells (SK-Hep1-GPC3), then confirmed by binding to GPC3+ HepG2 cells, both with flow cytometry (see Methods). 0.2 million SK-Hep1-GPC3 cells were co-incubated with the phage library (about 1×10⁷ pfu) for 1 hours at 4° C. The cell/phage mixture was washed in PBST, incubated with mouse anti-M13 antibody for 1 hour at 4° C., washed again in PBST, then incubated for 30 minutes in the dark at 4° C. with PE-conjugated anti-mouse IgG, and subjected to FACS analysis.

The 36 positive clones from the initial SK-Hep1-GPC3 screen were further validated for cell surface hGPC3 binding against the GPC3+ HepG2 cell line using the same procedure. 33 phage clones demonstrated specific binding to GPC3⁺ HepG2 cells (Table 4) using FACS analysis. FACS was performed as described in Methods. Briefly, a commercial mouse anti-human GPC3 antibody (1G12, Santa Cruz Biotech sc-65443) was diluted and incubated for one hour at 4° C. with GPC3+ HepG2 cells. The cells were washed in PBS and a PE-conjugated mouse anti-IgG secondary antibody (Vector Labs #EI-2007) was added and incubated for another 30 minutes at 4° C. in the dark. Then cells were washed with PBS and fixed. FACS analysis of 14 exemplary GPC3⁺ HepG2 bound clones is shown in FIGS. 1A-1G, demonstrating strong cell surface-bound GPC3 binding. Helper phages were also used for incubation with GPC3+ HepG2 cells, serving as a control.

Figure 2A:
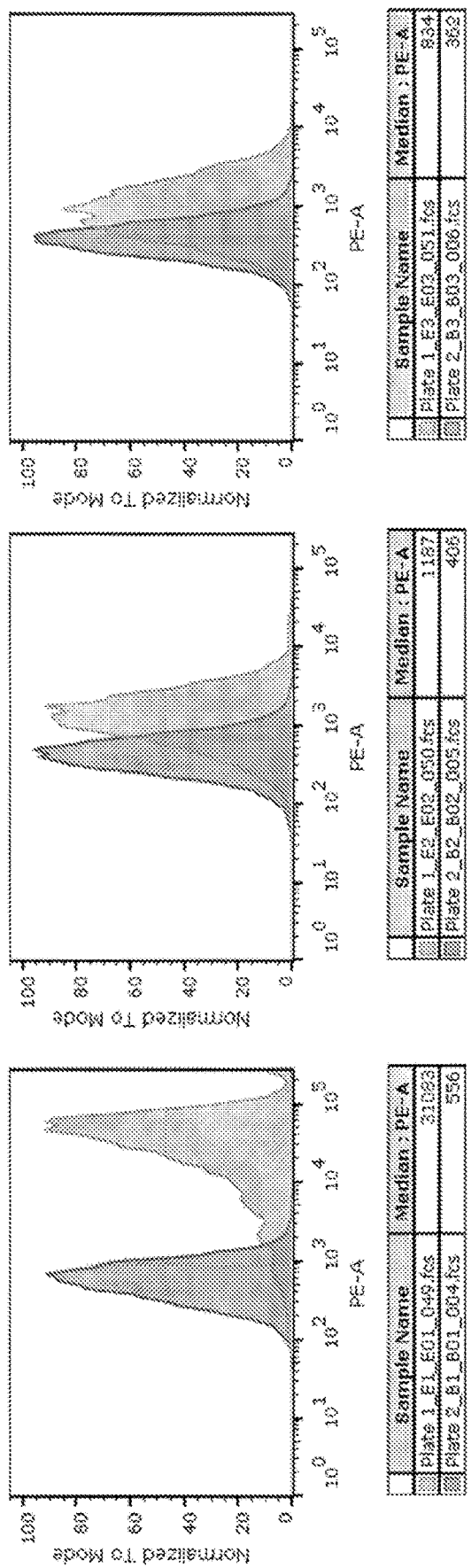
FIGS. 2A-2E show FACS analysis of the binding of 5 exemplary GPC3A phage clones to GPC3$^+$ HepG2 cell line and HepG2 GPC3-knockout cell lines (HepG2-GPC3-KO-2 and HepG2-GPC3-KO-3). Helper phages were used as a negative control.
Figure 2B:
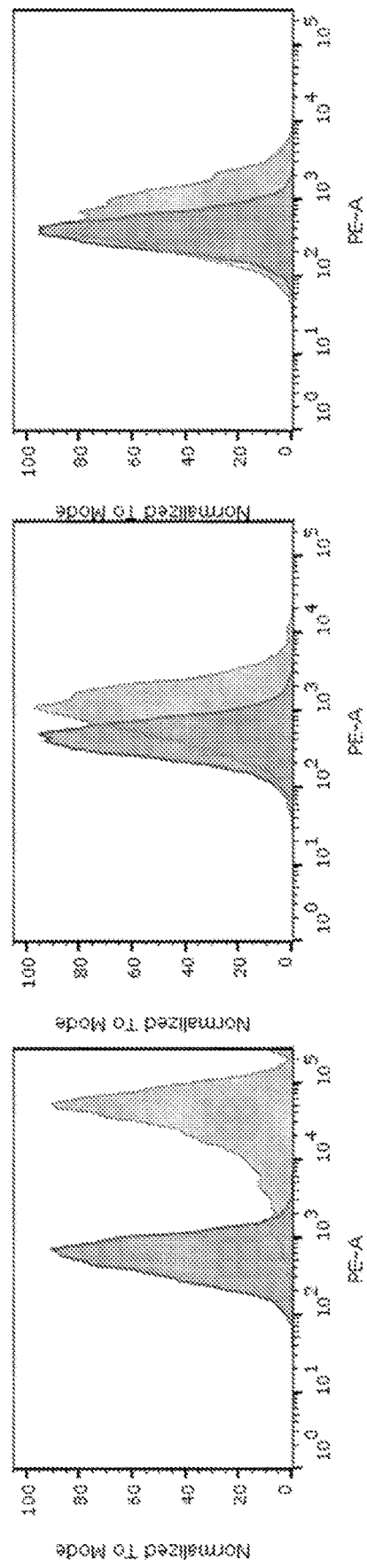
Figure 2C:
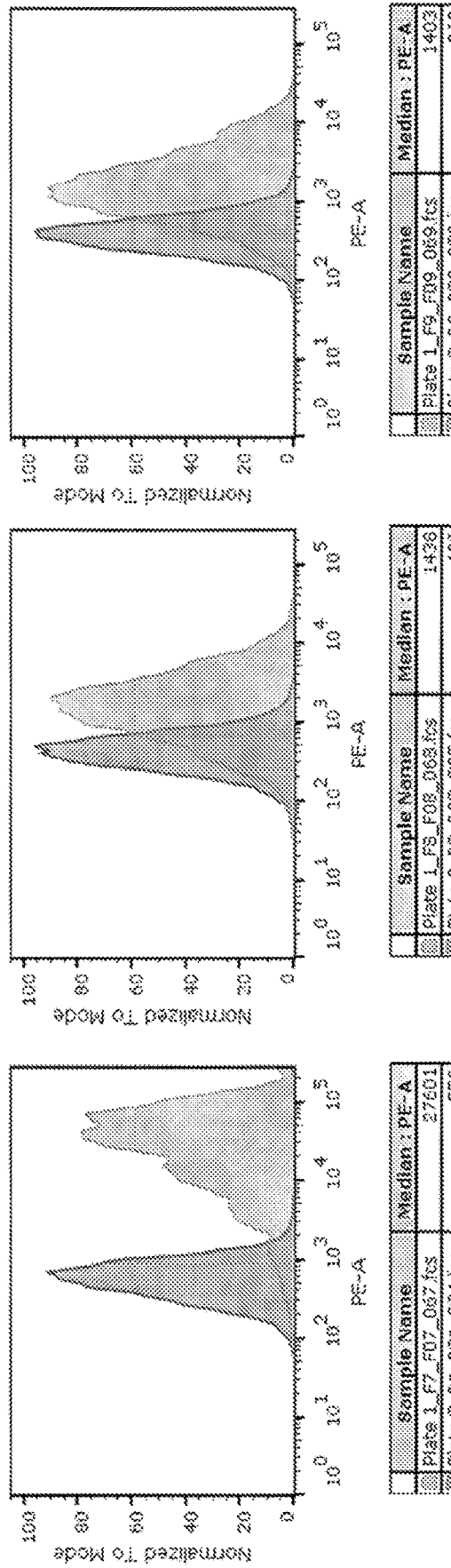
Figure 2D:
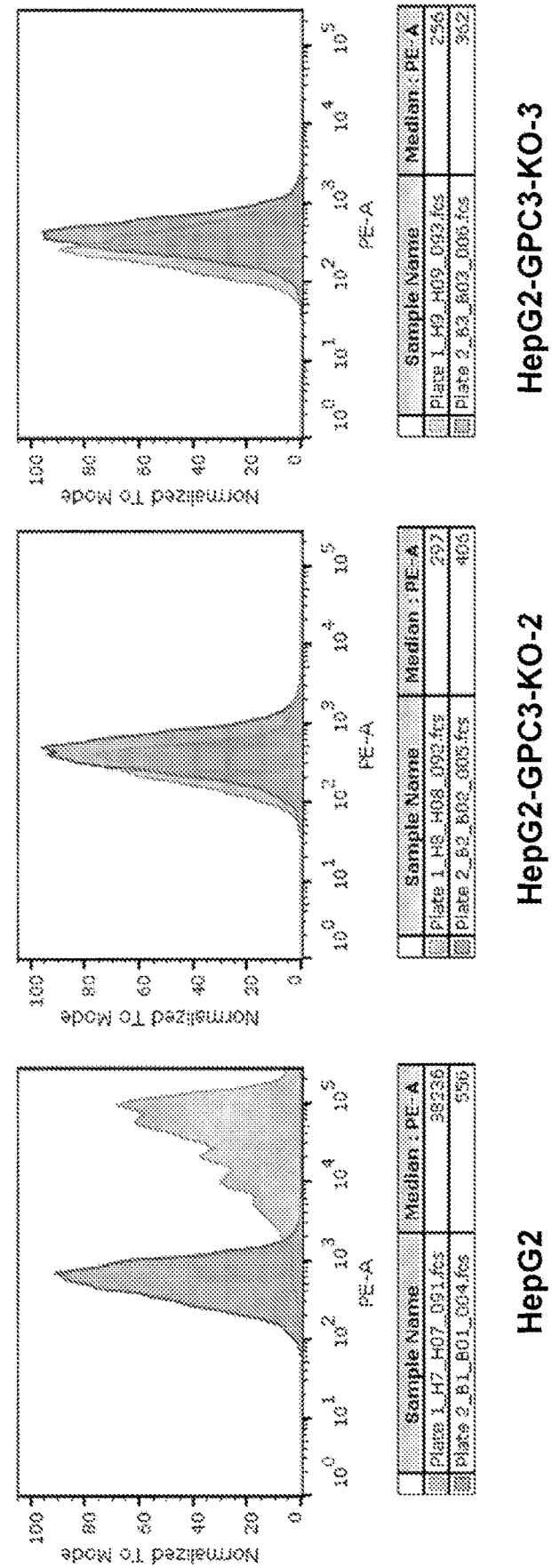
Figure 2E:
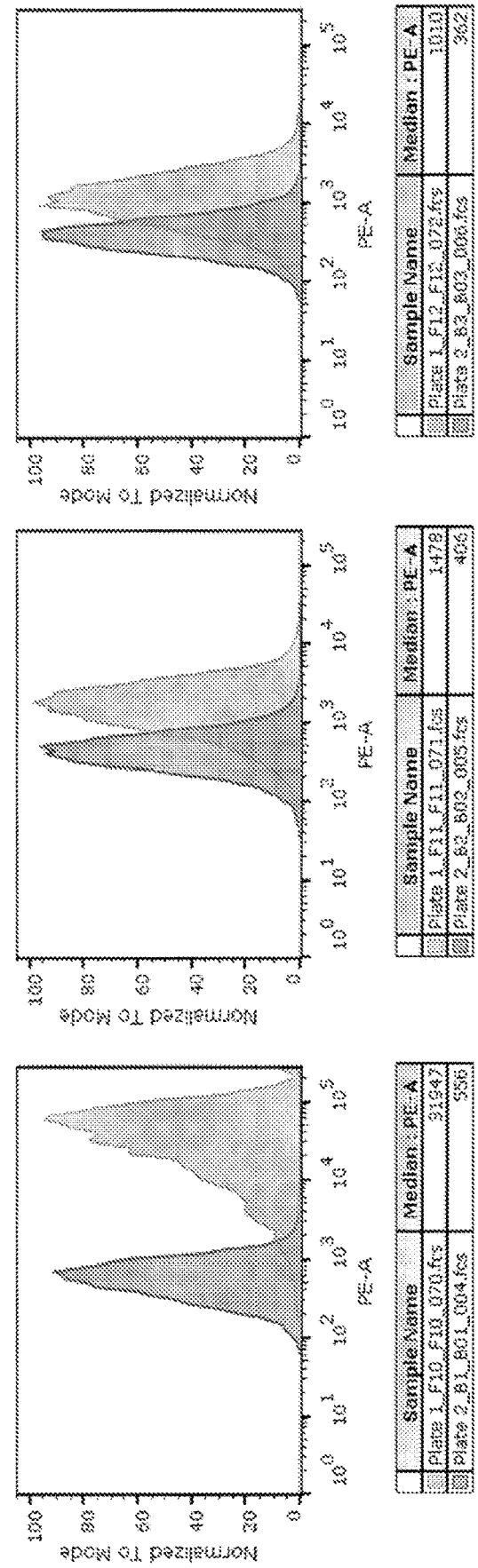

The phage clones from the GPC3A screen were further tested for binding to GPC3 knockout cell lines HepG2-GPC3-KO-2 and HepG2-GPC3-KO-3 made by Eureka Therapeutics (see "Generation of HepG2 GPC3 knockout (HepG2-GPC3-KO) cells" in Methods). Of the 33 clones identified by binding to the GPC3⁺ HepG2 cell line, five clones (GPC3A-34, 37, 38, 58 and 62) showed little or no binding to HepG2-GPC3-KO cell lines (HepG2-GPC3-KO-2 and HepG2-GPC3-KO-3), demonstrating their high specificity for GPC3 positive cell binding. FACS analysis is exemplified in FIGS. 2A-2F: GPC3A-39 (FIG. 2A), GPC3A-46 (FIG. 2B), GPC3A-56 (FIG. 2C), and GPC3A-64 (FIG. 2E) showed significant binding to GPC3⁺ HepG2 cell line, and relatively low levels of binding to HepG2-GPC3-KO cell lines; while GPC3A-58 (FIG. 2D) demonstrated high level of binding to GPC3⁺ HepG2 cell line and nearly no binding to HepG2-GPC3-KO cell lines. A few clones showed high levels of binding to both GPC3⁺ HepG2 and HepG2-GPC3-KO cell lines (data not shown).

Binding of GPC3A phage clones to soluble GPC3 was tested by ELISA. Three forms of soluble biotinylated GPC3 protein (GPC3$_{(560)}$, R&D Systems GPC3 protein [Cat. 2119-GP-0505], and GPC3-51mer) were used to coat 96 well ELISA plates as described (see Method). All clones were able to bind GPC3$_{(560)}$ and GPC3 (R&D Systems), with clones GPC3A-37, -42, -43 and -47 displaying the least binding to GPC3$_{(560)}$ and no binding to GPC3-51mer (data not shown).

TABLE 4

|  | Cell panning SK-Hep1-GPC3 cells (GPC3A) | Cell/ELISA panning GPC3-51mer SK-Hep1-GPC3 cells (GPC3B) |
|---|---|---|
| No. of clones (FACS screening) | 540 | 368 |
| Cell-surface GPC3 binding unique clones | 33 | 14 |
| GPC3 knockout cell binding clones | 5 | 4 |
| Clones converted to bispecific antibodies | 20 | 14 |
| Target cell killing by bispecific antibodies | 16 | 1 |

Panning Strategies and Phage Library Screening Using a 51Mer GPC3 Fragment (GPC3B)

On the other hand, three types of phage library panning were implemented using a biotinylated C-terminal 51mer hGPC3 fragment (bt-GPC3-51mer, see Methods). This screening strategy was named GPC3B and outlined in Table 4.

Plate Panning

A plate panning screen was performed using a biotinylated GPC3-51mer fragment (see Methods) in a volume of 100 μl at 2 ug/ml in PBS and added to a Streptavidin coated 96-well ELISA plate, allowing for incubation at 4° C. overnight. The plate was blocked with 5% non-fat dried milk (NFDM) in PBS for 2 hours at room temperature. After two additional washes, 100 μl of phage library (with a titer of 2×10¹² pfu/ml) was added into individual wells. 138 phage clones were tested. Plates were incubated for 2 hours at 4° C. and washed with PBSTB 6 times. The wells were eluted by trypsin (100 μl at 1 mg/ml) for 10 minutes at room temperature. The eluted phages were recovered according to standard methods. Three rounds of plate panning were conducted to enrich for specific phage binding against the hGPC3-51mer fragment. Using this screen, of the 138 isolated phage clones, 99 were positive by ELISA and 53 unique clones were identified.

Plate Plus Cell Panning

A second panning screen was performed on 138 isolated phage clones with two rounds of plate panning followed by one round of cell panning, using the SK-Hep1 cell line for subtraction panning and the SK-Hep1-GPC3 cell line for positive panning. In the third round of cell panning, about 4×10⁷ SK-Hep1 cells were used for subtraction panning of each phage library by co-incubation for 2 hours at room temperature. About 1×10⁷ SK-Hep1-GPC3 cells were used for positive panning of each phage library, also by co-incubation for 2 hours at 4° C. The cell/phage mixture was washed 4 times in 10% FBS in PBS and twice with PBS only. Specific bound phages were eluted with trypsin (1 ml at 1 mg/ml) for 10 minutes at room temperature. The eluted phages were rescued using standard techniques. Using this panning method, of 138 clones, a further 14 unique clones were isolated.

Bead Panning

A bead panning screen was also performed for additional 92 isolated phage clones. 50 μl DYNABEADS® were washed 2 times in PBST and resuspended in 500 μl of phage library (with titer of 2×10¹² pfu/ml). The phage/beads mixture was incubated for 2 hours at room temperature to deplete phages showing non-specific binding to streptavidin. Another 50 μl of DYNABEADS® were prepared using the same washing procedure and resuspended in 500 μl bt-GPC3-51mer fragment solution at 2.4 μg/ml in 2.5% PBSM, allowed for incubation for 15 minutes at room temperature, then washed twice. The phage library was aspirated and mixed with the bt-GPC3-51mer fragment/bead mixture, then incubated for 2 hours at 4° C. and washed with PBSM 5-10 times. The bound phages were eluted using trypsin (400 µl at 1 mg/ml) for 10 minutes at room temperature and rescued using standard techniques. Three rounds of bead panning were conducted to enrich for GPC3-specific phage binding against the hGPC3-51mer fragment. A further 62 unique clones were isolated using the bead panning method.

Of all these 129 unique clones identified from the GPC3B screen, 20 were tested for their ability to bind GPC3+ HepG2 cells using flow cytometry. For positive cell panning, 0.2 million GPC3+ HepG2 cells were suspended in 50 µl of 5% FBS in PBS and 0.05% $NaN_3$. For subtraction panning, 0.2 million HepG2-GPC3 knockout cells (HepG2-GPC3-KO-2) were suspended in 50 µl of 5% FBS in PBS and 0.05% $NaN_3$. GPC3B phages and negative control phages (helper phages) were added at about $1.0 \times 10^{11}$ pfu/mL in PBS and incubated at 4° C. for 1 hour. The mixture was washed in PBST, and a 200-fold dilution of mouse anti-M13 antibody (see Methods) was added in a volume of 100 µl in 5% FBS (in PBS) and 0.05% $NaN_3$ and incubated for another hour at 4° C. The mixture was washed again in PBS and secondary PE-anti-mouse IgG antibody was added at a 200-fold dilution in 100 µl of 5% FBS in PBS and 0.05% $NaN_3$ and incubated in the dark at 4° C. for another hour. The mixture was washed twice in PBS and fixed in fixation buffer at a three-fold dilution in a volume of 150 µl. Of the 20 clones tested, none of them showed binding to HepG2-GPC3-KO-2 cells. As exemplified in FIGS. 3A-3D, GPC3B phage clones #81, #87 and #115 showed strong binding to GPC3+ HepG2 cells, while GPC3B-80 clone showed weak binding, but none of them showed any binding to HepG2-GPC3-KO-2 cells.

These 20 clones from GPC3B screen were further tested for their binding to soluble biotinylated $GPC3_{(560)}$ and GPC3-51mer using an ELISA assay (see Methods). 16 out of the 20 clones showed strong binding to bt-GPC3-51mer and even stronger binding to soluble bt-$GPC3_{(560)}$. 3 clones showed strong binding to bt-GPC3-51mer but no binding to soluble bt-$GPC3_{(560)}$. 1 clone failed to bind either soluble protein (data not shown).

Example 2. Anti-GPC3 Bispecific Antibody Constructs

Generation of Bispecific Antibody Constructs Using Human Anti-GPC3 Antibodies

This example demonstrates the construction of multi-specific anti-GPC3 molecules using human scFv fragments specific for human GPC3. In particular, this example demonstrates the construction of bispecific antibodies having a first antibody moiety (e.g., scFv) that binds human GPC3 in native format (cell-surface expressed) and a second antibody moiety (e.g., scFv) that binds CD3 on T cells. These multi-specific anti-GPC3 molecules (e.g., tandem di-scFv anti-GPC3 T cell engager) described herein can be used for directing T cells to kill target cells that express human GPC3.

Bispecific antibodies (referred to as "L2K") were generated using scFv sequences of the human GPC3-specific phage clones showing specific cell surface-GPC3 binding and little or no GPC3-KO cell binding (from both GPC3A and GPC3B screenings). The bispecific antibodies were constructed using a single-chain format comprising the $V_L$-$V_H$ scFv sequence of a human GPC3-specific phage clone at the N-terminus and an anti-human CD3ε mouse monoclonal scFv at the C-terminus (anti-GPC3×CD3 di-scFv; e.g., see Brischwein, K. et al., *Mol. Immunol.* 43:1129-1143, 2006). Exemplary anti-GPC3×CD3 di-scFv antibodies derived from GPC3A-34, GPC3B-87, GPC3A-37, GPC3A-45, GPC3A-46, GPC3A-55, and GPC3A-58 antibody clones comprise the amino acid sequences of SEQ ID NOs: 488, 489 and 511-515 respectively.

DNA fragments encoding the anti-human GPC3 scFv and the anti-human CD3εscFv were synthesized by Genewiz or Genscript and subcloned into a mammalian expression vector pQD-T (Eureka Therapeutics, Inc.) using standard recombinant DNA technology. A hexahistidine tag was inserted at the C-terminus for purification and detection. HEK293 cells were transfected with the bispecific antibody expression vector and cultured for seven days for bispecific anti-GPC3 antibody production. Bispecific antibodies were purified from HEK293 cell supernatants using HisTrap HP column (GE healthcare) by FPLC AKTA system or His GraviTrap columns (GE healthcare) based on the cell culture volume. HEK293 cell culture supernatant was clarified and loaded onto the column with low imidazole concentration (20 mM), and then an isocratic high imidazole concentration elution buffer (500 mM) was used to elute bound bispecific anti-GPC3 antibodies. Molecular weights of purified human GPC3 bispecific antibodies were measured under non-reducing conditions by gel electrophoresis. A band (~98 kD) corresponding to the bispecific anti-GPC3 antibodies (anti-GPC3 scFv-anti-CD3 scFv) was observed as the major species on the gel (data not shown).

Taken together, this example demonstrates the successful construction of bispecific anti-GPC3 molecules having a first antibody moiety that is specific for human GPC3 expressed on the cell surface (i.e., native format) and a second antibody moiety that is specific for CD3. Further characterization of such bispecific molecules is described below. 20 unique clones from GPC3A screen and 14 unique clones from GPC3B screen were selected for generating bispecific anti-GPC3 antibodies and further characterization (Table 4).

Anti-GPC3 Bispecific Antibodies (GPC3A L2K) Binding to Human Hepatocellular Carcinoma Cell Lines HCC cell lines expressing GPC3 were tested for anti-GPC3 bispecific antibody binding by flow cytometry, using human GPC3+ HepG2 cells, GPC3-negative SK-Hep1 cells, and SK-Hep1-GPC3 (GPC3 over-expressing) cells in two experiments.

A control-L2K bispecific antibody was similarly generated as above by fusing a non-GPC3 binding scFv with an anti-human CD3εscFv, with a hexahistidine tag inserted at the C-terminus for purification and detection. This control-L2K antibody was used as a negative GPC3 binding control.

GPC3A L2K bispecific antibodies or control-L2K bispecific antibody were incubated with GPC3-negative SK-Hep1 cells and (separately) SK-Hep1-GPC3 cells for 1 hour at 4° C., at a final concentration of 5 µg/ml in 5% FBS in PBS with 0.05% $NaN_3$. Cells were then washed once with PBS. APC-conjugated anti-His tag mouse antibody (R&D Systems) was added to the washed cells in a volume of 100 µl, at 20-fold dilution of 5% FBS in PBS and 0.05% $NAN_3$ and incubated for 1 hour at 4° C. in the dark. The cells were then washed twice with PBS. The cells were fixed in 3-fold dilution of fixation buffer (BioLegend) in PBS in a volume of 150 µl. As shown in FIGS. 4A and 4B, GPC3A L2K bispecific antibodies failed to bind to GPC3-negative SK-Hep1 cells and bound well to GPC3 over-expressing SK-Hep1-GPC3 cells.

GPC3A L2K bispecific antibodies or control-L2K bispecific antibody were incubated with GPC3+ HepG2 cells for 1 hour at a final concentration of 5 µg/ml in 5% FBS in PBS with and 0.05% NaN₃ at 4° C., then washed once with PBS. APC-conjugated anti-His tag mouse antibody (R&D Systems) was added in a volume of 100 µl, a 20-fold dilution of 5% FBS in PBS and 0.05% NaN₃ and incubated for 1 hour at 4° C. in the dark, then washed twice with PBS. The cells were fixed in 3-fold dilution of fixation buffer (BioLegend) in PBS in a volume of 150 µl. FIGS. 5A-5B demonstrate significant binding of GPC3A L2K bispecific antibodies to GPC3+ HepG2 cells, as compared to the binding between the control-L2K antibody and GPC3+ HepG2 cells.

Anti-GPC3 Bispecific Antibodies (GPC3B L2K) Binding to Human Hepatocellular Carcinoma Cell Lines Anti-GPC3×CD3 di-scFv antibodies derived from B screen (GPC3B L2K bispecific antibodies) are similarly tested by flow cytometry, using human GPC3+ HepG2 cells, HepG2-GPC3-KO cells, GPC3-negative SK-Hep1 cells, and SK-Hep1-GPC3 (GPC3 over-expressing) cells in two experiments.

GPC3B L2K bispecific antibodies or control-L2K bispecific antibody are incubated with GPC3-negative SK-Hep1 cells and (separately) SK-Hep1-GPC3 cells for 1 hour at 4° C., at a final concentration of 5 µg/ml in 5% FBS in PBS with 0.05% NaN₃. Cells are then washed once with PBS. APC-conjugated anti-His tag mouse antibody (R&D Systems) is added to the washed cells in a volume of 100 µl, at 20-fold dilution of 5% FBS in PBS and 0.05% NaN₃ and incubated for 1 hour at 4° C. in the dark. The cells are then washed twice with PBS. The cells are fixed in 3-fold dilution of fixation buffer (BioLegend) in PBS in a volume of 150 µl. FACS analysis is performed to compare the binding of GPC3B L2K bispecific antibodies to GPC3-negative SK-Hep1 cells and GPC3 over-expressing SK-Hep1-GPC3 cells. GPC3B L2K bispecific antibodies demonstrating cell surface-bound human GPC3 specificity are expected to show significant binding to SK-Hep1-GPC3 cells, and little or no binding to GPC3-negative SK-Hep1 cells.

GPC3B L2K bispecific antibodies and control L2K bispecific antibody are also tested for binding to GPC3+ HepG2 cells. The two sets of antibodies are incubated with GPC3+ HepG2 cells for 1 hour at a final concentration of 5 µg/ml in 5% FBS in PBS with and 0.05% NaN₃ at 4° C., then washed once with PBS. APC-conjugated anti-His tag mouse antibody (R&D Systems) is added in a volume of 100 µl, a 20-fold dilution of 5% FBS in PBS and 0.05% NaN₃ and incubated for 1 hour at 4° C. in the dark, then washed twice with PBS. The cells are fixed in 3-fold dilution of fixation buffer (BioLegend) in PBS in a volume of 150 µl. FACS analysis is performed to compare the binding of GPC3B L2K bispecific antibodies and control L2K bispecific antibodies to GPC3+ HepG2 cells. GPC3B L2K bispecific antibodies demonstrating cell surface-bound human GPC3 specificity are expected to show significant binding to GPC3+ HepG2 cells, while little or no binding to these cells are expected to see for control L2K bispecific antibodies.

GPC3B L2K bispecific antibodies and control-L2K bispecific antibody are also incubated with HepG2-GPC3-KO cells for 1 hour at 4° C., at a final concentration of 5 µg/ml in 5% FBS in PBS with 0.05% NaN₃. Cells are then be washed once with PBS. APC-conjugated anti-His tag mouse antibody (R&D Systems) is added to the washed cells in a volume of 100 µl, at 20-fold dilution of 5% FBS in PBS and 0.05% NAN₃ and incubated for 1 hour at 4° C. in the dark. The cells are then washed twice with PBS. The cells are fixed in 3-fold dilution of fixation buffer (BioLegend) in PBS in a volume of 150 µl. FACS analysis is performed to compare the binding of GPC3B L2K bispecific antibodies and control IgG1 isotype antibodies to HepG2-GPC3-KO cells. GPC3B L2K bispecific antibodies demonstrating cell surface-bound human GPC3 specificity are expected to show little or no binding to HepG2-GPC3-KO cells, similar to IgG1 isotype control antibodies.

Example 3. Characterization of Human GPC3 Bispecific Antibodies

Competition for Binding to Human Liver Cell Lines with Soluble GPC3

Figure 6:
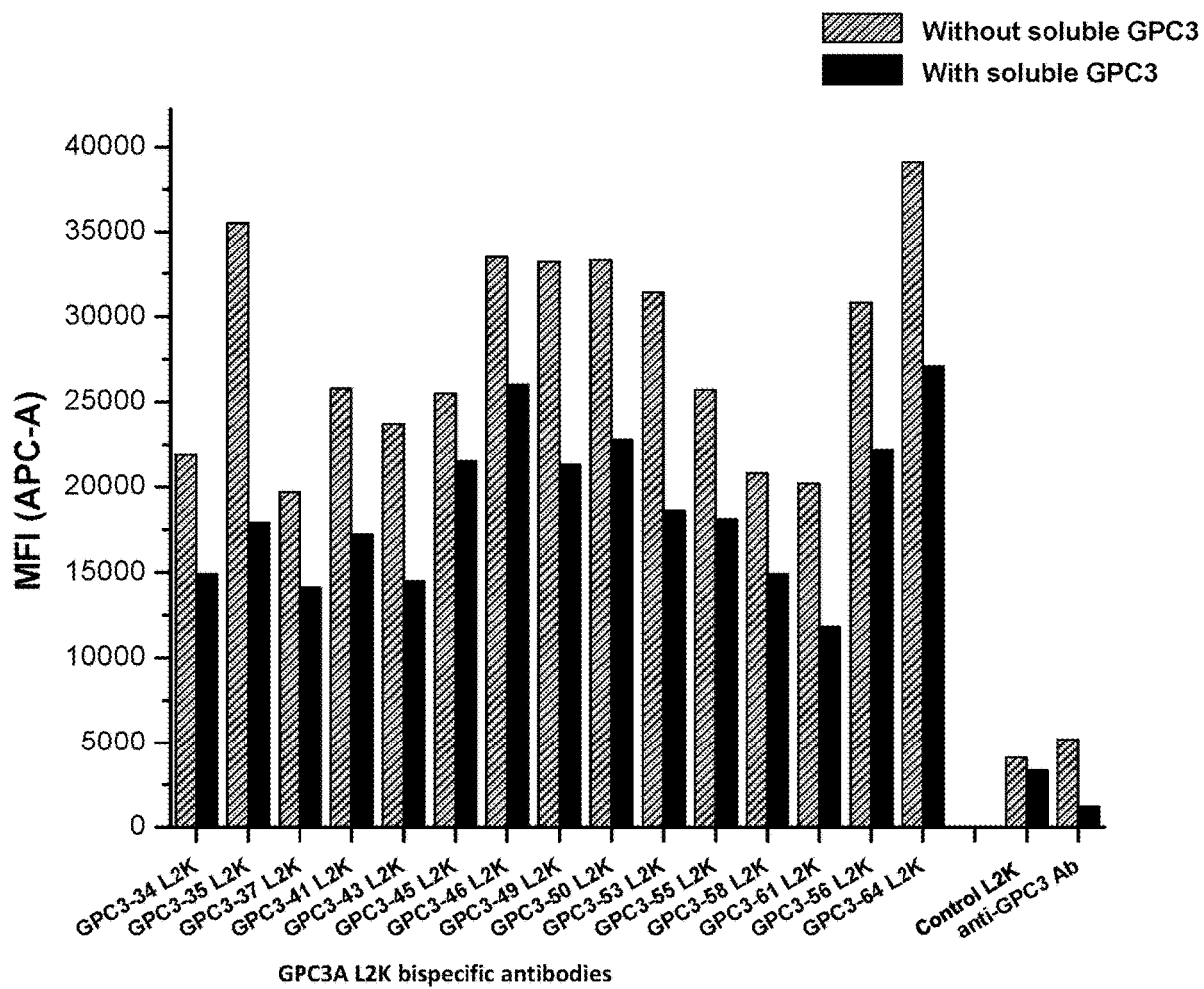
FIG. 6 shows FACS analysis of the binding of GPC3A L2K bispecific antibodies to GPC3+ HepG2 cells in a competition assay provided with or without soluble GPC3 antigen. A negative control L2K bispecific antibody and a commercial anti-GPC3 (1G12) antibody were used for comparison purposes.

Antibodies raised against cell surface-bound GPC3 were tested for their ability to bind GPC3+ HepG2 cells in a competitive binding assay (IC50) using the recombinant biotinylated GPC3(560) protein (see Methods). Anti-GPC3 L2K antibodies (derived from the GPC3A screen) or control-L2K bispecific antibody were premixed with various concentrations of the soluble bt-GPC3(560) protein and incubated at 4° C. for one hour; HepG2 cells were then added and the mixture was incubated for another hour at 4° C. APC-conjugated anti-His tag antibody (R&D Systems, #IC050A) was added at a 20-fold dilution to detect L2K antibody binding (L2K antibodies carry a C-terminal His tag). Streptavidin-PE (Vector Labs EI-2007) was also added at a 200-fold dilution and incubated for 30 minutes at 4° C. in the dark to monitor the soluble bt-GPC3(560) protein. Mouse anti-GPC3 antibody positive control (1G12, Santa Cruz #sc-65443) was treated with or without soluble bt-GPC3(560) protein under the same conditions using PE-conjugated anti-mouse IgG (H+L). Table 5 shows the IC50 values for the six GPC3A L2K antibodies tested. All GPC3 L2Ks showed much higher IC50 values than the anti-GPC3 positive control antibody (1G12), with GPC3A-37 and GPC3A-46 showing the highest values, i.e. least affected by the presence of soluble GPC3. As can be seen from FIG. 6, the median fluorescence intensity (MFI) of all GPC3A L2K bispecific antibodies demonstrated significantly stronger binding to GPC3 present on HepG2 cells than both the control-L2K bispecific antibody and the anti-GPC3 positive control antibody (1G12). Moreover, most GPC3A L2K bispecific antibodies demonstrated much higher specificity for cell surface-bound GPC3 than for soluble bt-GPC3(560) protein in the competition assay, such as GPC3A-37 and GPC3A-46 clones.

TABLE 5

| GPC3 × CD3 Bispecific antibody clone | IC₅₀ (µg/ml) |
| --- | --- |
| GPC3A-34 L2K | 2.4 |
| GPC3A-37 L2K | 4.6 |
| GPC3A-45 L2K | 1.2 |
| GPC3A-46 L2K | 4.1 |
| GPC3A-55 L2K | 2.7 |
| GPC3A-58 L2K | 2.4 |
| NC16 L2K negative control | — |
| Anti-GPC3 positive control Ab | 0.25 |

Similarly, the clone GPC3B-87 L2K was tested for its ability to bind to GPC3+ HepG2 cells in a competitive binding assay (IC₅₀) using the recombinant biotinylated GPC3$_{(560)}$ protein as described above. GC33 L2K (GC33 antibody converted to an L2K) and an anti-CD19 L2K were used as controls. Briefly, the GPC3B-87 L2K bispecific antibody or control-L2K bispecific antibodies were premixed with various concentrations of the soluble bt-GPC3$_{(560)}$ protein and incubated at 4° C. for one hour; HepG2 cells were added and the mixture incubated for another hour at 4° C. APC-conjugated anti-His tag antibody (R&D Systems, #IC050A) was then added at a 20-fold dilution to detect L2K antibody binding (L2K antibodies carry a C-terminal His tag). Streptavidin-PE (Vector Labs EI-2007) was also added at a 200-fold dilution and incubated for 30 minutes at 4° C. in the dark to monitor the soluble bt-GPC3$_{(560)}$ protein. Mouse anti-GPC3 antibody positive control (1G12, Santa Cruz #sc-65443) was treated with or without soluble bt-GPC3$_{(560)}$ protein under the same conditions using PE-conjugated anti-mouse IgG (H+L). FACS analysis was performed.

As shown in FIG. 10 and Table 12, both GPC3B-87 L2K (IC$_{50}$ 0.12 µg/ml) and GC33 L2K (IC$_{50}$ 0.86 µg/ml) showed much lower IC$_{50}$ than the GPC3A L2Ks tested (IC$_{50}$ between 1.2 and 4.6 µg/ml). This suggests that binding of GPC3B-87 L2K and GC33 L2K to cell surface GPC3 can be more easily competed off by soluble GPC3 than binding of GPC3A L2Ks to cell surface GPC3.

TABLE 12

| GPC3 × CD3 Bispecific antibody clone | IC$_{50}$ (µg/ml) |
|---|---|
| GPC3B-87 L2K | 0.12 |
| anti-CD19 L2K negative control | — |
| GC33 L2K | 0.86 |

Binding Affinity of GPC3A and GPC3B L2K Clones to HepG2 Cells

HCC cell lines expressing GPC3 were tested for anti-GPC3 bispecific antibody (GPC3 L2K clones) binding by flow cytometry, using human GPC3+ HepG2 cells.

A control-L2K bispecific antibody was generated by fusing a non-GPC3 binding scFv with an anti-human CD3εscFv, with a hexahistidine tag inserted at the C-terminus for purification and detection. This control-L2K antibody, designated ET-901 L2K, was used as a negative control for GPC3 binding. The reference anti-GPC3 bispecific antibody was also similarly generated using the scFv of GC33, and was designated GC33 L2K.

GPC3A L2K clones (GPC3A-34 L2K, GPC3A-37 L2K, GPC3A-45 L2K, GPC3A-46 L2K, GPC3A-55 L2K, and GPC3A-58 L2K), GPC3B L2K clone (GPC3B-87 L2K), reference GC33 L2K bispecific antibody, or negative control anti-CD19 L2K were incubated with GPC3 positive HepG2 cells for 1 hour at a final concentration of 5 µg/ml in 5% FBS in PBS and 0.05% NaN$_3$ at 4° C., then washed once with PBS. APC-conjugated anti-His tag mouse antibody (R&D Systems) was added in a volume of 100 µl, a 20-fold dilution of 5% FBS in PBS and 0.05% NaN$_3$ and incubated for 1 hour at 4° C. in the dark, then washed twice with PBS. The cells were fixed in 3-fold dilution of fixation buffer (BioLegend) in PBS in a volume of 150 µl. As a separate control, HepG2 cells were also incubated with APC-conjugated anti-His tag mouse antibody (R&D Systems) in the absence of any L2K bispecific antibody. FIG. 11 demonstrated significant binding of GPC3A L2K clones to GPC3 positive HepG2 cells.

Specifically, 6 GPC3A L2K bispecific antibody clones (GPC3A-34 L2K, GPC3A-37 L2K, GPC3A-45 L2K, GPC3A-46 L2K, GPC3A-55 L2K, GPC3A-58 L2K) and 1 GPC3B L2K bispecific antibody clone (GPC3B-87 L2K) were assayed by FACS to determine their binding affinity to GPC3+ HepG2 cells, along with reference anti-GPC3 GC33 L2K. The 6 GPC3A L2K clones showed EC$_{50}$ between 0.045-0.12 µg/ml, with apparent K$_d$ values between 0.86-2.4 nM. The GPC3B L2K clone (GPC3B-87 L2K) showed much weaker binding, with EC$_{50}$ at 4.3 µg/ml, and an apparent K$_d$ of 84 nM. GC33 L2K showed an EC$_{50}$ of 0.14 µg/ml, with an apparent K$_d$ of 2.7 nM. Compared to GC33 L2K (K$_d$=2.7 nM), all GPC3A L2K clones showed higher binding affinity, especially GPC3A-37 L2K (K$_d$=0.92 nM), GPC3A-46 L2K (K$_d$=1.0 nM) and GPC3A-55 L2K (K$_d$=0.86 nM) (See Table 13 and FIG. 11).

TABLE 13

| GPC3 × CD3 Bispecific antibody clone | EC$_{50}$ (µg/ml) | Apparent K$_d$ (nM) |
|---|---|---|
| GPC3A-34 L2K | 0.11 | 2.0 |
| GPC3A-37 L2K | 0.048 | 0.92 |
| GPC3A-45 L2K | 0.12 | 2.4 |
| GPC3A-46 L2K | 0.050 | 1.0 |
| GPC3A-55 L2K | 0.045 | 0.86 |
| GPC3A-58 L2K | 0.12 | 2.4 |
| GPC3B-87 L2K | 4.3 | 81 |
| Anti-GPC3 positive control Ab | 0.14 | 2.7 |

T Cell-Mediated Cytotoxicity Assay

Tumor cytotoxicity was assayed using an LDH Cytotoxicity Assay (Promega). Human T cells (AllCells) or Ficoll-purified cells from whole blood (Blood Centers of the Pacific) were activated and expanded with CD3/CD28 DYNABEADS® (Invitrogen) according to manufacturer's specifications. Activated T cells were cultured and maintained in RPMI1640 medium with 10% FBS plus 100 U/mL IL-2 and used at day 7-14 post-activation. T cells were >99% CD3$^+$ by FACS analysis. Activated T cells and target cells were co-cultured at a 5:1 ratio with bispecific antibodies (0.2 µg/ml; GPC3A L2K or GPC3B L2K) for 16 hours. Cytotoxicity was determined by measuring LDH activity in culture supernatants.

As shown in FIG. 7A and FIG. 7B, bispecific anti-GPC3× CD3 antibodies, derived from both GPC3A and GPC3B screens effectively mediated killing of cancer cells in a human GPC3-specific manner. A monoclonal antibody GC33, which was derived from mice immunized with a C-terminal human GPC3 fragment (see Methods), was also tested for GPC3-specific killing (FIG. 7B), The results show that GC33's cancer cell killing capability was not GPC3 specific, because GC33 mediated killing of GPC3 knockout cell line HepG-GPC3-KO-2 as well as GPC3-positive cell lines HepG2 and SK-Hep1-GPC3. On the other hand, GPC3A L2K bispecific antibodies #43, #53, #58 and #61 (among others; FIG. 7A) and GPC3B L2K bispecific antibody #87 (FIG. 7B) mediated robust killing of GPC3-positive cells (HepG2 and SK-Hep1-GPC3), while having no significant effect on GPC3-negative cell lines (SK-Hep1 and HepG2-GPC3-KO cells).

Example 4. Construction of Mouse Anti-hGPC3 Monospecific IgG Antibodies

Full-length mouse anti-human GPC3 (hGPC3) monospecific IgG antibodies were constructed using heavy chain and light chain variable region sequences of GPC3A-39, 46, 51, 56, 58 and 64 (SEQ ID NOs: 311 and 362, 318 and 369, 323 and 374, 328 and 379, 330 and 381, 336 and 387, for V$_H$ and V$_L$ respectively) to fuse to mouse IgG1 constant region and Fc region sequences using a cloning plasmid expressing the Fe region of murine IgG1 heavy chain and a plasmid expressing the IgG light chain. The resulting antibody clones were named anti-GPC3 mIgG1 clones A-39, -46, -51, -56, -58, and -64. The sequence of an exemplary anti-GPC3 mIgG1 A-39 comprises a heavy chain comprising the amino acid sequence of SEQ ID NO: 505, and a light chain comprising the amino acid sequence of SEQ ID NO: 506. A full-length GPC3B monospecific IgG antibody and a. full-length GC33 antibody are constructed in the same fashion and are named anti-GPC3 mIgG1 clone B-87, and anti-GPC3 mIgG1-GC33, respectively, using heavy chain and light chain variable regions of the GPC3B clone 87 (SEQ ID NOs: 350 and 401) and heavy chain and light chain variable regions of the anti-GPC3 antibody GC33 (SEQ ID NOs: 503 and 504).

In brief, full-length mouse IgG1 of the selected phage clones were produced in HEK293 and Chinese hamster ovary (CHO) cell lines, as described (Tomimatsu, K. et al., Biosci. Biotechnol. Biochem. 73(7):1465-1469, 2009) (data not shown). The GPC3 clone variable regions were subcloned into mammalian expression vectors with mouse IgG1 heavy chain and light chain constant regions. Molecular weight of the purified full-length IgG antibodies was measured under both reducing and non-reducing conditions by electrophoresis to determine protein purity, which was calculated to be in excess of 95% (data not shown).

Anti-GPC3 mIgG1 antibodies were tested for the binding towards GPC3-positive HepG2 and GPC3-negative SK-Hep1 cells by flow cytometry. 10 µg/mL of constructed antibody was added to cells on ice for 1 hour. After washing, PE conjugated anti-mouse IgG (H and L) (Vector Labs #EI-2007) was added (30 minutes at 4° C. in the dark and washed twice) to detect antibody binding. As can be seen from FIG. 9A, all anti-GPC3 mIgGs were found to bind to GPC3-positive HepG2 cells, while the secondary antibody and a control antibody alone (control mIgG1) did not bind to the same cells. None of the anti-GPC3 mIgGs or control mIgG1 displayed binding to SK-Hep1 cells (FIG. 9B). The same FACS analysis is performed with the anti-GPC3 mIgG1 clone B-87 and mIgG-GC33 antibodies.

Reactivity of GPC3A mIgG1 Antibodies Against Rat GPC3 by ELISA

GPC3-specific and negative control (ET-901) mouse chimeric IgG1 were tested for binding towards rat GPC3 peptide in an ELISA assay. Antibodies were tested at 3× serial dilution, starting from 100 ng/mL, for a total of 8 concentrations. Biotinylated rat GPC3 was coated onto streptavidin plates in a volume of 100 µL at 2 ug/ml in PBS and added to a Streptavidin coated 96-well ELISA plate, allowing for incubation at 4° C. overnight. The plate was blocked with 5% non-fat dried milk (NFDM) in PBS for 2 hours at room temperature. Each of the GPC3A mIgG1 clones (A-34, -46, -53, -58, -61), as well as the negative control ET-901 mIgG1, constituted at 5 µg/mL in PBST buffer, was respectively incubated with separate rat bt-GPC3-coated wells for 1 hour at room temperature. The plates were washed with PBST, and incubated with anti-mouse Fc (Bethyl Labs #A90-131P, 1:2000 dilution) for 30 minutes at room temperature. After washing with PBST, the reaction was developed with 1-STEP™ Ultra TMB-ELISA Substrate Solution (Thermofisher Scientific #34028) and stopped with 2N sulfuric acid. 4 out of 5 GPC3A mIgG1 clones (A-34, -46, -58, -61) reacted with rat bt-GPC3, as compared to negative control anti-CD19 mIgG1 (FIG. 12). GPC3A-53 mIgG1 clone did not react with rat bt-GPC3. In an accompanying experiment, all GPC3A mIgG1 clones tested (A-34, -46, -53, -58, -61) reacted with human GPC3 (FIG. 12).

Example 5. Binding Profile Determination of Anti-hGPC3 Monospecific and Bispecific Antibodies to Cell-Surface and Soluble GPC3

This example demonstrates GPC3 binding profile for selected monospecific and bispecific antibodies. In particular, this example describes the epitope-binding site characterization of selected anti-hGPC3 monospecific mIgG1 clones (as described in Example 4). On the other hand, this example also describes the binding profile of selected anti-hGPC3 monospecific mIgG1 clones and human anti-hGPC3 anti-CD3 bispecific antibodies (GPC3A L2K and GPC3B L2K, as described in Example 2) of the present invention, along with clone GC33 mIgG1 and bispecific GC33-L2K, to soluble recombinant human GPC3 (i.e., human $GPC3_{(560)}$, residues 1-560aa of hGPC3) or GPC3 antigen on cancer cell surface, such as GPC3-positive HepG2 and SK-Hep1-GPC3 cells.

Epitope Binding Site Characterization for GPC3A mIgG Clones

GPC3 epitope binning was carried out to determine if distinct epitopes are recognized by reference GC33-mIgG1 and the anti-hGPC3 monospecific mIgG1 clones GPC3A-37 mIgG and GPC3A-55 mIgG. A first pair of mIgG protein and GPC3 was allowed to react for the first mIgG to occupy its binding epitope on GPC3 before addition of a second distinct mIgG in order to determine whether the two mIgG proteins bind to different epitopes. Briefly, binding affinity was determined and binding parameters were calculated using a 1:1 binding site, partial fit model. After the first pairing of a mIgG protein and GPC3 (where one entity of the pair is immobilized to a streptavidin-biosensor), a spike in signal detected by the biosensor reflects binding between the first mIgG and GPC3, and after washing, the first pair of mIgG/GPC3 remains bound to the streptavidin-coated plate. Subsequently, upon adding a second mIgG to the immobilized pair of GPC3/first mIgG, a further spike in signal reflects binding between the second mIgG and the immobilized GPC3, indicating the second mIgG reacted with the unbound epitopes left open on GPC3 after reaction with the first mIgG. Therefore, a spike in signal upon addition of the second mIgG demonstrates that the first and second mIgGs bind to distinct epitopes. On the contrary, the absence of spikes in signal upon addition of the second mIgG may demonstrate that the first and second mIgGs bind to the same epitope.

In a linear format of GPC3 epitope binning, 5 µg/mL biotinylated GPC3 was loaded onto a streptavidin biosensor. After washing off excess antigens, mIgG proteins were sequentially added, where the first mIgG was added at 50 µg/mL, followed by the second mIgG at 100 µg/mL. Specifically, GC33-mIgG1 was first added at 50 µg/mL, triggering a spike in signal, thereby indicating specific binding of GC33-mIgG1 to a GPC3 epitope (FIG. 13). Subsequently, either GPC3A-37 mIgG or GPC3A-55 mIgG was added at 100 µg/mL. In both cases, a second spike was recorded upon the addition of either GPC3A-37 mIgG or A-55 mIgG (FIG. 13), indicating that GPC3A-37 mIgG and GC33-mIgG1 bind to distinct epitopes, and that GPC3A-55 mIgG and GC33-mIgG1 also bind to distinct epitopes.

In an additional experiment, GPC3A-37 mIgG was first added at 50 µg/mL, which triggered a spike in signal, thereby indicating specific binding of GPC3A-37 mIgG to a GPC3 epitope. Subsequently, GPC3A-55 mIgG was added at 100 µg/mL, which triggered a second spike, indicating that GPC3A-37 mIgG and GPC3A-55 mIgG bound to distinct epitopes (FIG. 13). Combining the above results, GC33 mIgG1, GPC3A-37 mIgG and GPC3A-55 mIgG each binds to a distinct epitope on GPC3.

In a sandwich format of GPC3 epitope binning, a mIgG protein was biotinylated and immobilized on Streptavidin biosensors, at 5 µg/mL. After washing off excess mIgGs, GPC3 was added to the immobilized antibody at 10 µg/mL and stayed bound to the immobilized mIgG. After washing, a second mIgG was then added at 10 µg/mL and binding was monitored.

Specifically, each of GC33-mIgG, GPC3A-37 mIgG and GPC3A-55 mIgG protein (as the first mIgG1) was biotinylated and immobilized respectively on Streptavidin biosensors at 5 µg/mL. After washing off excess mIgGs, 10 µg/mL of GPC3 was added to the immobilized antibody, which triggered a spike for each of the three tested mIgG's, thereby indicating specific binding of each of GC33-mIgG, GPC3A-37 mIgG and GPC3A-55 mIgG to a GPC3 epitope. After washing off excess GPC3 antigens, 10 µg/mL of a second mIgG (different from the first mIgG) was added and binding was monitored. Similar to the linear format of epitope binning, the subsequent addition of a second, different mIgG triggered a further spike in signal (FIG. 14); therefore indicating that GC33-mIgG1, GPC3A-37 mIgG and GPC3A-55 mIgG each binds to a distinct epitope on GPC3.

GPC3-L2K Binding to Soluble Recombinant Human GPC3 Protein

The binding properties of anti-hGPC3 anti-hGPC3 L2K bispecific antibodies (GPC3A L2K derived from clones GPC3A-34, GPC3A-37, GPC3A-45, GPC3A-46, GPC3A-55, GPC3A-58) to biotinylated recombinant GPC3$_{(560)}$ (bt-GPC3$_{(560)}$) was measured by surface plasmon resonance technology using a BIACORE™ X100 instrument (GE Healthcare) and a Biotin CAPture Kit (GE Healthcare, Cat #28-9202-33) in single-cycle kinetics mode according to the manufacturer's instructions. All of the proteins used in the assay were diluted in HBS-E buffer prior to use. Briefly, 5-10 µg/ml of bt-GPC3$_{(560)}$ was immobilized onto a sensor chip pre-functionalized with CAPture Reagent and injected onto the flow cell. Affinity of the L2K bispecific antibodies for immobilized antigen was measured by injection of the various bispecific antibodies at 0.3-5 mg/ml with a 90 second association phase followed by a 90 second dissociation phase at a flow rate of 30 µl/min. At the end of each run, the surface of the sensor chip was regenerated using the reagents provided in the Biotin CAPture kit. Binding constants were determined by nonlinear regression analysis using a 1:1 binding model (BIACORE™ X-100 evaluation software, FIGS. 15A and 15B). The association-on-rate-$k_{on}$, affinity constant-$k_a$, dissociation constant-$k_d$, and equilibrium dissociation constant-$K_d$ were then calculated for each L2K clone (Table 14).

TABLE 14

| GPC3 × CD3 Bispecific antibody clone | $k_a$ (1/Ms) | $k_d$ (Vs) | $K_d$ (nM) |
|---|---|---|---|
| GPC3A-34 L2K | 4.00E+05 | 0.001398 | 3.5 |
| GPC3A-37 L2K | 5.67E+05 | 0.002886 | 5.1 |
| GPC3A-45 L2K | 1.28E+05 | 0.000455 | 3.5 |
| GPC3A-46 L2K | 3.99E+05 | 0.001289 | 3.2 |
| GPC3A-55 L2K | 7.05E+05 | 0.001606 | 2.3 |
| GPC3A-58 L2K | 3.68E+05 | 0.00188 | 5.1 |

Binding to HepG2 (GPC3-positive) Cells

HepG2 cells are tested for anti-hGPC3 mIgG1 or BsAb binding with dose dependency. Briefly, HepG2 cells are incubated with anti-hGPC3 mIgG1 or BsAb at 10, 3.3, 1.1, 0.37, 0.12, 0.041, 0.014 or 0 µg/ml on ice for 1 hour. After a round of brief washing with PBS buffer, BsAbs are detected with the secondary antibody APC-labeled anti-His tag antibody. mIgG1 antibodies are detected with a PE-labeled anti-mouse secondary antibody. The anti-GPC3 mIgG1 or BsAbs are evaluated for their affinity towards HepG2 cells by EC50 of the dose dependence curve (MFI vs. BsAb concentration). Furthermore, apparent $K_d$ is determined based on EC50 value. The $EC_{50}$ or apparent $K_d$ ratios of mIgG1 clones of the invention against clone GC33 mIgG1 are calculated. The $EC_{50}$ or apparent $K_d$ ratios of BsAb clones of the invention against clone GC33 BsAb are also calculated.

Example 6. Construction and Characterization of Anti-GPC3 Chimeric Antigen Receptors Anti-GPC3 CARs were constructed using a lentiviral CAR expression vector. Each of the scFvs derived from anti-GPC3 clones (GPC3A-34, GPC3A-37, GPC3A-45, GPC3A-46, GPC3A-55, GPC3A-58 and GPC3B-87; referred herein as "GPC3A-CAR" or "GPC3B-CAR") were grafted onto the CAR expression vector. An scFv derived from GC33 was also used to construct a GC33 CAR. Each CAR construct comprises an intracellular signaling domain of CD28 and an intracellular signaling domain of CD3ζ. Exemplary CARs derived from GPC3A-34, GPC3A-37, GPC3A-45, GPC3A-46, GPC3A-55, and GPC3A-58 antibody clones comprise the amino acid sequences of SEQ ID NOs: 491 and 516-521 respectively.

Human primary T-cells were activated by stimulation with CD3/CD28 beads (DYNABEADS®, Invitrogen) in the presence of interleukin-7 and interleukin-15 for one day. Concentrated lentiviruses were applied to T-cells in Retronectin (Takara) coated 6-well plates for 72 hours, at an MOI of 6. Transduction efficiencies are shown in Table 15.

TABLE 15

| T cells | Transduction efficiency (CAR positive %) |
|---|---|
| GC33-CAR | 95.9 |
| GPC3A-CAR-34 | 66.8 |
| GPC3A-CAR-37 | 85.9 |
| GPC3A-CAR-45 | 80.7 |
| GPC3A-CAR-46 | 91.9 |
| GPC3A-CAR-55 | 76.7 |
| GPC3A-CAR-58 | 95.5 |
| GPC3A-CAR-87 | 94.1 |
| Mock | 0.67 |

Functional assessment of the transduced CAR T cells (GPC3A, GPC3B or GC33 CAR-T cells) was performed using a LDH Cytotoxicity Assay. CAR-T cells and target cells (HepG2, HepG2-GPC3-KO, SK-Hep1, or SK-Hep1-GPC3) were mixed at an effector-to-target ratio of 2:1, in which 100,000 target cells were seeded per test well and treated with 200,000 CAR-T cells (infected CAR T cells were normalized to be 67% CAR-positive). The LDH cytotoxicity assay was performed after overnight incubation.

A panel of seven GPC3A or GPC3B CARs, as well as the GC33 CAR were transduced into T cells and tested against the target cell lines HepG2, HepG2-GPC3-KO, SK-Hep1, and SK-Hep1-GPC3. T cells transduced with the CAR constructs, GPC3A-CAR-37, GPC3A-CAR-45, GPC3A-CAR-46, GPC3A-CAR-55, GPC3A-CAR-58, GPC3B-CAR-87) specifically killed GPC3 positive cell lines such as HepG2 and SK-Hep1-GPC3 (FIG. 16). GPC3-negative cells such as wild-type SK-Hep1 or HepG2-GPC3-KO, however, were poorly recognized by the same CAR T cells. In these LDH cytotoxicity experiments, CAR-Ts comprising GPC3A-CAR-37, GPC3A-CAR-55, and GPC3A-CAR-58

CAR displayed high efficiency in killing GPC3-positive target cells but low non-specific killing of GPC3 negative cells (FIG. 16).

In a second batch of LDH cytotoxicity assays, CAR-T cells and target cells (HepG2, HepG2-GPC3-KO, SK-Hep1, SK-Hep1-GPC3, JHH-5, A498 or PANC-1) were mixed at an effector-to-target ratio of 2:1, in which 100,000 cells were seeded per test well and treated with 200,000 anti-GPC3 CAR positive T cells (infected CAR T cells were normalized to be 37.1% positive for CAR). Transduction efficiencies of the CAR-T cells are shown in Table 16. The LDH assay was performed after overnight incubation.

TABLE 16

| T cells | Transduction efficiency (CAR positive %) |
| --- | --- |
| GC33-CAR | 74.4 |
| GPC3A-CAR-34 | 51.2 |
| GPC3A-CAR-37 | 69.2 |
| GPC3A-CAR-45 | 58.8 |
| GPC3A-CAR-46 | 60.3 |
| GPC3A-CAR-55 | 37.1 |
| GPC3A-CAR-58 | 78 |
| GPC3A-CAR-87 | 74.8 |
| Mock | 0.67 |

As shown in FIGS. 17A and 17B, T cells transduced with the CAR constructs, GPC3A-CAR-37, GPC3A-CAR-45, GPC3A-CAR-46, GPC3A-CAR-55, and GPC3B-CAR-87 specifically killed GPC3 positive cell lines HepG2, SK-Hep1-GPC3, and JHH-5. GPC-negative target cells such as A-498, PANC-1, wild-type SK-Hep1 cells and HepG2-GPC3-KO, however, were poorly recognized by the same CAR-T cells (FIGS. 16A and 16B). These experiments demonstrate therapeutic benefit in employing the anti-GPC3 GPC3A or GPC3B CAR-Ts in specifically targeting GPC3 expressing tumor cells without significant effects on GPC3 negative cells.

Example 7. Construction and Characterization of T Cells Transduced with Anti-AFP caTCR-1 and Anti-CD3/Anti-GPC3 Bispecific Antibody Primary T cells were transduced with a lentivirus encoding either anti-AFP caTCR (SEQ ID NOs: 522 and 523) or anti-AFP caTCR+anti-GPC3/anti-CD3 BsAb (SEQ ID NO: 511). Measurements of the percentages of caTCR-positive cells were determined to assess transduction efficiency. The anti-AFP caTCR was under the control of the EF1-alpha promoter (SEQ ID NO: 527) and the anti-GPC3/anti-CD3 BsAb was under the control of an NFAT-derived promoter (SEQ ID NO: 526) comprising 6 NFAT response elements (SEQ ID NO: 524) and a minimal TA promoter (SEQ ID NO: 525). T-cells were matched at the indicated receptor positive percentages by mixing with mock T-cells. Two cell lines were used: HEPG2 (AFP+/GPC3+) and HepG2-GPC3-KO (AFP+/GPC3−) at an effector-to-target ratio of 2.5:1. Specific T-cell lysis was measured after 16 hr incubation using the Cytox 96 Non-radioactive Cytotoxicity Assay (Promega).

In vitro killing data shows that the expression of the anti-GPC3/anti-CD3 BsAb in T-cells transduced with the anti-AFP caTCR+anti-GPC3/anti-CD3 BsAb increased the potency of the transduced T-cells compared to T cell transduced only with the anti-AFP caTCR in a GPC3-dependent manner, throughout a range of T-cell doses (FIG. 18). Reactions that demonstrated an increase in cytotoxic potency also showed increases in the amounts of cytokines (IFNγ, TNFα, and IL-2) released (FIG. 19). Thus, the induced expression of the anti-GPC3/anti-CD3 BsAb increased the potency and cytokine production of T-cells.

To directly measure the cytotoxicity of antigen-induced anti-GPC3/anti-CD3 BsAbs apart from the anti-AFP caTCR T-cell toxicity, we used transwells with BsAb permeable membranes. $2.5 \times 10^5$ SK-HEP1-GPC3 (GPC3$^+$) or SK-HEP1 (GPC3$^-$) tumor cells and $4 \times 10^6$ receptor-negative "mock" T-cells were seeded together in the lower chamber. $2.5 \times 10^5$ anti-AFP caTCR transfected T-cells along with $2.5 \times 10^5$ corresponding target cells SK-HEP1-MG (AFP$^+$) or SK-HEP1 (AFP$^-$) were seeded together in the upper chamber. When anti-AFP caTCR+anti-GPC3/anti-CD3 BsAb T-cells were stimulated with AFP positive (SK-Hep1-MG) tumor cells, the secreted anti-GPC3/anti-CD3 BsAbs passed through the transwell membrane and were able to stimulate the lysis of GPC3-positive SK-Hep1-GPC3 tumor cells (FIG. 20). These results demonstrate that the anti-AFP caTCR+anti-GPC3/anti-CD3 BsAb T-cells were able to secrete specific fully functional anti-GPC3/anti-CD3 BsAbs in response to caTCR receptor engagement, and that therapeutic effects of such BsAbs can be used in an additive fashion to caTCR therapy.

Example 8. Construction and Characterization of T Cells Transduced with Anti-AFP caTCR-1 and Anti-GPC3 Chimeric Stimulatory Receptor A nucleic acid fragment encoding the anti-AFP binding moiety (SEQ ID NOs: 528 and 529) was used to generate caTCR-1 constructs (caTCR-1-0 or caTCR-1-TM5). A nucleic acid fragment encoding the anti-GPC3 binding moiety (SEQ ID NOs: 309 and 360) was used to generate a CSR (i.e., CSR1) comprising CD28 transmembrane and intracellular signaling sequences (SEQ ID NO: 530).

In Vitro Killing

HEPG2 cells (human liver cancer cells expressing AFP and GPC3) and HEPG2-GPC3-KO cells were used as target cells for T-cell stimulation at an effector-to-target ratio of 2.5:1. Specific T-cell lysis was measured after 16 hr incubation using the Cytox 96 Non-radioactive Cytotoxicity Assay (Promega).

Expression of anti-GPC3-CSR (SEQ ID NO: 531) with either anti-AFP-caTCR-1-0 (SEQ ID NOs: 532, 533) or anti-AFP-caTCR-1-TM5 (SEQ ID NOs: 534, 535) resulted in fully functional cytotoxic T-cells capable of lysing HEPG2 cells in vitro (FIG. 21). T cells expressing only the caTCR-1-0 had much less specific killing (about 15%) than those expressing both caTCR-1 (caTCR-1-0 or caTCR-1-TM5) and the CSR (between about 55% to about 65%). By contrast, specific killing was reduced to about 10% for T cells expressing both the caTCR and CSR when using HEPG2-GPC3-KO target cells (FIG. 21), indicating that engagement of the CSR with its target ligand is responsible for the increased cytotoxicity.

Cytokine Secretion

The concentration of cytokines released into the supernatant of the in vitro killing experiments was measured with a Bioplex200 (Luminex) using the Bio-plex Pro Human Cytokine 8-plex kit (BioRad). The CSR-positive and caTCR-positive T-cells released more cytotoxic cytokines than T-cells expressing ca-TCR-1-0 alone for the HEPG2 target cells expressing both the caTCR target antigen and the CSR target ligand (FIG. 22). By contrast, there we little or no difference between the T cells expressing ca-TCR-1-0 alone or both a caTCR and the CSR for the HEPG2-GPC3-KO target cells lacking the CSR target ligand (FIG. 22).

Intracellular Cytokine Expression

T-cells were stimulated with target cells (HEPG2) at an E:T ratio 1:2 in the presence of secretion inhibitor brefeldin A (BFA) for 4 hours. T-cells were permeabilized and cytokine specific antibodies were used to detect cytokines expressed in response to tumor stimulation. The percent of cytokine-positive cells was determined using flow cytometry. The CSR-positive and caTCR-positive T-cells expressed more intracellular cytokines than T-cells expressing ca-TCR-1-0 alone (Table 17).

TABLE 17

| % Positive | HEPG2 | T-cell Alone |
|---|---|---|
| Intracellular TNFα Expression in CD8 + T-cells | | |
| CSR | 0.3 | 0.2 |
| caTCR-1-0 | 14.7 | 0.1 |
| caTCR-1-0 + CSR | 17.0 | 0.1 |
| caTCR-1-TM5 + CSR | 15.7 | 0.1 |
| Intracellular IL-2 Expression in CD4 + T-cells | | |
| CSR | 0.1 | 0.04 |
| caTCR-1-0 | 8.2 | 0.11 |
| caTCR-1-0 + CSR | 9.8 | 0.05 |
| caTCR-1-TM5 + CSR | 11.2 | 0.03 |
| Intracellular IFNγ Expression in CD8 + T-cells | | |
| CSR | 0.2 | 0.08 |
| caTCR-1-0 | 3.1 | 0.2 |
| caTCR-1-0 + CSR | 4.5 | 0.1 |
| caTCR-1-TM5 + CSR | 5.1 | 0.06 |

Taken together, the results indicate that the addition of the CSR increases the sensitivity and responsiveness of caTCR plus CSR T-cells having a different caTCR target antigen and CSR target ligand. The increased quantity of cytokines expressed in and released from these CSR-caTCR double positive T cells provides further evidence that the co-stimulation of both caTCR-1 and CSR raises the cytotoxic potential of the T-cells.

Degranulation

T cells were mixed with fluorescently-conjugated anti-CD107a and stimulated with HEPG2 target cells at an E:T ratio of 1:2 in the presence of the endocytosis inhibitor monensin for 4 hours. Engagement of the CSR on caTCR T-cells increased T-cell degranulation, further demonstrating that the CSR makes therapeutic T-cells more reactive towards the intended tumor cells (FIG. 23).

Proliferation

T-cells were labeled with the intracellular dye CFSE, and dye dilution and number of CFSE-positive cells remaining at the indicated day was measured.

Respective T-cells were serum starved overnight and labeled with CFSE using CellTrace CFSE (Thermo Fisher C34554). 100,000 T-cells were incubated at an E:T ratio of 2:1 and flow cytometry was used to observe serial dilution of the CFSE dye as the T-cells divide at the indicated day. The total number of T-cells was counted by FACs.

CFSE dilution increased with CSR stimulation, indicating these T-cells had a higher proliferation potential (FIG. 24). Importantly there is also an increase in the cell number, meaning that the cells not only proliferate better but their persistence is also maintained (Table 18).

TABLE 18

| # of T-Cells Persisting After Engagement with HEPG2 | | | |
|---|---|---|---|
| | Day 3 | Day 5 | Day 7 |
| CSR | 7,147 | 4,519 | 3,055 |
| caTCR1-0 | 5,674 | 4,362 | 3,372 |
| caTCR1-0 + CSR | 31,422 | 18,689 | 8,833 |
| caTCR-1-TM5 + CSR | 28,874 | 21,978 | 9,471 |

The results show that we were able to simultaneously stimulate both CSR and caTCR with ligand positive tumor cells, and that the co-stimulation of CSR and caTCR enhanced the cytotoxicity, proliferation potential, and persistence of caTCR T-cells. These are all characteristics that will increase therapeutic potential of caTCR-based therapies using adoptive transfer.

Example 9: In Vivo Efficacy Study of T Cells Transduced with Anti-AFP caTCR-1 and Anti-GPC3 CSR The in vivo anti-tumor activity of T cells expressing both anti-AFP caTCR-1 and anti-GPC3 CSR-1 (see, Example 8 for construct information) was tested in an established human AFP$^+$/HLA-A2$^+$ Hep G2 liver cancer xenograft model. Hep G2 cells were implanted subcutaneously (s.c.) over the right flank of SCID-Beige mice. When tumors reached ~100 mm$^3$, mice were intratumorally (i.t.) injected with either (1) 5×10$^6$ un-transduced donor-matched (Mock) T cells, (2) 2×10$^6$ T cells expressing an anti-AFP CAR comprising the same anti-AFP binding moiety (SEQ ID NOs: 528 and 529), or (3) 2×10$^6$ T cells expressing both anti-AFP caTCR-1 and anti-GPC3 CSR-1 (n=6 mice/group). Health effects resulting from the T cell infusions in mice were assessed by monitoring their general appearance, body weight, and other clinical signs of adverse response (including hypothermia, labored respiration, and hind-limb paralysis/weakness).

As shown in FIG. 25, both anti-AFP CAR T cell treatment and anti-AFP caTCR-1/anti-GPC3 CSR-1 T cell treatment resulted in profound and significant (****$P<0.0001$; Dunnett's multiple comparison test) tumor growth inhibition. All anti-AFP CAR-T treated and anti-AFP caTCR-1/anti-GPC3 CSR-1 T cell-treated mice demonstrated normal gait, posture, and activity/responsiveness for the duration of the study. In addition, anti-AFP CAR-T treated and anti-AFP caTCR-1/anti-GPC3 CSR-1 T cell-treated mice did not lose body weight during the study. Overall, the lack of observable abnormal parameters in treated mice demonstrates the safety of the anti-AFP caTCR-1/anti-GPC3 CSR-1 T cell therapy.

What is claimed is:

1. An isolated anti-Glypican-3 (anti-GPC3) construct comprising an antibody moiety specifically recognizing GPC3 (anti-GPC3 antibody moiety), wherein the anti-GPC3 antibody moiety comprises:

(1) a heavy chain complementarity determining region (HC-CDR) 1 comprising the amino acid sequence of SEQ ID NO: 3, an HC-CDR2 comprising the amino acid sequence of SEQ ID NO: 54, an HC-CDR3 comprising the amino acid sequence of SEQ ID NO: 105, a light chain complementarity determining region (LC-CDR) 1 comprising the amino acid sequence of SEQ ID NO: 156, an LC-CDR2 comprising the amino acid sequence of SEQ ID NO: 207, and an LC-CDR3 comprising the amino acid sequence of SEQ ID NO: 258;

(2) an HC-CDR1 comprising the amino acid sequence of SEQ ID NO: 21, an HC-CDR2 comprising the amino acid sequence of SEQ ID NO: 72, an HC-CDR3 comprising the amino acid sequence of SEQ ID NO: 123, an LC-CDR1 comprising the amino acid sequence of SEQ ID NO: 174, an LC-CDR2 comprising the amino acid sequence of SEQ ID NO: 225, and an LC-CDR3 comprising the amino acid sequence of SEQ ID NO: 276;

(3) an HC-CDR1 comprising the amino acid sequence of SEQ ID NO: 24, an HC-CDR2 comprising the amino acid sequence of SEQ ID NO: 75, an HC-CDR3 comprising the amino acid sequence of SEQ ID NO: 126, an LC-CDR1 comprising the amino acid sequence of SEQ ID NO: 177, an LC-CDR2 comprising the amino acid sequence of SEQ ID NO: 228, and an LC-CDR3 comprising the amino acid sequence of SEQ ID NO: 279;

(4) an HC-CDR1 comprising the amino acid sequence of SEQ ID NO: 1, an HC-CDR2 comprising the amino acid sequence of SEQ ID NO: 52, an HC-CDR3 comprising the amino acid sequence of SEQ ID NO: 103, an LC-CDR1 comprising the amino acid sequence of SEQ ID NO: 154, an LC-CDR2 comprising the amino acid sequence of SEQ ID NO: 205, and an LC-CDR3 comprising the amino acid sequence of SEQ ID NO: 256;

(5) an HC-CDR1 comprising the amino acid sequence of SEQ ID NO: 11, an HC-CDR2 comprising the amino acid sequence of SEQ ID NO: 62, an HC-CDR3 comprising the amino acid sequence of SEQ ID NO: 113, an LC-CDR1 comprising the amino acid sequence of SEQ ID NO: 164, an LC-CDR2 comprising the amino acid sequence of SEQ ID NO: 215, and an LC-CDR3 comprising the amino acid sequence of SEQ ID NO: 266; or (6) an HC-CDR1 comprising the amino acid sequence of SEQ ID NO: 12, an HC-CDR2 comprising the amino acid sequence of SEQ ID NO: 63, an HC-CDR3 comprising the amino acid sequence of SEQ ID NO: 114, an LC-CDR1 comprising the amino acid sequence of SEQ ID NO: 165, an LC-CDR2 comprising the amino acid sequence of SEQ ID NO: 216, and an LC-CDR3 comprising the amino acid sequence of SEQ ID NO: 267.

2. The isolated anti-GPC3 construct of claim 1, wherein the anti-GPC3 antibody moiety comprises:
(1) i) a heavy chain variable domain (VH) comprising the amino acid sequence of SEQ ID NO: 309, or a variant thereof having at least about 95% sequence identity to SEQ ID NO: 309; and ii) a light chain variable domain (VL) comprising the amino acid sequence of SEQ ID NO: 360, or a variant thereof having at least about 95% sequence identity to SEQ ID NO: 360;
(2) i) a VH comprising the amino acid sequence of SEQ ID NO: 327, or a variant thereof having at least about 95% sequence identity to SEQ ID NO: 327; and ii) a VL comprising the amino acid sequence of SEQ ID NO: 378, or a variant thereof having at least about 95% sequence identity to SEQ ID NO: 378;
(3) i) a VH comprising the amino acid sequence of SEQ ID NO: 330, or a variant thereof having at least about 95% sequence identity to SEQ ID NO: 330 and ii) a VL comprising the amino acid sequence of SEQ ID NO: 381, or a variant thereof having at least about 95% sequence identity to SEQ ID NO: 381;
(4) i) a VH comprising the amino acid sequence of SEQ ID NO: 307, or a variant thereof having at least about 95% sequence identity to SEQ ID NO: 307; and ii) a VL comprising the amino acid sequence of SEQ ID NO: 358, or a variant thereof having at least about 95% sequence identity to SEQ ID NO: 358; or
(5) i) a VH comprising the amino acid sequence of SEQ ID NO: 317, or a variant thereof having at least about 95% sequence identity to SEQ ID NO: 317; and ii) a VL comprising the amino acid sequence of SEQ ID NO: 368, or a variant thereof having at least about 95% sequence identity to SEQ ID NO: 368.

3. The isolated anti-GPC3 construct of claim 1, wherein the anti-GPC3 antibody moiety is fused to an Fc fragment optionally via a linker.

4. The isolated anti-GPC3 construct of claim 1, wherein the isolated anti-GPC3 construct is a tandem scFv comprising two scFvs linked by a peptide linker.

5. The isolated anti-GPC3 construct of claim 1, wherein the isolated anti-GPC3 construct is a chimeric antigen receptor (CAR) comprising:
(a) an extracellular domain comprising the anti-GPC3 antibody moiety;
(b) a transmembrane domain; and
(c) an intracellular signaling domain.

6. The isolated anti-GPC3 construct of claim 1, wherein the isolated anti-GPC3 construct is a chimeric antibody-T cell receptor (TCR) construct (caTCR) comprising:
(a) an extracellular domain comprising the anti-GPC3 antibody moiety; and
(b) a TCR module (TCRM) comprising i) a first TCR domain (TCRD) comprising a first TCR transmembrane domain (TCR-TM) and ii) a second TCRD comprising a second TCR-TM, wherein the TCRM facilitates recruitment of at least one TCR-associated signaling molecule.

7. The isolated anti-GPC3 construct of claim 1, wherein the isolated anti-GPC3 construct is an immunoconjugate comprising the anti-GPC3 antibody moiety and an effector molecule.

8. The isolated anti-GPC3 construct of claim 7, wherein the effector molecule is a label.

9. An isolated nucleic acid encoding the polypeptide components of the isolated anti-GPC3 construct of claim 8.

10. An isolated host cell comprising the isolated anti-GPC3 construct of claim 8.

11. An effector cell expressing the isolated anti-GPC3 construct of claim 5.

12. A pharmaceutical composition comprising the isolated anti-GPC3 construct of claim 8, and a pharmaceutically acceptable carrier.

13. A kit comprising the isolated anti-GPC3 construct of claim 1.

14. A method of treating an individual having a GPC3-positive cancer, comprising administering to the individual an effective amount of the isolated anti-GPC3 construct of claim 8, wherein:
i) the isolated anti-GPC3 construct is expressed on the cell surface of an immune effector cell;
ii) the isolated anti-GPC3 construct further comprises a second antigen-binding moiety specifically recognizing a cell surface antigen on an immune effector cell; or
iii) the isolated anti-GPC3 construct further comprises an effector molecule, wherein the effector molecule is a therapeutic agent selected from the group consisting of a drug, a toxin, a radioisotope, a protein, a peptide, and a nucleic acid.

15. A method of diagnosing an individual having a GPC3-positive disease, comprising:
   a) administering an effective amount of the isolated anti-GPC3 construct of claim 8 to the individual; and
   b) determining the level of the label in the individual, wherein a level of the label above a threshold level indicates that the individual has the GPC3-positive disease.

16. A method of diagnosing an individual having a GPC3-positive disease, comprising:
   a) contacting a sample derived from the individual with the isolated anti-GPC3 construct of claim 8; and
   b) determining the number of cells bound with the isolated anti-GPC3 construct in the sample, wherein a value for the number of cells bound with the isolated anti-GPC3 construct above a threshold level indicates that the individual has the GPC3-positive disease.

17. A method of producing an isolated anti-GPC3 construct, comprising:
   (a) culturing a host cell comprising the isolated nucleic acid of claim 9 under a condition effective to express the isolated anti-GPC3 construct; and
   (b) obtaining the expressed anti-GPC3 construct from said host cell.

18. The isolated anti-GPC3 construct of claim 1, wherein the isolated anti-GPC3 construct is a chimeric co-stimulatory receptor (CSR) comprising:
   (a) an extracellular ligand-binding module comprising the anti-GPC3 antibody moiety;
   (b) a transmembrane module; and
   (c) an intracellular co-stimulatory immune cell signaling module.

19. The isolated anti-GPC3 construct of claim 1, wherein the anti-GPC3 antibody moiety comprises an HC-CDR1 comprising the amino acid sequence of SEQ ID NO: 3, an HC-CDR2 comprising the amino acid sequence of SEQ ID NO: 54, an HC-CDR3 comprising the amino acid sequence of SEQ ID NO: 105, an LC-CDR1 comprising the amino acid sequence of SEQ ID NO: 156, an LC-CDR2 comprising the amino acid sequence of SEQ ID NO: 207, and an LC-CDR3 comprising the amino acid sequence of SEQ ID NO: 258.

20. The isolated anti-GPC3 construct of claim 19, wherein the anti-GPC3 antibody moiety comprises a VH comprising the amino acid sequence of SEQ ID NO: 309, and a VL comprising the amino acid sequence of SEQ ID NO: 360.

21. The isolated anti-GPC3 construct of claim 1, wherein the anti-GPC3 antibody moiety comprises an HC-CDR1 comprising the amino acid sequence of SEQ ID NO: 21, an HC-CDR2 comprising the amino acid sequence of SEQ ID NO: 72, an HC-CDR3 comprising the amino acid sequence of SEQ ID NO: 123, an LC-CDR1 comprising the amino acid sequence of SEQ ID NO: 174, an LC-CDR2 comprising the amino acid sequence of SEQ ID NO: 225, and an LC-CDR3 comprising the amino acid sequence of SEQ ID NO: 276.

22. The isolated anti-GPC3 construct of claim 21, wherein the anti-GPC3 antibody moiety comprises a VH comprising the amino acid sequence of SEQ ID NO: 327, and a VL comprising the amino acid sequence of SEQ ID NO: 378.

23. The isolated anti-GPC3 construct of claim 1, wherein the anti-GPC3 antibody moiety comprises an HC-CDR1 comprising the amino acid sequence of SEQ ID NO: 24, an HC-CDR2 comprising the amino acid sequence of SEQ ID NO: 75, an HC-CDR3 comprising the amino acid sequence of SEQ ID NO: 126, an LC-CDR1 comprising the amino acid sequence of SEQ ID NO: 177, an LC-CDR2 comprising the amino acid sequence of SEQ ID NO: 228, and an LC-CDR3 comprising the amino acid sequence of SEQ ID NO: 279.

24. The isolated anti-GPC3 construct of claim 23, wherein the anti-GPC3 antibody moiety comprises a VH comprising the amino acid sequence of SEQ ID NO: 330, and a VL comprising the amino acid sequence of SEQ ID NO: 381.

25. The effector cell of claim 11, wherein the effector cell is a T cell.

\* \* \* \* \*

UNITED STATES PATENT AND TRADEMARK OFFICE
CERTIFICATE OF CORRECTION

| | | |
|---|---|---|
| PATENT NO. | : 11,447,564 B2 | Page 1 of 1 |
| APPLICATION NO. | : 16/608377 | |
| DATED | : September 20, 2022 | |
| INVENTOR(S) | : Pengbo Zhang et al. | |

It is certified that error appears in the above-identified patent and that said Letters Patent is hereby corrected as shown below:

In the Claims

At Column 652, Claim number 9, Line number 44, delete "claim 8" and insert --claim 1--
At Column 652, Claim number 10, Line number 46, delete "claim 8" and insert --claim 1--
At Column 652, Claim number 12, Line number 50, delete "claim 8" and insert --claim 1--
At Column 652, Claim number 14, Line number 57, delete "claim 8" and insert --claim 1--

Signed and Sealed this
Ninth Day of July, 2024

Katherine Kelly Vidal
*Director of the United States Patent and Trademark Office*

SEQUENCE LISTING

<160> NUMBER OF SEQ ID NOS: 536

<210> SEQ ID NO 1
<211> LENGTH: 8
<212> TYPE: PRT
<213> ORGANISM: Artificial Sequence
<220> FEATURE:
<223> OTHER INFORMATION: GPC3A-034 HCDR1

<400> SEQUENCE: 1

Gly Gly Ser Phe Ser Gly Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: GPC3A-035 HCDR1

<400> SEQUENCE: 2

Gly Tyr Thr Phe Thr Gly Tyr Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: GPC3A-037 HCDR1

<400> SEQUENCE: 3

Gly Phe Thr Phe Ser Ser Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: GPC3A-038 HCDR1

<400> SEQUENCE: 4

Gly Tyr Thr Phe Thr Ser Tyr Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: GPC3A-039 HCDR1

<400> SEQUENCE: 5

Gly Phe Thr Phe Ser Ser Tyr Ala
1               5

<210> SEQ ID NO 6
<211> LENGTH: 8
<212> TYPE: PRT
<213> ORGANISM: Artificial Sequence
<220> FEATURE:
<223> OTHER INFORMATION: GPC3A-040 HCDR1

<400> SEQUENCE: 6

Gly Tyr Thr Phe Thr Gly Tyr Tyr
1               5

```
<210> SEQ ID NO 7
<211> LENGTH: 8
<212> TYPE: PRT
<213> ORGANISM: Artificial Sequence
<220> FEATURE:
<223> OTHER INFORMATION: GPC3A-041 HCDR1

<400> SEQUENCE: 7

Gly Tyr Thr Phe Thr Gly Tyr Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: GPC3A-042 HCDR1

<400> SEQUENCE: 8

Gly Tyr Ser Phe Thr Gly Tyr Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: GPC3A-043 HCDR1

<400> SEQUENCE: 9

Gly Tyr Thr Phe Thr Asp Tyr Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: GPC3A-044 HCDR1

<400> SEQUENCE: 10

Gly Gly Ser Phe Ser Gly Tyr Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: GPC3A-045 HCDR1

<400> SEQUENCE: 11

Gly Phe Thr Phe Ser Asp Tyr Tyr
1               5

<210> SEQ ID NO 12
<211> LENGTH: 8
<212> TYPE: PRT
<213> ORGANISM: Artificial Sequence
<220> FEATURE:
<223> OTHER INFORMATION: GPC3A-046 HCDR1

<400> SEQUENCE: 12

Gly Tyr Arg Phe Ser Asn Tyr Gly
1               5
```

<210> SEQ ID NO 13
<211> LENGTH: 8
<212> TYPE: PRT
<213> ORGANISM: Artificial Sequence
<220> FEATURE:
<223> OTHER INFORMATION: GPC3A-047 HCDR1

<400> SEQUENCE: 13

Gly Tyr Thr Phe Thr Gly Tyr Tyr
1               5

<210> SEQ ID NO 14
<211> LENGTH: 8
<212> TYPE: PRT
<213> ORGANISM: Artificial Sequence
<220> FEATURE:
<223> OTHER INFORMATION: GPC3A-048 HCDR1

<400> SEQUENCE: 14

Gly Phe Thr Phe Ser Ser Tyr Ala
1               5

<210> SEQ ID NO 15
<211> LENGTH: 8
<212> TYPE: PRT
<213> ORGANISM: Artificial Sequence
<220> FEATURE:
<223> OTHER INFORMATION: GPC3A-049 HCDR1

<400> SEQUENCE: 15

Gly Tyr Thr Phe Thr Gly Tyr Tyr
1               5

<210> SEQ ID NO 16
<211> LENGTH: 8
<212> TYPE: PRT
<213> ORGANISM: Artificial Sequence
<220> FEATURE:
<223> OTHER INFORMATION: GPC3A-050 HCDR1

<400> SEQUENCE: 16

Gly Tyr Ser Phe Thr Gly Tyr Tyr
1               5

<210> SEQ ID NO 17
<211> LENGTH: 8
<212> TYPE: PRT
<213> ORGANISM: Artificial Sequence
<220> FEATURE:
<223> OTHER INFORMATION: GPC3A-051 HCDR1

<400> SEQUENCE: 17

Gly Gly Ala Phe Ser Ser Tyr Ala
1               5

<210> SEQ ID NO 18
<211> LENGTH: 8
<212> TYPE: PRT
<213> ORGANISM: Artificial Sequence
<220> FEATURE:
<223> OTHER INFORMATION: GPC3A-052 HCDR1

<400> SEQUENCE: 18

Gly Tyr Thr Phe Thr Gly Tyr Tyr
1               5

```
<210> SEQ ID NO 19
<211> LENGTH: 10
<212> TYPE: PRT
<213> ORGANISM: Artificial Sequence
<220> FEATURE:
<223> OTHER INFORMATION: GPC3A-053 HCDR1

<400> SEQUENCE: 19

Gly Gly Ser Ile Ser Ser Ser Tyr Tyr
1               5                   10

<210> SEQ ID NO 20
<211> LENGTH: 8
<212> TYPE: PRT
<213> ORGANISM: Artificial Sequence
<220> FEATURE:
<223> OTHER INFORMATION: GPC3A-054 HCDR1

<400> SEQUENCE: 20

Gly Tyr Thr Phe Thr Ser Tyr Gly
1               5

<210> SEQ ID NO 21
<211> LENGTH: 8
<212> TYPE: PRT
<213> ORGANISM: Artificial Sequence
<220> FEATURE:
<223> OTHER INFORMATION: GPC3A-055 HCDR1

<400> SEQUENCE: 21

Gly Tyr Thr Phe Thr Ser Tyr Tyr
1               5

<210> SEQ ID NO 22
<211> LENGTH: 8
<212> TYPE: PRT
<213> ORGANISM: Artificial Sequence
<220> FEATURE:
<223> OTHER INFORMATION: GPC3A-056 HCDR1

<400> SEQUENCE: 22

Gly Tyr Ser Phe Asn Asp Tyr Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: GPC3A-057 HCDR1

<400> SEQUENCE: 23

Gly Phe Thr Phe Ser Ser Tyr Ala
1               5

<210> SEQ ID NO 24
<211> LENGTH: 8
<212> TYPE: PRT
<213> ORGANISM: Artificial Sequence
<220> FEATURE:
<223> OTHER INFORMATION: GPC3A-058 HCDR1

<400> SEQUENCE: 24

Gly Tyr Thr Phe Ala Ser His Gly
1               5

<210> SEQ ID NO 25
```

```
<211> LENGTH: 8
<212> TYPE: PRT
<213> ORGANISM: Artificial Sequence
<220> FEATURE:
<223> OTHER INFORMATION: GPC3A-059 HCDR1

<400> SEQUENCE: 25

Gly Tyr Thr Phe Thr Arg Tyr Gly
1               5

<210> SEQ ID NO 26
<211> LENGTH: 8
<212> TYPE: PRT
<213> ORGANISM: Artificial Sequence
<220> FEATURE:
<223> OTHER INFORMATION: GPC3A-060 HCDR1

<400> SEQUENCE: 26

Gly Tyr Thr Phe Asn Ser Tyr Ala
1               5

<210> SEQ ID NO 27
<211> LENGTH: 8
<212> TYPE: PRT
<213> ORGANISM: Artificial Sequence
<220> FEATURE:
<223> OTHER INFORMATION: GPC3A-061 HCDR1

<400> SEQUENCE: 27

Gly Tyr Thr Phe Thr Ser Tyr Gly
1               5

<210> SEQ ID NO 28
<211> LENGTH: 8
<212> TYPE: PRT
<213> ORGANISM: Artificial Sequence
<220> FEATURE:
<223> OTHER INFORMATION: GPC3A-062 HCDR1

<400> SEQUENCE: 28

Gly Gly Thr Phe Ser Ser Tyr Ala
1               5

<210> SEQ ID NO 29
<211> LENGTH: 8
<212> TYPE: PRT
<213> ORGANISM: Artificial Sequence
<220> FEATURE:
<223> OTHER INFORMATION: GPC3A-063 HCDR1

<400> SEQUENCE: 29

Gly Tyr Thr Phe Thr Ser Tyr Tyr
1               5

<210> SEQ ID NO 30
<211> LENGTH: 8
<212> TYPE: PRT
<213> ORGANISM: Artificial Sequence
<220> FEATURE:
<223> OTHER INFORMATION: GPC3A-064 HCDR1

<400> SEQUENCE: 30

Gly Tyr Thr Phe Thr Ile Tyr Gly
1               5

<210> SEQ ID NO 31
<211> LENGTH: 8
```

```
<212> TYPE: PRT
<213> ORGANISM: Artificial Sequence
<220> FEATURE:
<223> OTHER INFORMATION: GPC3A-067 HCDR1

<400> SEQUENCE: 31

Gly Gly Thr Phe Ser Ser Tyr Ala
1               5

<210> SEQ ID NO 32
<211> LENGTH: 8
<212> TYPE: PRT
<213> ORGANISM: Artificial Sequence
<220> FEATURE:
<223> OTHER INFORMATION: GPC3B-54 HCDR1

<400> SEQUENCE: 32

Gly Tyr Thr Phe Ile Asp Tyr Tyr
1               5

<210> SEQ ID NO 33
<211> LENGTH: 8
<212> TYPE: PRT
<213> ORGANISM: Artificial Sequence
<220> FEATURE:
<223> OTHER INFORMATION: GPC3B-60 HCDR1

<400> SEQUENCE: 33

Gly Tyr Thr Phe Thr Ser Tyr Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: GPC3B-63 HCDR1

<400> SEQUENCE: 34

Gly Tyr Thr Phe Thr Ser Tyr Tyr
1               5

<210> SEQ ID NO 35
<211> LENGTH: 8
<212> TYPE: PRT
<213> ORGANISM: Artificial Sequence
<220> FEATURE:
<223> OTHER INFORMATION: GPC3B-66 HCDR1

<400> SEQUENCE: 35

Gly Tyr Thr Phe Ile Gly Gln Tyr
1               5

<210> SEQ ID NO 36
<211> LENGTH: 8
<212> TYPE: PRT
<213> ORGANISM: Artificial Sequence
<220> FEATURE:
<223> OTHER INFORMATION: GPC3B-68 HCDR1

<400> SEQUENCE: 36

Gly Gly Thr Phe Ser Ser Tyr Ala
1               5

<210> SEQ ID NO 37
<211> LENGTH: 8
<212> TYPE: PRT
```

```
<213> ORGANISM: Artificial Sequence
<220> FEATURE:
<223> OTHER INFORMATION: GPC3B-71 HCDR1

<400> SEQUENCE: 37

Gly Phe Thr Phe Ser Arg Tyr Thr
1               5

<210> SEQ ID NO 38
<211> LENGTH: 8
<212> TYPE: PRT
<213> ORGANISM: Artificial Sequence
<220> FEATURE:
<223> OTHER INFORMATION: GPC3B-76 HCDR1

<400> SEQUENCE: 38

Gly Tyr Thr Phe Thr Asp Tyr Tyr
1               5

<210> SEQ ID NO 39
<211> LENGTH: 8
<212> TYPE: PRT
<213> ORGANISM: Artificial Sequence
<220> FEATURE:
<223> OTHER INFORMATION: GPC3B-78 HCDR1

<400> SEQUENCE: 39

Gly Tyr Thr Phe Thr Ser Tyr Tyr
1               5

<210> SEQ ID NO 40
<211> LENGTH: 8
<212> TYPE: PRT
<213> ORGANISM: Artificial Sequence
<220> FEATURE:
<223> OTHER INFORMATION: GPC3B-80 HCDR1

<400> SEQUENCE: 40

Gly Gly Thr Leu Ser Arg Phe Ala
1               5

<210> SEQ ID NO 41
<211> LENGTH: 8
<212> TYPE: PRT
<213> ORGANISM: Artificial Sequence
<220> FEATURE:
<223> OTHER INFORMATION: GPC3B-81 HCDR1

<400> SEQUENCE: 41

Gly Tyr Thr Phe Thr Gly Tyr Tyr
1               5

<210> SEQ ID NO 42
<211> LENGTH: 8
<212> TYPE: PRT
<213> ORGANISM: Artificial Sequence
<220> FEATURE:
<223> OTHER INFORMATION: GPC3B-82 HCDR1

<400> SEQUENCE: 42

Gly Tyr Ser Phe Thr Ser Tyr Tyr
1               5

<210> SEQ ID NO 43
<211> LENGTH: 8
<212> TYPE: PRT
<213> ORGANISM: Artificial Sequence
```

```
<220> FEATURE:
<223> OTHER INFORMATION: GPC3B-85 HCDR1

<400> SEQUENCE: 43

Gly Tyr Thr Phe Thr Ser Tyr Ala
1               5

<210> SEQ ID NO 44
<211> LENGTH: 8
<212> TYPE: PRT
<213> ORGANISM: Artificial Sequence
<220> FEATURE:
<223> OTHER INFORMATION: GPC3B-87 HCDR1

<400> SEQUENCE: 44

Gly Gly Thr Phe Gly Ser Tyr Ala
1               5

<210> SEQ ID NO 45
<211> LENGTH: 8
<212> TYPE: PRT
<213> ORGANISM: Artificial Sequence
<220> FEATURE:
<223> OTHER INFORMATION: GPC3B-92 HCDR1

<400> SEQUENCE: 45

Gly Tyr Thr Phe Ser Asn Tyr Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: GPC3B-93 HCDR1

<400> SEQUENCE: 46

Gly Tyr Thr Phe Thr Ser Tyr Tyr
1               5

<210> SEQ ID NO 47
<211> LENGTH: 8
<212> TYPE: PRT
<213> ORGANISM: Artificial Sequence
<220> FEATURE:
<223> OTHER INFORMATION: GPC3B-110 HCDR1

<400> SEQUENCE: 47

Gly Gly Thr Phe Thr Thr Tyr Ser
1               5

<210> SEQ ID NO 48
<211> LENGTH: 8
<212> TYPE: PRT
<213> ORGANISM: Artificial Sequence
<220> FEATURE:
<223> OTHER INFORMATION: GPC3B-113 HCDR1

<400> SEQUENCE: 48

Gly Tyr Thr Leu Thr Glu Leu Ser
1               5

<210> SEQ ID NO 49
<211> LENGTH: 8
<212> TYPE: PRT
<213> ORGANISM: Artificial Sequence
<220> FEATURE:
```

```
<223> OTHER INFORMATION: GPC3B-115 HCDR1

<400> SEQUENCE: 49

Gly Tyr Thr Phe Thr Ala Tyr Tyr
1               5

<210> SEQ ID NO 50
<211> LENGTH: 8
<212> TYPE: PRT
<213> ORGANISM: Artificial Sequence
<220> FEATURE:
<223> OTHER INFORMATION: GPC3B-119 HCDR1

<400> SEQUENCE: 50

Gly Tyr Thr Phe Thr Ser Tyr Ala
1               5

<210> SEQ ID NO 51
<211> LENGTH: 8
<212> TYPE: PRT
<213> ORGANISM: Artificial Sequence
<220> FEATURE:
<223> OTHER INFORMATION: GPC3B-125 HCDR1

<400> SEQUENCE: 51

Gly Tyr Thr Phe Thr Ser Tyr Ala
1               5

<210> SEQ ID NO 52
<211> LENGTH: 7
<212> TYPE: PRT
<213> ORGANISM: Artificial Sequence
<220> FEATURE:
<223> OTHER INFORMATION: GPC3A-034 HCDR2

<400> SEQUENCE: 52

Ile Asn His Ser Gly Ser Thr
1               5

<210> SEQ ID NO 53
<211> LENGTH: 8
<212> TYPE: PRT
<213> ORGANISM: Artificial Sequence
<220> FEATURE:
<223> OTHER INFORMATION: GPC3A-035 HCDR2

<400> SEQUENCE: 53

Ile Asn Pro Asn Ser Gly Gly Thr
1               5

<210> SEQ ID NO 54
<211> LENGTH: 8
<212> TYPE: PRT
<213> ORGANISM: Artificial Sequence
<220> FEATURE:
<223> OTHER INFORMATION: GPC3A-037 HCDR2

<400> SEQUENCE: 54

Ile Tyr Ser Gly Gly Ser Ser Thr
1               5

<210> SEQ ID NO 55
<211> LENGTH: 8
<212> TYPE: PRT
<213> ORGANISM: Artificial Sequence
<220> FEATURE:
<223> OTHER INFORMATION: GPC3A-038 HCDR2
```

```
<400> SEQUENCE: 55

Ile Asn Pro Ser Gly Gly Ser Thr
1               5

<210> SEQ ID NO 56
<211> LENGTH: 7
<212> TYPE: PRT
<213> ORGANISM: Artificial Sequence
<220> FEATURE:
<223> OTHER INFORMATION: GPC3A-039 HCDR2

<400> SEQUENCE: 56

Ile Gly Thr Gly Gly Gly Thr
1               5

<210> SEQ ID NO 57
<211> LENGTH: 8
<212> TYPE: PRT
<213> ORGANISM: Artificial Sequence
<220> FEATURE:
<223> OTHER INFORMATION: GPC3A-040 HCDR2

<400> SEQUENCE: 57

Ile Asn Pro Asn Ser Gly Gly Thr
1               5

<210> SEQ ID NO 58
<211> LENGTH: 8
<212> TYPE: PRT
<213> ORGANISM: Artificial Sequence
<220> FEATURE:
<223> OTHER INFORMATION: GPC3A-041 HCDR2

<400> SEQUENCE: 58

Ile Asn Pro Asn Ser Gly Gly Thr
1               5

<210> SEQ ID NO 59
<211> LENGTH: 8
<212> TYPE: PRT
<213> ORGANISM: Artificial Sequence
<220> FEATURE:
<223> OTHER INFORMATION: GPC3A-042 HCDR2

<400> SEQUENCE: 59

Met Asn Pro Arg Ser Gly Gly Thr
1               5

<210> SEQ ID NO 60
<211> LENGTH: 8
<212> TYPE: PRT
<213> ORGANISM: Artificial Sequence
<220> FEATURE:
<223> OTHER INFORMATION: GPC3A-043 HCDR2

<400> SEQUENCE: 60

Val Asp Pro Glu Asp Gly Glu Thr
1               5

<210> SEQ ID NO 61
<211> LENGTH: 7
<212> TYPE: PRT
<213> ORGANISM: Artificial Sequence
<220> FEATURE:
<223> OTHER INFORMATION: GPC3A-044 HCDR2
```

```
<400> SEQUENCE: 61

Ile Asn His Ser Gly Ser Thr
1               5

<210> SEQ ID NO 62
<211> LENGTH: 8
<212> TYPE: PRT
<213> ORGANISM: Artificial Sequence
<220> FEATURE:
<223> OTHER INFORMATION: GPC3A-045 HCDR2

<400> SEQUENCE: 62

Ile Ser Ser Ser Gly Ser Thr Ile
1               5

<210> SEQ ID NO 63
<211> LENGTH: 8
<212> TYPE: PRT
<213> ORGANISM: Artificial Sequence
<220> FEATURE:
<223> OTHER INFORMATION: GPC3A-046 HCDR2

<400> SEQUENCE: 63

Ile Ser Gly Ser Asn Gly Asn Thr
1               5

<210> SEQ ID NO 64
<211> LENGTH: 8
<212> TYPE: PRT
<213> ORGANISM: Artificial Sequence
<220> FEATURE:
<223> OTHER INFORMATION: GPC3A-047 HCDR2

<400> SEQUENCE: 64

Ile Asn Pro Asn Ser Gly Gly Thr
1               5

<210> SEQ ID NO 65
<211> LENGTH: 8
<212> TYPE: PRT
<213> ORGANISM: Artificial Sequence
<220> FEATURE:
<223> OTHER INFORMATION: GPC3A-048 HCDR2

<400> SEQUENCE: 65

Ile Ser Tyr Asp Gly Ser Asn Lys
1               5

<210> SEQ ID NO 66
<211> LENGTH: 8
<212> TYPE: PRT
<213> ORGANISM: Artificial Sequence
<220> FEATURE:
<223> OTHER INFORMATION: GPC3A-049 HCDR2

<400> SEQUENCE: 66

Ile Asn Pro Asn Ser Gly Gly Thr
1               5

<210> SEQ ID NO 67
<211> LENGTH: 8
<212> TYPE: PRT
<213> ORGANISM: Artificial Sequence
<220> FEATURE:
<223> OTHER INFORMATION: GPC3A-050 HCDR2

<400> SEQUENCE: 67
```

Met Asn Pro Arg Ser Gly Gly Thr
1               5

<210> SEQ ID NO 68
<211> LENGTH: 8
<212> TYPE: PRT
<213> ORGANISM: Artificial Sequence
<220> FEATURE:
<223> OTHER INFORMATION: GPC3A-051 HCDR2

<400> SEQUENCE: 68

Ile Ile Pro Ile Phe Gly Thr Ala
1               5

<210> SEQ ID NO 69
<211> LENGTH: 8
<212> TYPE: PRT
<213> ORGANISM: Artificial Sequence
<220> FEATURE:
<223> OTHER INFORMATION: GPC3A-052 HCDR2

<400> SEQUENCE: 69

Ile Asn Pro Asn Ser Gly Gly Thr
1               5

<210> SEQ ID NO 70
<211> LENGTH: 7
<212> TYPE: PRT
<213> ORGANISM: Artificial Sequence
<220> FEATURE:
<223> OTHER INFORMATION: GPC3A-053 HCDR2

<400> SEQUENCE: 70

Ile Tyr Tyr Ser Gly Ser Thr
1               5

<210> SEQ ID NO 71
<211> LENGTH: 8
<212> TYPE: PRT
<213> ORGANISM: Artificial Sequence
<220> FEATURE:
<223> OTHER INFORMATION: GPC3A-054 HCDR2

<400> SEQUENCE: 71

Ile Ser Ala Tyr Asn Gly Asn Thr
1               5

<210> SEQ ID NO 72
<211> LENGTH: 8
<212> TYPE: PRT
<213> ORGANISM: Artificial Sequence
<220> FEATURE:
<223> OTHER INFORMATION: GPC3A-055 HCDR2

<400> SEQUENCE: 72

Ile Asn Pro Ser Gly Gly Ser Thr
1               5

<210> SEQ ID NO 73
<211> LENGTH: 8
<212> TYPE: PRT
<213> ORGANISM: Artificial Sequence
<220> FEATURE:
<223> OTHER INFORMATION: GPC3A-056 HCDR2

<400> SEQUENCE: 73

```
Ile Asn Pro Asn Asn Gly Asp Thr
1               5

<210> SEQ ID NO 74
<211> LENGTH: 8
<212> TYPE: PRT
<213> ORGANISM: Artificial Sequence
<220> FEATURE:
<223> OTHER INFORMATION: GPC3A-057 HCDR2

<400> SEQUENCE: 74

Ile Ser Gly Ser Gly Gly Ser Thr
1               5

<210> SEQ ID NO 75
<211> LENGTH: 8
<212> TYPE: PRT
<213> ORGANISM: Artificial Sequence
<220> FEATURE:
<223> OTHER INFORMATION: GPC3A-058 HCDR2

<400> SEQUENCE: 75

Ile Ser Pro Tyr Thr Gly Asn Thr
1               5

<210> SEQ ID NO 76
<211> LENGTH: 8
<212> TYPE: PRT
<213> ORGANISM: Artificial Sequence
<220> FEATURE:
<223> OTHER INFORMATION: GPC3A-059 HCDR2

<400> SEQUENCE: 76

Ile Ser Ala Tyr Ser Asp Lys Thr
1               5

<210> SEQ ID NO 77
<211> LENGTH: 8
<212> TYPE: PRT
<213> ORGANISM: Artificial Sequence
<220> FEATURE:
<223> OTHER INFORMATION: GPC3A-060 HCDR2

<400> SEQUENCE: 77

Ile Ser Ala Tyr Asn Gly Asn Thr
1               5

<210> SEQ ID NO 78
<211> LENGTH: 8
<212> TYPE: PRT
<213> ORGANISM: Artificial Sequence
<220> FEATURE:
<223> OTHER INFORMATION: GPC3A-061 HCDR2

<400> SEQUENCE: 78

Ile Ser Ala Tyr Asn Gly Asn Thr
1               5

<210> SEQ ID NO 79
<211> LENGTH: 8
<212> TYPE: PRT
<213> ORGANISM: Artificial Sequence
<220> FEATURE:
<223> OTHER INFORMATION: GPC3A-062 HCDR2

<400> SEQUENCE: 79

Ile Ile Pro Lys Ile Gly Thr Ala
```

```
1               5

<210> SEQ ID NO 80
<211> LENGTH: 8
<212> TYPE: PRT
<213> ORGANISM: Artificial Sequence
<220> FEATURE:
<223> OTHER INFORMATION: GPC3A-063 HCDR2

<400> SEQUENCE: 80

Ile Asn Pro Ser Gly Gly Ser Ala
1               5

<210> SEQ ID NO 81
<211> LENGTH: 8
<212> TYPE: PRT
<213> ORGANISM: Artificial Sequence
<220> FEATURE:
<223> OTHER INFORMATION: GPC3A-064 HCDR2

<400> SEQUENCE: 81

Ile Ser Pro Tyr Asn Asp Asn Thr
1               5

<210> SEQ ID NO 82
<211> LENGTH: 8
<212> TYPE: PRT
<213> ORGANISM: Artificial Sequence
<220> FEATURE:
<223> OTHER INFORMATION: GPC3A-067 HCDR2

<400> SEQUENCE: 82

Ile Ile Pro Ile Phe Gly Ile Thr
1               5

<210> SEQ ID NO 83
<211> LENGTH: 8
<212> TYPE: PRT
<213> ORGANISM: Artificial Sequence
<220> FEATURE:
<223> OTHER INFORMATION: GPC3B-54 HCDR2

<400> SEQUENCE: 83

Ile Ile Pro Ile Phe Gly Thr Ala
1               5

<210> SEQ ID NO 84
<211> LENGTH: 8
<212> TYPE: PRT
<213> ORGANISM: Artificial Sequence
<220> FEATURE:
<223> OTHER INFORMATION: GPC3B-60 HCDR2

<400> SEQUENCE: 84

Ile Asn Pro Ser Gly Gly Ser Thr
1               5

<210> SEQ ID NO 85
<211> LENGTH: 8
<212> TYPE: PRT
<213> ORGANISM: Artificial Sequence
<220> FEATURE:
<223> OTHER INFORMATION: GPC3B-63 HCDR2

<400> SEQUENCE: 85

Ile Asn Pro Ser Gly Gly Ser Thr
1               5
```

```
<210> SEQ ID NO 86
<211> LENGTH: 8
<212> TYPE: PRT
<213> ORGANISM: Artificial Sequence
<220> FEATURE:
<223> OTHER INFORMATION: GPC3B-66 HCDR2

<400> SEQUENCE: 86

Ile Asn Pro Met Thr Gly Val Thr
1               5

<210> SEQ ID NO 87
<211> LENGTH: 8
<212> TYPE: PRT
<213> ORGANISM: Artificial Sequence
<220> FEATURE:
<223> OTHER INFORMATION: GPC3B-68 HCDR2

<400> SEQUENCE: 87

Ile Ile Pro Ile Leu Gly Ile Ala
1               5

<210> SEQ ID NO 88
<211> LENGTH: 8
<212> TYPE: PRT
<213> ORGANISM: Artificial Sequence
<220> FEATURE:
<223> OTHER INFORMATION: GPC3B-71 HCDR2

<400> SEQUENCE: 88

Ile Ser Ser Ser Gly Ser Tyr Ile
1               5

<210> SEQ ID NO 89
<211> LENGTH: 8
<212> TYPE: PRT
<213> ORGANISM: Artificial Sequence
<220> FEATURE:
<223> OTHER INFORMATION: GPC3B-76 HCDR2

<400> SEQUENCE: 89

Ile Asn Pro Asn Ser Gly Gly Thr
1               5

<210> SEQ ID NO 90
<211> LENGTH: 8
<212> TYPE: PRT
<213> ORGANISM: Artificial Sequence
<220> FEATURE:
<223> OTHER INFORMATION: GPC3B-78 HCDR2

<400> SEQUENCE: 90

Ile Asn Pro Ser Gly Gly Ser Thr
1               5

<210> SEQ ID NO 91
<211> LENGTH: 8
<212> TYPE: PRT
<213> ORGANISM: Artificial Sequence
<220> FEATURE:
<223> OTHER INFORMATION: GPC3B-80 HCDR2

<400> SEQUENCE: 91

Ile Ile Pro Ile Phe Arg Thr Ala
1               5
```

<210> SEQ ID NO 92
<211> LENGTH: 8
<212> TYPE: PRT
<213> ORGANISM: Artificial Sequence
<220> FEATURE:
<223> OTHER INFORMATION: GPC3B-81 HCDR2

<400> SEQUENCE: 92

Ile Asn Pro Asn Ser Gly Gly Thr
1               5

<210> SEQ ID NO 93
<211> LENGTH: 8
<212> TYPE: PRT
<213> ORGANISM: Artificial Sequence
<220> FEATURE:
<223> OTHER INFORMATION: GPC3B-82 HCDR2

<400> SEQUENCE: 93

Ile Asn Pro Ser Gly Gly Ser Thr
1               5

<210> SEQ ID NO 94
<211> LENGTH: 8
<212> TYPE: PRT
<213> ORGANISM: Artificial Sequence
<220> FEATURE:
<223> OTHER INFORMATION: GPC3B-85 HCDR2

<400> SEQUENCE: 94

Ile Asn Thr Asn Thr Gly Asn Pro
1               5

<210> SEQ ID NO 95
<211> LENGTH: 8
<212> TYPE: PRT
<213> ORGANISM: Artificial Sequence
<220> FEATURE:
<223> OTHER INFORMATION: GPC3B-87 HCDR2

<400> SEQUENCE: 95

Ile Ile Pro Val Leu Gly Arg Thr
1               5

<210> SEQ ID NO 96
<211> LENGTH: 8
<212> TYPE: PRT
<213> ORGANISM: Artificial Sequence
<220> FEATURE:
<223> OTHER INFORMATION: GPC3B-92 HCDR2

<400> SEQUENCE: 96

Ile Asn Pro Ser Gly Gly Thr Thr
1               5

<210> SEQ ID NO 97
<211> LENGTH: 8
<212> TYPE: PRT
<213> ORGANISM: Artificial Sequence
<220> FEATURE:
<223> OTHER INFORMATION: GPC3B-93 HCDR2

<400> SEQUENCE: 97

Ile Asn Pro Ser Gly Gly Ser Thr
1               5

```
<210> SEQ ID NO 98
<211> LENGTH: 8
<212> TYPE: PRT
<213> ORGANISM: Artificial Sequence
<220> FEATURE:
<223> OTHER INFORMATION: GPC3B-110 HCDR2

<400> SEQUENCE: 98

Ile Ile Pro Thr Phe Gly Thr Thr
1               5

<210> SEQ ID NO 99
<211> LENGTH: 8
<212> TYPE: PRT
<213> ORGANISM: Artificial Sequence
<220> FEATURE:
<223> OTHER INFORMATION: GPC3B-113 HCDR2

<400> SEQUENCE: 99

Phe Asp Pro Glu Asp Gly Glu Thr
1               5

<210> SEQ ID NO 100
<211> LENGTH: 8
<212> TYPE: PRT
<213> ORGANISM: Artificial Sequence
<220> FEATURE:
<223> OTHER INFORMATION: GPC3B-115 HCDR2

<400> SEQUENCE: 100

Ile Asn Ala Asn Thr Gly Gly Thr
1               5

<210> SEQ ID NO 101
<211> LENGTH: 8
<212> TYPE: PRT
<213> ORGANISM: Artificial Sequence
<220> FEATURE:
<223> OTHER INFORMATION: GPC3B-119 HCDR2

<400> SEQUENCE: 101

Ile Asn Thr Asn Thr Gly Asn Pro
1               5

<210> SEQ ID NO 102
<211> LENGTH: 8
<212> TYPE: PRT
<213> ORGANISM: Artificial Sequence
<220> FEATURE:
<223> OTHER INFORMATION: GPC3B-125 HCDR2

<400> SEQUENCE: 102

Ile Asn Thr Asn Thr Gly Asn Pro
1               5

<210> SEQ ID NO 103
<211> LENGTH: 10
<212> TYPE: PRT
<213> ORGANISM: Artificial Sequence
<220> FEATURE:
<223> OTHER INFORMATION: GPC3A-034 HCDR3

<400> SEQUENCE: 103

Ala Arg Gly Tyr Gly Gly Arg Phe Asp Tyr
1               5                   10

<210> SEQ ID NO 104
```

```
<211> LENGTH: 10
<212> TYPE: PRT
<213> ORGANISM: Artificial Sequence
<220> FEATURE:
<223> OTHER INFORMATION: GPC3A-035 HCDR3

<400> SEQUENCE: 104

Ala Arg Ser Trp Thr Ser Gly Phe Asp Tyr
1               5                   10

<210> SEQ ID NO 105
<211> LENGTH: 11
<212> TYPE: PRT
<213> ORGANISM: Artificial Sequence
<220> FEATURE:
<223> OTHER INFORMATION: GPC3A-037 HCDR3

<400> SEQUENCE: 105

Ala Arg Thr Ser Tyr Leu Asn His Gly Asp Tyr
1               5                   10

<210> SEQ ID NO 106
<211> LENGTH: 9
<212> TYPE: PRT
<213> ORGANISM: Artificial Sequence
<220> FEATURE:
<223> OTHER INFORMATION: GPC3A-038 HCDR3

<400> SEQUENCE: 106

Ala Arg Lys Val Thr Gly Tyr Asp Ser
1               5

<210> SEQ ID NO 107
<211> LENGTH: 10
<212> TYPE: PRT
<213> ORGANISM: Artificial Sequence
<220> FEATURE:
<223> OTHER INFORMATION: GPC3A-039 HCDR3

<400> SEQUENCE: 107

Ala Arg Tyr Gly Arg Lys Ser Ile Asp Ala
1               5                   10

<210> SEQ ID NO 108
<211> LENGTH: 10
<212> TYPE: PRT
<213> ORGANISM: Artificial Sequence
<220> FEATURE:
<223> OTHER INFORMATION: GPC3A-040 HCDR3

<400> SEQUENCE: 108

Ala Arg Arg Gly Tyr Tyr Gly Tyr Asp Ser
1               5                   10

<210> SEQ ID NO 109
<211> LENGTH: 10
<212> TYPE: PRT
<213> ORGANISM: Artificial Sequence
<220> FEATURE:
<223> OTHER INFORMATION: GPC3A-041 HCDR3

<400> SEQUENCE: 109

Ala Arg Ser Gly Lys Tyr Tyr Gly Asp Lys
1               5                   10

<210> SEQ ID NO 110
<211> LENGTH: 10
```

```
<212> TYPE: PRT
<213> ORGANISM: Artificial Sequence
<220> FEATURE:
<223> OTHER INFORMATION: GPC3A-042 HCDR3

<400> SEQUENCE: 110

Ala Arg Ser Ser Tyr Tyr Trp Ala Asp Ser
1               5                   10

<210> SEQ ID NO 111
<211> LENGTH: 17
<212> TYPE: PRT
<213> ORGANISM: Artificial Sequence
<220> FEATURE:
<223> OTHER INFORMATION: GPC3A-043 HCDR3

<400> SEQUENCE: 111

Ala Arg Glu Leu Arg Asp Val Ala Tyr Tyr Pro Trp Gly Val Glu Asp
1               5                   10                  15

Phe

<210> SEQ ID NO 112
<211> LENGTH: 10
<212> TYPE: PRT
<213> ORGANISM: Artificial Sequence
<220> FEATURE:
<223> OTHER INFORMATION: GPC3A-044 HCDR3

<400> SEQUENCE: 112

Ala Arg Tyr Tyr Val Pro Tyr Leu Ser Asp
1               5                   10

<210> SEQ ID NO 113
<211> LENGTH: 9
<212> TYPE: PRT
<213> ORGANISM: Artificial Sequence
<220> FEATURE:
<223> OTHER INFORMATION: GPC3A-045 HCDR3

<400> SEQUENCE: 113

Ala Arg Ala Ser Asp Leu Tyr Gly Asp
1               5

<210> SEQ ID NO 114
<211> LENGTH: 14
<212> TYPE: PRT
<213> ORGANISM: Artificial Sequence
<220> FEATURE:
<223> OTHER INFORMATION: GPC3A-046 HCDR3

<400> SEQUENCE: 114

Ala Arg Gly Asn Arg Arg Tyr Tyr Ser Pro Ile Ile Asp Pro
1               5                   10

<210> SEQ ID NO 115
<211> LENGTH: 11
<212> TYPE: PRT
<213> ORGANISM: Artificial Sequence
<220> FEATURE:
<223> OTHER INFORMATION: GPC3A-047 HCDR3

<400> SEQUENCE: 115

Ala Arg Ser Asp Tyr Gly Ser Leu Tyr Asp Lys
1               5                   10

<210> SEQ ID NO 116
```

```
<211> LENGTH: 10
<212> TYPE: PRT
<213> ORGANISM: Artificial Sequence
<220> FEATURE:
<223> OTHER INFORMATION: GPC3A-048 HCDR3

<400> SEQUENCE: 116

Ala Arg Ser Ser Phe Val Ala Thr Asp Tyr
1               5                   10

<210> SEQ ID NO 117
<211> LENGTH: 14
<212> TYPE: PRT
<213> ORGANISM: Artificial Sequence
<220> FEATURE:
<223> OTHER INFORMATION: GPC3A-049 HCDR3

<400> SEQUENCE: 117

Ala Arg His Gly Gly Ile Gly Ser Met Arg Ser Phe Asp Gln
1               5                   10

<210> SEQ ID NO 118
<211> LENGTH: 10
<212> TYPE: PRT
<213> ORGANISM: Artificial Sequence
<220> FEATURE:
<223> OTHER INFORMATION: GPC3A-050 HCDR3

<400> SEQUENCE: 118

Ala Arg Ser Gly Tyr Arg Trp Leu Asp Val
1               5                   10

<210> SEQ ID NO 119
<211> LENGTH: 14
<212> TYPE: PRT
<213> ORGANISM: Artificial Sequence
<220> FEATURE:
<223> OTHER INFORMATION: GPC3A-051 HCDR3

<400> SEQUENCE: 119

Ala Arg Met Leu Tyr Leu Ser Gly Arg Tyr Tyr Trp Asp Ser
1               5                   10

<210> SEQ ID NO 120
<211> LENGTH: 10
<212> TYPE: PRT
<213> ORGANISM: Artificial Sequence
<220> FEATURE:
<223> OTHER INFORMATION: GPC3A-052 HCDR3

<400> SEQUENCE: 120

Ala Arg Ser His Ser Ser Gly Tyr Asp Lys
1               5                   10

<210> SEQ ID NO 121
<211> LENGTH: 10
<212> TYPE: PRT
<213> ORGANISM: Artificial Sequence
<220> FEATURE:
<223> OTHER INFORMATION: GPC3A-053 HCDR3

<400> SEQUENCE: 121

Ala Arg Trp Trp Ser Gly Ser Tyr Asp Thr
1               5                   10

<210> SEQ ID NO 122
<211> LENGTH: 12
```

```
<212> TYPE: PRT
<213> ORGANISM: Artificial Sequence
<220> FEATURE:
<223> OTHER INFORMATION: GPC3A-054 HCDR3

<400> SEQUENCE: 122

Ala Arg Ile Pro Met Tyr Ser Gly Ser Ser Asp Tyr
1               5                   10

<210> SEQ ID NO 123
<211> LENGTH: 10
<212> TYPE: PRT
<213> ORGANISM: Artificial Sequence
<220> FEATURE:
<223> OTHER INFORMATION: GPC3A-055 HCDR3

<400> SEQUENCE: 123

Ala Arg Trp His Gly Gly Pro Tyr Asp Tyr
1               5                   10

<210> SEQ ID NO 124
<211> LENGTH: 15
<212> TYPE: PRT
<213> ORGANISM: Artificial Sequence
<220> FEATURE:
<223> OTHER INFORMATION: GPC3A-056 HCDR3

<400> SEQUENCE: 124

Ala Arg Phe Ser Thr His Asn Trp Trp Trp Pro Thr Tyr Asp Tyr
1               5                   10                  15

<210> SEQ ID NO 125
<211> LENGTH: 13
<212> TYPE: PRT
<213> ORGANISM: Artificial Sequence
<220> FEATURE:
<223> OTHER INFORMATION: GPC3A-057 HCDR3

<400> SEQUENCE: 125

Ala Arg Tyr Asn Tyr Met Ser Ser Gly Phe Tyr Asp Arg
1               5                   10

<210> SEQ ID NO 126
<211> LENGTH: 13
<212> TYPE: PRT
<213> ORGANISM: Artificial Sequence
<220> FEATURE:
<223> OTHER INFORMATION: GPC3A-058 HCDR3

<400> SEQUENCE: 126

Ala Arg Gly Lys Arg Thr Leu Ala Ser Cys Phe Asp Tyr
1               5                   10

<210> SEQ ID NO 127
<211> LENGTH: 10
<212> TYPE: PRT
<213> ORGANISM: Artificial Sequence
<220> FEATURE:
<223> OTHER INFORMATION: GPC3A-059 HCDR3

<400> SEQUENCE: 127

Ala Arg Ser Arg Trp Ser Tyr Met Asp Val
1               5                   10

<210> SEQ ID NO 128
<211> LENGTH: 12
<212> TYPE: PRT
```

```
<213> ORGANISM: Artificial Sequence
<220> FEATURE:
<223> OTHER INFORMATION: GPC3A-060 HCDR3

<400> SEQUENCE: 128

Ala Arg Glu Gly Tyr Gly Ser Trp Ala Met Asp Gln
1               5                   10

<210> SEQ ID NO 129
<211> LENGTH: 10
<212> TYPE: PRT
<213> ORGANISM: Artificial Sequence
<220> FEATURE:
<223> OTHER INFORMATION: GPC3A-061 HCDR3

<400> SEQUENCE: 129

Ala Arg Lys Gly Ser Ser Gln Phe Asp Gln
1               5                   10

<210> SEQ ID NO 130
<211> LENGTH: 16
<212> TYPE: PRT
<213> ORGANISM: Artificial Sequence
<220> FEATURE:
<223> OTHER INFORMATION: GPC3A-062 HCDR3

<400> SEQUENCE: 130

Ala Arg Met Tyr Met Asp Met Gly Trp Gly Trp Gly Tyr Trp Asp Trp
1               5                   10                  15

<210> SEQ ID NO 131
<211> LENGTH: 12
<212> TYPE: PRT
<213> ORGANISM: Artificial Sequence
<220> FEATURE:
<223> OTHER INFORMATION: GPC3A-063 HCDR3

<400> SEQUENCE: 131

Ala Arg Asp Arg Leu Ala Ser Asp Ala Phe Asp Ile
1               5                   10

<210> SEQ ID NO 132
<211> LENGTH: 13
<212> TYPE: PRT
<213> ORGANISM: Artificial Sequence
<220> FEATURE:
<223> OTHER INFORMATION: GPC3A-064 HCDR3

<400> SEQUENCE: 132

Ala Arg Met Gly Val Gly Trp Gly Tyr Ala Gln Asp Ser
1               5                   10

<210> SEQ ID NO 133
<211> LENGTH: 9
<212> TYPE: PRT
<213> ORGANISM: Artificial Sequence
<220> FEATURE:
<223> OTHER INFORMATION: GPC3A-067 HCDR3

<400> SEQUENCE: 133

Ala Arg Gly Ala Glu Met Ser Asp Tyr
1               5

<210> SEQ ID NO 134
<211> LENGTH: 13
<212> TYPE: PRT
<213> ORGANISM: Artificial Sequence
```

```
<220> FEATURE:
<223> OTHER INFORMATION: GPC3B-54 HCDR3

<400> SEQUENCE: 134

Ala Arg Glu Arg Arg Tyr Ser Ser Ser Pro Ser Asp His
1               5                   10

<210> SEQ ID NO 135
<211> LENGTH: 12
<212> TYPE: PRT
<213> ORGANISM: Artificial Sequence
<220> FEATURE:
<223> OTHER INFORMATION: GPC3B-60 HCDR3

<400> SEQUENCE: 135

Ala Arg Ser Leu Tyr Ser Gln Pro Tyr Ile Asp Gly
1               5                   10

<210> SEQ ID NO 136
<211> LENGTH: 15
<212> TYPE: PRT
<213> ORGANISM: Artificial Sequence
<220> FEATURE:
<223> OTHER INFORMATION: GPC3B-63 HCDR3

<400> SEQUENCE: 136

Ala Arg Ser Leu His Ala Met Arg Trp Ser Gln Thr Met Asp Ser
1               5                   10                  15

<210> SEQ ID NO 137
<211> LENGTH: 11
<212> TYPE: PRT
<213> ORGANISM: Artificial Sequence
<220> FEATURE:
<223> OTHER INFORMATION: GPC3B-66 HCDR3

<400> SEQUENCE: 137

Ala Arg Phe Ser Ser Gly Tyr Ser Arg Asp Thr
1               5                   10

<210> SEQ ID NO 138
<211> LENGTH: 10
<212> TYPE: PRT
<213> ORGANISM: Artificial Sequence
<220> FEATURE:
<223> OTHER INFORMATION: GPC3B-68 HCDR3

<400> SEQUENCE: 138

Ala Arg Tyr Gly Tyr Glu Gly His Asp Thr
1               5                   10

<210> SEQ ID NO 139
<211> LENGTH: 13
<212> TYPE: PRT
<213> ORGANISM: Artificial Sequence
<220> FEATURE:
<223> OTHER INFORMATION: GPC3B-71 HCDR3

<400> SEQUENCE: 139

Ala Arg Gln Gly His Met Trp Tyr Val Pro Val Asp Ala
1               5                   10

<210> SEQ ID NO 140
<211> LENGTH: 5
<212> TYPE: PRT
<213> ORGANISM: Artificial Sequence
<220> FEATURE:
```

<223> OTHER INFORMATION: GPC3B-76 HCDR3

<400> SEQUENCE: 140

Ala Arg Asn Tyr Asp
1               5

<210> SEQ ID NO 141
<211> LENGTH: 10
<212> TYPE: PRT
<213> ORGANISM: Artificial Sequence
<220> FEATURE:
<223> OTHER INFORMATION: GPC3B-78 HCDR3

<400> SEQUENCE: 141

Ala Arg Gly Tyr Ser Ser Phe Phe Asp Ser
1               5                   10

<210> SEQ ID NO 142
<211> LENGTH: 15
<212> TYPE: PRT
<213> ORGANISM: Artificial Sequence
<220> FEATURE:
<223> OTHER INFORMATION: GPC3B-80 HCDR3

<400> SEQUENCE: 142

Ala Arg Met Ser Lys Tyr Tyr Gly Ser Tyr Ser Ser Tyr Asp Glu
1               5                   10                  15

<210> SEQ ID NO 143
<211> LENGTH: 7
<212> TYPE: PRT
<213> ORGANISM: Artificial Sequence
<220> FEATURE:
<223> OTHER INFORMATION: GPC3B-81 HCDR3

<400> SEQUENCE: 143

Ala Arg Gly Leu Trp Asp Ser
1               5

<210> SEQ ID NO 144
<211> LENGTH: 14
<212> TYPE: PRT
<213> ORGANISM: Artificial Sequence
<220> FEATURE:
<223> OTHER INFORMATION: GPC3B-82 HCDR3

<400> SEQUENCE: 144

Ala Arg Tyr Pro Val Tyr Met Glu Thr Ser Asp Phe Asp Ser
1               5                   10

<210> SEQ ID NO 145
<211> LENGTH: 18
<212> TYPE: PRT
<213> ORGANISM: Artificial Sequence
<220> FEATURE:
<223> OTHER INFORMATION: GPC3B-85 HCDR3

<400> SEQUENCE: 145

Ala Arg Ser Ser Leu Tyr Trp Met Gly Ser Lys Trp Ser Arg Gln Thr
1               5                   10                  15

Asp Met

<210> SEQ ID NO 146
<211> LENGTH: 6
<212> TYPE: PRT
<213> ORGANISM: Artificial Sequence

```
<220> FEATURE:
<223> OTHER INFORMATION: GPC3B-87 HCDR3

<400> SEQUENCE: 146

Ala Arg Thr Asn Asp Ser
1               5

<210> SEQ ID NO 147
<211> LENGTH: 13
<212> TYPE: PRT
<213> ORGANISM: Artificial Sequence
<220> FEATURE:
<223> OTHER INFORMATION: GPC3B-92 HCDR3

<400> SEQUENCE: 147

Ala Arg Pro Ser Met Trp Thr Ser Ser Met Gly Asp Val
1               5                   10

<210> SEQ ID NO 148
<211> LENGTH: 16
<212> TYPE: PRT
<213> ORGANISM: Artificial Sequence
<220> FEATURE:
<223> OTHER INFORMATION: GPC3B-93 HCDR3

<400> SEQUENCE: 148

Ala Arg Tyr Thr Ala Leu Lys Pro Arg Gly Ile Tyr Ser Val Asp Ser
1               5                   10                  15

<210> SEQ ID NO 149
<211> LENGTH: 18
<212> TYPE: PRT
<213> ORGANISM: Artificial Sequence
<220> FEATURE:
<223> OTHER INFORMATION: GPC3B-110 HCDR3

<400> SEQUENCE: 149

Ala Arg Tyr Tyr Trp Arg Gly Gly Ser Gly Gln Gly Ser Val Thr Ser
1               5                   10                  15

Asp Tyr

<210> SEQ ID NO 150
<211> LENGTH: 7
<212> TYPE: PRT
<213> ORGANISM: Artificial Sequence
<220> FEATURE:
<223> OTHER INFORMATION: GPC3B-113 HCDR3

<400> SEQUENCE: 150

Ala Arg Tyr Ser Gly Asp Tyr
1               5

<210> SEQ ID NO 151
<211> LENGTH: 13
<212> TYPE: PRT
<213> ORGANISM: Artificial Sequence
<220> FEATURE:
<223> OTHER INFORMATION: GPC3B-115 HCDR3

<400> SEQUENCE: 151

Ala Arg Ile Ser Gly Tyr His Ser Ser Gly Trp Asp Tyr
1               5                   10

<210> SEQ ID NO 152
<211> LENGTH: 10
<212> TYPE: PRT
```

```
<213> ORGANISM: Artificial Sequence
<220> FEATURE:
<223> OTHER INFORMATION: GPC3B-119 HCDR3

<400> SEQUENCE: 152

Ala Arg Gly Tyr Tyr Gly Lys Tyr Asp Lys
1               5                   10

<210> SEQ ID NO 153
<211> LENGTH: 7
<212> TYPE: PRT
<213> ORGANISM: Artificial Sequence
<220> FEATURE:
<223> OTHER INFORMATION: GPC3B-125 HCDR3

<400> SEQUENCE: 153

Ala Arg Gln Ser His Asp Glu
1               5

<210> SEQ ID NO 154
<211> LENGTH: 8
<212> TYPE: PRT
<213> ORGANISM: Artificial Sequence
<220> FEATURE:
<223> OTHER INFORMATION: GPC3A-034 LCDR1

<400> SEQUENCE: 154

Ser Ser Asn Ile Gly Ser Asn Asn
1               5

<210> SEQ ID NO 155
<211> LENGTH: 8
<212> TYPE: PRT
<213> ORGANISM: Artificial Sequence
<220> FEATURE:
<223> OTHER INFORMATION: GPC3A-035 LCDR1

<400> SEQUENCE: 155

Ser Ser Asn Ile Gly Ser Asn Tyr
1               5

<210> SEQ ID NO 156
<211> LENGTH: 8
<212> TYPE: PRT
<213> ORGANISM: Artificial Sequence
<220> FEATURE:
<223> OTHER INFORMATION: GPC3A-037 LCDR1

<400> SEQUENCE: 156

Arg Ser Asn Ile Gly Ser Asp Tyr
1               5

<210> SEQ ID NO 157
<211> LENGTH: 6
<212> TYPE: PRT
<213> ORGANISM: Artificial Sequence
<220> FEATURE:
<223> OTHER INFORMATION: GPC3A-038 LCDR1

<400> SEQUENCE: 157

Asn Ile Gly Ser Lys Ser
1               5

<210> SEQ ID NO 158
<211> LENGTH: 6
<212> TYPE: PRT
<213> ORGANISM: Artificial Sequence
```

```
<220> FEATURE:
<223> OTHER INFORMATION: GPC3A-039 LCDR1

<400> SEQUENCE: 158

Asn Ile Gly Ser Lys Ser
1               5

<210> SEQ ID NO 159
<211> LENGTH: 8
<212> TYPE: PRT
<213> ORGANISM: Artificial Sequence
<220> FEATURE:
<223> OTHER INFORMATION: GPC3A-040 LCDR1

<400> SEQUENCE: 159

Ser Ser Asn Ile Gly Ser Asn Tyr
1               5

<210> SEQ ID NO 160
<211> LENGTH: 8
<212> TYPE: PRT
<213> ORGANISM: Artificial Sequence
<220> FEATURE:
<223> OTHER INFORMATION: GPC3A-041 LCDR1

<400> SEQUENCE: 160

Ser Ser Asn Ile Gly Ser Asn Tyr
1               5

<210> SEQ ID NO 161
<211> LENGTH: 8
<212> TYPE: PRT
<213> ORGANISM: Artificial Sequence
<220> FEATURE:
<223> OTHER INFORMATION: GPC3A-042 LCDR1

<400> SEQUENCE: 161

Ser Ser Asp Ile Gly Ser Asn Ser
1               5

<210> SEQ ID NO 162
<211> LENGTH: 8
<212> TYPE: PRT
<213> ORGANISM: Artificial Sequence
<220> FEATURE:
<223> OTHER INFORMATION: GPC3A-043 LCDR1

<400> SEQUENCE: 162

Ser Ser Asn Ile Gly Thr Asn Tyr
1               5

<210> SEQ ID NO 163
<211> LENGTH: 6
<212> TYPE: PRT
<213> ORGANISM: Artificial Sequence
<220> FEATURE:
<223> OTHER INFORMATION: GPC3A-044 LCDR1

<400> SEQUENCE: 163

Asn Ile Gly Tyr Lys Gly
1               5

<210> SEQ ID NO 164
<211> LENGTH: 8
<212> TYPE: PRT
<213> ORGANISM: Artificial Sequence
<220> FEATURE:
```

<223> OTHER INFORMATION: GPC3A-045 LCDR1

<400> SEQUENCE: 164

Thr Ser Asn Ile Gly Thr Asn Thr
1               5

<210> SEQ ID NO 165
<211> LENGTH: 8
<212> TYPE: PRT
<213> ORGANISM: Artificial Sequence
<220> FEATURE:
<223> OTHER INFORMATION: GPC3A-046 LCDR1

<400> SEQUENCE: 165

Ser Ser Asn Phe Gly Ser Asn Thr
1               5

<210> SEQ ID NO 166
<211> LENGTH: 8
<212> TYPE: PRT
<213> ORGANISM: Artificial Sequence
<220> FEATURE:
<223> OTHER INFORMATION: GPC3A-047 LCDR1

<400> SEQUENCE: 166

Arg Ser Asn Ile Ala Ser Asn Asp
1               5

<210> SEQ ID NO 167
<211> LENGTH: 6
<212> TYPE: PRT
<213> ORGANISM: Artificial Sequence
<220> FEATURE:
<223> OTHER INFORMATION: GPC3A-048 LCDR1

<400> SEQUENCE: 167

Asn Ile Gly Ser Lys Ser
1               5

<210> SEQ ID NO 168
<211> LENGTH: 8
<212> TYPE: PRT
<213> ORGANISM: Artificial Sequence
<220> FEATURE:
<223> OTHER INFORMATION: GPC3A-049 LCDR1

<400> SEQUENCE: 168

Ser Ser Asn Ile Gly Ser Asn Tyr
1               5

<210> SEQ ID NO 169
<211> LENGTH: 8
<212> TYPE: PRT
<213> ORGANISM: Artificial Sequence
<220> FEATURE:
<223> OTHER INFORMATION: GPC3A-050 LCDR1

<400> SEQUENCE: 169

Ser Ser Asn Ile Gly Ser Asn Thr
1               5

<210> SEQ ID NO 170
<211> LENGTH: 9
<212> TYPE: PRT
<213> ORGANISM: Artificial Sequence
<220> FEATURE:
<223> OTHER INFORMATION: GPC3A-051 LCDR1

<400> SEQUENCE: 170

Ser Ser Asn Ile Gly Ala Gly Tyr Asp
1               5

<210> SEQ ID NO 171
<211> LENGTH: 8
<212> TYPE: PRT
<213> ORGANISM: Artificial Sequence
<220> FEATURE:
<223> OTHER INFORMATION: GPC3A-052 LCDR1

<400> SEQUENCE: 171

Ser Ser Asn Ile Gly Ser Asn Tyr
1               5

<210> SEQ ID NO 172
<211> LENGTH: 8
<212> TYPE: PRT
<213> ORGANISM: Artificial Sequence
<220> FEATURE:
<223> OTHER INFORMATION: GPC3A-053 LCDR1

<400> SEQUENCE: 172

Ser Ser Asn Ile Gly Ser Asn Tyr
1               5

<210> SEQ ID NO 173
<211> LENGTH: 8
<212> TYPE: PRT
<213> ORGANISM: Artificial Sequence
<220> FEATURE:
<223> OTHER INFORMATION: GPC3A-054 LCDR1

<400> SEQUENCE: 173

Ser Ser Asn Ile Gly Ser Asn Tyr
1               5

<210> SEQ ID NO 174
<211> LENGTH: 6
<212> TYPE: PRT
<213> ORGANISM: Artificial Sequence
<220> FEATURE:
<223> OTHER INFORMATION: GPC3A-055 LCDR1

<400> SEQUENCE: 174

Asn Ile Gly Ser Lys Ser
1               5

<210> SEQ ID NO 175
<211> LENGTH: 6
<212> TYPE: PRT
<213> ORGANISM: Artificial Sequence
<220> FEATURE:
<223> OTHER INFORMATION: GPC3A-056 LCDR1

<400> SEQUENCE: 175

Gln Ser Ile Ser Ser Tyr
1               5

<210> SEQ ID NO 176
<211> LENGTH: 6
<212> TYPE: PRT
<213> ORGANISM: Artificial Sequence
<220> FEATURE:
<223> OTHER INFORMATION: GPC3A-057 LCDR1

<400> SEQUENCE: 176

Asn Ile Gly Ser Lys Ser
1               5

<210> SEQ ID NO 177
<211> LENGTH: 6
<212> TYPE: PRT
<213> ORGANISM: Artificial Sequence
<220> FEATURE:
<223> OTHER INFORMATION: GPC3A-058 LCDR1

<400> SEQUENCE: 177

Asn Ile Gly Ser Lys Ser
1               5

<210> SEQ ID NO 178
<211> LENGTH: 6
<212> TYPE: PRT
<213> ORGANISM: Artificial Sequence
<220> FEATURE:
<223> OTHER INFORMATION: GPC3A-059 LCDR1

<400> SEQUENCE: 178

Asn Ile Gly Ser Lys Ser
1               5

<210> SEQ ID NO 179
<211> LENGTH: 6
<212> TYPE: PRT
<213> ORGANISM: Artificial Sequence
<220> FEATURE:
<223> OTHER INFORMATION: GPC3A-060 LCDR1

<400> SEQUENCE: 179

Asn Ile Gly Ser Glu Ser
1               5

<210> SEQ ID NO 180
<211> LENGTH: 6
<212> TYPE: PRT
<213> ORGANISM: Artificial Sequence
<220> FEATURE:
<223> OTHER INFORMATION: GPC3A-061 LCDR1

<400> SEQUENCE: 180

Asn Ile Gly Ser Lys Ser
1               5

<210> SEQ ID NO 181
<211> LENGTH: 9
<212> TYPE: PRT
<213> ORGANISM: Artificial Sequence
<220> FEATURE:
<223> OTHER INFORMATION: GPC3A-062 LCDR1

<400> SEQUENCE: 181

Ser Ser Asn Ile Gly Ala Gly Tyr Asp
1               5

<210> SEQ ID NO 182
<211> LENGTH: 8
<212> TYPE: PRT
<213> ORGANISM: Artificial Sequence
<220> FEATURE:
<223> OTHER INFORMATION: GPC3A-063 LCDR1

<400> SEQUENCE: 182

Trp Ser Asn Ile Gly Ser Tyr Thr
1               5

<210> SEQ ID NO 183
<211> LENGTH: 6
<212> TYPE: PRT
<213> ORGANISM: Artificial Sequence
<220> FEATURE:
<223> OTHER INFORMATION: GPC3A-064 LCDR1

<400> SEQUENCE: 183

Asn Ile Gly Ser Lys Ser
1               5

<210> SEQ ID NO 184
<211> LENGTH: 6
<212> TYPE: PRT
<213> ORGANISM: Artificial Sequence
<220> FEATURE:
<223> OTHER INFORMATION: GPC3A-067 LCDR1

<400> SEQUENCE: 184

Asn Ile Gly Ser Lys Ser
1               5

<210> SEQ ID NO 185
<211> LENGTH: 8
<212> TYPE: PRT
<213> ORGANISM: Artificial Sequence
<220> FEATURE:
<223> OTHER INFORMATION: GPC3B-54 LCDR1

<400> SEQUENCE: 185

Asn Ser Asn Ile Gly Ser Asp Thr
1               5

<210> SEQ ID NO 186
<211> LENGTH: 6
<212> TYPE: PRT
<213> ORGANISM: Artificial Sequence
<220> FEATURE:
<223> OTHER INFORMATION: GPC3B-60 LCDR1

<400> SEQUENCE: 186

Asn Leu Glu Asn Lys Phe
1               5

<210> SEQ ID NO 187
<211> LENGTH: 11
<212> TYPE: PRT
<213> ORGANISM: Artificial Sequence
<220> FEATURE:
<223> OTHER INFORMATION: GPC3B-63 LCDR1

<400> SEQUENCE: 187

Gln Ser Leu Leu His Ser Asn Gly Tyr Asn Tyr
1               5                   10

<210> SEQ ID NO 188
<211> LENGTH: 6
<212> TYPE: PRT
<213> ORGANISM: Artificial Sequence
<220> FEATURE:
<223> OTHER INFORMATION: GPC3B-66 LCDR1

<400> SEQUENCE: 188

Asn Ile Gly Ser Lys Ser
1               5

<210> SEQ ID NO 189
<211> LENGTH: 8
<212> TYPE: PRT
<213> ORGANISM: Artificial Sequence
<220> FEATURE:
<223> OTHER INFORMATION: GPC3B-68 LCDR1

<400> SEQUENCE: 189

Ser Ser Asn Ile Gly Asn Asn Tyr
1               5

<210> SEQ ID NO 190
<211> LENGTH: 6
<212> TYPE: PRT
<213> ORGANISM: Artificial Sequence
<220> FEATURE:
<223> OTHER INFORMATION: GPC3B-71 LCDR1

<400> SEQUENCE: 190

Asn Ile Gly Ser Lys Ser
1               5

<210> SEQ ID NO 191
<211> LENGTH: 8
<212> TYPE: PRT
<213> ORGANISM: Artificial Sequence
<220> FEATURE:
<223> OTHER INFORMATION: GPC3B-76 LCDR1

<400> SEQUENCE: 191

Ser Ser Asn Ile Gly Asn Asn Tyr
1               5

<210> SEQ ID NO 192
<211> LENGTH: 6
<212> TYPE: PRT
<213> ORGANISM: Artificial Sequence
<220> FEATURE:
<223> OTHER INFORMATION: GPC3B-78 LCDR1

<400> SEQUENCE: 192

Lys Leu Gly Asp Lys Tyr
1               5

<210> SEQ ID NO 193
<211> LENGTH: 8
<212> TYPE: PRT
<213> ORGANISM: Artificial Sequence
<220> FEATURE:
<223> OTHER INFORMATION: GPC3B-80 LCDR1

<400> SEQUENCE: 193

Ser Ser Asn Ile Gly Ser Asn Thr
1               5

<210> SEQ ID NO 194
<211> LENGTH: 6
<212> TYPE: PRT
<213> ORGANISM: Artificial Sequence
<220> FEATURE:
<223> OTHER INFORMATION: GPC3B-81 LCDR1

<400> SEQUENCE: 194

Asn Ile Gly Ser Lys Ser

```
1               5

<210> SEQ ID NO 195
<211> LENGTH: 9
<212> TYPE: PRT
<213> ORGANISM: Artificial Sequence
<220> FEATURE:
<223> OTHER INFORMATION: GPC3B-82 LCDR1

<400> SEQUENCE: 195

Ser Ser Asn Ile Gly Ala Gly Phe Asp
1               5

<210> SEQ ID NO 196
<211> LENGTH: 8
<212> TYPE: PRT
<213> ORGANISM: Artificial Sequence
<220> FEATURE:
<223> OTHER INFORMATION: GPC3B-85 LCDR1

<400> SEQUENCE: 196

Ser Ser Asn Ile Gly Ser Asn Thr
1               5

<210> SEQ ID NO 197
<211> LENGTH: 11
<212> TYPE: PRT
<213> ORGANISM: Artificial Sequence
<220> FEATURE:
<223> OTHER INFORMATION: GPC3B-87 LCDR1

<400> SEQUENCE: 197

Gln Ser Leu Leu His Ser Asn Gly Tyr Asn Tyr
1               5                   10

<210> SEQ ID NO 198
<211> LENGTH: 6
<212> TYPE: PRT
<213> ORGANISM: Artificial Sequence
<220> FEATURE:
<223> OTHER INFORMATION: GPC3B-92 LCDR1

<400> SEQUENCE: 198

Thr Leu Ala Lys Arg Tyr
1               5

<210> SEQ ID NO 199
<211> LENGTH: 8
<212> TYPE: PRT
<213> ORGANISM: Artificial Sequence
<220> FEATURE:
<223> OTHER INFORMATION: GPC3B-93 LCDR1

<400> SEQUENCE: 199

Ser Gly Ser Ile Ala Ser Asn Tyr
1               5

<210> SEQ ID NO 200
<211> LENGTH: 8
<212> TYPE: PRT
<213> ORGANISM: Artificial Sequence
<220> FEATURE:
<223> OTHER INFORMATION: GPC3B-110 LCDR1

<400> SEQUENCE: 200

Ser Ser Asn Ile Gly Ser Asn Thr
1               5
```

<210> SEQ ID NO 201
<211> LENGTH: 8
<212> TYPE: PRT
<213> ORGANISM: Artificial Sequence
<220> FEATURE:
<223> OTHER INFORMATION: GPC3B-113 LCDR1

<400> SEQUENCE: 201

Ser Ser Asn Ile Gly Ser Asn Ser
1               5

<210> SEQ ID NO 202
<211> LENGTH: 6
<212> TYPE: PRT
<213> ORGANISM: Artificial Sequence
<220> FEATURE:
<223> OTHER INFORMATION: GPC3B-115 LCDR1

<400> SEQUENCE: 202

Asn Ile Gly Ser Lys Ser
1               5

<210> SEQ ID NO 203
<211> LENGTH: 8
<212> TYPE: PRT
<213> ORGANISM: Artificial Sequence
<220> FEATURE:
<223> OTHER INFORMATION: GPC3B-119 LCDR1

<400> SEQUENCE: 203

Ser Ser Asn Ile Gly Asn Asn Tyr
1               5

<210> SEQ ID NO 204
<211> LENGTH: 9
<212> TYPE: PRT
<213> ORGANISM: Artificial Sequence
<220> FEATURE:
<223> OTHER INFORMATION: GPC3B-125 LCDR1

<400> SEQUENCE: 204

Ser Ser Asp Val Gly Gly Tyr Asn Tyr
1               5

<210> SEQ ID NO 205
<211> LENGTH: 3
<212> TYPE: PRT
<213> ORGANISM: Artificial Sequence
<220> FEATURE:
<223> OTHER INFORMATION: GPC3A-034 LCDR2

<400> SEQUENCE: 205

Ser Asn His
1

<210> SEQ ID NO 206
<211> LENGTH: 3
<212> TYPE: PRT
<213> ORGANISM: Artificial Sequence
<220> FEATURE:
<223> OTHER INFORMATION: GPC3A-035 LCDR2

<400> SEQUENCE: 206

Lys Asn Phe
1

```
<210> SEQ ID NO 207
<211> LENGTH: 3
<212> TYPE: PRT
<213> ORGANISM: Artificial Sequence
<220> FEATURE:
<223> OTHER INFORMATION: GPC3A-037 LCDR2

<400> SEQUENCE: 207

Gly Asp Asn
1

<210> SEQ ID NO 208
<211> LENGTH: 3
<212> TYPE: PRT
<213> ORGANISM: Artificial Sequence
<220> FEATURE:
<223> OTHER INFORMATION: GPC3A-038 LCDR2

<400> SEQUENCE: 208

Tyr Asp Ser
1

<210> SEQ ID NO 209
<211> LENGTH: 3
<212> TYPE: PRT
<213> ORGANISM: Artificial Sequence
<220> FEATURE:
<223> OTHER INFORMATION: GPC3A-039 LCDR2

<400> SEQUENCE: 209

Tyr Asp Ser
1

<210> SEQ ID NO 210
<211> LENGTH: 3
<212> TYPE: PRT
<213> ORGANISM: Artificial Sequence
<220> FEATURE:
<223> OTHER INFORMATION: GPC3A-040 LCDR2

<400> SEQUENCE: 210

Ser Asn Asn
1

<210> SEQ ID NO 211
<211> LENGTH: 3
<212> TYPE: PRT
<213> ORGANISM: Artificial Sequence
<220> FEATURE:
<223> OTHER INFORMATION: GPC3A-041 LCDR2

<400> SEQUENCE: 211

Lys Asn Phe
1

<210> SEQ ID NO 212
<211> LENGTH: 3
<212> TYPE: PRT
<213> ORGANISM: Artificial Sequence
<220> FEATURE:
<223> OTHER INFORMATION: GPC3A-042 LCDR2

<400> SEQUENCE: 212

Ser Thr Gln
1
```

```
<210> SEQ ID NO 213
<211> LENGTH: 3
<212> TYPE: PRT
<213> ORGANISM: Artificial Sequence
<220> FEATURE:
<223> OTHER INFORMATION: GPC3A-043 LCDR2

<400> SEQUENCE: 213

Arg Asn Asn
1

<210> SEQ ID NO 214
<211> LENGTH: 3
<212> TYPE: PRT
<213> ORGANISM: Artificial Sequence
<220> FEATURE:
<223> OTHER INFORMATION: GPC3A-044 LCDR2

<400> SEQUENCE: 214

Asp Asp Ser
1

<210> SEQ ID NO 215
<211> LENGTH: 3
<212> TYPE: PRT
<213> ORGANISM: Artificial Sequence
<220> FEATURE:
<223> OTHER INFORMATION: GPC3A-045 LCDR2

<400> SEQUENCE: 215

Ser Asn Asn
1

<210> SEQ ID NO 216
<211> LENGTH: 3
<212> TYPE: PRT
<213> ORGANISM: Artificial Sequence
<220> FEATURE:
<223> OTHER INFORMATION: GPC3A-046 LCDR2

<400> SEQUENCE: 216

Ser Asn Thr
1

<210> SEQ ID NO 217
<211> LENGTH: 3
<212> TYPE: PRT
<213> ORGANISM: Artificial Sequence
<220> FEATURE:
<223> OTHER INFORMATION: GPC3A-047 LCDR2

<400> SEQUENCE: 217

Lys Lys Asn
1

<210> SEQ ID NO 218
<211> LENGTH: 3
<212> TYPE: PRT
<213> ORGANISM: Artificial Sequence
<220> FEATURE:
<223> OTHER INFORMATION: GPC3A-048 LCDR2

<400> SEQUENCE: 218

Tyr Asp Ser
1

<210> SEQ ID NO 219
```

```
<211> LENGTH: 3
<212> TYPE: PRT
<213> ORGANISM: Artificial Sequence
<220> FEATURE:
<223> OTHER INFORMATION: GPC3A-049 LCDR2

<400> SEQUENCE: 219

Arg Asn Asn
1

<210> SEQ ID NO 220
<211> LENGTH: 3
<212> TYPE: PRT
<213> ORGANISM: Artificial Sequence
<220> FEATURE:
<223> OTHER INFORMATION: GPC3A-050 LCDR2

<400> SEQUENCE: 220

Ser Asn Asn
1

<210> SEQ ID NO 221
<211> LENGTH: 3
<212> TYPE: PRT
<213> ORGANISM: Artificial Sequence
<220> FEATURE:
<223> OTHER INFORMATION: GPC3A-051 LCDR2

<400> SEQUENCE: 221

Gly Asn Ser
1

<210> SEQ ID NO 222
<211> LENGTH: 3
<212> TYPE: PRT
<213> ORGANISM: Artificial Sequence
<220> FEATURE:
<223> OTHER INFORMATION: GPC3A-052 LCDR2

<400> SEQUENCE: 222

Arg Asn Asn
1

<210> SEQ ID NO 223
<211> LENGTH: 3
<212> TYPE: PRT
<213> ORGANISM: Artificial Sequence
<220> FEATURE:
<223> OTHER INFORMATION: GPC3A-053 LCDR2

<400> SEQUENCE: 223

Gly Asn Ser
1

<210> SEQ ID NO 224
<211> LENGTH: 3
<212> TYPE: PRT
<213> ORGANISM: Artificial Sequence
<220> FEATURE:
<223> OTHER INFORMATION: GPC3A-054 LCDR2

<400> SEQUENCE: 224

Arg Asn Asn
1

<210> SEQ ID NO 225
<211> LENGTH: 3
```

```
<212> TYPE: PRT
<213> ORGANISM: Artificial Sequence
<220> FEATURE:
<223> OTHER INFORMATION: GPC3A-055 LCDR2

<400> SEQUENCE: 225

Tyr Asp Ser
1

<210> SEQ ID NO 226
<211> LENGTH: 3
<212> TYPE: PRT
<213> ORGANISM: Artificial Sequence
<220> FEATURE:
<223> OTHER INFORMATION: GPC3A-056 LCDR2

<400> SEQUENCE: 226

Ala Ala Ser
1

<210> SEQ ID NO 227
<211> LENGTH: 3
<212> TYPE: PRT
<213> ORGANISM: Artificial Sequence
<220> FEATURE:
<223> OTHER INFORMATION: GPC3A-057 LCDR2

<400> SEQUENCE: 227

Tyr Asp Ser
1

<210> SEQ ID NO 228
<211> LENGTH: 3
<212> TYPE: PRT
<213> ORGANISM: Artificial Sequence
<220> FEATURE:
<223> OTHER INFORMATION: GPC3A-058 LCDR2

<400> SEQUENCE: 228

Asp Asp Ser
1

<210> SEQ ID NO 229
<211> LENGTH: 3
<212> TYPE: PRT
<213> ORGANISM: Artificial Sequence
<220> FEATURE:
<223> OTHER INFORMATION: GPC3A-059 LCDR2

<400> SEQUENCE: 229

Tyr Asp Ser
1

<210> SEQ ID NO 230
<211> LENGTH: 3
<212> TYPE: PRT
<213> ORGANISM: Artificial Sequence
<220> FEATURE:
<223> OTHER INFORMATION: GPC3A-060 LCDR2

<400> SEQUENCE: 230

Asp Asp Asp
1

<210> SEQ ID NO 231
<211> LENGTH: 3
<212> TYPE: PRT
```

<213> ORGANISM: Artificial Sequence
<220> FEATURE:
<223> OTHER INFORMATION: GPC3A-061 LCDR2

<400> SEQUENCE: 231

Tyr Asp Ser
1

<210> SEQ ID NO 232
<211> LENGTH: 3
<212> TYPE: PRT
<213> ORGANISM: Artificial Sequence
<220> FEATURE:
<223> OTHER INFORMATION: GPC3A-062 LCDR2

<400> SEQUENCE: 232

Gly Asn Ser
1

<210> SEQ ID NO 233
<211> LENGTH: 3
<212> TYPE: PRT
<213> ORGANISM: Artificial Sequence
<220> FEATURE:
<223> OTHER INFORMATION: GPC3A-063 LCDR2

<400> SEQUENCE: 233

Gly Asn Asn
1

<210> SEQ ID NO 234
<211> LENGTH: 3
<212> TYPE: PRT
<213> ORGANISM: Artificial Sequence
<220> FEATURE:
<223> OTHER INFORMATION: GPC3A-064 LCDR2

<400> SEQUENCE: 234

Asp Asp Thr
1

<210> SEQ ID NO 235
<211> LENGTH: 3
<212> TYPE: PRT
<213> ORGANISM: Artificial Sequence
<220> FEATURE:
<223> OTHER INFORMATION: GPC3A-067 LCDR2

<400> SEQUENCE: 235

Tyr Asp Ser
1

<210> SEQ ID NO 236
<211> LENGTH: 3
<212> TYPE: PRT
<213> ORGANISM: Artificial Sequence
<220> FEATURE:
<223> OTHER INFORMATION: GPC3B-54 LCDR2

<400> SEQUENCE: 236

Arg Asp Asn
1

<210> SEQ ID NO 237
<211> LENGTH: 3
<212> TYPE: PRT
<213> ORGANISM: Artificial Sequence

```
<220> FEATURE:
<223> OTHER INFORMATION: GPC3B-60 LCDR2

<400> SEQUENCE: 237

Glu Asp Asn
1

<210> SEQ ID NO 238
<211> LENGTH: 3
<212> TYPE: PRT
<213> ORGANISM: Artificial Sequence
<220> FEATURE:
<223> OTHER INFORMATION: GPC3B-63 LCDR2

<400> SEQUENCE: 238

Leu Gly Ser
1

<210> SEQ ID NO 239
<211> LENGTH: 3
<212> TYPE: PRT
<213> ORGANISM: Artificial Sequence
<220> FEATURE:
<223> OTHER INFORMATION: GPC3B-66 LCDR2

<400> SEQUENCE: 239

Tyr Asp Ser
1

<210> SEQ ID NO 240
<211> LENGTH: 3
<212> TYPE: PRT
<213> ORGANISM: Artificial Sequence
<220> FEATURE:
<223> OTHER INFORMATION: GPC3B-68 LCDR2

<400> SEQUENCE: 240

Asp Asn Ile
1

<210> SEQ ID NO 241
<211> LENGTH: 3
<212> TYPE: PRT
<213> ORGANISM: Artificial Sequence
<220> FEATURE:
<223> OTHER INFORMATION: GPC3B-71 LCDR2

<400> SEQUENCE: 241

Tyr Asp Ser
1

<210> SEQ ID NO 242
<211> LENGTH: 3
<212> TYPE: PRT
<213> ORGANISM: Artificial Sequence
<220> FEATURE:
<223> OTHER INFORMATION: GPC3B-76 LCDR2

<400> SEQUENCE: 242

Asp Asn Asn
1

<210> SEQ ID NO 243
<211> LENGTH: 3
<212> TYPE: PRT
<213> ORGANISM: Artificial Sequence
<220> FEATURE:
```

<223> OTHER INFORMATION: GPC3B-78 LCDR2

<400> SEQUENCE: 243

Gln Asp Asn
1

<210> SEQ ID NO 244
<211> LENGTH: 3
<212> TYPE: PRT
<213> ORGANISM: Artificial Sequence
<220> FEATURE:
<223> OTHER INFORMATION: GPC3B-80 LCDR2

<400> SEQUENCE: 244

Ser Asn Asn
1

<210> SEQ ID NO 245
<211> LENGTH: 3
<212> TYPE: PRT
<213> ORGANISM: Artificial Sequence
<220> FEATURE:
<223> OTHER INFORMATION: GPC3B-81 LCDR2

<400> SEQUENCE: 245

Tyr Asp Ser
1

<210> SEQ ID NO 246
<211> LENGTH: 3
<212> TYPE: PRT
<213> ORGANISM: Artificial Sequence
<220> FEATURE:
<223> OTHER INFORMATION: GPC3B-82 LCDR2

<400> SEQUENCE: 246

Asp Asn Asn
1

<210> SEQ ID NO 247
<211> LENGTH: 3
<212> TYPE: PRT
<213> ORGANISM: Artificial Sequence
<220> FEATURE:
<223> OTHER INFORMATION: GPC3B-85 LCDR2

<400> SEQUENCE: 247

Ser Asn Asn
1

<210> SEQ ID NO 248
<211> LENGTH: 3
<212> TYPE: PRT
<213> ORGANISM: Artificial Sequence
<220> FEATURE:
<223> OTHER INFORMATION: GPC3B-87 LCDR2

<400> SEQUENCE: 248

Leu Gly Ser
1

<210> SEQ ID NO 249
<211> LENGTH: 3
<212> TYPE: PRT
<213> ORGANISM: Artificial Sequence
<220> FEATURE:
<223> OTHER INFORMATION: GPC3B-92 LCDR2

```
<400> SEQUENCE: 249

Arg Asp Thr
1

<210> SEQ ID NO 250
<211> LENGTH: 3
<212> TYPE: PRT
<213> ORGANISM: Artificial Sequence
<220> FEATURE:
<223> OTHER INFORMATION: GPC3B-93 LCDR2

<400> SEQUENCE: 250

Glu Asp Asn
1

<210> SEQ ID NO 251
<211> LENGTH: 3
<212> TYPE: PRT
<213> ORGANISM: Artificial Sequence
<220> FEATURE:
<223> OTHER INFORMATION: GPC3B-110 LCDR2

<400> SEQUENCE: 251

Ser Ser Asn
1

<210> SEQ ID NO 252
<211> LENGTH: 3
<212> TYPE: PRT
<213> ORGANISM: Artificial Sequence
<220> FEATURE:
<223> OTHER INFORMATION: GPC3B-113 LCDR2

<400> SEQUENCE: 252

Ser Asn Asn
1

<210> SEQ ID NO 253
<211> LENGTH: 3
<212> TYPE: PRT
<213> ORGANISM: Artificial Sequence
<220> FEATURE:
<223> OTHER INFORMATION: GPC3B-115 LCDR2

<400> SEQUENCE: 253

Asp Asp Ser
1

<210> SEQ ID NO 254
<211> LENGTH: 3
<212> TYPE: PRT
<213> ORGANISM: Artificial Sequence
<220> FEATURE:
<223> OTHER INFORMATION: GPC3B-119 LCDR2

<400> SEQUENCE: 254

Asp Asn Asn
1

<210> SEQ ID NO 255
<211> LENGTH: 3
<212> TYPE: PRT
<213> ORGANISM: Artificial Sequence
<220> FEATURE:
<223> OTHER INFORMATION: GPC3B-125 LCDR2
```

```
<400> SEQUENCE: 255

Glu Val Ser
1

<210> SEQ ID NO 256
<211> LENGTH: 11
<212> TYPE: PRT
<213> ORGANISM: Artificial Sequence
<220> FEATURE:
<223> OTHER INFORMATION: GPC3A-034 LCDR3

<400> SEQUENCE: 256

Ala Ala Trp Asp Asp Ser Leu Asp Gly Tyr Leu
1               5                   10

<210> SEQ ID NO 257
<211> LENGTH: 11
<212> TYPE: PRT
<213> ORGANISM: Artificial Sequence
<220> FEATURE:
<223> OTHER INFORMATION: GPC3A-035 LCDR3

<400> SEQUENCE: 257

Ala Ala Trp Asp Asp Ala Leu Ser Gly Tyr Val
1               5                   10

<210> SEQ ID NO 258
<211> LENGTH: 11
<212> TYPE: PRT
<213> ORGANISM: Artificial Sequence
<220> FEATURE:
<223> OTHER INFORMATION: GPC3A-037 LCDR3

<400> SEQUENCE: 258

Gly Thr Trp Asp Tyr Thr Leu Asn Gly Val Val
1               5                   10

<210> SEQ ID NO 259
<211> LENGTH: 11
<212> TYPE: PRT
<213> ORGANISM: Artificial Sequence
<220> FEATURE:
<223> OTHER INFORMATION: GPC3A-038 LCDR3

<400> SEQUENCE: 259

Gln Val Trp Asp Ser Ser Ser Asp His Val Val
1               5                   10

<210> SEQ ID NO 260
<211> LENGTH: 11
<212> TYPE: PRT
<213> ORGANISM: Artificial Sequence
<220> FEATURE:
<223> OTHER INFORMATION: GPC3A-039 LCDR3

<400> SEQUENCE: 260

Gln Val Trp Asp Ser Ser Ser Asp His Trp Val
1               5                   10

<210> SEQ ID NO 261
<211> LENGTH: 11
<212> TYPE: PRT
<213> ORGANISM: Artificial Sequence
<220> FEATURE:
<223> OTHER INFORMATION: GPC3A-040 LCDR3

<400> SEQUENCE: 261
```

```
Ala Ala Trp Asp Asp Ser Leu Ser Gly Tyr Val
1               5                   10

<210> SEQ ID NO 262
<211> LENGTH: 11
<212> TYPE: PRT
<213> ORGANISM: Artificial Sequence
<220> FEATURE:
<223> OTHER INFORMATION: GPC3A-041 LCDR3

<400> SEQUENCE: 262

Ala Ala Trp Asp Asp Ala Leu Ser Gly Tyr Val
1               5                   10

<210> SEQ ID NO 263
<211> LENGTH: 11
<212> TYPE: PRT
<213> ORGANISM: Artificial Sequence
<220> FEATURE:
<223> OTHER INFORMATION: GPC3A-042 LCDR3

<400> SEQUENCE: 263

Ala Thr Trp Asp Asp Ser Leu Asn Gly Tyr Val
1               5                   10

<210> SEQ ID NO 264
<211> LENGTH: 11
<212> TYPE: PRT
<213> ORGANISM: Artificial Sequence
<220> FEATURE:
<223> OTHER INFORMATION: GPC3A-043 LCDR3

<400> SEQUENCE: 264

Ala Val Trp Asp Asp Ser Leu Ser Gly Val Val
1               5                   10

<210> SEQ ID NO 265
<211> LENGTH: 11
<212> TYPE: PRT
<213> ORGANISM: Artificial Sequence
<220> FEATURE:
<223> OTHER INFORMATION: GPC3A-044 LCDR3

<400> SEQUENCE: 265

Gln Val Trp Asp Ser Ser Ser Asp His Val Val
1               5                   10

<210> SEQ ID NO 266
<211> LENGTH: 11
<212> TYPE: PRT
<213> ORGANISM: Artificial Sequence
<220> FEATURE:
<223> OTHER INFORMATION: GPC3A-045 LCDR3

<400> SEQUENCE: 266

Ala Ala Trp Asp Asp Ser Leu Asn Gly Val Val
1               5                   10

<210> SEQ ID NO 267
<211> LENGTH: 11
<212> TYPE: PRT
<213> ORGANISM: Artificial Sequence
<220> FEATURE:
<223> OTHER INFORMATION: GPC3A-046 LCDR3

<400> SEQUENCE: 267
```

```
Ala Ala Trp Asp Asp Ser Leu Thr Gly Val Val
1               5                   10

<210> SEQ ID NO 268
<211> LENGTH: 11
<212> TYPE: PRT
<213> ORGANISM: Artificial Sequence
<220> FEATURE:
<223> OTHER INFORMATION: GPC3A-047 LCDR3

<400> SEQUENCE: 268

Ala Ala Trp Asp Asp Asn Leu Ser Gly Tyr Val
1               5                   10

<210> SEQ ID NO 269
<211> LENGTH: 11
<212> TYPE: PRT
<213> ORGANISM: Artificial Sequence
<220> FEATURE:
<223> OTHER INFORMATION: GPC3A-048 LCDR3

<400> SEQUENCE: 269

Gln Val Trp Asp Ser Ser Ser Asp Arg Gly Val
1               5                   10

<210> SEQ ID NO 270
<211> LENGTH: 9
<212> TYPE: PRT
<213> ORGANISM: Artificial Sequence
<220> FEATURE:
<223> OTHER INFORMATION: GPC3A-049 LCDR3

<400> SEQUENCE: 270

Ala Ala Trp Asp Asp Ser Leu Ser Gly
1               5

<210> SEQ ID NO 271
<211> LENGTH: 11
<212> TYPE: PRT
<213> ORGANISM: Artificial Sequence
<220> FEATURE:
<223> OTHER INFORMATION: GPC3A-050 LCDR3

<400> SEQUENCE: 271

Ala Ala Trp Asp Asp Ser Leu Asn Gly Pro Val
1               5                   10

<210> SEQ ID NO 272
<211> LENGTH: 11
<212> TYPE: PRT
<213> ORGANISM: Artificial Sequence
<220> FEATURE:
<223> OTHER INFORMATION: GPC3A-051 LCDR3

<400> SEQUENCE: 272

Gln Ser Tyr Asp Ser Ser Leu Ser Gly Tyr Val
1               5                   10

<210> SEQ ID NO 273
<211> LENGTH: 11
<212> TYPE: PRT
<213> ORGANISM: Artificial Sequence
<220> FEATURE:
<223> OTHER INFORMATION: GPC3A-052 LCDR3

<400> SEQUENCE: 273

Ala Ala Trp Asp Asp Ser Leu Ser Gly Tyr Val
```

```
<210> SEQ ID NO 274
<211> LENGTH: 12
<212> TYPE: PRT
<213> ORGANISM: Artificial Sequence
<220> FEATURE:
<223> OTHER INFORMATION: GPC3A-053 LCDR3

<400> SEQUENCE: 274

Gln Ser Tyr Asp Ser Ser Leu Ser Gly Ser Asn Val
1               5                   10

<210> SEQ ID NO 275
<211> LENGTH: 11
<212> TYPE: PRT
<213> ORGANISM: Artificial Sequence
<220> FEATURE:
<223> OTHER INFORMATION: GPC3A-054 LCDR3

<400> SEQUENCE: 275

Ala Ala Trp Asp Asp Ser Leu Ser Gly Tyr Val
1               5                   10

<210> SEQ ID NO 276
<211> LENGTH: 11
<212> TYPE: PRT
<213> ORGANISM: Artificial Sequence
<220> FEATURE:
<223> OTHER INFORMATION: GPC3A-055 LCDR3

<400> SEQUENCE: 276

Gln Val Trp Asp Ser Ser Ser Asp His Tyr Val
1               5                   10

<210> SEQ ID NO 277
<211> LENGTH: 9
<212> TYPE: PRT
<213> ORGANISM: Artificial Sequence
<220> FEATURE:
<223> OTHER INFORMATION: GPC3A-056 LCDR3

<400> SEQUENCE: 277

Gln Gln Ser Tyr Ser Thr Pro Ile Thr
1               5

<210> SEQ ID NO 278
<211> LENGTH: 11
<212> TYPE: PRT
<213> ORGANISM: Artificial Sequence
<220> FEATURE:
<223> OTHER INFORMATION: GPC3A-057 LCDR3

<400> SEQUENCE: 278

Gln Val Trp Asp Ser Ser Ser Asp His Val Val
1               5                   10

<210> SEQ ID NO 279
<211> LENGTH: 10
<212> TYPE: PRT
<213> ORGANISM: Artificial Sequence
<220> FEATURE:
<223> OTHER INFORMATION: GPC3A-058 LCDR3

<400> SEQUENCE: 279

Gln Val Trp Asp Ser Ser Ser Asp His Val
1               5                   10
```

<210> SEQ ID NO 280
<211> LENGTH: 10
<212> TYPE: PRT
<213> ORGANISM: Artificial Sequence
<220> FEATURE:
<223> OTHER INFORMATION: GPC3A-059 LCDR3

<400> SEQUENCE: 280

Gln Val Trp Asp Ser Ser Ser Asp His Val
1               5                   10

<210> SEQ ID NO 281
<211> LENGTH: 9
<212> TYPE: PRT
<213> ORGANISM: Artificial Sequence
<220> FEATURE:
<223> OTHER INFORMATION: GPC3A-060 LCDR3

<400> SEQUENCE: 281

Gln Thr Trp Asp Ser Ser Thr Ala Ile
1               5

<210> SEQ ID NO 282
<211> LENGTH: 11
<212> TYPE: PRT
<213> ORGANISM: Artificial Sequence
<220> FEATURE:
<223> OTHER INFORMATION: GPC3A-061 LCDR3

<400> SEQUENCE: 282

Gln Val Trp Asp Ser Ser Ser Asp His Tyr Val
1               5                   10

<210> SEQ ID NO 283
<211> LENGTH: 12
<212> TYPE: PRT
<213> ORGANISM: Artificial Sequence
<220> FEATURE:
<223> OTHER INFORMATION: GPC3A-062 LCDR3

<400> SEQUENCE: 283

Gln Ser Tyr Asp Ser Ser Leu Ser Gly Ser Tyr Val
1               5                   10

<210> SEQ ID NO 284
<211> LENGTH: 11
<212> TYPE: PRT
<213> ORGANISM: Artificial Sequence
<220> FEATURE:
<223> OTHER INFORMATION: GPC3A-063 LCDR3

<400> SEQUENCE: 284

Ala Ala Trp Asp Asp Asn Leu Asn Gly Val Val
1               5                   10

<210> SEQ ID NO 285
<211> LENGTH: 11
<212> TYPE: PRT
<213> ORGANISM: Artificial Sequence
<220> FEATURE:
<223> OTHER INFORMATION: GPC3A-064 LCDR3

<400> SEQUENCE: 285

Gln Val Trp Asp Arg Ser Ser Ala His Trp Val
1               5                   10

<210> SEQ ID NO 286
<211> LENGTH: 11
<212> TYPE: PRT
<213> ORGANISM: Artificial Sequence
<220> FEATURE:
<223> OTHER INFORMATION: GPC3A-067 LCDR3

<400> SEQUENCE: 286

Gln Val Trp Asp Ser Ser Asp His Val Val
1               5                   10

<210> SEQ ID NO 287
<211> LENGTH: 11
<212> TYPE: PRT
<213> ORGANISM: Artificial Sequence
<220> FEATURE:
<223> OTHER INFORMATION: GPC3B-54 LCDR3

<400> SEQUENCE: 287

Thr Thr Trp Asp Asp Ser Leu Asn Gly Leu Val
1               5                   10

<210> SEQ ID NO 288
<211> LENGTH: 11
<212> TYPE: PRT
<213> ORGANISM: Artificial Sequence
<220> FEATURE:
<223> OTHER INFORMATION: GPC3B-60 LCDR3

<400> SEQUENCE: 288

Gln Thr Trp Asp Ser Pro Thr Gly Leu Phe Val
1               5                   10

<210> SEQ ID NO 289
<211> LENGTH: 9
<212> TYPE: PRT
<213> ORGANISM: Artificial Sequence
<220> FEATURE:
<223> OTHER INFORMATION: GPC3B-63 LCDR3

<400> SEQUENCE: 289

Met Gln Ala Leu Gln Thr Pro Pro Thr
1               5

<210> SEQ ID NO 290
<211> LENGTH: 12
<212> TYPE: PRT
<213> ORGANISM: Artificial Sequence
<220> FEATURE:
<223> OTHER INFORMATION: GPC3B-66 LCDR3

<400> SEQUENCE: 290

Gln Val Trp Asp Ser Ser Ser Asp His Leu Tyr Val
1               5                   10

<210> SEQ ID NO 291
<211> LENGTH: 11
<212> TYPE: PRT
<213> ORGANISM: Artificial Sequence
<220> FEATURE:
<223> OTHER INFORMATION: GPC3B-68 LCDR3

<400> SEQUENCE: 291

Gly Thr Trp Asp Ser Ser Leu Ser Ala Gly Val
1               5                   10

```
<210> SEQ ID NO 292
<211> LENGTH: 11
<212> TYPE: PRT
<213> ORGANISM: Artificial Sequence
<220> FEATURE:
<223> OTHER INFORMATION: GPC3B-71 LCDR3

<400> SEQUENCE: 292

Gln Val Trp Asp Ser Ser Asp His Tyr Val
1               5                   10

<210> SEQ ID NO 293
<211> LENGTH: 11
<212> TYPE: PRT
<213> ORGANISM: Artificial Sequence
<220> FEATURE:
<223> OTHER INFORMATION: GPC3B-76 LCDR3

<400> SEQUENCE: 293

Gly Thr Trp Asp Ser Ser Leu Ser Ala Gly Val
1               5                   10

<210> SEQ ID NO 294
<211> LENGTH: 9
<212> TYPE: PRT
<213> ORGANISM: Artificial Sequence
<220> FEATURE:
<223> OTHER INFORMATION: GPC3B-78 LCDR3

<400> SEQUENCE: 294

Gln Thr Trp Asp Arg Ser Thr Tyr Val
1               5

<210> SEQ ID NO 295
<211> LENGTH: 9
<212> TYPE: PRT
<213> ORGANISM: Artificial Sequence
<220> FEATURE:
<223> OTHER INFORMATION: GPC3B-80 LCDR3

<400> SEQUENCE: 295

Ala Ala Trp Asp Asp Ser Leu Asn Gly
1               5

<210> SEQ ID NO 296
<211> LENGTH: 12
<212> TYPE: PRT
<213> ORGANISM: Artificial Sequence
<220> FEATURE:
<223> OTHER INFORMATION: GPC3B-81 LCDR3

<400> SEQUENCE: 296

Gln Val Trp Asp Ser Ser Ser Asp Leu Leu Tyr Val
1               5                   10

<210> SEQ ID NO 297
<211> LENGTH: 11
<212> TYPE: PRT
<213> ORGANISM: Artificial Sequence
<220> FEATURE:
<223> OTHER INFORMATION: GPC3B-82 LCDR3

<400> SEQUENCE: 297

Gln Ser Phe Asp Ser Ser Leu Ser Gly Trp Val
1               5                   10

<210> SEQ ID NO 298
```

```
<211> LENGTH: 11
<212> TYPE: PRT
<213> ORGANISM: Artificial Sequence
<220> FEATURE:
<223> OTHER INFORMATION: GPC3B-85 LCDR3

<400> SEQUENCE: 298

Ala Ala Trp Asp Asp Ser Leu Asn Gly Tyr Val
1               5                   10

<210> SEQ ID NO 299
<211> LENGTH: 9
<212> TYPE: PRT
<213> ORGANISM: Artificial Sequence
<220> FEATURE:
<223> OTHER INFORMATION: GPC3B-87 LCDR3

<400> SEQUENCE: 299

Met Gln Ala Leu Gln Thr Pro Trp Thr
1               5

<210> SEQ ID NO 300
<211> LENGTH: 10
<212> TYPE: PRT
<213> ORGANISM: Artificial Sequence
<220> FEATURE:
<223> OTHER INFORMATION: GPC3B-92 LCDR3

<400> SEQUENCE: 300

Gln Ser Ala Asp Asn Ser Arg Thr Phe Val
1               5                   10

<210> SEQ ID NO 301
<211> LENGTH: 9
<212> TYPE: PRT
<213> ORGANISM: Artificial Sequence
<220> FEATURE:
<223> OTHER INFORMATION: GPC3B-93 LCDR3

<400> SEQUENCE: 301

Gln Ser Tyr Asp Ser Ser Asn Trp Val
1               5

<210> SEQ ID NO 302
<211> LENGTH: 11
<212> TYPE: PRT
<213> ORGANISM: Artificial Sequence
<220> FEATURE:
<223> OTHER INFORMATION: GPC3B-110 LCDR3

<400> SEQUENCE: 302

Ala Ala Trp Asp Asp Ser Leu Asn Gly Pro Val
1               5                   10

<210> SEQ ID NO 303
<211> LENGTH: 11
<212> TYPE: PRT
<213> ORGANISM: Artificial Sequence
<220> FEATURE:
<223> OTHER INFORMATION: GPC3B-113 LCDR3

<400> SEQUENCE: 303

Ala Ala Trp Asp Asp Ser Leu Asn Gly Val Leu
1               5                   10

<210> SEQ ID NO 304
<211> LENGTH: 12
```

```
<212> TYPE: PRT
<213> ORGANISM: Artificial Sequence
<220> FEATURE:
<223> OTHER INFORMATION: GPC3B-115 LCDR3

<400> SEQUENCE: 304

Gln Val Trp Asp Ser Ser Asp Pro Leu Tyr Val
1               5                   10

<210> SEQ ID NO 305
<211> LENGTH: 11
<212> TYPE: PRT
<213> ORGANISM: Artificial Sequence
<220> FEATURE:
<223> OTHER INFORMATION: GPC3B-119 LCDR3

<400> SEQUENCE: 305

Ala Thr Trp Asp Asn Ser Leu Ser Ala Leu Ile
1               5                   10

<210> SEQ ID NO 306
<211> LENGTH: 10
<212> TYPE: PRT
<213> ORGANISM: Artificial Sequence
<220> FEATURE:
<223> OTHER INFORMATION: GPC3B-125 LCDR3

<400> SEQUENCE: 306

Ser Ser Tyr Thr Ser Ser Thr Thr Val Ile
1               5                   10

<210> SEQ ID NO 307
<211> LENGTH: 116
<212> TYPE: PRT
<213> ORGANISM: Artificial Sequence
<220> FEATURE:
<223> OTHER INFORMATION: GPC3A-034 VH

<400> SEQUENCE: 307

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Glu Leu Ser Ser Val Thr Ala Ala Asp Thr Ala Val Tyr Tyr Cys Ala
                85                  90                  95

Arg Gly Tyr Gly Gly Arg Phe Asp Tyr Trp Gly Gln Gly Thr Leu Val
            100                 105                 110

Thr Val Ser Ser
        115

<210> SEQ ID NO 308
<211> LENGTH: 117
<212> TYPE: PRT
<213> ORGANISM: Artificial Sequence
<220> FEATURE:
<223> OTHER INFORMATION: GPC3A-035 VH

<400> SEQUENCE: 308
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Trp Thr Ser Gly Phe Asp Tyr Trp Gly Gln Gly Thr Leu
            100                 105                 110

Val Thr Val Ser Ser
        115

<210> SEQ ID NO 309
<211> LENGTH: 118
<212> TYPE: PRT
<213> ORGANISM: Artificial Sequence
<220> FEATURE:
<223> OTHER INFORMATION: GPC3A-037 VH

<400> SEQUENCE: 309

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Ser Tyr Leu Asn His Gly Asp Tyr Trp Gly Gln Gly Thr
            100                 105                 110

Leu Val Thr Val Ser Ser
        115

<210> SEQ ID NO 310
<211> LENGTH: 116
<212> TYPE: PRT
<213> ORGANISM: Artificial Sequence
<220> FEATURE:
<223> OTHER INFORMATION: GPC3A-038 VH

<400> SEQUENCE: 310

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe

```
                    50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                    85                  90                  95

Ala Arg Lys Val Thr Gly Tyr Asp Ser Trp Gly Gln Gly Thr Leu Val
                100                 105                 110

Thr Val Ser Ser
        115

<210> SEQ ID NO 311
<211> LENGTH: 116
<212> TYPE: PRT
<213> ORGANISM: Artificial Sequence
<220> FEATURE:
<223> OTHER INFORMATION: GPC3A-039 VH

<400> SEQUENCE: 311

Gln Val Gln Leu Val Gln Ser Gly Gly Gly Leu Val His Pro Gly Gly
 1               5                  10                  15

Ser Leu Arg Leu Ser Cys Ala Gly Ser Gly Phe Thr Phe Ser Ser Tyr
                20                  25                  30

Ala Met His Trp Val Arg Gln Ala Pro Gly Lys Gly Leu Glu Trp Val
                35                  40                  45

Ser Ala Ile Gly Thr Gly Gly Thr Tyr Tyr Ala Asp Ser Val Lys
                50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                85                  90                  95

Arg Tyr Gly Arg Lys Ser Ile Asp Ala Trp Gly Gln Gly Thr Leu Val
                100                 105                 110

Thr Val Ser Ser
        115

<210> SEQ ID NO 312
<211> LENGTH: 117
<212> TYPE: PRT
<213> ORGANISM: Artificial Sequence
<220> FEATURE:
<223> OTHER INFORMATION: GPC3A-040 VH

<400> SEQUENCE: 312

Gln Val Gln Leu Val Gln Ser Gly Ala Glu Val Lys Lys Pro Gly Ala
 1               5                  10                  15

Ser Val Thr Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
                35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Arg Gly Tyr Tyr Gly Tyr Asp Ser Trp Gly Gln Gly Thr Leu
                100                 105                 110
```

```
Val Thr Val Ser Ser
        115

<210> SEQ ID NO 313
<211> LENGTH: 117
<212> TYPE: PRT
<213> ORGANISM: Artificial Sequence
<220> FEATURE:
<223> OTHER INFORMATION: GPC3A-041 VH

<400> SEQUENCE: 313

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Met Tyr Tyr Cys
                85                  90                  95

Ala Arg Ser Gly Lys Tyr Tyr Gly Asp Lys Trp Gly Gln Gly Thr Leu
            100                 105                 110

Val Thr Val Ser Ser
        115

<210> SEQ ID NO 314
<211> LENGTH: 117
<212> TYPE: PRT
<213> ORGANISM: Artificial Sequence
<220> FEATURE:
<223> OTHER INFORMATION: GPC3A-042 VH

<400> SEQUENCE: 314

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
                20                  25                  30

Tyr Val Tyr Trp Met Arg Gln Ala Pro Gly Lys Gly Leu Glu Trp Met
            35                  40                  45

Gly Trp Met Asn Pro Arg Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Ser Ser Tyr Tyr Trp Ala Asp Ser Trp Gly Gln Gly Thr Leu
            100                 105                 110

Val Thr Val Ser Ser
        115

<210> SEQ ID NO 315
<211> LENGTH: 124
<212> TYPE: PRT
<213> ORGANISM: Artificial Sequence
<220> FEATURE:
<223> OTHER INFORMATION: GPC3A-043 VH
```

<400> SEQUENCE: 315

Glu Val Gln Leu Val Gln Ser Gly Ala Glu Val Lys Lys Pro Gly Ala
1               5                   10                  15

Thr Val Lys Val Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Leu Arg Asp Val Ala Tyr Tyr Pro Trp Gly Val Glu Asp
            100                 105                 110

Phe Trp Gly Gln Gly Thr Leu Val Thr Val Ser Ser
        115                 120

<210> SEQ ID NO 316
<211> LENGTH: 116
<212> TYPE: PRT
<213> ORGANISM: Artificial Sequence
<220> FEATURE:
<223> OTHER INFORMATION: GPC3A-044 VH

<400> SEQUENCE: 316

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Tyr Val Pro Tyr Leu Ser Asp Trp Gly Gln Gly Thr Leu Val
            100                 105                 110

Thr Val Ser Ser
        115

<210> SEQ ID NO 317
<211> LENGTH: 116
<212> TYPE: PRT
<213> ORGANISM: Artificial Sequence
<220> FEATURE:
<223> OTHER INFORMATION: GPC3A-045 VH

<400> SEQUENCE: 317

Gln Met Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ala Ser Asp Leu Tyr Gly Asp Trp Gly Gln Gly Thr Leu Val
            100                 105                 110

Thr Val Ser Ser
            115

<210> SEQ ID NO 318
<211> LENGTH: 121
<212> TYPE: PRT
<213> ORGANISM: Artificial Sequence
<220> FEATURE:
<223> OTHER INFORMATION: GPC3A-046 VH

<400> SEQUENCE: 318

Gln Val Gln Leu Val Gln Ser Gly Ala Glu Val Lys Lys Pro Gly Ala
 1               5                  10                  15

Ser Val Thr Val Ser Cys Lys Ala Ser Gly Tyr Arg Phe Ser Asn Tyr
             20                  25                  30

Gly Val Ser Trp Val Arg Gln Ala Pro Gly Gln Gly Leu Glu Trp Met
         35                  40                  45

Gly Trp Ile Ser Gly Ser Asn Gly Asn Thr Asn Tyr Ala Gln Lys Phe
     50                  55                  60

Leu Gly Arg Val Thr Met Thr Thr Asp Thr Ser Thr Thr Thr Ala Tyr
 65                  70                  75                  80

Met Glu Leu Ser Ser Leu Arg Ser Asp Asp Thr Ala Val Tyr Tyr Cys
                 85                  90                  95

Ala Arg Gly Asn Arg Arg Tyr Tyr Ser Pro Ile Ile Asp Pro Trp Gly
            100                 105                 110

Gln Gly Thr Leu Val Thr Val Ser Ser
            115                 120

<210> SEQ ID NO 319
<211> LENGTH: 118
<212> TYPE: PRT
<213> ORGANISM: Artificial Sequence
<220> FEATURE:
<223> OTHER INFORMATION: GPC3A-047 VH

<400> SEQUENCE: 319

Gln Val Gln Leu Val Gln Ser Gly Ala Glu Val Lys Lys Pro Gly Ala
 1               5                  10                  15

Ser Val Lys Val Ser Cys Lys Ala Pro Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser Asp Tyr Gly Ser Leu Tyr Asp Lys Trp Gly Gln Gly Thr
            100                 105                 110

-continued

Leu Val Thr Val Ser Ser
        115

<210> SEQ ID NO 320
<211> LENGTH: 117
<212> TYPE: PRT
<213> ORGANISM: Artificial Sequence
<220> FEATURE:
<223> OTHER INFORMATION: GPC3A-048 VH

<400> SEQUENCE: 320

Glu Val Gln Leu Val Glu Ser Gly Gly Glu Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Phe Val Ala Thr Asp Tyr Trp Gly Gln Gly Thr Leu
            100                 105                 110

Val Thr Val Ser Ser
        115

<210> SEQ ID NO 321
<211> LENGTH: 121
<212> TYPE: PRT
<213> ORGANISM: Artificial Sequence
<220> FEATURE:
<223> OTHER INFORMATION: GPC3A-049 VH

<400> SEQUENCE: 321

Gln Val Gln Leu Val Gln Ser Gly Ala Glu Val Lys Glu Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg His Gly Gly Ile Gly Ser Met Arg Ser Phe Asp Gln Trp Gly
            100                 105                 110

Gln Gly Thr Leu Val Thr Val Ser Ser
        115                 120

<210> SEQ ID NO 322
<211> LENGTH: 117
<212> TYPE: PRT
<213> ORGANISM: Artificial Sequence
<220> FEATURE:
<223> OTHER INFORMATION: GPC3A-050 VH

<400> SEQUENCE: 322

Gln Ile Thr Leu Lys Glu Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Val Tyr Trp Met Arg Gln Ala Pro Gly Lys Gly Leu Glu Trp Met
        35                  40                  45

Gly Trp Met Asn Pro Arg Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Thr Tyr Tyr Cys
                85                  90                  95

Ala Arg Ser Gly Tyr Arg Trp Leu Asp Val Trp Gly Gln Gly Thr Leu
            100                 105                 110

Val Thr Val Ser Ser
        115

<210> SEQ ID NO 323
<211> LENGTH: 121
<212> TYPE: PRT
<213> ORGANISM: Artificial Sequence
<220> FEATURE:
<223> OTHER INFORMATION: GPC3A-051 VH

<400> SEQUENCE: 323

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Leu Tyr Leu Ser Gly Arg Tyr Tyr Trp Asp Ser Trp Gly
            100                 105                 110

Gln Gly Thr Leu Val Thr Val Ser Ser
        115                 120

<210> SEQ ID NO 324
<211> LENGTH: 117
<212> TYPE: PRT
<213> ORGANISM: Artificial Sequence
<220> FEATURE:
<223> OTHER INFORMATION: GPC3A-052 VH

<400> SEQUENCE: 324

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
            50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Ser His Ser Ser Gly Tyr Asp Lys Trp Gly Gln Gly Thr Leu
                100                 105                 110

Val Thr Val Ser Ser
            115

<210> SEQ ID NO 325
<211> LENGTH: 118
<212> TYPE: PRT
<213> ORGANISM: Artificial Sequence
<220> FEATURE:
<223> OTHER INFORMATION: GPC3A-053 VH

<400> SEQUENCE: 325

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
                 20                  25                  30

Ser Tyr Tyr Trp Gly Trp Ile Arg Gln Pro Pro Gly Lys Gly Leu Glu
             35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Trp Trp Ser Gly Ser Tyr Asp Tyr Asp Trp Gly Gln Gly Thr
                100                 105                 110

Leu Val Thr Val Ser Ser
            115

<210> SEQ ID NO 326
<211> LENGTH: 119
<212> TYPE: PRT
<213> ORGANISM: Artificial Sequence
<220> FEATURE:
<223> OTHER INFORMATION: GPC3A-054 VH

<400> SEQUENCE: 326

Gln Met Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Ile Pro Met Tyr Ser Gly Ser Ser Asp Tyr Trp Gly Gln Gly

Thr Leu Val Thr Val Ser Ser
        115

<210> SEQ ID NO 327
<211> LENGTH: 117
<212> TYPE: PRT
<213> ORGANISM: Artificial Sequence
<220> FEATURE:
<223> OTHER INFORMATION: GPC3A-055 VH

<400> SEQUENCE: 327

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp His Gly Gly Pro Tyr Asp Tyr Trp Gly Gln Gly Thr Leu
            100                 105                 110

Val Thr Val Ser Ser
        115

<210> SEQ ID NO 328
<211> LENGTH: 122
<212> TYPE: PRT
<213> ORGANISM: Artificial Sequence
<220> FEATURE:
<223> OTHER INFORMATION: GPC3A-056 VH

<400> SEQUENCE: 328

Gln Val Gln Leu Gln Gln Ser Gly Ala Glu Val Lys Lys Phe Gly Ala
1               5                   10                  15

Ser Val Lys Val Ser Cys Lys Ala Ser Gly Tyr Ser Phe Asn Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Asn Gly Asp Thr Lys Tyr Glu Lys Lys Trp
    50                  55                  60

Gln Gly Arg Val Thr Met Thr Arg Asp Thr Ser Ile Thr Thr Ala Tyr
65                  70                  75                  80

Met Glu Leu Ser Ser Leu Arg Ser Asp Asp Thr Ala Val Tyr Tyr Cys
                85                  90                  95

Ala Arg Phe Ser Thr His Asn Trp Trp Pro Thr Tyr Asp Tyr Trp
            100                 105                 110

Gly Gln Gly Thr Leu Val Thr Val Ser Ser
        115                 120

<210> SEQ ID NO 329
<211> LENGTH: 120
<212> TYPE: PRT
<213> ORGANISM: Artificial Sequence
<220> FEATURE:

<223> OTHER INFORMATION: GPC3A-057 VH

<400> SEQUENCE: 329

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Tyr Met Ser Ser Gly Phe Tyr Asp Arg Trp Gly Gln
            100                 105                 110

Gly Thr Leu Val Thr Val Ser Ser
        115                 120

<210> SEQ ID NO 330
<211> LENGTH: 120
<212> TYPE: PRT
<213> ORGANISM: Artificial Sequence
<220> FEATURE:
<223> OTHER INFORMATION: GPC3A-058 VH

<400> SEQUENCE: 330

Gln Val Gln Leu Val Gln Ser Gly Ala Asp Val Arg Lys Pro Gly Ala
1               5                   10                  15

Ser Val Lys Val Ser Cys Lys Ala Ser Gly Tyr Thr Phe Ala Ser His
            20                  25                  30

Gly Ile Ser Trp Val Arg Gln Ala Pro Gly Gln Gly Leu Glu Trp Leu
        35                  40                  45

Gly Trp Ile Ser Pro Tyr Thr Gly Asn Thr Asn Tyr Ala Gln Lys Phe
    50                  55                  60

Gln Gly Arg Val Thr Met Ala Thr Asp Thr Ser Thr Ser Thr Ala Tyr
65                  70                  75                  80

Met Glu Leu Arg Ser Leu Arg Ser Asp Asp Thr Ala Ile Tyr Tyr Cys
                85                  90                  95

Ala Arg Gly Lys Arg Thr Leu Ala Ser Cys Phe Asp Tyr Trp Gly Gln
            100                 105                 110

Gly Thr Leu Val Thr Val Ser Ser
        115                 120

<210> SEQ ID NO 331
<211> LENGTH: 117
<212> TYPE: PRT
<213> ORGANISM: Artificial Sequence
<220> FEATURE:
<223> OTHER INFORMATION: GPC3A-059 VH

<400> SEQUENCE: 331

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Arg Tyr
            20                  25                  30

Gly Ile Thr Trp Val Arg Gln Ala Pro Gly Gln Gly Leu Glu Trp Met

```
                35                  40                  45

Gly Trp Ile Ser Ala Tyr Ser Asp Lys Thr Asn Tyr Ala Gln Lys Leu
 50                  55                  60

Gln Gly Arg Val Thr Met Thr Thr Asp Ile Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Arg Trp Ser Tyr Met Asp Val Trp Gly Gln Gly Thr Leu
            100                 105                 110

Val Thr Val Ser Ser
            115

<210> SEQ ID NO 332
<211> LENGTH: 119
<212> TYPE: PRT
<213> ORGANISM: Artificial Sequence
<220> FEATURE:
<223> OTHER INFORMATION: GPC3A-060 VH

<400> SEQUENCE: 332

Gln Val Gln Leu Val Gln Ser Gly Gly Glu Val Lys Lys Pro Gly Ala
  1               5                  10                  15

Ser Val Lys Val Ser Cys Lys Ala Ser Gly Tyr Thr Phe Asn Ser Tyr
                 20                  25                  30

Ala Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Asn Thr Ala Phe
 65                  70                  75                  80

Met Glu Leu Arg Ser Leu Arg Ser Asp Asp Thr Ala Val Tyr Tyr Cys
                 85                  90                  95

Ala Arg Glu Gly Tyr Gly Ser Trp Ala Met Asp Gln Trp Gly Gln Gly
            100                 105                 110

Thr Leu Val Thr Val Ser Ser
            115

<210> SEQ ID NO 333
<211> LENGTH: 117
<212> TYPE: PRT
<213> ORGANISM: Artificial Sequence
<220> FEATURE:
<223> OTHER INFORMATION: GPC3A-061 VH

<400> SEQUENCE: 333

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Thr Pro Gly Gln Gly Leu Glu Trp Met
             35                  40                  45

Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

Ala Arg Lys Gly Ser Ser Gln Phe Asp Gln Trp Gly Gln Gly Thr Leu
            100                 105                 110

Val Thr Val Ser Ser
        115

<210> SEQ ID NO 334
<211> LENGTH: 123
<212> TYPE: PRT
<213> ORGANISM: Artificial Sequence
<220> FEATURE:
<223> OTHER INFORMATION: GPC3A-062 VH

<400> SEQUENCE: 334

Gln Met Gln Leu Val Gln Ser Gly Ser Glu Leu Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Lys Ile Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Met Tyr Met Asp Met Gly Trp Gly Trp Gly Tyr Trp Asp Trp
            100                 105                 110

Trp Gly Gln Gly Thr Leu Val Thr Val Ser Ser
        115                 120

<210> SEQ ID NO 335
<211> LENGTH: 119
<212> TYPE: PRT
<213> ORGANISM: Artificial Sequence
<220> FEATURE:
<223> OTHER INFORMATION: GPC3A-063 VH

<400> SEQUENCE: 335

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Ala Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Leu Ala Ser Asp Ala Phe Asp Ile Trp Gly Gln Gly
            100                 105                 110

Thr Met Val Thr Val Ser Ser
        115

<210> SEQ ID NO 336
<211> LENGTH: 120
<212> TYPE: PRT
<213> ORGANISM: Artificial Sequence

<220> FEATURE:
<223> OTHER INFORMATION: GPC3A-064 VH

<400> SEQUENCE: 336

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
                20                  25                  30

Gly Ile Ser Trp Val Arg Gln Ala Pro Gly Gln Gly Leu Glu Trp Met
            35                  40                  45

Gly Trp Ile Ser Pro Tyr Asn Asp Asn Thr Ile Tyr Ala Gln Lys Val
        50                  55                  60

Gln Gly Arg Val Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Met Gly Val Gly Trp Gly Tyr Ala Gln Asp Ser Trp Gly Gln
            100                 105                 110

Gly Thr Leu Val Thr Val Ser Ser
        115                 120

<210> SEQ ID NO 337
<211> LENGTH: 116
<212> TYPE: PRT
<213> ORGANISM: Artificial Sequence
<220> FEATURE:
<223> OTHER INFORMATION: GPC3A-067 VH

<400> SEQUENCE: 337

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Phe Gly Ile Thr Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Glu Met Ser Asp Tyr Trp Gly Gln Gly Thr Leu Val
            100                 105                 110

Thr Val Ser Ser
        115

<210> SEQ ID NO 338
<211> LENGTH: 120
<212> TYPE: PRT
<213> ORGANISM: Artificial Sequence
<220> FEATURE:
<223> OTHER INFORMATION: GPC3B-54 VH

<400> SEQUENCE: 338

Glu Val Gln Leu Val Gln Ser Gly Ala Glu Val Lys Lys Pro Gly Ala
1               5                   10                  15

Ser Val Lys Leu Ser Cys Lys Thr Ser Gly Tyr Thr Phe Ile Asp Tyr
                20                  25                  30

```
Tyr Val Tyr Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Gly Ser Glu Asp Thr Ala Val Tyr Tyr Cys
                 85                  90                  95

Ala Arg Glu Arg Arg Tyr Ser Ser Pro Ser Asp His Trp Gly Gln
                100                 105                 110

Gly Thr Leu Val Thr Val Ser Ser
        115                 120
```

<210> SEQ ID NO 339
<211> LENGTH: 119
<212> TYPE: PRT
<213> ORGANISM: Artificial Sequence
<220> FEATURE:
<223> OTHER INFORMATION: GPC3B-60 VH

<400> SEQUENCE: 339

```
Glu Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
             35                  40                  45

Gly Ile Ile Asn Pro Ser Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Leu Tyr Ser Gln Pro Tyr Ile Asp Gly Trp Ser Gln Gly
                100                 105                 110

Thr Leu Val Thr Val Ser Ser
        115
```

<210> SEQ ID NO 340
<211> LENGTH: 122
<212> TYPE: PRT
<213> ORGANISM: Artificial Sequence
<220> FEATURE:
<223> OTHER INFORMATION: GPC3B-63 VH

<400> SEQUENCE: 340

```
Gln Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
             35                  40                  45

Gly Ile Ile Asn Pro Ser Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95
```

```
Ala Arg Ser Leu His Ala Met Arg Trp Ser Gln Thr Met Asp Ser Trp
            100                 105                 110

Gly Gln Gly Thr Leu Val Thr Val Ser Ser
        115                 120
```

<210> SEQ ID NO 341
<211> LENGTH: 118
<212> TYPE: PRT
<213> ORGANISM: Artificial Sequence
<220> FEATURE:
<223> OTHER INFORMATION: GPC3B-66 VH

<400> SEQUENCE: 341

```
Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Ile Gly Gln
            20                  25                  30

Tyr Leu His Trp Val Arg Gln Ala Pro Gly Gln Gly Leu Glu Trp Met
        35                  40                  45

Gly Arg Ile Asn Pro Met Thr Gly Val Thr Asn Tyr Ala Pro Lys Phe
    50                  55                  60

Gln Gly Arg Val Thr Met Thr Arg Asp Thr Ser Ile Ser Thr Gly Tyr
65                  70                  75                  80

Met Glu Ile Ser Arg Leu Arg Ser Asp Asp Thr Ala Val Tyr Tyr Cys
                85                  90                  95

Ala Arg Phe Ser Ser Gly Tyr Ser Arg Asp Thr Trp Gly Gln Gly Thr
            100                 105                 110

Leu Val Thr Val Ser Ser
        115
```

<210> SEQ ID NO 342
<211> LENGTH: 117
<212> TYPE: PRT
<213> ORGANISM: Artificial Sequence
<220> FEATURE:
<223> OTHER INFORMATION: GPC3B-68 VH

<400> SEQUENCE: 342

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Gly Tyr Glu Gly His Asp Thr Trp Gly Gln Gly Thr Leu
            100                 105                 110

Val Thr Val Ser Ser
        115
```

<210> SEQ ID NO 343
<211> LENGTH: 120
<212> TYPE: PRT

```
<213> ORGANISM: Artificial Sequence
<220> FEATURE:
<223> OTHER INFORMATION: GPC3B-71 VH

<400> SEQUENCE: 343

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Thr Met Asn Trp Val Arg Gln Ala Pro Gly Lys Gly Leu Glu Trp Val
        35                  40                  45

Ser Ser Ile Ser Ser Ser Gly Ser Tyr Ile Tyr Tyr Ala Asp Ser Val
50                  55                  60

Lys Gly Arg Phe Thr Ile Ser Arg Asp Asn Ala Lys Asn Ser Leu Phe
65                  70                  75                  80

Leu Gln Met Asp Ser Leu Arg Ala Glu Asp Thr Ala Val Tyr Tyr Cys
                85                  90                  95

Ala Arg Gln Gly His Met Trp Tyr Val Pro Val Asp Ala Trp Gly Gln
            100                 105                 110

Gly Thr Leu Val Thr Val Ser Ser
        115                 120

<210> SEQ ID NO 344
<211> LENGTH: 112
<212> TYPE: PRT
<213> ORGANISM: Artificial Sequence
<220> FEATURE:
<223> OTHER INFORMATION: GPC3B-76 VH

<400> SEQUENCE: 344

Gln Met Gln Leu Val Gln Ser Gly Ala Glu Val Lys Glu Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Tyr Asp Trp Gly Gln Gly Thr Leu Val Thr Val Ser Ser
            100                 105                 110

<210> SEQ ID NO 345
<211> LENGTH: 117
<212> TYPE: PRT
<213> ORGANISM: Artificial Sequence
<220> FEATURE:
<223> OTHER INFORMATION: GPC3B-78 VH

<400> SEQUENCE: 345

Gln Met Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45
```

```
Gly Ile Ile Asn Pro Ser Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Ser Phe Phe Asp Ser Trp Gly Gln Gly Thr Leu
            100                 105                 110

Val Thr Val Ser Ser
            115
```

<210> SEQ ID NO 346
<211> LENGTH: 122
<212> TYPE: PRT
<213> ORGANISM: Artificial Sequence
<220> FEATURE:
<223> OTHER INFORMATION: GPC3B-80 VH

<400> SEQUENCE: 346

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Leu Ser Arg Phe
                20                  25                  30

Ala Ile Ser Trp Val Arg Gln Ala Pro Gly Gln Gly Leu Glu Trp Met
            35                  40                  45

Gly Gly Ile Ile Pro Ile Phe Arg Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Ser Lys Tyr Tyr Gly Ser Tyr Ser Ser Tyr Asp Glu Trp
            100                 105                 110

Gly Gln Gly Thr Leu Val Thr Val Ser Ser
        115                 120
```

<210> SEQ ID NO 347
<211> LENGTH: 114
<212> TYPE: PRT
<213> ORGANISM: Artificial Sequence
<220> FEATURE:
<223> OTHER INFORMATION: GPC3B-81 VH

<400> SEQUENCE: 347

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Leu Trp Asp Ser Trp Gly Gln Gly Thr Leu Val Thr Val
```

Ser Ser

<210> SEQ ID NO 348
<211> LENGTH: 121
<212> TYPE: PRT
<213> ORGANISM: Artificial Sequence
<220> FEATURE:
<223> OTHER INFORMATION: GPC3B-82 VH

<400> SEQUENCE: 348

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Met Ser Ser Leu Arg Ser Glu Asp Thr Ala Val Tyr Tyr Cys
                85                  90                  95

Ala Arg Tyr Pro Val Tyr Met Glu Thr Ser Asp Phe Asp Ser Trp Gly
            100                 105                 110

Ser Arg Tyr Ser Gly Asp Arg Leu Leu
        115                 120

<210> SEQ ID NO 349
<211> LENGTH: 125
<212> TYPE: PRT
<213> ORGANISM: Artificial Sequence
<220> FEATURE:
<223> OTHER INFORMATION: GPC3B-85 VH

<400> SEQUENCE: 349

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Ser Leu Tyr Trp Met Gly Ser Lys Trp Ser Arg Gln Thr
            100                 105                 110

Asp Met Trp Gly Gln Gly Thr Leu Val Thr Val Ser Ser
        115                 120                 125

<210> SEQ ID NO 350
<211> LENGTH: 113
<212> TYPE: PRT
<213> ORGANISM: Artificial Sequence
<220> FEATURE:
<223> OTHER INFORMATION: GPC3B-87 VH

<400> SEQUENCE: 350

Glu Val Gln Leu Val Gln Ser Gly Ala Glu Val Arg Lys Pro Gly Ser
1               5                   10                  15

Ser Val Lys Val Ser Cys Gln Ala Ser Gly Gly Thr Phe Gly Ser Tyr
            20                  25                  30

Ala Ile Ser Trp Val Arg Gln Ala Pro Gly Gln Gly Leu Glu Trp Met
        35                  40                  45

Gly Arg Ile Ile Pro Val Leu Gly Arg Thr Lys Tyr Ala Gln Lys Phe
50                  55                  60

Gln Gly Arg Val Thr Val Thr Ala Asp Thr Ser Thr Ser Thr Val Tyr
65                  70                  75                  80

Met Glu Leu Thr Ser Leu Thr Ser Glu Asp Thr Ala Val Tyr Tyr Cys
                85                  90                  95

Ala Arg Thr Asn Asp Ser Trp Gly Gln Gly Thr Leu Val Thr Val Ser
            100                 105                 110

Ser

<210> SEQ ID NO 351
<211> LENGTH: 120
<212> TYPE: PRT
<213> ORGANISM: Artificial Sequence
<220> FEATURE:
<223> OTHER INFORMATION: GPC3B-92 VH

<400> SEQUENCE: 351

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Thr Thr Thr Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Ser Met Trp Thr Ser Ser Met Gly Asp Val Trp Gly Gln
            100                 105                 110

Gly Thr Leu Val Thr Val Ser Ser
        115                 120

<210> SEQ ID NO 352
<211> LENGTH: 123
<212> TYPE: PRT
<213> ORGANISM: Artificial Sequence
<220> FEATURE:
<223> OTHER INFORMATION: GPC3B-93 VH

<400> SEQUENCE: 352

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

```
Gly Ile Ile Asn Pro Ser Gly Gly Ser Thr Arg Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Thr Ala Leu Lys Pro Arg Gly Ile Tyr Ser Val Asp Ser
            100                 105                 110

Trp Gly Gln Gly Thr Leu Val Thr Val Ser Ser
        115                 120

<210> SEQ ID NO 353
<211> LENGTH: 125
<212> TYPE: PRT
<213> ORGANISM: Artificial Sequence
<220> FEATURE:
<223> OTHER INFORMATION: GPC3B-110 VH

<400> SEQUENCE: 353

Glu Val Gln Leu Val Gln Ser Gly Ala Glu Val Lys Lys Pro Gly Ser
1               5                   10                  15

Ser Val Lys Val Ser Cys Gln Ala Ser Gly Gly Thr Phe Thr Thr Tyr
            20                  25                  30

Ser Ile Asn Trp Val Arg Gln Ala Pro Gly Gln Gly Leu Glu Trp Met
        35                  40                  45

Gly Gly Ile Ile Pro Thr Phe Gly Thr Thr Asn Tyr Ala Gln Asn Phe
    50                  55                  60

Gln Asp Arg Val Thr Ile Ser Ala Asp Glu Ser Thr Asn Thr Ala Tyr
65                  70                  75                  80

Met Glu Leu Thr Ser Leu Arg Ser Glu Asp Thr Ala Val Tyr Tyr Cys
                85                  90                  95

Ala Arg Tyr Tyr Trp Arg Gly Gly Ser Gly Gln Gly Ser Val Thr Ser
            100                 105                 110

Asp Tyr Trp Gly Gln Gly Thr Leu Val Thr Val Ser Ser
        115                 120                 125

<210> SEQ ID NO 354
<211> LENGTH: 114
<212> TYPE: PRT
<213> ORGANISM: Artificial Sequence
<220> FEATURE:
<223> OTHER INFORMATION: GPC3B-113 VH

<400> SEQUENCE: 354

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Ser Gly Asp Tyr Trp Gly Gln Gly Thr Leu Val Thr Val
            100                 105                 110
```

Ser Ser

<210> SEQ ID NO 355
<211> LENGTH: 120
<212> TYPE: PRT
<213> ORGANISM: Artificial Sequence
<220> FEATURE:
<223> OTHER INFORMATION: GPC3B-115 VH

<400> SEQUENCE: 355

Gln Val Gln Leu Val Gln Ser Gly Ala Glu Val Lys Arg Pro Gly Ala
1               5                   10                  15

Thr Ile Lys Val Ser Cys Lys Thr Ser Gly Tyr Thr Phe Thr Ala Tyr
            20                  25                  30

Tyr Thr His Trp Val Arg Gln Ala Pro Gly Gln Gly Leu Glu Trp Val
        35                  40                  45

Gly Arg Ile Asn Ala Asn Thr Gly Gly Thr Asp Tyr Ala Pro Lys Phe
    50                  55                  60

Arg Asp Arg Val Ile Met Thr Arg Asp Thr Ser Ile Ser Thr Ala Tyr
65                  70                  75                  80

Met Glu Leu Gly Arg Leu Thr Ser Glu Asp Thr Ala Val Tyr Tyr Cys
                85                  90                  95

Ala Arg Ile Ser Gly Tyr His Ser Ser Gly Trp Asp Tyr Trp Gly Gln
            100                 105                 110

Gly Thr Leu Val Thr Val Ser Ser
        115                 120

<210> SEQ ID NO 356
<211> LENGTH: 117
<212> TYPE: PRT
<213> ORGANISM: Artificial Sequence
<220> FEATURE:
<223> OTHER INFORMATION: GPC3B-119 VH

<400> SEQUENCE: 356

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Tyr Tyr Gly Lys Tyr Asp Lys Trp Gly Gln Gly Thr Leu
            100                 105                 110

Val Thr Val Ser Ser
        115

<210> SEQ ID NO 357
<211> LENGTH: 114
<212> TYPE: PRT
<213> ORGANISM: Artificial Sequence
<220> FEATURE:
<223> OTHER INFORMATION: GPC3B-125 VH

<400> SEQUENCE: 357

Gln Met Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gln Ser His Asp Glu Trp Gly Gln Gly Thr Leu Val Thr Val
            100                 105                 110

Ser Ser

<210> SEQ ID NO 358
<211> LENGTH: 111
<212> TYPE: PRT
<213> ORGANISM: Artificial Sequence
<220> FEATURE:
<223> OTHER INFORMATION: GPC3A-034 VL

<400> SEQUENCE: 358

Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Asn Val Ile Trp Tyr Gln Gln Leu Pro Gly Ala Ala Pro Lys Leu Leu
        35                  40                  45

Ile Tyr Ser Asn His Arg Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asp Gly Tyr Leu Phe Gly Thr Gly Thr Lys Val Thr Val Leu Gly
            100                 105                 110

<210> SEQ ID NO 359
<211> LENGTH: 111
<212> TYPE: PRT
<213> ORGANISM: Artificial Sequence
<220> FEATURE:
<223> OTHER INFORMATION: GPC3A-035 VL

<400> SEQUENCE: 359

Gln Ala Val Leu Thr Gln Pro Pro Ser Ala Ser Gln Thr Pro Gly Gln
1               5                   10                  15

Met Val Thr Ile Ser Cys Ser Gly Thr Ser Asn Ile Gly Ser Asn
            20                  25                  30

Tyr Val Phe Trp Tyr Gln Gln Leu Pro Gly Thr Ala Pro Lys Leu Leu
        35                  40                  45

Ile Tyr Lys Asn Phe Gln Arg Pro Ser Gly Val Pro Gly Arg Phe Ser
    50                  55                  60

Gly Ser Lys Ser Gly Thr Ala Ala Ser Leu Ala Ile Ser Gly Leu Arg

```
                65                  70                  75                  80
Ser Glu Asp Glu Ala Asp Tyr Phe Cys Ala Ala Trp Asp Asp Ala Leu
                        85                  90                  95

Ser Gly Tyr Val Phe Gly Ala Gly Thr Lys Val Thr Val Leu Gly
                100                 105                 110

<210> SEQ ID NO 360
<211> LENGTH: 111
<212> TYPE: PRT
<213> ORGANISM: Artificial Sequence
<220> FEATURE:
<223> OTHER INFORMATION: GPC3A-037 VL

<400> SEQUENCE: 360

Gln Ser Val Leu Thr Gln Pro Pro Ser Val Ser Ala Ala Pro Gly Gln
1               5                   10                  15

Arg Val Thr Ile Ser Cys Ser Gly Thr Arg Ser Asn Ile Gly Ser Asp
                20                  25                  30

Tyr Val Ser Trp Tyr Gln His Leu Pro Gly Thr Ala Pro Lys Leu Leu
                35                  40                  45

Val Tyr Gly Asp Asn Leu Arg Pro Ser Gly Ile Pro Asp Arg Phe Ser
            50                  55                  60

Ala Ser Lys Ser Gly Thr Ser Ala Thr Leu Gly Ile Thr Gly Leu Gln
65              70                  75                  80

Thr Gly Asp Glu Ala Asp Tyr Tyr Cys Gly Thr Trp Asp Tyr Thr Leu
                        85                  90                  95

Asn Gly Val Val Phe Gly Gly Gly Thr Lys Leu Thr Val Leu Gly
                100                 105                 110

<210> SEQ ID NO 361
<211> LENGTH: 109
<212> TYPE: PRT
<213> ORGANISM: Artificial Sequence
<220> FEATURE:
<223> OTHER INFORMATION: GPC3A-038 VL

<400> SEQUENCE: 361

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
                35                  40                  45

Tyr Asp Ser Asp Arg Pro Ser Gly Ile Pro Glu Arg Phe Ser Gly Ser
            50                  55                  60

Asn Ser Gly Asn Thr Ala Thr Leu Thr Ile Ser Arg Val Glu Ala Gly
65              70                  75                  80

Asp Glu Ala Asp Tyr Tyr Cys Gln Val Trp Asp Ser Ser Ser Asp His
                        85                  90                  95

Val Val Phe Gly Gly Gly Thr Lys Leu Thr Val Leu Gly
                100                 105

<210> SEQ ID NO 362
<211> LENGTH: 109
<212> TYPE: PRT
<213> ORGANISM: Artificial Sequence
<220> FEATURE:
<223> OTHER INFORMATION: GPC3A-039 VL

<400> SEQUENCE: 362
```

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
                35                  40                  45

Tyr Asp Ser Asp Arg Pro Ser Gly Ile Pro Glu Arg Phe Ser Gly Ser
            50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly
                100                 105
```

<210> SEQ ID NO 363
<211> LENGTH: 111
<212> TYPE: PRT
<213> ORGANISM: Artificial Sequence
<220> FEATURE:
<223> OTHER INFORMATION: GPC3A-040 VL

<400> SEQUENCE: 363

```
Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
                35                  40                  45

Ile Tyr Ser Asn Asn Gln Arg Pro Ser Gly Val Pro Asp Arg Phe Ser
            50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly
                100                 105                 110
```

<210> SEQ ID NO 364
<211> LENGTH: 111
<212> TYPE: PRT
<213> ORGANISM: Artificial Sequence
<220> FEATURE:
<223> OTHER INFORMATION: GPC3A-041 VL

<400> SEQUENCE: 364

```
Gln Ala Val Leu Thr Gln Pro Pro Ser Ala Ser Gln Thr Pro Gly Gln
1               5                   10                  15

Met Val Thr Ile Ser Cys Ser Gly Thr Ser Ser Asn Ile Gly Ser Asn
                20                  25                  30

Tyr Val Phe Trp Tyr Gln Gln Leu Pro Gly Thr Ala Pro Lys Leu Leu
                35                  40                  45

Ile Tyr Lys Asn Phe Gln Arg Pro Ser Gly Val Pro Gly Arg Phe Ser
            50                  55                  60

Gly Ser Lys Ser Gly Thr Ala Ala Ser Leu Ala Ile Ser Gly Leu Arg
65                  70                  75                  80

Ser Glu Asp Glu Ala Asp Tyr Phe Cys Ala Ala Trp Asp Asp Ala Leu
```

```
                85                  90                  95

Ser Gly Tyr Val Phe Gly Ala Gly Thr Lys Val Thr Val Leu Gly
            100                 105                 110

<210> SEQ ID NO 365
<211> LENGTH: 111
<212> TYPE: PRT
<213> ORGANISM: Artificial Sequence
<220> FEATURE:
<223> OTHER INFORMATION: GPC3A-042 VL

<400> SEQUENCE: 365

Ser Tyr Val Leu Thr Gln Pro Pro Ser Ala Ser Gly Thr Pro Gly Gln
1               5                   10                  15

Arg Val Thr Ile Ser Cys Phe Gly Ser Ser Ser Asp Ile Gly Ser Asn
            20                  25                  30

Ser Val Phe Trp Tyr Gln Gln Leu Pro Gly Ala Ala Pro Lys Leu Leu
        35                  40                  45

Ile Tyr Ser Thr Gln Tyr Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Glu Tyr His Cys Ala Thr Trp Asp Asp Ser Leu
                85                  90                  95

Asn Gly Tyr Val Phe Gly Ser Gly Thr Lys Val Thr Val Leu Gly
            100                 105                 110

<210> SEQ ID NO 366
<211> LENGTH: 111
<212> TYPE: PRT
<213> ORGANISM: Artificial Sequence
<220> FEATURE:
<223> OTHER INFORMATION: GPC3A-043 VL

<400> SEQUENCE: 366

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Asn
            20                  25                  30

Tyr Val Tyr Trp Tyr Gln Gln Leu Pro Gly Thr Ala Pro Lys Leu Ile
        35                  40                  45

Ile Tyr Arg Asn Asn Gln Arg Pro Ser Gly Val Pro Asp Arg Phe Ser
    50                  55                  60

Gly Ser Glu Ser Gly Thr Ser Ala Ser Leu Ala Ile Ser Gly Leu Arg
65                  70                  75                  80

Ser Glu Asp Glu Ala Asp Tyr Tyr Cys Ala Val Trp Asp Asp Ser Leu
                85                  90                  95

Ser Gly Val Val Phe Gly Gly Gly Thr Lys Leu Thr Val Leu Gly
            100                 105                 110

<210> SEQ ID NO 367
<211> LENGTH: 109
<212> TYPE: PRT
<213> ORGANISM: Artificial Sequence
<220> FEATURE:
<223> OTHER INFORMATION: GPC3A-044 VL

<400> SEQUENCE: 367

Ser Tyr Val Leu Thr Gln Pro Pro Ser Val Ser Val Ala Pro Gly Lys
1               5                   10                  15
```

```
Thr Ala Arg Ile Thr Cys Gly Gly Asp Asn Ile Gly Tyr Lys Gly Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Val Val Phe Gly Gly Gly Thr Lys Leu Thr Val Leu Gly
            100                 105
```

<210> SEQ ID NO 368
<211> LENGTH: 111
<212> TYPE: PRT
<213> ORGANISM: Artificial Sequence
<220> FEATURE:
<223> OTHER INFORMATION: GPC3A-045 VL

<400> SEQUENCE: 368

```
Gln Ser Val Leu Thr Gln Pro Pro Ser Val Ser Gly Thr Pro Gly Gln
1               5                   10                  15

Arg Val Ile Ile Ser Cys Pro Gly Ser Thr Ser Asn Ile Gly Thr Asn
            20                  25                  30

Thr Val Asn Trp Tyr Gln Gln Phe Pro Gly Thr Ala Pro Lys Leu Leu
        35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly
            100                 105                 110
```

<210> SEQ ID NO 369
<211> LENGTH: 111
<212> TYPE: PRT
<213> ORGANISM: Artificial Sequence
<220> FEATURE:
<223> OTHER INFORMATION: GPC3A-046 VL

<400> SEQUENCE: 369

```
Gln Ala Val Leu Thr Gln Pro Pro Ser Val Ser Gly Thr Pro Gly Gln
1               5                   10                  15

Arg Val Thr Ile Ser Cys Ser Gly Ser Ser Ser Asn Phe Gly Ser Asn
            20                  25                  30

Thr Val His Trp Tyr Gln Gln Val Pro Gly Thr Ala Pro Lys Leu Leu
        35                  40                  45

Ile Phe Ser Asn Thr Gln Arg Pro Ser Glu Ile Pro Asp Arg Phe Ser
 50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Thr Gly Val Val Phe Gly Gly Gly Thr Lys Leu Thr Val Leu Gly
```

<210> SEQ ID NO 370
<211> LENGTH: 111
<212> TYPE: PRT
<213> ORGANISM: Artificial Sequence
<220> FEATURE:
<223> OTHER INFORMATION: GPC3A-047 VL

<400> SEQUENCE: 370

```
Leu Pro Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Ala Ser Asn
            20                  25                  30

Asp Val Tyr Trp Tyr Gln Gln Leu Pro Gly Thr Ala Pro Lys Arg Leu
        35                  40                  45

Ile Tyr Lys Lys Asn Gln Arg Pro Ser Gly Val Pro Asp Arg Phe Ser
    50                  55                  60

Ala Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Asn Leu
                85                  90                  95

Ser Gly Tyr Val Phe Gly Thr Gly Thr Lys Val Thr Val Leu Gly
            100                 105                 110
```

<210> SEQ ID NO 371
<211> LENGTH: 109
<212> TYPE: PRT
<213> ORGANISM: Artificial Sequence
<220> FEATURE:
<223> OTHER INFORMATION: GPC3A-048 VL

<400> SEQUENCE: 371

```
Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Phe Tyr Cys Gln Val Trp Asp Ser Ser Ser Asp Arg
                85                  90                  95

Gly Val Phe Gly Gly Gly Thr Lys Leu Thr Val Leu Gly
            100                 105
```

<210> SEQ ID NO 372
<211> LENGTH: 111
<212> TYPE: PRT
<213> ORGANISM: Artificial Sequence
<220> FEATURE:
<223> OTHER INFORMATION: GPC3A-049 VL

<400> SEQUENCE: 372

```
Gln Ala Val Leu Thr Gln Pro Ser Ser Ala Ser Gly Thr Pro Gly Gln
1               5                   10                  15

Arg Val Thr Ile Ser Cys Ser Gly Gly Ser Ser Asn Ile Gly Ser Asn
            20                  25                  30
```

```
Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Trp Val Phe Gly Gly Arg Thr Lys Leu Thr Val Leu Gly
                100                 105                 110

<210> SEQ ID NO 373
<211> LENGTH: 111
<212> TYPE: PRT
<213> ORGANISM: Artificial Sequence
<220> FEATURE:
<223> OTHER INFORMATION: GPC3A-050 VL

<400> SEQUENCE: 373

Gln Ala Val Leu Thr Gln Pro Ser Ser Ala Ser Gly Thr Pro Gly Gln
 1               5                  10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Thr Gly Thr Lys Val Thr Val Leu Gly
                100                 105                 110

<210> SEQ ID NO 374
<211> LENGTH: 112
<212> TYPE: PRT
<213> ORGANISM: Artificial Sequence
<220> FEATURE:
<223> OTHER INFORMATION: GPC3A-051 VL

<400> SEQUENCE: 374

Gln Ala Val Leu Thr Gln Pro Ser Ser Ala Ser Gly Ala Pro Gly Gln
 1               5                  10                  15

Arg Val Thr Ile Ser Cys Thr Gly Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Tyr Val Phe Gly Thr Gly Thr Lys Val Thr Val Leu Gly
                100                 105                 110
```

<210> SEQ ID NO 375
<211> LENGTH: 111
<212> TYPE: PRT
<213> ORGANISM: Artificial Sequence
<220> FEATURE:
<223> OTHER INFORMATION: GPC3A-052 VL

<400> SEQUENCE: 375

Gln Ala Val Leu Thr Gln Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Ser Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly
            100                 105                 110

<210> SEQ ID NO 376
<211> LENGTH: 112
<212> TYPE: PRT
<213> ORGANISM: Artificial Sequence
<220> FEATURE:
<223> OTHER INFORMATION: GPC3A-053 VL

<400> SEQUENCE: 376

Gln Ser Val Leu Thr Gln Pro Pro Ser Ala Ser Ala Ala Pro Gly Gln
1               5                   10                  15

Arg Val Thr Ile Ser Cys Ser Gly Thr Ser Asn Ile Gly Ser Asn
            20                  25                  30

Tyr Val Trp Trp Tyr Gln Gln Leu Pro Gly Ala Ala Pro Arg Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Ser Gly Ser Asn Val Phe Gly Thr Gly Thr Lys Val Thr Val Leu Gly
            100                 105                 110

<210> SEQ ID NO 377
<211> LENGTH: 111
<212> TYPE: PRT
<213> ORGANISM: Artificial Sequence
<220> FEATURE:
<223> OTHER INFORMATION: GPC3A-054 VL

<400> SEQUENCE: 377

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

```
Ile Tyr Arg Asn Asn Gln Arg Pro Ser Gly Val Pro Asp Arg Phe Ser
         50                  55                  60
Gly Ser Lys Ser Gly Thr Ser Ala Ser Leu Ala Ile Ser Gly Leu Arg
 65                  70                  75                  80
Ser Glu Asp Glu Ala Asp Tyr Tyr Cys Ala Ala Trp Asp Asp Ser Leu
                 85                  90                  95
Ser Gly Tyr Val Phe Gly Thr Gly Thr Lys Val Thr Val Leu Gly
            100                 105                 110
```

<210> SEQ ID NO 378
<211> LENGTH: 109
<212> TYPE: PRT
<213> ORGANISM: Artificial Sequence
<220> FEATURE:
<223> OTHER INFORMATION: GPC3A-055 VL

<400> SEQUENCE: 378

```
Gln Pro Val Leu Thr Gln Pro Pro Ser Val Ser Val Ala Pro Gly Lys
 1               5                  10                  15
Thr Ala Arg Ile Thr Cys Gly Gly Asn Asn Ile Gly Ser Lys Ser Val
             20                  25                  30
His Trp Tyr Gln Gln Lys Pro Gly Gln Ala Pro Val Leu Val Ile Tyr
         35                  40                  45
Tyr Asp Ser Asp Arg Pro Ser Gly Ile Pro Glu Arg Phe Ser Gly Ser
     50                  55                  60
Asn Ser Gly Asn Thr Ala Thr Leu Thr Ile Ser Arg Val Glu Ala Gly
 65                  70                  75                  80
Asp Glu Ala Asp Tyr Tyr Cys Gln Val Trp Asp Ser Ser Ser Asp His
                 85                  90                  95
Tyr Val Phe Gly Thr Gly Thr Lys Val Thr Val Leu Gly
            100                 105
```

<210> SEQ ID NO 379
<211> LENGTH: 108
<212> TYPE: PRT
<213> ORGANISM: Artificial Sequence
<220> FEATURE:
<223> OTHER INFORMATION: GPC3A-056 VL

<400> SEQUENCE: 379

```
Asp Ile Gln Leu Thr Gln Ser Pro Ser Ser Leu Ser Ala Ser Val Gly
 1               5                  10                  15
Asp Arg Val Thr Ile Thr Cys Arg Ala Ser Gln Ser Ile Ser Ser Tyr
             20                  25                  30
Leu Asn Trp Tyr Gln Gln Lys Pro Gly Lys Ala Pro Lys Leu Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ser Thr Pro Ile
                 85                  90                  95
Thr Phe Gly Gln Gly Thr Arg Leu Glu Ile Lys Arg
            100                 105
```

<210> SEQ ID NO 380
<211> LENGTH: 109
<212> TYPE: PRT

<213> ORGANISM: Artificial Sequence
<220> FEATURE:
<223> OTHER INFORMATION: GPC3A-057 VL

<400> SEQUENCE: 380

Glu Ile Val Leu Thr Gln Ser Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Val Val Phe Gly Gly Gly Thr Lys Val Glu Ile Lys Arg
            100                 105

<210> SEQ ID NO 381
<211> LENGTH: 108
<212> TYPE: PRT
<213> ORGANISM: Artificial Sequence
<220> FEATURE:
<223> OTHER INFORMATION: GPC3A-058 VL

<400> SEQUENCE: 381

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Phe Gly Thr Gly Thr Lys Val Thr Val Leu Gly
            100                 105

<210> SEQ ID NO 382
<211> LENGTH: 108
<212> TYPE: PRT
<213> ORGANISM: Artificial Sequence
<220> FEATURE:
<223> OTHER INFORMATION: GPC3A-059 VL

<400> SEQUENCE: 382

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

Tyr Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Phe Gly Thr Gly Thr Lys Val Thr Val Leu Gly
            100                 105

<210> SEQ ID NO 383
<211> LENGTH: 107
<212> TYPE: PRT
<213> ORGANISM: Artificial Sequence
<220> FEATURE:
<223> OTHER INFORMATION: GPC3A-060 VL

<400> SEQUENCE: 383

Ser Tyr Val Leu Thr Gln Pro Pro Ser Val Ser Val Ala Pro Gly Lys
1               5                   10                  15

Thr Ala Arg Leu Thr Cys Gly Gly Asn Asn Ile Gly Ser Glu Ser Val
            20                  25                  30

His Trp Tyr Gln Gln Lys Pro Gly Gln Ala Pro Leu Leu Val Val Tyr
        35                  40                  45

Asp Asp Asp Arg Pro Ser Gly Ile Pro Glu Arg Phe Ser Gly Ser
    50                  55                  60

Asn Ser Glu Asp Thr Ala Thr Leu Thr Ile Ser Gly Thr Gln Ala Leu
65                  70                  75                  80

Asp Glu Ala Glu Tyr Tyr Cys Gln Thr Trp Asp Ser Ser Thr Ala Ile
                85                  90                  95

Phe Gly Thr Gly Thr Lys Leu Thr Val Leu Gly
            100                 105

<210> SEQ ID NO 384
<211> LENGTH: 109
<212> TYPE: PRT
<213> ORGANISM: Artificial Sequence
<220> FEATURE:
<223> OTHER INFORMATION: GPC3A-061 VL

<400> SEQUENCE: 384

Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly
            100                 105

<210> SEQ ID NO 385
<211> LENGTH: 113
<212> TYPE: PRT
<213> ORGANISM: Artificial Sequence
<220> FEATURE:
<223> OTHER INFORMATION: GPC3A-062 VL

<400> SEQUENCE: 385

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Trp Pro Ser Gly Val Pro Asp Arg Phe
    50                  55                  60

Ser Gly Ser Lys Ser Gly Thr Ser Ala Ser Leu Ala Ile Thr Gly Leu
65              70                  75                  80

Arg Ala Glu Asp Glu Ala Asp Tyr Tyr Cys Gln Ser Tyr Asp Ser Ser
                85                  90                  95

Leu Ser Gly Ser Tyr Val Phe Gly Thr Gly Thr Lys Val Thr Val Leu
            100                 105                 110

Gly

<210> SEQ ID NO 386
<211> LENGTH: 111
<212> TYPE: PRT
<213> ORGANISM: Artificial Sequence
<220> FEATURE:
<223> OTHER INFORMATION: GPC3A-063 VL

<400> SEQUENCE: 386

Gln Thr Val Val Thr Gln Pro Pro Ser Ala Ser Gly Thr Pro Gly Gln
1               5                   10                  15

Arg Val Thr Ile Ser Cys Ser Gly Ser Trp Ser Asn Ile Gly Ser Tyr
                20                  25                  30

Thr Val Asn Trp Tyr Gln His Leu Pro Gly Thr Ala Pro Lys Leu Leu
            35                  40                  45

Ile Ser Gly Asn Asn Gln Arg Pro Ser Gly Val Pro Gly Arg Phe Ser
    50                  55                  60

Gly Ser Lys Ser Gly Thr Ser Ala Ser Leu Ala Ile Ser Gly Leu Gln
65              70                  75                  80

Ser Glu Asp Glu Ala Asp Tyr His Cys Ala Ala Trp Asp Asp Asn Leu
                85                  90                  95

Asn Gly Val Val Phe Gly Gly Gly Thr Lys Leu Thr Val Leu Gly
            100                 105                 110

<210> SEQ ID NO 387
<211> LENGTH: 109
<212> TYPE: PRT
<213> ORGANISM: Artificial Sequence
<220> FEATURE:
<223> OTHER INFORMATION: GPC3A-064 VL

<400> SEQUENCE: 387

Leu Pro Val Leu Thr Gln Pro Pro Ser Leu Ser Val Ala Pro Gly Lys
1               5                   10                  15

Thr Ala Arg Leu Thr Cys Gly Gly Asn Asn Ile Gly Ser Lys Ser Val
                20                  25                  30

His Trp Tyr His Gln Lys Pro Gly Gln Ala Pro Val Leu Val Val Tyr
            35                  40                  45

Asp Asp Thr Asp Arg Pro Ser Gly Ile Pro Glu Arg Phe Ser Gly Ser
    50                  55                  60

-continued

Asn Ser Gly Asn Thr Ala Ala Leu Thr Ile Ser Arg Val Glu Val Gly
65                  70                  75                  80

Asp Glu Ala Asp Tyr Tyr Cys Gln Val Trp Asp Arg Ser Ser Ala His
                85                  90                  95

Trp Val Phe Gly Gly Gly Thr Lys Leu Thr Val Leu Gly
            100                 105

<210> SEQ ID NO 388
<211> LENGTH: 109
<212> TYPE: PRT
<213> ORGANISM: Artificial Sequence
<220> FEATURE:
<223> OTHER INFORMATION: GPC3A-067 VL

<400> SEQUENCE: 388

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Val Val Phe Gly Gly Gly Thr Lys Leu Thr Val Leu Gly
            100                 105

<210> SEQ ID NO 389
<211> LENGTH: 111
<212> TYPE: PRT
<213> ORGANISM: Artificial Sequence
<220> FEATURE:
<223> OTHER INFORMATION: GPC3B-54 VL

<400> SEQUENCE: 389

Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asp
                20                  25                  30

Thr Val Asn Trp Tyr Gln Gln Leu Pro Gly Thr Ala Pro Lys Leu Leu
            35                  40                  45

Ile Tyr Arg Asp Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Thr Thr Trp Asp Asp Ser Leu
                85                  90                  95

Asn Gly Leu Val Phe Gly Gly Gly Thr Lys Val Thr Val Leu Gly
            100                 105                 110

<210> SEQ ID NO 390
<211> LENGTH: 109
<212> TYPE: PRT
<213> ORGANISM: Artificial Sequence
<220> FEATURE:
<223> OTHER INFORMATION: GPC3B-60 VL

<400> SEQUENCE: 390

Ser Tyr Val Leu Thr Gln Pro Pro Ser Val Ser Val Ser Pro Gly Gln
1               5                   10                  15

Thr Ala Thr Ile Ala Cys Ser Gly Asp Asn Leu Glu Asn Lys Phe Val
            20                  25                  30

Tyr Trp Tyr His Gln Lys Pro Gly Gln Ser Pro Val Leu Val Met Tyr
        35                  40                  45

Glu Asp Asn Lys Arg Pro Ser Gly Ile Pro Glu Arg Phe Ser Gly Ser
50                  55                  60

Asn Ser Gly Asn Thr Ala Ala Leu Thr Ile Ser Gly Ala Gln Pro Met
65                  70                  75                  80

Asp Glu Ala Asp Tyr Tyr Cys Gln Thr Trp Asp Ser Pro Thr Gly Leu
                85                  90                  95

Phe Val Phe Gly Thr Gly Thr Lys Val Thr Val Leu Gly
            100                 105

<210> SEQ ID NO 391
<211> LENGTH: 113
<212> TYPE: PRT
<213> ORGANISM: Artificial Sequence
<220> FEATURE:
<223> OTHER INFORMATION: GPC3B-63 VL

<400> SEQUENCE: 391

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Thr Phe Gly Gln Gly Thr Lys Val Glu Ile Lys
            100                 105                 110

Arg

<210> SEQ ID NO 392
<211> LENGTH: 110
<212> TYPE: PRT
<213> ORGANISM: Artificial Sequence
<220> FEATURE:
<223> OTHER INFORMATION: GPC3B-66 VL

<400> SEQUENCE: 392

Gln Ala Val Leu Thr Gln Pro Pro Ser Val Ser Val Ala Pro Gly Lys
1               5                   10                  15

Thr Ala Ser Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly

```
                65                  70                  75                  80

Asp Glu Ala Asp Tyr Tyr Cys Gln Val Trp Asp Ser Ser Asp His
                85                  90                  95

Leu Tyr Val Phe Gly Thr Gly Thr Lys Val Thr Val Leu Gly
            100                 105                 110

<210> SEQ ID NO 393
<211> LENGTH: 111
<212> TYPE: PRT
<213> ORGANISM: Artificial Sequence
<220> FEATURE:
<223> OTHER INFORMATION: GPC3B-68 VL

<400> SEQUENCE: 393

Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
                35                  40                  45

Ile Tyr Asp Asn Ile Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu Gly
            100                 105                 110

<210> SEQ ID NO 394
<211> LENGTH: 109
<212> TYPE: PRT
<213> ORGANISM: Artificial Sequence
<220> FEATURE:
<223> OTHER INFORMATION: GPC3B-71 VL

<400> SEQUENCE: 394

Ser Tyr Val Leu Thr Gln Pro Pro Ser Val Ser Val Ala Pro Gly Lys
1               5                   10                  15

Thr Ala Arg Val Thr Cys Gly Gly Asn Asn Ile Gly Ser Lys Ser Val
                20                  25                  30

His Trp Tyr Gln Gln Lys Pro Gly Gln Ala Pro Val Leu Val Met Tyr
            35                  40                  45

Tyr Asp Ser Asp Arg Pro Ser Gly Ile Pro Glu Arg Phe Ser Gly Ser
50                  55                  60

Asn Ser Gly Asn Thr Ala Thr Leu Thr Ile Ser Ser Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly
            100                 105

<210> SEQ ID NO 395
<211> LENGTH: 111
<212> TYPE: PRT
<213> ORGANISM: Artificial Sequence
<220> FEATURE:
<223> OTHER INFORMATION: GPC3B-76 VL

<400> SEQUENCE: 395
```

```
Gln Ser Val Val Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Ala Tyr Tyr Cys Gly Thr Trp Asp Ser Ser Leu
                85                  90                  95

Ser Ala Gly Val Phe Gly Thr Gly Thr Lys Val Thr Val Leu Gly
                100                 105                 110

<210> SEQ ID NO 396
<211> LENGTH: 107
<212> TYPE: PRT
<213> ORGANISM: Artificial Sequence
<220> FEATURE:
<223> OTHER INFORMATION: GPC3B-78 VL

<400> SEQUENCE: 396

Leu Pro Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
                20                  25                  30

Tyr Trp Tyr Gln Gln Lys Pro Gly Gln Ser Pro Val Leu Val Ile Tyr
            35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Ala Ala Asp Tyr Tyr Cys Gln Thr Trp Asp Arg Ser Thr Tyr Val
                85                  90                  95

Phe Gly Thr Gly Thr Lys Val Thr Val Leu Gly
                100                 105

<210> SEQ ID NO 397
<211> LENGTH: 112
<212> TYPE: PRT
<213> ORGANISM: Artificial Sequence
<220> FEATURE:
<223> OTHER INFORMATION: GPC3B-80 VL

<400> SEQUENCE: 397

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Tyr Leu Ala Ile Ser Gly Leu Gln
65                  70                  75                  80

Ser Glu Asp Glu Ala Asp Tyr Tyr Cys Ala Ala Trp Asp Asp Ser Leu
```

```
                    85                  90                  95

Asn Gly Trp Gly Val Phe Gly Gly Gly Thr Lys Leu Thr Val Leu Gly
            100                 105                 110
```

<210> SEQ ID NO 398
<211> LENGTH: 110
<212> TYPE: PRT
<213> ORGANISM: Artificial Sequence
<220> FEATURE:
<223> OTHER INFORMATION: GPC3B-81 VL

<400> SEQUENCE: 398

```
Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Leu
                85                  90                  95

Leu Tyr Val Phe Gly Thr Gly Thr Lys Val Thr Val Leu Gly
            100                 105                 110
```

<210> SEQ ID NO 399
<211> LENGTH: 112
<212> TYPE: PRT
<213> ORGANISM: Artificial Sequence
<220> FEATURE:
<223> OTHER INFORMATION: GPC3B-82 VL

<400> SEQUENCE: 399

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Asp Asn Asn Asn Arg Pro Ser Gly Val Pro Asp Arg Phe
    50                  55                  60

Ser Gly Ser Lys Ser Asp Thr Ser Ala Ser Leu Ala Ile Thr Gly Leu
65                  70                  75                  80

Gln Ala Glu Asp Glu Ala Asp Tyr Tyr Cys Gln Ser Phe Asp Ser Ser
                85                  90                  95

Leu Ser Gly Trp Val Phe Gly Gly Gly Thr Lys Leu Thr Val Leu Gly
            100                 105                 110
```

<210> SEQ ID NO 400
<211> LENGTH: 111
<212> TYPE: PRT
<213> ORGANISM: Artificial Sequence
<220> FEATURE:
<223> OTHER INFORMATION: GPC3B-85 VL

<400> SEQUENCE: 400

```
Gln Ala Val Leu Thr Gln Pro Pro Ser Ala Ser Gly Thr Pro Gly Gln
1               5                   10                  15
```

-continued

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly
            100                 105                 110

<210> SEQ ID NO 401
<211> LENGTH: 113
<212> TYPE: PRT
<213> ORGANISM: Artificial Sequence
<220> FEATURE:
<223> OTHER INFORMATION: GPC3B-87 VL

<400> SEQUENCE: 401

Asp Val Val Met Thr Gln Ser Pro Leu Ser Leu Pro Val Thr Pro Gly
1               5                   10                  15

Glu Pro Ala Ser Val Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

Arg

<210> SEQ ID NO 402
<211> LENGTH: 108
<212> TYPE: PRT
<213> ORGANISM: Artificial Sequence
<220> FEATURE:
<223> OTHER INFORMATION: GPC3B-92 VL

<400> SEQUENCE: 402

Gln Ser Val Leu Thr Gln Pro Pro Ser Val Ser Val Ser Pro Gly Gln
1               5                   10                  15

Thr Ala Arg Ile Thr Cys Ser Gly Glu Thr Leu Ala Lys Arg Tyr Ala
            20                  25                  30

His Trp Tyr Gln Gln Lys Pro Gly Gln Ala Pro Val Leu Leu Ile Tyr
        35                  40                  45

Arg Asp Thr Glu Arg Pro Ser Gly Ile Pro Glu Arg Phe Ser Gly Ser
50                  55                  60

Ser Ser Gly Thr Thr Ile Thr Leu Thr Ile Thr Gly Val Gln Ala Glu
65                  70                  75                  80

Asp Glu Ala Asp Tyr Tyr Cys Gln Ser Ala Asp Asn Ser Arg Thr Phe
                85                  90                  95

```
Val Phe Gly Pro Gly Thr Lys Val Thr Val Leu Gly
            100                 105
```

<210> SEQ ID NO 403
<211> LENGTH: 111
<212> TYPE: PRT
<213> ORGANISM: Artificial Sequence
<220> FEATURE:
<223> OTHER INFORMATION: GPC3B-93 VL

<400> SEQUENCE: 403

```
Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Trp Val Phe Gly Gly Thr Lys Leu Thr Val Leu Gly
            100                 105                 110
```

<210> SEQ ID NO 404
<211> LENGTH: 111
<212> TYPE: PRT
<213> ORGANISM: Artificial Sequence
<220> FEATURE:
<223> OTHER INFORMATION: GPC3B-110 VL

<400> SEQUENCE: 404

```
Gln Ser Val Leu Thr Gln Pro Pro Ser Ala Ser Gly Thr Pro Gly Gln
1               5                   10                  15

Arg Val Thr Val Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Leu Tyr Ser Ser Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly
            100                 105                 110
```

<210> SEQ ID NO 405
<211> LENGTH: 111
<212> TYPE: PRT
<213> ORGANISM: Artificial Sequence
<220> FEATURE:
<223> OTHER INFORMATION: GPC3B-113 VL

<400> SEQUENCE: 405

```
Ser Tyr Glu Leu Thr Gln Pro Pro Ser Ala Ser Gly Thr Pro Gly Gln
1               5                   10                  15
```

```
Arg Val Thr Ile Ser Cys Ser Gly Ser Ser Asn Ile Gly Ser Asn
            20                  25                  30

Ser Val Ser Trp Tyr Gln His Leu Pro Gly Val Ala Pro Lys Leu Leu
        35                  40                  45

Ile Tyr Ser Asn Asn Gln Arg Pro Ser Gly Val Pro Asp Arg Phe Ser
 50                  55                  60

Gly Ser Lys Thr Gly Thr Ser Ala Ser Leu Ala Ile Ser Gly Leu Gln
65                  70                  75                  80

Ser Glu Asp Glu Gly Asp Tyr Tyr Cys Ala Ala Trp Asp Asp Ser Leu
            85                  90                  95

Asn Gly Val Leu Phe Gly Gly Gly Thr Lys Leu Thr Val Leu Gly
            100                 105                 110
```

<210> SEQ ID NO 406
<211> LENGTH: 110
<212> TYPE: PRT
<213> ORGANISM: Artificial Sequence
<220> FEATURE:
<223> OTHER INFORMATION: GPC3B-115 VL

<400> SEQUENCE: 406

```
Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp Pro
            85                  90                  95

Leu Tyr Val Phe Gly Thr Gly Thr Lys Val Thr Val Leu Gly
            100                 105                 110
```

<210> SEQ ID NO 407
<211> LENGTH: 111
<212> TYPE: PRT
<213> ORGANISM: Artificial Sequence
<220> FEATURE:
<223> OTHER INFORMATION: GPC3B-119 VL

<400> SEQUENCE: 407

```
Gln Ser Val Val Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Ile Pro Gly Thr Ala Pro Lys Leu Leu
        35                  40                  45

Ile Tyr Asp Asn Asn Lys Arg Pro Ser Gly Ile Pro Asp Arg Phe Ser
 50                  55                  60

Gly Ser Arg Ser Gly Thr Ser Ala Thr Leu Gly Ile Thr Gly Leu Gln
65                  70                  75                  80

Thr Gly Asp Glu Ala His Tyr Tyr Cys Ala Thr Trp Asp Asn Ser Leu
            85                  90                  95

Ser Ala Leu Ile Phe Gly Gly Gly Thr Lys Val Thr Val Leu Gly
            100                 105                 110
```

<210> SEQ ID NO 408
<211> LENGTH: 111
<212> TYPE: PRT
<213> ORGANISM: Artificial Sequence
<220> FEATURE:
<223> OTHER INFORMATION: GPC3B-125 VL

<400> SEQUENCE: 408

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Phe Gln Gln His Pro Gly Lys Ala Pro Lys Leu
        35                  40                  45

Ile Ile Tyr Glu Val Ser Asn Arg Pro Ser Gly Val Ser Asp Arg Phe
    50                  55                  60

Ser Gly Ser Lys Ser Gly Ser Thr Ala Ser Leu Thr Ile Ser Gly Leu
65                  70                  75                  80

Gln Ala Glu Asp Glu Ala Asn Tyr Tyr Cys Ser Ser Tyr Thr Ser Ser
                85                  90                  95

Thr Thr Val Ile Phe Gly Gly Gly Thr Lys Leu Thr Val Leu Gly
            100                 105                 110
```

<210> SEQ ID NO 409
<211> LENGTH: 248
<212> TYPE: PRT
<213> ORGANISM: Artificial Sequence
<220> FEATURE:
<223> OTHER INFORMATION: GPC3A-034 scFv

<400> SEQUENCE: 409

```
Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Asn Val Ile Trp Tyr Gln Gln Leu Pro Gly Ala Ala Pro Lys Leu Leu
        35                  40                  45

Ile Tyr Ser Asn His Arg Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asp Gly Tyr Leu Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
            115                 120                 125

Leu Glu Met Ala Gln Val Gln Leu Gln Gln Trp Gly Ala Gly Leu Leu
        130                 135                 140

Lys Pro Ser Glu Thr Leu Ser Leu Thr Cys Ala Val Tyr Gly Gly Ser
145                 150                 155                 160

Phe Ser Gly Tyr Tyr Trp Ser Trp Ile Arg Gln Pro Pro Gly Lys Gly
                165                 170                 175

Leu Glu Trp Ile Gly Glu Ile Asn His Ser Gly Ser Thr Asn Tyr Asn
            180                 185                 190

Pro Ser Leu Lys Ser Arg Val Thr Ile Ser Val Asp Thr Ser Lys Asn
```

```
                195                 200                 205
Gln Phe Ser Leu Glu Leu Ser Ser Val Thr Ala Ala Asp Thr Ala Val
    210                 215                 220
Tyr Tyr Cys Ala Arg Gly Tyr Gly Arg Phe Asp Tyr Trp Gly Gln
225                 230                 235                 240
Gly Thr Leu Val Thr Val Ser Ser
                245

<210> SEQ ID NO 410
<211> LENGTH: 249
<212> TYPE: PRT
<213> ORGANISM: Artificial Sequence
<220> FEATURE:
<223> OTHER INFORMATION: GPC3A-035 scFv

<400> SEQUENCE: 410

Gln Ala Val Leu Thr Gln Pro Pro Ser Ala Ser Gln Thr Pro Gly Gln
1               5                   10                  15
Met Val Thr Ile Ser Cys Ser Gly Thr Ser Ser Asn Ile Gly Ser Asn
                20                  25                  30
Tyr Val Phe Trp Tyr Gln Gln Leu Pro Gly Thr Ala Pro Lys Leu Leu
            35                  40                  45
Ile Tyr Lys Asn Phe Gln Arg Pro Ser Gly Val Pro Gly Arg Phe Ser
        50                  55                  60
Gly Ser Lys Ser Gly Thr Ala Ala Ser Leu Ala Ile Ser Gly Leu Arg
65                  70                  75                  80
Ser Glu Asp Glu Ala Asp Tyr Phe Cys Ala Ala Trp Asp Asp Ala Leu
                85                  90                  95
Ser Gly Tyr Val Phe Gly Ala Gly Thr Lys Val Thr Val Leu Gly Ser
            100                 105                 110
Arg Gly Gly Gly Gly Ser Gly Gly Gly Gly Ser Gly Gly Gly Gly Ser
        115                 120                 125
Leu Glu Met Ala Gln Val Gln Leu Val Gln Ser Gly Ala Glu Val Lys
    130                 135                 140
Lys Pro Gly Ala Ser Val Lys Val Ser Cys Lys Ala Ser Gly Tyr Thr
145                 150                 155                 160
Phe Thr Gly Tyr Tyr Met His Trp Val Arg Gln Ala Pro Gly Gln Gly
                165                 170                 175
Leu Glu Trp Met Gly Trp Ile Asn Pro Asn Ser Gly Gly Thr Asn Tyr
            180                 185                 190
Ala Gln Lys Phe Gln Gly Arg Val Thr Met Thr Arg Asp Thr Ser Ile
        195                 200                 205
Ser Thr Ala Tyr Met Glu Leu Ser Arg Leu Arg Ser Asp Asp Thr Ala
    210                 215                 220
Val Tyr Tyr Cys Ala Arg Ser Trp Thr Ser Gly Phe Asp Tyr Trp Gly
225                 230                 235                 240
Gln Gly Thr Leu Val Thr Val Ser Ser
                245

<210> SEQ ID NO 411
<211> LENGTH: 250
<212> TYPE: PRT
<213> ORGANISM: Artificial Sequence
<220> FEATURE:
<223> OTHER INFORMATION: GPC3A-037 scFv

<400> SEQUENCE: 411
```

```
Gln Ser Val Leu Thr Gln Pro Pro Ser Val Ser Ala Ala Pro Gly Gln
1               5                   10                  15

Arg Val Thr Ile Ser Cys Ser Gly Thr Arg Ser Asn Ile Gly Ser Asp
            20                  25                  30

Tyr Val Ser Trp Tyr Gln His Leu Pro Gly Thr Ala Pro Lys Leu Leu
        35                  40                  45

Val Tyr Gly Asp Asn Leu Arg Pro Ser Gly Ile Pro Asp Arg Phe Ser
    50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Tyr Thr Leu
                85                  90                  95

Asn Gly Val Val Phe Gly Gly Gly Thr Lys Leu Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Gln Val Gln Leu Val Glu Ser Gly Gly Gly Leu Val
    130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
            165                 170                 175

Leu Glu Trp Val Ser Val Ile Tyr Ser Gly Gly Ser Ser Thr Tyr Tyr
            180                 185                 190

Ala Asp Ser Val Lys Gly Arg Phe Thr Ile Ser Arg Asp Asn Ser Lys
            195                 200                 205

Asn Thr Leu Tyr Leu Gln Met Asn Ser Leu Arg Ala Glu Asp Thr Ala
    210                 215                 220

Val Tyr Tyr Cys Ala Arg Thr Ser Tyr Leu Asn His Gly Asp Tyr Trp
225                 230                 235                 240

Gly Gln Gly Thr Leu Val Thr Val Ser Ser
                245                 250

<210> SEQ ID NO 412
<211> LENGTH: 246
<212> TYPE: PRT
<213> ORGANISM: Artificial Sequence
<220> FEATURE:
<223> OTHER INFORMATION: GPC3A-038 scFv

<400> SEQUENCE: 412

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Ser Arg Gly
            100                 105                 110
```

Gly Gly Gly Ser Gly Gly Gly Ser Gly Gly Gly Ser Leu Glu
            115                 120                 125

Met Ala Gln Val Gln Leu Val Gln Ser Gly Ala Glu Val Lys Lys Pro
    130                 135                 140

Gly Ala Ser Val Lys Val Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
                165                 170                 175

Trp Met Gly Ile Ile Asn Pro Ser Gly Gly Ser Thr Ser Tyr Ala Gln
            180                 185                 190

Lys Phe Gln Gly Arg Val Thr Met Thr Arg Asp Thr Ser Thr Ser Thr
        195                 200                 205

Val Tyr Met Glu Leu Ser Ser Leu Arg Ser Glu Asp Thr Ala Val Tyr
    210                 215                 220

Tyr Cys Ala Arg Lys Val Thr Gly Tyr Asp Ser Trp Gly Gln Gly Thr
225                 230                 235                 240

Leu Val Thr Val Ser Ser
                245

<210> SEQ ID NO 413
<211> LENGTH: 246
<212> TYPE: PRT
<213> ORGANISM: Artificial Sequence
<220> FEATURE:
<223> OTHER INFORMATION: GPC3A-039 scFv

<400> SEQUENCE: 413

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Ser Arg Gly
            100                 105                 110

Gly Gly Gly Ser Gly Gly Gly Ser Gly Gly Gly Ser Leu Glu
        115                 120                 125

Met Ala Gln Val Gln Leu Val Gln Ser Gly Gly Gly Leu Val His Pro
    130                 135                 140

Gly Gly Ser Leu Arg Leu Ser Cys Ala Gly Ser Gly Phe Thr Phe Ser
145                 150                 155                 160

Ser Tyr Ala Met His Trp Val Arg Gln Ala Pro Gly Lys Gly Leu Glu
                165                 170                 175

Trp Val Ser Ala Ile Gly Thr Gly Gly Gly Thr Tyr Tyr Ala Asp Ser
            180                 185                 190

Val Lys Gly Arg Phe Thr Ile Ser Arg Asp Asn Ala Lys Asn Ser Leu
        195                 200                 205

Tyr Leu Gln Met Asn Ser Leu Arg Ala Glu Asp Thr Ala Val Tyr Tyr
    210                 215                 220

Cys Ala Arg Tyr Gly Arg Lys Ser Ile Asp Ala Trp Gly Gln Gly Thr
225                 230                 235                 240

Leu Val Thr Val Ser Ser
                245

<210> SEQ ID NO 414
<211> LENGTH: 249
<212> TYPE: PRT
<213> ORGANISM: Artificial Sequence
<220> FEATURE:
<223> OTHER INFORMATION: GPC3A-040 scFv

<400> SEQUENCE: 414

Leu Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
                35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
            115                 120                 125

Leu Glu Met Ala Gln Val Gln Leu Val Gln Ser Gly Ala Glu Val Lys
        130                 135                 140

Lys Pro Gly Ala Ser Val Thr Val Ser Cys Lys Ala Ser Gly Tyr Thr
145                 150                 155                 160

Phe Thr Gly Tyr Tyr Met His Trp Val Arg Gln Ala Pro Gly Gln Gly
                165                 170                 175

Leu Glu Trp Met Gly Trp Ile Asn Pro Asn Ser Gly Gly Thr Asn Tyr
            180                 185                 190

Ala Gln Lys Phe Gln Gly Arg Val Thr Met Thr Arg Asp Thr Ser Ile
        195                 200                 205

Ser Thr Ala Tyr Met Glu Leu Ser Arg Leu Arg Ser Asp Asp Thr Ala
    210                 215                 220

Val Tyr Tyr Cys Ala Arg Arg Gly Tyr Tyr Gly Tyr Asp Ser Trp Gly
225                 230                 235                 240

Gln Gly Thr Leu Val Thr Val Ser Ser
                245

<210> SEQ ID NO 415
<211> LENGTH: 249
<212> TYPE: PRT
<213> ORGANISM: Artificial Sequence
<220> FEATURE:
<223> OTHER INFORMATION: GPC3A-041 scFv

<400> SEQUENCE: 415

Gln Ala Val Leu Thr Gln Pro Pro Ser Ala Ser Gln Thr Pro Gly Gln
1               5                   10                  15

Met Val Thr Ile Ser Cys Ser Gly Thr Ser Ser Asn Ile Gly Ser Asn
            20                  25                  30

Tyr Val Phe Trp Tyr Gln Gln Leu Pro Gly Thr Ala Pro Lys Leu Leu
            35                  40                  45

Ile Tyr Lys Asn Phe Gln Arg Pro Ser Gly Val Pro Gly Arg Phe Ser
 50                  55                  60

Gly Ser Lys Ser Gly Thr Ala Ala Ser Leu Ala Ile Ser Gly Leu Arg
 65                  70                  75                  80

Ser Glu Asp Glu Ala Asp Tyr Phe Cys Ala Ala Trp Asp Asp Ala Leu
                 85                  90                  95

Ser Gly Tyr Val Phe Gly Ala Gly Thr Lys Val Thr Val Leu Gly Ser
                100                 105                 110

Arg Gly Gly Gly Gly Ser Gly Gly Gly Ser Gly Gly Gly Gly Ser
                115                 120                 125

Leu Glu Met Ala Glu Val Gln Leu Val Gln Ser Gly Ala Glu Val Lys
            130                 135                 140

Lys Pro Gly Ala Ser Val Lys Val Ser Cys Lys Ala Ser Gly Tyr Thr
145                 150                 155                 160

Phe Thr Gly Tyr Tyr Met His Trp Val Arg Gln Ala Pro Gly Gln Gly
                165                 170                 175

Leu Glu Trp Met Gly Trp Ile Asn Pro Asn Ser Gly Gly Thr Asn Tyr
            180                 185                 190

Ala Gln Lys Phe Gln Gly Arg Val Thr Met Thr Arg Asp Thr Ser Ile
                195                 200                 205

Ser Thr Ala Tyr Met Glu Leu Ser Arg Leu Arg Ser Asp Asp Thr Ala
            210                 215                 220

Met Tyr Tyr Cys Ala Arg Ser Gly Lys Tyr Tyr Gly Asp Lys Trp Gly
225                 230                 235                 240

Gln Gly Thr Leu Val Thr Val Ser Ser
                245

<210> SEQ ID NO 416
<211> LENGTH: 249
<212> TYPE: PRT
<213> ORGANISM: Artificial Sequence
<220> FEATURE:
<223> OTHER INFORMATION: GPC3A-042 scFv

<400> SEQUENCE: 416

Ser Tyr Val Leu Thr Gln Pro Pro Ser Ala Ser Gly Thr Pro Gly Gln
 1               5                  10                  15

Arg Val Thr Ile Ser Cys Phe Gly Ser Ser Ser Asp Ile Gly Ser Asn
             20                  25                  30

Ser Val Phe Trp Tyr Gln Gln Leu Pro Gly Ala Ala Pro Lys Leu Leu
            35                  40                  45

Ile Tyr Ser Thr Gln Tyr Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Glu Tyr His Cys Ala Thr Trp Asp Asp Ser Leu
                 85                  90                  95

Asn Gly Tyr Val Phe Gly Ser Gly Thr Lys Val Thr Val Leu Gly Ser
                100                 105                 110

Arg Gly Gly Gly Gly Ser Gly Gly Gly Gly Ser Gly Gly Gly Gly Ser
                115                 120                 125

Leu Glu Met Ala Gln Val Gln Leu Gln Gln Ser Gly Ala Glu Val Lys
            130                 135                 140

```
Lys Pro Gly Ala Ser Val Lys Val Ser Cys Lys Ala Ser Gly Tyr Ser
145                 150                 155                 160

Phe Thr Gly Tyr Tyr Val Tyr Trp Met Arg Gln Ala Pro Gly Lys Gly
            165                 170                 175

Leu Glu Trp Met Gly Trp Met Asn Pro Arg Ser Gly Gly Thr Asn Tyr
            180                 185                 190

Ala Gln Lys Phe Gln Gly Arg Val Thr Met Thr Arg Asp Thr Ser Ile
            195                 200                 205

Ser Thr Ala Tyr Met Glu Leu Ser Arg Leu Thr Ser Asp Asp Thr Ala
        210                 215                 220

Val Tyr Tyr Cys Ala Arg Ser Ser Tyr Tyr Trp Ala Asp Ser Trp Gly
225                 230                 235                 240

Gln Gly Thr Leu Val Thr Val Ser Ser
                245
```

<210> SEQ ID NO 417
<211> LENGTH: 256
<212> TYPE: PRT
<213> ORGANISM: Artificial Sequence
<220> FEATURE:
<223> OTHER INFORMATION: GPC3A-043 scFv

<400> SEQUENCE: 417

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Asn
            20                  25                  30

Tyr Val Tyr Trp Tyr Gln Gln Leu Pro Gly Thr Ala Pro Lys Leu Ile
        35                  40                  45

Ile Tyr Arg Asn Asn Gln Arg Pro Ser Gly Val Pro Asp Arg Phe Ser
    50                  55                  60

Gly Ser Glu Ser Gly Thr Ser Ala Ser Leu Ala Ile Ser Gly Leu Arg
65                  70                  75                  80

Ser Glu Asp Glu Ala Asp Tyr Tyr Cys Ala Val Trp Asp Asp Ser Leu
                85                  90                  95

Ser Gly Val Val Phe Gly Gly Gly Thr Lys Leu Thr Val Leu Gly Ser
            100                 105                 110

Arg Gly Gly Gly Ser Gly Gly Gly Ser Gly Gly Gly Ser
        115                 120                 125

Leu Glu Met Ala Glu Val Gln Leu Val Gln Ser Gly Ala Glu Val Lys
        130                 135                 140

Lys Pro Gly Ala Thr Val Lys Val Ser Cys Lys Val Ser Gly Tyr Thr
145                 150                 155                 160

Phe Thr Asp Tyr Tyr Met His Trp Val Gln Gln Ala Pro Gly Lys Gly
            165                 170                 175

Leu Glu Trp Met Gly Leu Val Asp Pro Glu Asp Gly Glu Thr Ile Tyr
            180                 185                 190

Ala Glu Lys Phe Gln Gly Arg Val Thr Ile Thr Ala Asp Thr Ser Thr
            195                 200                 205

Asp Thr Ala Tyr Met Glu Leu Ser Ser Leu Arg Ser Glu Asp Thr Ala
        210                 215                 220

Val Tyr Tyr Cys Ala Arg Glu Leu Arg Asp Val Ala Tyr Tyr Pro Trp
225                 230                 235                 240

Gly Val Glu Asp Phe Trp Gly Gln Gly Thr Leu Val Thr Val Ser Ser
            245                 250                 255
```

<210> SEQ ID NO 418
<211> LENGTH: 246
<212> TYPE: PRT
<213> ORGANISM: Artificial Sequence
<220> FEATURE:
<223> OTHER INFORMATION: GPC3A-044 scFv

<400> SEQUENCE: 418

```
Ser Tyr Val Leu Thr Gln Pro Pro Ser Val Ser Val Ala Pro Gly Lys
1               5                   10                  15

Thr Ala Arg Ile Thr Cys Gly Gly Asp Asn Ile Gly Tyr Lys Gly Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Gln Val Gln Leu Gln Gln Trp Gly Ala Gly Leu Leu Lys Pro
    130                 135                 140

Ser Glu Thr Leu Ser Leu Thr Cys Ala Val Tyr Gly Gly Ser Phe Ser
145                 150                 155                 160

Gly Tyr Tyr Trp Ser Trp Ile Arg Gln Pro Pro Gly Lys Gly Leu Glu
                165                 170                 175

Trp Ile Gly Glu Ile Asn His Ser Gly Ser Thr Asn Tyr Asn Pro Ser
            180                 185                 190

Leu Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Val Tyr Tyr
    210                 215                 220

Cys Ala Arg Tyr Tyr Val Pro Tyr Leu Ser Asp Trp Gly Gln Gly Thr
225                 230                 235                 240

Leu Val Thr Val Ser Ser
                245
```

<210> SEQ ID NO 419
<211> LENGTH: 248
<212> TYPE: PRT
<213> ORGANISM: Artificial Sequence
<220> FEATURE:
<223> OTHER INFORMATION: GPC3A-045 scFv

<400> SEQUENCE: 419

```
Gln Ser Val Leu Thr Gln Pro Pro Ser Val Ser Gly Thr Pro Gly Gln
1               5                   10                  15

Arg Val Ile Ile Ser Cys Pro Gly Ser Thr Ser Asn Ile Gly Thr Asn
            20                  25                  30

Thr Val Asn Trp Tyr Gln Gln Phe Pro Gly Thr Ala Pro Lys Leu Leu
        35                  40                  45

Ile Tyr Ser Asn Asn Gln Arg Pro Ser Gly Val Pro Asp Arg Phe Ser
```

```
            50                  55                  60
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Val Val Phe Gly Gly Gly Thr Lys Leu Thr Val Leu Gly Ser
            100                 105                 110

Arg Gly Gly Gly Gly Ser Gly Gly Gly Ser Gly Gly Gly Gly Gly Ser
            115                 120                 125

Leu Glu Met Ala Gln Met Gln Leu Val Gln Ser Gly Gly Gly Leu Val
        130                 135                 140

Lys Pro Gly Gly Ser Leu Arg Leu Ser Cys Ala Ala Ser Gly Phe Thr
145                 150                 155                 160

Phe Ser Asp Tyr Tyr Met Ser Trp Ile Arg Gln Ala Pro Gly Lys Gly
                165                 170                 175

Leu Glu Trp Val Ser Tyr Ile Ser Ser Ser Gly Ser Thr Ile Tyr Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
    210                 215                 220

Val Tyr Tyr Cys Ala Arg Ala Ser Asp Leu Tyr Gly Asp Trp Gly Gln
225                 230                 235                 240

Gly Thr Leu Val Thr Val Ser Ser
                245

<210> SEQ ID NO 420
<211> LENGTH: 253
<212> TYPE: PRT
<213> ORGANISM: Artificial Sequence
<220> FEATURE:
<223> OTHER INFORMATION: GPC3A-046 scFv

<400> SEQUENCE: 420

Gln Ala Val Leu Thr Gln Pro Pro Ser Val Ser Gly Thr Pro Gly Gln
 1               5                  10                  15

Arg Val Thr Ile Ser Cys Ser Gly Ser Ser Asn Phe Gly Ser Asn
                 20                  25                  30

Thr Val His Trp Tyr Gln Gln Val Pro Gly Thr Ala Pro Lys Leu Leu
             35                  40                  45

Ile Phe Ser Asn Thr Gln Arg Pro Ser Glu Ile Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Thr Gly Val Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Gln Val Gln Leu Val Gln Ser Gly Ala Glu Val Lys
        130                 135                 140

Lys Pro Gly Ala Ser Val Thr Val Ser Cys Lys Ala Ser Gly Tyr Arg
145                 150                 155                 160

Phe Ser Asn Tyr Gly Val Ser Trp Val Arg Gln Ala Pro Gly Gln Gly
```

```
                    165                 170                 175
Leu Glu Trp Met Gly Trp Ile Ser Gly Ser Asn Gly Asn Thr Asn Tyr
                180                 185                 190

Ala Gln Lys Phe Leu Gly Arg Val Thr Met Thr Thr Asp Thr Ser Thr
            195                 200                 205

Thr Thr Ala Tyr Met Glu Leu Ser Ser Leu Arg Ser Asp Asp Thr Ala
210                 215                 220

Val Tyr Tyr Cys Ala Arg Gly Asn Arg Arg Tyr Tyr Ser Pro Ile Ile
225                 230                 235                 240

Asp Pro Trp Gly Gln Gly Thr Leu Val Thr Val Ser Ser
                245                 250

<210> SEQ ID NO 421
<211> LENGTH: 250
<212> TYPE: PRT
<213> ORGANISM: Artificial Sequence
<220> FEATURE:
<223> OTHER INFORMATION: GPC3A-047 scFv

<400> SEQUENCE: 421

Leu Pro Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Ala Ser Asn
            20                  25                  30

Asp Val Tyr Trp Tyr Gln Gln Leu Pro Gly Thr Ala Pro Lys Arg Leu
        35                  40                  45

Ile Tyr Lys Lys Asn Gln Arg Pro Ser Gly Val Pro Asp Arg Phe Ser
50                  55                  60

Ala Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Asn Leu
                85                  90                  95

Ser Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Lys
    130                 135                 140

Lys Pro Gly Ala Ser Val Lys Val Ser Cys Lys Ala Pro Gly Tyr Thr
145                 150                 155                 160

Phe Thr Gly Tyr Tyr Met His Trp Val Arg Gln Ala Pro Gly Gln Gly
                165                 170                 175

Leu Glu Trp Met Gly Trp Ile Asn Pro Asn Ser Gly Gly Thr Asn Tyr
            180                 185                 190

Ala Gln Lys Phe Gln Gly Arg Val Thr Met Thr Arg Asp Thr Ser Ile
        195                 200                 205

Ser Thr Ala Tyr Met Glu Leu Ser Arg Leu Arg Ser Asp Asp Thr Ala
210                 215                 220

Val Tyr Tyr Cys Ala Arg Ser Asp Tyr Gly Ser Leu Tyr Asp Lys Trp
225                 230                 235                 240

Gly Gln Gly Thr Leu Val Thr Val Ser Ser
                245                 250

<210> SEQ ID NO 422
<211> LENGTH: 247
<212> TYPE: PRT
```

<213> ORGANISM: Artificial Sequence
<220> FEATURE:
<223> OTHER INFORMATION: GPC3A-048 scFv

<400> SEQUENCE: 422

Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Phe Tyr Cys Gln Val Trp Asp Ser Ser Asp Arg
                85                  90                  95

Gly Val Phe Gly Gly Gly Thr Lys Leu Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Glu Ser Gly Gly Gly Glu Val Gln Pro
130                 135                 140

Gly Arg Ser Leu Arg Leu Ser Cys Ala Ala Ser Gly Phe Thr Phe Ser
145                 150                 155                 160

Ser Tyr Ala Met His Trp Val Arg Gln Ala Pro Gly Lys Gly Leu Glu
                165                 170                 175

Trp Val Ala Val Ile Ser Tyr Asp Gly Ser Asn Lys Tyr Tyr Ala Asp
            180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Arg Ser Ser Phe Val Ala Thr Asp Tyr Trp Gly Gln Gly
225                 230                 235                 240

Thr Leu Val Thr Val Ser Ser
            245

<210> SEQ ID NO 423
<211> LENGTH: 253
<212> TYPE: PRT
<213> ORGANISM: Artificial Sequence
<220> FEATURE:
<223> OTHER INFORMATION: GPC3A-049 scFv

<400> SEQUENCE: 423

Gln Ala Val Leu Thr Gln Pro Ser Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

```
Ser Glu Asp Glu Ala Asp Tyr Tyr Cys Ala Ala Trp Asp Asp Ser Leu
                85                  90                  95

Ser Gly Trp Val Phe Gly Gly Arg Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Lys
    130                 135                 140

Glu Pro Gly Ala Ser Val Lys Val Ser Cys Lys Ala Ser Gly Tyr Thr
145                 150                 155                 160

Phe Thr Gly Tyr Tyr Met His Trp Val Arg Gln Ala Pro Gly Gln Gly
                165                 170                 175

Leu Glu Trp Met Gly Trp Ile Asn Pro Asn Ser Gly Gly Thr Asn Tyr
            180                 185                 190

Ala Gln Lys Phe Gln Gly Arg Val Thr Met Thr Arg Asp Thr Ser Ile
        195                 200                 205

Ser Thr Ala Tyr Met Glu Leu Ser Arg Leu Arg Ser Asp Asp Thr Ala
    210                 215                 220

Val Tyr Tyr Cys Ala Arg His Gly Gly Ile Gly Ser Met Arg Ser Phe
225                 230                 235                 240

Asp Gln Trp Gly Gln Gly Thr Leu Val Thr Val Ser Ser
                245                 250

<210> SEQ ID NO 424
<211> LENGTH: 249
<212> TYPE: PRT
<213> ORGANISM: Artificial Sequence
<220> FEATURE:
<223> OTHER INFORMATION: GPC3A-050 scFv

<400> SEQUENCE: 424

Gln Ala Val Leu Thr Gln Pro Ser Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Ile Thr Leu Lys Glu Ser Gly Ala Glu Val Lys
    130                 135                 140

Lys Pro Gly Ala Ser Val Lys Val Ser Cys Lys Ala Ser Gly Tyr Ser
145                 150                 155                 160

Phe Thr Gly Tyr Tyr Val Tyr Trp Met Arg Gln Ala Pro Gly Lys Gly
                165                 170                 175

Leu Glu Trp Met Gly Trp Met Asn Pro Arg Ser Gly Gly Thr Asn Tyr
            180                 185                 190
```

```
Ala Gln Lys Phe Gln Gly Arg Val Thr Met Thr Arg Asp Thr Ser Ile
            195                 200                 205

Ser Thr Ala Tyr Met Glu Leu Ser Arg Leu Thr Ser Asp Asp Thr Ala
        210                 215                 220

Thr Tyr Tyr Cys Ala Arg Ser Gly Tyr Arg Trp Leu Asp Val Trp Gly
225                 230                 235                 240

Gln Gly Thr Leu Val Thr Val Ser Ser
                245
```

<210> SEQ ID NO 425
<211> LENGTH: 254
<212> TYPE: PRT
<213> ORGANISM: Artificial Sequence
<220> FEATURE:
<223> OTHER INFORMATION: GPC3A-051 scFv

<400> SEQUENCE: 425

```
Gln Ala Val Leu Thr Gln Pro Ser Ser Ala Ser Gly Ala Pro Gly Gln
1               5                   10                  15

Arg Val Thr Ile Ser Cys Thr Gly Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
        115                 120                 125

Ser Leu Glu Met Ala Gln Val Gln Leu Val Gln Ser Gly Ala Glu Val
    130                 135                 140

Lys Lys Pro Gly Ser Ser Val Lys Val Ser Cys Lys Ala Ser Gly Gly
145                 150                 155                 160

Ala Phe Ser Ser Tyr Ala Ile Ser Trp Val Arg Gln Ala Pro Gly Gln
                165                 170                 175

Gly Leu Glu Trp Met Gly Gly Ile Ile Pro Ile Phe Gly Thr Ala Asn
            180                 185                 190

Tyr Ala Gln Lys Phe Gln Gly Arg Val Thr Ile Thr Ala Asp Glu Ser
        195                 200                 205

Thr Ser Thr Ala Tyr Met Glu Leu Ser Ser Leu Arg Ser Glu Asp Thr
    210                 215                 220

Ala Val Tyr Tyr Cys Ala Arg Met Leu Tyr Leu Ser Gly Arg Tyr Tyr
225                 230                 235                 240

Trp Asp Ser Trp Gly Gln Gly Thr Leu Val Thr Val Ser Ser
                245                 250
```

<210> SEQ ID NO 426
<211> LENGTH: 249
<212> TYPE: PRT
<213> ORGANISM: Artificial Sequence
<220> FEATURE:
<223> OTHER INFORMATION: GPC3A-052 scFv

<400> SEQUENCE: 426

Gln Ala Val Leu Thr Gln Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Ser Gly Thr Ala Pro Lys Leu Leu
            35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly Ser
            100                 105                 110

Arg Gly Gly Gly Gly Ser Gly Gly Gly Ser Gly Gly Gly Gly Ser
            115                 120                 125

Leu Glu Met Ala Glu Val Gln Leu Val Glu Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Gly Tyr Tyr Met His Trp Val Arg Gln Ala Pro Gly Gln Gly
            165                 170                 175

Leu Glu Trp Met Gly Trp Ile Asn Pro Asn Ser Gly Gly Thr Asn Tyr
            180                 185                 190

Ala Gln Lys Phe Gln Gly Arg Val Thr Met Thr Arg Asp Thr Ser Ile
            195                 200                 205

Ser Thr Ala Tyr Met Glu Leu Ser Arg Leu Arg Ser Asp Asp Thr Ala
    210                 215                 220

Val Tyr Tyr Cys Ala Arg Ser His Ser Ser Gly Tyr Asp Lys Trp Gly
225                 230                 235                 240

Gln Gly Thr Leu Val Thr Val Ser Ser
            245

<210> SEQ ID NO 427
<211> LENGTH: 251
<212> TYPE: PRT
<213> ORGANISM: Artificial Sequence
<220> FEATURE:
<223> OTHER INFORMATION: GPC3A-053 scFv

<400> SEQUENCE: 427

Gln Ser Val Leu Thr Gln Pro Ser Ala Ser Ala Ala Pro Gly Gln
1               5                   10                  15

Arg Val Thr Ile Ser Cys Ser Gly Thr Ser Ser Asn Ile Gly Ser Asn
            20                  25                  30

Tyr Val Trp Trp Tyr Gln Gln Leu Pro Gly Ala Ala Pro Arg Leu Leu
            35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Ser Ser Leu
                85                  90                  95

Ser Gly Ser Asn Val Phe Gly Thr Gly Thr Lys Val Thr Val Leu Gly
            100                 105                 110

Ser Arg Gly Gly Gly Ser Gly Gly Gly Ser Gly Gly Gly
            115                 120                 125

Ser Leu Glu Met Ala Gln Leu Gln Leu Gln Glu Ser Gly Pro Gly Leu
        130                 135                 140

Val Lys Pro Ser Glu Thr Leu Ser Leu Thr Cys Thr Val Ser Gly Gly
145                 150                 155                 160

Ser Ile Ser Ser Ser Tyr Tyr Trp Gly Trp Ile Arg Gln Pro Pro
                165                 170                 175

Gly Lys Gly Leu Glu Trp Ile Gly Ser Ile Tyr Tyr Ser Gly Ser Thr
        180                 185                 190

Tyr Tyr Asn Pro Ser Leu Lys Ser Arg Val Thr Ile Ser Val Asp Thr
        195                 200                 205

Ser Lys Asn Gln Phe Ser Leu Lys Leu Ser Ser Val Thr Ala Ala Asp
        210                 215                 220

Thr Ala Val Tyr Tyr Cys Ala Arg Trp Trp Ser Gly Ser Tyr Asp Thr
225                 230                 235                 240

Trp Gly Gln Gly Thr Leu Val Thr Val Ser Ser
                245                 250

<210> SEQ ID NO 428
<211> LENGTH: 251
<212> TYPE: PRT
<213> ORGANISM: Artificial Sequence
<220> FEATURE:
<223> OTHER INFORMATION: GPC3A-054 scFv

<400> SEQUENCE: 428

Ser Tyr Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Met Gln Leu Val Gln Ser Gly Ala Glu Val Lys
        130                 135                 140

Lys Pro Gly Ala Ser Val Lys Val Ser Cys Lys Ala Ser Gly Tyr Thr
145                 150                 155                 160

Phe Thr Ser Tyr Gly Ile Ser Trp Val Arg Gln Ala Pro Gly Gln Gly
                165                 170                 175

Leu Glu Trp Met Gly Trp Ile Ser Ala Tyr Asn Gly Asn Thr Asn Tyr
        180                 185                 190

Ala Gln Lys Leu Gln Gly Arg Val Thr Met Thr Thr Asp Thr Ser Thr
        195                 200                 205

Ser Thr Ala Tyr Met Glu Leu Arg Ser Leu Arg Ser Asp Asp Thr Ala
        210                 215                 220

```
Val Tyr Tyr Cys Ala Arg Ile Pro Met Tyr Ser Ser Asp Tyr
225                 230                 235                 240

Trp Gly Gln Gly Thr Leu Val Thr Val Ser Ser
                245                 250

<210> SEQ ID NO 429
<211> LENGTH: 247
<212> TYPE: PRT
<213> ORGANISM: Artificial Sequence
<220> FEATURE:
<223> OTHER INFORMATION: GPC3A-055 scFv

<400> SEQUENCE: 429

Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly Ser Arg Gly
            100                 105                 110

Gly Gly Gly Ser Gly Gly Gly Gly Ser Gly Gly Gly Ser Leu Glu
        115                 120                 125

Met Ala Gln Val Gln Leu Val Gln Ser Gly Ala Glu Val Lys Lys Pro
    130                 135                 140

Gly Ala Ser Val Lys Val Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
                165                 170                 175

Trp Met Gly Ile Ile Asn Pro Ser Gly Gly Ser Thr Ser Tyr Ala Gln
            180                 185                 190

Lys Phe Gln Gly Arg Val Thr Met Thr Arg Asp Thr Ser Thr Ser Thr
        195                 200                 205

Val Tyr Met Glu Leu Ser Ser Leu Arg Ser Glu Asp Thr Ala Val Tyr
    210                 215                 220

Tyr Cys Ala Arg Trp His Gly Gly Pro Tyr Asp Tyr Trp Gly Gln Gly
225                 230                 235                 240

Thr Leu Val Thr Val Ser Ser
                245

<210> SEQ ID NO 430
<211> LENGTH: 251
<212> TYPE: PRT
<213> ORGANISM: Artificial Sequence
<220> FEATURE:
<223> OTHER INFORMATION: GPC3A-056 scFv

<400> SEQUENCE: 430

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
```

```
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Tyr Ser Thr Pro Ile
                85                  90                  95
Thr Phe Gly Gln Gly Thr Arg Leu Glu Ile Lys Arg Ser Arg Gly Gly
            100                 105                 110
Gly Gly Ser Gly Gly Gly Ser Gly Gly Gly Ser Leu Glu Met
        115                 120                 125
Ala Gln Val Gln Leu Gln Ser Gly Ala Glu Val Lys Lys Phe Gly
        130                 135                 140
Ala Ser Val Lys Val Ser Cys Lys Ala Ser Gly Tyr Ser Phe Asn Asp
145                 150                 155                 160
Tyr Tyr Ile His Trp Val Arg Gln Ala Pro Gly Gln Gly Leu Glu Trp
                165                 170                 175
Met Gly Trp Ile Asn Pro Asn Asn Gly Asp Thr Lys Tyr Glu Lys Lys
            180                 185                 190
Trp Gln Gly Arg Val Thr Met Thr Arg Asp Thr Ser Ile Thr Thr Ala
        195                 200                 205
Tyr Met Glu Leu Ser Ser Leu Arg Ser Asp Asp Thr Ala Val Tyr Tyr
    210                 215                 220
Cys Ala Arg Phe Ser Thr His Asn Trp Trp Pro Thr Tyr Asp Tyr
225                 230                 235                 240
Trp Gly Gln Gly Thr Leu Val Thr Val Ser Ser
                245                 250

<210> SEQ ID NO 431
<211> LENGTH: 250
<212> TYPE: PRT
<213> ORGANISM: Artificial Sequence
<220> FEATURE:
<223> OTHER INFORMATION: GPC3A-057 scFv

<400> SEQUENCE: 431

Glu Ile Val Leu Thr Gln Ser Pro Ser Val Ser Val Ala Pro Gly Lys
1               5                   10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Ile Tyr
        35                  40                  45
Tyr Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Ser Asp His
                85                  90                  95
Val Val Phe Gly Gly Gly Thr Lys Val Glu Ile Lys Arg Ser Arg Gly
            100                 105                 110
Gly Gly Gly Ser Gly Gly Gly Gly Ser Gly Gly Gly Ser Leu Glu
        115                 120                 125
Met Ala Glu Val Gln Leu Val Glu Ser Gly Gly Gly Leu Ile Gln Pro
```

```
            130                 135                 140
Gly Gly Ser Leu Arg Leu Ser Cys Ala Ala Ser Gly Phe Thr Phe Ser
145                 150                 155                 160

Ser Tyr Ala Met Ser Trp Val Arg Gln Ala Pro Gly Lys Gly Leu Glu
                165                 170                 175

Trp Val Ser Ala Ile Ser Gly Ser Gly Gly Ser Thr Tyr Tyr Ala Asp
                180                 185                 190

Ser Val Lys Gly Arg Phe Thr Ile Ser Arg Asp Asn Ser Lys Asn Thr
                195                 200                 205

Leu Tyr Leu Gln Met Asn Ser Leu Arg Ala Glu Asp Thr Ala Val Tyr
            210                 215                 220

Tyr Cys Ala Arg Tyr Asn Tyr Met Ser Gly Phe Tyr Asp Arg Trp
225                 230                 235                 240

Gly Gln Gly Thr Leu Val Thr Val Ser Ser
                245                 250

<210> SEQ ID NO 432
<211> LENGTH: 249
<212> TYPE: PRT
<213> ORGANISM: Artificial Sequence
<220> FEATURE:
<223> OTHER INFORMATION: GPC3A-058 scFv

<400> SEQUENCE: 432

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
                35                  40                  45

Asp Asp Ser Asp Arg Pro Ser Gly Ile Pro Glu Arg Phe Ser Gly Ser
            50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Phe Gly Thr Gly Thr Lys Val Thr Val Leu Gly Ser Arg Gly Gly
                100                 105                 110

Gly Gly Ser Gly Gly Gly Gly Ser Gly Gly Gly Gly Ser Leu Glu Met
            115                 120                 125

Ala Gln Val Gln Leu Val Gln Ser Gly Ala Asp Val Arg Lys Pro Gly
            130                 135                 140

Ala Ser Val Lys Val Ser Cys Lys Ala Ser Gly Tyr Thr Phe Ala Ser
145                 150                 155                 160

His Gly Ile Ser Trp Val Arg Gln Ala Pro Gly Gln Gly Leu Glu Trp
                165                 170                 175

Leu Gly Trp Ile Ser Pro Tyr Thr Gly Asn Thr Asn Tyr Ala Gln Lys
                180                 185                 190

Phe Gln Gly Arg Val Thr Met Ala Thr Asp Thr Ser Thr Ser Thr Ala
                195                 200                 205

Tyr Met Glu Leu Arg Ser Leu Arg Ser Asp Asp Thr Ala Ile Tyr Tyr
            210                 215                 220

Cys Ala Arg Gly Lys Arg Thr Leu Ala Ser Cys Phe Asp Tyr Trp Gly
225                 230                 235                 240

Gln Gly Thr Leu Val Thr Val Ser Ser
```

-continued

245

<210> SEQ ID NO 433
<211> LENGTH: 246
<212> TYPE: PRT
<213> ORGANISM: Artificial Sequence
<220> FEATURE:
<223> OTHER INFORMATION: GPC3A-059 scFv

<400> SEQUENCE: 433

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

Tyr Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Phe Gly Thr Gly Thr Lys Val Thr Val Leu Gly Ser Arg Gly Gly
            100                 105                 110

Gly Gly Ser Gly Gly Gly Gly Ser Gly Gly Gly Gly Ser Leu Glu Met
        115                 120                 125

Ala Gln Val Gln Leu Val Gln Ser Gly Ala Glu Val Lys Lys Pro Gly
    130                 135                 140

Ala Ser Val Thr Val Ser Cys Lys Ala Ser Gly Tyr Thr Phe Thr Arg
145                 150                 155                 160

Tyr Gly Ile Thr Trp Val Arg Gln Ala Pro Gly Gln Gly Leu Glu Trp
                165                 170                 175

Met Gly Trp Ile Ser Ala Tyr Ser Asp Lys Thr Asn Tyr Ala Gln Lys
            180                 185                 190

Leu Gln Gly Arg Val Thr Met Thr Thr Asp Ile Ser Thr Asn Thr Ala
        195                 200                 205

Tyr Met Glu Leu Ser Ser Leu Arg Ser Glu Asp Thr Ala Val Tyr Tyr
    210                 215                 220

Cys Ala Arg Ser Arg Trp Ser Tyr Met Asp Val Trp Gly Gln Gly Thr
225                 230                 235                 240

Leu Val Thr Val Ser Ser
                245

<210> SEQ ID NO 434
<211> LENGTH: 247
<212> TYPE: PRT
<213> ORGANISM: Artificial Sequence
<220> FEATURE:
<223> OTHER INFORMATION: GPC3A-060 scFv

<400> SEQUENCE: 434

Ser Tyr Val Leu Thr Gln Pro Pro Ser Val Ser Val Ala Pro Gly Lys
1               5                   10                  15

Thr Ala Arg Leu Thr Cys Gly Gly Asn Asn Ile Gly Ser Glu Ser Val
            20                  25                  30

His Trp Tyr Gln Gln Lys Pro Gly Gln Ala Pro Leu Leu Val Val Tyr
        35                  40                  45

Asp Asp Asp Arg Pro Ser Gly Ile Pro Glu Arg Phe Ser Gly Ser
50              55                  60

Asn Ser Glu Asp Thr Ala Thr Leu Thr Ile Ser Gly Thr Gln Ala Leu
65                  70                  75                  80

Asp Glu Ala Glu Tyr Tyr Cys Gln Thr Trp Asp Ser Ser Thr Ala Ile
                85                  90                  95

Phe Gly Thr Gly Thr Lys Leu Thr Val Leu Gly Ser Arg Gly Gly Gly
            100                 105                 110

Gly Ser Gly Gly Gly Gly Ser Gly Gly Gly Gly Ser Leu Glu Met Ala
            115                 120                 125

Gln Val Gln Leu Val Gln Ser Gly Gly Glu Val Lys Lys Pro Gly Ala
130                 135                 140

Ser Val Lys Val Ser Cys Lys Ala Ser Gly Tyr Thr Phe Asn Ser Tyr
145                 150                 155                 160

Ala Ile Ser Trp Val Arg Gln Ala Pro Gly Gln Gly Leu Glu Trp Met
                165                 170                 175

Gly Trp Ile Ser Ala Tyr Asn Gly Asn Thr Asn Tyr Ala Gln Lys Leu
            180                 185                 190

Gln Gly Arg Val Thr Met Thr Thr Asp Thr Ser Thr Asn Thr Ala Phe
            195                 200                 205

Met Glu Leu Arg Ser Leu Arg Ser Asp Asp Thr Ala Val Tyr Tyr Cys
210                 215                 220

Ala Arg Glu Gly Tyr Gly Ser Trp Ala Met Asp Gln Trp Gly Gln Gly
225                 230                 235                 240

Thr Leu Val Thr Val Ser Ser
                245

<210> SEQ ID NO 435
<211> LENGTH: 247
<212> TYPE: PRT
<213> ORGANISM: Artificial Sequence
<220> FEATURE:
<223> OTHER INFORMATION: GPC3A-061 scFv

<400> SEQUENCE: 435

Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
50              55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly Ser Arg Gly
            100                 105                 110

Gly Gly Gly Ser Gly Gly Gly Gly Ser Gly Gly Gly Gly Ser Leu Glu
            115                 120                 125

Met Ala Gln Val Gln Leu Val Gln Ser Gly Ala Glu Val Lys Lys Pro
130                 135                 140

Gly Ala Ser Val Lys Val Ser Cys Lys Ala Ser Gly Tyr Thr Phe Thr
145                 150                 155                 160

Ser Tyr Gly Ile Ser Trp Val Arg Gln Thr Pro Gly Gln Gly Leu Glu
            165                 170                 175

Trp Met Gly Trp Ile Ser Ala Tyr Asn Gly Asn Thr Asn Tyr Ala Gln
            180                 185                 190

Lys Leu Gln Gly Arg Val Thr Met Thr Thr Asp Thr Ser Thr Ser Thr
            195                 200                 205

Ala Tyr Met Glu Leu Ser Ser Leu Arg Ser Glu Asp Thr Ala Val Tyr
            210                 215                 220

Tyr Cys Ala Arg Lys Gly Ser Ser Gln Phe Asp Gln Trp Gly Gln Gly
225                 230                 235                 240

Thr Leu Val Thr Val Ser Ser
            245

<210> SEQ ID NO 436
<211> LENGTH: 257
<212> TYPE: PRT
<213> ORGANISM: Artificial Sequence
<220> FEATURE:
<223> OTHER INFORMATION: GPC3A-062 scFv

<400> SEQUENCE: 436

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Trp Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Arg Ala Glu Asp Glu Ala Asp Tyr Tyr Cys Gln Ser Tyr Asp Ser Ser
            85                  90                  95

Leu Ser Gly Ser Tyr Val Phe Gly Thr Gly Thr Lys Val Thr Val Leu
            100                 105                 110

Gly Ser Arg Gly Gly Gly Gly Ser Gly Gly Gly Ser Gly Gly Gly
            115                 120                 125

Gly Ser Leu Glu Met Ala Gln Met Gln Leu Val Gln Ser Gly Ser Glu
130                 135                 140

Leu Lys Lys Pro Gly Ala Ser Val Lys Val Ser Cys Lys Ala Ser Gly
145                 150                 155                 160

Gly Thr Phe Ser Ser Tyr Ala Ile Ser Trp Val Arg Gln Ala Pro Gly
            165                 170                 175

Gln Gly Leu Glu Trp Met Gly Gly Ile Ile Pro Lys Ile Gly Thr Ala
            180                 185                 190

Asn Tyr Ala Gln Lys Phe Gln Gly Arg Val Thr Ile Thr Ala Asp Glu
            195                 200                 205

Ser Thr Ser Thr Ala Tyr Met Glu Leu Ser Ser Leu Arg Ser Glu Asp
            210                 215                 220

Thr Ala Met Tyr Tyr Cys Ala Arg Met Tyr Met Asp Met Gly Trp Gly
225                 230                 235                 240

Trp Gly Tyr Trp Asp Trp Trp Gly Gln Gly Thr Leu Val Thr Val Ser
            245                 250                 255

Ser

<210> SEQ ID NO 437
<211> LENGTH: 251
<212> TYPE: PRT
<213> ORGANISM: Artificial Sequence
<220> FEATURE:
<223> OTHER INFORMATION: GPC3A-063 scFv

<400> SEQUENCE: 437

```
Gln Thr Val Val Thr Gln Pro Pro Ser Ala Ser Gly Thr Pro Gly Gln
1               5                   10                  15

Arg Val Thr Ile Ser Cys Ser Gly Ser Trp Ser Asn Ile Gly Ser Tyr
            20                  25                  30

Thr Val Asn Trp Tyr Gln His Leu Pro Gly Thr Ala Pro Lys Leu Leu
        35                  40                  45

Ile Ser Gly Asn Asn Gln Arg Pro Ser Gly Val Pro Gly Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr His Cys Ala Ala Trp Asp Asp Asn Leu
                85                  90                  95

Asn Gly Val Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
                165                 170                 175

Leu Glu Trp Met Gly Ile Ile Asn Pro Ser Gly Gly Ser Ala Ser Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Ser Leu Arg Ser Glu Asp Thr Ala
    210                 215                 220

Val Tyr Tyr Cys Ala Arg Asp Arg Leu Ala Ser Asp Ala Phe Asp Ile
225                 230                 235                 240

Trp Gly Gln Gly Thr Met Val Thr Val Ser Ser
                245                 250
```

<210> SEQ ID NO 438
<211> LENGTH: 250
<212> TYPE: PRT
<213> ORGANISM: Artificial Sequence
<220> FEATURE:
<223> OTHER INFORMATION: GPC3A-064 scFv

<400> SEQUENCE: 438

```
Leu Pro Val Leu Thr Gln Pro Pro Ser Leu Ser Val Ala Pro Gly Lys
1               5                   10                  15

Thr Ala Arg Leu Thr Cys Gly Gly Asn Asn Ile Gly Ser Lys Ser Val
            20                  25                  30

His Trp Tyr His Gln Lys Pro Gly Gln Ala Pro Val Leu Val Val Tyr
        35                  40                  45

Asp Asp Thr Asp Arg Pro Ser Gly Ile Pro Glu Arg Phe Ser Gly Ser
    50                  55                  60
```

```
Asn Ser Gly Asn Thr Ala Ala Leu Thr Ile Ser Arg Val Glu Val Gly
 65                  70                  75                  80

Asp Glu Ala Asp Tyr Tyr Cys Gln Val Trp Asp Arg Ser Ser Ala His
                 85                  90                  95

Trp Val Phe Gly Gly Gly Thr Lys Leu Thr Val Leu Gly Ser Arg Gly
            100                 105                 110

Gly Gly Gly Ser Gly Gly Gly Ser Gly Gly Gly Ser Leu Glu
        115                 120                 125

Met Ala Gln Met Gln Leu Val Gln Ser Gly Ala Glu Val Lys Lys Pro
130                 135                 140

Gly Ala Ser Val Lys Val Ser Cys Lys Ala Ser Gly Tyr Thr Phe Thr
145                 150                 155                 160

Ile Tyr Gly Ile Ser Trp Val Arg Gln Ala Pro Gly Gln Gly Leu Glu
                165                 170                 175

Trp Met Gly Trp Ile Ser Pro Tyr Asn Asp Asn Thr Ile Tyr Ala Gln
            180                 185                 190

Lys Val Gln Gly Arg Val Thr Met Thr Thr Asp Thr Ser Thr Ser Thr
        195                 200                 205

Ala Tyr Met Glu Leu Arg Ser Leu Arg Ser Asp Asp Thr Ala Val Tyr
210                 215                 220

Tyr Cys Ala Arg Met Gly Val Gly Trp Gly Tyr Ala Gln Asp Ser Trp
225                 230                 235                 240

Gly Gln Gly Thr Leu Val Thr Val Ser Ser
                245                 250

<210> SEQ ID NO 439
<211> LENGTH: 246
<212> TYPE: PRT
<213> ORGANISM: Artificial Sequence
<220> FEATURE:
<223> OTHER INFORMATION: GPC3A-067 scFv

<400> SEQUENCE: 439

Gln Ser Val Leu Thr Gln Pro Pro Ser Val Ser Val Ala Pro Gly Lys
  1               5                  10                  15

Thr Ala Arg Ile Thr Cys Gly Gly Asn Asn Ile Gly Ser Lys Ser Val
                 20                  25                  30

His Trp Tyr Gln Gln Lys Pro Gly Gln Ala Pro Val Leu Val Ile Tyr
             35                  40                  45

Tyr Asp Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu Gly Ser Arg Gly
            100                 105                 110

Gly Gly Gly Ser Gly Gly Gly Ser Gly Gly Gly Ser Leu Glu
        115                 120                 125

Met Ala Glu Val Gln Leu Val Gln Ser Gly Ala Glu Val Lys Lys Pro
130                 135                 140

Gly Ser Ser Val Lys Val Ser Cys Lys Ala Ser Gly Gly Thr Phe Ser
145                 150                 155                 160

Ser Tyr Ala Ile Ser Trp Val Arg Gln Ala Pro Gly Gln Gly Leu Glu
                165                 170                 175
```

```
Trp Met Gly Arg Ile Ile Pro Ile Phe Gly Ile Thr Asn Tyr Ala Gln
            180                 185                 190

Lys Phe Gln Gly Arg Val Thr Ile Thr Ala Asp Lys Ser Thr Ser Thr
        195                 200                 205

Ala Tyr Met Glu Leu Ser Ser Leu Arg Ser Glu Asp Thr Ala Val Tyr
    210                 215                 220

Tyr Cys Ala Arg Gly Ala Glu Met Ser Asp Tyr Trp Gly Gln Gly Thr
225                 230                 235                 240

Leu Val Thr Val Ser Ser
                245
```

<210> SEQ ID NO 440
<211> LENGTH: 252
<212> TYPE: PRT
<213> ORGANISM: Artificial Sequence
<220> FEATURE:
<223> OTHER INFORMATION: GPC3B-54 scFv

<400> SEQUENCE: 440

```
Gln Ser Val Leu Thr Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asp
            20                  25                  30

Thr Val Asn Trp Tyr Gln Gln Leu Pro Gly Thr Ala Pro Lys Leu Leu
        35                  40                  45

Ile Tyr Arg Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Thr Thr Trp Asp Asp Ser Leu
                85                  90                  95

Asn Gly Leu Val Phe Gly Gly Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Ala Ser Val Lys Leu Ser Cys Lys Thr Ser Gly Tyr Thr
145                 150                 155                 160

Phe Ile Asp Tyr Tyr Val Tyr Trp Val Arg Gln Ala Pro Gly Gln Gly
                165                 170                 175

Leu Glu Trp Met Gly Gly Ile Ile Pro Ile Phe Gly Thr Ala Asn Tyr
            180                 185                 190

Ala Gln Lys Phe Gln Gly Arg Val Thr Ile Thr Ala Asp Lys Ser Thr
        195                 200                 205

Ser Thr Ala Tyr Met Glu Leu Ser Ser Leu Gly Ser Glu Asp Thr Ala
    210                 215                 220

Val Tyr Tyr Cys Ala Arg Glu Arg Arg Tyr Ser Ser Pro Ser Asp
225                 230                 235                 240

His Trp Gly Gln Gly Thr Leu Val Thr Val Ser Ser
                245                 250
```

<210> SEQ ID NO 441
<211> LENGTH: 249
<212> TYPE: PRT
<213> ORGANISM: Artificial Sequence
<220> FEATURE:

<223> OTHER INFORMATION: GPC3B-60 scFv

<400> SEQUENCE: 441

```
Ser Tyr Val Leu Thr Gln Pro Pro Ser Val Ser Val Ser Pro Gly Gln
1               5                   10                  15

Thr Ala Thr Ile Ala Cys Ser Gly Asp Asn Leu Glu Asn Lys Phe Val
            20                  25                  30

Tyr Trp Tyr His Gln Lys Pro Gly Gln Ser Pro Val Leu Val Met Tyr
        35                  40                  45

Glu Asp Asn Lys Arg Pro Ser Gly Ile Pro Glu Arg Phe Ser Gly Ser
    50                  55                  60

Asn Ser Gly Asn Thr Ala Ala Leu Thr Ile Ser Gly Ala Gln Pro Met
65                  70                  75                  80

Asp Glu Ala Asp Tyr Tyr Cys Gln Thr Trp Asp Ser Pro Thr Gly Leu
                85                  90                  95

Phe Val Phe Gly Thr Gly Thr Lys Val Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Glu Val Gln Leu Val Glu Ser Gly Ala Glu Val Lys Lys Pro
    130                 135                 140

Gly Ala Ser Val Lys Val Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
                165                 170                 175

Trp Met Gly Ile Ile Asn Pro Ser Gly Gly Ser Thr Ser Tyr Ala Gln
            180                 185                 190

Lys Phe Gln Gly Arg Val Thr Met Thr Arg Asp Thr Ser Thr Ser Thr
        195                 200                 205

Val Tyr Met Glu Leu Ser Ser Leu Arg Ser Glu Asp Thr Ala Val Tyr
    210                 215                 220

Tyr Cys Ala Arg Ser Leu Tyr Ser Gln Pro Tyr Ile Asp Gly Trp Ser
225                 230                 235                 240

Gln Gly Thr Leu Val Thr Val Ser Ser
                245
```

<210> SEQ ID NO 442
<211> LENGTH: 256
<212> TYPE: PRT
<213> ORGANISM: Artificial Sequence
<220> FEATURE:
<223> OTHER INFORMATION: GPC3B-63 scFv

<400> SEQUENCE: 442

```
Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95
```

Leu Gln Thr Pro Pro Thr Phe Gly Gln Gly Thr Lys Val Glu Ile Lys
            100                 105                 110

Arg Ser Arg Gly Gly Gly Ser Gly Gly Gly Ser Gly Gly Gly
            115                 120                 125

Gly Ser Leu Glu Met Ala Gln Val Gln Leu Val Gln Ser Gly Ala Glu
            130                 135                 140

Val Lys Lys Pro Gly Ala Ser Val Lys Val Ser Cys Lys Ala Ser Gly
145                 150                 155                 160

Tyr Thr Phe Thr Ser Tyr Tyr Met His Trp Val Arg Gln Ala Pro Gly
                165                 170                 175

Gln Gly Leu Glu Trp Met Gly Ile Ile Asn Pro Ser Gly Gly Ser Thr
            180                 185                 190

Ser Tyr Ala Gln Lys Phe Gln Gly Arg Val Thr Met Thr Arg Asp Thr
            195                 200                 205

Ser Thr Ser Thr Val Tyr Met Glu Leu Ser Ser Leu Arg Ser Glu Asp
            210                 215                 220

Thr Ala Val Tyr Tyr Cys Ala Arg Ser Leu His Ala Met Arg Trp Ser
225                 230                 235                 240

Gln Thr Met Asp Ser Trp Gly Gln Gly Thr Leu Val Thr Val Ser Ser
                245                 250                 255

<210> SEQ ID NO 443
<211> LENGTH: 249
<212> TYPE: PRT
<213> ORGANISM: Artificial Sequence
<220> FEATURE:
<223> OTHER INFORMATION: GPC3B-66 scFv

<400> SEQUENCE: 443

Gln Ala Val Leu Thr Gln Pro Pro Ser Val Ser Val Ala Pro Gly Lys
1               5                   10                  15

Thr Ala Ser Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Leu Tyr Val Phe Gly Thr Gly Thr Lys Val Thr Val Leu Gly Ser Arg
            100                 105                 110

Gly Gly Gly Gly Ser Gly Gly Gly Ser Gly Gly Gly Ser Leu
            115                 120                 125

Glu Met Ala Gln Val Gln Leu Val Gln Ser Gly Ala Glu Val Lys Arg
            130                 135                 140

Pro Gly Ala Ser Val Lys Val Ser Cys Lys Ala Ser Gly Tyr Thr Phe
145                 150                 155                 160

Ile Gly Gln Tyr Leu His Trp Val Arg Gln Ala Pro Gly Gln Gly Leu
                165                 170                 175

Glu Trp Met Gly Arg Ile Asn Pro Met Thr Gly Val Thr Asn Tyr Ala
            180                 185                 190

Pro Lys Phe Gln Gly Arg Val Thr Met Thr Arg Asp Thr Ser Ile Ser
            195                 200                 205

```
Thr Gly Tyr Met Glu Ile Ser Arg Leu Arg Ser Asp Asp Thr Ala Val
    210                 215                 220

Tyr Tyr Cys Ala Arg Phe Ser Ser Gly Tyr Ser Arg Asp Thr Trp Gly
225                 230                 235                 240

Gln Gly Thr Leu Val Thr Val Ser Ser
                245

<210> SEQ ID NO 444
<211> LENGTH: 249
<212> TYPE: PRT
<213> ORGANISM: Artificial Sequence
<220> FEATURE:
<223> OTHER INFORMATION: GPC3B-68 scFv

<400> SEQUENCE: 444

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Ile Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu Gly Ser
            100                 105                 110

Arg Gly Gly Gly Ser Gly Gly Gly Ser Gly Gly Gly Ser
        115                 120                 125

Leu Glu Met Ala Gln Val Gln Leu Val Gln Ser Gly Ala Glu Val Lys
    130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Arg Ile Ile Pro Ile Leu Gly Ile Ala Asn Tyr
            180                 185                 190

Ala Gln Lys Phe Gln Gly Arg Val Thr Ile Thr Ala Asp Lys Ser Thr
        195                 200                 205

Ser Thr Ala Tyr Met Glu Leu Ser Ser Leu Arg Ser Glu Asp Thr Ala
    210                 215                 220

Val Tyr Tyr Cys Ala Arg Tyr Gly Tyr Glu Gly His Asp Thr Trp Gly
225                 230                 235                 240

Gln Gly Thr Leu Val Thr Val Ser Ser
                245

<210> SEQ ID NO 445
<211> LENGTH: 250
<212> TYPE: PRT
<213> ORGANISM: Artificial Sequence
<220> FEATURE:
<223> OTHER INFORMATION: GPC3B-71 scFv

<400> SEQUENCE: 445

Ser Tyr Val Leu Thr Gln Pro Pro Ser Val Ser Val Ala Pro Gly Lys
```

```
             1               5                  10                 15
            Thr Ala Arg Val Thr Cys Gly Gly Asn Asn Ile Gly Ser Lys Ser Val
                            20                 25                 30
            His Trp Tyr Gln Gln Lys Pro Gly Gln Ala Pro Val Leu Val Met Tyr
                            35                 40                 45
            Tyr Asp Ser Asp Arg Pro Ser Gly Ile Pro Glu Arg Phe Ser Gly Ser
                            50                 55                 60
            Asn Ser Gly Asn Thr Ala Thr Leu Thr Ile Ser Ser Val Glu Ala Gly
            65                             70                 75                 80
            Asp Glu Ala Asp Tyr Tyr Cys Gln Val Trp Asp Ser Ser Ser Asp His
                                85                 90                 95
            Tyr Val Phe Gly Thr Gly Thr Lys Val Thr Val Leu Gly Ser Arg Gly
                            100                105                110
            Gly Gly Gly Ser Gly Gly Gly Ser Gly Gly Gly Gly Ser Leu Glu
                            115                120                125
            Met Ala Glu Val Gln Leu Val Glu Ser Gly Gly Leu Val Lys Pro
            130                            135                140
            Gly Gly Ser Leu Arg Leu Ser Cys Ala Ala Ser Gly Phe Thr Phe Ser
            145                            150                155                160
            Arg Tyr Thr Met Asn Trp Val Arg Gln Ala Pro Gly Lys Gly Leu Glu
                            165                170                175
            Trp Val Ser Ser Ile Ser Ser Ser Gly Ser Tyr Ile Tyr Tyr Ala Asp
                            180                185                190
            Ser Val Lys Gly Arg Phe Thr Ile Ser Arg Asp Asn Ala Lys Asn Ser
                            195                200                205
            Leu Phe Leu Gln Met Asp Ser Leu Arg Ala Glu Asp Thr Ala Val Tyr
                            210                215                220
            Tyr Cys Ala Arg Gln Gly His Met Trp Tyr Val Pro Val Asp Ala Trp
            225                            230                235                240
            Gly Gln Gly Thr Leu Val Thr Val Ser Ser
                            245                250

<210> SEQ ID NO 446
<211> LENGTH: 244
<212> TYPE: PRT
<213> ORGANISM: Artificial Sequence
<220> FEATURE:
<223> OTHER INFORMATION: GPC3B-76 scFv

<400> SEQUENCE: 446

Gln Ser Val Val Thr Gln Pro Pro Ser Val Ser Ala Ala Pro Gly Gln
1               5                  10                 15

Lys Val Thr Ile Ser Cys Ser Gly Ser Ser Ser Asn Ile Gly Asn Asn
                20                 25                 30

Tyr Val Ser Trp Tyr Gln Gln Leu Pro Gly Thr Ala Pro Lys Leu Leu
                35                 40                 45

Ile Tyr Asp Asn Asn Lys Arg Pro Ser Gly Ile Pro Asp Arg Phe Ser
            50                 55                 60

Gly Ser Lys Ser Gly Thr Ser Ala Thr Leu Gly Ile Thr Gly Leu Gln
65                             70                 75                 80

Thr Gly Asp Glu Ala Ala Tyr Tyr Cys Gly Thr Trp Asp Ser Ser Leu
                            85                 90                 95

Ser Ala Gly Val Phe Gly Thr Gly Thr Lys Val Thr Val Leu Gly Ser
                100                105                110

Arg Gly Gly Gly Gly Ser Gly Gly Gly Gly Ser Gly Gly Gly Gly Ser
```

```
                115                 120                 125
Leu Glu Met Ala Gln Met Gln Leu Val Gln Ser Gly Ala Glu Val Lys
    130                 135                 140

Glu Pro Gly Ala Ser Val Lys Val Ser Cys Lys Ala Ser Gly Tyr Thr
145                 150                 155                 160

Phe Thr Asp Tyr Tyr Ile His Trp Val Arg Gln Ala Pro Gly Gln Gly
                165                 170                 175

Leu Glu Trp Met Gly Trp Ile Asn Pro Asn Ser Gly Gly Thr Asn Tyr
            180                 185                 190

Ala Gln Lys Phe Gln Gly Arg Val Thr Met Thr Arg Asp Thr Ser Ile
        195                 200                 205

Ser Thr Ala Tyr Met Glu Leu Ser Arg Leu Arg Ser Asp Asp Thr Ala
    210                 215                 220

Val Tyr Tyr Cys Ala Arg Asn Tyr Asp Trp Gly Gln Gly Thr Leu Val
225                 230                 235                 240

Thr Val Ser Ser

<210> SEQ ID NO 447
<211> LENGTH: 245
<212> TYPE: PRT
<213> ORGANISM: Artificial Sequence
<220> FEATURE:
<223> OTHER INFORMATION: GPC3B-78 scFv

<400> SEQUENCE: 447

Leu Pro Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Ala Ala Asp Tyr Tyr Cys Gln Thr Trp Asp Arg Ser Thr Tyr Val
                85                  90                  95

Phe Gly Thr Gly Thr Lys Val Thr Val Leu Gly Ser Arg Gly Gly Gly
            100                 105                 110

Gly Ser Gly Gly Gly Ser Gly Gly Gly Gly Ser Leu Glu Met Ala
        115                 120                 125

Gln Met Gln Leu Val Gln Ser Gly Ala Glu Val Lys Lys Pro Gly Ala
    130                 135                 140

Ser Val Lys Val Ser Cys Lys Ala Ser Gly Tyr Thr Phe Thr Ser Tyr
145                 150                 155                 160

Tyr Met His Trp Val Arg Gln Ala Pro Gly Gln Gly Leu Glu Trp Met
                165                 170                 175

Gly Ile Ile Asn Pro Ser Gly Gly Ser Thr Ser Tyr Ala Gln Lys Phe
            180                 185                 190

Gln Gly Arg Val Thr Met Thr Arg Asp Thr Ser Thr Ser Thr Val Tyr
        195                 200                 205

Met Glu Leu Ser Ser Leu Arg Ser Glu Asp Thr Ala Val Tyr Tyr Cys
    210                 215                 220

Ala Arg Gly Tyr Ser Ser Phe Phe Asp Ser Trp Gly Gln Gly Thr Leu
225                 230                 235                 240
```

<210> SEQ ID NO 448
<211> LENGTH: 255
<212> TYPE: PRT
<213> ORGANISM: Artificial Sequence
<220> FEATURE:
<223> OTHER INFORMATION: GPC3B-80 scFv

<400> SEQUENCE: 448

```
Gln Ala Val Leu Thr Gln Pro Pro Ser Ala Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Tyr Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Trp Gly Val Phe Gly Gly Gly Thr Lys Leu Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Gln Val Gln Leu Val Gln Ser Gly Ala Glu Val
    130                 135                 140

Lys Lys Pro Gly Ser Ser Val Lys Val Ser Cys Lys Ala Ser Gly Gly
145                 150                 155                 160

Thr Leu Ser Arg Phe Ala Ile Ser Trp Val Arg Gln Ala Pro Gly Gln
                165                 170                 175

Gly Leu Glu Trp Met Gly Gly Ile Ile Pro Ile Phe Arg Thr Ala Asn
            180                 185                 190

Tyr Ala Gln Lys Phe Gln Gly Arg Val Thr Ile Thr Ala Asp Glu Ser
        195                 200                 205

Thr Ser Thr Ala Tyr Met Glu Leu Ser Ser Leu Arg Ser Glu Asp Thr
    210                 215                 220

Ala Val Tyr Tyr Cys Ala Arg Met Ser Lys Tyr Tyr Gly Ser Tyr Ser
225                 230                 235                 240

Ser Tyr Asp Glu Trp Gly Gln Gly Thr Leu Val Thr Val Ser Ser
                245                 250                 255
```

<210> SEQ ID NO 449
<211> LENGTH: 245
<212> TYPE: PRT
<213> ORGANISM: Artificial Sequence
<220> FEATURE:
<223> OTHER INFORMATION: GPC3B-81 scFv

<400> SEQUENCE: 449

```
Ser Tyr Glu Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
```

```
            35                  40                  45
Tyr Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Asp Leu
                 85                  90                  95

Leu Tyr Val Phe Gly Thr Gly Thr Lys Val Thr Val Leu Gly Ser Arg
                100                 105                 110

Gly Gly Gly Gly Ser Gly Gly Gly Ser Gly Gly Gly Ser Leu
            115                 120                 125

Glu Met Ala Glu Val Gln Leu Val Gln Ser Gly Ala Glu Val Lys Lys
130                 135                 140

Pro Gly Ala Ser Val Lys Val Ser Cys Lys Ala Ser Gly Tyr Thr Phe
145                 150                 155                 160

Thr Gly Tyr Tyr Met His Trp Val Arg Gln Ala Pro Gly Gln Gly Leu
                165                 170                 175

Glu Trp Met Gly Arg Ile Asn Pro Asn Ser Gly Gly Thr Asn Tyr Ala
                180                 185                 190

Gln Lys Phe Gln Gly Arg Val Thr Met Thr Arg Asp Thr Ser Ile Ser
                195                 200                 205

Thr Ala Tyr Met Glu Leu Ser Arg Leu Arg Ser Asp Asp Thr Ala Val
210                 215                 220

Tyr Tyr Cys Ala Arg Gly Leu Trp Asp Ser Trp Gly Gln Gly Thr Leu
225                 230                 235                 240

Val Thr Val Ser Ser
                245

<210> SEQ ID NO 450
<211> LENGTH: 254
<212> TYPE: PRT
<213> ORGANISM: Artificial Sequence
<220> FEATURE:
<223> OTHER INFORMATION: GPC3B-82 scFv

<400> SEQUENCE: 450

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
             20                  25                  30

Phe Asp Val His Trp Tyr Gln Gln Leu Pro Gly Thr Ala Pro Lys Leu
         35                  40                  45

Leu Ile Tyr Asp Asn Asn Asn Arg Pro Ser Gly Val Pro Asp Arg Phe
 50                  55                  60

Ser Gly Ser Lys Ser Asp Thr Ser Ala Ser Leu Ala Ile Thr Gly Leu
 65                  70                  75                  80

Gln Ala Glu Asp Glu Ala Asp Tyr Tyr Cys Gln Ser Phe Asp Ser Ser
                 85                  90                  95

Leu Ser Gly Trp Val Phe Gly Gly Gly Thr Lys Leu Thr Val Leu Gly
                100                 105                 110

Ser Arg Gly Gly Gly Gly Ser Gly Gly Gly Gly Ser Gly Gly Gly Gly
            115                 120                 125

Ser Leu Glu Met Ala Glu Val Gln Leu Val Gln Ser Gly Ala Glu Val
130                 135                 140

Lys Lys Pro Gly Glu Ser Leu Lys Ile Ser Cys Lys Gly Ser Gly Tyr
```

```
145                 150                 155                 160
Ser Phe Thr Ser Tyr Tyr Met His Trp Val Arg Gln Ala Pro Gly Gln
                165                 170                 175

Gly Leu Glu Trp Met Gly Ile Ile Asn Pro Ser Gly Gly Ser Thr Ser
                180                 185                 190

Tyr Ala Gln Lys Phe Gln Gly Arg Val Thr Met Thr Arg Asp Thr Ser
                195                 200                 205

Thr Ser Thr Val Tyr Met Glu Met Ser Ser Leu Arg Ser Glu Asp Thr
            210                 215                 220

Ala Val Tyr Tyr Cys Ala Arg Tyr Pro Val Tyr Met Glu Thr Ser Asp
225                 230                 235                 240

Phe Asp Ser Trp Gly Ser Arg Tyr Ser Gly Asp Arg Leu Leu
                245                 250

<210> SEQ ID NO 451
<211> LENGTH: 257
<212> TYPE: PRT
<213> ORGANISM: Artificial Sequence
<220> FEATURE:
<223> OTHER INFORMATION: GPC3B-85 scFv

<400> SEQUENCE: 451

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Thr Val Asn Trp Tyr Gln Gln Leu Pro Gly Thr Ala Pro Lys Leu Leu
                35                  40                  45

Ile Tyr Ser Asn Asn Gln Arg Pro Ser Gly Val Pro Asp Arg Phe Ser
            50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu Gly Ser
                100                 105                 110

Arg Gly Gly Gly Gly Ser Gly Gly Gly Ser Gly Gly Gly Gly Ser
                115                 120                 125

Leu Glu Met Ala Gln Val Gln Leu Val Gln Ser Gly Ser Glu Leu Lys
            130                 135                 140

Lys Pro Gly Ala Ser Val Lys Val Ser Cys Lys Ala Ser Gly Tyr Thr
145                 150                 155                 160

Phe Thr Ser Tyr Ala Met Asn Trp Val Arg Gln Ala Pro Gly Gln Gly
                165                 170                 175

Leu Glu Trp Met Gly Trp Ile Asn Thr Asn Thr Gly Asn Pro Thr Tyr
                180                 185                 190

Ala Gln Gly Phe Thr Gly Arg Phe Val Phe Ser Leu Asp Thr Ser Val
                195                 200                 205

Ser Thr Ala Tyr Leu Gln Ile Ser Ser Leu Lys Ala Glu Asp Thr Ala
            210                 215                 220

Val Tyr Tyr Cys Ala Arg Ser Ser Leu Tyr Trp Met Gly Ser Lys Trp
225                 230                 235                 240

Ser Arg Gln Thr Asp Met Trp Gly Gln Gly Thr Leu Val Thr Val Ser
                245                 250                 255

Ser
```

<210> SEQ ID NO 452
<211> LENGTH: 247
<212> TYPE: PRT
<213> ORGANISM: Artificial Sequence
<220> FEATURE:
<223> OTHER INFORMATION: GPC3B-87 scFv

<400> SEQUENCE: 452

```
Asp Val Val Met Thr Gln Ser Pro Leu Ser Leu Pro Val Thr Pro Gly
1               5                   10                  15

Glu Pro Ala Ser Val Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

Arg Ser Arg Gly Gly Gly Gly Ser Gly Gly Gly Gly Ser Gly Gly Gly
        115                 120                 125

Gly Ser Leu Glu Met Ala Glu Val Gln Leu Val Gln Ser Gly Ala Glu
    130                 135                 140

Val Arg Lys Pro Gly Ser Ser Val Lys Val Ser Cys Gln Ala Ser Gly
145                 150                 155                 160

Gly Thr Phe Gly Ser Tyr Ala Ile Ser Trp Val Arg Gln Ala Pro Gly
                165                 170                 175

Gln Gly Leu Glu Trp Met Gly Arg Ile Ile Pro Val Leu Gly Arg Thr
            180                 185                 190

Lys Tyr Ala Gln Lys Phe Gln Gly Arg Val Thr Val Thr Ala Asp Thr
        195                 200                 205

Ser Thr Ser Thr Val Tyr Met Glu Leu Thr Ser Leu Thr Ser Glu Asp
    210                 215                 220

Thr Ala Val Tyr Tyr Cys Ala Arg Thr Asn Asp Ser Trp Gly Gln Gly
225                 230                 235                 240

Thr Leu Val Thr Val Ser Ser
            245
```

<210> SEQ ID NO 453
<211> LENGTH: 249
<212> TYPE: PRT
<213> ORGANISM: Artificial Sequence
<220> FEATURE:
<223> OTHER INFORMATION: GPC3B-92 scFv

<400> SEQUENCE: 453

```
Gln Ser Val Leu Thr Gln Pro Pro Ser Val Ser Val Ser Pro Gly Gln
1               5                   10                  15

Thr Ala Arg Ile Thr Cys Ser Gly Glu Thr Leu Ala Lys Arg Tyr Ala
            20                  25                  30

His Trp Tyr Gln Gln Lys Pro Gly Gln Ala Pro Val Leu Leu Ile Tyr
        35                  40                  45

Arg Asp Thr Glu Arg Pro Ser Gly Ile Pro Glu Arg Phe Ser Gly Ser
```

-continued

```
                50                  55                  60
Ser Ser Gly Thr Thr Ile Thr Leu Thr Ile Thr Gly Val Gln Ala Glu
 65                  70                  75                  80

Asp Glu Ala Asp Tyr Tyr Cys Gln Ser Ala Asp Asn Ser Arg Thr Phe
                 85                  90                  95

Val Phe Gly Pro Gly Thr Lys Val Thr Val Leu Gly Ser Arg Gly Gly
                100                 105                 110

Gly Gly Ser Gly Gly Gly Gly Ser Gly Gly Gly Ser Leu Glu Met
            115                 120                 125

Ala Glu Val Gln Leu Val Gln Ser Gly Ala Glu Val Lys Lys Pro Gly
145                 150                 155                 160

Ala Ser Val Lys Val Ser Cys Lys Ala Ser Gly Tyr Thr Phe Ser Asn
145                 150                 155                 160

Tyr Tyr Met His Trp Val Arg Gln Ala Pro Gly Gln Gly Leu Glu Trp
                165                 170                 175

Met Gly Ile Ile Asn Pro Ser Gly Gly Thr Thr Thr Tyr Ala Gln Lys
                180                 185                 190

Phe Gln Gly Arg Val Thr Met Thr Arg Asp Thr Ser Thr Ser Thr Val
            195                 200                 205

Tyr Met Glu Leu Ser Ser Leu Arg Ser Glu Asp Thr Ala Val Tyr Tyr
210                 215                 220

Cys Ala Arg Pro Ser Met Trp Thr Ser Ser Met Gly Asp Val Trp Gly
225                 230                 235                 240

Gln Gly Thr Leu Val Thr Val Ser Ser
            245
```

<210> SEQ ID NO 454
<211> LENGTH: 255
<212> TYPE: PRT
<213> ORGANISM: Artificial Sequence
<220> FEATURE:
<223> OTHER INFORMATION: GPC3B-93 scFv

<400> SEQUENCE: 454

```
Asn Phe Met Leu Thr Gln Pro His Ser Val Ser Glu Ser Pro Gly Lys
 1               5                  10                  15

Thr Val Thr Ile Ser Cys Thr Gly Ser Ser Gly Ser Ile Ala Ser Asn
                20                  25                  30

Tyr Val Gln Trp Tyr Gln Gln Arg Pro Gly Ser Ala Pro Thr Thr Val
             35                  40                  45

Ile Tyr Glu Asp Asn Gln Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Asn Trp Val Phe Gly Gly Gly Thr Lys Leu Thr Val Leu Gly Ser
                100                 105                 110

Arg Gly Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Val Lys
130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Gly
```

```
                165                 170                 175
Leu Glu Trp Met Gly Ile Ile Asn Pro Ser Gly Gly Ser Thr Arg Tyr
            180                 185                 190

Ala Gln Lys Phe Gln Gly Arg Val Thr Met Thr Arg Asp Thr Ser Thr
            195                 200                 205

Ser Thr Val Tyr Met Glu Leu Ser Ser Leu Arg Ser Glu Asp Thr Ala
    210                 215                 220

Val Tyr Tyr Cys Ala Arg Tyr Thr Ala Leu Lys Pro Arg Gly Ile Tyr
225                 230                 235                 240

Ser Val Asp Ser Trp Gly Gln Gly Thr Leu Val Thr Val Ser Ser
                245                 250                 255

<210> SEQ ID NO 455
<211> LENGTH: 257
<212> TYPE: PRT
<213> ORGANISM: Artificial Sequence
<220> FEATURE:
<223> OTHER INFORMATION: GPC3B-110 scFv

<400> SEQUENCE: 455

Gln Ser Val Leu Thr Gln Pro Pro Ser Ala Ser Gly Thr Pro Gly Gln
1               5                   10                  15

Arg Val Thr Val Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Leu Tyr Ser Ser Asn Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65              70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Glu Val Gln Leu Val Gln Ser Gly Ala Glu Val Lys
    130                 135                 140

Lys Pro Gly Ser Ser Val Lys Val Ser Cys Gln Ala Ser Gly Gly Thr
145                 150                 155                 160

Phe Thr Thr Tyr Ser Ile Asn Trp Val Arg Gln Ala Pro Gly Gln Gly
                165                 170                 175

Leu Glu Trp Met Gly Gly Ile Ile Pro Thr Phe Gly Thr Thr Asn Tyr
            180                 185                 190

Ala Gln Asn Phe Gln Asp Arg Val Thr Ile Ser Ala Asp Glu Ser Thr
            195                 200                 205

Asn Thr Ala Tyr Met Glu Leu Thr Ser Leu Arg Ser Glu Asp Thr Ala
    210                 215                 220

Val Tyr Tyr Cys Ala Arg Tyr Tyr Trp Arg Gly Gly Ser Gly Gln Gly
225                 230                 235                 240

Ser Val Thr Ser Asp Tyr Trp Gly Gln Gly Thr Leu Val Thr Val Ser
                245                 250                 255

Ser

<210> SEQ ID NO 456
```

<211> LENGTH: 246
<212> TYPE: PRT
<213> ORGANISM: Artificial Sequence
<220> FEATURE:
<223> OTHER INFORMATION: GPC3B-113 scFv

<400> SEQUENCE: 456

Ser Tyr Glu Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Ser Val Ser Trp Tyr Gln His Leu Pro Gly Val Ala Pro Lys Leu Leu
        35                  40                  45
Ile Tyr Ser Asn Asn Gln Arg Pro Ser Gly Val Pro Asp Arg Phe Ser
    50                  55                  60
Gly Ser Lys Thr Gly Thr Ser Ala Ser Leu Ala Ile Ser Gly Leu Gln
65                  70                  75                  80
Ser Glu Asp Glu Gly Asp Tyr Tyr Cys Ala Ala Trp Asp Asp Ser Leu
                85                  90                  95
Asn Gly Val Leu Phe Gly Gly Gly Thr Lys Leu Thr Val Leu Gly Ser
            100                 105                 110
Arg Gly Gly Gly Gly Ser Gly Gly Gly Gly Ser Gly Gly Gly Gly Ser
        115                 120                 125
Leu Glu Met Ala Gln Val Gln Leu Val Gln Ser Gly Ala Glu Val Lys
    130                 135                 140
Lys Pro Gly Ala Ser Val Lys Val Ser Cys Lys Val Ser Gly Tyr Thr
145                 150                 155                 160
Leu Thr Glu Leu Ser Met His Trp Val Arg Gln Ala Pro Gly Lys Gly
                165                 170                 175
Leu Glu Trp Met Gly Gly Phe Asp Pro Glu Asp Gly Glu Thr Ile Tyr
            180                 185                 190
Ala Gln Lys Phe Gln Gly Arg Val Thr Met Thr Glu Asp Thr Ser Thr
        195                 200                 205
Asp Thr Ala Tyr Met Glu Leu Ser Ser Leu Arg Ser Glu Asp Thr Ala
    210                 215                 220
Val Tyr Tyr Cys Ala Arg Tyr Ser Gly Asp Tyr Trp Gly Gln Gly Thr
225                 230                 235                 240
Leu Val Thr Val Ser Ser
                245

<210> SEQ ID NO 457
<211> LENGTH: 251
<212> TYPE: PRT
<213> ORGANISM: Artificial Sequence
<220> FEATURE:
<223> OTHER INFORMATION: GPC3B-115 scFv

<400> SEQUENCE: 457

Ser Tyr Glu Leu Thr Gln Pro Pro Ser Val Ser Val Ala Pro Gly Lys
1               5                   10                  15
Thr Ala Arg Ile Thr Cys Gly Gly Asn Asn Ile Gly Ser Lys Ser Val
            20                  25                  30
His Trp Tyr Gln Gln Lys Pro Gly Gln Ala Pro Val Leu Val Val Tyr
        35                  40                  45
Asp Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly

```
                65                  70                  75                  80
Asp Glu Ala Asp Tyr Tyr Cys Gln Val Trp Asp Ser Ser Asp Pro
                    85                  90                  95

Leu Tyr Val Phe Gly Thr Gly Thr Lys Val Thr Val Leu Gly Ser Arg
                100                 105                 110

Gly Gly Gly Gly Ser Gly Gly Gly Gly Ser Gly Gly Gly Gly Ser Leu
            115                 120                 125

Glu Met Ala Gln Val Gln Leu Val Gln Ser Gly Ala Glu Val Lys Arg
        130                 135                 140

Pro Gly Ala Thr Ile Lys Val Ser Cys Lys Thr Ser Gly Tyr Thr Phe
145                 150                 155                 160

Thr Ala Tyr Tyr Thr His Trp Val Arg Gln Ala Pro Gly Gln Gly Leu
                165                 170                 175

Glu Trp Val Gly Arg Ile Asn Ala Asn Thr Gly Thr Asp Tyr Ala
                180                 185                 190

Pro Lys Phe Arg Asp Arg Val Ile Met Thr Arg Asp Thr Ser Ile Ser
                195                 200                 205

Thr Ala Tyr Met Glu Leu Gly Arg Leu Thr Ser Glu Asp Thr Ala Val
        210                 215                 220

Tyr Tyr Cys Ala Arg Ile Ser Gly Tyr His Ser Ser Gly Trp Asp Tyr
225                 230                 235                 240

Trp Gly Gln Gly Thr Leu Val Thr Val Ser Ser
                245                 250

<210> SEQ ID NO 458
<211> LENGTH: 249
<212> TYPE: PRT
<213> ORGANISM: Artificial Sequence
<220> FEATURE:
<223> OTHER INFORMATION: GPC3B-119 scFv

<400> SEQUENCE: 458

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Ile Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Arg Ser Gly Thr Ser Ala Thr Leu Gly Ile Thr Gly Leu Gln
65                  70                  75                  80

Thr Gly Asp Glu Ala His Tyr Tyr Cys Ala Thr Trp Asp Asn Ser Leu
                85                  90                  95

Ser Ala Leu Ile Phe Gly Gly Gly Thr Lys Val Thr Val Leu Gly Ser
                100                 105                 110

Arg Gly Gly Gly Gly Ser Gly Gly Gly Gly Ser Gly Gly Gly Gly Ser
            115                 120                 125

Leu Glu Met Ala Gln Val Gln Leu Val Gln Ser Gly Ser Glu Leu Lys
        130                 135                 140

Lys Pro Gly Ala Ser Val Lys Val Ser Cys Lys Ala Ser Gly Tyr Thr
145                 150                 155                 160

Phe Thr Ser Tyr Ala Met Asn Trp Val Arg Gln Ala Pro Gly Gln Gly
                165                 170                 175

Leu Glu Trp Met Gly Trp Ile Asn Thr Asn Thr Gly Asn Pro Thr Tyr
```

```
                180                 185                 190
Ala Gln Gly Phe Thr Gly Arg Phe Val Phe Ser Leu Asp Thr Ser Val
            195                 200                 205

Ser Thr Ala Tyr Leu Gln Ile Ser Ser Leu Lys Ala Glu Asp Thr Ala
        210                 215                 220

Val Tyr Tyr Cys Ala Arg Gly Tyr Gly Lys Tyr Asp Lys Trp Gly
225                 230                 235                 240

Gln Gly Thr Leu Val Thr Val Ser Ser
                245

<210> SEQ ID NO 459
<211> LENGTH: 246
<212> TYPE: PRT
<213> ORGANISM: Artificial Sequence
<220> FEATURE:
<223> OTHER INFORMATION: GPC3B-125 scFv

<400> SEQUENCE: 459

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Phe Gln Gln His Pro Gly Lys Ala Pro Lys Leu
        35                  40                  45

Ile Ile Tyr Glu Val Ser Asn Arg Pro Ser Gly Val Ser Asp Arg Phe
    50                  55                  60

Ser Gly Ser Lys Ser Gly Ser Thr Ala Ser Leu Thr Ile Ser Gly Leu
65                  70                  75                  80

Gln Ala Glu Asp Glu Ala Asn Tyr Tyr Cys Ser Ser Tyr Thr Ser Ser
                85                  90                  95

Thr Thr Val Ile Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Met Gln Leu Val Gln Ser Gly Ser Glu Leu Lys
    130                 135                 140

Lys Pro Gly Ala Ser Val Lys Val Ser Cys Lys Ala Ser Gly Tyr Thr
145                 150                 155                 160

Phe Thr Ser Tyr Ala Met Asn Trp Val Arg Gln Ala Pro Gly Gln Gly
                165                 170                 175

Leu Glu Trp Met Gly Trp Ile Asn Thr Asn Thr Gly Asn Pro Thr Tyr
            180                 185                 190

Ala Gln Gly Phe Thr Gly Arg Phe Val Phe Ser Leu Asp Thr Ser Val
        195                 200                 205

Ser Thr Ala Tyr Leu Gln Ile Ser Ser Leu Lys Ala Glu Asp Thr Ala
    210                 215                 220

Val Tyr Tyr Cys Ala Arg Gln Ser His Asp Glu Trp Gly Gln Gly Thr
225                 230                 235                 240

Leu Val Thr Val Ser Ser
                245

<210> SEQ ID NO 460
<211> LENGTH: 580
<212> TYPE: PRT
<213> ORGANISM: Artificial Sequence
<220> FEATURE:
<223> OTHER INFORMATION: P51654 human GPC3 full-length (UNIPROT)
```

<400> SEQUENCE: 460

```
Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg Ser Ala Tyr Tyr Pro Glu Asp Leu Phe Ile
        355                 360                 365

Asp Lys Lys Val Leu Lys Val Ala His Val Glu His Glu Glu Thr Leu
    370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
```

-continued

```
                        405                 410                 415

Glu Asn Asp Thr Leu Cys Trp Asn Gly Gln Glu Leu Val Glu Arg Tyr
            420                 425                 430

Ser Gln Lys Ala Ala Arg Asn Gly Met Lys Asn Gln Phe Asn Leu His
            435                 440                 445

Glu Leu Lys Met Lys Gly Pro Glu Pro Val Val Ser Gln Ile Ile Asp
            450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                485                 490                 495

Asp Cys Gly Asp Asp Glu Asp Glu Cys Ile Gly Gly Ser Gly Asp Gly
                500                 505                 510

Met Ile Lys Val Lys Asn Gln Leu Arg Phe Leu Ala Glu Leu Ala Tyr
            515                 520                 525

Asp Leu Asp Val Asp Asp Ala Pro Gly Asn Ser Gln Gln Ala Thr Pro
            530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580

<210> SEQ ID NO 461
<211> LENGTH: 560
<212> TYPE: PRT
<213> ORGANISM: Artificial Sequence
<220> FEATURE:
<223> OTHER INFORMATION: Amino acids 1-560 of SEQ ID NO: 460
      human GPC3 full-length (UNIPROT)

<400> SEQUENCE: 461

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
            115                 120                 125

Met Phe Lys Asn Asn Tyr Pro Ser Leu Thr Pro Gln Ala Phe Glu Phe
        130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175
```

```
Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
            245                 250                 255

Thr Arg Met Trp Tyr Cys Ser Tyr Cys Gln Gly Leu Met Met Val Lys
        260                 265                 270

Pro Cys Gly Gly Tyr Cys Asn Val Val Met Gln Gly Cys Met Ala Gly
    275                 280                 285

Val Val Glu Ile Asp Lys Tyr Trp Arg Glu Tyr Ile Leu Ser Leu Glu
290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
            325                 330                 335

Asn Ala Gly Lys Leu Thr Thr Thr Ile Gly Lys Leu Cys Ala His Ser
        340                 345                 350

Gln Gln Arg Gln Tyr Arg Ser Ala Tyr Tyr Pro Glu Asp Leu Phe Ile
    355                 360                 365

Asp Lys Lys Val Leu Lys Val Ala His Val Glu His Glu Thr Leu
370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
            405                 410                 415

Glu Asn Asp Thr Leu Cys Trp Asn Gly Gln Glu Leu Val Glu Arg Tyr
        420                 425                 430

Ser Gln Lys Ala Ala Arg Asn Gly Met Lys Asn Gln Phe Asn Leu His
    435                 440                 445

Glu Leu Lys Met Lys Gly Pro Glu Pro Val Val Ser Gln Ile Ile Asp
450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
            485                 490                 495

Asp Cys Gly Asp Asp Glu Asp Glu Cys Ile Gly Gly Ser Gly Asp Gly
        500                 505                 510

Met Ile Lys Val Lys Asn Gln Leu Arg Phe Leu Ala Glu Leu Ala Tyr
    515                 520                 525

Asp Leu Asp Val Asp Ala Pro Gly Asn Ser Gln Gln Ala Thr Pro
530                 535                 540

Lys Asp Asn Glu Ile Ser Thr Phe His Asn Leu Gly Asn Val His Ser
545                 550                 555                 560

<210> SEQ ID NO 462
<211> LENGTH: 556
<212> TYPE: PRT
<213> ORGANISM: Artificial Sequence
<220> FEATURE:
<223> OTHER INFORMATION: Amino acids 25-580 of SEQ ID NO: 460
```

-continued human GPC3 full-length (UNIPROT)

<400> SEQUENCE: 462

| | | | | | | | | | | | | | | |
|---|---|---|---|---|---|---|---|---|---|---|---|---|---|---|
| Gln | Pro | Pro | Pro | Pro | Pro | Asp | Ala | Thr | Cys | His | Gln | Val | Arg | Ser |
| 1 | | | | 5 | | | | | 10 | | | | | 15 |
| Phe | Phe | Gln | Arg | Leu | Gln | Pro | Gly | Leu | Lys | Trp | Val | Pro | Glu | Thr | Pro |
| | | | 20 | | | | | 25 | | | | | 30 | | |
| Val | Pro | Gly | Ser | Asp | Leu | Gln | Val | Cys | Leu | Pro | Lys | Gly | Pro | Thr | Cys |
| | | | 35 | | | | | 40 | | | | | 45 | | |
| Cys | Ser | Arg | Lys | Met | Glu | Glu | Lys | Tyr | Gln | Leu | Thr | Ala | Arg | Leu | Asn |
| | 50 | | | | | 55 | | | | | 60 | | | | |
| Met | Glu | Gln | Leu | Leu | Gln | Ser | Ala | Ser | Met | Glu | Leu | Lys | Phe | Leu | Ile |
| 65 | | | | | 70 | | | | | 75 | | | | | 80 |
| Ile | Gln | Asn | Ala | Ala | Val | Phe | Gln | Glu | Ala | Phe | Glu | Ile | Val | Val | Arg |
| | | | | 85 | | | | | 90 | | | | | 95 | |
| His | Ala | Lys | Asn | Tyr | Thr | Asn | Ala | Met | Phe | Lys | Asn | Asn | Tyr | Pro | Ser |
| | | | 100 | | | | | 105 | | | | | 110 | | |
| Leu | Thr | Pro | Gln | Ala | Phe | Glu | Phe | Val | Gly | Glu | Phe | Phe | Thr | Asp | Val |
| | | 115 | | | | | 120 | | | | | 125 | | | |
| Ser | Leu | Tyr | Ile | Leu | Gly | Ser | Asp | Ile | Asn | Val | Asp | Asp | Met | Val | Asn |
| | | 130 | | | | | 135 | | | | | 140 | | | |
| Glu | Leu | Phe | Asp | Ser | Leu | Phe | Pro | Val | Ile | Tyr | Thr | Gln | Leu | Met | Asn |
| 145 | | | | | 150 | | | | | 155 | | | | | 160 |
| Pro | Gly | Leu | Pro | Asp | Ser | Ala | Leu | Asp | Ile | Asn | Glu | Cys | Leu | Arg | Gly |
| | | | 165 | | | | | 170 | | | | | 175 | | |
| Ala | Arg | Arg | Asp | Leu | Lys | Val | Phe | Gly | Asn | Phe | Pro | Lys | Leu | Ile | Met |
| | | | 180 | | | | | 185 | | | | | 190 | | |
| Thr | Gln | Val | Ser | Lys | Ser | Leu | Gln | Val | Thr | Arg | Ile | Phe | Leu | Gln | Ala |
| | | | 195 | | | | | 200 | | | | | 205 | | |
| Leu | Asn | Leu | Gly | Ile | Glu | Val | Ile | Asn | Thr | Thr | Asp | His | Leu | Lys | Phe |
| | | 210 | | | | | 215 | | | | | 220 | | | |
| Ser | Lys | Asp | Cys | Gly | Arg | Met | Leu | Thr | Arg | Met | Trp | Tyr | Cys | Ser | Tyr |
| 225 | | | | | 230 | | | | | 235 | | | | | 240 |
| Cys | Gln | Gly | Leu | Met | Met | Val | Lys | Pro | Cys | Gly | Gly | Tyr | Cys | Asn | Val |
| | | | | 245 | | | | | 250 | | | | | 255 | |
| Val | Met | Gln | Gly | Cys | Met | Ala | Gly | Val | Val | Glu | Ile | Asp | Lys | Tyr | Trp |
| | | | 260 | | | | | 265 | | | | | 270 | | |
| Arg | Glu | Tyr | Ile | Leu | Ser | Leu | Glu | Glu | Leu | Val | Asn | Gly | Met | Tyr | Arg |
| | | | 275 | | | | | 280 | | | | | 285 | | |
| Ile | Tyr | Asp | Met | Glu | Asn | Val | Leu | Leu | Gly | Leu | Phe | Ser | Thr | Ile | His |
| | | | 290 | | | | | 295 | | | | | 300 | | |
| Asp | Ser | Ile | Gln | Tyr | Val | Gln | Lys | Asn | Ala | Gly | Lys | Leu | Thr | Thr | Thr |
| 305 | | | | | 310 | | | | | 315 | | | | | 320 |
| Ile | Gly | Lys | Leu | Cys | Ala | His | Ser | Gln | Gln | Arg | Gln | Tyr | Arg | Ser | Ala |
| | | | | 325 | | | | | 330 | | | | | 335 | |
| Tyr | Tyr | Pro | Glu | Asp | Leu | Phe | Ile | Asp | Lys | Lys | Val | Leu | Lys | Val | Ala |
| | | | 340 | | | | | 345 | | | | | 350 | | |
| His | Val | Glu | His | Glu | Glu | Thr | Leu | Ser | Ser | Arg | Arg | Arg | Glu | Leu | Ile |
| | | | 355 | | | | | 360 | | | | | 365 | | |
| Gln | Lys | Leu | Lys | Ser | Phe | Ile | Ser | Phe | Tyr | Ser | Ala | Leu | Pro | Gly | Tyr |
| | | 370 | | | | | 375 | | | | | 380 | | | |
| Ile | Cys | Ser | His | Ser | Pro | Val | Ala | Glu | Asn | Asp | Thr | Leu | Cys | Trp | Asn |
| 385 | | | | | 390 | | | | | 395 | | | | | 400 |

Gly Gln Glu Leu Val Glu Arg Tyr Ser Gln Lys Ala Ala Arg Asn Gly
                405                 410                 415

Met Lys Asn Gln Phe Asn Leu His Glu Leu Lys Met Lys Gly Pro Glu
            420                 425                 430

Pro Val Val Ser Gln Ile Ile Asp Lys Leu Lys His Ile Asn Gln Leu
        435                 440                 445

Leu Arg Thr Met Ser Met Pro Lys Gly Arg Val Leu Asp Lys Asn Leu
    450                 455                 460

Asp Glu Glu Gly Phe Glu Ser Gly Asp Cys Gly Asp Asp Glu Asp Glu
465                 470                 475                 480

Cys Ile Gly Gly Ser Gly Asp Gly Met Ile Lys Val Lys Asn Gln Leu
                485                 490                 495

Arg Phe Leu Ala Glu Leu Ala Tyr Asp Leu Asp Val Asp Asp Ala Pro
            500                 505                 510

Gly Asn Ser Gln Gln Ala Thr Pro Lys Asp Asn Glu Ile Ser Thr Phe
        515                 520                 525

His Asn Leu Gly Asn Val His Ser Pro Leu Lys Leu Leu Thr Ser Met
    530                 535                 540

Ala Ile Ser Val Val Cys Phe Phe Leu Val His
545                 550                 555

<210> SEQ ID NO 463
<211> LENGTH: 536
<212> TYPE: PRT
<213> ORGANISM: Artificial Sequence
<220> FEATURE:
<223> OTHER INFORMATION: Amino acids 25-560 of SEQ ID NO: 460
      human GPC3 full-length (UNIPROT)

<400> SEQUENCE: 463

Gln Pro Pro Pro Pro Pro Asp Ala Thr Cys His Gln Val Arg Ser
1               5                   10                  15

Phe Phe Gln Arg Leu Gln Pro Gly Leu Lys Trp Val Pro Glu Thr Pro
            20                  25                  30

Val Pro Gly Ser Asp Leu Gln Val Cys Leu Pro Lys Gly Pro Thr Cys
        35                  40                  45

Cys Ser Arg Lys Met Glu Glu Lys Tyr Gln Leu Thr Ala Arg Leu Asn
    50                  55                  60

Met Glu Gln Leu Leu Gln Ser Ala Ser Met Glu Leu Lys Phe Leu Ile
65                  70                  75                  80

Ile Gln Asn Ala Ala Val Phe Gln Glu Ala Phe Glu Ile Val Val Arg
                85                  90                  95

His Ala Lys Asn Tyr Thr Asn Ala Met Phe Lys Asn Asn Tyr Pro Ser
            100                 105                 110

Leu Thr Pro Gln Ala Phe Glu Phe Val Gly Glu Phe Phe Thr Asp Val
        115                 120                 125

Ser Leu Tyr Ile Leu Gly Ser Asp Ile Asn Val Asp Asp Met Val Asn
    130                 135                 140

Glu Leu Phe Asp Ser Leu Phe Pro Val Ile Tyr Thr Gln Leu Met Asn
145                 150                 155                 160

Pro Gly Leu Pro Asp Ser Ala Leu Asp Ile Asn Glu Cys Leu Arg Gly
                165                 170                 175

Ala Arg Arg Asp Leu Lys Val Phe Gly Asn Phe Pro Lys Leu Ile Met
            180                 185                 190

Thr Gln Val Ser Lys Ser Leu Gln Val Thr Arg Ile Phe Leu Gln Ala
        195                 200                 205

Leu Asn Leu Gly Ile Glu Val Ile Asn Thr Thr Asp His Leu Lys Phe
210                 215                 220

Ser Lys Asp Cys Gly Arg Met Leu Thr Arg Met Trp Tyr Cys Ser Tyr
225                 230                 235                 240

Cys Gln Gly Leu Met Met Val Lys Pro Cys Gly Gly Tyr Cys Asn Val
            245                 250                 255

Val Met Gln Gly Cys Met Ala Gly Val Val Glu Ile Asp Lys Tyr Trp
            260                 265                 270

Arg Glu Tyr Ile Leu Ser Leu Glu Glu Leu Val Asn Gly Met Tyr Arg
            275                 280                 285

Ile Tyr Asp Met Glu Asn Val Leu Leu Gly Leu Phe Ser Thr Ile His
            290                 295                 300

Asp Ser Ile Gln Tyr Val Gln Lys Asn Ala Gly Lys Leu Thr Thr Thr
305                 310                 315                 320

Ile Gly Lys Leu Cys Ala His Ser Gln Gln Arg Gln Tyr Arg Ser Ala
            325                 330                 335

Tyr Tyr Pro Glu Asp Leu Phe Ile Asp Lys Lys Val Leu Lys Val Ala
            340                 345                 350

His Val Glu His Glu Glu Thr Leu Ser Ser Arg Arg Arg Glu Leu Ile
            355                 360                 365

Gln Lys Leu Lys Ser Phe Ile Ser Phe Tyr Ser Ala Leu Pro Gly Tyr
370                 375                 380

Ile Cys Ser His Ser Pro Val Ala Glu Asn Asp Thr Leu Cys Trp Asn
385                 390                 395                 400

Gly Gln Glu Leu Val Glu Arg Tyr Ser Gln Lys Ala Ala Arg Asn Gly
            405                 410                 415

Met Lys Asn Gln Phe Asn Leu His Glu Leu Lys Met Lys Gly Pro Glu
            420                 425                 430

Pro Val Val Ser Gln Ile Ile Asp Lys Leu Lys His Ile Asn Gln Leu
            435                 440                 445

Leu Arg Thr Met Ser Met Pro Lys Gly Arg Val Leu Asp Lys Asn Leu
450                 455                 460

Asp Glu Glu Gly Phe Glu Ser Gly Asp Cys Gly Asp Asp Glu Asp Glu
465                 470                 475                 480

Cys Ile Gly Gly Ser Gly Asp Gly Met Ile Lys Val Lys Asn Gln Leu
            485                 490                 495

Arg Phe Leu Ala Glu Leu Ala Tyr Asp Leu Asp Val Asp Asp Ala Pro
            500                 505                 510

Gly Asn Ser Gln Gln Ala Thr Pro Lys Asp Asn Glu Ile Ser Thr Phe
            515                 520                 525

His Asn Leu Gly Asn Val His Ser
530                 535

<210> SEQ ID NO 464
<211> LENGTH: 334
<212> TYPE: PRT
<213> ORGANISM: Artificial Sequence
<220> FEATURE:
<223> OTHER INFORMATION: Amino acids 25-358 of SEQ ID NO: 460
      human GPC3 full-length (UNIPROT)

<400> SEQUENCE: 464

Gln Pro Pro Pro Pro Pro Asp Ala Thr Cys His Gln Val Arg Ser
1               5                   10                  15

Phe Phe Gln Arg Leu Gln Pro Gly Leu Lys Trp Val Pro Glu Thr Pro

```
            20              25              30
Val Pro Gly Ser Asp Leu Gln Val Cys Leu Pro Lys Gly Pro Thr Cys
        35              40              45

Cys Ser Arg Lys Met Glu Glu Lys Tyr Gln Leu Thr Ala Arg Leu Asn
50              55              60

Met Glu Gln Leu Leu Gln Ser Ala Ser Met Glu Leu Lys Phe Leu Ile
65              70              75              80

Ile Gln Asn Ala Ala Val Phe Gln Glu Ala Phe Glu Ile Val Val Arg
            85              90              95

His Ala Lys Asn Tyr Thr Asn Ala Met Phe Lys Asn Asn Tyr Pro Ser
            100             105             110

Leu Thr Pro Gln Ala Phe Glu Phe Val Gly Glu Phe Phe Thr Asp Val
        115             120             125

Ser Leu Tyr Ile Leu Gly Ser Asp Ile Asn Val Asp Asp Met Val Asn
        130             135             140

Glu Leu Phe Asp Ser Leu Phe Pro Val Ile Tyr Thr Gln Leu Met Asn
145             150             155             160

Pro Gly Leu Pro Asp Ser Ala Leu Asp Ile Asn Glu Cys Leu Arg Gly
            165             170             175

Ala Arg Arg Asp Leu Lys Val Phe Gly Asn Phe Pro Lys Leu Ile Met
            180             185             190

Thr Gln Val Ser Lys Ser Leu Gln Val Thr Arg Ile Phe Leu Gln Ala
        195             200             205

Leu Asn Leu Gly Ile Glu Val Ile Asn Thr Thr Asp His Leu Lys Phe
        210             215             220

Ser Lys Asp Cys Gly Arg Met Leu Thr Arg Met Trp Tyr Cys Ser Tyr
225             230             235             240

Cys Gln Gly Leu Met Met Val Lys Pro Cys Gly Gly Tyr Cys Asn Val
            245             250             255

Val Met Gln Gly Cys Met Ala Gly Val Val Glu Ile Asp Lys Tyr Trp
            260             265             270

Arg Glu Tyr Ile Leu Ser Leu Glu Glu Leu Val Asn Gly Met Tyr Arg
        275             280             285

Ile Tyr Asp Met Glu Asn Val Leu Leu Gly Leu Phe Ser Thr Ile His
        290             295             300

Asp Ser Ile Gln Tyr Val Gln Lys Asn Ala Gly Lys Leu Thr Thr Thr
305             310             315             320

Ile Gly Lys Leu Cys Ala His Ser Gln Gln Arg Gln Tyr Arg
            325             330

<210> SEQ ID NO 465
<211> LENGTH: 202
<212> TYPE: PRT
<213> ORGANISM: Artificial Sequence
<220> FEATURE:
<223> OTHER INFORMATION: Amino acids 359-560 of SEQ ID NO: 460
      human GPC3 full-length (UNIPROT)

<400> SEQUENCE: 465

Ser Ala Tyr Tyr Pro Glu Asp Leu Phe Ile Asp Lys Lys Val Leu Lys
1               5               10              15

Val Ala His Val Glu His Glu Glu Thr Leu Ser Ser Arg Arg Arg Glu
            20              25              30

Leu Ile Gln Lys Leu Lys Ser Phe Ile Ser Phe Tyr Ser Ala Leu Pro
        35              40              45
```

```
Gly Tyr Ile Cys Ser His Ser Pro Val Ala Glu Asn Asp Thr Leu Cys
        50                  55                  60

Trp Asn Gly Gln Glu Leu Val Glu Arg Tyr Ser Gln Lys Ala Ala Arg
 65                  70                  75                  80

Asn Gly Met Lys Asn Gln Phe Asn Leu His Glu Leu Lys Met Lys Gly
                 85                  90                  95

Pro Glu Pro Val Val Ser Gln Ile Ile Asp Lys Leu Lys His Ile Asn
            100                 105                 110

Gln Leu Leu Arg Thr Met Ser Met Pro Lys Gly Arg Val Leu Asp Lys
        115                 120                 125

Asn Leu Asp Glu Glu Gly Phe Glu Ser Gly Asp Cys Gly Asp Asp Glu
130                 135                 140

Asp Glu Cys Ile Gly Gly Ser Gly Asp Gly Met Ile Lys Val Lys Asn
145                 150                 155                 160

Gln Leu Arg Phe Leu Ala Glu Leu Ala Tyr Asp Leu Asp Val Asp Asp
                165                 170                 175

Ala Pro Gly Asn Ser Gln Gln Ala Thr Pro Lys Asp Asn Glu Ile Ser
            180                 185                 190

Thr Phe His Asn Leu Gly Asn Val His Ser
        195                 200

<210> SEQ ID NO 466
<211> LENGTH: 222
<212> TYPE: PRT
<213> ORGANISM: Artificial Sequence
<220> FEATURE:
<223> OTHER INFORMATION: Amino acids 359-580 of SEQ ID NO: 460
      human GPC3 full-length (UNIPROT)

<400> SEQUENCE: 466

Ser Ala Tyr Tyr Pro Glu Asp Leu Phe Ile Asp Lys Lys Val Leu Lys
 1               5                  10                  15

Val Ala His Val Glu His Glu Glu Thr Leu Ser Ser Arg Arg Arg Glu
             20                  25                  30

Leu Ile Gln Lys Leu Lys Ser Phe Ile Ser Phe Tyr Ser Ala Leu Pro
         35                  40                  45

Gly Tyr Ile Cys Ser His Ser Pro Val Ala Glu Asn Asp Thr Leu Cys
        50                  55                  60

Trp Asn Gly Gln Glu Leu Val Glu Arg Tyr Ser Gln Lys Ala Ala Arg
 65                  70                  75                  80

Asn Gly Met Lys Asn Gln Phe Asn Leu His Glu Leu Lys Met Lys Gly
                 85                  90                  95

Pro Glu Pro Val Val Ser Gln Ile Ile Asp Lys Leu Lys His Ile Asn
            100                 105                 110

Gln Leu Leu Arg Thr Met Ser Met Pro Lys Gly Arg Val Leu Asp Lys
        115                 120                 125

Asn Leu Asp Glu Glu Gly Phe Glu Ser Gly Asp Cys Gly Asp Asp Glu
130                 135                 140

Asp Glu Cys Ile Gly Gly Ser Gly Asp Gly Met Ile Lys Val Lys Asn
145                 150                 155                 160

Gln Leu Arg Phe Leu Ala Glu Leu Ala Tyr Asp Leu Asp Val Asp Asp
                165                 170                 175

Ala Pro Gly Asn Ser Gln Gln Ala Thr Pro Lys Asp Asn Glu Ile Ser
            180                 185                 190

Thr Phe His Asn Leu Gly Asn Val His Ser Pro Leu Lys Leu Leu Thr
        195                 200                 205
```

```
Ser Met Ala Ile Ser Val Val Cys Phe Phe Phe Leu Val His
    210                 215                 220
```

<210> SEQ ID NO 467
<211> LENGTH: 51
<212> TYPE: PRT
<213> ORGANISM: Artificial Sequence
<220> FEATURE:
<223> OTHER INFORMATION: Amino acids 510-560 of SEQ ID NO: 460
      human GPC3 full-length (UNIPROT)

<400> SEQUENCE: 467

```
Gly Asp Gly Met Ile Lys Val Lys Asn Gln Leu Arg Phe Leu Ala Glu
1               5                   10                  15

Leu Ala Tyr Asp Leu Asp Val Asp Ala Pro Gly Asn Ser Gln Gln
            20                  25                  30

Ala Thr Pro Lys Asp Asn Glu Ile Ser Thr Phe His Asn Leu Gly Asn
            35                  40                  45

Val His Ser
        50
```

<210> SEQ ID NO 468
<211> LENGTH: 358
<212> TYPE: PRT
<213> ORGANISM: Artificial Sequence
<220> FEATURE:
<223> OTHER INFORMATION: Amino acids 1-358 of SEQ ID NO: 460
      human GPC3 full-length (UNIPROT)

<400> SEQUENCE: 468

```
Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Asp
            20                  25                  30

Ala Thr Cys His Gln Val Arg Ser Phe Phe Gln Arg Leu Gln Pro Gly
            35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220
```

```
Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
            245                 250                 255

Thr Arg Met Trp Tyr Cys Ser Tyr Cys Gln Gly Leu Met Met Val Lys
        260                 265                 270

Pro Cys Gly Gly Tyr Cys Asn Val Val Met Gln Gly Cys Met Ala Gly
        275                 280                 285

Val Val Glu Ile Asp Lys Tyr Trp Arg Glu Tyr Ile Leu Ser Leu Glu
    290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                325                 330                 335

Asn Ala Gly Lys Leu Thr Thr Thr Ile Gly Lys Leu Cys Ala His Ser
            340                 345                 350

Gln Gln Arg Gln Tyr Arg
        355
```

<210> SEQ ID NO 469
<211> LENGTH: 2
<212> TYPE: PRT
<213> ORGANISM: Artificial Sequence
<220> FEATURE:
<223> OTHER INFORMATION: Linker amino acid sequence
<220> FEATURE:
<221> NAME/KEY: Variant
<222> LOCATION: (1)..(2)
<223> OTHER INFORMATION: Can be present in repeats of at least one

<400> SEQUENCE: 469

```
Gly Ser
1
```

<210> SEQ ID NO 470
<211> LENGTH: 5
<212> TYPE: PRT
<213> ORGANISM: Artificial Sequence
<220> FEATURE:
<223> OTHER INFORMATION: Linker amino acid sequence
<220> FEATURE:
<221> NAME/KEY: Variant
<222> LOCATION: (1)..(5)
<223> OTHER INFORMATION: Can be present in repeats of at least one

<400> SEQUENCE: 470

```
Gly Ser Gly Gly Ser
1               5
```

<210> SEQ ID NO 471
<211> LENGTH: 5
<212> TYPE: PRT
<213> ORGANISM: Artificial Sequence
<220> FEATURE:
<223> OTHER INFORMATION: Linker amino acid sequence
<220> FEATURE:
<221> NAME/KEY: Variant
<222> LOCATION: (1)..(5)
<223> OTHER INFORMATION: Can be present in repeats of at least one

<400> SEQUENCE: 471

```
Gly Gly Gly Gly Ser
1               5
```

```
<210> SEQ ID NO 472
<211> LENGTH: 4
<212> TYPE: PRT
<213> ORGANISM: Artificial Sequence
<220> FEATURE:
<223> OTHER INFORMATION: Linker amino acid sequence
<220> FEATURE:
<221> NAME/KEY: Variant
<222> LOCATION: (1)..(4)
<223> OTHER INFORMATION: Can be present in repeats of at least one

<400> SEQUENCE: 472

Gly Gly Gly Ser
1

<210> SEQ ID NO 473
<211> LENGTH: 21
<212> TYPE: PRT
<213> ORGANISM: Artificial Sequence
<220> FEATURE:
<223> OTHER INFORMATION: Linker amino acid sequence

<400> SEQUENCE: 473

Ser Arg Gly Gly Gly Gly Ser Gly Gly Gly Gly Ser Gly Gly Gly Gly
1               5                   10                  15

Ser Leu Glu Met Ala
            20

<210> SEQ ID NO 474
<211> LENGTH: 7
<212> TYPE: PRT
<213> ORGANISM: Artificial Sequence
<220> FEATURE:
<223> OTHER INFORMATION: Linker amino acid sequence

<400> SEQUENCE: 474

Thr Ser Gly Gly Gly Gly Ser
1               5

<210> SEQ ID NO 475
<211> LENGTH: 22
<212> TYPE: PRT
<213> ORGANISM: Artificial Sequence
<220> FEATURE:
<223> OTHER INFORMATION: Linker amino acid sequence

<400> SEQUENCE: 475

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 476
<211> LENGTH: 6
<212> TYPE: PRT
<213> ORGANISM: Artificial Sequence
<220> FEATURE:
<223> OTHER INFORMATION: His-tag amino acid sequence

<400> SEQUENCE: 476

His His His His His His
1               5

<210> SEQ ID NO 477
<211> LENGTH: 25
<212> TYPE: PRT
```

```
<213> ORGANISM: Artificial Sequence
<220> FEATURE:
<223> OTHER INFORMATION: His-tag and HA-tag amino acid sequence

<400> SEQUENCE: 477

Thr Ser Gly Gln Ala Gly Gln His His His His His His Gly Ala Tyr
1               5                   10                  15

Pro Tyr Asp Val Pro Asp Tyr Ala Ser
            20                  25

<210> SEQ ID NO 478
<211> LENGTH: 5
<212> TYPE: PRT
<213> ORGANISM: Artificial Sequence
<220> FEATURE:
<223> OTHER INFORMATION: Fc hinge amino acid sequence

<400> SEQUENCE: 478

Cys Pro Pro Cys Pro
1               5

<210> SEQ ID NO 479
<211> LENGTH: 8
<212> TYPE: PRT
<213> ORGANISM: Artificial Sequence
<220> FEATURE:
<223> OTHER INFORMATION: Anti-CD3 antibody HC-CDR1 amino acid sequence

<400> SEQUENCE: 479

Gly Tyr Thr Phe Thr Arg Tyr Thr
1               5

<210> SEQ ID NO 480
<211> LENGTH: 8
<212> TYPE: PRT
<213> ORGANISM: Artificial Sequence
<220> FEATURE:
<223> OTHER INFORMATION: Anti-CD3 antibody HC-CDR2 amino acid sequence

<400> SEQUENCE: 480

Ile Asn Pro Ser Arg Gly Tyr Thr
1               5

<210> SEQ ID NO 481
<211> LENGTH: 12
<212> TYPE: PRT
<213> ORGANISM: Artificial Sequence
<220> FEATURE:
<223> OTHER INFORMATION: Anti-CD3 antibody HC-CDR3 amino acid sequence

<400> SEQUENCE: 481

Ala Arg Tyr Tyr Asp Asp His Tyr Cys Leu Asp Tyr
1               5                   10

<210> SEQ ID NO 482
<211> LENGTH: 5
<212> TYPE: PRT
<213> ORGANISM: Artificial Sequence
<220> FEATURE:
<223> OTHER INFORMATION: Anti-CD3 antibody LC-CDR1 amino acid sequence

<400> SEQUENCE: 482

Gln Ser Val Ser Tyr
1               5

<210> SEQ ID NO 483
```

```
<211> LENGTH: 3
<212> TYPE: PRT
<213> ORGANISM: Artificial Sequence
<220> FEATURE:
<223> OTHER INFORMATION: Anti-CD3 antibody LC-CDR2 amino acid sequence

<400> SEQUENCE: 483

Asp Thr Ser
1

<210> SEQ ID NO 484
<211> LENGTH: 9
<212> TYPE: PRT
<213> ORGANISM: Artificial Sequence
<220> FEATURE:
<223> OTHER INFORMATION: Anti-CD3 antibody LC-CDR3 amino acid sequence

<400> SEQUENCE: 484

Gln Gln Trp Ser Ser Asn Pro Leu Thr
1               5

<210> SEQ ID NO 485
<211> LENGTH: 119
<212> TYPE: PRT
<213> ORGANISM: Artificial Sequence
<220> FEATURE:
<223> OTHER INFORMATION: Anti-CD3 antibody VH amino acid sequence

<400> SEQUENCE: 485

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115

<210> SEQ ID NO 486
<211> LENGTH: 106
<212> TYPE: PRT
<213> ORGANISM: Artificial Sequence
<220> FEATURE:
<223> OTHER INFORMATION: Anti-CD3 antibody VL amino acid sequence

<400> SEQUENCE: 486

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Ala Arg Phe Ser Gly Ser
    50                  55                  60
```

```
Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 487
<211> LENGTH: 243
<212> TYPE: PRT
<213> ORGANISM: Artificial Sequence
<220> FEATURE:
<223> OTHER INFORMATION: Anti-CD3 scFv amino acid sequence

<400> SEQUENCE: 487

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Ile
            35                  40                  45

Gly Tyr Ile Asn Pro Ser Arg Gly Tyr Thr Asn Tyr Ala Asp Ser Val
        50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys

<210> SEQ ID NO 488
<211> LENGTH: 498
<212> TYPE: PRT
<213> ORGANISM: Artificial Sequence
<220> FEATURE:
<223> OTHER INFORMATION: Anti-nGPC3 (GPC3A-034) scFv-anti-CD3 scFv
      amino acid sequence

<400> SEQUENCE: 488

Gln Pro Val Leu Thr Gln Pro Pro Ser Ala Ser Gly Thr Pro Gly Gln
```

-continued

```
1               5                   10                  15
Arg Val Thr Ile Ser Cys Ser Gly Ser Ser Asn Ile Gly Ser Asn
                20                  25                  30

Asn Val Ile Trp Tyr Gln Gln Leu Pro Gly Ala Ala Pro Lys Leu Leu
                35                  40                  45

Ile Tyr Ser Asn His Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asp Gly Tyr Leu Phe Gly Thr Gly Thr Lys Val Thr Val Leu Gly Ser
                100                 105                 110

Arg Gly Gly Gly Gly Ser Gly Gly Gly Ser Gly Gly Gly Ser
                115                 120                 125

Leu Glu Met Ala Gln Val Gln Leu Gln Gln Trp Gly Ala Gly Leu Leu
    130                 135                 140

Lys Pro Ser Glu Thr Leu Ser Leu Thr Cys Ala Val Tyr Gly Gly Ser
145                 150                 155                 160

Phe Ser Gly Tyr Tyr Trp Ser Trp Ile Arg Gln Pro Pro Gly Lys Gly
                165                 170                 175

Leu Glu Trp Ile Gly Glu Ile Asn His Ser Gly Ser Thr Asn Tyr Asn
                180                 185                 190

Pro Ser Leu Lys Ser Arg Val Thr Ile Ser Val Asp Thr Ser Lys Asn
                195                 200                 205

Gln Phe Ser Leu Glu Leu Ser Ser Val Thr Ala Ala Asp Thr Ala Val
    210                 215                 220

Tyr Tyr Cys Ala Arg Gly Tyr Gly Gly Arg Phe Asp Tyr Trp Gly Gln
225                 230                 235                 240

Gly Thr Leu Val Thr Val Ser Ser Thr Ser Gly Gly Gly Gly Ser Asp
                245                 250                 255

Val Gln Leu Val Gln Ser Gly Ala Glu Val Lys Lys Pro Gly Ala Ser
                260                 265                 270

Val Lys Val Ser Cys Lys Ala Ser Gly Tyr Thr Phe Thr Arg Tyr Thr
    275                 280                 285

Met His Trp Val Arg Gln Ala Pro Gly Gln Gly Leu Glu Trp Ile Gly
    290                 295                 300

Tyr Ile Asn Pro Ser Arg Gly Tyr Thr Asn Tyr Ala Asp Ser Val Lys
305                 310                 315                 320

Gly Arg Phe Thr Ile Thr Thr Asp Lys Ser Thr Ser Thr Ala Tyr Met
                325                 330                 335

Glu Leu Ser Ser Leu Arg Ser Glu Asp Thr Ala Thr Tyr Tyr Cys Ala
                340                 345                 350

Arg Tyr Tyr Asp Asp His Tyr Cys Leu Asp Tyr Trp Gly Gln Gly Thr
                355                 360                 365

Thr Val Thr Val Ser Ser Gly Glu Gly Thr Ser Thr Gly Ser Gly Gly
    370                 375                 380

Ser Gly Gly Ser Gly Gly Ala Asp Asp Ile Val Leu Thr Gln Ser Pro
385                 390                 395                 400

Ala Thr Leu Ser Leu Ser Pro Gly Glu Arg Ala Thr Leu Ser Cys Arg
                405                 410                 415

Ala Ser Gln Ser Val Ser Tyr Met Asn Trp Tyr Gln Gln Lys Pro Gly
                420                 425                 430
```

```
Lys Ala Pro Lys Arg Trp Ile Tyr Asp Thr Ser Lys Val Ala Ser Gly
            435                 440                 445

Val Pro Ala Arg Phe Ser Gly Ser Gly Ser Gly Thr Asp Tyr Ser Leu
        450                 455                 460

Thr Ile Asn Ser Leu Glu Ala Glu Asp Ala Ala Thr Tyr Tyr Cys Gln
465                 470                 475                 480

Gln Trp Ser Ser Asn Pro Leu Thr Phe Gly Gly Gly Thr Lys Val Glu
                485                 490                 495

Ile Lys

<210> SEQ ID NO 489
<211> LENGTH: 497
<212> TYPE: PRT
<213> ORGANISM: Artificial Sequence
<220> FEATURE:
<223> OTHER INFORMATION: Anti-GPC3 (GPC3B-87) scFv-anti-CD3 scFv
      amino acid sequence

<400> SEQUENCE: 489

Asp Val Val Met Thr Gln Ser Pro Leu Ser Leu Pro Val Thr Pro Gly
1               5                   10                  15

Glu Pro Ala Ser Val Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

Arg Ser Arg Gly Gly Gly Gly Ser Gly Gly Gly Gly Ser Gly Gly Gly
        115                 120                 125

Gly Ser Leu Glu Met Ala Glu Val Gln Leu Val Gln Ser Gly Ala Glu
    130                 135                 140

Val Arg Lys Pro Gly Ser Ser Val Lys Val Ser Cys Gln Ala Ser Gly
145                 150                 155                 160

Gly Thr Phe Gly Ser Tyr Ala Ile Ser Trp Val Arg Gln Ala Pro Gly
                165                 170                 175

Gln Gly Leu Glu Trp Met Gly Arg Ile Ile Pro Val Leu Gly Arg Thr
            180                 185                 190

Lys Tyr Ala Gln Lys Phe Gln Gly Arg Val Thr Val Thr Ala Asp Thr
        195                 200                 205

Ser Thr Ser Thr Val Tyr Met Glu Leu Thr Ser Leu Thr Ser Glu Asp
    210                 215                 220

Thr Ala Val Tyr Tyr Cys Ala Arg Thr Asn Asp Ser Trp Gly Gln Gly
225                 230                 235                 240

Thr Leu Val Thr Val Ser Ser Thr Ser Gly Gly Gly Gly Ser Asp Val
                245                 250                 255

Gln Leu Val Gln Ser Gly Ala Glu Val Lys Lys Pro Gly Ala Ser Val
            260                 265                 270

Lys Val Ser Cys Lys Ala Ser Gly Tyr Thr Phe Thr Arg Tyr Thr Met
        275                 280                 285
```

```
His Trp Val Arg Gln Ala Pro Gly Gln Gly Leu Glu Trp Ile Gly Tyr
    290                 295                 300

Ile Asn Pro Ser Arg Gly Tyr Thr Asn Tyr Ala Asp Ser Val Lys Gly
305                 310                 315                 320

Arg Phe Thr Ile Thr Thr Asp Lys Ser Thr Ser Thr Ala Tyr Met Glu
                325                 330                 335

Leu Ser Ser Leu Arg Ser Glu Asp Thr Ala Thr Tyr Tyr Cys Ala Arg
            340                 345                 350

Tyr Tyr Asp Asp His Tyr Cys Leu Asp Tyr Trp Gly Gln Gly Thr Thr
        355                 360                 365

Val Thr Val Ser Ser Gly Glu Gly Thr Ser Thr Gly Ser Gly Gly Ser
    370                 375                 380

Gly Gly Ser Gly Gly Ala Asp Asp Ile Val Leu Thr Gln Ser Pro Ala
385                 390                 395                 400

Thr Leu Ser Leu Ser Pro Gly Glu Arg Ala Thr Leu Ser Cys Arg Ala
                405                 410                 415

Ser Gln Ser Val Ser Tyr Met Asn Trp Tyr Gln Gln Lys Pro Gly Lys
            420                 425                 430

Ala Pro Lys Arg Trp Ile Tyr Asp Thr Ser Lys Val Ala Ser Gly Val
        435                 440                 445

Pro Ala Arg Phe Ser Gly Ser Gly Ser Gly Thr Asp Tyr Ser Leu Thr
    450                 455                 460

Ile Asn Ser Leu Glu Ala Glu Asp Ala Ala Thr Tyr Tyr Cys Gln Gln
465                 470                 475                 480

Trp Ser Ser Asn Pro Leu Thr Phe Gly Gly Thr Lys Val Glu Ile
                485                 490                 495

Lys

<210> SEQ ID NO 490
<211> LENGTH: 18
<212> TYPE: PRT
<213> ORGANISM: Artificial Sequence
<220> FEATURE:
<223> OTHER INFORMATION: Linker amino acid sequence

<400> SEQUENCE: 490

Gly Glu Gly Thr Ser Thr Gly Ser Gly Gly Ser Gly Gly Ser Gly Gly
1               5                   10                  15

Ala Asp

<210> SEQ ID NO 491
<211> LENGTH: 470
<212> TYPE: PRT
<213> ORGANISM: Artificial Sequence
<220> FEATURE:
<223> OTHER INFORMATION: GPC3A-034 scFv-CAR amino acid sequence

<400> SEQUENCE: 491

Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Asn Val Ile Trp Tyr Gln Gln Leu Pro Gly Ala Ala Pro Lys Leu Leu
        35                  40                  45

Ile Tyr Ser Asn His Arg Arg Pro Ser Gly Val Pro Asp Arg Phe Ser
    50                  55                  60
```

```
Gly Ser Arg Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asp Gly Tyr Leu Phe Gly Thr Gly Thr Lys Val Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Gln Gln Trp Gly Ala Gly Leu Leu
    130                 135                 140

Lys Pro Ser Glu Thr Leu Ser Leu Thr Cys Ala Val Tyr Gly Gly Ser
145                 150                 155                 160

Phe Ser Gly Tyr Tyr Trp Ser Trp Ile Arg Gln Pro Pro Gly Lys Gly
                165                 170                 175

Leu Glu Trp Ile Gly Glu Ile Asn His Ser Gly Ser Thr Asn Tyr Asn
            180                 185                 190

Pro Ser Leu Lys Ser Arg Val Thr Ile Ser Val Asp Thr Ser Lys Asn
        195                 200                 205

Gln Phe Ser Leu Glu Leu Ser Ser Val Thr Ala Ala Asp Thr Ala Val
    210                 215                 220

Tyr Tyr Cys Ala Arg Gly Tyr Gly Gly Arg Phe Asp Tyr Trp Gly Gln
225                 230                 235                 240

Gly Thr Leu Val Thr Val Ser Ser Ala Ala Ile Glu Val Met Tyr
                245                 250                 255

Pro Pro Pro Tyr Leu Asp Asn Glu Lys Ser Asn Gly Thr Ile Ile His
            260                 265                 270

Val Lys Gly Lys His Leu Cys Pro Ser Pro Leu Phe Pro Gly Pro Ser
        275                 280                 285

Lys Pro Phe Trp Val Leu Val Val Val Gly Gly Val Leu Ala Cys Tyr
    290                 295                 300

Ser Leu Leu Val Thr Val Ala Phe Ile Ile Phe Trp Val Arg Ser Lys
305                 310                 315                 320

Arg Ser Arg Leu Leu His Ser Asp Tyr Met Asn Met Thr Pro Arg Arg
                325                 330                 335

Pro Gly Pro Thr Arg Lys His Tyr Gln Pro Tyr Ala Pro Pro Arg Asp
            340                 345                 350

Phe Ala Ala Tyr Arg Ser Arg Val Lys Phe Ser Arg Ser Ala Asp Ala
        355                 360                 365

Pro Ala Tyr Gln Gln Gly Gln Asn Gln Leu Tyr Asn Glu Leu Asn Leu
    370                 375                 380

Gly Arg Arg Glu Glu Tyr Asp Val Leu Asp Lys Arg Gly Arg Asp
385                 390                 395                 400

Pro Glu Met Gly Gly Lys Pro Arg Arg Lys Asn Pro Gln Glu Gly Leu
                405                 410                 415

Tyr Asn Glu Leu Gln Lys Asp Lys Met Ala Glu Ala Tyr Ser Glu Ile
            420                 425                 430

Gly Met Lys Gly Glu Arg Arg Arg Gly Lys Gly His Asp Gly Leu Tyr
        435                 440                 445

Gln Gly Leu Ser Thr Ala Thr Lys Asp Thr Tyr Asp Ala Leu His Met
    450                 455                 460

Gln Ala Leu Pro Pro Arg
465                 470
```

<210> SEQ ID NO 492
<211> LENGTH: 287
<212> TYPE: PRT
<213> ORGANISM: Artificial Sequence
<220> FEATURE:
<223> OTHER INFORMATION: GPC3A-034 (VHCH)-TCR delta amino acid sequence

<400> SEQUENCE: 492

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Glu Leu Ser Ser Val Thr Ala Ala Asp Thr Ala Val Tyr Tyr Cys Ala
                85                  90                  95

Arg Gly Tyr Gly Gly Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Glu Val Lys Thr Asp
    210                 215                 220

Ser Thr Asp His Val Lys Pro Lys Glu Thr Glu Asn Thr Lys Gln Pro
225                 230                 235                 240

Ser Lys Ser Cys His Lys Pro Lys Ala Ile Val His Thr Glu Lys Val
                245                 250                 255

Asn Met Met Ser Leu Thr Val Leu Gly Leu Arg Met Leu Phe Ala Lys
            260                 265                 270

Thr Val Ala Val Asn Phe Leu Leu Thr Ala Lys Leu Phe Phe Leu
        275                 280                 285
```

<210> SEQ ID NO 493
<211> LENGTH: 283
<212> TYPE: PRT
<213> ORGANISM: Artificial Sequence
<220> FEATURE:
<223> OTHER INFORMATION: GPC3A-034 (VLCL)-TCR gamma amino acid sequence

<400> SEQUENCE: 493

```
Gln Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30
```

Asn Val Ile Trp Tyr Gln Gln Leu Pro Gly Ala Ala Pro Lys Leu Leu
            35                  40                  45

Ile Tyr Ser Asn His Arg Arg Pro Ser Gly Val Pro Asp Arg Phe Ser
 50                  55                  60

Gly Ser Arg Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asp Gly Tyr Leu Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Pro Ile Lys Thr Asp Val Ile Thr
    210                 215                 220

Met Asp Pro Lys Asp Asn Cys Ser Lys Asp Ala Asn Asp Thr Leu Leu
225                 230                 235                 240

Leu Gln Leu Thr Asn Thr Ser Ala Tyr Tyr Met Tyr Leu Leu Leu Leu
                245                 250                 255

Leu Lys Ser Val Val Tyr Phe Ala Ile Ile Thr Cys Cys Leu Leu Arg
            260                 265                 270

Arg Thr Ala Phe Cys Cys Asn Gly Glu Lys Ser
        275                 280

<210> SEQ ID NO 494
<211> LENGTH: 219
<212> TYPE: PRT
<213> ORGANISM: Artificial Sequence
<220> FEATURE:
<223> OTHER INFORMATION: CD28-CD3 zeta CAR domain fusion amino acid
      sequence

<400> SEQUENCE: 494

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser Arg Val Lys Phe Ser
            100                 105                 110

Arg Ser Ala Asp Ala Pro Ala Tyr Gln Gln Gly Gln Asn Gln Leu Tyr
        115                 120                 125

Asn Glu Leu Asn Leu Gly Arg Arg Glu Tyr Asp Val Leu Asp Lys
    130                 135                 140

Arg Arg Gly Arg Asp Pro Glu Met Gly Gly Lys Pro Arg Arg Lys Asn
145                 150                 155                 160

Pro Gln Glu Gly Leu Tyr Asn Glu Leu Gln Lys Asp Lys Met Ala Glu
                165                 170                 175

Ala Tyr Ser Glu Ile Gly Met Lys Gly Glu Arg Arg Arg Gly Lys Gly
                180                 185                 190

His Asp Gly Leu Tyr Gln Gly Leu Ser Thr Ala Thr Lys Asp Thr Tyr
            195                 200                 205

Asp Ala Leu His Met Gln Ala Leu Pro Pro Arg
    210                 215

<210> SEQ ID NO 495
<211> LENGTH: 68
<212> TYPE: PRT
<213> ORGANISM: Artificial Sequence
<220> FEATURE:
<223> OTHER INFORMATION: TCR delta chain amino acid sequence

<400> SEQUENCE: 495

Glu Val Lys Thr Asp Ser Thr Asp His Val Pro Lys Glu Thr Glu
1               5                   10                  15

Asn Thr Lys Gln Pro Ser Lys Ser Cys His Lys Pro Lys Ala Ile Val
            20                  25                  30

His Thr Glu Lys Val Asn Met Met Ser Leu Thr Val Leu Gly Leu Arg
        35                  40                  45

Met Leu Phe Ala Lys Thr Val Ala Val Asn Phe Leu Leu Thr Ala Lys
    50                  55                  60

Leu Phe Phe Leu
65

<210> SEQ ID NO 496
<211> LENGTH: 67
<212> TYPE: PRT
<213> ORGANISM: Artificial Sequence
<220> FEATURE:
<223> OTHER INFORMATION: TCR gamma chain amino acid sequence

<400> SEQUENCE: 496

Pro Ile Lys Thr Asp Val Ile Thr Met Asp Pro Lys Asp Asn Cys Ser
1               5                   10                  15

Lys Asp Ala Asn Asp Thr Leu Leu Leu Gln Leu Thr Asn Thr Ser Ala
            20                  25                  30

Tyr Tyr Met Tyr Leu Leu Leu Leu Lys Ser Val Val Tyr Phe Ala
        35                  40                  45

Ile Ile Thr Cys Cys Leu Leu Arg Arg Thr Ala Phe Cys Cys Asn Gly
    50                  55                  60

Glu Lys Ser
65

<210> SEQ ID NO 497
<211> LENGTH: 5
<212> TYPE: PRT
<213> ORGANISM: Artificial Sequence
<220> FEATURE:
<223> OTHER INFORMATION: GC33 antibody HC-CDR1 amino acid sequence

```
<400> SEQUENCE: 497

Asp Tyr Glu Met His
1               5

<210> SEQ ID NO 498
<211> LENGTH: 17
<212> TYPE: PRT
<213> ORGANISM: Artificial Sequence
<220> FEATURE:
<223> OTHER INFORMATION: GC33 antibody HC-CDR2 amino acid sequence

<400> SEQUENCE: 498

Ala Leu Asp Pro Lys Thr Gly Asp Thr Ala Tyr Ser Gln Lys Phe Lys
1               5                   10                  15

Gly

<210> SEQ ID NO 499
<211> LENGTH: 6
<212> TYPE: PRT
<213> ORGANISM: Artificial Sequence
<220> FEATURE:
<223> OTHER INFORMATION: GC33 antibody HC-CDR3 amino acid sequence

<400> SEQUENCE: 499

Phe Tyr Ser Tyr Thr Tyr
1               5

<210> SEQ ID NO 500
<211> LENGTH: 16
<212> TYPE: PRT
<213> ORGANISM: Artificial Sequence
<220> FEATURE:
<223> OTHER INFORMATION: GC33 antibody LC-CDR1 amino acid sequence

<400> SEQUENCE: 500

Arg Ser Ser Gln Ser Leu Val His Ser Asn Gly Asn Thr Tyr Leu His
1               5                   10                  15

<210> SEQ ID NO 501
<211> LENGTH: 7
<212> TYPE: PRT
<213> ORGANISM: Artificial Sequence
<220> FEATURE:
<223> OTHER INFORMATION: GC33 antibody LC-CDR2 amino acid sequence

<400> SEQUENCE: 501

Lys Val Ser Asn Arg Phe Ser
1               5

<210> SEQ ID NO 502
<211> LENGTH: 9
<212> TYPE: PRT
<213> ORGANISM: Artificial Sequence
<220> FEATURE:
<223> OTHER INFORMATION: GC33 antibody LC-CDR3 amino acid sequence

<400> SEQUENCE: 502

Ser Gln Asn Thr His Val Pro Pro Thr
1               5

<210> SEQ ID NO 503
<211> LENGTH: 116
<212> TYPE: PRT
<213> ORGANISM: Artificial Sequence
<220> FEATURE:
```

<223> OTHER INFORMATION: GC33 antibody VH amino acid sequence

<400> SEQUENCE: 503

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asp Tyr
            20                  25                  30

Glu Met His Trp Val Lys Gln Thr Pro Val His Gly Leu Lys Trp Met
        35                  40                  45

Ile Gly Ala Leu Asp Pro Lys Thr Gly Asp Thr Ala Tyr Ser Gln Lys
    50                  55                  60

Phe Lys Gly Lys Ala Thr Leu Thr Ala Asp Lys Ser Ser Thr Ala
65                  70                  75                  80

Tyr Met Glu Leu Arg Ser Leu Thr Ser Glu Asp Ser Ala Val Tyr Tyr
                85                  90                  95

Cys Thr Arg Phe Tyr Ser Tyr Thr Tyr Trp Gly Gln Gly Thr Leu Val
            100                 105                 110

Thr Val Ser Ala
        115

<210> SEQ ID NO 504
<211> LENGTH: 112
<212> TYPE: PRT
<213> ORGANISM: Artificial Sequence
<220> FEATURE:
<223> OTHER INFORMATION: GC33 antibody VL amino acid sequence

<400> SEQUENCE: 504

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Pro Thr Phe Gly Ser Gly Thr Lys Leu Glu Ile Lys
            100                 105                 110

<210> SEQ ID NO 505
<211> LENGTH: 440
<212> TYPE: PRT
<213> ORGANISM: Artificial Sequence
<220> FEATURE:
<223> OTHER INFORMATION: GPC3A-039 mouse heavy chain amino acid sequence

<400> SEQUENCE: 505

Gln Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Gly Thr Tyr Tyr Ala Asp Ser Val Lys

```
                50              55              60
Gly Arg Phe Thr Ile Ser Arg Asp Asn Ala Lys Asn Ser Leu Tyr Leu
 65                      70                  75                  80

Gln Met Asn Ser Leu Arg Ala Glu Asp Thr Ala Val Tyr Tyr Cys Ala
                     85                  90                  95

Arg Tyr Gly Arg Lys Ser Ile Asp Ala Trp Gly Gln Gly Thr Leu Val
            100                 105                 110

Thr Val Ser Ser Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

Val Asp Lys Lys Ile Val Pro Arg Asp Cys Gly Cys Lys Pro Cys Ile
210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
                245                 250                 255

Val Ala Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285

Phe Asn Ser Thr Phe Arg Ser Val Ser Glu Leu Pro Ile Met His Gln
290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
                325                 330                 335

Lys Ala Pro Gln Val Tyr Thr Ile Pro Pro Pro Lys Glu Gln Met Ala
            340                 345                 350

Lys Asp Lys Val Ser Leu Thr Cys Met Ile Thr Asp Phe Phe Pro Glu
        355                 360                 365

Asp Ile Thr Val Glu Trp Gln Trp Asn Gly Gln Pro Ala Glu Asn Tyr
370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His Thr Glu Lys
            420                 425                 430

Ser Leu Ser His Ser Pro Gly Lys
        435                 440

<210> SEQ ID NO 506
<211> LENGTH: 214
<212> TYPE: PRT
<213> ORGANISM: Artificial Sequence
```

<220> FEATURE:
<223> OTHER INFORMATION: GPC3A-039 mouse light chain amino acid sequence

<400> SEQUENCE: 506

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Gln Pro Lys
            100                 105                 110

Ser Ser Pro Ser Val Thr Leu Phe Pro Pro Ser Ser Glu Glu Leu Glu
        115                 120                 125

Thr Asn Lys Ala Thr Leu Val Cys Thr Ile Thr Asp Phe Tyr Pro Gly
130                 135                 140

Val Val Thr Val Asp Trp Lys Val Asp Gly Thr Pro Val Thr Gln Gly
145                 150                 155                 160

Met Glu Thr Thr Gln Pro Ser Lys Gln Ser Asn Asn Lys Tyr Met Ala
                165                 170                 175

Ser Ser Tyr Leu Thr Leu Thr Ala Arg Ala Trp Glu Arg His Ser Ser
            180                 185                 190

Tyr Ser Cys Gln Val Thr His Glu Gly His Thr Val Glu Lys Ser Leu
        195                 200                 205

Ser Arg Ala Asp Cys Ser
    210

<210> SEQ ID NO 507
<211> LENGTH: 324
<212> TYPE: PRT
<213> ORGANISM: Artificial Sequence
<220> FEATURE:
<223> OTHER INFORMATION: Mouse IgG1 heavy chain constant domain
      amino acid sequence

<400> SEQUENCE: 507

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

```
Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Ala Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
                195                 200                 205

Ile Glu Lys Thr Ile Ser Lys Thr Lys Gly Arg Pro Lys Ala Pro Gln
210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
                260                 265                 270

Pro Ile Met Asp Thr Asp Gly Ser Tyr Phe Val Tyr Ser Lys Leu Asn
                275                 280                 285

Val Gln Lys Ser Asn Trp Glu Ala Gly Asn Thr Phe Thr Cys Ser Val
                290                 295                 300

Leu His Glu Gly Leu His Asn His His Thr Glu Lys Ser Leu Ser His
305                 310                 315                 320

Ser Pro Gly Lys

<210> SEQ ID NO 508
<211> LENGTH: 105
<212> TYPE: PRT
<213> ORGANISM: Artificial Sequence
<220> FEATURE:
<223> OTHER INFORMATION: Mouse lambda light chain constant domain
      amino acid sequence

<400> SEQUENCE: 508

Gln Pro Lys Ser Ser Pro Ser Val Thr Leu Phe Pro Pro Ser Ser Glu
1               5                   10                  15

Glu Leu Glu Thr Asn Lys Ala Thr Leu Val Cys Thr Ile Thr Asp Phe
                20                  25                  30

Tyr Pro Gly Val Val Thr Val Asp Trp Lys Val Asp Gly Thr Pro Val
            35                  40                  45

Thr Gln Gly Met Glu Thr Thr Gln Pro Ser Lys Gln Ser Asn Asn Lys
    50                  55                  60

Tyr Met Ala Ser Ser Tyr Leu Thr Leu Thr Ala Arg Ala Trp Glu Arg
65                  70                  75                  80

His Ser Ser Tyr Ser Cys Gln Val Thr His Glu Gly His Thr Val Glu
                85                  90                  95

Lys Ser Leu Ser Arg Ala Asp Cys Ser
            100                 105

<210> SEQ ID NO 509
<211> LENGTH: 20
<212> TYPE: PRT
<213> ORGANISM: Artificial Sequence
<220> FEATURE:
```

<223> OTHER INFORMATION: Signal peptide amino acid sequence

<400> SEQUENCE: 509

Met Glu Thr Asp Thr Leu Leu Leu Trp Val Leu Leu Leu Trp Val Pro
1               5                   10                  15

Gly Ser Thr Gly
        20

<210> SEQ ID NO 510
<211> LENGTH: 228
<212> TYPE: PRT
<213> ORGANISM: Artificial Sequence
<220> FEATURE:
<223> OTHER INFORMATION: GC33 antibody amino acid sequence

<400> SEQUENCE: 510

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asp Tyr
            20                  25                  30

Glu Met His Trp Val Lys Gln Thr Pro Val His Gly Leu Lys Trp Met
        35                  40                  45

Ile Gly Ala Leu Asp Pro Lys Thr Gly Asp Thr Ala Tyr Ser Gln Lys
    50                  55                  60

Phe Lys Gly Lys Ala Thr Leu Thr Ala Asp Lys Ser Ser Ser Thr Ala
65                  70                  75                  80

Tyr Met Glu Leu Arg Ser Leu Thr Ser Glu Asp Ser Ala Val Tyr Tyr
                85                  90                  95

Cys Thr Arg Phe Tyr Ser Tyr Thr Tyr Trp Gly Gln Gly Thr Leu Val
            100                 105                 110

Thr Val Ser Ala Asp Val Val Met Thr Gln Thr Pro Leu Ser Leu Pro
        115                 120                 125

Val Ser Leu Gly Asp Gln Ala Ser Ile Ser Cys Arg Ser Ser Gln Ser
    130                 135                 140

Leu Val His Ser Asn Gly Asn Thr Tyr Leu His Trp Tyr Leu Gln Lys
145                 150                 155                 160

Pro Gly Gln Ser Pro Lys Leu Leu Ile Tyr Lys Val Ser Asn Arg Phe
                165                 170                 175

Ser Gly Val Pro Asp Arg Phe Ser Gly Ser Gly Ser Gly Thr Asp Phe
            180                 185                 190

Thr Leu Lys Ile Ser Arg Val Glu Ala Glu Asp Leu Gly Val Tyr Phe
        195                 200                 205

Cys Ser Gln Asn Thr His Val Pro Pro Thr Phe Gly Ser Gly Thr Lys
    210                 215                 220

Leu Glu Ile Lys
225

<210> SEQ ID NO 511
<211> LENGTH: 500
<212> TYPE: PRT
<213> ORGANISM: Artificial Sequence
<220> FEATURE:
<223> OTHER INFORMATION: Anti-nGPC3 (GPC3A-037) scFv-anti-CD3 scFv
    amino acid sequence

<400> SEQUENCE: 511

Gln Ser Val Leu Thr Gln Pro Pro Ser Val Ser Ala Ala Pro Gly Gln
1               5                   10                  15

```
Arg Val Thr Ile Ser Cys Ser Gly Thr Arg Ser Asn Ile Gly Ser Asp
             20                  25                  30

Tyr Val Ser Trp Tyr Gln His Leu Pro Gly Thr Ala Pro Lys Leu Leu
         35                  40                  45

Val Tyr Gly Asp Asn Leu Arg Pro Ser Gly Ile Pro Asp Arg Phe Ser
 50                  55                  60

Ala Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Tyr Thr Leu
                 85                  90                  95

Asn Gly Val Val Phe Gly Gly Gly Thr Lys Leu Thr Val Leu Gly Ser
                100                 105                 110

Arg Gly Gly Gly Gly Ser Gly Gly Gly Ser Gly Gly Gly Gly Ser
                115                 120                 125

Leu Glu Met Ala Gln Val Gln Leu Val Glu Ser Gly Gly Gly Leu Val
130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Val Ile Tyr Ser Gly Gly Ser Ser Thr Tyr Tyr
                180                 185                 190

Ala Asp Ser Val Lys Gly Arg Phe Thr Ile Ser Arg Asp Asn Ser Lys
                195                 200                 205

Asn Thr Leu Tyr Leu Gln Met Asn Ser Leu Arg Ala Glu Asp Thr Ala
210                 215                 220

Val Tyr Tyr Cys Ala Arg Thr Ser Tyr Leu Asn His Gly Asp Tyr Trp
225                 230                 235                 240

Gly Gln Gly Thr Leu Val Thr Val Ser Ser Gly Gly Gly Gly
                245                 250                 255

Ser Asp Val Gln Leu Val Gln Ser Gly Ala Glu Val Lys Lys Pro Gly
                260                 265                 270

Ala Ser Val Lys Val Ser Cys Lys Ala Ser Gly Tyr Thr Phe Thr Arg
                275                 280                 285

Tyr Thr Met His Trp Val Arg Gln Ala Pro Gly Gln Gly Leu Glu Trp
290                 295                 300

Ile Gly Tyr Ile Asn Pro Ser Arg Gly Tyr Thr Asn Tyr Ala Asp Ser
305                 310                 315                 320

Val Lys Gly Arg Phe Thr Ile Thr Thr Asp Lys Ser Thr Ser Thr Ala
                325                 330                 335

Tyr Met Glu Leu Ser Ser Leu Arg Ser Glu Asp Thr Ala Thr Tyr Tyr
                340                 345                 350

Cys Ala Arg Tyr Tyr Asp Asp His Tyr Cys Leu Asp Tyr Trp Gly Gln
                355                 360                 365

Gly Thr Thr Val Thr Val Ser Ser Gly Glu Gly Thr Ser Thr Gly Ser
370                 375                 380

Gly Gly Ser Gly Gly Ser Gly Gly Ala Asp Asp Ile Val Leu Thr Gln
385                 390                 395                 400

Ser Pro Ala Thr Leu Ser Leu Ser Pro Gly Glu Arg Ala Thr Leu Ser
                405                 410                 415

Cys Arg Ala Ser Gln Ser Val Ser Tyr Met Asn Trp Tyr Gln Gln Lys
                420                 425                 430

Pro Gly Lys Ala Pro Lys Arg Trp Ile Tyr Asp Thr Ser Lys Val Ala
```

-continued

```
                435                 440                 445
Ser Gly Val Pro Ala Arg Phe Ser Gly Ser Gly Ser Gly Thr Asp Tyr
        450                 455                 460

Ser Leu Thr Ile Asn Ser Leu Glu Ala Glu Asp Ala Ala Thr Tyr Tyr
465                 470                 475                 480

Cys Gln Gln Trp Ser Ser Asn Pro Leu Thr Phe Gly Gly Gly Thr Lys
                        485                 490                 495

Val Glu Ile Lys
            500

<210> SEQ ID NO 512
<211> LENGTH: 498
<212> TYPE: PRT
<213> ORGANISM: Artificial Sequence
<220> FEATURE:
<223> OTHER INFORMATION: Anti-nGPC3 (GPC3A-045) scFv-anti-CD3 scFv
      amino acid sequence

<400> SEQUENCE: 512

Gln Ser Val Leu Thr Gln Pro Pro Ser Val Ser Gly Thr Pro Gly Gln
1               5                   10                  15

Arg Val Ile Ile Ser Cys Pro Gly Ser Thr Ser Asn Ile Gly Thr Asn
            20                  25                  30

Thr Val Asn Trp Tyr Gln Gln Phe Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Gln Met Gln Leu Val Gln Ser Gly Gly Gly Leu Val
    130                 135                 140

Lys Pro Gly Gly Ser Leu Arg Leu Ser Cys Ala Ala Ser Gly Phe Thr
145                 150                 155                 160

Phe Ser Asp Tyr Tyr Met Ser Trp Ile Arg Gln Ala Pro Gly Lys Gly
                165                 170                 175

Leu Glu Trp Val Ser Tyr Ile Ser Ser Ser Gly Ser Thr Ile Tyr Tyr
            180                 185                 190

Ala Asp Ser Val Lys Gly Arg Phe Thr Ile Ser Arg Asp Asn Ala Lys
        195                 200                 205

Asn Ser Leu Tyr Leu Gln Met Asn Ser Leu Arg Ala Glu Asp Thr Ala
    210                 215                 220

Val Tyr Tyr Cys Ala Arg Ala Ser Asp Leu Tyr Gly Asp Trp Gly Gln
225                 230                 235                 240

Gly Thr Leu Val Thr Val Ser Ser Thr Ser Gly Gly Gly Gly Ser Asp
                245                 250                 255

Val Gln Leu Val Gln Ser Gly Ala Glu Val Lys Lys Pro Gly Ala Ser
            260                 265                 270

Val Lys Val Ser Cys Lys Ala Ser Gly Tyr Thr Phe Thr Arg Tyr Thr
        275                 280                 285
```

```
Met His Trp Val Arg Gln Ala Pro Gly Gln Gly Leu Glu Trp Ile Gly
    290                 295                 300
Tyr Ile Asn Pro Ser Arg Gly Tyr Thr Asn Tyr Ala Asp Ser Val Lys
305                 310                 315                 320
Gly Arg Phe Thr Ile Thr Thr Asp Lys Ser Thr Ser Thr Ala Tyr Met
                325                 330                 335
Glu Leu Ser Ser Leu Arg Ser Glu Asp Thr Ala Thr Tyr Tyr Cys Ala
            340                 345                 350
Arg Tyr Tyr Asp Asp His Tyr Cys Leu Asp Tyr Trp Gly Gln Gly Thr
        355                 360                 365
Thr Val Thr Val Ser Ser Gly Glu Gly Thr Ser Thr Gly Ser Gly Gly
    370                 375                 380
Ser Gly Gly Ser Gly Gly Ala Asp Asp Ile Val Leu Thr Gln Ser Pro
385                 390                 395                 400
Ala Thr Leu Ser Leu Ser Pro Gly Glu Arg Ala Thr Leu Ser Cys Arg
                405                 410                 415
Ala Ser Gln Ser Val Ser Tyr Met Asn Trp Tyr Gln Gln Lys Pro Gly
            420                 425                 430
Lys Ala Pro Lys Arg Trp Ile Tyr Asp Thr Ser Lys Val Ala Ser Gly
        435                 440                 445
Val Pro Ala Arg Phe Ser Gly Ser Gly Ser Gly Thr Asp Tyr Ser Leu
    450                 455                 460
Thr Ile Asn Ser Leu Glu Ala Glu Asp Ala Ala Thr Tyr Tyr Cys Gln
465                 470                 475                 480
Gln Trp Ser Ser Asn Pro Leu Thr Phe Gly Gly Gly Thr Lys Val Glu
                485                 490                 495
Ile Lys

<210> SEQ ID NO 513
<211> LENGTH: 503
<212> TYPE: PRT
<213> ORGANISM: Artificial Sequence
<220> FEATURE:
<223> OTHER INFORMATION: Anti-nGPC3 (GPC3A-046) scFv-anti-CD3 scFv
      amino acid sequence

<400> SEQUENCE: 513

Gln Ala Val Leu Thr Gln Pro Pro Ser Val Ser Gly Thr Pro Gly Gln
1               5                   10                  15
Arg Val Thr Ile Ser Cys Ser Gly Ser Ser Asn Phe Gly Ser Asn
                20                  25                  30
Thr Val His Trp Tyr Gln Gln Val Pro Gly Thr Ala Pro Lys Leu Leu
            35                  40                  45
Ile Phe Ser Asn Thr Gln Arg Pro Ser Glu Ile Pro Asp Arg Phe Ser
        50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Thr Gly Val Val Phe Gly Gly Gly Thr Lys Leu Thr Val Leu Gly Ser
            100                 105                 110
Arg Gly Gly Gly Gly Ser Gly Gly Gly Gly Ser Gly Gly Gly Gly Ser
        115                 120                 125
Leu Glu Met Ala Gln Val Gln Leu Val Gln Ser Gly Ala Glu Val Lys
    130                 135                 140
```

-continued

```
Lys Pro Gly Ala Ser Val Thr Val Ser Cys Lys Ala Ser Gly Tyr Arg
145                 150                 155                 160

Phe Ser Asn Tyr Gly Val Ser Trp Val Arg Gln Ala Pro Gly Gln Gly
            165                 170                 175

Leu Glu Trp Met Gly Trp Ile Ser Gly Ser Asn Gly Asn Thr Asn Tyr
        180                 185                 190

Ala Gln Lys Phe Leu Gly Arg Val Thr Met Thr Thr Asp Thr Ser Thr
    195                 200                 205

Thr Thr Ala Tyr Met Glu Leu Ser Ser Leu Arg Ser Asp Asp Thr Ala
210                 215                 220

Val Tyr Tyr Cys Ala Arg Gly Asn Arg Arg Tyr Tyr Ser Pro Ile Ile
225                 230                 235                 240

Asp Pro Trp Gly Gln Gly Thr Leu Val Thr Val Ser Ser Thr Ser Gly
            245                 250                 255

Gly Gly Gly Ser Asp Val Gln Leu Val Gln Ser Gly Ala Glu Val Lys
        260                 265                 270

Lys Pro Gly Ala Ser Val Lys Val Ser Cys Lys Ala Ser Gly Tyr Thr
    275                 280                 285

Phe Thr Arg Tyr Thr Met His Trp Val Arg Gln Ala Pro Gly Gln Gly
290                 295                 300

Leu Glu Trp Ile Gly Tyr Ile Asn Pro Ser Arg Gly Tyr Thr Asn Tyr
305                 310                 315                 320

Ala Asp Ser Val Lys Gly Arg Phe Thr Ile Thr Thr Asp Lys Ser Thr
            325                 330                 335

Ser Thr Ala Tyr Met Glu Leu Ser Ser Leu Arg Ser Glu Asp Thr Ala
        340                 345                 350

Thr Tyr Tyr Cys Ala Arg Tyr Tyr Asp Asp His Tyr Cys Leu Asp Tyr
    355                 360                 365

Trp Gly Gln Gly Thr Thr Val Thr Val Ser Ser Gly Glu Gly Thr Ser
370                 375                 380

Thr Gly Ser Gly Gly Ser Gly Gly Ser Gly Gly Ala Asp Asp Ile Val
385                 390                 395                 400

Leu Thr Gln Ser Pro Ala Thr Leu Ser Leu Ser Pro Gly Glu Arg Ala
            405                 410                 415

Thr Leu Ser Cys Arg Ala Ser Gln Ser Val Ser Tyr Met Asn Trp Tyr
        420                 425                 430

Gln Gln Lys Pro Gly Lys Ala Pro Lys Arg Trp Ile Tyr Asp Thr Ser
    435                 440                 445

Lys Val Ala Ser Gly Val Pro Ala Arg Phe Ser Gly Ser Gly Ser Gly
450                 455                 460

Thr Asp Tyr Ser Leu Thr Ile Asn Ser Leu Glu Ala Glu Asp Ala Ala
465                 470                 475                 480

Thr Tyr Tyr Cys Gln Gln Trp Ser Ser Asn Pro Leu Thr Phe Gly Gly
            485                 490                 495

Gly Thr Lys Val Glu Ile Lys
            500

<210> SEQ ID NO 514
<211> LENGTH: 497
<212> TYPE: PRT
<213> ORGANISM: Artificial Sequence
<220> FEATURE:
<223> OTHER INFORMATION: Anti-nGPC3 (GPC3A-055) scFv-anti-CD3 scFv
      amino acid sequence

<400> SEQUENCE: 514
```

```
Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Tyr Val Phe Gly Thr Gly Thr Lys Val Thr Val Leu Gly Ser Arg Gly
                100                 105                 110

Gly Gly Gly Ser Gly Gly Gly Gly Ser Gly Gly Gly Ser Leu Glu
            115                 120                 125

Met Ala Gln Val Gln Leu Val Gln Ser Gly Ala Glu Val Lys Lys Pro
            130                 135                 140

Gly Ala Ser Val Lys Val Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
            165                 170                 175

Trp Met Gly Ile Ile Asn Pro Ser Gly Gly Ser Thr Ser Tyr Ala Gln
            180                 185                 190

Lys Phe Gln Gly Arg Val Thr Met Thr Arg Asp Thr Ser Thr Ser Thr
            195                 200                 205

Val Tyr Met Glu Leu Ser Ser Leu Arg Ser Glu Asp Thr Ala Val Tyr
            210                 215                 220

Tyr Cys Ala Arg Trp His Gly Pro Tyr Asp Tyr Trp Gly Gln Gly
225                 230                 235                 240

Thr Leu Val Thr Val Ser Ser Thr Ser Gly Gly Gly Ser Asp Val
                245                 250                 255

Gln Leu Val Gln Ser Gly Ala Glu Val Lys Lys Pro Gly Ala Ser Val
            260                 265                 270

Lys Val Ser Cys Lys Ala Ser Gly Tyr Thr Phe Thr Arg Tyr Thr Met
            275                 280                 285

His Trp Val Arg Gln Ala Pro Gly Gln Gly Leu Glu Trp Ile Gly Tyr
            290                 295                 300

Ile Asn Pro Ser Arg Gly Tyr Thr Asn Tyr Ala Asp Ser Val Lys Gly
305                 310                 315                 320

Arg Phe Thr Ile Thr Thr Asp Lys Ser Thr Ser Thr Ala Tyr Met Glu
            325                 330                 335

Leu Ser Ser Leu Arg Ser Glu Asp Thr Ala Thr Tyr Tyr Cys Ala Arg
            340                 345                 350

Tyr Tyr Asp Asp His Tyr Cys Leu Asp Tyr Trp Gly Gln Gly Thr Thr
            355                 360                 365

Val Thr Val Ser Ser Gly Glu Gly Thr Ser Thr Gly Ser Gly Gly Ser
            370                 375                 380

Gly Gly Ser Gly Gly Ala Asp Asp Ile Val Leu Thr Gln Ser Pro Ala
385                 390                 395                 400

Thr Leu Ser Leu Ser Pro Gly Glu Arg Ala Thr Leu Ser Cys Arg Ala
            405                 410                 415
```

-continued

```
Ser Gln Ser Val Ser Tyr Met Asn Trp Tyr Gln Gln Lys Pro Gly Lys
            420                 425                 430

Ala Pro Lys Arg Trp Ile Tyr Asp Thr Ser Lys Val Ala Ser Gly Val
        435                 440                 445

Pro Ala Arg Phe Ser Gly Ser Gly Ser Gly Thr Asp Tyr Ser Leu Thr
    450                 455                 460

Ile Asn Ser Leu Glu Ala Glu Asp Ala Ala Thr Tyr Tyr Cys Gln Gln
465                 470                 475                 480

Trp Ser Ser Asn Pro Leu Thr Phe Gly Gly Gly Thr Lys Val Glu Ile
                485                 490                 495

Lys

<210> SEQ ID NO 515
<211> LENGTH: 499
<212> TYPE: PRT
<213> ORGANISM: Artificial Sequence
<220> FEATURE:
<223> OTHER INFORMATION: Anti-nGPC3 (GPC3A-058) scFv-anti-CD3 scFv
      amino acid sequence

<400> SEQUENCE: 515

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Phe Gly Thr Gly Thr Lys Val Thr Val Leu Gly Ser Arg Gly Gly
            100                 105                 110

Gly Gly Ser Gly Gly Gly Gly Ser Gly Gly Gly Gly Ser Leu Glu Met
        115                 120                 125

Ala Gln Val Gln Leu Val Gln Ser Gly Ala Asp Val Arg Lys Pro Gly
    130                 135                 140

Ala Ser Val Lys Val Ser Cys Lys Ala Ser Gly Tyr Thr Phe Ala Ser
145                 150                 155                 160

His Gly Ile Ser Trp Val Arg Gln Ala Pro Gly Gln Gly Leu Glu Trp
                165                 170                 175

Leu Gly Trp Ile Ser Pro Tyr Thr Gly Asn Thr Asn Tyr Ala Gln Lys
            180                 185                 190

Phe Gln Gly Arg Val Thr Met Ala Thr Asp Thr Ser Thr Ser Thr Ala
        195                 200                 205

Tyr Met Glu Leu Arg Ser Leu Arg Ser Asp Asp Thr Ala Ile Tyr Tyr
    210                 215                 220

Cys Ala Arg Gly Lys Arg Thr Leu Ala Ser Cys Phe Asp Tyr Trp Gly
225                 230                 235                 240

Gln Gly Thr Leu Val Thr Val Ser Ser Thr Ser Gly Gly Gly Gly Ser
                245                 250                 255

Asp Val Gln Leu Val Gln Ser Gly Ala Glu Val Lys Lys Pro Gly Ala
            260                 265                 270
```

```
Ser Val Lys Val Ser Cys Lys Ala Ser Gly Tyr Thr Phe Thr Arg Tyr
            275                 280                 285

Thr Met His Trp Val Arg Gln Ala Pro Gly Gln Gly Leu Glu Trp Ile
        290                 295                 300

Gly Tyr Ile Asn Pro Ser Arg Gly Tyr Thr Asn Tyr Ala Asp Ser Val
305                 310                 315                 320

Lys Gly Arg Phe Thr Ile Thr Thr Asp Lys Ser Thr Ser Thr Ala Tyr
                325                 330                 335

Met Glu Leu Ser Ser Leu Arg Ser Glu Asp Thr Ala Thr Tyr Tyr Cys
            340                 345                 350

Ala Arg Tyr Tyr Asp Asp His Tyr Cys Leu Asp Tyr Trp Gly Gln Gly
        355                 360                 365

Thr Thr Val Thr Val Ser Ser Gly Glu Gly Thr Ser Thr Gly Ser Gly
    370                 375                 380

Gly Ser Gly Gly Ser Gly Gly Ala Asp Asp Ile Val Leu Thr Gln Ser
385                 390                 395                 400

Pro Ala Thr Leu Ser Leu Ser Pro Gly Glu Arg Ala Thr Leu Ser Cys
                405                 410                 415

Arg Ala Ser Gln Ser Val Ser Tyr Met Asn Trp Tyr Gln Gln Lys Pro
            420                 425                 430

Gly Lys Ala Pro Lys Arg Trp Ile Tyr Asp Thr Ser Lys Val Ala Ser
        435                 440                 445

Gly Val Pro Ala Arg Phe Ser Gly Ser Gly Ser Gly Thr Asp Tyr Ser
    450                 455                 460

Leu Thr Ile Asn Ser Leu Glu Ala Glu Asp Ala Ala Thr Tyr Tyr Cys
465                 470                 475                 480

Gln Gln Trp Ser Ser Asn Pro Leu Thr Phe Gly Gly Gly Thr Lys Val
                485                 490                 495

Glu Ile Lys

<210> SEQ ID NO 516
<211> LENGTH: 472
<212> TYPE: PRT
<213> ORGANISM: Artificial Sequence
<220> FEATURE:
<223> OTHER INFORMATION: ET230-37-28Z CAR amino acid sequence

<400> SEQUENCE: 516

Gln Ser Val Leu Thr Gln Pro Pro Ser Val Ser Ala Ala Pro Gly Gln
1               5                   10                  15

Arg Val Thr Ile Ser Cys Ser Gly Thr Arg Ser Asn Ile Gly Ser Asp
            20                  25                  30

Tyr Val Ser Trp Tyr Gln His Leu Pro Gly Thr Ala Pro Lys Leu Leu
        35                  40                  45

Val Tyr Gly Asp Asn Leu Arg Pro Ser Gly Ile Pro Asp Arg Phe Ser
    50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Tyr Thr Leu
                85                  90                  95

Asn Gly Val Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Gln Val Gln Leu Val Glu Ser Gly Gly Gly Leu Val
```

```
                130                 135                 140
Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Val Ile Tyr Ser Gly Gly Ser Ser Thr Tyr Tyr
            180                 185                 190

Ala Asp Ser Val Lys Gly Arg Phe Thr Ile Ser Arg Asp Asn Ser Lys
        195                 200                 205

Asn Thr Leu Tyr Leu Gln Met Asn Ser Leu Arg Ala Glu Asp Thr Ala
    210                 215                 220

Val Tyr Tyr Cys Ala Arg Thr Ser Tyr Leu Asn His Gly Asp Tyr Trp
225                 230                 235                 240

Gly Gln Gly Thr Leu Val Thr Val Ser Ala Ala Ile Glu Val
                245                 250                 255

Met Tyr Pro Pro Pro Tyr Leu Asp Asn Glu Lys Ser Asn Gly Thr Ile
                260                 265                 270

Ile His Val Lys Gly Lys His Leu Cys Pro Ser Pro Leu Phe Pro Gly
                275                 280                 285

Pro Ser Lys Pro Phe Trp Val Leu Val Val Val Gly Gly Val Leu Ala
            290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
                340                 345                 350

Arg Asp Phe Ala Ala Tyr Arg Ser Arg Val Lys Phe Ser Arg Ser Ala
            355                 360                 365

Asp Ala Pro Ala Tyr Gln Gln Gly Gln Asn Gln Leu Tyr Asn Glu Leu
        370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
                420                 425                 430

Glu Ile Gly Met Lys Gly Glu Arg Arg Arg Gly Lys Gly His Asp Gly
            435                 440                 445

Leu Tyr Gln Gly Leu Ser Thr Ala Thr Lys Asp Thr Tyr Asp Ala Leu
        450                 455                 460

His Met Gln Ala Leu Pro Pro Arg
465                 470

<210> SEQ ID NO 517
<211> LENGTH: 248
<212> TYPE: PRT
<213> ORGANISM: Artificial Sequence
<220> FEATURE:
<223> OTHER INFORMATION: ET230-45-28Z CAR amino acid sequence

<400> SEQUENCE: 517

Gln Ser Val Leu Thr Gln Pro Pro Ser Val Ser Gly Thr Pro Gly Gln
1               5                   10                  15

Arg Val Ile Ile Ser Cys Pro Gly Ser Thr Ser Asn Ile Gly Thr Asn
```

```
            20                  25                  30
Thr Val Asn Trp Tyr Gln Gln Phe Pro Gly Thr Ala Pro Lys Leu Leu
         35                  40                  45
Ile Tyr Ser Asn Asn Gln Arg Pro Ser Gly Val Pro Asp Arg Phe Ser
     50                  55                  60
Gly Ser Lys Ser Gly Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Ser Leu
                 85                  90                  95
Asn Gly Val Val Phe Gly Gly Gly Thr Lys Leu Thr Val Leu Gly Ser
             100                 105                 110
Arg Gly Gly Gly Gly Ser Gly Gly Gly Ser Gly Gly Gly Gly Ser
             115                 120                 125
Leu Glu Met Ala Gln Met Gln Leu Val Gln Ser Gly Gly Gly Leu Val
             130                 135                 140
Lys Pro Gly Gly Ser Leu Arg Leu Ser Cys Ala Ala Ser Gly Phe Thr
145                 150                 155                 160
Phe Ser Asp Tyr Tyr Met Ser Trp Ile Arg Gln Ala Pro Gly Lys Gly
                 165                 170                 175
Leu Glu Trp Val Ser Tyr Ile Ser Ser Ser Gly Ser Thr Ile Tyr Tyr
             180                 185                 190
Ala Asp Ser Val Lys Gly Arg Phe Thr Ile Ser Arg Asp Asn Ala Lys
             195                 200                 205
Asn Ser Leu Tyr Leu Gln Met Asn Ser Leu Arg Ala Glu Asp Thr Ala
         210                 215                 220
Val Tyr Tyr Cys Ala Arg Ala Ser Asp Leu Tyr Gly Asp Trp Gly Gln
225                 230                 235                 240
Gly Thr Leu Val Thr Val Ser Ser
                 245
```

<210> SEQ ID NO 518
<211> LENGTH: 253
<212> TYPE: PRT
<213> ORGANISM: Artificial Sequence
<220> FEATURE:
<223> OTHER INFORMATION: ET230-46-28Z CAR amino acid sequence

<400> SEQUENCE: 518

```
Gln Ala Val Leu Thr Gln Pro Pro Ser Val Ser Gly Thr Pro Gly Gln
  1               5                  10                  15
Arg Val Thr Ile Ser Cys Ser Gly Ser Ser Ser Asn Phe Gly Ser Asn
             20                  25                  30
Thr Val His Trp Tyr Gln Gln Val Pro Gly Thr Ala Pro Lys Leu Leu
         35                  40                  45
Ile Phe Ser Asn Thr Gln Arg Pro Ser Glu Ile Pro Asp Arg Phe Ser
     50                  55                  60
Gly Ser Lys Ser Gly Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Ser Leu
                 85                  90                  95
Thr Gly Val Val Phe Gly Gly Gly Thr Lys Leu Thr Val Leu Gly Ser
             100                 105                 110
Arg Gly Gly Gly Gly Ser Gly Gly Gly Ser Gly Gly Gly Gly Ser
             115                 120                 125
Leu Glu Met Ala Gln Val Gln Leu Val Gln Ser Gly Ala Glu Val Lys
```

```
                130               135               140
Lys Pro Gly Ala Ser Val Thr Val Ser Cys Lys Ala Ser Gly Tyr Arg
145                 150               155                 160

Phe Ser Asn Tyr Gly Val Ser Trp Val Arg Gln Ala Pro Gly Gln Gly
                165               170                 175

Leu Glu Trp Met Gly Trp Ile Ser Ser Asn Gly Asn Thr Asn Tyr
                180               185                 190

Ala Gln Lys Phe Leu Gly Arg Val Thr Met Thr Thr Asp Thr Ser Thr
                195               200                 205

Thr Thr Ala Tyr Met Glu Leu Ser Ser Leu Arg Ser Asp Asp Thr Ala
    210               215                 220

Val Tyr Tyr Cys Ala Arg Gly Asn Arg Arg Tyr Tyr Ser Pro Ile Ile
225                 230               235                 240

Asp Pro Trp Gly Gln Gly Thr Leu Val Thr Val Ser Ser
                245               250

<210> SEQ ID NO 519
<211> LENGTH: 247
<212> TYPE: PRT
<213> ORGANISM: Artificial Sequence
<220> FEATURE:
<223> OTHER INFORMATION: ET230-55-28Z CAR amino acid sequence

<400> SEQUENCE: 519

Gln Pro Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Val Leu Gly Ser Arg Gly
            100                 105                 110

Gly Gly Gly Ser Gly Gly Gly Gly Ser Gly Gly Gly Gly Ser Leu Glu
        115                 120                 125

Met Ala Gln Val Gln Leu Val Gln Ser Gly Ala Glu Val Lys Lys Pro
    130                 135                 140

Gly Ala Ser Val Lys Val Ser Cys Lys Ala Ser Gly Tyr Thr Phe Thr
145                 150                 155                 160

Ser Tyr Tyr Met His Trp Val Arg Gln Ala Pro Gly Gln Gly Leu Glu
                165                 170                 175

Trp Met Gly Ile Ile Asn Pro Ser Gly Gly Ser Thr Ser Tyr Ala Gln
            180                 185                 190

Lys Phe Gln Gly Arg Val Thr Met Thr Arg Asp Thr Ser Thr Ser Thr
        195                 200                 205

Val Tyr Met Glu Leu Ser Ser Leu Arg Ser Glu Asp Thr Ala Val Tyr
    210                 215                 220

Tyr Cys Ala Arg Trp His Gly Gly Pro Tyr Asp Tyr Trp Gly Gln Gly
225                 230                 235                 240

Thr Leu Val Thr Val Ser Ser
```

<210> SEQ ID NO 520
<211> LENGTH: 249
<212> TYPE: PRT
<213> ORGANISM: Artificial Sequence
<220> FEATURE:
<223> OTHER INFORMATION: ET230-58-28Z CAR amino acid sequence

<400> SEQUENCE: 520

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Phe Gly Thr Gly Thr Lys Val Thr Val Leu Gly Ser Arg Gly Gly
            100                 105                 110

Gly Gly Ser Gly Gly Gly Gly Ser Gly Gly Gly Gly Ser Leu Glu Met
        115                 120                 125

Ala Gln Val Gln Leu Val Gln Ser Gly Ala Asp Val Arg Lys Pro Gly
    130                 135                 140

Ala Ser Val Lys Val Ser Cys Lys Ala Ser Gly Tyr Thr Phe Ala Ser
145                 150                 155                 160

His Gly Ile Ser Trp Val Arg Gln Ala Pro Gly Gln Gly Leu Glu Trp
                165                 170                 175

Leu Gly Trp Ile Ser Pro Tyr Thr Gly Asn Thr Asn Tyr Ala Gln Lys
            180                 185                 190

Phe Gln Gly Arg Val Thr Met Ala Thr Asp Thr Ser Thr Ser Thr Ala
        195                 200                 205

Tyr Met Glu Leu Arg Ser Leu Arg Ser Asp Asp Thr Ala Ile Tyr Tyr
    210                 215                 220

Cys Ala Arg Gly Lys Arg Thr Leu Ala Ser Cys Phe Asp Tyr Trp Gly
225                 230                 235                 240

Gln Gly Thr Leu Val Thr Val Ser Ser
                245

<210> SEQ ID NO 521
<211> LENGTH: 247
<212> TYPE: PRT
<213> ORGANISM: Artificial Sequence
<220> FEATURE:
<223> OTHER INFORMATION: ET230-87-28Z CAR amino acid sequence

<400> SEQUENCE: 521

Asp Val Val Met Thr Gln Ser Pro Leu Ser Leu Pro Val Thr Pro Gly
1               5                   10                  15

Glu Pro Ala Ser Val Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50              55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Ala
            85                  90                  95

Leu Gln Thr Pro Trp Thr Phe Gly Gln Gly Thr Lys Val Glu Ile Lys
            100                 105                 110

Arg Ser Arg Gly Gly Gly Gly Ser Gly Gly Gly Gly Ser Gly Gly Gly
            115                 120                 125

Gly Ser Leu Glu Met Ala Glu Val Gln Leu Val Gln Ser Gly Ala Glu
130                 135                 140

Val Arg Lys Pro Gly Ser Ser Val Lys Val Ser Cys Gln Ala Ser Gly
145                 150                 155                 160

Gly Thr Phe Gly Ser Tyr Ala Ile Ser Trp Val Arg Gln Ala Pro Gly
            165                 170                 175

Gln Gly Leu Glu Trp Met Gly Arg Ile Ile Pro Val Leu Gly Arg Thr
            180                 185                 190

Lys Tyr Ala Gln Lys Phe Gln Gly Arg Val Thr Val Thr Ala Asp Thr
195                 200                 205

Ser Thr Ser Thr Val Tyr Met Glu Leu Thr Ser Leu Thr Ser Glu Asp
210                 215                 220

Thr Ala Val Tyr Tyr Cys Ala Arg Thr Asn Asp Ser Trp Gly Gln Gly
225                 230                 235                 240

Thr Leu Val Thr Val Ser Ser
                245

<210> SEQ ID NO 522
<211> LENGTH: 288
<212> TYPE: PRT
<213> ORGANISM: Artificial Sequence
<220> FEATURE:
<223> OTHER INFORMATION: anti-AFP158/HLA-A*02:01-caTCR-6MD delta

<400> SEQUENCE: 522

Glu Val Gln Leu Val Gln Ser Gly Ala Glu Val Lys Lys Pro Gly Glu
1               5                   10                  15

Ser Leu Thr Ile Ser Cys Lys Ala Ser Gly Tyr Ser Phe Pro Asn Tyr
            20                  25                  30

Trp Ile Thr Trp Val Arg Gln Met Ser Gly Gly Leu Glu Trp Met
            35                  40                  45

Gly Arg Ile Asp Pro Gly Asp Ser Tyr Thr Thr Tyr Asn Pro Ser Phe
            50                  55                  60

Gln Gly His Val Thr Ile Ser Ile Asp Lys Ser Thr Asn Thr Ala Tyr
65              70                  75                  80

Leu His Trp Asn Ser Leu Lys Ala Ser Asp Thr Ala Met Tyr Tyr Cys
            85                  90                  95

Ala Arg Tyr Tyr Val Ser Leu Val Asp Ile Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Glu Val Lys Thr
    210                 215                 220

Asp Ser Thr Asp His Val Lys Pro Lys Glu Thr Glu Asn Thr Lys Gln
225                 230                 235                 240

Pro Ser Lys Ser Cys His Lys Pro Lys Ala Ile Val His Thr Glu Lys
                245                 250                 255

Val Asn Met Met Ser Leu Thr Val Leu Gly Leu Arg Met Leu Phe Ala
            260                 265                 270

Lys Thr Val Ala Val Asn Phe Leu Leu Thr Ala Lys Leu Phe Phe Leu
        275                 280                 285

<210> SEQ ID NO 523
<211> LENGTH: 283
<212> TYPE: PRT
<213> ORGANISM: Artificial Sequence
<220> FEATURE:
<223> OTHER INFORMATION: anti-AFP158/HLA-A*02:01-caTCR-6MD gamma

<400> SEQUENCE: 523

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Glu Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Gly
                85                  90                  95

Ser Arg Ala Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Pro Ile Lys Thr Asp Val Ile Thr
    210                 215                 220

Met Asp Pro Lys Asp Asn Cys Ser Lys Asp Ala Asn Asp Thr Leu Leu
225                 230                 235                 240

-continued

```
Leu Gln Leu Thr Asn Thr Ser Ala Tyr Tyr Met Tyr Leu Leu Leu Leu
            245                 250                 255

Leu Lys Ser Val Val Tyr Phe Ala Ile Ile Thr Cys Cys Leu Leu Arg
        260                 265                 270

Arg Thr Ala Phe Cys Cys Asn Gly Glu Lys Ser
        275                 280

<210> SEQ ID NO 524
<211> LENGTH: 180
<212> TYPE: DNA
<213> ORGANISM: Artificial Sequence
<220> FEATURE:
<223> OTHER INFORMATION: 6NFAT response element

<400> SEQUENCE: 524
ggaggaaaaa ctgtttcata cagaaggcgt ggaggaaaaa ctgtttcata cagaaggcgt      60
ggaggaaaaa ctgtttcata cagaaggcgt ggaggaaaaa ctgtttcata cagaaggcgt     120
ggaggaaaaa ctgtttcata cagaaggcgt ggaggaaaaa ctgtttcata cagaaggcgt     180

<210> SEQ ID NO 525
<211> LENGTH: 149
<212> TYPE: DNA
<213> ORGANISM: Artificial Sequence
<220> FEATURE:
<223> OTHER INFORMATION: TA promoter

<400> SEQUENCE: 525
gccgccccga ctgcatctgc gtgttccaat tcgccaatga caagacgctg ggcggggttt      60
gtgtcatcat agaactaaag acatgcaaat atatttcttc ggggacacc gccagcaaac      120 gcgagcaacg ggccacgggg atgaagcag                                         149

<210> SEQ ID NO 526
<211> LENGTH: 335
<212> TYPE: DNA
<213> ORGANISM: Artificial Sequence
<220> FEATURE:
<223> OTHER INFORMATION: NFAT-derived promoter

<400> SEQUENCE: 526
ggaggaaaaa ctgtttcata cagaaggcgt ggaggaaaaa ctgtttcata cagaaggcgt      60
ggaggaaaaa ctgtttcata cagaaggcgt ggaggaaaaa ctgtttcata cagaaggcgt     120
ggaggaaaaa ctgtttcata cagaaggcgt ggaggaaaaa ctgtttcata cagaaggcgt     180
ctcgaggccg ccccgactgc atctgcgtgt tccaattcgc caatgacaag acgctgggcg     240
gggtttgtgt catcatagaa ctaaagacat gcaaatatat ttcttccggg gacaccgcca     300
gcaaacgcga gcaacgggcc acggggatga agcag                               335

<210> SEQ ID NO 527
<211> LENGTH: 544
<212> TYPE: DNA
<213> ORGANISM: Artificial Sequence
<220> FEATURE:
<223> OTHER INFORMATION: EF1-alpha promoter

<400> SEQUENCE: 527
ggatctgcga tcgctccggt gcccgtcagt gggcagagcg cacatcgccc acagtccccg      60
agaagttggg gggaggggtc ggcaattgaa cgggtgccta gagaaggtgg cgcggggtaa     120
actgggaaag tgatgtcgtg tactggctcc gcctttttcc cgagggtggg ggagaaccgt     180
```

```
atataagtgc agtagtcgcc gtgaacgttc tttttcgcaa cgggtttgcc gccagaacac    240
agctgaagct tcgaggggct cgcatctctc cttcacgcgc cgccgcccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctac                                                                544
```

<210> SEQ ID NO 528
<211> LENGTH: 117
<212> TYPE: PRT
<213> ORGANISM: Artificial Sequence
<220> FEATURE:
<223> OTHER INFORMATION: EF1-alpha promoter

<400> SEQUENCE: 528

Glu Val Gln Leu Val Gln Ser Gly Ala Glu Val Lys Lys Pro Gly Glu
1               5                   10                  15

Ser Leu Thr Ile Ser Cys Lys Ala Ser Gly Tyr Ser Phe Pro Asn Tyr
            20                  25                  30

Trp Ile Thr Trp Val Arg Gln Met Ser Gly Gly Leu Glu Trp Met
        35                  40                  45

Gly Arg Ile Asp Pro Gly Asp Ser Tyr Thr Thr Tyr Asn Pro Ser Phe
    50                  55                  60

Gln Gly His Val Thr Ile Ser Ile Asp Lys Ser Thr Asn Thr Ala Tyr
65                  70                  75                  80

Leu His Trp Asn Ser Leu Lys Ala Ser Asp Thr Ala Met Tyr Tyr Cys
                85                  90                  95

Ala Arg Tyr Tyr Val Ser Leu Val Asp Ile Trp Gly Gln Gly Thr Leu
            100                 105                 110

Val Thr Val Ser Ser
        115

<210> SEQ ID NO 529
<211> LENGTH: 110
<212> TYPE: PRT
<213> ORGANISM: Artificial Sequence
<220> FEATURE:
<223> OTHER INFORMATION: IgVL domain of anti-AFP antibody

<400> SEQUENCE: 529

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Glu Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Gly
                85                  90                  95

Ser Arg Ala Val Phe Gly Gly Gly Thr Lys Leu Thr Val Leu
            100                 105                 110

<210> SEQ ID NO 530
<211> LENGTH: 110
<212> TYPE: PRT
<213> ORGANISM: Artificial Sequence
<220> FEATURE:
<223> OTHER INFORMATION: CSR1

<400> SEQUENCE: 530

```
Ala Ala Ala Ile Glu Val Met Tyr Pro Pro Tyr Leu Asp Asn Glu
1               5                   10                  15

Lys Ser Asn Gly Thr Ile Ile His Val Lys Gly Lys His Leu Cys Pro
                20                  25                  30

Ser Pro Leu Phe Pro Gly Pro Ser Lys Pro Phe Trp Val Leu Val Val
            35                  40                  45

Val Gly Gly Val Leu Ala Cys Tyr Ser Leu Leu Val Thr Val Ala Phe
50                  55                  60

Ile Ile Phe Trp Val Arg Ser Lys Arg Ser Arg Leu Leu His Ser Asp
65                  70                  75                  80

Tyr Met Asn Met Thr Pro Arg Arg Pro Gly Pro Thr Arg Lys His Tyr
                85                  90                  95

Gln Pro Tyr Ala Pro Pro Arg Asp Phe Ala Ala Tyr Arg Ser
            100                 105                 110
```

<210> SEQ ID NO 531
<211> LENGTH: 360
<212> TYPE: PRT
<213> ORGANISM: Artificial Sequence
<220> FEATURE:
<223> OTHER INFORMATION: Anti-GPC3 CSR

<400> SEQUENCE: 531

```
Gln Ser Val Leu Thr Gln Pro Pro Ser Val Ser Ala Ala Pro Gly Gln
1               5                   10                  15

Arg Val Thr Ile Ser Cys Ser Gly Thr Arg Ser Asn Ile Gly Ser Asp
                20                  25                  30

Tyr Val Ser Trp Tyr Gln His Leu Pro Gly Thr Ala Pro Lys Leu Leu
            35                  40                  45

Val Tyr Gly Asp Asn Leu Arg Pro Ser Gly Ile Pro Asp Arg Phe Ser
50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Tyr Thr Leu
                85                  90                  95

Asn Gly Val Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
            115                 120                 125

Leu Glu Met Ala Gln Val Gln Leu Val Glu Ser Gly Gly Gly Leu Val
            130                 135                 140

Gln Pro Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Val Ile Tyr Ser Gly Gly Ser Ser Thr Tyr Tyr
            180                 185                 190

Ala Asp Ser Val Lys Gly Arg Phe Thr Ile Ser Arg Asp Asn Ser Lys
            195                 200                 205
```

```
Asn Thr Leu Tyr Leu Gln Met Asn Ser Leu Arg Ala Glu Asp Thr Ala
            210                 215                 220

Val Tyr Tyr Cys Ala Arg Thr Ser Tyr Leu Asn His Gly Asp Tyr Trp
225                 230                 235                 240

Gly Gln Gly Thr Leu Val Thr Val Ser Ala Ala Ile Glu Val
                245                 250                 255

Met Tyr Pro Pro Tyr Leu Asp Asn Glu Lys Ser Asn Gly Thr Ile
            260                 265                 270

Ile His Val Lys Gly Lys His Leu Cys Pro Ser Pro Leu Phe Pro Gly
            275                 280                 285

Pro Ser Lys Pro Phe Trp Val Leu Val Val Val Gly Gly Val Leu Ala
            290                 295                 300

Cys Tyr Ser Leu Leu Val Thr Val Ala Phe Ile Ile Phe Trp Val Arg
305                 310                 315                 320

Ser Lys Arg Ser Arg Leu Leu His Ser Asp Tyr Met Asn Met Thr Pro
                325                 330                 335

Arg Arg Pro Gly Pro Thr Arg Lys His Tyr Gln Pro Tyr Ala Pro Pro
                340                 345                 350

Arg Asp Phe Ala Ala Tyr Arg Ser
                355                 360

<210> SEQ ID NO 532
<211> LENGTH: 288
<212> TYPE: PRT
<213> ORGANISM: Artificial Sequence
<220> FEATURE:
<223> OTHER INFORMATION: anti-AFP158/HLA-A*02:01-caTCR-1-0 delta

<400> SEQUENCE: 532

Glu Val Gln Leu Val Gln Ser Gly Ala Glu Val Lys Lys Pro Gly Glu
1               5                   10                  15

Ser Leu Thr Ile Ser Cys Lys Ala Ser Gly Tyr Ser Phe Pro Asn Tyr
                20                  25                  30

Trp Ile Thr Trp Val Arg Gln Met Ser Gly Gly Leu Glu Trp Met
            35                  40                  45

Gly Arg Ile Asp Pro Gly Asp Ser Tyr Thr Thr Tyr Asn Pro Ser Phe
50                  55                  60

Gln Gly His Val Thr Ile Ser Ile Asp Lys Ser Thr Asn Thr Ala Tyr
65                  70                  75                  80

Leu His Trp Asn Ser Leu Lys Ala Ser Asp Thr Ala Met Tyr Tyr Cys
                85                  90                  95

Ala Arg Tyr Tyr Val Ser Leu Val Asp Ile Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205
```

```
Thr Lys Val Asp Lys Arg Val Glu Pro Lys Ser Cys Glu Val Lys Thr
    210                 215                 220
Asp Ser Thr Asp His Val Lys Pro Lys Glu Thr Glu Asn Thr Lys Gln
225                 230                 235                 240
Pro Ser Lys Ser Cys His Lys Pro Lys Ala Ile Val His Thr Glu Lys
            245                 250                 255
Val Asn Met Met Ser Leu Thr Val Leu Gly Leu Arg Met Leu Phe Ala
            260                 265                 270
Lys Thr Val Ala Val Asn Phe Leu Leu Thr Ala Lys Leu Phe Phe Leu
            275                 280                 285

<210> SEQ ID NO 533
<211> LENGTH: 283
<212> TYPE: PRT
<213> ORGANISM: Artificial Sequence
<220> FEATURE:
<223> OTHER INFORMATION: anti-AFP158/HLA-A*02:01-caTCR-1-0 gamma

<400> SEQUENCE: 533

Gln Ser Val Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Tyr Val Ser Trp Tyr Gln Gln His Pro Gly Lys Ala Pro Lys Leu
        35                  40                  45
Met Ile Tyr Asp Val Asn Asn Arg Pro Ser Glu Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Ser Ser Tyr Thr Thr Gly
                85                  90                  95
Ser Arg Ala Val Phe Gly Gly Gly Thr Lys Leu Thr Val Leu Gly Gln
            100                 105                 110
Pro Lys Ala Asn Pro Thr Val Thr Leu Phe Pro Pro Ser Ser Glu Glu
        115                 120                 125
Leu Gln Ala Asn Lys Ala Thr Leu Val Cys Leu Ile Ser Asp Phe Tyr
    130                 135                 140
Pro Gly Ala Val Thr Val Ala Trp Lys Ala Asp Gly Ser Pro Val Lys
145                 150                 155                 160
Ala Gly Val Glu Thr Thr Lys Pro Ser Lys Gln Ser Asn Asn Lys Tyr
                165                 170                 175
Ala Ala Ser Ser Tyr Leu Ser Leu Thr Pro Glu Gln Trp Lys Ser His
            180                 185                 190
Arg Ser Tyr Ser Cys Gln Val Thr His Glu Gly Ser Thr Val Glu Lys
        195                 200                 205
Thr Val Ala Pro Thr Glu Cys Ser Pro Ile Lys Thr Asp Val Ile Thr
    210                 215                 220
Met Asp Pro Lys Asp Asn Cys Ser Lys Asp Ala Asn Asp Thr Leu Leu
225                 230                 235                 240
Leu Gln Leu Thr Asn Thr Ser Ala Tyr Tyr Met Tyr Leu Leu Leu Leu
                245                 250                 255
Leu Lys Ser Val Val Tyr Phe Ala Ile Ile Thr Cys Cys Leu Leu Arg
            260                 265                 270
Arg Thr Ala Phe Cys Cys Asn Gly Glu Lys Ser
        275                 280
```

<210> SEQ ID NO 534
<211> LENGTH: 288
<212> TYPE: PRT
<213> ORGANISM: Artificial Sequence
<220> FEATURE:
<223> OTHER INFORMATION: anti-AFP158/HLA-A*02:01-caTCR-1-TM5 delta

<400> SEQUENCE: 534

Glu Val Gln Leu Val Gln Ser Gly Ala Glu Val Lys Lys Pro Gly Glu
1               5                   10                  15

Ser Leu Thr Ile Ser Cys Lys Ala Ser Gly Tyr Ser Phe Pro Asn Tyr
            20                  25                  30

Trp Ile Thr Trp Val Arg Gln Met Ser Gly Gly Leu Glu Trp Met
        35                  40                  45

Gly Arg Ile Asp Pro Gly Asp Ser Tyr Thr Thr Tyr Asn Pro Ser Phe
    50                  55                  60

Gln Gly His Val Thr Ile Ser Ile Asp Lys Ser Thr Asn Thr Ala Tyr
65                  70                  75                  80

Leu His Trp Asn Ser Leu Lys Ala Ser Asp Thr Ala Met Tyr Tyr Cys
                85                  90                  95

Ala Arg Tyr Tyr Val Ser Leu Val Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Glu Val Lys Thr
    210                 215                 220

Asp Ser Thr Asp His Val Lys Pro Lys Glu Thr Glu Asn Thr Lys Gln
225                 230                 235                 240

Pro Ser Lys Ser Cys His Lys Pro Lys Ala Ile Val His Thr Glu Lys
                245                 250                 255

Val Asn Met Met Ser Leu Thr Val Leu Gly Leu Arg Val Leu Phe Ala
            260                 265                 270

Lys Thr Val Ala Val Asn Phe Leu Leu Thr Ala Lys Leu Phe Phe Leu
        275                 280                 285

<210> SEQ ID NO 535
<211> LENGTH: 283
<212> TYPE: PRT
<213> ORGANISM: Artificial Sequence
<220> FEATURE:
<223> OTHER INFORMATION: anti-AFP158/HLA-A*02:01-caTCR-1-TM5 gamma

<400> SEQUENCE: 535

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr

```
                    20                  25                  30
Asn Tyr Val Ser Trp Tyr Gln Gln His Pro Gly Lys Ala Pro Lys Leu
                35                  40                  45
Met Ile Tyr Asp Val Asn Asn Arg Pro Ser Glu Val Ser Asn Arg Phe
 50                  55                  60
Ser Gly Ser Lys Ser Gly Asn Thr Ala Ser Leu Thr Ile Ser Gly Leu
 65                  70                  75                  80
Gln Ala Glu Asp Glu Ala Asp Tyr Tyr Cys Ser Ser Tyr Thr Thr Gly
                85                  90                  95
Ser Arg Ala Val Phe Gly Gly Gly Thr Lys Leu Thr Val Leu Gly Gln
                100                 105                 110
Pro Lys Ala Asn Pro Thr Val Thr Leu Phe Pro Pro Ser Ser Glu Glu
                115                 120                 125
Leu Gln Ala Asn Lys Ala Thr Leu Val Cys Leu Ile Ser Asp Phe Tyr
                130                 135                 140
Pro Gly Ala Val Thr Val Ala Trp Lys Ala Asp Gly Ser Pro Val Lys
145                 150                 155                 160
Ala Gly Val Glu Thr Thr Lys Pro Ser Lys Gln Ser Asn Asn Lys Tyr
                165                 170                 175
Ala Ala Ser Ser Tyr Leu Ser Leu Thr Pro Glu Gln Trp Lys Ser His
                180                 185                 190
Arg Ser Tyr Ser Cys Gln Val Thr His Glu Gly Ser Thr Val Glu Lys
                195                 200                 205
Thr Val Ala Pro Thr Glu Cys Ser Pro Ile Lys Thr Asp Val Ile Thr
                210                 215                 220
Met Asp Pro Lys Asp Asn Cys Ser Lys Asp Ala Asn Asp Thr Leu Leu
225                 230                 235                 240
Leu Gln Leu Thr Asn Thr Ser Ala Tyr Leu Val Tyr Leu Leu Leu Leu
                245                 250                 255
Leu Lys Ser Val Val Tyr Phe Val Ile Val Thr Cys Cys Leu Leu Arg
                260                 265                 270
Arg Thr Ala Phe Cys Cys Asn Gly Glu Lys Ser
                275                 280

<210> SEQ ID NO 536
<211> LENGTH: 43
<212> TYPE: PRT
<213> ORGANISM: Artificial Sequence
<220> FEATURE:
<223> OTHER INFORMATION: GPC33 fragment

<400> SEQUENCE: 536

Leu Ala Glu Leu Ala Tyr Asp Leu Asp Val Asp Asp Ala Pro Gly Asn
1               5                   10                  15
Ser Gln Gln Ala Thr Pro Lys Asp Asn Glu Ile Ser Thr Phe His Asn
                20                  25                  30
Leu Gly Asn Val His Ser Pro Leu Lys Leu Leu
                35                  40
```